(12) United States Patent
Sheppard et al.

(10) Patent No.: US 11,104,921 B2
(45) Date of Patent: Aug. 31, 2021

(54) MICROORGANISMS FOR THE PRODUCTION OF INSECT PHEROMONES AND RELATED COMPOUNDS

(71) Applicant: Provivi, Inc., Santa Monica, CA (US)

(72) Inventors: Micah Sheppard, Los Angeles, CA (US); Thomas Heel, Los Angeles, CA (US); Peter Meinhold, Topanga, CA (US); Keith Wampler, Santa Monica, CA (US); Pedro Coelho, Santa Monica, CA (US); Effendi Leonard, Anaheim Hills, CA (US)

(73) Assignee: Provivi, Inc., Santa Monica, CA (US)

( * ) Notice: Subject to any disclaimer, the term of this patent is extended or adjusted under 35 U.S.C. 154(b) by 0 days.

(21) Appl. No.: 16/614,144

(22) PCT Filed: May 17, 2018

(86) PCT No.: PCT/US2018/033151
§ 371 (c)(1),
(2) Date: Nov. 15, 2019

(87) PCT Pub. No.: WO2018/213554
PCT Pub. Date: Nov. 22, 2018

(65) Prior Publication Data
US 2020/0140902 A1    May 7, 2020

Related U.S. Application Data

(60) Provisional application No. 62/507,654, filed on May 17, 2017.

(51) Int. Cl.
| | |
|---|---|
| *C12N 1/20* | (2006.01) |
| *C12P 7/64* | (2006.01) |
| *C12N 9/04* | (2006.01) |
| *C12N 9/02* | (2006.01) |
| *C12N 9/10* | (2006.01) |
| *C12N 15/81* | (2006.01) |

(52) U.S. Cl.
CPC ............. *C12P 7/64* (2013.01); *C12N 9/0006* (2013.01); *C12N 9/0008* (2013.01); *C12N 9/0071* (2013.01); *C12N 9/1029* (2013.01); *C12N 15/815* (2013.01)

(58) Field of Classification Search
CPC ............... C12N 9/0071; C12N 15/815; C12Y 114/19001; C12P 7/6409
See application file for complete search history.

(56) References Cited

U.S. PATENT DOCUMENTS

| | | |
|---|---|---|
| 4,231,947 A | 11/1980 | Schrock |
| 4,245,131 A | 1/1981 | Schrock |
| 4,427,595 A | 1/1984 | Schrock |
| 4,681,956 A | 7/1987 | Schrock |
| 4,727,215 A | 2/1988 | Schrock |
| 5,087,710 A | 2/1992 | Schrock et al. |
| 5,124,491 A | 6/1992 | Fleckenstein et al. |
| 5,142,073 A | 8/1992 | Schrock et al. |
| 5,146,033 A | 9/1992 | Schrock et al. |
| 6,121,473 A | 9/2000 | Schrock et al. |
| 6,291,742 B1 | 9/2001 | Somerville et al. |
| 6,346,652 B1 | 2/2002 | Schrock et al. |
| 7,169,959 B2 | 1/2007 | Heck et al. |
| 7,700,833 B2 | 4/2010 | Renz et al. |
| 8,110,093 B2 | 2/2012 | Friedman et al. |
| 8,110,670 B2 | 2/2012 | Hu et al. |
| 8,268,599 B2 | 9/2012 | Schirmer et al. |
| 8,283,143 B2 | 10/2012 | Hu et al. |

(Continued)

FOREIGN PATENT DOCUMENTS

| | | |
|---|---|---|
| CN | 1656226 A | 8/2005 |
| CN | 101490241 A | 7/2009 |

(Continued)

OTHER PUBLICATIONS

Chandrasekhar, et al., "One pot conversion of carboxylic acids to aldehydes with DIBAL-H". Tetrahedron Letters (Feb. 19, 1998); 39(8): 909-910.
Extended European Search Report for Application No. EP 17810850.2 dated Feb. 18, 2020, 9 pages.
Kuemmel and Chapman, "The 9-hexadecenoic and 11-octadecenoic acid content of natural fats and oils". Lipids (1968); 3(4): 313-316.
Vickery, J.R., "The fatty acid composition of the seed oils of proteaceae: A chemotaxonomic study". Phytochemistry (Jan. 1971); 10(1): 123-130.

(Continued)

*Primary Examiner* — Tekchand Saidha

(74) *Attorney, Agent, or Firm* — Cooley LLP

(57) ABSTRACT

The present application relates to recombinant microorganisms useful in the biosynthesis of unsaturated $C_6$-$C_{24}$ fatty alcohols, aldehydes, and acetates which may be useful as insect pheromones, fragrances, flavors, and polymer intermediates. The recombinant microorganisms may express enzymes or enzyme variants useful for production of and/or may be modified to down regulate pathways to shunt production toward unsaturated $C_6$-$C_{24}$ fatty alcohols, aldehydes, and acetates. The $C_6$-$C_{24}$ fatty alcohols, aldehydes, and acetates described herein may be used as substrates for metathesis reactions to expand the repertoire of target compounds and pheromones. Also provided are methods of producing unsaturated $C_6$-$C_{24}$ fatty alcohols, aldehydes, and acetates using the recombinant microorganisms, as well as compositions comprising the recombinant microorganisms and/or optionally one or more of the product alcohols, aldehydes, or acetates.

19 Claims, 54 Drawing Sheets

Specification includes a Sequence Listing.

(56) References Cited

U.S. PATENT DOCUMENTS

| | | |
|---|---|---|
| 8,535,916 B2 | 9/2013 | Del Cardayre et al. |
| 8,658,404 B2 | 2/2014 | Schirmer et al. |
| 8,987,531 B2 | 3/2015 | Grubbs et al. |
| 9,017,984 B2 | 4/2015 | Hu et al. |
| 9,068,201 B2 | 6/2015 | Hu et al. |
| 9,200,299 B2 | 12/2015 | Friedman et al. |
| 9,598,706 B2 | 3/2017 | Keasling et al. |
| 9,776,179 B2 | 10/2017 | Wampler et al. |
| 10,017,455 B2 | 7/2018 | Hu et al. |
| 10,093,950 B2 | 10/2018 | Gatter et al. |
| 10,308,962 B1 | 6/2019 | Leonard et al. |
| 2006/0078973 A1 | 4/2006 | Renz et al. |
| 2007/0282148 A1 | 12/2007 | Berlin et al. |
| 2008/0009598 A1 | 1/2008 | Herrmann et al. |
| 2008/0119678 A1 | 5/2008 | Hock et al. |
| 2008/0207911 A1 | 8/2008 | Herrmann et al. |
| 2008/0221345 A1 | 9/2008 | Winde et al. |
| 2008/0275247 A1 | 11/2008 | Kadyrov et al. |
| 2010/0087644 A1 | 4/2010 | Mauduit et al. |
| 2010/0113795 A1 | 5/2010 | Arlt et al. |
| 2010/0170826 A1 | 7/2010 | Friedman et al. |
| 2010/0174068 A1 | 7/2010 | Grela et al. |
| 2010/0199548 A1 | 8/2010 | Del Cardayre et al. |
| 2010/0235934 A1 | 9/2010 | Friedman et al. |
| 2010/0242345 A1 | 9/2010 | Keasling et al. |
| 2010/0251601 A1 | 10/2010 | Hu et al. |
| 2011/0015430 A1 | 1/2011 | Schrock et al. |
| 2011/0282068 A1 | 1/2011 | Herrmann et al. |
| 2011/0040099 A1 | 2/2011 | Kadyrov et al. |
| 2011/0065915 A1 | 3/2011 | Malcolmson et al. |
| 2011/0077421 A1 | 3/2011 | Schrock |
| 2011/0097769 A1 | 4/2011 | Del Cardayre et al. |
| 2011/0237815 A1 | 9/2011 | Hock et al. |
| 2011/0256599 A1 | 10/2011 | Hu et al. |
| 2012/0123133 A1 | 5/2012 | Berlin et al. |
| 2012/0142979 A1 | 6/2012 | Keasling et al. |
| 2012/0264983 A1 | 10/2012 | Hu et al. |
| 2012/0302710 A1 | 11/2012 | Hoveyda et al. |
| 2012/0323000 A1 | 12/2012 | Hoveyda et al. |
| 2013/0079515 A1 | 3/2013 | Grela et al. |
| 2013/0116434 A1 | 5/2013 | Schrock et al. |
| 2013/0144060 A1 | 6/2013 | Mauduit et al. |
| 2013/0211096 A1 | 8/2013 | Arlt et al. |
| 2013/0245339 A1 | 9/2013 | Keasling et al. |
| 2013/0261312 A1 | 10/2013 | Allen et al. |
| 2013/0274482 A1 | 10/2013 | Schrock et al. |
| 2013/0281688 A1 | 10/2013 | Di Biase et al. |
| 2013/0281706 A1 | 10/2013 | Hock et al. |
| 2013/0296511 A1 | 11/2013 | Ung et al. |
| 2014/0171607 A1 | 6/2014 | Grela et al. |
| 2014/0330018 A1 | 11/2014 | Czirok et al. |
| 2014/0378637 A1 | 12/2014 | Schrock et al. |
| 2015/0018557 A1 | 1/2015 | Nolan et al. |
| 2015/0038723 A1 | 2/2015 | Herrmann et al. |
| 2015/0045558 A1 | 2/2015 | Plenio et al. |
| 2015/0125933 A1 | 5/2015 | Groban et al. |
| 2015/0166465 A1 | 6/2015 | Chen et al. |
| 2015/0275188 A1 | 10/2015 | Hu et al. |
| 2016/0046914 A1 | 2/2016 | Hom et al. |
| 2016/0076058 A1 | 3/2016 | Friedman et al. |
| 2016/0108436 A1 | 4/2016 | Coelho et al. |
| 2016/0222419 A1* | 8/2016 | Stuart .................. C12N 9/0008 |
| 2016/0304913 A1 | 10/2016 | Gatter et al. |
| 2017/0275651 A1 | 9/2017 | Keasling et al. |
| 2017/0327799 A1 | 11/2017 | Hu et al. |
| 2018/0162916 A1 | 6/2018 | Borodina et al. |
| 2018/0371510 A1 | 12/2018 | Gatter et al. |
| 2019/0031594 A1 | 1/2019 | Hu et al. |
| 2019/0136272 A1 | 5/2019 | Otte et al. |
| 2019/0338317 A1 | 11/2019 | Leonard et al. |
| 2019/0376094 A1 | 12/2019 | Friedman et al. |
| 2020/0017890 A1 | 1/2020 | Sanchez-Riera et al. |

FOREIGN PATENT DOCUMENTS

| | | |
|---|---|---|
| CN | 102264910 A | 11/2011 |
| CN | 102807470 A | 12/2012 |
| CN | 103842502 A | 6/2014 |
| CN | 104370701 A | 2/2015 |
| CN | 104781411 A | 7/2015 |
| CN | 104968672 A | 10/2015 |
| CN | 108138202 A | 6/2018 |
| EP | 15174099 | 6/2015 |
| JP | H10-506783 A | 7/1998 |
| WO | WO 1991/009825 A1 | 7/1991 |
| WO | WO 1992/019631 A1 | 11/1992 |
| WO | WO 2007/075427 A1 | 7/2007 |
| WO | WO 2007/136762 A2 | 11/2007 |
| WO | WO 2007/140954 A1 | 12/2007 |
| WO | WO 2008/066754 A1 | 6/2008 |
| WO | WO 2008/100251 A1 | 8/2008 |
| WO | WO 2008/113041 A2 | 9/2008 |
| WO | WO 2008/119082 A2 | 10/2008 |
| WO | WO 2008/147781 A2 | 12/2008 |
| WO | WO 2009/126831 A1 | 10/2009 |
| WO | WO 2010/037550 A1 | 4/2010 |
| WO | WO 2010/144296 A2 | 12/2010 |
| WO | WO 2011/040963 A1 | 4/2011 |
| WO | WO 2011/069134 A3 | 6/2011 |
| WO | WO 2011/091980 A1 | 8/2011 |
| WO | WO 2011/097642 A1 | 8/2011 |
| WO | WO 2012/087964 A1 | 6/2012 |
| WO | WO 2012/167171 A3 | 12/2012 |
| WO | WO 2012/168183 A1 | 12/2012 |
| WO | WO 2013/135776 A1 | 3/2013 |
| WO | WO 2013/070725 A1 | 5/2013 |
| WO | WO 2014/001291 A1 | 1/2014 |
| WO | WO 2014/008054 A2 | 1/2014 |
| WO | WO 2014/067767 A1 | 5/2014 |
| WO | WO 2014/134333 A1 | 9/2014 |
| WO | WO 2014/139679 A3 | 9/2014 |
| WO | WO 2014/155185 A1 | 10/2014 |
| WO | WO 2014/169014 A1 | 10/2014 |
| WO | WO 2014/172534 A1 | 10/2014 |
| WO | WO 2015/003814 A1 | 1/2015 |
| WO | WO 2015/003815 A1 | 1/2015 |
| WO | WO 2015/042306 A1 | 3/2015 |
| WO | WO 2015/077752 A1 | 5/2015 |
| WO | WO 2015/086684 A1 | 6/2015 |
| WO | WO 2015/171057 A1 | 11/2015 |
| WO | WO 2016/099568 A1 | 6/2016 |
| WO | WO 2016/159869 A1 | 10/2016 |
| WO | WO 2016/207339 A1 | 12/2016 |
| WO | WO 2017/087846 A1 | 5/2017 |
| WO | WO 2017/214133 A2 | 12/2017 |
| WO | WO 2018/213554 A1 | 11/2018 |

OTHER PUBLICATIONS

Wang, et al., "Comparative study of sex pheromone composition and biosynthesis in Helicoverpa armigera, H. assulta and their hybrid". Insect Biochemistry and Molecular Biology (Jun. 2005); 35(6): 575-583. Epub Mar. 16, 2005.

Zhu and Jackson, "Metabolic engineering of Yarrowia lipolytica for industrial applications". Current Opinion in Biotechnology (Dec. 2015); 36: 65-72.

Mauersberger, Stephan, "Cytochromes P450 of the Alkane-Utilising Yeast *Yarrowia lipolytica*", pp. 227-262 in G. Barth (ed.), Yarrowia lipolytica, Microbiology Monographs vol. 25, Springer-Verlag Berlin Heidelberg (2013); 273 pages.

U.S. Appl. No. 15/983,706, filed May 18, 2018, now U.S. Pat. No. 10,308,962, Patented.

U.S. Appl. No. 16/307,282, filed Dec. 5, 2018, Pending.

U.S. Appl. No. 16/420,566, filed May 23, 2019, Pending.

[Author Unknown] "NP 001037017: (11Z)-hexadec-11-enoyl-CoA conjugase [Bombyx mori]," NCBI Protein, Jul. 5, 2004 (Jul. 5, 2004), pp. 1-4. Retrieved from the Internet: <https://www.ncbi.nlm.nih.gov/protein/162809332> on Jan. 18, 2017 (Jan. 18, 2017). Entire document.

(56) References Cited

OTHER PUBLICATIONS

Adrio, J.L., "Oleaginous Yeasts: Promising Platforms for the Production of Oleochemicals and Biofuels". Biotechnol Bioeng. (Sep. 2017); 114(9): 1915-1920. Epub May 29, 2017.

Ando, et. Al., "Lepidopteran Sex Pheromones". Topics in Current Chemistry (2004); 239: 51-96.

Ayciriex, et al., "YPR139c/LOA1 encodes a novel lysophosphatidic acid acyltransferase associated with lipid droplets and involved in TAG homeostasis." Mol Biol Cell (2012); 23 (2): 233-246.

Baba, et al., "Construction of Escherichia coli K-12 in-frame, single-gene knockout mutants: the Keio collection." Molecular Systems Biology (2006); 2 (1): 1-11.

Beisson, et al., "The acyltransferase GPAT5 is required for the synthesis of suberin in seed coat and root of Arabidopsis." Plant Cell (2007); 19 (1): 351-368.

Benghezal, et al., "SLC1 and SLC4 Encode Partially Redundant Acyl-Coenzyme A 1-Acylglycerol-3-phosphate O-Acyltransferases of Budding Yeast." The Journal of Biological Chemistry (2007); 282 (42): 30845-30855.

Blom, et al., "Sequence and structure-based prediction of eukaryotic protein phosphorylation sites." J. Mol. Biol. (1999); 294 (5): 1351-1362.

Bredeweg, et al., "A molecular genetic toolbox for Yarrowia lipolytica." Biotechnol Biofuels (2017); 10: 2, pp. 1-22, ePub Jan. 3, 2017.

Broun, et al., "Catalytic plasticity of fatty acid modification enzymes underlying chemical diversity of plant lipids." Science (1998); 282 (5392): 1315-1317.

Brown, et al., "Limnanthes douglasii lysophosphatidic acid acyltransferases: immunological quantification, acyl selectivity and functional replacement of the Escherichia coli plsC gene." Biochemical Journal (2002); 364 (3): 795-805.

Chen, et al., "The yeast acylglycerol acyltransferase LCA1 is a key component of Lands cycle for phosphatidylcholine turnover." FEBS Letters (2007); 581 (28): 5511-5516.

Choi, et al., "Regulatory elements that control transcription activation and unsaturated fatty acid-mediated repression of the Saccharomyces cerevisiae OLE1 gene." J Biol. Chem. (1996); 271 (7): 3581-3589.

Colby, et al., "Calculating synergistic and antagonistic responses of herbicide combinations." Weeds, (1967); 15 (1): 20-22.

GenBank entry AF272342.1, Helicoverpa zea acyl-CoA delta-11 desaturase (PGDs1) mRNA, complete cds, Aug. 30, 2001, 2 pages, (https://www.ncbi.nlm.nih.gov/nuccore/AF272342.1), retrieved on Jan. 6, 2020.

Dahlqvist, et al., "Phospholipid:diacylglycerol acyltransferase: An enzyme that catalyzes the acyl-CoA-independent formation of triacylglycerol in yeast and plants." Proc Natl Acad Sci USA (2000); 97 (12): 6487-6492.

Devos and Valencia. "Practical limits of function prediction." Proteins: Structure, Function, and Genetics (2000); 41 (1): 98-107.

Ding, et al., "Analysis of the Agrotis segetum pheromone gland transcriptome in the light of sex pheromone biosynthesis" BMC Genomics (2015); 16 (711): 1-21.

EBI Accession EAY76846. Oryza sativa triacylglycerol lipase, Dec. 29, 2008 [online]. [Retrieved Sep. 21, 2008]. 3 Pages, Retrieved from the internet: <URL: https:/lwww.ebi.ac.uk/ena/data/view/EAY76846&display=text>.

Endo, et al., "Chelated ruthenium catalysts for Z-selective olefin metathesis" J Am Chem Soc. (2011); 133 (22): 8525-8527.

Extended European Search Report for Application No. EP 16867255.8 dated Feb. 5, 2019, 12 pages.

Flook, et al. "Z-Selective and Syndioselective Ring-Opening Metathesis Polymerization (ROMP) Initiated by MonoAryloxidePyrrolide (MAP) Catalysts" Macromolecules (2010) 43(18):7515-7522.

Gatter, et al., "A newly identified fatty alcohol oxidase gene is mainly responsible for the oxidation of long-chain ω-hydroxy fatty acids in Yarrowia lipolytica." FEMS Yeast Res. (Sep. 2014); 14(6): 858-872. Epub Jul. 2, 2014.

GenBank Accession AAL49962.1. Diacylglycerol acyltransferase 1 [Bos Taurus], Feb. 11, 2002 [online]. [Retrieved Sep. 21, 2002]. 2 pages, Retrieved from the internet:< URL: https://www.ncbi.nlm.nih.gov/protein/AAL49962.1/>.

GenBank Accession KTA99184.1 Alcohol O-acetyltransferase 2 [Candida] glabrata]. Feb. 9, 2016 [online]. [Retrieved Sep. 21, 2018]. 1 page, Retrieved from the internet:< URL: https://www.ncbi.nlm.nih.gov/protein/KTA99184.1/>.

GenBank Accession AKD01723.1 Alcohol dehydrogenase 12 [Helicoverpa armigera], Apr. 25, 2015 [online]. [retrieved Sep. 21, 2018]. 1 page, Retrieved from the internet:< URL: https://www.ncbi.nlm.nih.gov/protein/AKD01723.1/>.

Goelz and Cronan Jr., "The positional distribution of fatty acids in Escherichia coli phospholipids is not regulated by sn-glycerol 3-phosphate levels." J Bacteriol (1980); 144 (1): 462-464.

Gonzalez, et al., "Fatty acid-responsive control of mRNA stability. Unsaturated fatty acid-induced degradation of the Saccharomyces OLEI transcript" J. Biol. Chem. (1996); 271 (42): 25801-25809.

Greenway and Silbert, "Altered acyltransferase activity in Escherichia coli associated with mutations in acyl coenzyme A synthetase." The Journal of Biological Chemistry (1983); 258 (21): 13034-13042.

Groot, et al., "The Genetic Basis of Pheromone Evolution in Moths." Annu Rev Entomol. (2016); 61: 99-117. Epub Nov. 4, 2015.

Hagström, et al., "A moth pheromone brewery: production of (Z)-11-hexadecenol by heterologous co-expression of two biosynthetic genes from a noctuid moth in a yeast cell factory" Microb. Cell Fact. (2013); 12: 125, pp. 1-11.

Hagstrom, et al., "Semi-selective fatty acyl reductases from four heliothine moths influence the specific pheromone composition" PLoS One (2012); 7 (5): e37230: 1-11.

Halford, B. "Olefin Metathesis for Macrocycles—Organic Synthesis: Tungsten catalysts make macrocyclic olefins with Z-selectivity" Chem. Eng. News (2011); 89 (45): 11.

Hartung, et al., "Highly Z-selective and enantioselective ring-opening/cross-metathesis catalyzed by a resolved stereogenic-at-Ru complex" J Am Chem Soc. (2013); 135 (28): 10183-10185.

Heath, et al., "Periodicity of Female Sex Pheromone Titer and Release in Heliothis subflexa and H. virescens (Lepidoptera: Noctuidae)". Annals of the Entomological Society of America (Mar. 1, 1991); vol. 84, Issue 2, pp. 182-189.

Heier, et al., "Identification of Yju3p as functional orthologue of mammalian monoglyceride lipase in the yeast Saccharomyces cerevisiae." Biochimica et Biophysica Acta (2010); 1801 (9): 1063-1071.

Herbert, et al., "Concise syntheses of insect pheromones using Z-selective cross metathesis" Angew Chem Int Ed Engl. (2013); 52 (1): 310-314.

Hobbs, et al., "Cloning of a cDNA encoding diacylglycerol acyltransferase from Arabidopsis thaliana and its functional expression." FEBS Lett (1999); 452 (3): 145-149.

Ingrell, et al., "NetPhosYeast: prediction of protein phosphorylation sites in yeast." Bioinformatics (2007); 23 (7): 895-897.

Iwama, et al., "Alcohol dehydrogenases and an alcohol oxidase involved in the assimilation of exogenous fatty alcohols in Yarrowia lipolytica." FEMS Yeast Research (May 2015); 15(3): fov014, pp. 1-12.

Jain, et al., "Identification of a Novel Lysophospholipid Acyltransferase in Saccharomyces cerevisiae." The Journal of Biological Chemistry (2007); 282 (42): 30562-30569.

Jako, et al., "Seed-Specific Over-Expression of an Arabidopsis cDNA Encoding a Diacylglycerol Acyltransferase Enhances Seed Oil Content and Seed Weight." Plant Physiol (2001); 126 (2): 861-874.

Jurenka and Rafaeli, "Regulatory Role of PBAN in Sex Pheromone Biosynthesis of Heliothine Moths." Front. Endocrinol. (2011); 2 (46): 1-8.

Kajiwara, et al., "Molecular cloning and characterization of the Δ9 fatty acid desaturase gene and its promoter from Saccharomyces kluyveri" FEMS Yeast. Res. (2002); 2: 333-339.

Kalscheuer and Steinbüchel, "A Novel Bifunctional Wax Ester Synthase/Acyl-CoA:Diacylglycerol Acyltransferase Mediates Wax

(56) References Cited

OTHER PUBLICATIONS

Ester and Triacylglycerol Biosynthesis in Acinetobacter calcoaceticus ADP1." The Journal of Biological Chemistry (2002); 278 (10): 8075-8082.

Keitz, et al., "Cis-selective ring-opening metathesis polymerization with ruthenium catalysts" J Am Chem Soc. (2012); 134 (4): 2040-2043.

Keitz, et al., "Improved ruthenium catalysts for Z-selective olefin metathesis" J Am Chem Soc. (2012); 134 (1): 693-699.

Kito, et al., "Inhibition of L-Glycerol 3-Phosphate Acyltransferase from *Escherichia coli* by cis-9, 10-Methylenehexadecanoic Acid." The Journal of Biochemistry (1972); 71 (1): 99-105.

Lardizabal, et al., "DGAT2 is a new diacylglycerol acyltransferase gene family: purification, cloning, and expression in insect cells of two polypeptides from Mortierella ramanniana with diacylglycerol acyltransferase activity." The Journal of Biological Chemistry (2001); 276 (42): 38862-38869.

Lassner, et al., "Lysophosphatidic Acid Acyltransferase from Meadowfoam Mediates Insertion of Erucic Acid at the sn-2 Position of Triacylglycerol in Transgenic Rapeseed Oil." Plant Physiol (1995); 109 (4): 1389-1394.

Lee, D. "Organic chemistry: Overcoming catalytic bias" Nature (2011) 471 (7339): 452-453.

Liénard, et al., "Sex pheromone biosynthetic pathways are conserved between moths and the butterfly *Bicyclus anynana*." Nature Communications (2014); 5: 3957, pp. 1-12.

Lewin, et al., "Analysis of Amino Acid Motifs Diagnostic for the sn-Glycerol-3-phosphate Acyltransferase Reaction." Biochemistry (1999); 38 (18): 5764-5771.

Li, et al., "Identification of acyltransferases required for cutin biosynthesis and production of cutin with suberin-like monomers." Proc Natl Acad Sci USA (2007); 104 (46): 18339-18344.

Liu, et al., "Functional and Topological Analysis of Yeast Acyl-CoA:Diacylglycerol Acyltransferase 2, an Endoplasmic Reticulum Enzyme Essential for Triacylglycerol Biosynthesis." The Journal of Biological Chemistry (2011); 286 (15): 13115-13126.

Lu, et al., "Acyl-phosphates initiate membrane phospholipid synthesis in Gram-positive pathogens." Mol Cell (2006); 23 (5): 765-772.

Maniatis, et al,. "Regulation of inducible and tissue-specific gene expression" Science (1987); 236 (4806): 1237-1245.

Marx, et al, "Stereoselective access to Z and E macrocycles by ruthenium-catalyzed Z-selective ring-closing metathesis and ethenolysis" J Am Chem Soc. (2013); 135 (1): 94-97.

Mauersberger, et al., "Insertional Mutagenesis in the n-Alkane-Assimilating Yeast *Yarrowia lipolytica*: Generation of Tagged Mutations in Genes Involved in Hydrophobic Substrate Utilization." J. Bacteriology (2001); 183 (17): 5102-5109.

Meek, et al. "Z-selective catalytic olefin cross-metathesis for natural product synthesis" Nature (2011); 471 (7339): 461-466.

Miller, W. T., "Tyrosine kinase signaling and the emergence of multicellularity" Biochimica et Biophysica Acta (BBA)—Molecular Cell Research (2012); 1823 (6): 1053-1057.

Moss, et al. "Determination of cellular fatty acid compositions of various yeasts by gas-liquid chromatography" J Clin Microbiol. (1982); 16 (6): 1073-1079.

Moto, et al., "Involvement of a bifunctional fatty-acyl desaturase in the biosynthesis of the silkmoth, *Bombyx mori*, sex pheromone." PNAS (2004); 101 (23): 8631-8636.

Murata, et al., "Modes of Fatty-Acid Desaturation in Cyanobacteria." Plant Cell Physiol (1992); 33(7): 933-941.

Nagiec, et al., "A suppressor gene that enables *Saccharomyces cerevisiae* to grow without making sphingolipids encodes a protein that resembles an *Escherichia coli* fatty acyltransferase." The Journal of Biological Chemistry (1993); 268 (29): 22156-22163.

Nishida, et al., "The gene and the RNA for the precursor to the plastid-located glycerol-3-phosphate acyltransferase of *Arabidopsis thaliana*." Plant Mol Biol. (1993); 21 (2): 267-277.

Oelkers, et al., "The DGA1 gene determines a second triglyceride synthetic pathway in yeast." The Journal of Biological Chemistry (2002); 277 (11): 8877-8881.

Okuyama and Wakil, "Positional Specificities of Acyl Coenzyme A:Glycerophosphate and Acyl Coenzyme A:Monoacylglycerophosphate Acyltransferases in *Escherichia coli*." The Journal of Biological Chemistry (1973); 248 (14): 5197-5205.

Ondi, et al. "High activity, stabilized formulations, efficient synthesis and industrial use of Mo- and W-based metathesis catalysts" XiMo Technology Updates, 2015: http://www.ximoinc.com/files/ximo/uploads/download/Summary_3.11.15.pdf.

PCT/US2016/062852, International Preliminary Report on Patentability, dated May 22, 2018, 10 pages.

PCT/US2016/062852, International Search Report and Written Opinion, dated Feb. 7, 2017, 13 pages.

PCT/US2016/062852, Third Party Observation filed by Danmarks Tekniske Universitet dated Oct. 5, 2017 with WIPO, 7 pages.

PCT/US2017/036136, Invitation to Pay Additional Fees, dated Sep. 20, 2017, 3 pages.

PCT/US2017/036136, International Search Report and Written Opinion, dated Nov. 17, 2017, 15 pages.

PCT/US2017/036136, International Preliminary Report on Patentability, dated Dec. 11, 2018, 10 pages.

PCT/US2018/033151, Invitation to Pay Additional Fees, dated Aug. 14, 2018, 6 pages.

PCT/US2018/033151, International Search Report and Written Opinion, dated Oct. 15, 2018, 22 pages.

PCT/US2018/033151, International Preliminary Report on Patentability, dated Nov. 19, 2019, 14 pages.

Peryshkov, et al. "B(C6F5)3 Activation of Oxo Tungsten complexes that are relevant to olefin metathesis" Organometallics (2013); 32 (19): 5256-5259.

Peryshkov, et al., "Z-Selective olefin metathesis reactions promoted by tungsten oxo alkylidene complexes" J Am Chem Soc. (2011); 133 (51): 20754-20757.

Riekhof, et al., "Identification and Characterization of the Major Lysophosphatidylethanolamine Acyltransferase in *Saccharomyces cerevisiae*." The Journal of Biological Chemistry (2007); 282 (39): 28344-28352.

Rock, et al., "Phospholipid synthesis in *Escherichia coli*. Characteristics of fatty acid transfer from acyl-acyl carrier protein to sn-glycerol 3-phosphate." The Journal of Biological Chemistry (1981); 256 (2): 736-742.

Rosenfield, et al., "Structural and functional conservation and divergence among acyl-CoA desaturases of two noctuid species, the corn earworm, *Helicoverpa zea*, and the cabbage looper, *Trichoplusia ni*." Insect. Biochem. Mol. Biol. (2001); 31 (10): 949-964.

Sandager, et al., "Storage lipid synthesis is non-essential in yeast." J Biol Chem (2002); 277 (8): 6478-6482.

Schrock, et al. "Z-Selective and syndioselective ring-opening metathesis polymerization (ROMP) Initiated by monoaryloxidepyrrolide (MAP) catalysts" Macromolecules (2010); 43 (18): 7515-7522.

Seffernick, et al., "Melamine deaminase and Atrazine chlorohydrolase: 98 percent identical but functionally different." J. Bacteriol. (2001); 183 (8): 2405-2410.

Sheng and Feng, "Metabolic engineering of yeast to produce fatty acid-derived biofuels: bottlenecks and solutions". Frontiers in Microbiology (2015) vol. 6, 11 pages.

Shi, et al., "Improving Production of Malonyl Coenzyme A-Derived Metabolites by Abolishing Snf1-Dependent Regulation of Acc1." mBio (2014); 5 (3): e01130-14: 1-8.

Shi and Zhao, "Metabolic Engineering of Oleaginous Yeasts for Production of Fuels and Chemicals". Front Microbiol. (Nov. 8, 2017); 8: 2185. Published online Nov. 8, 2017.

Sorger and Daum, "Synthesis of Triacylglycerols by the Acyl-Coenzyme A:Diacyl-Glycerol Acyltransferase Dga1p in Lipid Particles of the Yeast *Saccharomyces cerevisiae*." J Bacteriol (2002); 184 (2):519-524.

Ståhl, et al., "Cloning and Functional Characterization of a Phospholipid:Diacylglycerol Acyltransferase from *Arabidopsis*." Plant Physiology (2004); 135 (3):1324-1335.

Stelinski, et al., "Sprayable microencapsulated sex pheromone formulations for mating disruption of four *tortricid* species: effects

(56) References Cited

OTHER PUBLICATIONS of application height, rate, frequency, and sticker adjuvant" J Econ. Entomol. (2007); 100(4): 1360-1369.
Stöveken, et al., "The Wax Ester Synthase/Acyl Coenzyme A:Diacylglycerol Acyltransferase from *Acinetobacter* sp. Strain ADP1: Characterization of a Novel Type of Acyltransferase." J Bacteriol (2005); 187 (4): 1369-1376.
Takai et al. "Construction and characterization of a Yarrowia lipolytica mutant lacking genes encoding cytochromes P450 subfamily 52." Fungal Genet Biol. (2012); 49 (1): 58-64. Epub Nov. 17, 2011.
Third Party Observations filed Jan. 8, 2020, in European Application No. 16867255.8, 19 pages.
European Patent Office Communication dated Jan. 13, 2020 transmitting Third Party Observations filed Jan. 8, 2020, in European Application No. 16867255.8, 1 page.
Townsend, et al. "Z-selective metathesis homocoupling of 1,3-dienes by molybdenum and tungsten monoaryloxide pyrrolide (MAP) complexes" J Am Chem Soc. (2012); 134 (28): 11334-11337.
UniProtKB-O74934 (ACOX1_YARLI): 9 (nine) pages downloaded on Oct. 23, 2018 from https://www.uniprot.org/uniprot/074934.
Uniprot Accession A0A178WDE4. Acyl-coenzyme A oxidase, Apr. 12, 2017 [online]. [Retrieved on Aug. 10, 2018]. 1 page, Retrieved from the internet: <URL: https://www.uniprot.org/uniproVAOA178WDE4.txt?version=7>.
Uniprot Accession R8XW24. Acinetobacter calcoaceticus—Fatty acyl-CoA reductase, Apr. 13, 2013 [online]. [Retrieved Sep. 21, 2018]. 1 page, Retrieved from the internet: <URL: https://www.uniprot.org/uniprot/R8XW24.txt?version=14>.
Uthoff, et al., "Thio Wax Ester Biosynthesis Utilizing the Unspecific Bifunctional Wax Ester Synthase/Acyl Coenzyme A:Diacylglycerol Acyltransferase of *Acinetobacter* sp. Strain ADP1." Appl. Environ. Microbiol. (2005); 71 (2): 790-796.
Wahl, et al., "Antagonistic regulation of dgkA and plsB genes of phospholipid synthesis by multiple stress responses in *Escherichia coli*." Molecular Microbiology (2011); 80 (5): 1260-1275.
Wang, et al. "Efficient and selective formation of macrocyclic disubstituted Z alkenes by ring-closing metathesis (RCM) reactions catalyzed by Mo- or W-based monoaryloxide pyrrolide (MAP) complexes: applications to total syntheses of epilachnene, yuzu lactone, ambrettolide, epothilone C, and nakadomarin A" Chemistry (2013); 19 (8): 2726-2740.
Wang, et al., "Exploring fatty alcohol-producing capability of Yarrowia lipolytica." Biotechnology for Biofuels (2016); 9: 107, pp. 1-10.
Wang, et al., "Mo-Based Complexes with Two Aryloxides and a Pentafluoroimido Ligand: Catalysts for Efficient Z-Selective Synthesis of a Macrocyclic Trisubstituted Alkene by Ring-Closing Metathesis." Angew Chem Int Ed Engl., (2013); 52 (7): 1939-1943.
Whisstock and Lesk, "Prediction of protein function from protein sequence and structure." Q. Rev. Biophysics. (2003); 36 (3): 307-340.
Witkowski, et al., "Conversion of a β-ketoacyl synthase to a malonyl decarboxylase by replacement of the active-site cysteine with glutamine." Biochemistry (1999); 38 (36): 11643-11650.
Xia, et al., "Large Number of putative chemoreception and pheromone biosynthesis genes revealed by analyzing transcriptome from ovipositor-pheromone glands of Chilo suppressalis." Scientific Reports (Jan. 2015); 5: 7888. Epub Jan. 20, 2015.
Yoshimura, et al., "Involvement of the YneS/YgiH and PlsX proteins in phospholipid biosynthesis in both Bacillus subtilis and *Escherichia coli*." BMC Microbiology (2007); 7: 69, 13 pages.
Yousuf, et al., " Microbial conversion of olive oil mill wastewaters into lipids suitable for biodiesel production." J Agric. Food Chem. (2010); 58 (15): 8630- 8635.
Yu, et al., "Enol Ethers as Substrates for Efficient Z- and Enantioselective Ring-Opening/Cross-Metathesis Reactions Promoted by Stereogenic-at-Mo Complexes: Utility in Chemical Synthesis and Mechanistic Attributes." J Am. Chem. Soc. (2012); 134(5): 2788-2799.
Yu, et al., "Synthesis of macrocyclic natural products by catalyst-controlled stereoselective ring-closing metathesis" Nature (2011); 479 (7371): 88-93.
Zhao, et al. "Endo-selective enyne ring-closing metathesis promoted by stereogenic-at-W mono-pyrrolide complexes" Org Lett. (2011); 13 (4): 784-787.
Zheng and Zou, "The initial step of the glycerolipid pathway: identification of glycerol 3-phosphate/dihydroxyacetone phosphate dual substrate acyltransferases in *Saccharomyces cerevisiae*." The Journal of Biological Chemistry (2001); 276 (45): 417104-417116.
Zou, et al., "The *Arabidopsis thaliana* TAG1 mutant has a mutation in a diacylglycerol acyltransferase gene." The Plant Journal (1999); 19 (6): 645-653.
Extended European Search Report for Application No. EP 18803040.7 dated Feb. 26, 2021, 7 pages.
Flook, et al., "Synthesis of cis,syndiotactic ROMP Polymers Containing Alternating Enantiomers", J. Am. Chem. Soc. (Jan. 25, 2011); 133(6): 1784-1786.
GenBank Accession No. AAD03775.1, "acyl-CoA delta11 desaturase [Trichoplusia ni]", Jan. 11, 1999.
GenBank Accession No. AAF81787.1, "acyl-CoA delta-11 desaturase [Helicoverpa Zea]", Aug. 30, 2001, 1 page.
GenBank Accession No. AAF81790.2, "acyl-CoA delta-9 desaturase [Helicoverpa zea]", Aug. 30, 2001, 2 pages.
GenBank Accession No. AAM28480.2, "acyl-CoA desaturase HassGATD [Helicoverpa assulta]", May 22, 2003, 2 pages.
GenBank Accession No. AAM28481.2, "acyl-CoA desaturase HassKPSE [Helicoverpa assulta]", May 22, 2003, 1 page.
GenBank Accession No. AAM28483.2, "acyl-CoA desaturase HassLPAQ [Helicoverpa assulta]", May 22, 2003, 2 pages.
GenBank Accession No. AAM28484.2, "acyl-CoA desaturase HassNPVE [Helicoverpa assulta]", May 22, 2003, 1 page.
GenBank Accession No. AF416738.1, "Argyrotaenia velutinana acyl-CoA delta-11 desaturase mRNA, complete cds", Oct. 17, 2001, 2 pages.
GenBank Accession No. AF482906.2, "Helicoverpa assulta acyl-CoA desaturase HassKPSE mRNA, complete cds", May 22, 2003, 1 page.
GenBank Accession No. AF545481.1, "Choristoneura rosaceana acyl-CoA Z/E11 desaturase mRNA, complete cds", Mar. 8, 2005, 2 pages.
GenBank Accession No. AKU76402.1, "acyl-CoA desaturase 3 [Helicoverpa armigera]", Dec. 31, 2015, 2 pages.
GenBank Accession No. AKU76404.1, "acyl-CoA desaturase 5 [Helicoverpa armigera]", Dec. 31, 2015, 2 pages.
GenBank Accession No. AKU76405.1, "acyl-CoA desaturase 6 [Helicoverpa armigera]", Dec. 31, 2015, 1 page.
GenBank Accession No. AKU76408.1, "acyl-CoA desaturase 2 [Helicoverpa assulta]", Dec. 31, 2015, 1 page.
GenBank Accession No. AKU76409.1, "acyl-CoA desaturase 3 [Helicoverpa assulta]", Dec. 31, 2015, 1 page.
GenBank Accession No. AKU76410.1, "acyl-CoA desaturase 4 [Helicoverpa assulta]", Dec. 31, 2015, 1 page.
GenBank Accession No. AKU76411.1, "acyl-CoA desaturase 5 [Helicoverpa assulta]", Dec. 31, 2015, 1 page.
GenBank Accession No. AKU76412.1, "acyl-CoA desaturase 6 [Helicoverpa assulta]", Dec. 31, 2015, 2 pages.
GenBank Accession No. ATJ44449.1, "desaturase MPVE [Helicoverpa armigera]", Oct. 18, 2017, 1 page.
GenBank Accession No. ATJ44454.1, "desaturase LPAQ [Helicoverpa armigera]", Oct. 18, 2017, 2 pages.
GenBank Accession No. ATJ44456.1, "desaturase PDSN [Helicoverpa armigera]", Oct. 18, 2017, 1 page.
GenBank Accession No. ATJ44457.1, "desaturase IPAE [Helicoverpa armigera]", Oct. 18, 2017, 2 pages.
GenBank Accession No. ATJ44509.1, "desaturase KSVE [Helicoverpa assulta]", Oct. 18, 2017, 1 page.
GenBank Accession No. ATJ44511.1, "desaturase MPVE [Helicoverpa assulta]", Oct. 18, 2017, 1 page.
GenBank Accession No. ATJ44514.1, "desaturase PDSN [Helicoverpa assulta]", Oct. 18, 2017, 1 page.

(56) References Cited

OTHER PUBLICATIONS

GenBank Accession No. AY493438.1, "Thalassiosira pseudonana delta-11 fatty acid desaturase (desN) gene, complete cds", Apr. 6, 2004, 2 pages.
GenBank Accession No. EU152335.1, "Lampronia capitella acyl-CoA-delta11-desaturase mRNA, complete cds", Oct. 12, 2008, 2 pages.
GenBank Accession No. JX679209.1, "Agrotis segetum fatty acyl delta-11 desaturase (D11) mRNA, complete cds", Aug. 3, 2014, 1 page.
GenBank Accession No. JX964774.1, "Amyelois transitella delta 11 desaturase mRNA, complete cds", Sep. 3, 2014, 2 pages.
GenBank Accession No. PZC81408.1, "hypothetical protein B5X24_HaOG212613 [Helicoverpa armigera]", Jun. 15, 2018, 2 pages.
GenBank Accession No. PZC82682.1, "hypothetical protein B5X24 HaOG209780 [Helicoverpa armigera]", Jun. 15, 2018, 2 pages.
GenBank Accession No. PZC86045.1, "hypothetical protein B5X24_HaOG213003 [Helicoverpa armigera]", Jun. 15, 2018, 2 pages.
GenBank Accession No. PZC86046.1, "hypothetical protein B5X24_HaOG213004 [Helicoverpa armigera]", Jun. 15, 2018, 2 pages.
GenBank Accession No. XP_021183629.1, "acyl-CoA Delta(11) desaturase [Helicoverpa armigera]", Jun. 1, 2017, 2 pages.
GenBank Accession No. XP_021185492.1, "acyl-CoA Delta(11) desaturase-like [Helicoverpa armigera]", Jun. 1, 2017, 1 page.
GenBank Accession No. XP_021187735.1, "acyl-CoA Delta(11) desaturase-like [Helicoverpa armigera]", Jun. 1, 2017, 2 pages.
GenBank Accession No. XP_021182948.1, "acyl-CoA Delta(11) desaturase-like [Helicoverpa armigera]", Jun. 1, 2017, 2 pages.
GenBank Accession No. XP_021183600.1, "acyl-CoA Delta(11) desaturase-like isoform X1 [Helicoverpa armigera]", Jun. 1, 2017, 1 page.
GenBank Accession No. XP_021183601.1, "acyl-CoA Delta(11) desaturase-like isoform X2 [Helicoverpa armigera]", Jun. 1, 2017, 1 page.
GenBank Accession No. XP_021183624.1, "stearoyl-CoA desaturase 5 [Helicoverpa armigera]", Jun. 1, 2017, 2 pages.
GenBank Accession No. XP_021183628.1, "acyl-CoA Delta(11) desaturase [Helicoverpa armigera]", Jun. 1, 2017, 2 pages.
GenBank Accession No. XP_021183660.1, "acyl-CoA Delta(11) desaturase-like [Helicoverpa armigera]", Jun. 1, 2017, 1 page.
GenBank Accession No. XP_021183696.1, "acyl-CoA Delta(11) desaturase-like [Helicoverpa armigera]", Jun. 1, 2017, 1 page.
GenBank Accession No. XP_021190176.1, "acyl-CoA Delta(11) desaturase-like [Helicoverpa armigera]", Jun. 1, 2017, 1 page.
GenBank Accession No. XP_021195328.1, "stearoyl-CoA desaturase 5-like [Helicoverpa armigera]", Jun. 1, 2017, 2 pages.
GenBank Accession No. XP_021195974.1, "Low Quality Protein: acyl-CoA Delta(11) desaturase-like [Helicoverpa armigera]", Jun. 1, 2017, 2 pages.
GenBank Accession No. XP_021200693.1, "acyl-CoA Delta(11) desaturase-like [Helicoverpa armigera]", Jun. 1, 2017, 1 page.
Gerber and Schrock, "Synthesis of methylidene complexes that contain a 2,6-dimesitylphenylimido ligand and ethenolysis of 2,3-dicarbomethoxynorbornadiene" Organometallics (2013); 32 (19): 5573-5580.
Los and Murata, "Structure and expression of fatty acid desaturases", Biochimica et Biophysica Acta (Oct. 2, 1998); 1394(1): 3-15.
Marinescu, et al. "Synthesis of variations of Sterogenic-at-Metal Imido Alkylidene Complexes of Molybdenum" Organometallics (2012); 31: 6336-6343.
Shanklin, et al., "Eight Histidine Residues Are Catalytically Essential in a Membrane-Associated Iron Enzyme, Stearoyl-CoA Desaturase, and Are Conserved in Alkane Hydroxylase and Xylene Monooxygenase", Biochemistry (Jan. 1, 1994), 33 (43): 12787-12794.

\* cited by examiner

US 11,104,921 B2

MICROORGANISMS FOR THE PRODUCTION OF INSECT PHEROMONES AND RELATED COMPOUNDS

CROSS REFERENCE TO RELATED APPLICATIONS

This application claims priority to U.S. Provisional Application Ser. No. 62/507,654, filed on May 17, 2017, which is hereby incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is PRVI_020_01WO_SeqList_ST25.txt. The text file is about 240 KB, was created on May 17, 2018, and is being submitted electronically via EFS-Web.

TECHNICAL FIELD

This application relates to recombinant microorganisms useful in the biosynthesis of unsaturated $C_6$-$C_{24}$ fatty alcohols, aldehydes, and acetates which may be useful as insect pheromones, fragrances, flavors, and polymer intermediates. The application further relates to methods of producing unsaturated $C_6$-$C_{24}$ fatty alcohols, aldehydes, and acetates using the recombinant microorganisms, as well as compositions comprising one or more of these compounds and/or the recombinant microorganisms.

BACKGROUND

As the global demand for food grows, there is an increasing need for effective pest control. Conventional insecticides are among the most popular chemical control agents because they are readily available, rapid acting, and highly reliable. However, the overuse, misuse, and abuse of these chemicals have led to resistant pests, alteration of the natural ecology, and in some cases, environmental damage.

The use of insect pheromones to control pest populations has gained increasing popularity as a viable, safe, and environmentally friendly alternative to conventional insecticides. Since their discovery in the late 1950s, these molecules have shown efficacy in reducing insect populations through a variety of methods, including mass trappings, attract and kill, and mating disruption. The latter method in particular represents a non-toxic means of pest control and utilizes the ability of synthetic pheromones to mask naturally occurring pheromones, thereby causing confusion and mating disruption.

Although pheromones have significant potential in agricultural insect control, the cost of synthesizing pheromones using currently available techniques is very high, which prohibits widespread use of this sustainable technology beyond high-value crops. Thus, there is an existing need to develop novel technologies for the cost-efficient production of insect pheromones and related fragrances, flavors, and polymer intermediates. The present inventors address this need with the development of recombinant microorganisms capable of producing a wide-range of unsaturated $C_6$-$C_{24}$ fatty alcohols, aldehydes, and acetates including synthetic insect pheromones from low-cost feedstocks.

SUMMARY OF THE DISCLOSURE

The present application relates to recombinant microorganisms having a biosynthesis pathway for the production of one or more compounds selected from unsaturated $C_6$-$C_{24}$ fatty alcohols, aldehydes, and acetates. The recombinant microorganisms described herein may be used for the production of at least one compound, such as an insect pheromone, a fragrance, or a flavoring agent, selected from unsaturated $C_6$-$C_{24}$ fatty alcohols, aldehydes, and acetates.

In one embodiment, the recombinant microorganism comprises a biosynthesis pathway for the production of an unsaturated $C_6$-$C_{24}$ fatty aldehyde or fatty alcohol. Accordingly, in a first aspect, the application relates to a recombinant microorganism capable of producing an unsaturated $C_6$-$C_{24}$ fatty aldehyde or fatty alcohol from an endogenous or exogenous source of saturated $C_6$-$C_{24}$ fatty acyl-CoA, wherein the recombinant microorganism expresses (a): at least one exogenous nucleic acid molecule encoding a fatty-acyl desaturase that catalyzes the conversion of a saturated $C_6$-$C_{24}$ fatty acyl-CoA to a corresponding mono- or poly-unsaturated $C_6$-$C_{24}$ fatty acyl-CoA; and (b): at least one exogenous nucleic acid molecule encoding a fatty aldehyde forming fatty-acyl reductase that catalyzes the conversion of the mono- or poly-unsaturated $C_6$-$C_{24}$ fatty acyl-CoA from into the corresponding mono- or poly-unsaturated $C_6$-$C_{24}$ fatty aldehyde. In some embodiments, the mono- or poly-unsaturated $C_6$-$C_{24}$ fatty aldehyde is an insect pheromone. In some embodiments, the mono- or poly-unsaturated $C_6$-$C_{24}$ fatty aldehyde is a fragrance or flavoring agent. In some embodiments, the recombinant microorganism further comprises at least one endogenous or exogenous nucleic acid molecule encoding an acetyl transferase capable of catalyzing the conversion of the mono- or poly-unsaturated $C_6$-$C_{24}$ fatty alcohol from (b) into a corresponding mono- or poly-unsaturated $C_6$-$C_{24}$ fatty acetate. (c) at least one exogenous nucleic acid molecule encoding a fatty alcohol forming fatty-acyl reductase that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol. In some embodiments, the mono- or poly-unsaturated $C_6$-$C_{24}$ fatty alcohol is an insect pheromone. In some embodiments, the mono- or poly-unsaturated $C_6$-$C_{24}$ fatty alcohol is a fragrance or flavoring agent. In some embodiments, the recombinant microorganism further comprises at least one endogenous or exogenous nucleic acid molecule encoding an alcohol oxidase or an alcohol dehydrogenase, wherein the alcohol oxidase or alcohol dehydrogenase is capable of catalyzing the conversion of the mono- or poly-unsaturated $C_6$-$C_{24}$ fatty alcohol from (b) into a corresponding mono- or poly-unsaturated $C_6$-$C_{24}$ fatty aldehyde. In some embodiments, the recombinant microorganism further comprises at least one endogenous or exogenous nucleic acid molecule encoding an acetyl transferase capable of catalyzing the conversion of the mono- or poly-unsaturated $C_6$-$C_{24}$ fatty alcohol from (b) into a corresponding mono- or poly-unsaturated $C_6$-$C_{24}$ fatty acetate.

In some embodiments, the fatty-acyl desaturase is a desaturase capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms.

In some embodiments, the fatty-acyl desaturase is capable of generating a double bond at position C5, C6, C7, C8, C9, C10, C11, C12, or C13 in the fatty acid or its derivatives, such as, for example, fatty acid CoA esters.

In one exemplary embodiment, the fatty-acyl desaturase is a Z11 desaturase. In various embodiments described herein, the Z11 desaturase, or the nucleic acid sequence that encodes it, can be isolated from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana*. Further Z11-desaturases, or the nucleic acid sequences encoding them, can be isolated from *Bombyx mori, Manduca sexta, Diatraea grandiosella, Earias insulana, Earias vittella, Plutella xylostella, Bombyx mori* or *Diaphania nindalis*. In exemplary embodiments, the Z11 desaturase comprises a sequence selected from GenBank Accession Nos. JX679209, JX964774, AF416738, AF545481, EU152335, AAD03775, AAF81787, and AY493438. In some embodiments, a nucleic acid sequence encoding a Z11 desaturase from organisms of the species *Agrotis segetum, Amyelois transitella, Argyrotaenia velutiana, Choristoneura rosaceana, Lampronia capitella, Trichoplusia ni, Helicoverpa zea, or Thalassiosira pseudonana* is codon optimized. In some embodiments, the Z11 desaturase comprises a nucleotide sequence selected from SEQ ID NOs: 9, 18, 24 and 26 from *Trichoplusia ni*. In some embodiments, the Z11 desaturase comprises an amino acid sequence set forth in SEQ ID NO: 49 from *Trichoplusia ni*. In other embodiments, the Z11 desaturase comprises a nucleotide sequence selected from SEQ ID NOs: 10 and 16 from *Agrotis segetum*. In some embodiments, the Z11 desaturase comprises an amino acid sequence set forth in SEQ ID NO: 53 from *Agrotis segetum*. In some embodiments, the Z11 desaturase comprises a nucleotide sequence selected from SEQ ID NOs: 11 and 23 from *Thalassiosira pseudonana*. In some embodiments, the Z11 desaturase comprises an amino acid sequence selected from SEQ ID NOs: 50 and 51 from *Thalassiosira pseudonana*. In certain embodiments, the Z11 desaturase comprises a nucleotide sequence selected from SEQ ID NOs: 12, 17 and 30 from *Amyelois transitella*. In some embodiments, the Z11 desaturase comprises an amino acid sequence set forth in SEQ ID NO: 52 from *Amyelois transitella*. In further embodiments, the Z11 desaturase comprises a nucleotide sequence selected from SEQ ID NOs: 13, 19, 25, 27 and 31 from *Helicoverpa zea*. In some embodiments, the Z11 desaturase comprises an amino acid sequence set forth in SEQ ID NO: 54 from *Helicoverpa zea*. In some embodiments, the Z11 desaturase comprises an amino acid sequence set forth in SEQ ID NO: 39 from *S. inferens*. In some embodiments, the Z11 desaturase comprises an amino acid sequence set forth in GenBank Accession nos. AF416738, AGH12217.1, AH21943.1, CAJ43430.2, AF441221, AAF81787.1, AF545481, AJ271414, AY362879, ABX71630.1 and NP001299594.1, Q9N9Z8, ABX71630.1 and AIM40221.1. In some embodiments, the Z11 desaturase comprises a chimeric polypeptide. In some embodiments, a complete or partial Z11 desaturase is fused to another polypeptide. In certain embodiments, the N-terminal native leader sequence of a Z11 desaturase is replaced by an oleosin leader sequence from another species. In certain embodiments, the Z11 desaturase comprises a nucleotide sequence selected from SEQ ID NOs: 15, 28 and 29. In some embodiments, the Z11 desaturase comprises an amino acid sequence selected from SEQ ID NOs: 61, 62, 63, 78, 79 and 80.

In certain embodiments, the Z11 desaturase catalyzes the conversion of a fatty acyl-CoA into a mono- or polyunsaturated product selected from Z11-13:Acyl-CoA, E11-13:Acyl-CoA, (Z,Z)-7,11-13:Acyl-CoA, Z11-14:Acyl-CoA, E11-14:Acyl-CoA, (E,E)-9,11-14:Acyl-CoA, (E,Z)-9,11-14:Acyl-CoA, (Z,E)-9,11-14:Acyl-CoA, (Z,Z)-9,11-14:Acyl-CoA, (E,Z)-9,11-15:Acyl-CoA, (Z,Z)-9,11-15:Acyl-CoA, Z11-16:Acyl-CoA, E11-16:Acyl-CoA, (E,Z)-6,11-16:Acyl-CoA, (E,Z)-7,11-16:Acyl-CoA, (E,Z)-8,11-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA. (E,E)-11,13-16:Acyl-CoA, (E,Z)-11,13-16:Acyl-CoA, (Z,E)-11,13-16:Acyl-CoA, (Z,Z)-11,13-16:Acyl-CoA, (Z,E)-11,14-16:Acyl-CoA, (E,E,Z)-4,6,11-16:Acyl-CoA, (Z,Z,E)-7,11,13-16:Acyl-CoA, (E,E,Z,Z)-4,6,11,13-16:Acyl-CoA, Z11-17:Acyl-CoA, (Z,Z)-8,11-17:Acyl-CoA, Z11-18:Acyl-CoA, E11-18:Acyl-CoA, (Z,Z)-11,13-18:Acyl-CoA, (E,E)-11,14-18:Acyl-CoA, or combinations thereof.

In another exemplary embodiment, the fatty-acyl desaturase is a Z9 desaturase. In various embodiments described herein, the Z9 desaturase, or the nucleic acid sequence that encodes it, can be isolated from organisms of the species *Ostrinia furnacalis, Ostrinia nobilalis, Choristoneura rosaceana, Lampronia capitella, Helicoverpa assulta,* or *Helicoverpa zea*. In exemplary embodiments, the Z9 desaturase comprises a sequence selected from GenBank Accession Nos. AY057862, AF243047, AF518017, EU152332. AF482906, and AAF81788. In some embodiments, a nucleic acid sequence encoding a Z9 desaturase is codon optimized. In some embodiments, the Z9 desaturase comprises a nucleotide sequence set forth in SEQ ID NO: 20 from *Ostrinia furnacalis*. In some embodiments, the Z9 desaturase comprises an amino acid sequence set forth in SEQ ID NO: 58 from *Ostrinia furnacalis*. In other embodiments, the Z9 desaturase comprises a nucleotide sequence set forth in SEQ ID NO: 21 from *Lampronia capitella*. In some embodiments, the Z9 desaturase comprises an amino acid sequence set forth in SEQ ID NO: 59 from *Lampronia capitella*. In some embodiments, the Z9 desaturase comprises a nucleotide sequence set forth in SEQ ID NO: 22 from *Helicoverpa zea*. In some embodiments, the Z9 desaturase comprises an amino acid sequence set forth in SEQ ID NO: 60 from *Helicoverpa zea*. Other Z9 desaturases of the present disclosure include SEQ ID Nos: 95, 97, 99, 101, 103, and 105. In some embodiments, the overexpression of a Z9-18 specific desaturase can increase the membrane fluidity to improve the diffusion of fatty alcohols into the supernatant.

In certain embodiments, the Z9 desaturase catalyzes the conversion of a fatty acyl-CoA into a monounsaturated or polyunsaturated product selected from Z9-11:Acyl-CoA, Z9-12:Acyl-CoA, E9-12:Acyl-CoA, (E,E)-7,9-12:Acyl-CoA, (E,Z)-7,9-12:Acyl-CoA, (Z,E)-7,9-12:Acyl-CoA, (Z,Z)-7,9-12:Acyl-CoA, Z9-13:Acyl-CoA, E9-13:Acyl-CoA, (E,Z)-5,9-13:Acyl-CoA, (Z,E)-5,9-13:Acyl-CoA, (Z,Z)-5,9-13:Acyl-CoA, Z9-14:Acyl-CoA, E9-14:Acyl-CoA, (E,Z)-4,9-14:Acyl-CoA, (E,E)-9,11-14:Acyl-CoA, (E,Z)-9,11-14:Acyl-CoA, (Z,E)-9,11-14:Acyl-CoA, (Z,Z)-9,11-14:Acyl-CoA, (E,E)-9,12-14:Acyl-CoA, (Z,E)-9,12-14:Acyl-CoA, (Z,Z)-9,12-14:Acyl-CoA, Z9-15:Acyl-CoA, E9-15:Acyl-CoA, (Z,E)-6,9-15:Acyl-CoA, Z9-16:Acyl-CoA, E9-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA, Z9-17:Acyl-CoA, E9-18:Acyl-CoA, Z9-18:Acyl-CoA, (E,E)-5,9-18:Acyl-CoA, (E,E)-9,12-18:Acyl-CoA, (Z,Z)-9,12-18:Acyl-CoA, (Z,Z,Z)-3,6,9-18:Acyl-CoA, (E,E,E)-9,12,15-18:Acyl-CoA, (Z,Z,Z)-9,12,15-18:Acyl-CoA, or combinations thereof.

In some embodiments, the recombinant microorganism may express a bifunctional desaturase capable of catalyzing the subsequent desaturation of two double bonds.

In some embodiments, the recombinant microorganism may express more than one exogenous nucleic acid molecule encoding a fatty-acyl desaturase that catalyzes the conversion of a saturated $C_6$-$C_{24}$ fatty acyl-CoA to a corresponding mono- or poly-unsaturated $C_6$-$C_{24}$ fatty acyl-CoA. For instance, the recombinant microorganism may express an exogenous nucleic acid molecule encoding a Z11 desaturase and another exogenous nucleic acid molecule encoding a Z9 desaturase.

In some embodiments, the recombinant microorganism may express a fatty-acyl conjugase that acts independently or together with a fatty-acyl desaturase to catalyze the conversion of a saturated or monounsaturated fatty acyl-CoA to a conjugated polyunsaturated fatty acyl-CoA.

In one embodiment, the disclosure provides a recombinant microorganism capable of producing a polyunsaturated $C_6$-$C_{24}$ aldehyde or fatty alcohol from an endogenous or exogenous source of saturated or monounsaturated $C_6$-$C_{24}$ fatty acyl-CoA, wherein the recombinant microorganism expresses: (a) at least one exogenous nucleic acid molecule encoding a fatty acyl conjugase that catalyzes the conversion of a saturated or monounsaturated $C_6$-$C_{24}$ fatty acyl-CoA to a corresponding polyunsaturated $C_6$-$C_{24}$ fatty acyl-CoA; and (b) at least one exogenous nucleic acid molecule encoding a fatty aldehyde or fatty alcohol forming fatty-acyl reductase that catalyzes the conversion of the polyunsaturated $C_6$-$C_{24}$ fatty acyl-CoA from (a) into the corresponding polyunsaturated $C_6$-$C_{24}$ fatty aldehyde or fatty alcohol.

In another embodiment, the recombinant microorganism expresses at least two exogenous nucleic acid molecules encoding fatty-acyl conjugases that catalyze the conversion of a saturated or monounsaturated $C_6$-$C_{24}$ fatty acyl-CoA to a corresponding polyunsaturated $C_6$-$C_{24}$ fatty acyl-CoA.

In a further embodiment, the disclosure provides a recombinant microorganism capable of producing a polyunsaturated $C_6$-$C_{24}$ fatty alcohol from an endogenous or exogenous source of saturated or monounsaturated $C_4$-$C_{24}$ fatty acyl-CoA, wherein the recombinant microorganism expresses: (a) at least one exogenous nucleic acid molecule encoding a fatty-acyl desaturase and at least one exogenous nucleic acid molecule encoding a fatty acyl conjugase that catalyze the conversion of a saturated or monounsaturated $C_6$-$C_{24}$ fatty acyl-CoA to a corresponding polyunsaturated $C_6$-$C_{24}$ fatty acyl-CoA; and (b) at least one exogenous nucleic acid molecule encoding a fatty alcohol forming fatty-acyl reductase that catalyzes the conversion of the polyunsaturated $C_6$-$C_{24}$ fatty acyl-CoA from (a) into the corresponding polyunsaturated $C_6$-$C_{24}$ fatty alcohol.

In another embodiment, the recombinant microorganism expresses at least two exogenous nucleic acid molecules encoding fatty-acyl desaturases and at least two exogenous nucleic acid molecules encoding fatty-acyl conjugases that catalyze the conversion of a saturated or monounsaturated $C_6$-$C_{24}$ fatty acyl-CoA to a corresponding polyunsaturated $C_6$-$C_{24}$ fatty acyl-CoA.

In yet a further embodiment, the fatty-acyl conjugase is a conjugase capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms.

In certain embodiments, the conjugase, or the nucleic acid sequence that encodes it, can be isolated from organisms of the species *Cydia pomonella, Cydia nigricana, Lobesia botrana, Myelois cribrella, Plodia interpunctella, Dendrolimus punctatus, Lampronia capitella, Spodoptera litura, Amyelois transitella, Manduca sexta, Bombyx mori, Calendula officinalis, Trichosanthes kirilowli, Punica granatum, Momordica charantia, Impatiens balsamina*, and *Epiphyas postvittana*. In exemplary embodiments, the conjugase comprises a sequence selected from GenBank Accession No. or Uniprot database: A0A059TBF5, A0A0M3L9E8, A0A0M3L9S4, A0A0M3LAH8, A0A0M3LAS8, A0A0M3LAH8, B6CBS4, XP_013183656.1, XP_004923568.2, ALA65425.1, NP_001296494.1, NP_001274330.1, Q4A181, Q75PL7, Q9FPP8, AY178444, AY178446, AF182521, AF182520, Q95UJ3.

In various embodiments described herein, the fatty alcohol forming acyl-CoA reductase, i.e., fatty alcohol forming fatty-acyl reductase, or the nucleic acid sequence that encodes it, can be isolated from organisms of the species *Agrotis segetum, Spodoptera littoralis, Helicoverpa amigera, Spodoptera exigua, Euglena gracilis*, or *Yponomeuta evonymellus*. In exemplary embodiments, the reductase comprises a sequence selected from GenBank Accession Nos. JX679210 and HG423128, and UniProt Accession No. I3PN86. In some embodiments, a nucleic acid sequence encoding a fatty-acyl reductase from organisms of the species *Agrotis segetum, Spodoptera littoralis, Helicoverpa amigera, Spodoptera exigua, Euglena gracilis*, or *Yponomeuta evonymellus* is codon optimized. In some embodiments, the reductase comprises a nucleotide sequence set forth in SEQ ID NO: 1 from *Agrotis segetum*. In some embodiments, the fatty acyl reductase comprises an amino acid sequence set forth in SEQ ID NO: 55 from *Agrotis segetum*. In other embodiments, the reductase comprises a nucleotide sequence set forth in SEQ ID NO: 2 from *Spodoptera littoralis*. In some embodiments, the fatty acyl reductase comprises an amino acid sequence set forth in SEQ ID NO: 56 from *Spodoptera littoralis*. In some embodiments, the reductase comprises a nucleotide sequence selected from SEQ ID NOs: 3, 32, 40, 72, 74, 76 and 81. In some embodiments, the fatty acyl reductase comprises an amino acid sequence set forth in SEQ ID NO: 55 from *Agrotis segetum*. In other embodiments, the fatty acyl reductase comprises an amino acid sequence set forth in SEQ ID NO: 56 from *Spodoptera littoralis*. In some embodiments, the fatty acyl reductase comprises an amino acid sequence selected from SEQ ID NOs: 41 and 57 from *Helicoverpa armigera*. In some embodiments, the fatty acyl reductase comprises an amino acid sequence selected from SEQ ID NOs: 73 and 82 from *Spodoptera exigua*. In some embodiments, the fatty acyl reductase comprises an amino acid sequence set forth in SEQ ID NO: 75 from *Euglena gracilis*. In some embodiments, the fatty acyl reductase comprises an amino acid sequence set forth in SEQ ID NO: 77 from *Yponomeuta evonymellus*.

In some embodiments, the present disclosure teaches using multiple fatty acyl reductase enzymes. In some embodiments, the present disclosure teaches recombinant microorganisms comprising multiple copies of the same fatty acyl reductase. In other embodiments, the present disclosure teaches recombinant microorganisms comprising two or more different fatty acyl reductases. In some embodiments, the different fatty acyl reductases utilize different co-factors. For example, the fatty acyl reductase from *Euglena gracilis* (SEQ ID NO: 75) uses NADH instead of NADPH as reducing equivalent. In some embodiments, this can allow for co-factor balancing using two or more different reductases.

In some embodiments, the fatty acyl reductase is a mutated fatty acyl reductase and comprises an amino acid sequence selected from SEQ ID NOs: 42-48. In some embodiments, the fatty acyl reductase is a mutated fatty acyl reductase and comprises a nucleotide sequence selected from SEQ ID NOs: 83-89.

In certain embodiments, the fatty alcohol forming fatty-acyl reductase catalyzes the conversion of a mono- or poly-unsaturated fatty acyl-CoA into a fatty alcohol product selected from (Z)-3-hexenol, (Z)-3-nonenol, (Z)-5-decenol, (E)-5-decenol, (Z)-7-dodecenol, (E)-7-dodecenol, (E)-8-dodecenol, (Z)-8-dodecenol, (Z)-9-dodecenol, (E)-9-dodecenol, (Z)-9-tetradecenol, (E)-9-tetradecenol, (Z)-9-hexadecenol, (Z)-11-tetradecenol, (Z)-7-hexadecenol, (Z)-11-hexadecenol, (E)-11-hexadecenol (E)-11-tetradecenol, or (Z,Z)-11,13-hexadecadienol, (11Z,13E)-hexadecadienol, (E,E)-8,10-dodecadienol, (E,Z)-7,9-dodecadienol, (Z)-13-octadecenol, or combinations thereof.

In some embodiments, the recombinant microorganism may express more than one exogenous nucleic acid molecule encoding a fatty alcohol forming fatty-acyl reductase that catalyzes the conversion of a mono- or poly-unsaturated $C_6$-$C_{24}$ fatty acyl-CoA to a corresponding mono- or poly-unsaturated $C_6$-$C_{24}$ fatty alcohol.

In a further embodiment, the disclosure provides a recombinant microorganism capable of producing a mono- or poly-unsaturated $\leq C_{18}$ fatty alcohol from an endogenous or exogenous source of saturated $C_6$-$C_{24}$ fatty acid, wherein the recombinant microorganism comprises: (a) at least one exogenous nucleic acid molecule encoding a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA; (b) at least one exogenous nucleic acid molecule encoding an acyl-CoA oxidase that catalyzes the conversion of the mono- or poly-unsaturated $C_6$-$C_{24}$ fatty acyl-CoA from (a) into a mono- or poly-unsaturated $\leq C_{18}$ fatty acyl-CoA after one or more successive cycle of acyl-CoA oxidase activity, with a given cycle producing a mono- or poly-unsaturated $C_4$-$C_{22}$ fatty acyl-CoA intermediate with a two carbon truncation relative to a starting mono- or poly-unsaturated $C_6$-$C_{24}$ fatty acyl-CoA substrate in that cycle; and (c) at least one exogenous nucleic acid molecule encoding a fatty alcohol forming fatty acyl reductase that catalyzes the conversion of the mono- or poly-unsaturated $\leq C_{18}$ fatty acyl-CoA from (b) into the corresponding mono- or poly-unsaturated $\leq C_{18}$ fatty alcohol. In some embodiments, the fatty acyl desaturase is selected from an *Argyrotaenia velutinana, Spodoptera litura, Sesamia inferens, Manduca sexta, Ostrinia nubilalis, Helicoverpa zea, Choristoneura rosaceana, Drosophila melanogaster, Spodoptera littoralis, Lamproninia capitella, Amyelois transitella, Trichoplusia ni, Agrotis segetum, Ostrinia furnicalis,* and *Thalassiosira pseudonana* derived fatty acyl desaturase. In some embodiments, the fatty acyl desaturase has at least 99%, 98%, 97%, 96%, 95%, 94%, 93%, 92%, 91%, 90%, 89%, 88%, 87%, 86%, 85% 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, or 50% sequence identity to a fatty acyl desaturase selected from the group consisting of: SEQ ID NOs: 39, 49-54, 58-63, 78-80 and GenBank Accession nos. AF416738, AGH12217.1, AH21943.1, CAJ43430.2, AF441221, AAF81787.1, AF545481, AJ271414, AY362879, ABX71630.1, NP001299594.1, Q9N9Z8, ABX71630.1 and AIM40221.1. In some embodiments, the acyl-CoA oxidase is selected from Table 5a. In other embodiments, the fatty alcohol forming fatty acyl reductase is selected from an *Agrotis segetum, Spodoptera exigua, Spodoptera littoralis, Euglena gracilis, Yponomeuta evonymellus* and *Helicoverpa armigera* derived fatty alcohol forming fatty acyl reductase. In further embodiments, the fatty alcohol forming fatty acyl reductase has at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, or 50% sequence identity to a fatty alcohol forming fatty acyl reductase selected from the group consisting of: SEQ ID NOs: 1-3, 32, 41-48, 55-57, 73, 75, 77 and 82. In some embodiments, the recombinant microorganism is a yeast selected from the group consisting of *Yarrowia lipolytica, Saccharomyces cerevisiae, Candida albicans, Candida tropicalis* and *Candida viswanathii*.

In some embodiments, the recombinant microorganism further comprises at least one endogenous or exogenous nucleic acid molecule encoding an acyltransferase that preferably stores $\leq C_{18}$ fatty acyl-CoA. In some embodiments, the acyltransferase is selected from the group consisting of glycerol-3-phosphate acyl transferase (GPAT), lysophosphatidic acid acyltransferase (LPAAT), glycerolphospholipid acyltransferase (GPLAT) and diacylglycerol acyltransferases (DGAT). In some preferred embodiments, the acyltransferase is selected from Table 5b.

In some embodiments, the recombinant microorganism further comprises at least one endogenous or exogenous nucleic acid molecule encoding an acylglycerol lipase that preferably hydrolyzes ester bonds of >C16, of >C14, of >C12 or of >C10 acylglycerol substrates. In some embodiments, the acylglycerol lipase is selected from Table 5c.

In some embodiments, the recombinant microorganism comprises a deletion, disruption, mutation, and/or reduction in the activity of one or more endogenous enzymes that catalyzes a reaction in a pathway that competes with the biosynthesis pathway for the production of a mono- or poly-unsaturated $\leq C_{18}$ fatty alcohol. In further embodiments, the recombinant microorganism comprises a deletion, disruption, mutation, and/or reduction in the activity of one or more endogenous enzyme selected from: (i) one or more acyl-CoA oxidase; (ii) one or more acyltransferase; (iii) one or more acylglycerol lipase and/or sterol ester esterase; (iv) one or more (fatty) alcohol dehydrogenase; (v) one or more (fatty) alcohol oxidase; and (vi) one or more cytochrome P450 monooxygenase.

In some preferred embodiments, one or more genes of the microbial host encoding acyl-CoA oxidases are deleted or down-regulated to eliminate or reduce the truncation of desired fatty acyl-CoAs beyond a desired chain-length. In some embodiments, the recombinant microorganism comprises a deletion, disruption, mutation, and/or reduction in the activity of one or more endogenous acyl-CoA oxidase enzyme selected from the group consisting of *Y. lipolytica* POX1 (YALI0E32835g), *Y. lipolytica* POX2 (YALI0F10857g). *Y. lipolytica* POX3 (YALI0D24750g), *Y. lipolytica* POX4 (YALI0E27654g), *Y. lipolytica* POX5 (YALI0C23859g), *Y. lipolytica* POX6 (YALI0E06567g); *S. cerevisiae* POX1 (YGL205W); *Candida* POX2 (CaO19.1655, CaO19.9224, CTRG_02374, M18259), *Candida* POX4 (CaO19.1652, CaO19.9221, CTRG_02377, M12160), and *Candida* POX5 (CaO19.5723, CaO19.13146, CTRG_02721, M12161).

In some embodiments, a recombinant microorganism capable of producing a mono- or poly-unsaturated $\leq C_{18}$ fatty alcohol, fatty aldehyde and/or fatty acetate from an endogenous or exogenous source of saturated $C_6$-$C_{24}$ fatty acid is provided, wherein the recombinant microorganism expresses one or more acyl-CoA oxidase enzymes, and wherein the recombinant microorganism is manipulated to delete, disrupt, mutate, and/or reduce the activity of one or more endogenous acyl-CoA oxidase enzymes. In some embodiments, the one or more acyl-CoA oxidase enzymes being expressed are different from the one or more endogenous acyl-CoA oxidase enzymes being deleted or downregulated. In other embodiments, the one or more acyl-CoA oxidase enzymes that are expressed regulate chain length of the mono- or poly-unsaturated ≤$C_{18}$ fatty alcohol, fatty aldehyde and/or fatty acetate. In other embodiments, the one or more acyl-CoA oxidase enzymes being expressed are selected from Table 5a.

In some embodiments, the recombinant microorganism comprises a deletion, disruption, mutation, and/or reduction in the activity of one or more endogenous acyltransferase enzyme selected from the group consisting of *Y. lipolytica* YALI0C00209g, *Y. lipolytica* YALI0E18964g, *Y. lipolytica* YALI0F19514g, *Y. lipolytica* YALI0C14014g, *Y. lipolytica* YALI0E16797g, *Y. lipolytica* YALI0E32769g, and *Y. lipolytica* YALI0D07986g, *S. cerevisiae* YBL011w, *S. cerevisiae* YDL052c, *S. cerevisiae* YOR175C, *S. cerevisiae* YPR139C, *S. cerevisiae* YNR008w, and *S. cerevisiae* YOR245c, and *Candida* I503_02577, *Candida* CTRG_02630, *Candida* CaO19.250, *Candida* CaO19.7881, *Candida* CTRG_02437, *Candida* CaO19.1881, *Candida* CaO19.9437, *Candida* CTRG_01687, *Candida* CaO19.1043, *Candida* CaO19.8645, *Candida* CTRG_04750. *Candida* CaO19.13439, *Candida* CTRG_04390, *Candida* CaO19.6941, *Candida* CaO19.14203, and *Candida* CTRG_06209.

In some embodiments, a recombinant microorganism capable of producing a mono- or poly-unsaturated ≤$C_{18}$ fatty alcohol, fatty aldehyde and/or fatty acetate from an endogenous or exogenous source of saturated $C_6$-$C_{24}$ fatty acid is provided, wherein the recombinant microorganism expresses one or more acyltransferase enzymes, and wherein the recombinant microorganism is manipulated to delete, disrupt, mutate, and/or reduce the activity of one or more endogenous acyltransferase enzymes. In some preferred embodiments, one or more genes of the microbial host encoding GPATs, LPAATs, GPLATs and/or DGATs are deleted or downregulated, and replaced with one or more GPATs, LPAATs, GPLATs, or DGATs which prefer to store short-chain fatty acyl-CoAs. In some embodiments, the one or more acyltransferase enzymes being expressed are different from the one or more endogenous acyltransferase enzymes being deleted or downregulated. In other embodiments, the one or more acyltransferase enzymes being expressed are selected from Table 5b.

In some preferred embodiments, one or more genes of the microbial host encoding acylglycerol lipases (mono-, di-, or triacylglycerol lipases) and sterol ester esterases are deleted or downregulated and replaced with one or more acylglycerol lipases which prefer long chain acylglycerol substrates. In some embodiments, the recombinant microorganism comprises a deletion, disruption, mutation, and/or reduction in the activity of one or more endogenous acylglycerol lipase and/or sterol ester esterase enzyme selected from the group consisting of *Y. lipolytica* YALI0E32035g, *Y. lipolytica* YALI0D17534g, *Y. lipolytica* YALI0F10010g, *Y. lipolytica* YALI0C14520g, and *Y. lipolytica* YALI0E00528g, *S. cerevisiae* YKL140w, *S. cerevisiae* YMR313c, *S. cerevisiae* YKR089c, *S. cerevisiae* YOR081c, *S. cerevisiae* YKL094W, *S. cerevisiae* YLL012W, and *S. cerevisiae* YLR020C, and *Candida* CaO19.2050, *Candida* CaO19.9598, *Candida* CTRG_01138, *Candida* W5Q_03398, *Candida* CTRG_00057, *Candida* CaO19.5426, *Candida* CaO19.12881, *Candida* CTRG_06185, *Candida* CaO19.4864. *Candida* CaO19.12328. *Candida* CTRG_03360, *Candida* CaO19.6501. *Candida* CaO19.13854, *Candida* CTRG_05049, *Candida* CaO19.1887, *Candida* CaO19.9443, *Candida* CTRG_01683, and *Candida* CTRG_04630.

In some embodiments, the recombinant microorganism comprises a deletion, disruption, mutation, and/or reduction in the activity of one or more endogenous cytochrome P450 monooxygenases selected from the group consisting of *Y. lipolytica* YALI0E25982g (ALK1), *Y. lipolytica* YALI0F01320g (ALK2), *Y. lipolytica* YALI0E23474g (ALK3), *Y. lipolytica* YALI0B13816g (ALK4), *Y. lipolytica* YALI0B13838g (ALK5), *Y. lipolytica* YALI0B01848g (ALK6), *Y. lipolytica* YALI0A15488g (ALK7), *Y. lipolytica* YALI0C12122g (ALK8), *Y. lipolytica* YALI0B06248g (ALK9), *Y. lipolytica* YALI0B20702g (ALK10), *Y. lipolytica* YALI0C10054g (ALK11) and *Y. lipolytica* YALI0A20130g (ALK12).

In some embodiments, a recombinant microorganism capable of producing a mono- or poly-unsaturated ≤$C_{18}$ fatty alcohol, fatty aldehyde and/or fatty acetate from an endogenous or exogenous source of saturated $C_6$-$C_{24}$ fatty acid is provided, wherein the recombinant microorganism expresses one or more acylglycerol lipase and/or sterol ester esterase enzymes, and wherein the recombinant microorganism is manipulated to delete, disrupt, mutate, and/or reduce the activity of one or more endogenous acylglycerol lipase and/or sterol ester esterase enzymes. In some embodiments, the one or more acylglycerol lipase and/or sterol ester esterase enzymes being expressed are different from the one or more endogenous acylglycerol lipase and/or sterol ester esterase enzymes being deleted or downregulated. In some embodiments, the one or more endogenous or exogenous acylglycerol lipase and/or sterol ester esterase enzymes being expressed prefer to hydrolyze ester bonds of long-chain acylglycerols. In other embodiments, the one or more acylglycerol lipase and/or sterol ester esterase enzymes being expressed are selected from Table 5c.

In some embodiments, the fatty acyl desaturase catalyzes the conversion of a fatty acyl-CoA into a mono- or poly-unsaturated intermediate selected from E5-10:Acyl-CoA, E7-12:Acyl-CoA. E9-14:Acyl-CoA, E11-16:Acyl-CoA, E13-18:Acyl-CoA, Z7-12:Acyl-CoA, Z9-14:Acyl-CoA, Z11-16:Acyl-CoA, Z13-18:Acyl-CoA, Z8-12:Acyl-CoA, Z10-14:Acyl-CoA, Z12-16:Acyl-CoA, Z14-18:Acyl-CoA, Z7-10:Acyl-coA, Z9-12:Acyl-CoA, Z11-14:Acyl-CoA, Z13-16:Acyl-CoA, Z5-18:Acyl-CoA, E7-10:Acyl-CoA, E9-12:Acyl-CoA, E11-14:Acyl-CoA, E13-16:Acyl-CoA, E15-18:Acyl-CoA, E5Z7-12:Acyl-CoA, E7Z9-12:Acyl-CoA, E9Z11-14:Acyl-CoA, E11Z13-16:Acyl-CoA, E13Z15-18:Acyl-CoA, E6E8-10:Acyl-CoA, E8E10-12:Acyl-CoA, E10E12-14:Acyl-CoA, E12E14-16:Acyl-CoA, Z5E8-10:Acyl-CoA, Z7E10-12:Acyl-CoA, Z9E12-14:Acyl-CoA, Z11E14-16:Acyl-CoA, Z13E16-18:Acyl-CoA, Z3-10:Acyl-CoA, Z5-12:Acyl-CoA, Z7-14:Acyl-CoA, Z9-16:Acyl-CoA, Z11-18:Acyl-CoA, Z3Z5-10:Acyl-CoA, Z5Z7-12:Acyl-CoA, Z7Z9-14:Acyl-CoA, Z9Z11-16:Acyl-CoA, Z11Z13-16:Acyl-CoA, and Z13Z15-18:Acyl-CoA. In further embodiments, the mono- or poly-unsaturated ≤$C_{18}$ fatty alcohol is selected from the group consisting of E5-10:OH, Z8-12:OH, Z9-12:OH, Z11-14:OH, Z11-16:OH, E11-14:OH. E8E10-12:OH, E7Z9-12:OH, Z11Z13-16OH, Z9-14:OH, Z9-16:OH, and Z13-18:OH.

In some embodiments, the recombinant microorganism further comprises at least one endogenous or exogenous nucleic acid molecule encoding an aldehyde forming fatty acyl-CoA reductase capable of catalyzing the conversion of the mono- or poly-unsaturated ≤$C_{18}$ fatty acid into a corresponding ≤$C_{18}$ fatty aldehyde. In some preferred embodiments, the aldehyde forming fatty acyl-CoA reductase is selected from the group consisting of *Acinetobacter calcoaceticus* A0A1C4HN78, *A. calcoaceticus* N9DA85, *A. calcoaceticus* R8XW24, *A. calcoaceticus* A0A1A0GGM5, *A. calcoaceticus* A0A117N158, and *Nostoc punctiforme* YP_001865324. In some embodiments, the recombinant microorganism further comprises at least one endogenous or exogenous nucleic acid molecule encoding an alcohol oxidase or an alcohol dehydrogenase capable of catalyzing the conversion of the mono- or poly-unsaturated ≤$C_{18}$ fatty alcohol into a corresponding ≤$C_{18}$ fatty aldehyde. In some preferred embodiments, the ≤$C_{18}$ fatty aldehyde is selected from the group consisting of Z9-16:Ald, Z11-16:Ald, Z11Z13-16:Ald, and Z13-18:Ald.

In some embodiments, the recombinant microorganism further comprises: at least one endogenous or exogenous nucleic acid molecule encoding an enzyme selected from an alcohol oxidase, an alcohol dehydrogenase capable of catalyzing the conversion of the mono- or poly-unsaturated ≤$C_{18}$ fatty alcohol into a corresponding ≤$C_{18}$ fatty aldehyde; and at least one endogenous or exogenous nucleic acid molecule encoding an acetyl transferase capable of catalyzing the conversion of the mono- or poly-unsaturated ≤$C_{18}$ fatty alcohol into a corresponding ≤$C_{18}$ fatty acetate. In some preferred embodiments, the mono- or poly-unsaturated ≤$C_{18}$ fatty aldehyde and ≤$C_{18}$ fatty acetate is selected from the group consisting of E5-10:Ac, Z7-12:Ac, Z8-12:Ac, Z9-12:Ac, E7Z9-12:Ac, Z9-14:Ac, Z9E12-14:Ac, E11-14:Ac, Z11-14:Ac, Z11-16:Ac, Z9-16:Ac, Z9-16:Ald, Z11-16:Ald, Z11Z13-16:Ald, and Z13-18:Ald.

In some embodiments, the disclosure provides a method of engineering a microorganism that is capable of producing a mono- or poly-unsaturated ≤$C_{18}$ fatty alcohol from an endogenous or exogenous source of saturated $C_6$-$C_{24}$ fatty acid, wherein the method comprises introducing into a microorganism the following: (a) at least one exogenous nucleic acid molecule encoding a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA; (b) at least one exogenous nucleic acid molecule encoding an acyl-CoA oxidase that catalyzes the conversion of the mono- or poly-unsaturated $C_6$-$C_{24}$ fatty acyl-CoA from (a) into a mono- or poly-unsaturated ≤C18 fatty acyl-CoA after one or more successive cycle of acyl-CoA oxidase activity, with a given cycle producing a mono- or poly-unsaturated $C_4$-$C_{22}$ fatty acyl-CoA intermediate with a two carbon truncation relative to a starting mono- or poly-unsaturated $C_6$-$C_{24}$ fatty acyl-CoA substrate in that cycle; and (c) at least one exogenous nucleic acid molecule encoding a fatty alcohol forming fatty acyl reductase that catalyzes the conversion of the mono- or poly-unsaturated ≤C18 fatty acyl-CoA from (b) into the corresponding mono- or poly-unsaturated ≤$C_{18}$ fatty alcohol. In some embodiments, the microorganism is MATA ura3-302::SUC2 Δpox1 Δpox2 Δpox3 Δpox4 Δpox5 Δpox6 Δfadh Δadh1 Δadh2 Δadh3 Δadh4 Δadh5 Δadh6 Δadh7 Δfao1::URA3.

In some embodiments, the disclosure provides a method of producing a mono- or poly-unsaturated ≤$C_{18}$ fatty alcohol, fatty aldehyde or fatty acetate from an endogenous or exogenous source of saturated $C_6$-$C_{24}$ fatty acid, comprising: cultivating a recombinant microorganism described herein in a culture medium containing a feedstock that provides a carbon source adequate for the production of the mono- or poly-unsaturated ≤$C_{18}$ fatty alcohol, fatty aldehyde or fatty acetate. In some embodiments, the method further comprises a step of recovering the mono- or poly-unsaturated ≤$C_{18}$ fatty alcohol, fatty aldehyde or fatty acetate. In further embodiments, the recovery step comprises distillation. In yet further embodiments, the recovery step comprises membrane-based separation.

In some embodiments, the mono- or poly-unsaturated ≤$C_{18}$ fatty alcohol is converted into a corresponding ≤$C_{18}$ fatty aldehyde using chemical methods. In further embodiments, the chemical methods are selected from TEMPO-bleach, TEMPO-copper-air, TEMPO-PhI(OAc)$_2$, Swern oxidation and noble metal-air. In some embodiments, the mono- or poly-unsaturated ≤$C_{18}$ fatty alcohol is converted into a corresponding ≤$C_{18}$ fatty acetate using chemical methods. In further embodiments, the chemical methods utilize a chemical agent selected from the group consisting of acetyl chloride, acetic anhydride, butyryl chloride, butyric anhydride, propanoyl chloride and propionic anhydride in the presence of 4-N,N-dimethylaminopyridine (DMAP) or sodium acetate to esterify the mono- or poly-unsaturated ≤$C_{18}$ fatty alcohol to the corresponding ≤$C_{18}$ fatty acetate.

In a further embodiment, the disclosure provides a recombinant *Yarrowia lipolytica* microorganism capable of producing a mono- or poly-unsaturated $C_6$-$C_{24}$ fatty alcohol from an endogenous or exogenous source of saturated $C_6$-$C_{24}$ fatty acid, wherein the recombinant *Yarrowia lipolytica* microorganism comprises: (a) at least one nucleic acid molecule encoding a fatty acyl desaturase having at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, or 50% sequence identity to a fatty acyl desaturase selected from the group consisting of SEQ ID NOs: 54, 60, 62, 78, 79, 80, 95, 97, 99, 101, 103, and 105 that catalyzes the conversion of a saturated $C_6$-$C_{24}$ fatty acyl-CoA to a corresponding mono- or poly-unsaturated $C_6$-$C_{24}$ fatty acyl-CoA and (b) at least one nucleic acid molecule encoding a fatty alcohol forming fatty acyl reductase having 95% sequence identity to a fatty alcohol forming fatty acyl reductase selected from the group consisting of SEQ ID NOs: 41-48, 57, 73, 75 and 77 that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol.

In some embodiments, the recombinant *Yarrowia lipolytica* microorganism comprises a deletion, disruption, mutation, and/or reduction in the activity of one or more endogenous enzymes that catalyzes a reaction in a pathway that competes with the biosynthesis pathway for the production of a mono- or poly-unsaturated $C_6$-$C_{24}$ fatty alcohol. In some preferred embodiments, the recombinant *Yarrowia lipolytica* microorganism comprises a deletion, disruption, mutation, and/or reduction in the activity of one or more endogenous enzyme selected from the following: (i) one or more acyl-CoA oxidase selected from the group consisting of YALI0E32835g (POX1), YALI0F10857g (POX2), YALI0D24750g (POX3). YALI0E27654g (POX4), YALI0C23859g (POX5), YALI0E06567g (POX6); (ii) one or more (fatty) alcohol dehydrogenase selected from the group consisting of YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), YALI0E07766g (ADH7); (iii) a (fatty) alcohol oxidase YALI0B14014g (FAO1); (iv) one or more cytochrome P450 enzyme selected from the group consisting of YALI0E25982g (ALK1), YALI0F01320g (ALK2), YALI0E23474g (ALK3), YALI0B13816g (ALK4), YALI0B13838g (ALK5), YALI0B01848g (ALK6), YALI0A15488g (ALK7), (YALI0C12122g (ALK8), YALI0B06248g (ALK9), YALI0B20702g (ALK10), YALI0C10054g (ALK11) and YALI0A20130g (Alk12): YAS1 (YALI1C03349), Yas2 (YALI0E32417), Gsyl1 (YALI0F18502), HFD1 (YALI0F23793), HFD2 (YALI0E15400), HFD3 (YALI0A17875), HFD4 (YALI0B01298), SDR (YALI0A19536); and (v) one or more diacylglycerol acyltransferase selected from the group consisting of YALI0E32791g (DGA1) and YALI0D07986g (DGA2). In other preferred embodiments, the recombinant Yarrowia lipolytica microorganism comprises a deletion of one or more endogenous enzyme selected from the following: (i) one or more acyl-CoA oxidase selected from the group consisting of YALI0E32835g (POX1), YALI0F01857g (POX2), YALI0D24750g (POX3), YALI0E27654g (POX4), YALI0C23859g (POX5), YALI0E06567g (POX6); (ii) one or more (fatty) alcohol dehydrogenase selected from the group consisting of YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), YALI0E07766g (ADH7); (iii) a (fatty) alcohol oxidase YALI0B14014g (FAO1); (iv) one or more cytochrome P450 enzyme selected from the group consisting of YALI0E25982g (ALK1), YALI0F01320g (ALK2), YALI0E23474g (ALK3), YALI0B13816g (ALK4), YALI0B13838g (ALK5), YALI0B01848g (ALK6), YALI0A15488g (ALK7), (YALI0C12122g (ALK8), YALI0B06248g (ALK9), YALI0B20702g (ALK10). YALI0C10054g (ALK11) and YALI0A20130g (Alk12); and (v) one or more diacylglycerol acyltransferase selected from the group consisting of YALI0E32791g (DGA1) and YALI0D07986g (DGA2).

In some embodiments, the fatty acyl desaturase catalyzes the conversion of a saturated fatty acyl-CoA into a mono- or poly-unsaturated intermediate selected from Z9-14:Acyl-CoA, Z11-14:Acyl-CoA, E11-14:Acyl-CoA, Z9-16:Acyl-CoA, and Z11-16:Acyl-CoA. In other embodiments, the mono- or poly-unsaturated $C_6$-$C_{24}$ fatty alcohol is selected from the group consisting of Z9-14:OH, Z11-14:OH, E11-14:OH, Z9-16:OH, Z11-16:OH, Z11Z13-16:OH, and Z13-18:OH.

In some embodiments, the recombinant Yarrowia lipolytica microorganism further comprises at least one endogenous or exogenous nucleic acid molecule encoding an alcohol oxidase or an alcohol dehydrogenase capable of catalyzing the conversion of the mono- or poly-unsaturated $C_6$-$C_{24}$ fatty alcohol into a corresponding $C_6$-$C_{24}$ fatty aldehyde. In some embodiments, the alcohol dehydrogenase is selected from Table 3a. In some embodiments, the $C_6$-$C_{24}$ fatty aldehyde is selected from the group consisting of Z9-14:Ald, Z11-14:Ald, E11-14:Ald, Z9-16:Ald, Z11-16:Ald, Z11Z13-16:Ald and Z13-18:Ald.

In some embodiments, the recombinant Yarrowia lipolytica microorganism further comprises: at least one endogenous or exogenous nucleic acid molecule encoding an alcohol oxidase or an alcohol dehydrogenase capable of catalyzing the conversion of the mono- or poly-unsaturated $C_6$-$C_{24}$ fatty alcohol into a corresponding $C_6$-$C_{24}$ fatty aldehyde; and at least one endogenous or exogenous nucleic acid molecule encoding an acetyl transferase capable of catalyzing the conversion of the mono- or poly-unsaturated $C_6$-$C_{24}$ fatty alcohol into a corresponding $C_6$-$C_{24}$ fatty acetate. In some embodiments, the mono- or poly-unsaturated $C_6$-$C_{24}$ fatty aldehyde and $C_6$-$C_{24}$ fatty acetate is selected from the group consisting of Z9-14:Ac, Z11-14:Ac, E11-14:Ac, Z9-16:Ac, Z11-16:Ac, Z1Z13-16:Ac, Z13-18:Ac, Z9-14:Ald, Z11-14:Ald, E11-14:Ald, Z9-16:Ald, Z11-16:Ald, Z11Z13-16:Ald and Z13-18:Ald.

In some embodiments, the fatty acyl desaturase does not comprise a fatty acyl desaturase comprising an amino acid sequence selected from the group consisting of SEQ ID NOs: 64, 65, 66 and 67. In other embodiments, the fatty acyl desaturase does not comprise a fatty acyl desaturase selected from an *Amyelois transitella*, *Spodoptera littoralis*, *Agrotis segetum*, or *Trichoplusia ni* derived desaturase.

In some embodiments, the disclosure provides a method of engineering a Yarrowia lipolytica microorganism that is capable of producing a mono- or poly-unsaturated $C_6$-$C_{24}$ fatty alcohol from an endogenous or exogenous source of saturated $C_6$-$C_{24}$ fatty acid, wherein the method comprises introducing into the Yarrowia lipolytica microorganism the following: (a) at least one nucleic acid molecule encoding a fatty acyl desaturase having at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%& 61%, 60&% 59%, 58%, 57%, 56%, 55%, 54%, 53%, 52%, 51%, 50%, or 50% sequence identity to a fatty acyl desaturase selected from the group consisting of SEQ ID NOs: 39, 54, 60, 62, 78, 79, 80, 95, 97, 99, 101, 103, and 105 that catalyzes the conversion of a saturated $C_6$-$C_{24}$ fatty acyl-CoA to a corresponding mono- or poly-unsaturated $C_6$-$C_{24}$ fatty acyl-CoA; and (b) at least one nucleic acid molecule encoding a fatty alcohol forming fatty acyl reductase having 95% sequence identity to a fatty alcohol forming fatty acyl reductase selected from the group consisting of SEQ ID NOs: 41-48, 55, 56, 57, 73, 75 and 77 that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol. In some embodiments, the microorganism is MATA ura3-302::SUC2 Δpox1 Δpox2 Δpox3 Δpox4 Δpox5 Δpox6 Δfadh Δadh1 Δadh2 Δadh3 Δadh4 Δadh5 Δadh6 Δadh7 Δfao1::URA3.

In some embodiments, the disclosure provides a method of producing a mono- or poly-unsaturated $C_6$-$C_4$ fatty alcohol, fatty aldehyde or fatty acetate from an endogenous or exogenous source of saturated $C_6$-$C_{24}$ fatty acid, comprising: cultivating a recombinant microorganism described herein in a culture medium containing a feedstock that provides a carbon source adequate for the production of the mono- or poly-unsaturated $C_6$-$C_{24}$ fatty alcohol, fatty aldehyde or fatty acetate. In some embodiments, the method further comprises a step of recovering the mono- or poly-unsaturated $C_6$-$C_{24}$ fatty alcohol, fatty aldehyde or fatty acetate. In further embodiments, the recovery step comprises distillation. In yet further embodiments, the recovery step comprises membrane-based separation.

In some embodiments, the mono- or poly-unsaturated $C_6$-$C_{24}$ fatty alcohol is converted into a corresponding $C_6$-$C_{24}$ fatty aldehyde using chemical methods. In further embodiments, the chemical methods are selected from TEMPO-bleach, TEMPO-copper-air, TEMPO-PhI(OAc)$_2$, Swern oxidation and noble metal-air. In some embodiments, the mono- or poly-unsaturated $C_6$-$C_{24}$ fatty alcohol is converted into a corresponding $C_6$-$C_{24}$ fatty acetate using chemical methods. In further embodiments, the chemical methods utilize a chemical agent selected from the group consisting of acetyl chloride, acetic anhydride, butyryl chloride, butyric anhydride, propanoyl chloride and propionic anhydride in the presence of 4-N. N-dimethylaminopyridine (DMAP) or sodium acetate to esterify the mono- or poly-unsaturated $C_6$-$C_{24}$ fatty alcohol to the corresponding $C_6$-$C_{24}$ fatty acetate.

In addition to the biosynthetic pathway described in the first aspect above, the present application provides an additional biosynthetic pathway for the production of an unsaturated $C_6$-$C_{24}$ fatty alcohol utilizing a saturated $C_6$-$C_{24}$ fatty acyl-ACP intermediate derived from a $C_6$-$C_{24}$ fatty acid. Accordingly, in a second aspect, the application relates to a recombinant microorganism capable of producing an unsaturated $C_6$-$C_{24}$ fatty alcohol from an endogenous or exogenous source of $C_6$-$C_{24}$ fatty acid, wherein the recombinant microorganism expresses (a): at least one exogenous nucleic acid molecule encoding an acyl-ACP synthetase that catalyzes the conversion of a $C_6$-$C_{24}$ fatty acid to a corresponding saturated $C_6$-$C_{24}$ fatty acyl-ACP; (b) at least one exogenous nucleic acid molecule encoding a fatty-acyl-ACP desaturase that catalyzes the conversion of a saturated $C_6$-$C_{24}$ fatty acyl-ACP to a corresponding mono- or poly-unsaturated $C_6$-$C_{24}$ fatty acyl-ACP; (c) one or more endogenous or exogenous nucleic acid molecules encoding a fatty acid synthase complex that catalyzes the conversion of the mono- or poly-unsaturated $C_6$-$C_{24}$ fatty acyl-ACP from (b) to a corresponding mono- or poly-unsaturated $C_6$-$C_{24}$ fatty acyl-ACP with a two carbon elongation relative to the product of (b); (d): at least one exogenous nucleic acid molecule encoding a fatty aldehyde forming fatty-acyl reductase that catalyzes the conversion of the mono- or poly-unsaturated $C_6$-$C_{24}$ fatty acyl-ACP from (c) into a corresponding mono- or poly-unsaturated $C_6$-$C_{24}$ fatty aldehyde; and (e) at least one endogenous or exogenous nucleic acid molecule encoding a dehydrogenase that catalyzes the conversion of the mono- or poly-unsaturated $C_6$-$C_{24}$ fatty aldehyde $C_6$-$C_{24}$ from (d) into a corresponding mono- or poly-unsaturated $C_6$-$C_{24}$ fatty alcohol. In some embodiments, the mono- or poly-unsaturated $C_6$-$C_{24}$ fatty alcohol is an insect pheromone. In some embodiments, the mono- or poly-unsaturated $C_6$-$C_{24}$ fatty alcohol is a fragrance or flavoring agent. In some embodiments, the recombinant microorganism further comprises at least one endogenous or exogenous nucleic acid molecule encoding an alcohol oxidase or an alcohol dehydrogenase, wherein the alcohol oxidase or alcohol dehydrogenase is capable of catalyzing the conversion of the mono- or poly-unsaturated $C_6$-$C_{24}$ fatty alcohol from (e) into a corresponding mono- or poly-unsaturated $C_6$-$C_{24}$ fatty aldehyde. In some embodiments, the recombinant microorganism further comprises at least one endogenous or exogenous nucleic acid molecule encoding an acetyl transferase capable of catalyzing the conversion of the mono- or poly-unsaturated $C_6$-$C_{24}$ fatty alcohol from (e) into a corresponding mono- or poly-unsaturated $C_6$-$C_{24}$ fatty acetate.

In some embodiments, acyl-ACP synthetase is a synthetase capable of utilizing a fatty acid as a substrate that has a chain length of 6, 7, 8, 9, 10, 11, 12, 13, 14, 15, 16, 17, 18, 19, 20, 21, 22, 23, or 24 carbon atoms.

In various embodiments described herein, the acyl-ACP synthetase, or the nucleic acid that encodes it, can be isolated from organisms of the species *Vibrio harveyi, Rhodotorula gluntnis,* or *Yarrowia lipolytica.*

In some embodiments, the fatty-acyl-ACP desaturase is a soluble desaturase. In various embodiments described herein, the fatty-acyl-ACP desaturase, or the nucleic acid that encodes it, can be isolated from organisms of the species *Pelargonium hortorum, Asclepias syriaca,* or *Uncaria tomentosa.*

In some embodiments, the recombinant microorganism may express more than one exogenous nucleic acid molecule encoding a fatty-acyl desaturase that catalyzes the conversion of a saturated $C_6$-$C_{24}$ fatty acyl-ACP to a corresponding mono- or poly-unsaturated $C_6$-$C_{24}$ fatty acyl-ACP.

As described above, fatty acid elongation enzymes, i.e., a fatty acid synthase complex, can be utilized to extend the chain length of a mono- or poly-unsaturated $C_6$-$C_{24}$ fatty acyl-ACP by two additional carbons at the alpha carbon. In some embodiments, the two additional carbons are derived from endogenous malonyl-CoA. In one embodiment, the one or more nucleic acid molecules encoding a fatty acid synthase complex are endogenous nucleic acid molecules, i.e., the nucleic acid molecule(s) is/are native to the recombinant microorganism. In another embodiment, the one or more nucleic acid molecules encoding a fatty acid synthase complex are exogenous nucleic acid molecules.

In various embodiments described herein, the fatty aldehyde forming acyl-ACP reductase, i.e., fatty aldehyde forming fatty-acyl reductase, or the nucleic acid sequence that encodes it, can be isolated from organisms of the species can be isolated from organisms of the species *Pelargonium hortorum, Asclepias syriaca,* and *Uncaria tomentosa.*

As noted above, the recombinant microorganism according to the second aspect comprises at least one endogenous or exogenous nucleic acid molecule encoding a dehydrogenase capable of catalyzing the conversion of the mono- or poly-unsaturated $C_6$-$C_{24}$ fatty aldehyde from (d) into a corresponding mono- or poly-unsaturated $C_6$-$C_{24}$ fatty alcohol. In one embodiment, the dehydrogenase is encoded by an endogenous nucleic acid molecule. In another embodiment, the dehydrogenase is encoded by an exogenous nucleic acid molecule. In exemplary embodiments, the endogenous or exogenous nucleic acid molecule encoding a dehydrogenase is isolated from organisms of the species *Saccharomyces cerevisiae, Escherichia coli, Yarrowia lipolytica,* or *Candida tropicalis.*

In addition to the biosynthetic pathway described in the first and second aspects above, the present application provides an additional biosynthetic pathway for the production of an unsaturated $C_6$-$C_{24}$ fatty alcohol utilizing a saturated $C_6$-$C_{24}$ fatty acyl-ACP intermediate derived from a $C_6$-$C_{24}$ fatty acid. Accordingly, in a third aspect, the application relates to a recombinant microorganism capable of producing an unsaturated $C_6$-$C_{24}$ fatty alcohol from an endogenous or exogenous source of $C_6$-$C_{24}$ fatty acid, wherein the recombinant microorganism expresses (a): at least one exogenous nucleic acid molecule encoding an acyl-ACP synthetase that catalyzes the conversion of a $C_6$-$C_{24}$ fatty acid to a corresponding saturated $C_6$-$C_{24}$ fatty acyl-ACP; (b) at least one exogenous nucleic acid molecule encoding a fatty-acyl-ACP desaturase that catalyzes the conversion of a saturated $C_6$-$C_{24}$ fatty acyl-ACP to a corresponding mono- or poly-unsaturated $C_6$-$C_{24}$ fatty acyl-ACP; (c) at least one exogenous fatty acyl-ACP thioesterase that catalyzes the conversion of the mono- or poly-unsaturated $C_6$-$C_{24}$ fatty acyl-ACP from (b) to a corresponding mono- or poly-unsaturated $C_6$-$C_{24}$ fatty acid; (d) one or more endogenous or exogenous nucleic acid molecules encoding an elongase that catalyzes the conversion of the mono- or poly-unsaturated $C_6$-$C_{24}$ fatty acyl-CoA derived from CoA activation of the mono- or poly-unsaturated $C_6$-$C_{24}$ fatty acid from (c) to a corresponding mono- or poly-unsaturated $C_6$-$C_{24}$ fatty acyl-CoA with a two carbon or greater elongation relative to the product of (c); and (e): at least one exogenous nucleic acid molecule encoding a fatty alcohol forming fatty-acyl reductase that catalyzes the conversion of the mono- or poly-unsaturated $C_6$-$C_{24}$ fatty acyl-CoA from (d) into a corresponding mono- or poly-unsaturated $C_6$-$C_{24}$ fatty alcohol. In some embodiments, the mono- or poly-unsaturated $C_6$-$C_{24}$ fatty alcohol is an insect pheromone. In some embodiments, the mono- or poly-unsaturated $C_6$-$C_{24}$ fatty alcohol is a fragrance or flavoring agent. In some embodiments, the recombinant microorganism further comprises at least one endogenous or exogenous nucleic acid molecule encoding an alcohol oxidase or an alcohol dehydrogenase, wherein the alcohol oxidase or alcohol dehydrogenase is capable of catalyzing the conversion of the mono- or poly-unsaturated $C_6$-$C_{24}$ fatty alcohol from (e) into a corresponding mono- or poly-unsaturated $C_6$-$C_{24}$ fatty aldehyde. In some embodiments, the recombinant microorganism further comprises at least one endogenous or exogenous nucleic acid molecule encoding an acetyl transferase capable of catalyzing the conversion of the mono- or poly-unsaturated $C_6$-$C_{24}$ fatty alcohol from (e) into a corresponding mono- or poly-unsaturated $C_6$-$C_{24}$ fatty acetate.

In some embodiments according to this third aspect, a fatty acyl-ACP thioesterase can be utilized to convert a mono- or poly-unsaturated $C_6$-$C_{24}$ fatty acyl-ACP into a corresponding mono- or poly-unsaturated $C_6$-$C_{24}$ fatty acid. In a some embodiments, soluble fatty acyl-ACP thioesterases can be used to release free fatty acids for reactivation to a CoA thioester. Fatty acyl-ACP thioesterases that can be included within the embodiment include, but are not limited to, including Q41635, Q39473, P05521.2, AEM72519, AEM72520, AEM72521, AEM72523, AAC49784, CAB60830, EER87824, EER96252, ABN54268, AAO77182, CAH09236, ACL08376, and homologs thereof may be used. In some embodiments, the mono- or poly-unsaturated $C_6$-$C_{24}$ fatty acyl-CoA may serve as a substrate for an elongase, which can be utilized to extend the chain length of a mono- or poly-unsaturated $C_6$-$C_{24}$ fatty acyl-CoA by two additional carbons at the alpha carbon. In some embodiments, the two additional carbons are derived from endogenous malonyl-CoA.

As described above, in some embodiments, the recombinant microorganism according to the first, second, or third aspect further comprises at least one endogenous or exogenous nucleic acid molecule encoding an alcohol oxidase capable of catalyzing the conversion of a mono- or poly-unsaturated $C_6$-$C_{24}$ fatty alcohol into a corresponding mono- or poly-unsaturated $C_6$-$C_{24}$ fatty aldehyde. In certain embodiments, the alcohol oxidase, or the nucleic acid sequence that encodes it, can be isolated from organisms of the species *Candida boidinii, Komagataella pastoris, Tanacetum vulgare, Simmondsia chinensis, Arabidopsis thaliana, Lotus japonicas,* or *Candida tropicalis*. In exemplary embodiments, the alcohol oxidase comprises a sequence selected from GenBank Accession Nos. Q00922, F2QY27, Q6QIR6, Q8LDP0, and L7VFV2.

As described above, in some embodiments, the recombinant microorganism according to the first or second aspect further comprises at least one endogenous or exogenous nucleic acid molecule encoding an acetyl transferase capable of catalyzing the conversion of a $C_6$-$C_{24}$ fatty alcohol into a corresponding $C_6$-$C_{24}$ fatty acetate. In certain embodiments, the acetyl transferase, or the nucleic acid sequence that encodes it, can be isolated from organisms of the species *Saccharomyces cerevisiae, Danaus plexippus, Heliotis virescens, Bombyx mori, Agrotis ipsilon, Agrotis segetum, Euonymus alatus*. In exemplary embodiments, the acetyl transferase comprises a sequence selected from GenBank Accession Nos. AY242066, AY242065, AY242064, AY242063, AY242062, EHJ65205, ACX53812, NP_001182381, EHJ65977, EHJ68573, KJ579226, GU594061, KTA99184.1, AIN34693.1, AY605053, XP_002552712.1, XP_503024.1, XP_505595.1, and XP_505513.1.

In alternative embodiments, the fatty alcohol may be converted into a fatty acetate using chemical methods, e.g., via chemical catalysis utilizing a chemical agent such as acetyl chloride, acetic anhydride, butyryl chloride, butyric anhydride, propanoyl chloride and propionic anhydride.

In some embodiments, the recombinant microorganism comprising a biosynthesis pathway for the production of an unsaturated $C_6$-$C_{24}$ fatty alcohol, aldehyde, or acetate may further be engineered to express one or more nucleic acids encoding protein or polypeptide which, when expressed, is toxic to an insect. Exemplary toxicant producing genes suitable for the present disclosure can be obtained from entomopathogenic organism, such as *Bacillus thuringiensis. Pseudomonas aeruginosa, Serratia marcescens*, and members of the genus *Streptomyces*. In an exemplary embodiment, the recombinant microorganism comprising a biosynthesis pathway for the production of an unsaturated $C_6$-$C_{24}$ fatty alcohol, aldehyde, or acetate may further be engineered to express a nucleic acid encoding a *Bacillus thuringiensis* ("Bt") toxin. In additional or alternative embodiments, the recombinant microorganism comprising a biosynthesis pathway for the production of an unsaturated $C_6$-$C_{24}$ fatty alcohol, aldehyde, or acetate may further be engineered to express a nucleic acid encoding other toxic proteins such as spider venom.

In some embodiments, the recombinant microorganism comprising a biosynthesis pathway for the production of an unsaturated $C_6$-$C_{24}$ fatty alcohol, aldehyde, or acetate may further be engineered to express an RNAi molecule which, when expressed, produces an oligonucleotide that is toxic to an insect.

In some embodiments, the recombinant microorganism comprising a biosynthesis pathway for the production of an unsaturated $C_6$-$C_{24}$ fatty alcohol, aldehyde, or acetate may further be engineered to express a metabolic pathway which, when expressed, produces a small molecule that is toxic to an insect. Non-limiting examples of toxic small molecules include azadirachtin, spinosad, avermectin, pyrethrins, and various terpenoids.

In various embodiments described herein, the recombinant microorganism comprising a biosynthesis pathway for the production of an unsaturated $C_6$-$C_{24}$ fatty alcohol, aldehyde, or acetate may be a eukaryotic microorganism, such as a yeast, a filamentous fungi, or an algae, or alternatively, a prokaryotic microorganism, such as a bacterium. For instance, suitable host cells can include cells of a genus selected from the group consisting of *Yarrowia, Candida, Saccharomyces, Pichia, Hansenula, Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium,* and *Streptomyces*.

In some embodiments, the recombinant microorganism comprising a biosynthesis pathway for the production of an unsaturated $C_6$-$C_{24}$ fatty alcohol, aldehyde, or acetate is a yeast. Examples of suitable yeasts include yeasts of a genus selected from the group consisting of *Yarrowia, Candida, Saccharomyces, Pichia, Hansenula, Kluveromyces, Issatchenkia, Zygosaccharomyes, Debaryomyces, Schizosaccharomyces Pachysolen, Cyptococcus, Trichosporon, Rhodotorula,* or *Myxozyma*. In certain embodiments, the yeast is an oleaginous yeast. Exemplary oleaginous yeasts suitable for use in the present disclosure include members of the genera Yarrowia, Candida, Rhodotorula, Rhodosporidium, Cryptococcus, Trichosporon, and Lipomyces, including, but not limited to the species of Yarrowia lipolytica, Candida tropicalis, Rhodosporidium toruloides, Lipomyces starkey, L. lipoferus, C. revkaufi, C. pulcherrima, C. utilis, Rhodotorula minuta, Trichosporon pullans, T. cutaneum, Cryptococcus curvatus, R. glutinis, and R. graminis.

As will be understood in the art, endogenous enzymes can convert critical substrates and/or intermediates upstream of or within the unsaturated $C_6$-$C_{24}$ fatty alcohol, aldehyde, or acetate biosynthesis pathway into unwanted by-products. Accordingly, in some embodiments, the recombinant microorganism is manipulated to delete, disrupt, mutate, and/or reduce the activity of one or more endogenous enzymes that catalyzes a reaction in a pathway that competes with the unsaturated $C_6$-$C_{24}$ fatty alcohol, aldehyde, or acetate biosynthesis pathway.

In one embodiment, the recombinant microorganism is manipulated to delete, disrupt, mutate, and/or reduce the activity of one or more endogenous enzymes that catalyzes the conversion of a fatty acid into a ω-hydroxyfatty acid. In the context of a recombinant yeast microorganism, the recombinant yeast microorganism is engineered to delete, disrupt, mutate, and/or reduce the activity of one or more enzyme selected from XP_504406, XP_504857, XP_504311, XP_500855, XP_500856, XP_500402, XP_500097, XP_501748, XP_500560, XP_501148, XP_501667, XP_500273, BAA02041, CAA39366, CAA39367, BAA02210, BAA02211, BAA02212, BAA02213, BAA02214, AAO73952, AAO73953, AAO73954, AAO73955, AAO73956, AAO73958, AAO73959, AAO73960, AAO73961, AAO73957, XP_002546278, or homologs thereof. In the context of a recombinant bacterial microorganism, the recombinant bacterial microorganism is engineered to delete, disrupt, mutate, and/or reduce the activity of one or more enzyme selected from BAM49649, AAB80867, AAB17462, ADL27534, AAU24352, AAA87602, CAA34612, ABM17701, AAA25760, CABS 1047, AAC82967, WP_011027348, or homologs thereof.

In another embodiment, the recombinant microorganism is manipulated to delete, disrupt, mutate, and/or reduce the activity of one or more endogenous enzymes that catalyzes the conversion of a fatty acyl-CoA into α,β-enoyl-CoA. In the context of a recombinant yeast microorganism, the recombinant yeast microorganism is engineered to delete, disrupt, mutate, and/or reduce the activity of one or more enzyme selected from CAA04659, CAA04660, CAA04661, CAA04662, CAA04663, CAG79214, AAA34322, AAA34361, AAA34363, CAA29901, BAA04761, AAA34891, or homologs thereof. In the context of a recombinant bacterial microorganism, the recombinant bacterial microorganism is engineered to delete, disrupt, mutate, and/or reduce the activity of one or more enzyme selected from AAB08643, CAB15271, BAN55749, CAC44516, ADK16968, AEI37634, WP_000973047, WP_025433422, WP_035184107, WP_026484842, CEL80920, WP_026818657, WP_005293707, WP_005883960, or homologs thereof.

In embodiments where the recombinant microorganism is a yeast microorganism, the recombinant microorganism is manipulated to delete, disrupt, mutate, and/or reduce the activity of one or more enzyme involved in peroxisome assembly and/or peroxisome enzyme import. The recombinant yeast microorganism is engineered to delete, disrupt, mutate, and/or reduce the activity of one or more enzyme selected from XP_505754, XP_501986, XP_501311, XP_504845, XP_503326, XP_504029, XP_002549868, XP_002547156, XP_002545227, XP_002547350, XP_002546990, EIW11539, EIW08094, EIW11472, EIW09743, EIW08286, or homologs thereof.

In another embodiment, the recombinant microorganism is manipulated to delete, disrupt, mutate, and/or reduce the activity of one or more endogenous reductase or desaturase enzymes that interferes with the unsaturated $C_6$-$C_{24}$ fatty alcohol, aldehyde, or acetate, i.e., catalyzes the conversion of a pathway substrate or product into an unwanted by-product.

In another embodiment, the recombinant microorganism is manipulated to delete, disrupt, mutate, and/or reduce the activity of one or more endogenous alcohol oxidase or alcohol dehydrogenase enzymes that catalyzes the unwanted conversion of the desired product, e.g., unsaturated $C_6$-$C_{24}$ fatty alcohol into a corresponding unsaturated $C_6$-$C_{24}$ fatty aldehyde.

In another embodiment, the recombinant microorganism is manipulated to delete, disrupt, mutate, and/or reduce the activity of one or more endogenous enzymes that catalyzes a reaction in a pathway that competes with the biosynthesis pathway for one or more unsaturated fatty acyl-CoA intermediates. In one embodiment, the one or more endogenous enzymes comprise one or more diacylglycerol acyltransferases. In the context of a recombinant yeast microorganism, the recombinant yeast microorganism is engineered to delete, disrupt, mutate, and/or reduce the activity of one or more diacylglycerol acyltransferases selected from the group consisting of YALI0E32769g, YALI0D07986g and CTRG_06209, or homolog thereof. In another embodiment, the one or more endogenous enzymes comprise one or more glycerolphospholipid acyltransferases. In the context of a recombinant yeast microorganism, the recombinant yeast microorganism is engineered to delete, disrupt, mutate, and/or reduce the activity of one or more glycerolphospholipid acyltransferases selected from the group consisting of YALI0E16797g and CTG_04390, or homolog thereof. In another embodiment, the one or more endogenous enzymes comprise one or more acyl-CoA/sterol acyltransferases. In the context of a recombinant yeast microorganism, the recombinant yeast microorganism is engineered to delete, disrupt, mutate, and/or reduce the activity of one or more acyl-CoA/sterol acyltransferases selected from the group consisting of YALI0F06578g, CTRG_01764 and CTRG_01765, or homolog thereof.

In another embodiment, the recombinant microorganism is manipulated to delete, disrupt, mutate, and/or reduce the activity of one or more endogenous enzymes that catalyzes a reaction in a pathway that oxidizes fatty aldehyde intermediates. In one embodiment, the one or more endogenous enzymes comprise one or more fatty aldehyde dehydrogenases. In the context of a recombinant yeast microorganism, the recombinant yeast microorganism is engineered to delete, disrupt, mutate, and/or reduce the activity of one or more fatty aldehyde dehydrogenases selected from the group consisting of YALI0A17875g. YALI0E15400g, YALI0B01298g, YALI0F23793g, CTRG_05010 and CTRG_04471, or homolog thereof.

In another embodiment, the recombinant microorganism is manipulated to delete, disrupt, mutate, and/or reduce the activity of one or more endogenous enzymes that catalyzes a reaction in a pathway that consumes fatty acetate products. In one embodiment, the one or more endogenous enzymes comprise one or more sterol esterases. In the context of a recombinant yeast microorganism, the recombinant yeast microorganism is engineered to delete, disrupt, mutate, and/or reduce the activity of one or more sterol esterases selected from the group consisting of YALI0E32035g, YALI0E00528g, CTRG_01138, CTRG_01683 and CTRG_04630, or homolog thereof. In another embodiment, the one or more endogenous enzymes comprise one or more triacylglycerol lipases. In the context of a recombinant yeast microorganism, the recombinant yeast microorganism is engineered to delete, disrupt, mutate, and/or reduce the activity of one or more triacylglycerol lipases selected from the group consisting of YALI0D17534g, YALI0F10010g, CTRG_00057 and CTRG_06185, or homolog thereof. In another embodiment, the one or more endogenous enzymes comprise one or more monoacylglycerol lipases. In the context of a recombinant yeast microorganism, the recombinant yeast microorganism is engineered to delete, disrupt, mutate, and/or reduce the activity of one or more monoacylglycerol lipases selected from the group consisting of YALI0C14520g, CTRG_03360 and CTRG_05049, or homolog thereof. In another embodiment, the one or more endogenous enzymes comprise one or more extracellular lipases. In the context of a recombinant yeast microorganism, the recombinant yeast microorganism is engineered to delete, disrupt, mutate, and/or reduce the activity of one or more extracellular lipases selected from the group consisting of YALI0A20350g, YALI0D19184g, YALI0B09361g, CTRG_05930, CTRG_04188, CTRG_02799, CTRG_03052 and CTRG_03885, or homolog thereof.

In embodiments where the recombinant microorganism is a yeast microorganism, one or more of the exogenous unsaturated $C_6$-$C_{24}$ fatty alcohol, aldehyde, or acetate pathway genes encodes an enzyme that is localized to a yeast compartment selected from the group consisting of the cytosol, the mitochondria, or the endoplasmic reticulum. In an exemplary embodiment, one or more of the exogenous pathway genes encodes an enzyme that is localized to the endoplasmic reticulum. In another embodiment, at least two exogenous pathway genes encode an enzyme that is localized to the endoplasmic reticulum. In yet another embodiment, all exogenous pathway genes encodes an enzyme that is localized to the endoplasmic reticulum.

In additional embodiments, the present application provides methods of producing an unsaturated $C_6$-$C_{24}$ fatty alcohol, aldehyde, or acetate using a recombinant microorganism as described herein. In one embodiment, the method includes cultivating the recombinant microorganism in a culture medium containing a feedstock providing a carbon source until the unsaturated $C_6$-$C_{24}$ fatty alcohol, aldehyde, or acetate is produced and optionally, recovering the unsaturated $C_6$-$C_{24}$ fatty alcohol, aldehyde, or acetate. Once produced, the unsaturated $C_6$-$C_{24}$ fatty alcohol, aldehyde, or acetate may be isolated from the fermentation medium using various methods known in the art including, but not limited to, distillation, membrane-based separation gas stripping, solvent extraction, and expanded bed adsorption.

In some embodiments, the recombinant microorganism, e.g., a yeast, may be recovered and produced in dry particulate form. In embodiments involving yeast, the yeast may be dried to produce powdered yeast. In some embodiments, the process for producing powdered yeast comprises spray drying a liquid yeast composition in air, optionally followed by further drying. In some embodiments, the recombinant microorganism composition will comprise the unsaturated $C_6$-$C_{24}$ fatty alcohol, aldehyde, or acetate when dried.

As described herein, preferred recombinant microorganisms of the disclosure will have the ability to utilize alkanes and fatty acids as carbon sources. However, as will be understood in the art, a variety of carbon sources may be utilized, including but not limited to, various sugars (e.g., glucose, fructose, or sucrose), glycerol, alcohols (e.g., ethanol), organic acids, lignocellulose, proteins, carbon dioxide, carbon monoxide, as well as the aforementioned alkanes and fatty acids. In some embodiments, the recombinant microorganism will convert the carbon source to the unsaturated $C_6$-$C_{24}$ fatty alcohol, aldehyde, or acetate under aerobic conditions.

As highlighted above, the present application provides methods of producing one or more unsaturated $C_6$-$C_{24}$ fatty alcohols, aldehydes, or acetates using a recombinant microorganism as described herein. In some embodiments, the product is an insect pheromone. As will be appreciated by the skilled artisan equipped with the instant disclosure, a variety of different exogenous and endogenous enzymes can be expressed in a recombinant host microorganism to produce a desired insect pheromone. Exemplary insect pheromones in the form of fatty alcohols, fatty aldehydes, or fatty acetates capable of being generated using the recombinant microorganisms and methods described herein include, but are not limited to, (Z)-11-hexadecenal, (Z)-11-hexadecenyl acetate, (Z)-9-tetradecenyl acetate, (Z,Z)-11,13-hexadecadienal, (9Z,11E)-hexadecadienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, (Z)-13-hexadecenyl acetate, and (Z)-13-octadecenayl acetate, and (Z)-13-octadecenal.

In another embodiment of the present application, compositions comprising one of more of the insect pheromone-producing recombinant microorganisms described herein can be provided. In certain embodiments, the composition may further comprise one or more insect pheromones produced by the recombinant microorganism. In further embodiments, the may additionally comprise one or more toxic proteins or polypeptides produced by the recombinant microorganism.

BRIEF DESCRIPTION OF DRAWINGS

Illustrative embodiments of the disclosure are illustrated in the drawings, in which:

FIG. 11A: YPD+palmitoleic acid; FIG. 11B: YPD−palmitoleic acid; FIG. 11C: CM-Ura glucose+palmitoleic acid; FIG. 11D: CM-Ura glucose—palmitoleic acid, FIG. 11E: Map of strains in FIG. 11A-FIG. 11D. Dasher=GFP synthon.

FIG. 19A: Fragmentation pattern of an authentic standard. The m/z 297.3 was used in follow up experiments to selectively detect the alcohol. To also detect the internal standard, the masses 208 and 387.3 were included too. FIG. 19B: In addition to the detection of the specific mass fragment, the retention time was used as second stage confirmation. The retention time is 6.22. FIG. 19C: Comparison of the two different regioisomers 9Z- and 11Z-hexadcenol when detected in SIM mode (297.3) with the same method.

FIG. 21A: Negative (water-only) control transformation plate. FIG. 21B: pPV0137 mCherry transformation plate. FIG. 21C: Patch plates from negative control clones. FIG. 21D: Patch plates from pPV0137 clones.

FIG. 24A: The specific peak with an ion fragment of 245 m/z was only observed in *C. tropicalis* SPV053 expressing either the Z11-desaturase from *A. transitella* or *H. zea*. FIG. 24B: The fragmentation patterns of the authentic standard. FIG. 24D: The fragmentation patterns of the newly formed compound in samples with expressed desaturase from *H. zea* match those of the standard. FIG. 24E: The fragmentation patterns of the newly formed compound in samples with expressed desaturase from *A. transitella* match those of the standard. FIG. 24C: The fragmentation patterns of the mCherry control significantly differ from those of FIG. 24B. FIG. 24D and FIG. 24E.

FIG. 25A: Overall spectrum. The occurrence of the Z11-C16:1 peak is observable for the strains expressing the Z11-desaturases from *A. transitella* and *H. zea*. FIG. 25B: Zoom of the C14 to C18 area. A new peak is visible at 4.8 min, which could correspond to Z11-C14:1. Another peak near Z9-C18:1 is also visible, which could correspond to Z11-C18:1.

*amigera* derived FAR enzyme upon expression in yeast. The used server (world wide web address: cbs.dtu.dk/services/NetPhosYeast/; Blom, N., Gammeltoft, S. & Brunak, S. Sequence and structure-based prediction of eukaryotic protein phosphorylation sites1. *J. Mol. Biol.* 294, 1351-1362 (1999)) predicts phosphorylated amino acids specifically in yeast. The horizontal line resembles the threshold for possible phosphorylation sites.

Figure 45:
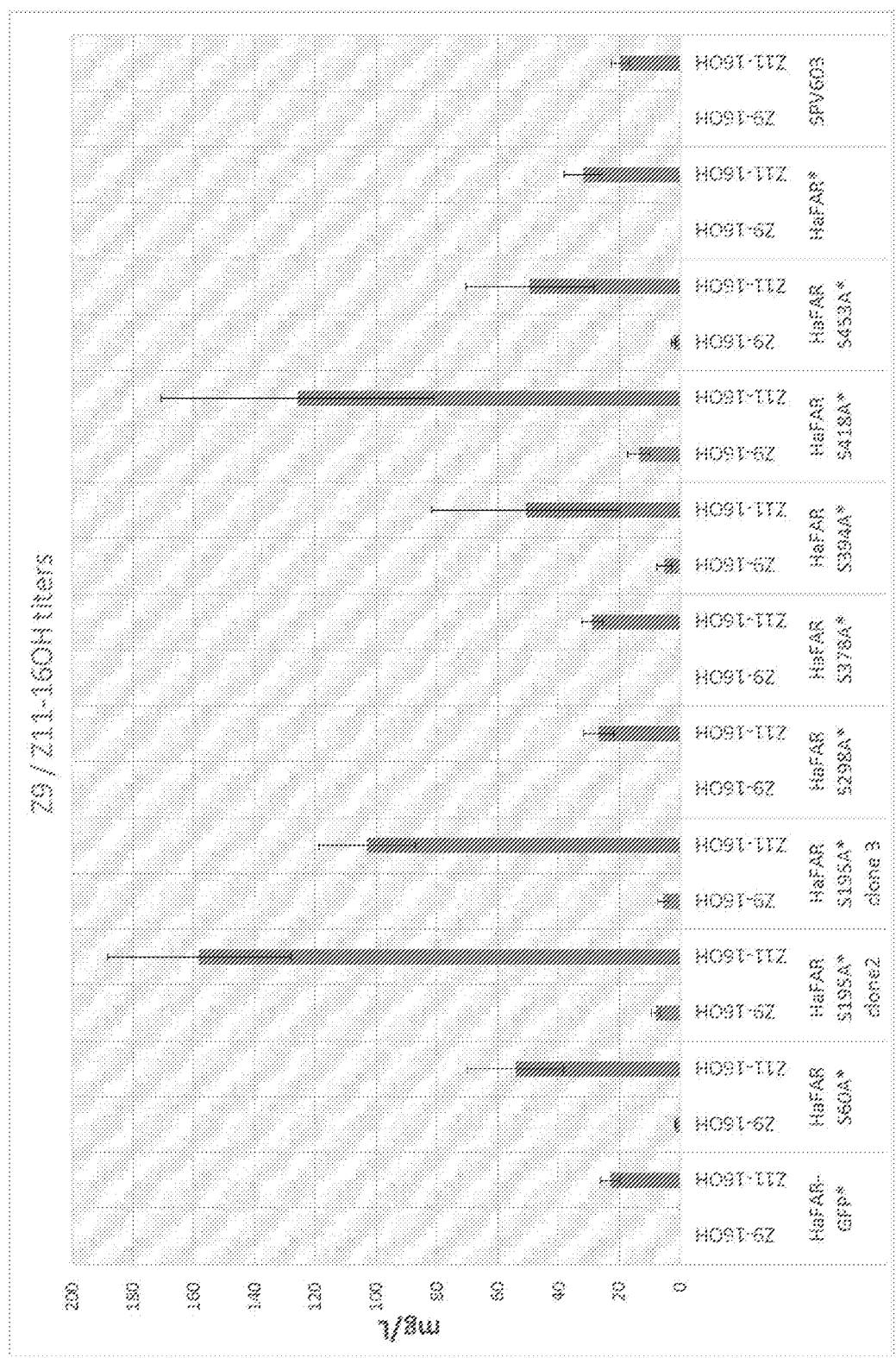

FIG. 45 shows analysis of the Z9/Z11-16OH titers of HaFAR mutant library upon expression in *Y. lipolytica* SPV603. * Indicates a second copy of the HaFAR enzyme in addition to the existing copy of the parental strain.

Figure 46:
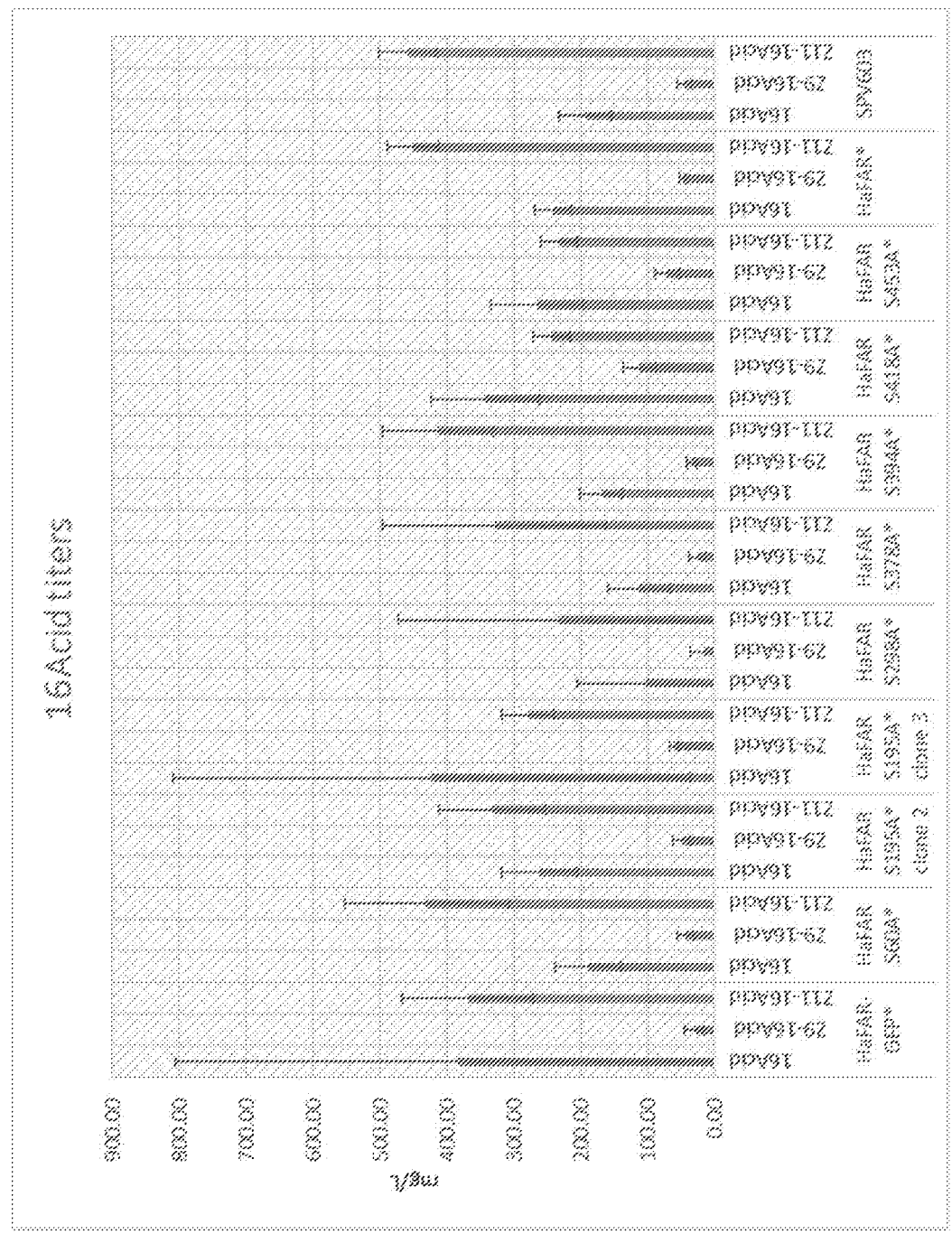

FIG. 46 shows analysis of the Z9/Z11-16Acid titers of HaFAR mutant library upon expression in *Y. lipolytica* SPV603. * Indicates a second copy of the HaFAR enzyme in addition to the existing copy in the parental strain.

Figure 47:
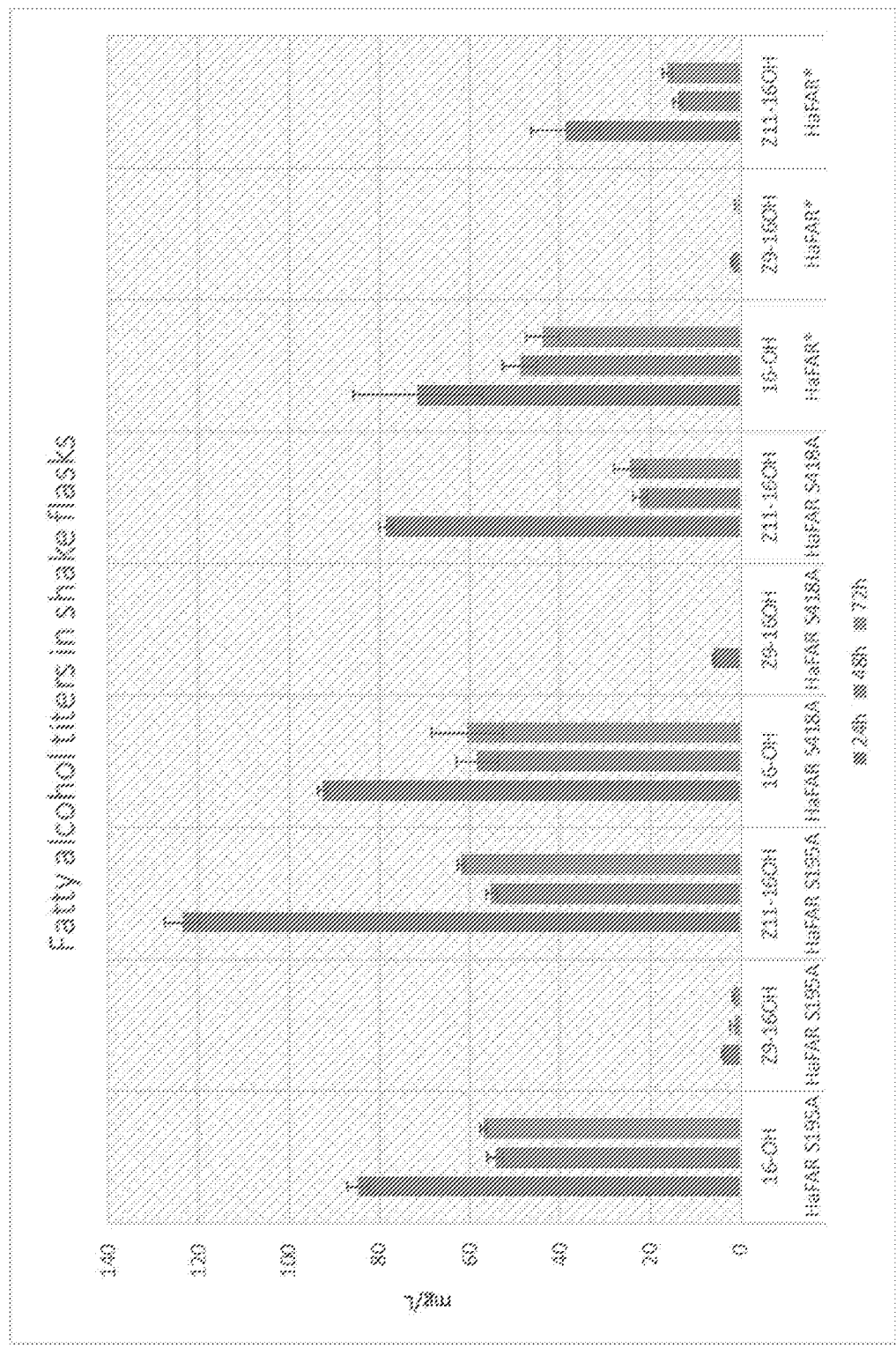

FIG. 47 shows analysis of the fatty alcohol titers of selected strains expressing HaFAR and derived mutants. Strains were cultivated in shake flasks over a period of 72 h after addition of 10 g/L methyl palmitate. * Indicates a second copy of the HaFAR enzyme in addition to the existing copy in the parental strain. The analysis is based on technical quadruplicates.

Figure 48:
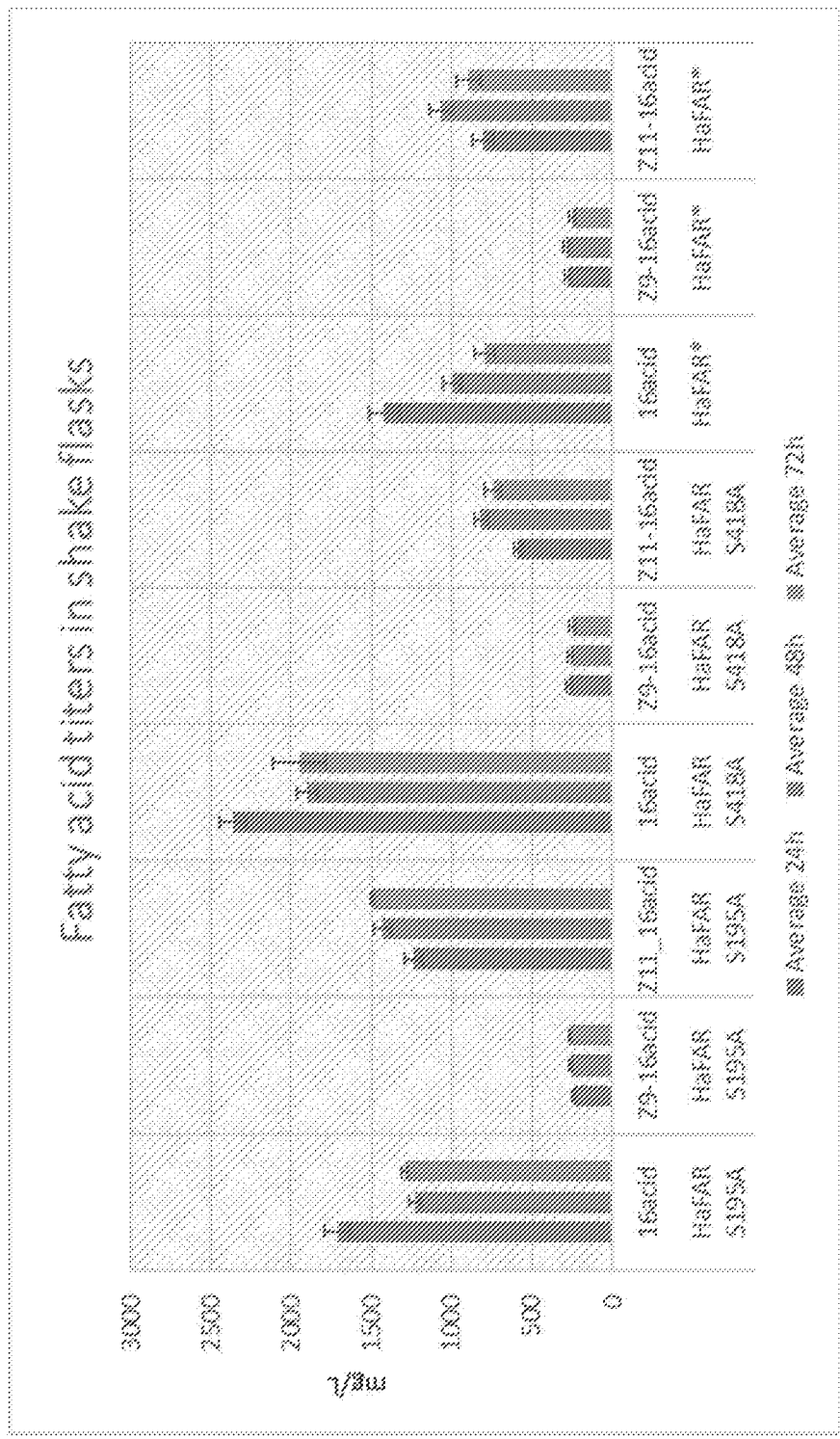

FIG. 48 shows analysis of the fatty acid titers of selected strains expressing HaFAR and derived mutants. Strains were cultivated in shake flasks over a period of 72 h after addition of 10 g/L methyl palmitate. * Indicates a second copy of the HaFAR enzyme in addition to the existing copy in the parental strain. The analysis is based on technical quadruplicates.

Figure 49:
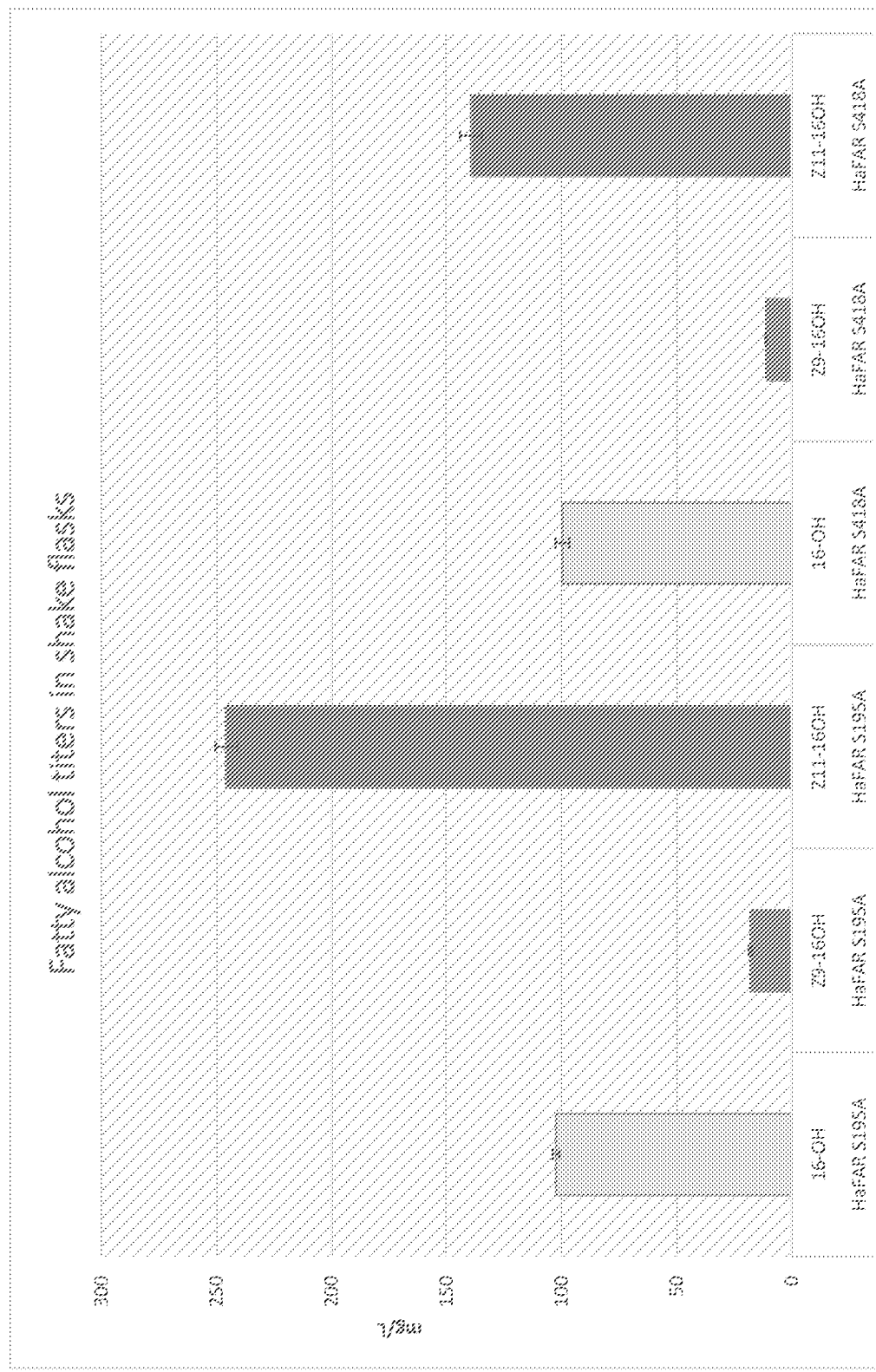

FIG. 49 shows analysis of the fatty alcohol titers of selected strains expressing HaFAR and derived mutants. Strains were cultivated in shake flasks over a period of 20 h upon addition of 10 g/L methyl palmitate. The analysis is based on technical quadruplicates.

Figure 50:
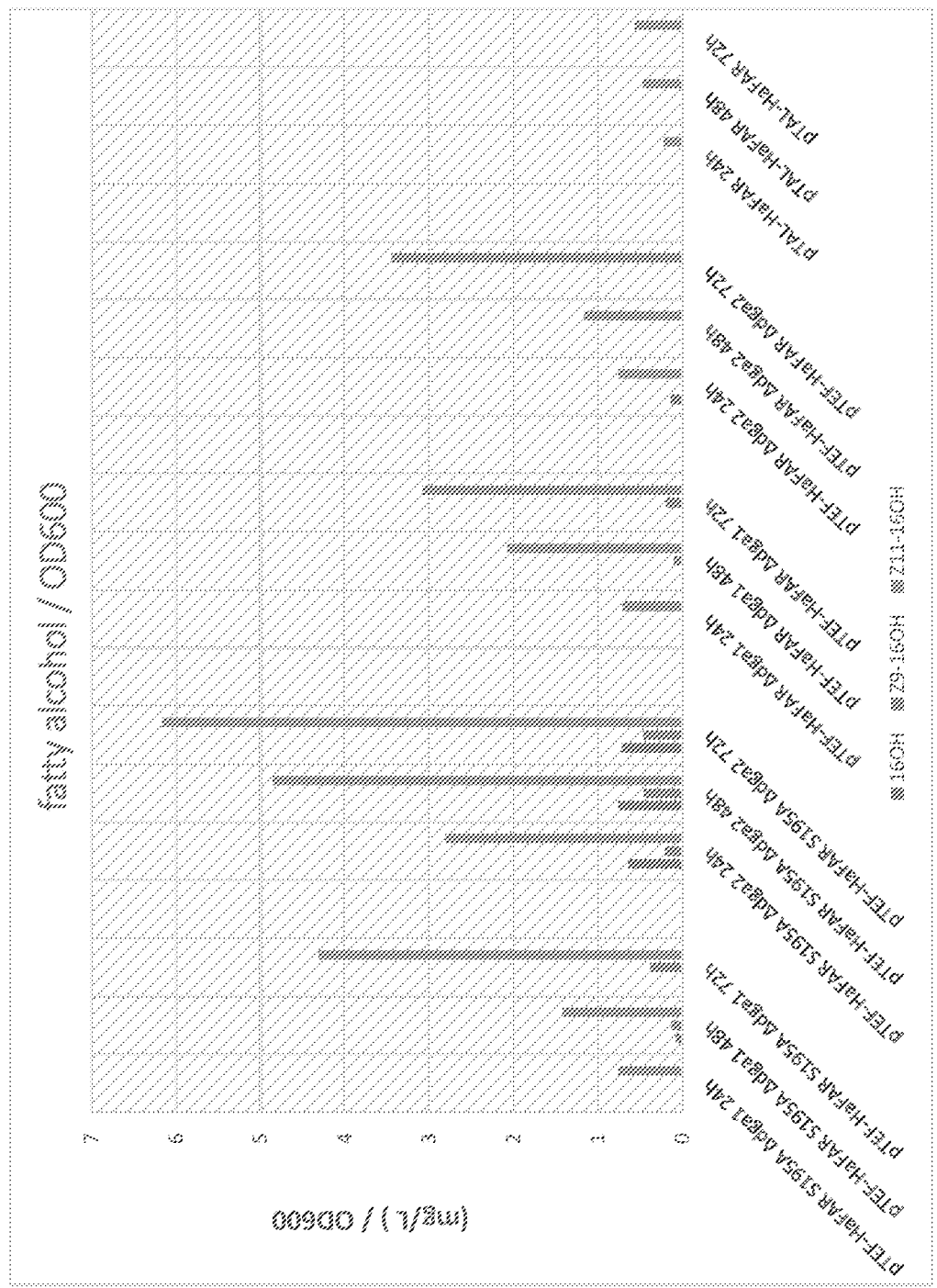

FIG. 50 shows analysis of the fatty alcohol titers of selected strains in a time course experiment in shake flasks. A copy of the enzyme HaFAR or HaS195A was introduced into the strains SPV1053 (Δdga1 ΔURA, ΔLeu, leu2::pTEF-HZ_Z11_desat_Hs-tXPR2_loxP) and SPV1054 (Δdga2 ΔURA, ΔLeu, leu2::pTEF-HZ_Z11_desat_Hs-tXPR2_loxP). Cultivation was performed as biological triplicates in shake flasks. Strains were cultivated in shake flasks over a period of 72 h upon addition of 10 g/L methyl palmitate.

Figure 51:
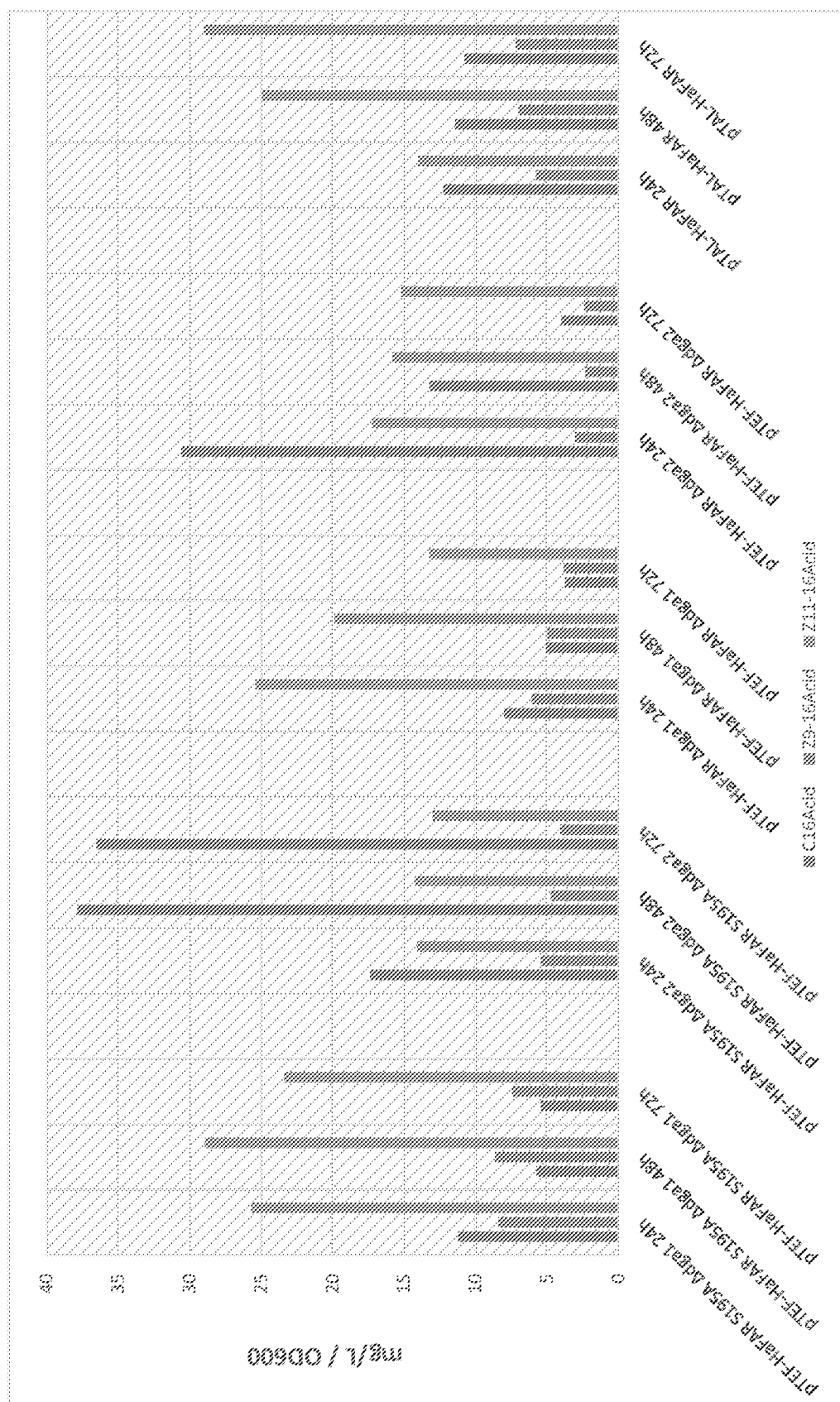

FIG. 51 shows analysis of the fatty acid titers of selected strains in a time course experiment in shake flasks. A copy of the enzyme HaFAR or HaS195A was introduced into the strains SPV1053 (Δdga1 ΔURA, ΔLeu, leu2::pTEF-HZ_Z1_desat_Hs-tXPR2_loxP) and SPV1054 (Δdga2 ΔURA, ΔLeu, leu2::pTEF-HZ_Z11_desat_Hs-tXPR2_loxP). Cultivation was performed as biological triplicates in shake flasks. Strains were cultivated in shake flasks over a period of 72 h upon addition of 10 g/L methyl palmitate.

Figure 52:
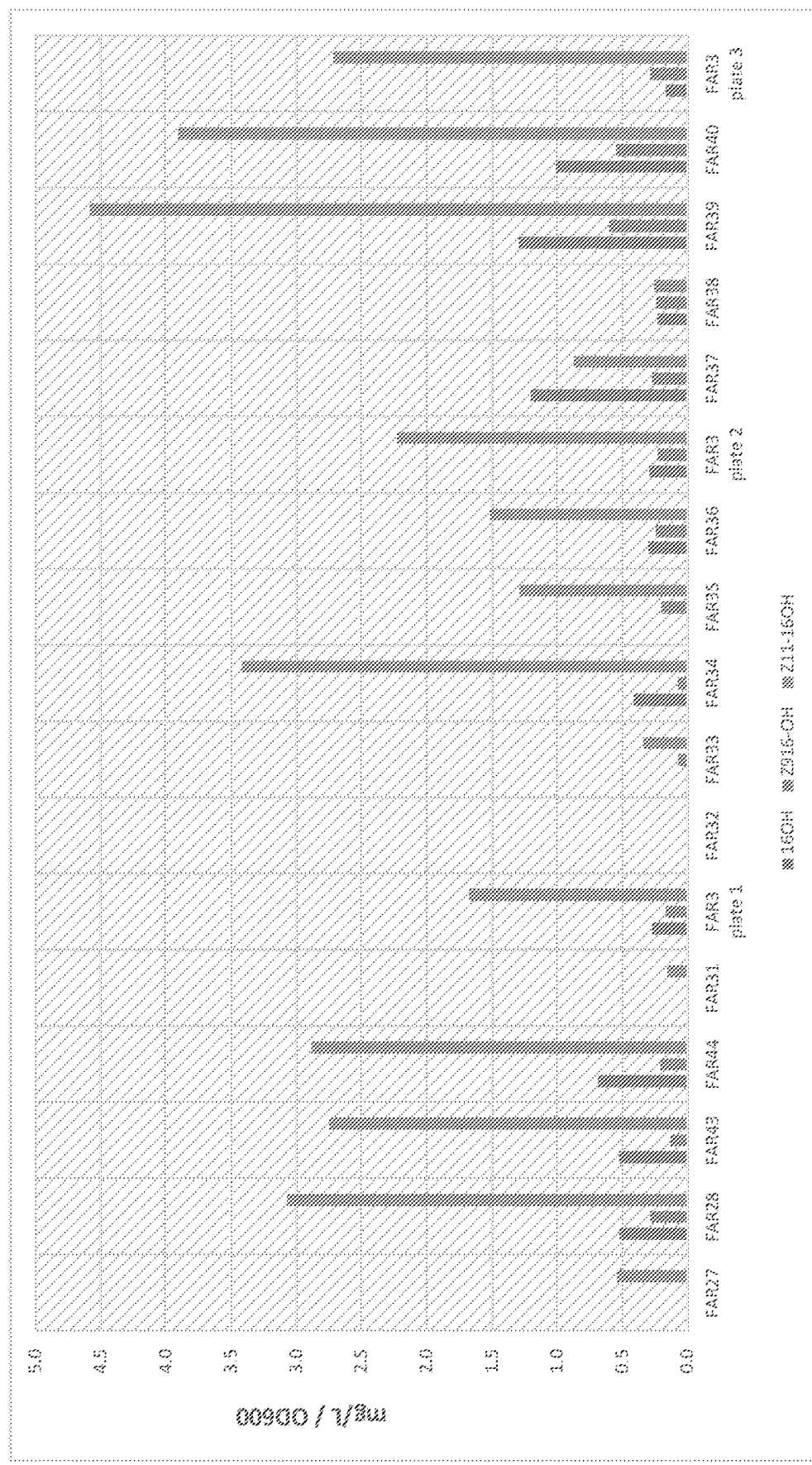

FIG. 52 shows analysis of the fatty alcohol titers of new strains in a FAR library screening in 24 well plates. A copy of each respective FAR enzyme from Table 24 was introduced into the strain SPV1054 (Δdga2 ΔURA, ΔLeu, leu2::pTEF-HZ_Z11_desat_Hs-tXPR2_loxP). Cultivation was performed as biological quadruplicates in 24 well plates. Strains were cultivated over a period of 96 h upon addition of 10 g/L methyl palmitate.

Figure 53:
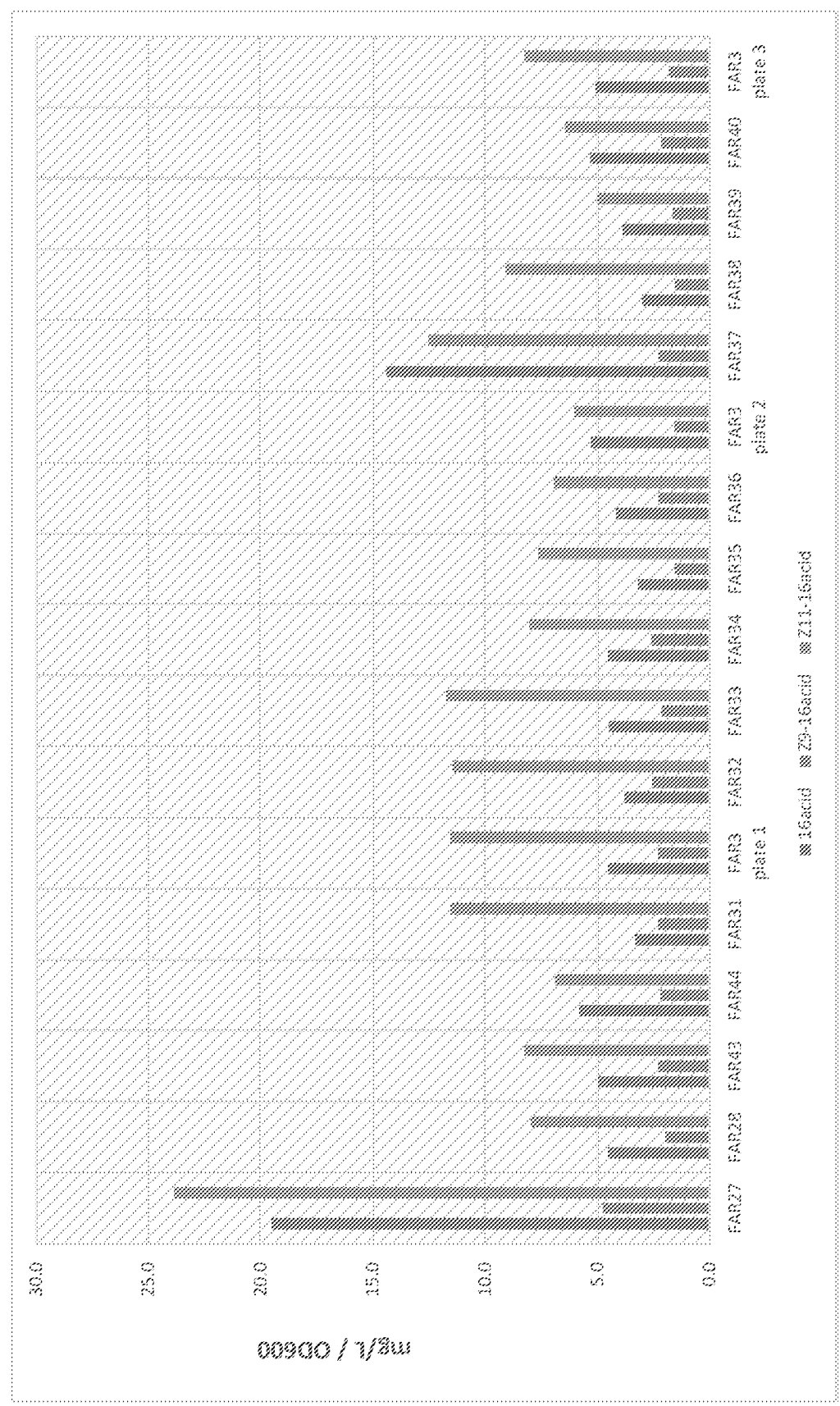

FIG. 53 shows analysis of the fatty acid titers of new strains in a FAR library screening in 24 well plates. A single copy of each respective FAR enzyme from Table 24 was introduced into the strain SPV1054 (Δdga2 ΔURA, ΔLeu, leu2::pTEF-HZ_Z11_desat_Hs-tXPR2_loxP). Cultivation was performed as biological quadruplicates in 24 well plates. Strains were cultivated over a period of 96 h upon addition of 10 g/L methyl palmitate.

Figure 54:
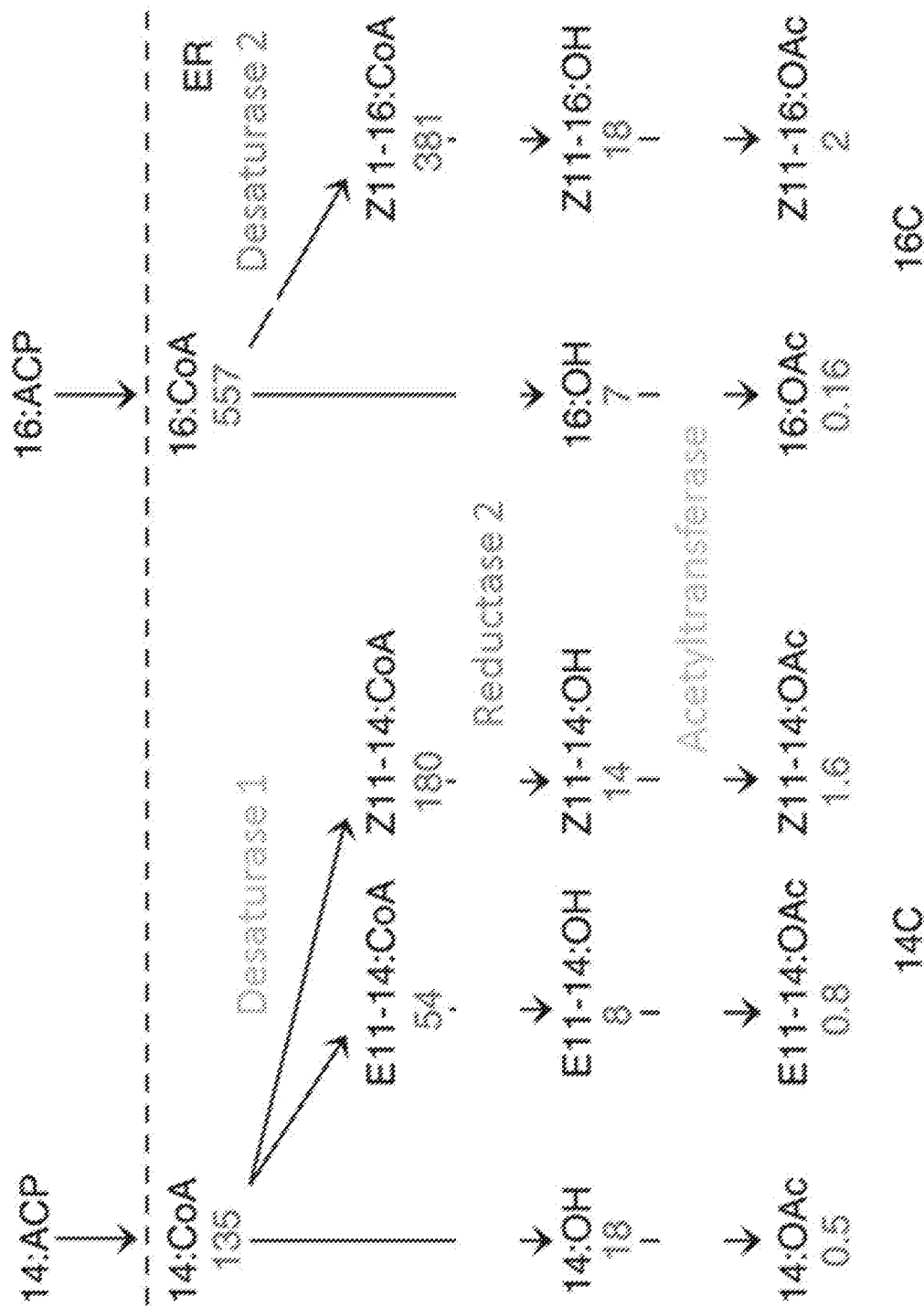

FIG. 54 shows a biosynthetic pathway capable of using tetradecyl-ACP (14:ACP) inputs to produce a blend of E- and Z-tetradecenyl acetate (E11-14:OAc and Z11-14:OAC) pheromones in a recombinant microorganism of the present disclosure.

SEQUENCES

A sequence listing for SEQ ID NO: 1-SEQ ID NO: 105 is part of this application and is incorporated by reference herein. The sequence listing is provided at the end of this document, and is separately provided in computer readable format.

DETAILED DESCRIPTION

Definitions

The following definitions and abbreviations are to be used for the interpretation of the disclosure.

As used herein and in the appended claims, the singular forms "a," "an," and "the" include plural referents unless the context clearly dictates otherwise. Thus, for example, reference to "a pheromone" includes a plurality of such pheromones and reference to "the microorganism" includes reference to one or more microorganisms, and so forth.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganism. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria): (3) Cyanobacteria, e.g., oxygenic phototrophs; (4) Spirochetes and related species; (5) Planctomyces: (6) Bacteroides, Flavobacteria: (7) Chlamydia; (8) Green sulfur bacteria: (9) Green non-sulfur bacteria (also anaerobic phototrophs); (10) Radioresistant micrococci and relatives; (11) *Thermotoga* and *Thermosipho thermophiles.*

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibro, Rhizobium, Chlamydia, Rickettsia, Treponema*, and *Fusobacterium.*

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces.*

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

As used herein, the term "non-naturally occurring," when used in reference to a microorganism organism or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "an endogenous or exogenous source of saturated $C_6$-$C_{24}$ fatty acid" as used herein refers to a source of saturated $C_6$-$C_{24}$ fatty acid originating from within the microorganism (endogenous), such as when a saturated $C_6$-$C_{24}$ fatty acid is produced or synthesized inside the microorganism, or originating from outside the microorganism (exogenous), such as when a saturated $C_6$-$C_{24}$ fatty acid is provided to the microorganism during the course of culturing or cultivating the microorganism in media in flasks or other containers.

The term "heterologous" as used herein in the context of a modified host cell refers to various molecules, e.g., polynucleotides, polypeptides, enzymes, etc., wherein at least one of the following is true; (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell, and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

As used herein, the term "homologous sequences" "homolog" "homologs" or "orthologs" refers to related sequences (nucleic or amino acid) that are functionally related to the referenced sequence. A functional relationship may be indicated in any one of a number of ways, including, but not limited to: (a) degree of sequence identity and/or (b) the same or similar biological function. Use of the term homolog in this disclosure refers to instances in which both (a) and (b) are indicated. The degree of sequence identity may vary, but in one embodiment, is at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, or 50% sequence identity when using standard sequence alignment programs known in the art (e.g., Clustal Omega alignment using default parameters). Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.). Thus, a reference to a homolog in the present disclosure will be understood as referencing a related sequence with the same or similar biological function, and a high degree of sequence identity as described above.

The term "fatty acid" as used herein refers to a compound of structure R—COOH, wherein R is a $C_6$ to $C_{24}$ saturated, unsaturated, linear, branched or cyclic hydrocarbon and the carboxyl group is at position 1. In a particular embodiment. R is a $C_6$ to $C_{24}$ saturated or unsaturated linear hydrocarbon and the carboxyl group is at position 1.

The term "fatty alcohol" as used herein refers to an aliphatic alcohol having the formula R—OH, wherein R is a $C_6$ to $C_{24}$ saturated, unsaturated, linear, branched or cyclic hydrocarbon. In a particular embodiment, R is a $C_6$ to $C_{24}$ saturated or unsaturated linear hydrocarbon.

The term "fatty acyl-CoA" refers to a compound having the structure R—(CO)—S—$R_1$, wherein $R_1$ is Coenzyme A, and the term "fatty acyl-ACP" refers to a compound having the structure R—(CO)—S—$R_1$, wherein $R_1$ is an acyl carrier protein ACP.

The term "short chain" or "short-chain" refers to fatty alcohols, fatty aldehydes, and/or fatty acetates, including pheromones, fragrances, flavors, and polymer intermediates with carbon chain length shorter than or equal to C18.

Introduction

The present disclosure addresses the need for novel technologies for the cost-efficient production of valuable products from low-cost feedstocks. Specifically, the present inventors have addressed this need with the development of recombinant microorganisms capable of producing a wide-range of unsaturated $C_6$-$C_{24}$ fatty alcohols, aldehydes, and acetates including synthetic insect pheromones, fragrances, flavors, and polymer intermediates from low-cost feedstocks. Thus, aspects of the disclosure are based on the inventors' discovery that recombinant microorganisms can be engineered in order to produce valuable products from low-cost feedstocks, which circumvents conventional synthetic methodologies to produce valuable products.

As discussed above, recombinant microorganisms can be engineered to synthesize mono- or poly-unsaturated $C_6$-$C_{24}$ fatty alcohols. Mono- or poly-unsaturated $C_6$-$C_{24}$ fatty alcohols synthesized as described herein can be further converted into the corresponding aldehydes or acetates. Thus, various embodiments of the present disclosure can be used to synthesize a variety of insect pheromones selected from fatty alcohols, aldehydes, and acetates. Additionally, embodiments described herein can also be used for the synthesis of fragrances, flavors, and polymer intermediates.

Engineering of the microbial hosts entail the expression of a non-native pheromone biosynthetic pathway which is comprised of but not limited to one or multiple fatty acyl desaturases, and fatty alcohol-forming or fatty aldehyde-forming reductases. Fatty acids produced by desaturation reactions can be stored intracellularly as triacylglycerides or reduced enzymatically by reductases to form fatty alcohols or aldehydes. Triacylglycerides containing unsaturated fatty acids can be extracted, esterified, and chemically reduced to produce unsaturated fatty alcohols. Fatty alcohols produced via the described pathways can be further converted into fatty aldehyde pheromones, and fatty acetate pheromones via subsequent chemical oxidation, and esterification methods, respectively. Methods of chemical oxidation and esterification are known in the arts. Fatty alcohols produced via the described pheromone biosynthetic pathway can also be further converted into fatty aldehyde pheromones, and fatty acetate pheromones using enzymatic conversion such as alcohol dehydrogenases, and acetyltransferase, respectively. Similarly, fatty acyl-CoA or fatty acyl-ACP formed as intermediates in the pheromone biosynthetic pathway can be released as free fatty acids by native or heterologously derived thioesterases, to become substrates for synthesis of pheromones using metathesis.

Pheromones

As described above, embodiments of the disclosure provide for the synthesis of one or more insect pheromones using a recombinant microorganism. A pheromone is a volatile chemical compound that is secreted by a particular insect for the function of chemical communication within the species. That is, a pheromone is secreted or excreted chemical factor that triggers a social response in members of the same species. There are, inter alia, alarm pheromones, food trail pheromones, sex pheromones, aggregation pheromones, epideictic pheromones, releaser pheromones, primer pheromones, and territorial pheromones, that affect behavior or physiology.

Non-limiting examples of insect pheromones which can be synthesized using the recombinant microorganisms and methods disclosed herein include linear alcohols, aldehydes, and acetates listed in Table 1.

TABLE 1

$C_6$-$C_{20}$ Linear Pheromones

| Name | Name |
|---|---|
| (E)-2-Decen-1-ol | (E,E)-10,12-Tetradecadien-1-ol |
| (E)-2-Decenyl acetate | (E,E)-10,12-Tetradecadienyl acetate |
| (E)-2-Decenal | (E,E)-10,12-Tetradecadienal |
| (Z)-2-Decen-1-ol | (E,Z)-10,12-Tetradecadienyl acetate |
| (Z)-2-Decenyl acetate | (Z,E)-10,12-Tetradecadienyl acetate |
| (Z)-2-Decenal | (Z,Z)-10,12-Tetradecadien-1-ol |
| (E)-3-Decen-1-ol | (Z,Z)-10,12-Tetradecadienyl acetate |
| (Z)-3-Decenyl acetate | (E,Z,Z)-3,8,11-Tetradecatrienyl acetate |
| (Z)-3-Decen-1-ol | (E)-8-Pentadecen-1-ol |
| (Z)-4-Decen-1-ol | (E)-8-Pentadecenyl acetate |
| (E)-4-Decenyl acetate | (Z)-8-Pentadecen-1-ol |
| (Z)-4-Decenyl acetate | (Z)-8-Pentadecenyl acetate |
| (Z)-4-Decenal | (Z)-9-Pentadecenyl acetate |
| (E)-5-Decen-1-ol | (E)-9-Pentadecenyl acetate |
| (E)-5-Decenyl acetate | (Z)-10-Pentadecenyl acetate |
| (Z)-5-Decen-1-ol | (Z)-10-Pentadecenal |
| (Z)-5-Decenyl acetate | (E)-12-Pentadecenyl acetate |
| (Z)-5-Decenal | (Z)-12-Pentadecenyl acetate |
| (E)-7-Decenyl acetate | (Z,Z)-6,9-Pentadecadien-1-ol |
| (Z)-7-Decenyl acetate | (Z,Z)-6,9-Pentadecadienyl acetate |
| (E)-8-Decen-1-ol | (Z,Z)-6,9-Pentadecadienal |
| (E,E)-2,4-Decadienal | (E,E)-8,10-Pentadecadienyl acetate |
| (E,Z)-2,4-Decadienal | (E,Z)-8,10-Pentadecadien-1-ol |
| (Z,Z)-2,4-Decadienal | (E,Z)-8,10-Pentadecadienyl acetate |
| (E,E)-3,5-Decadienyl acetate | (Z,E)-8,10-Pentadecadienyl acetate |
| (Z,E)-3,5-Decadienyl acetate | (Z,Z)-8,10-Pentadecadienyl acetate |
| (Z,Z)-4,7-Decadien-1-ol | (E,Z)-9,11-Pentadecadienal |
| (Z,Z)-4,7-Decadienyl acetate | (Z,Z)-9,11-Pentadecadienal |
| (E)-2-Undecenyl acetate | (Z)-3-Hexadecenyl acetate |
| (E)-2-Undecenal | (E)-5-Hexadecen-1-ol |
| (Z)-5-Undecenyl acetate | (E)-5-Hexadecenyl acetate |
| (Z)-7-Undecenyl acetate | (Z)-5-Hexadecen-1-ol |
| (Z)-8-Undecenyl acetate | (Z)-5-Hexadecenyl acetate |
| (Z)-9-Undecenyl acetate | (E)-6-Hexadecenyl acetate |
| (E)-2-Dodecenal | (E)-7-Hexadecen-1-ol |
| (Z)-3-Dodecen-1-ol | (E)-7-Hexadecenyl acetate |
| (E)-3-Dodecenyl acetate | (E)-7-Hexadecenal |
| (Z)-3-Dodecenyl acetate | (Z)-7-Hexadecen-1-ol |
| (E)-4-Dodecenyl acetate | (Z)-7-Hexadecenyl acetate |
| (E)-5-Dodecen-1-ol | (Z)-7-Hexadecenal |
| (E)-5-Dodecenyl acetate | (E)-8-Hexadecenyl acetate |
| (Z)-5-Dodecen-1-ol | (E)-9-Hexadecen-1-ol |
| (Z)-5-Dodecenyl acetate | (E)-9-Hexadecenyl acetate |
| (Z)-5-Dodecenal | (E)-9-Hexadecenal |
| (E)-6-Dodecen-1-ol | (Z)-9-Hexadecen-1-ol |
| (Z)-6-Dodecenyl acetate | (Z)-9-Hexadecenyl acetate |
| (E)-6-Dodecenal | (Z)-9-Hexadecenal |
| (E)-7-Dodecen-1-ol | (E)-10-Hexadecen-1-ol |
| (E)-7-Dodecenyl acetate | (E)-10-Hexadecenal |
| (E)-7-Dodecenal | (Z)-10-Hexadecenyl acetate |
| (Z)-7-Dodecen-1-ol | (Z)-10-Hexadecenal |
| (Z)-7-Dodecenyl acetate | (E)-11-Hexadecen-1-ol |
| (Z)-7-Dodecenal | (E)-11-Hexadecenyl acetate |
| (E)-8-Dodecen-1-ol | (E)-11-Hexadecenal |
| (E)-8-Dodecenyl acetate | (Z)-11-Hexadecen-1-ol |
| (E)-8-Dodecenal | (Z)-11-Hexadecenyl acetate |
| (Z)-8-Dodecen-1-ol | (Z)-11-Hexadecenal |
| (Z)-8-Dodecenyl acetate | (Z)-12-Hexadecenyl acetate |
| (E)-9-Dodecen-1-ol | (Z)-12-Hexadecenal |
| (E)-9-Dodecenyl acetate | (E)-14-Hexadecenal |
| (E)-9-Dodecenal | (Z)-14-Hexadecenyl acetate |
| (Z)-9-Dodecen-1-ol | (E,E)-1,3-Hexadecadien-1-ol |
| (Z)-9-Dodecenyl acetate | (E,Z)-4,6-Hexadecadien-1-ol |
| (Z)-9-Dodecenal | (E,Z)-4,6-Hexadecadienyl acetate |
| (E)-10-Dodecen-1-ol | (E,Z)-4,6-Hexadecadienal |
| (E)-10-Dodecenyl acetate | (E,Z)-6,11-Hexadecadienyl acetate |
| (E)-10-Dodecenal | (E,Z)-6,11-Hexadecadienal |
| (Z)-10-Dodecen-1-ol | (Z,Z)-7,10-Hexadecadien-1-ol |
| (Z)-10-Dodecenyl acetate | (Z,Z)-7,10-Hexadecadienyl acetate |
| (E,Z)-3,5-Dodecadienyl acetate | (Z,E)-7,11-Hexadecadien-1-ol |
| (Z,E)-3,5-Dodecadienyl acetate | (E,Z)-7,11-Hexadecadienyl acetate |
| (Z,Z)-3,6-Dodecadien-1-ol | (Z,E)-7,11-Hexadecadienal |
| (E,E)-4,10-Dodecadienyl acetate | (Z,Z)-7,11-Hexadecadien-1-ol |
| (E,E)-5,7-Dodecadien-1-ol | (Z,Z)-7,11-Hexadecadienyl acetate |
| (E,E)-5,7-Dodecadienyl acetate | (Z,Z)-7,11-Hexadecadienal |
| (E,Z)-5,7-Dodecadien-1-ol | (Z,Z)-8,10-Hexadecadienyl acetate |
| (E,Z)-5,7-Dodecadienyl acetate | (E,Z)-8,11-Hexadecadienal |
| (E,Z)-5,7-Dodecadienal | (E,E)-9,11-Hexadecadienal |
| (Z,E)-5,7-Dodecadien-1-ol | (E,Z)-9,11-Hexadecadienyl acetate |
| (Z,E)-5,7-Dodecadienyl acetate | (E,Z)-9,11-Hexadecadienal |
| (Z,E)-5,7-Dodecadienal | (Z,E)-9,11-Hexadecadienal |
| (Z,Z)-5,7-Dodecadienyl acetate | (Z,Z)-9,11-Hexadecadienal |
| (Z,Z)-5,7-Dodecadienal | (E,E)-10,12-Hexadecadien-1-ol |
| (E,E)-7,9-Dodecadienyl acetate | (E,E)-10,12-Hexadecadienyl acetate |
| (E,Z)-7,9-Dodecadien-1-ol | (E,E)-10,12-Hexadecadienal |
| (E,Z)-7,9-Dodecadienyl acetate | (E,Z)-10,12-Hexadecadien-1-ol |
| (E,Z)-7,9-Dodecadienal | (E,Z)-10,12-Hexadecadienyl acetate |
| (Z,E)-7,9-Dodecadien-1-ol | (E,Z)-10,12-Hexadecadienal |
| (Z,E)-7,9-Dodecadienyl acetate | (Z,E)-10,12-Hexadecadienyl acetate |
| (Z,E)-7,9-Dodecadienal | (Z,E)-10,12-Hexadecadienal |
| (Z,Z)-7,9-Dodecadienyl acetate | (Z,Z)-10,12-Hexadecadienal |
| (E,E)-8,10-Dodecadien-1-ol | (E,E)-11,13-Hexadecadien-1-ol |
| (E,E)-8,10-Dodecadienyl acetate | (E,E)-11,13-Hexadecadienyl acetate |
| (E,E)-8,10-Dodecadienal | (E,E)-11,13-Hexadecadienal |
| (E,Z)-8,10-Dodecadien-1-ol | (E,Z)-11,13-Hexadecadien-1-ol |
| (E,Z)-8,10-Dodecadienyl acetate | (E,Z)-11,13-Hexadecadienyl acetate |
| (E,Z)-8,10-Dodecadienal | (E,Z)-11,13-Hexadecadienal |
| (Z,E)-8,10-Dodecadien-1-ol | (Z,E)-11,13-Hexadecadien-1-ol |
| (Z,E)-8,10-Dodecadienyl acetate | (Z,E)-11,13-Hexadecadienyl acetate |
| (Z,E)-8,10-Dodecadienal | (Z,E)-11,13-Hexadecadienal |
| (Z,Z)-8,10-Dodecadien-1-ol | (Z,Z)-11,13-Hexadecadien-1-ol |
| (Z,Z)-8,10-Dodecadienyl acetate | (Z,Z)-11,13-Hexadecadienyl acetate |
| (Z,E,E)-3,6,8-Dodecatrien-1-ol | (Z,Z)-11,13-Hexadecadienal |
| (Z,Z,E)-3,6,8-Dodecatrien-1-ol | (E,E)-10,14-Hexadecadienal |
| (E)-2-Tridecenyl acetate | (Z,E)-11,14-Hexadecadienyl acetate |
| (Z)-2-Tridecenyl acetate | (E,E,Z)-4,6,10-Hexadecatrien-1-ol |
| (E)-3-Tridecenyl acetate | (E,E,Z)-4,6,10-Hexadecatrienyl acetate |
| (E)-4-Tridecenyl acetate | (E,Z,Z)-4,6,10-Hexadecatrien-1-ol |
| (Z)-4-Tridecenyl acetate | (E,Z,Z)-4,6,10-Hexadecatrienyl acetate |
| (Z)-4-Tridecenal | (E,E,Z)-4,6,11-Hexadecatrienyl acetate |
| (E)-6-Tridecenyl acetate | (E,E,Z)-4,6,11-Hexadecatrienal |
| (Z)-7-Tridecenyl acetate | (Z,Z,E)-7,11,13-Hexadecatrienal |
| (E)-8-Tridecenyl acetate | (E,E,E)-10,12,14-Hexadecatrienyl acetate |
| (Z)-8-Tridecenyl acetate | (E,E,E)-10,12,14-Hexadecatrienal |
| (E)-9-Tridecenyl acetate | (E,E,Z)-10,12,14-Hexadecatrienyl acetate |
| (Z)-9-Tridecenyl acetate | (E,E,Z)-10,12,14-Hexadecatrienal |
| (Z)-10-Tridecenyl acetate | (E,E,Z,Z)-4,6,11,13-Hexadecatetraenal |
| (E)-11-Tridecenyl acetate | (E)-2-Heptadecenal |
| (Z)-11-Tridecenyl acetate | (Z)-2-Heptadecenal |
| (E,Z)-4,7-Tridecadienyl acetate | (E)-8-Heptadecen-1-ol |
| (Z,Z)-4,7-Tridecadien-1-ol | (E)-8-Heptadecenyl acetate |
| (Z,Z)-4,7-Tridecadienyl acetate | (Z)-8-Heptadecen-1-ol |

TABLE 1-continued

C₆-C₂₀ Linear Pheromones

| Name | Name |
|---|---|
| (E,Z)-5,9-Tridecadienyl acetate | (Z)-9-Heptadecenal |
| (Z,E)-5,9-Tridecadienyl acetate | (E)-10-Heptadecenyl acetate |
| (Z,Z)-5,9-Tridecadienyl acetate | (Z)-11-Heptadecen-1-ol |
| (Z,Z)-7,11-Tridecadienyl acetate | (Z)-11-Heptadecenyl acetate |
| (E,Z,Z)-4,7,10-Tridecatrienyl acetate | (E,E)-4,8-Heptadecadienyl acetate |
| (E)-3-Tetradecen-1-ol | (Z,Z)-8,10-Heptadecadien-1-ol |
| (E)-3-Tetradecenyl acetate | (Z,Z)-8,11-Heptadecadienyl acetate |
| (Z)-3-Tetradecen-1-ol | (E)-2-Octadecenyl acetate |
| (Z)-3-Tetradecenyl acetate | (E)-2-Octadecenal |
| (E)-5-Tetradecen-1-ol | (Z)-2-Octadecenyl acetate |
| (E)-5-Tetradecenyl acetate | (Z)-2-Octadecenal |
| (E)-5-Tetradecenal | (E)-9-Octadecen-1-ol |
| (Z)-5-Tetradecen-1-ol | (E)-9-Octadecenyl acetate |
| (Z)-5-Tetradecenyl acetate | (E)-9-Octadecenal |
| (Z)-5-Tetradecenal | (Z)-9-Octadecen-1-ol |
| (E)-6-Tetradecenyl acetate | (Z)-9-Octadecenyl acetate |
| (Z)-6-Tetradecenyl acetate | (Z)-9-Octadecenal |
| (E)-7-Tetradecen-1-ol | (E)-11-Octadecen-1-ol |
| (E)-7-Tetradecenyl acetate | (E)-11-Octadecenal |
| (Z)-7-Tetradecen-1-ol | (Z)-11-Octadecen-1-ol |
| (Z)-7-Tetradecenyl acetate | (Z)-11-Octadecenyl acetate |
| (Z)-7-Tetradecenal | (Z)-11-Octadecenal |
| (E)-8-Tetradecenyl acetate | (E)-13-Octadecenyl acetate |
| (Z)-8-Tetradecen-1-ol | (E)-13-Octadecenal |
| (Z)-8-Tetradecenyl acetate | (Z)-13-Octadecen-1-ol |
| (Z)-8-Tetradecenal | (Z)-13-Octadecenyl acetate |
| (E)-9-Tetradecen-1-ol | (Z)-13-Octadecenal |
| (E)-9-Tetradecenyl acetate | (E)-14-Octadecenal |
| (Z)-9-Tetradecen-1-ol | (E,Z)-2,13-Octadecadien-1-ol |
| (Z)-9-Tetradecenyl acetate | (E,Z)-2,13-Octadecadienyl acetate |
| (Z)-9-Tetradecenal | (E,Z)-2,13-Octadecadienal |
| (E)-10-Tetradecenyl acetate | (Z,E)-2,13-Octadecadienyl acetate |
| (Z)-10-Tetradecenyl acetate | (Z,Z)-2,13-Octadecadien-1-ol |
| (E)-11-Tetradecen-1-ol | (Z,Z)-2,13-Octadecadienyl acetate |
| (E)-11-Tetradecenyl acetate | (E,E)-3,13-Octadecadienyl acetate |
| (E)-11-Tetradecenal | (E,Z)-3,13-Octadecadienyl acetate |
| (Z)-11-Tetradecen-1-ol | (E,Z)-3,13-Octadecadienal |
| (Z)-11-Tetradecenyl acetate | (Z,E)-3,13-Octadecadienyl acetate |
| (Z)-11-Tetradecenal | (Z,Z)-3,13-Octadecadienyl acetate |
| (E)-12-Tetradecenyl acetate | (Z,Z)-3,13-Octadecadienal |
| (Z)-12-Tetradecenyl acetate | (E,E)-5,9-Octadecadien-1-ol |
| (E,E)-2,4-Tetradecadienal | (E,E)-5,9-Octadecadienyl acetate |
| (E,E)-3,5-Tetradecadienyl acetate | (E,E)-9,12-Octadecadien-1-ol |
| (E,Z)-3,5-Tetradecadienyl acetate | (Z,Z)-9,12-Octadecadienyl acetate |
| (Z,E)-3,5-Tetradecadienyl acetate | (Z,Z)-9,12-Octadecadienal |
| (E,Z)-3,7-Tetradecadienyl acetate | (Z,Z)-11,13-Octadecadienal |
| (E,Z)-3,8-Tetradecadienyl acetate | (E,E)-11,14-Octadecadienal |
| (E,Z)-4,9-Tetradecadienyl acetate | (Z,Z)-13,15-Octadecadienal |
| (E,Z)-4,9-Tetradecadienal | (Z,Z,Z)-3,6,9-Octadecatrienyl acetate |
| (E,Z)-4,10-Tetradecadienyl acetate | (E,E,E)-9,12,15-Octadecatrien-1-ol |
| (E,E)-5,8-Tetradecadienal | (Z,Z,Z)-9,12,15-Octadecatrienyl acetate |
| (Z,Z)-5,8-Tetradecadien-1-ol | (Z,Z,Z)-9,12,15-Octadecatrienal |
| (Z,Z)-5,8-Tetradecadienyl acetate | |
| (Z,Z)-5,8-Tetradecadienal | |
| (E,E)-8,10-Tetradecadien-1-ol | |
| (E,E)-8,10-Tetradecadienyl acetate | |
| (E,E)-8,10-Tetradecadienal | |
| (E,Z)-8,10-Tetradecadienyl acetate | |
| (E,Z)-8,10-Tetradecadienal | |
| (Z,E)-8,10-Tetradecadien-1-ol | |
| (Z,E)-8,10-Tetradecadienyl acetate | |
| (Z,Z)-8,10-Tetradecadienal | |
| (E,E)-9,11-Tetradecadienyl acetate | |
| (E,Z)-9,11-Tetradecadienyl acetate | |
| (Z,E)-9,11-Tetradecadien-1-ol | |
| (Z,E)-9,11-Tetradecadienyl acetate | |
| (Z,E)-9,11-Tetradecadienal | |
| (Z,Z)-9,11-Tetradecadien-1-ol | |
| (Z,Z)-9,11-Tetradecadienyl acetate | |
| (Z,Z)-9,11-Tetradecadienal | |
| (E,E)-9,12-Tetradecadienyl acetate | |
| (Z,E)-9,12-Tetradecadien-1-ol | |
| (Z,E)-9,12-Tetradecadienyl acetate | |
| (Z,E)-9,12 -Tetradecadienal | |
| (Z,Z)-9,12-Tetradecadien-1-ol | |
| (Z,Z)-9,12-Tetradecadienyl acetate | |

In some aspects, the pheromones synthesized as taught in this disclosure include at least one pheromone listed in Table 2a to modulate the behavior of an insect listed in Table 2a. In other aspects, non-limiting examples of insect pheromones which can be synthesized using the recombinant microorganisms and methods disclosed herein include alcohols, aldehydes, and acetates listed in Table 2a. However, the microorganisms described herein are not limited to the synthesis of $C_6$-$C_{20}$ pheromones listed in Table 1 and Table 2a. Rather, the disclosed microorganisms can also be utilized in the synthesis of various $C_6$-$C_{24}$ mono- or poly-unsaturated fatty alcohols, aldehydes, and acetates, including fragrances, flavors, and polymer intermediates.

TABLE 2a

Exemplary pheromones that can be synthesized according to methods described in the present disclosure

| Name | Structure | Example of Biological importance |
|---|---|---|
| (Z)-3-hexen-1-ol | 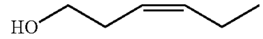 | See, Sugimoto et al. (2014) |
| (Z)-3-nonen-1-ol | 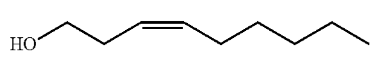 | West Indian Fruity Fly male sex pheromone |
| (Z)-5-decen-1-ol | 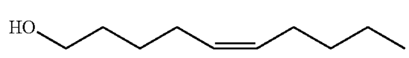 | |
| (Z)-5-decenyl acetate | 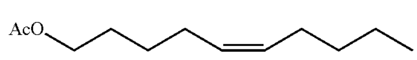 | *Agrotis segetum* sex pheromone component |
| (E)-5-decen-1-ol | 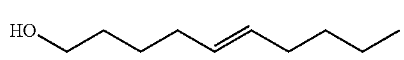 | *Anarsia lineatella* sex pheromone component |

TABLE 2a-continued

Exemplary pheromones that can be synthesized according to methods described in the present disclosure

| Name | Structure | Example of Biological importance |
|---|---|---|
| (E)-5-decenyl acetate | 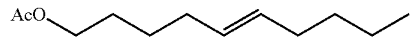 | *Anarsia lineatella* sex pheromone component |
| (Z)-7-dodecen-1-ol | 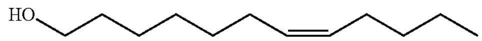 | |
| (Z)-7-dodecenyl acetate | 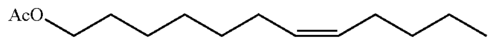 [SMILES: CCCC/C=C\CCCCCCOC(C)=O] | *Pseudoplusia includens* sex pheromone<br>*Argrotis segetum* sex pheromone component |
| (E)-8-dodcen-1-ol | 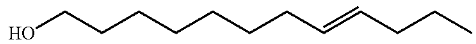 | Citrus Fruit Moth sex pheromone |
| (E)-8-dodecenyl acetate | 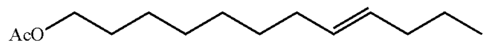 [SMILES: CCC/C=C/CCCCCCCOC(C)=O] | *Grapholitha molesta*, *Ecdytolopha aurantiana* sex pheromone component |
| (Z)-8-dodecen-1-ol | 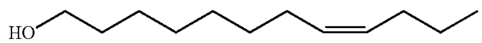 | *Grapholitha molesta*, *Ecdytolopha aurantiana* sex pheromone component |
| (Z)-8-dodecenyl acetate | 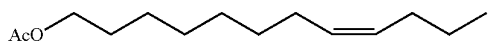 | *Grapholitha molesta* sex pheromone component |
| (Z)-9-dodecen-1-ol | 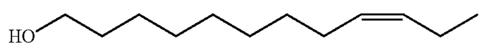 | |
| (Z)-9-dodecenyl acetate | 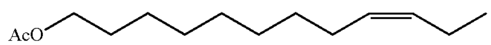 | *Eupoecilia ambiguella* sex pheromone |
| (E,E)-8,10-dodecadien-1-ol | 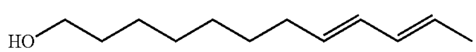 | *Cydia pomonella* |
| (7E,9Z)-dodecadienyl acetate | 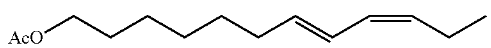 [SMILES: CC/C=C\C=C\CCCCCCOC(C)=O] | *Lobesia botrana* |
| (Z)-9-tetradecen-1-ol | 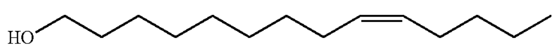 | |
| (Z)-9-tetradecenyl acetate | 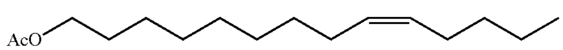 [SMILES: CCCC/C=C\CCCCCCCCOC(C)=O] | *Pandemis pyrusana, Naranga aenescens, Agrotis segetum* sex pheromone component |
| (Z)-11-tetradecen-1-ol | 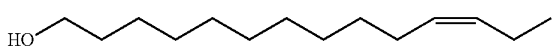 | |
| (Z)-11-tetradecenyl acetate | 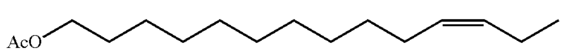 | *Pandemis pyrusana, Choristoneura roseceana* sex pheromone component |
| (E)-11-tetradecen-1-ol | 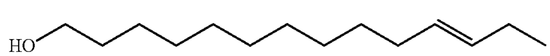 | |
| (E)-11-tetradecenyl acetate | 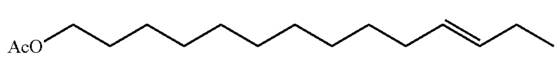 [SMILES: CC/C=C/CCCCCCCCCCOC(C)=O] | *Choristoneura roseceana, Crocidolomia pavonana* sex pheromone component |
| (Z)-7-hexadecen-1-ol | 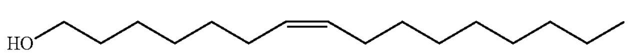 [SMILES: CCCCCCCC/C=C\CCCCCCO] | |
| (Z)-7-hexadecenal | 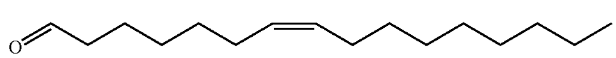 | *Diatraea considerata* sex pheromone component |
| (Z)-9-hexadecen-1-ol | 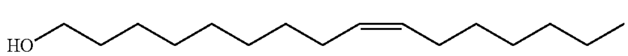 [SMILES: CCCCCC/C=C\CCCCCCCCO] | |

TABLE 2a-continued

Exemplary pheromones that can be synthesized according to methods described in the present disclosure

| Name | Structure | Example of Biological importance |
|---|---|---|
| (Z)-9-hexadecenal | 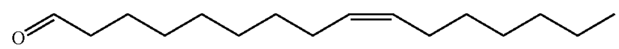 [SMILES: CCCCCC/C=C\CCCCCCCC=O] | *Helicoverpa zea, Helicoverpa amigera, Heliothis virescens* sex pheromone component |
| (Z)-9-hexadecenyl acetate | 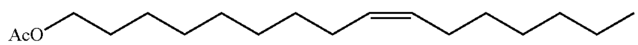 [SMILES: CCCCCC/C=C\CCCCCCCCOC(C)=O] | *Naranga aenescens* sex pheromone component |
| (Z)-11-hexadecen-1-ol | 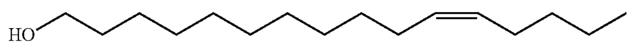 [SMILES: CCCC/C=C\CCCCCCCCCCO] | |
| (Z)-11-hexadecenal | 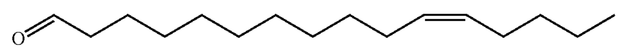 | *Platyptila carduidactyla, Heliothis virescens* sex pheromone *Helicoverpa zea, Helicoverpa armigera, Plutella xylostella, Diatraea considerate, Diatraea grandiosella, Diatraea saccharalis, Acrolepiopsis assectella* sex pheromone component |
| (Z)-11-hexadecenyl acetate | 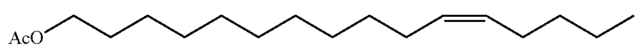 [SMILES: CCCC/C=C\CCCCCCCCCCOC(C)=O] | *Discestra trifolii* sex pheromone *Heliothis virescens, Plutella xylostella, Acrolespiopsis assectella, Crocidolomia pavonana, Naranga aenescens* sex pheromone component |
| (Z,Z)-11,13-hexadecadienal | 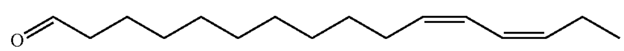 [SMILES: CC/C=C\C=C/CCCCCCCCCC=O] | *Amyelosis transitella* |
| (Z)-11,13-hexadecadian-1-ol | 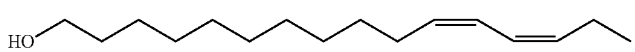 | *Amyelosis transitella* |
| (11Z,13E)-hexadecadien-1-ol | 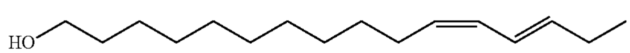 | *Amyelosis transitella* |
| (9Z,11E)-hexadecadienal | 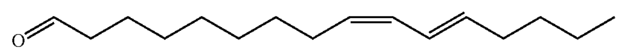 | |
| (Z)-13-octadecen-1-ol | 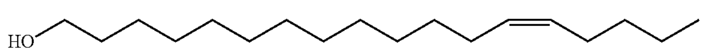 [SMILES: CCCC/C=C\CCCCCCCCCCCCO] | |
| (Z)-13-octadecenal | 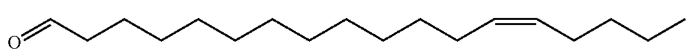 [SMILES: CCCC/C=C\CCCCCCCCCCCC=O] | *Diatraea considerata, Diatraea grandiosella* sex pheromone component |
| (Z,Z,Z,Z,Z)-3,6,9,12,15-tricosapentaene | 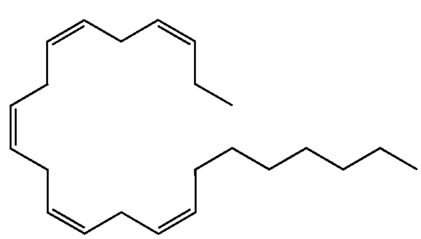 [SMILES: CC/C=C\C/C=C\C/C=C\C/C=C\C/C=C\CCCCCCC] | *Amyelosis transitella* |

Most pheromones comprise a hydrocarbon skeleton with the terminal hydrogen substituted by a functional group (Ryan M F (2002). Insect Chemoreception. Fundamental and Applied. Kluwer Academic Publishers). Table 2b shows some common functional groups, along with their formulas, prefixes and suffixes. The presence of one or more double bonds, generated by the loss of hydrogens from adjacent carbons, determines the degree of unsaturation of the molecule and alters the designation of a hydrocarbon from -ane (no multiple bonds) to -ene. The presence of two and three double bonds is indicated by ending the name with -diene and -triene, respectively. The position of each double bond is represented by a numeral corresponding to that of the carbon from which it begins, with each carbon numbered from that attached to the functional group. The carbon to which the functional group is attached is designated -1-. Pheromones may have, but are not limited to, hydrocarbon chain lengths numbering 10 (deca-), 12 (dodeca-), 14 (tetradeca-), 16 (hexadeca-), or 18 (octadeca-) carbons long. The presence of a double bond has another effect. It precludes rotation of the molecule by fixing it in one of two possible configurations, each representing geometric isomers that are different molecules. These are designated either E (from the German word Entgegen, opposite) or Z (Zusammen, together), when the carbon chains are connected on the opposite (trans) or same (cis) side, respectively, of the double bond.

TABLE 2b

Prefixes and suffixes for common functional groups

| Functional group | Formula | Prefix | Suffix |
|---|---|---|---|
| Alcohol | —OH | Hydroxy- | -ol |
| Aldehyde | —CH=O | Formyl- | -al |
| Amine | —NH$_2$ | Amino- | -amine |
| Carboxylic add | —COOH | Carboxy- | -oic add |
| Ester | —COOR | R-oxycarbonyl | -R-oate |
| Ketone | >C=O | Oxo- | -one |

From Howse, P E, Stevens, I D R and Jones, O T (1998). Insect pheromones and their use in pest management. London: Chapman and Hall.

Pheromones described herein can be referred to using IUPAC nomenclature or various abbreviations or variations known to one skilled in the art. For example, (11Z)-hexadecen-1-al, can also be written as Z-11-hexadecen-1-al, Z-11-hexadecenal, or Z-x-y:Ald, wherein x represents the position of the double bond and y represents the number of carbons in the hydrocarbon skeleton. Abbreviations used herein and known to those skilled in the art to identify functional groups on the hydrocarbon skeleton include "Ald," indicating an aldehyde. "OH," indicating an alcohol, and "Ac," indicating an acetyl. Also, the number of carbons in the chain can be indicated using numerals rather than using the written name. Thus, as used herein, an unsaturated carbon chain comprised of sixteen carbons can be written as hexadecene or 16.

Similar abbreviation and derivations are used herein to describe pheromone precursors. For example, the fatty acyl-CoA precursors of (11Z)-hexadecen-1-al can be identified as (11Z)-hexadecenyl-CoA or Z-11-16:Acyl-CoA.

The present disclosure relates to the synthesis of mono- or poly-unsaturated $C_6$-$C_{24}$ fatty alcohols, aldehydes, and acetates using a recombinant microorganism comprised of one or more heterologous enzymes, which catalyze substrate to product conversions for one or more steps in the synthesis process.

Desaturase

The present disclosure describes enzymes that desaturate fatty acyl substrates to corresponding unsaturated fatty acyl substrates.

In some embodiments, a desaturase is used to catalyze the conversion of a fatty acyl-CoA or acyl-ACP to a corresponding unsaturated fatty acyl-CoA or acyl-ACP. A desaturase is an enzyme that catalyzes the formation of a carbon-carbon double bond in a saturated fatty acid or fatty acid derivative, e.g., fatty acyl-CoA or fatty acyl-ACP (collectively referred to herein as "fatty acyl"), by removing at least two hydrogen atoms to produce a corresponding unsaturated fatty acid/acyl. Desaturases are classified with respect to the ability of the enzyme to selectively catalyze double bond formation at a subterminal carbon relative to the methyl end of the fatty acid/acyl or a subterminal carbon relative to the carbonyl end of the fatty acid/acyl. Omega (w) desaturases catalyze the formation of a carbon-carbon double bond at a fixed subterminal carbon relative to the methyl end of a fatty acid/acyl. For example, an $\omega^3$ desaturase catalyzes the formation of a double bond between the third and fourth carbon relative the methyl end of a fatty acid/acyl. Delta (Δ) desaturases catalyze the formation of a carbon-carbon double bond at a specific position relative to the carboxyl group of a fatty acid or the carbonyl group of a fatty acyl CoA. For example, a $\Delta^9$ desaturase catalyzes the formation of a double bond between the $C_9$ and $C_{10}$ carbons with respect to the carboxyl end of the fatty acid or the carbonyl group of a fatty acyl CoA.

As used herein, a desaturase can be described with reference to the location in which the desaturase catalyzes the formation of a double bond and the resultant geometric configuration (i.e., E/Z) of the unsaturated hydrocarbon. Accordingly, as used herein, a Z9 desaturase refers to a Δ desaturase that catalyzes the formation of a double bond between the $C_9$ and $C_{10}$ carbons with respect to the carbonyl end of a fatty acid/acyl, thereby orienting two hydrocarbons on opposing sides of the carbon-carbon double bonds in the cis or Z configuration. Similarly, as used herein, a Z11 desaturase refers to a Δ desaturase that catalyzes the formation of a double bond between the $C_{11}$ and $C_{12}$ carbons with respect to the carbonyl end of a fatty acid/acyl.

Desaturases have a conserved structural motif. This sequence motif of transmembrane desaturases is characterized by [HX3-4HX7-41(3 non-His)HX2-3(1 nonHis) HHX61-189(40 non-His)HX2-3(1 non-His)HH]. The sequence motif of soluble desaturases is characterized by two occurrences of [D/EEXXH].

In some embodiments, the desaturase is a fatty acyl-CoA desaturase that catalyzes the formation of a double bond in a fatty acyl-CoA. In some such embodiments, the fatty acyl-CoA desaturase described herein is capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms. Thus, the desaturase used in the recombinant microorganism can be selected based on the chain length of the substrate.

In some embodiments, the fatty acyl desaturase described herein is capable of catalyzing the formation of a double bond at a desired carbon relative to the terminal CoA on the unsaturated fatty acyl-CoA. Thus, in some embodiments, a desaturase can be selected for use in the recombinant microorganism which catalyzes double bond insertion at the 3, 4, 5, 6, 7, 8, 9, 10, 11, 12, or 13 position with respect to the carbonyl group on a fatty acyl-CoA.

In some embodiments, the fatty acyl desaturase described herein is capable of catalyzing the formation of a double bond in a saturated fatty acyl-CoA such that the resultant unsaturated fatty acyl-CoA has a cis or trans (i.e., Z or E) geometric configuration.

In some embodiments, the desaturase is a fatty acyl-ACP desaturase that catalyzes the formation of a double bond in a fatty acyl-ACP. In some embodiments, the fatty acyl-ACP desaturase described herein is capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms. Thus, the desaturase used in the recombinant microorganism can be selected based on the chain length of the substrate.

In some embodiments, the fatty acyl-ACP desaturase described herein is capable of catalyzing the formation of a double bond at a desired carbon relative to the terminal carbonyl on the unsaturated fatty acyl-ACP. Thus, in some embodiments, a desaturase can be selected for use in the recombinant microorganism which catalyzes double bond insertion at the 3, 4, 5, 6, 7, 8, 9, 10, 11, 12, or 13 position with respect to the carbonyl group on a fatty acyl-ACP.

In some embodiments, the fatty acyl desaturase described herein is capable of catalyzing the formation of a double bond in a saturated fatty acyl-CoA such that the resultant unsaturated fatty acyl-ACP has a cis or trans (i.e., Z or E) geometric configuration.

In one embodiment, the fatty acyl desaturase is a Z11 desaturase. In some embodiments, a nucleic acid sequence encoding a Z11 desaturase from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana* is codon optimized. In some embodiments, the Z11 desaturase comprises a nucleotide sequence selected from SEQ ID NOs: 9, 18, 24 and 26 from *Trichoplusia ni.* In some embodiments, the Z1 desaturase comprises an amino acid sequence set forth in SEQ ID NO: 49 from *Trichoplusia ni.* In other embodiments, the Z11 desaturase comprises a nucleotide sequence selected from SEQ ID NOs: 10 and 16 from *Agrotis segetum.* In some embodiments, the Z11 desaturase comprises an amino acid sequence set forth in SEQ ID NO: 53 from *Agrotis segetum.* In some embodiments, the Z11 desaturase comprises a nucleotide sequence selected from SEQ ID NOs: 11 and 23 from *Thalassiosira pseudonana.* In some embodiments, the Z11 desaturase comprises an amino acid sequence selected from SEQ ID NOs: 50 and 51 from *Thalassiosira pseudonana.* In certain embodiments, the Z11 desaturase comprises a nucleotide sequence selected from SEQ ID NOs: 12, 17 and 30 from *Amyelois transitella.* In some embodiments, the Z11 desaturase comprises an amino acid sequence set forth in SEQ ID NO: 52 from *Amyelois transitella.* In further embodiments, the Z11 desaturase comprises a nucleotide sequence selected from SEQ ID NOs: 13, 19, 25, 27 and 31 from *Helicoverpa zea.* In some embodiments, the Z11 desaturase comprises an amino acid sequence set forth in SEQ ID NO: 54 from *Helicoverpa zea.* In some embodiments, the Z11 desaturase comprises an amino acid sequence set forth in SEQ ID NO: 39 from *S. inferens.* In some embodiments, the Z11 desaturase comprises an amino acid sequence set forth in GenBank Accession nos. AF416738, AGH12217.1, AH21943.1, CAJ43430.2, AF441221, AAF81787.1, AF545481, AJ271414, AY362879, ABX71630.1 and NP001299594.1, Q9N9Z8, ABX71630.1 and AIM40221.1. In some embodiments, the Z11 desaturase comprises a chimeric polypeptide. In some embodiments, a complete or partial Z11 desaturase is fused to another polypeptide. In certain embodiments, the N-terminal native leader sequence of a Z11 desaturase is replaced by an oleosin leader sequence from another species. In certain embodiments, the Z11 desaturase comprises a nucleotide sequence selected from SEQ ID NOs: 15, 28 and 29. In some embodiments, the Z11 desaturase comprises an amino acid sequence selected from SEQ ID NOs: 61, 62, 63, 78, 79 and 80.

In one embodiment, the fatty acyl desaturase is a Z9 desaturase. In some embodiments, a nucleic acid sequence encoding a Z9 desaturase is codon optimized. In some embodiments, the Z9 desaturase comprises a nucleotide sequence set forth in SEQ ID NO: 20 from *Ostrinia furnacalis.* In some embodiments, the Z9 desaturase comprises an amino acid sequence set forth in SEQ ID NO: 58 from *Ostrinia furnacalis.* In other embodiments, the Z9 desaturase comprises a nucleotide sequence set forth in SEQ ID NO: 21 from *Lampronia capitella.* In some embodiments, the Z9 desaturase comprises an amino acid sequence set forth in SEQ ID NO: 59 from *Lampronia capitella.* In some embodiments, the Z9 desaturase comprises a nucleotide sequence set forth in SEQ ID NO: 22 from *Helicoverpa zea.* In some embodiments, the Z9 desaturase comprises an amino acid sequence set forth in SEQ ID NO: 60 from *Helicoverpa zea.*

Thus, in some embodiments, the present disclosure teaches a recombinant microorganism comprising a Z11 or Z9 desaturase exhibiting at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50% sequence identity with any one of SEQ ID Nos. selected from the group consisting of 39, 49, 50, 51, 52, 53, 54, 58, 59, 60, 61, 62, 63, 64, 65, 66, 67, 78, 79, 80, 95, 97, 99, 101, 103, and 105.

Thus, in some embodiments, the present disclosure teaches a recombinant microorganism comprising a nucleic acid molecule encoding for a Z11 or Z9 desaturase, wherein said nucleic acid molecule exhibits at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50% sequence identity with any one of SEQ ID Nos. selected from the group consisting of 9, 10, 11, 12, 13, 15, 16, 17, 18, 19, 20, 21, 22, 23, 24, 25, 26, 27, 28, 29, 30, 31, 68, 69, 70, 71, 94, 96, 98, 100, 102, and 104.

In some embodiments, the present disclosure teaches a recombinant microorganism comprising at least one nucleic acid molecule encoding a fatty acyl desaturase having at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50% sequence identity to a fatty acyl desaturase selected from the group consisting of SEQ ID NOs: 39, 54, 60, 62, 78, 79, 80, 95, 97, 99, 101, 103, and 105 that catalyzes the conversion of a saturated $C_6$-$C_{24}$ fatty acyl-CoA to a corresponding mono- or poly-unsaturated $C_6$-$C_{24}$ fatty acyl-CoA.

Fatty Acyl Reductase

The present disclosure describes enzymes that reduce fatty acyl substrates to corresponding fatty alcohols or aldehydes.

In some embodiments, a fatty alcohol forming fatty acyl-reductase is used to catalyze the conversion of a fatty acyl-CoA to a corresponding fatty alcohol. In some embodiments, a fatty aldehyde forming fatty acyl-reductase is used to catalyze the conversion of a fatty acyl-ACP to a corresponding fatty aldehyde. A fatty acyl reductase is an enzyme that catalyzes the reduction of a fatty acyl-CoA to a corresponding fatty alcohol or the reduction of a fatty acyl-ACP to a corresponding fatty aldehyde. A fatty acyl-CoA and fatty acyl-ACP has a structure of R—(CO)—S—$R_1$, wherein R is a $C_6$ to $C_{24}$ saturated, unsaturated, linear, branched or cyclic hydrocarbon, and $R_1$ represents CoA or ACP. In a particular embodiment, R is a $C_6$ to $C_{24}$ saturated or unsaturated linear hydrocarbon. "CoA" is a non-protein acyl carrier group involved in the synthesis and oxidation of fatty acids. "ACP" is an acyl carrier protein, i.e., a polypeptide or protein subunit, of fatty acid synthase used in the synthesis of fatty acids.

Thus, in some embodiments, the disclosure provides for a fatty alcohol forming fatty acyl-reductase which catalyzes the reduction of a fatty acyl-CoA to the corresponding fatty alcohol. For example, R—(CO)—S-CoA is converted to R—CH$_2$OH and CoA-SH when two molecules of NAD(P)H are oxidized to NAD(P)$^+$. Accordingly, in some such embodiments, a recombinant microorganism described herein can include a heterologous fatty alcohol forming fatty acyl-reductase, which catalyzes the reduction a fatty acyl-CoA to the corresponding fatty alcohol. In an exemplary embodiment, a recombinant microorganism disclosed herein includes at least one exogenous nucleic acid molecule encoding a fatty alcohol forming fatty-acyl reductase which catalyzes the conversion of a mono- or poly-unsaturated C$_6$-C$_{24}$ fatty acyl-CoA into the corresponding mono- or poly-unsaturated C$_6$-C$_{24}$ fatty alcohol.

In other embodiments, the disclosure provides for a fatty aldehyde forming fatty acyl-reductase which catalyzes the reduction of a fatty acyl-ACP to the corresponding fatty aldehyde. For example, R—(CO)—S-ACP is converted to R—(CO)—H and ACP-SH when one molecule of NAD(P)H is oxidized to NAD(P)$^+$. In some such embodiments, a recombinant microorganism described herein can include a heterologous fatty aldehyde forming fatty acyl-reductase, which catalyzes the reduction a fatty acyl-ACP to the corresponding fatty aldehyde. In an exemplary embodiment, a recombinant microorganism disclosed herein includes at least one exogenous nucleic acid molecule encoding a fatty aldehyde forming fatty-acyl reductase which catalyzes the conversion of a mono- or poly-unsaturated C$_6$-C$_{24}$ fatty acyl-ACP into the corresponding mono- or poly-unsaturated C$_6$-C$_{24}$ fatty aldehyde.

In some insect species the respective alcohol-forming fatty acyl reductase (FAR) enzymes are activated via site specific dephosphorylation (Jurenka, R. & Rafaeli, A. Regulatory Role of PBAN in Sex Pheromone Biosynthesis of Heliothine Moths. Front. Endocrinol. (Lausanne), 2: 46 (2011); Gilbert, L. I. Insect Endocrinology. (Academic Press)). Without being bound by any one theory, phosphorylation of heterologously expressed FAR enzymes in yeast such as *Y. lipolytica* can lead to inactivation, and results in low fatty alcohol titers. In some embodiments, a bioinformatic approach can be used to predict phosphorylated residues within FAR. Alanine substitution of serine and threonine residues has been shown to abolish phosphorylation (Shi, S., Chen, Y., Siewers, V. & Nielsen, J. Improving Production of Malonyl Coenzyme A-Derived Metabolites by Abolishing Snf1-Dependent Regulation of Acc1. mBio 5 (2014)). Thus, the impact of alanine substitutions to prevent phosphorylation of serine residues and its impact on fatty alcohol titers can be tested. In addition to alanine substitution, improvement of FAR activity can also be achieved by other amino acid substitutions.

In some embodiments, methods are provided to identify beneficial mutations of FAR based on selection and alteration of phosphorylation-sensitive residues upon its expression in a host microorganism. In a preferred embodiment, the host microorganism is yeast selected from the group consisting of *Yarrowia, Candida, Saccharomyces, Pichia, Hansenula*, and *Kluyveromyces*.

Other references for protein phosphorylation sites include: Blom, N., Gammeltoft, S. & Brunak. S. Sequence and structure-based prediction of eukaryotic protein phosphorylation sites1. J. Mol. Biol. 294, 1351-1362 (1999); Ingrell, C. R., Miller, M. L., Jensen, O. N. & Blom, N. NetPhosYcast: prediction of protein phosphorylation sites in yeast. Bioinforma. 23: 895-897 (2007); Miller, W. T. Tyrosine kinase signaling and the emergence of multicellularity. Biochim. Biophys. Acta 1823, 1053-1057 (2012), each of which is herein incorporated in its entirety.

In some embodiments, a nucleic acid sequence encoding a fatty-acyl reductase from organisms of the species *Agrotis segetum, Spodoptera exigua, Spodoptera littoralis, Euglena gracilis, Yponomeuta evonymellus* and *Helicoverpa armigera* is codon optimized. In some embodiments, the fatty acyl reductase comprises a nucleotide sequence set forth in SEQ ID NO: 1 from *Agrotis segetum*. In other embodiments, the fatty acyl reductase comprises a nucleotide sequence set forth in SEQ ID NO: 2 from *Spodoptera littoralis*. In some embodiments, the fatty acyl reductase comprises a nucleotide sequence selected from SEQ ID NOs: 3, 32, 40, 72, 74, 76 and 81. In some embodiments, the fatty acyl reductase comprises an amino acid sequence set forth in SEQ ID NO: 55 from *Agrotis segetum*. In other embodiments, the fatty acyl reductase comprises an amino acid sequence set forth in SEQ ID NO: 56 from *Spodoptera littoralis*. In some embodiments, the fatty acyl reductase comprises an amino acid sequence selected from SEQ ID NOs: 41 and 57 from *Helicoverpa armigera*. In some embodiments, the fatty acyl reductase comprises an amino acid sequence selected from SEQ ID NOs: 73 and 82 from *Spodoptera exigua*. In some embodiments, the fatty acyl reductase comprises an amino acid sequence set forth in SEQ ID NO: 75 from *Euglena gracilis*. In some embodiments, the fatty acyl reductase comprises an amino acid sequence set forth in SEQ ID NO: 77 from *Yponomeuta evonymellus*.

In some embodiments, the production of unsaturated fatty alcohols in a recombinant microorganism comprises the expression of one or more mutant FARs. In certain embodiments, *Helicoverpa amigera* fatty acyl-CoA reductase (HaFAR) variants are provided which have increased enzymatic activity relative to enzymatic activity of a wild type *Helicoverpa amigera* fatty acyl-CoA reductase encoded by an amino acid sequence set forth in SEQ ID NO: 41. In some embodiments, the increased enzymatic activity is a net activity increase in amount of fatty alcohol produced relative to the amount of fatty alcohol produced by a wild type enzymatic activity of HaFAR encoded by an amino acid sequence set forth in SEQ ID NO: 41. In some embodiments, a wild type HaFAR comprises a nucleotide sequence set forth in SEQ ID NO: 90. In some embodiments, a variant of a wild type HaFAR encoded by an amino acid sequence set forth in SEQ ID NO: 41 comprises point mutations at the following positions: S60X, S195X, S298X, S378X, S394X, S418X, and S453X, wherein X comprises an amino acid selected from F, L, M, I, V, P, T, A, Y, K, H, N, Q, K, D, E, C, W and R. In some embodiments, a variant of a wild type HaFAR encoded by an amino acid sequence set forth in SEQ ID NO: 41 comprises a combination of point mutations selected from mutations at the following amino acid positions: S60X, S195X, S298X, S378X. S394X, S418X, and S453X, wherein X comprises an amino acid selected from F, L, M, I, V, P, T, A, Y, K, H, N, Q, K, D, E, C, W and R. In some embodiments, the fatty acyl reductase is a mutated fatty acyl reductase and comprises an amino acid sequence selected from SEQ ID NOs: 42-48. In some embodiments, the fatty acyl reductase is a mutated fatty acyl reductase and comprises a nucleotide sequence selected from SEQ ID NOs: 83-89.

Thus, in some embodiments, the present disclosure teaches a recombinant microorganism comprising a fatty acyl reductase exhibiting at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58&, 57%, 56%, 55%, 54%, 53%, 52%, 51%, or 50% sequence identity with any one of SEQ ID Nos. selected from the group consisting of, 41, 42, 43, 44, 45, 46, 47, 48, 55, 56, 57, 73, 75, 77, and 82.

Thus, in some embodiments, the present disclosure teaches a recombinant microorganism comprising a nucleic acid molecule encoding for a fatty acyl reductase, wherein said nucleic acid molecule exhibits at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50% sequence identity with any one of SEQ ID Nos. selected from the group consisting of 1, 2, 3, 32, 37, 40, 72, 74, 76, 81, 83, 84, 85, 86, 87, 88, 89, and 90.

In some embodiments, the present disclosure teaches a recombinant microorganism comprising at least one nucleic acid molecule encoding a fatty acyl reductase having at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50% sequence identity to a fatty acyl reductase selected from the group consisting of SEQ ID NOs: 41-48, 57, 73, 75 and 77 that catalyzes the conversion of the mono- or poly-unsaturated $C_6$-$C_{24}$ fatty acyl-CoA into the corresponding mono- or poly-unsaturated $C_6$-$C_{24}$ fatty alcohol.

Acyl-ACP Synthetase

The present disclosure describes enzymes that ligate a fatty acid to the corresponding fatty acyl-ACP.

In some embodiments, an acyl-ACP synthetase is used to catalyze the conversion of a fatty acid to a corresponding fatty acyl-ACP. An acyl-ACP synthetase is an enzyme capable of ligating a fatty acid to ACP to produce a fatty acid acyl-ACP. In some embodiments, an acyl-ACP synthetase can be used to catalyze the conversion of a fatty acid to a corresponding fatty acyl-ACP. In some embodiments, the acyl-ACP synthetase is a synthetase capable of utilizing a fatty acid as a substrate that has a chain length of 6, 7, 8, 9, 10, 11, 12, 13, 14, 15, 16, 17, 18, 19, 20, 21, 22, 23, or 24 carbon atoms. In one such embodiment, a recombinant microorganism described herein can include a heterologous acyl-ACP synthetase, which catalyzes the conversion of a fatty acid to a corresponding fatty acyl-ACP. In an exemplary embodiment, a recombinant microorganism disclosed herein includes at least one exogenous nucleic acid molecule which encodes an acyl-ACP synthetase that catalyzes the conversion of a saturated $C_6$-$C_{24}$ fatty acid to a corresponding saturated $C_6$-$C_{24}$ fatty acyl-ACP.

Fatty Acid Synthase Complex

The present disclosure describes enzymes that catalyze the elongation of a carbon chain in fatty acid.

In some embodiments, a fatty acid synthase complex is used to catalyze initiation and elongation of a carbon chain in a fatty acid. A "fatty acid synthase complex" refers to a group of enzymes that catalyzes the initiation and elongation of a carbon chain on a fatty acid. The ACP along with the enzymes in the fatty acid synthase (FAS) pathway control the length, degree of saturation, and branching of the fatty acids produced. The steps in this pathway are catalyzed by enzymes of the fatty acid biosynthesis (fab) and acetyl-CoA carboxylase (ace) gene families. Depending upon the desired product, one or more of these genes can be attenuated, expressed or over-expressed. In exemplary embodiments, one or more of these genes is over-expressed.

There are two principal classes of fatty acid synthases. Type I (FAS I) systems utilize a single large, multifunctional polypeptide and are common to both mammals and fungi (although the structural arrangement of fungal and mammalian synthases differ). The Type I FAS system is also found in the CMN group of bacteria (corynebacteria, mycobacteria, and nocardia). The Type 11 FAS (FAS II) is characterized by the use of discrete, monofunctional enzymes for fatty acid synthesis, and is found in archaea and bacteria.

The mechanism of FAS I and FAS II elongation and reduction is the substantially similar, as the domains of the FAS I multienzyme polypeptides and FAS II enzymes are largely conserved.

Fatty acids are synthesized by a series of decarboxylative Claisen condensation reactions from acetyl-CoA and malonyl-CoA. The steps in this pathway are catalyzed by enzymes of the fatty acid biosynthesis (fab) and acetyl-CoA carboxylase (ace) gene families. For a description of this pathway, see, e.g., Heath et al. *Prog. Lipid Res.* 40:467, 2001, which is herein incorporated by reference in its entirety. Without being limited by theory, in bacteria, acetyl-CoA is carboxylated by acetyl-CoA carboxylase (Acc, a multi-subunit enzyme encoded by four separate genes, accABCD), to form malonyl-CoA. In yeast, acetyl-CoA is carboxylated by the yeast equivalents of the acetyl-CoA carboxylase, encoded by ACC1 and ACC2. In bacteria, the malonate group is transferred to ACP by malonyl-CoA:ACP transacylase (FabD) to form malonyl-ACP. In yeast, a malonyl-palmityl transferase domain adds malonyl from malonyl-CoA to the ACP domain of the FAS complex. A condensation reaction then occurs, where malonyl-ACP merges with acyl-CoA, resulting in 1-ketoacyl-ACP. In this manner, the hydrocarbon substrate is elongated by 2 carbons.

Following elongation, the β-keto group is reduced to the fully saturated carbon chain by the sequential action of a keto-reductase (KR), dehydratase (DH), and enol reductase (ER). The elongated fatty acid chain is carried between these active sites while attached covalently to the phosphopantetheine prosthetic group of ACP. First, the β-ketoacyl-ACP is reduced by NADPH to form β-hydroxyacyl-ACP. In bacteria, this step is catalyzed by β-ketoacyl-ACP reductase (FabG). The equivalent yeast reaction is catalyzed by the ketoreductase (KR) domain of FAS. β-hydroxyacyl-ACP is then dehydrated to form trans-2-enoyl-ACP, which is catalyzed by either β-hydroxyacyl-ACP dehydratase/isomerase (FabA) or β-hydroxyacyl-ACP dehydratase (FabZ) in bacteria or the dehydratase (DH) domain of FAS in yeast. NADPH-dependent trans-2-enoyl-ACP reductase I, II, or III (FabI, FabK, and FabL, respectively) in bacteria and the enol reductase (ER) domain of FAS in yeast reduces trans-2-enoyl-ACP to form acyl-ACP. Subsequent cycles are started by the condensation of malonyl-ACP with acyl-ACP by β-ketoacyl-ACP synthase I or β-ketoacyl-ACP synthase II (FabB and FabF, respectively, in bacteria or the beta-ketoacyl synthase (KS) domain in yeast).

In some embodiments, a fatty acid synthase complex can be used to catalyze elongation of a fatty acyl-ACP to a corresponding fatty acyl-ACP with a two carbon elongation relative to the substrate.

Dehydrogenase

The present disclosure describes enzymes that catalyze the conversion of a fatty aldehyde to a fatty alcohol. In some embodiments, an alcohol dehydrogenase (ADH, Table 3 and Table 3a) is used to catalyze the conversion of a fatty aldehyde to a fatty alcohol. A number of ADHs identified from alkanotrophic organisms. *Pseudomonas fluorescens* NRRL B-1244 (Hou et al. 1983), *Pseudomonas butanovora*

ATCC43655 (Vangnai and Arp 2001), and *Acinetobacter* sp, strain M-1 (Tani et al. 2000), have shown to be active on short to medium-chain alkyl alcohols ($C_2$ to $C_{14}$). Additionally, commercially available ADHs from Sigma, Horse liver ADH and Baker's yeast ADH have detectable activity for substrates with length $C_{10}$ and greater. The reported activities for the longer fatty alcohols may be impacted by the difficulties in solubilizing the substrates. For the yeast ADH from Sigma, little to no activity is observed for $C_{12}$ to $C_{14}$ aldehydes by (Tani et al. 2000), however, activity for $C_{12}$ and $C_{16}$ hydroxy-ω-fatty acids has been observed (Lu et al. 2010). Recently, two ADHs were characterized from *Geobacillus thermodenitrificans* NG80-2, an organism that degrades $C_{15}$ to $C_{36}$ alkanes using the LadA hydroxylase. Activity was detected from methanol to 1-triacontanol ($C_{30}$) for both ADHs, with 1-octanol being the preferred substrate for ADH2 and ethanol for ADH1 (Liu et al. 2009).

The use of ADHs in whole-cell bioconversions has been mostly focused on the production of chiral alcohols from ketones (Ernst et al. 2005) (Schroer et al. 2007). Using the ADH from *Lactobacillus brevis* and coupled cofactor regeneration with isopropanol. Schroer et al. reported the production of 797 g of (R)-methyl-3 hydroxybutanoate from methyl acetoacetate, with a space time yield of 29 g/L/h (Schroer et al. 2007). Examples of aliphatic alcohol oxidation in whole-cell transformations have been reported with commercially obtained *S. cerevisiae* for the conversion of hexanol to hexanal (Presecki et al. 2012) and 2-heptanol to 2-heptanone (Cappaert and Larroche 2004).

TABLE 3

Exemplary alcohol dehydrogenase enzymes.

| Organism | Gene Name | Accession No. |
| --- | --- | --- |
| Bactrocera oleae (Olive fruit fly) (Dacus oleae) | ADH | Q9NAR7 |
| Cupriavidus necator (Alcaligenes eutrophus) (Ralstonia eutropha) | adh | P14940 |
| Drosophila adiastola (Fruit fly) (Idiomyia adiastola) | Adh | Q00669 |
| Drosophila affinidisjuncta (Fruit fly) (Idiotnyia affinidisjuncta) | Adh | P21518 |
| Drosophila ambigua (Fruit fly) | Adh | P25139 |
| Drosophila borealis (Fruit fly) | Adh | P48584 |
| Drosophila differens (Fruit fly) | Adh | P22245 |
| Drosophila equinoxialis (Fruit fly) | Adh | Q9NG42 |
| Drosophila flavomontana (Fruit fly) | Adh | P48585 |
| Drosophiia guanche (Fruit fly) | Adh | Q09009 |
| Drsophila hawaiiensis (Fruit Fly) | Adh | P51549 |
| Drosophila heteroneura (Fruit fly) | Adh | P21898 |
| Drosophila immigrans (Fruit fly) | Adh | Q07588 |
| Drosophila insulatis (Fruit fly) | Adh | Q9NG40 |
| Drosophila lebanonensis (Fruit fly) (Scaptodrosophila lebanonensis) | Adh | P10807 |
| Drosophila mauritiana (Fruit fly) | Adh | P07162 |
| Drosophila madeirensis (Fruit fly) | Adh | Q09010 |
| Drosophila mimica (Fruit fly) (Idiomyia mimica) | Adh | Q00671 |
| Drosophila nigra (Fruit fly) (Idiomyia nigra) | Adh | Q00672 |
| Drosophila orena (Fruit fly) | Adh | P07159 |
| Drosophila pseudoobscura bogotana (Fruit fly) | Adh | P84328 |
| Drosophila picticornis (Fruit fly) (Idiomyia picticornis) | Adh | P23361 |
| Drosophila planitibia (Fruit fly) | Adh | P23277 |
| Drosophila paulistorum (Fruit fly) | Adh | Q9U8S9 |
| Drosophila silvestris (Fruit fly) | Adh | P23278 |
| Drosophila subobscura (Fruit fly) | Adh | Q03384 |
| Drosophila teissieri (Fruit fly) | Adh | P28484 |
| Drosophila tsacasi (Fruit fly) | Adh | P51550 |
| Fragaria ananassa (Strawberry) | ADH | P17648 |
| Malus domestica (Apple) (Pyrus malus) | ADH | P48977 |
| Scaptomyza albovittata (Fruit Fly) | Adh | P25988 |
| Scaptomyza crassifemur (Fruit fly) (Drosophila crassifemur) | Adh | Q00670 |
| Sulfolobus sp. (strain RC3) | adh | P50381 |
| Zaprionus tuberculatus (Vinegar fly) | Adh | P51552 |
| Geobacilius stearothermophilus (Bacillus stearothermophilus) | adh | P42327 |
| Drosophila mayaguana (Fruit fly) | Adh, Adh2 | P25721 |
| Drosophila melanogaster (Fruit fly) | Adh, CG3481 | P00334 |
| Drosophila pseudoobscura (Fruit fly) | Adh, GA17214 | Q6LCE4 |
| Drosophila simulans (Fruit fly) | Adh, GD23968 | Q24641 |
| Drosophila yakuba (Fruit fly) | Adh, GE19037 | P26719 |
| Drophila ananassae (Fruit fly) | Adh, GF14888 | Q50L96 |
| Drosophila erecta (Fruit fly) | Adh, GG25120 | P28483 |
| Drosophila grimshawi (fruit fly) (Idiomyia grimshawi) | Adh, GH13025 | P51551 |
| Drosophila willistoni (Fruit fly) | Adh, GK18290 | Q05114 |
| Drosophila persimilis Fruit fly) | Adh, GL25993 | P37473 |
| Drosophila sechellia (Fruit fly) | Adh, GM15656 | Q9GN94 |
| Cupriavidus necator (strain ATCC 17699/H16/DSM 428/Stainer 337) (Ralstonia eutropha) | adh, H16_A0757 | Q0KDL6 |

TABLE 3-continued

Exemplary alcohol dehydrogenase enzymes.

| Organism | Gene Name | Accession No. |
| --- | --- | --- |
| Mycobacterium tuberculosis (strain CDC 1551/Oshkosh) | adh, MT1581 | P9WQC2 |
| Staphylococcus aureus (strain MW2) | adh, MT0568 | Q8NXU1 |
| Mycobacterium tuberculosis (strain ATCC 25618/H37Rv) | adh, Rv1530 | P9WQC3 |
| Staphylococcus aureus (strain N315) | adh, SA0562 | Q7A742 |
| Staphylococcus aureus (strain bovine RF122/ET3-1) | adh, SAB0557 | Q2YSX0 |
| Sulfolobus acidocaldarius (strain ATCC 33909/DSM 639/JCM 8929/NBRC 15157/NCIMB 11770) | adh, Saci_2057 | Q4J781 |
| Staphylococcus aurcus (strain COL) | adh. SACOL06 | Q5H163 |
| Staphylococcus aureus (strain NCTC 8325) | adh, SAOUHSC_90608 | Q2G0G1 |
| Staphylococcus aureus (strain MRSA252) | adh, SAR0613 | Q6GJ63 |
| Staphylococcus aureus (strain MSSA476) | adh, SAS0573 | Q6GBM4 |
| Staphylococcus aureus (strain USA300) | adh, SAUSA300_0594 | Q2FJ31 |
| Staphylococcus aureus (strain Mu50/ATCC 700699) | adh, SAV0605 | Q99W07 |
| Staphylococcus epidermidis (strain ATCC 12228) | adh. SE_0375 | Q8CQ56 |
| Staphylococcus epiderdis (strain ATCC 35984/RP62A) | adh, SERP0257 | Q5HRD6 |
| Sulfolobus solfataricus (strain ATCC 35092/DSM 1617/JCM 11322/P2) | adh, SSO2536 | P39462 |
| Sulfolobus tokodaii (strain DSM 16993/JCM 10545 I NBRC 100140/7) | adh, STK_25770 | Q96XE0 |
| Anas platyrhynchos (Domestic duck) (Anas boschas) | ADH1 | P30350 |
| Apteryx australis (Brown kiwi) | ADH1 | P49645 |
| Ceratitis capitata (Mediterranean fruitfly) (Tephritis capitata) | ADH1 | P48814 |
| Ceratitis cosyra (Mango fruit fly) (Trypeta cosyra) | ADH1 | Q70UN9 |
| Gallus (Chicken) | ADH1 | P23991 |
| Columba livia (Domestic pigeon) | ADH1 | P86883 |
| Coumix japonica (Japanese quail) (Coturnix japonica) | ADH1 | P19631 |
| Drosophila hydei (Fruit fly) | Adh1 | P23236 |
| Drosophila montana (Fruit fly) | Adh1 | P48586 |
| Drosophila mettleri (Fruit fly) | Adh1 | P22246 |
| Drosophila mulleri (Fruit fly) | Adh1 | P07161 |
| Drosophila navojoa (Fruit fly) | Adh1 | P12854 |
| Geomys attwateri (Attwater's pocket gopher) (Geomys bursarius attwateri) | ADH1 | Q9Z2M2 |
| Geomys bursarius (Plains pocket gopher) | ADH1 | Q64413 |
| Geomys knoxjonesi (Knox Jones's pocket gopher) | ADH1 | Q64415 |
| Hordeum vulgare (Barley) | ADH1 | P05336 |
| Kluyveromyces marxianus (Yeast) (candida kefyr) | ADH1 | Q07288 |
| Zea mays (Maize) | ADH1 | P00333 |
| Mesocricetus auratus (Golden hamster) | ADH1 | P86885 |
| Pennisetum americanum Pearl millet) (Pennisetum glaucum) | ADH1 | P14219 |
| Petunia hybrida (Petunia) | ADH1 | P25141 |
| Oryctolagus cuniculus (Rabbit) | ADH1 | Q03505 |
| Solanum tuberosum (Potato) | ADH1 | P14673 |
| Struthio camelus (Ostrich) | ADH1 | P80338 |
| Trifolium repens (Creeping white clover) | ADH1 | P13603 |
| Zea luxurisns (Guaternalan teosinte) (Euchlaena luxurians) | ADH1 | Q07264 |
| Saccharomyces cerevisiae 'train ATCC204508/S288c) (Baker's yeast) | ADH1, ADC1, YOL:086C, O0947 | P00330 |
| Arabidopsis thaliana (Mouse-ear cress) | ADH1, ADH, At1g77120, F22K20.19 | P06525 |
| Schizosaccharomyces pombe (strain 972/ATCC 24843) (Fission yeast) | ADH1, adh, SPCC13B11.01 | P00332 |
| Drosophiia lacicola (Fruit fly) | Adh1, Adh-1 | O27404 |
| Mus musculus (Mouse) | Adh1, Adh-1 | P00329 |
| Peromyscus maniculatus (North American deer mouse) | ADH1, ADH-1 | P41680 |
| Rattus norvegicus (Rat) | Adh1, Adh-1 | P06757 |
| Drosophila virilis (Fruit fly) | Adh1, Adh-1, GJ18208 | B4M8Y0 |
| Scheffersomyces stipitis (strain ATCC 58785/CBS 6054/NBRC 10063/NRRL Y-11545) (Yeast) (Pichia stipitis) | ADH1, ADH2, PICST_68558 | O00097 |

TABLE 3-continued

Exemplary alcohol dehydrogenase enzymes.

| Organism | Gene Name | Accession No. |
|---|---|---|
| Aspergillus flavus (strain ATCC 200026/FGSC A1120/NRRL 3357/JCM 12722/SRRC 167) | adh1, AFLA_048690 | P41747 |
| Neurospora crassa strain ATCC 24698/74-OR23-1A/CBS 708.71/DSM 1257/FGSC 987) | adh-1, B17C10.210, NCU01754 | Q9P6C8 |
| Candida albicans (Yeast) | ADH1, CAD | P43067 |
| Oryza sativa subsp. japonica (Rice) | ADH1, DUPR11.3, Os11g0210300, LOC_Os11g10480, OsJ_032001 | Q2R8Z5 |
| Drosophila mojavensis (Fruit fly) | Adh1, GI17644 | P09370 |
| Kluyveromyces lactis strain ATCC 8585/CBS 2359/DSM 70799/NBRC 1267/NRRL Y-1140/WM37) (Yeast) (Candida sphaerica) | ADH1, KLLA0F21010g | P20369 |
| Oryza sativa subsp. indica (Rice) | ADH1, OsI_034290 | Q75ZX4 |
| Pongo abelii (Sumatran orangutan) (Pongo pygmaeus abelii) | ADH1A | Q5RBP7 |
| Homo sapiens (Human) | ADH1A, ADH1 | P07327 |
| Macaca mulatta (Rhesus macaque) | ADH1A, ADH1 | P28469 |
| Pan troglodytes (Chimpanzee) | ADH1B | Q5R1W2 |
| Papio hamadryas (Hamadryas baboon) | ADH1B | P14139 |
| Homo sapiens (Human) | ADH1B, ADH2 | P00325 |
| Homo sapiens (Human) | ADH1C, ADH3 | P00326 |
| Papio hamadiyas (Hamadryas baboon) | ADH1C, ADH3 | O97959 |
| Ceratitis capitata (Mediterranean fruit fly) (Tephritis capitata) | ADH2 | P48815 |
| Ceratitis cosyra (Mango fruit fly) (Trypeta cosyra) | ADH2 | Q70UP5 |
| Ceratitis rosa (Natal fruit fly) (Pterandrus rosa) | ADH2 | Q70UP6 |
| Drosophiia anizonae (Fruit fly) | Adh2 | P27581 |
| Drosophila buzzatii (Fruit fly) | Adh2 | P25720 |
| Drosophila hydei (Fruit fly) | Adh2 | P23237 |
| Drosophila montana (Fruit fly) | Adh2 | P48587 |
| Drosophila mulleri (Fruit fly) | Adh2 | P07160 |
| Drosophila wheeleri (Fruit fly) | Adh2 | P24267 |
| Entamoeba histolytica | ADH2 | Q24803 |
| Hordeum vulgare (Barley) | ADH2 | P10847 |
| Kluyveromyves marxianus (Yeast) (candida kefyr) | ADH2 | Q9P4C2 |
| Zea mays (Maize) | ADH2 | P04707 |
| Oryza sativa subsp. indica (Rice) | ADH2 | Q4R1E8 |
| Solarium lycopersicum (Tomato) (Lycopersicon esculentum) | ADH2 | P28032 |
| Solanum iiiberosum (Potato) | ADH2 | P14674 |
| Scheffersomyces stipitis (strain ATCC 58785/CBS 6054/NBRC 10063/NRRL Y-11545) (Yeast) (Pichia stipitis) | ADH2, ADH1, PICST_27980 | O13309 |
| Arabidopsis thaliana (Mouse-ear cress) | ADH2, ADHIII, FDH1, At5g43940, MRH10.4 | Q96533 |
| Saccharomyces cerevisiae (strain ATCC 204508/S288c) (Baker's yeast) | ADH2, ADR2, YMR303C, YM9952.05C | P00331 |
| Candida albicans (strain SC5314/ATCC MYA-2876) (Yeast) | ADH2, Ca41C10.04, Ca019.12579, Ca019.5113 | O94038 |
| Oryza sativa subsp. japonica (Rice) | ADH2, DUPR11.1 Os11g0210500, LOC_Os11g10510 | Q0ITW7 |
| Drosophila mojavensis (Fruit fly) | Adh2, GI17643 | P09369 |
| Kluyveromyces lactis (strain ATCC 8585/CBS 2359/DSM 70799/NBRC 1267/NRRL Y-1140/WM37) (Yeast) (Candida sphaerica) | ADH2, KLLA0F18260g | P49383 |
| Oryctolagus cuniculus (Rabbit) | ADH2-1 | O46649 |
| Oryctolagus cuniculus (Rabbit) | ADH2-2 | O46650 |
| Hordeum vulgare (Barley) | ADH3 | P10848 |
| Solanum tuberosum (Potato) | ADH3 | P14675 |
| Kluyveromyces lactis (strain ATCC 8585/CBS 2359/DSM 70799/NBRC 1267/NRRL Y-1140/WM37) (Yeast) (Candida sphaerica) | ADH3, KLLA0B09064g | P49384 |
| Saccharomyces cerevisiae (strain ATCC 204508/S288c) (Baker's yeast) | ADH3, YMR083W, YM9582.08 | P07246 |
| Homo sapiens (Human) | ADH4 | P08319 |
| Mus musculus (Mouse) | Adh4 | Q9QYY9 |
| Rattus norvegicus (Rat) | Adh4 | Q64563 |

TABLE 3-continued

Exemplary alcohol dehydrogenase enzymes.

| Organism | Gene Name | Accession No. |
| --- | --- | --- |
| Struthio camelus (Ostrich) | ADH4 | P80468 |
| Kluyveromyces lactis (strain ATCC 8585/CBS 2359/DSM 70799/NBRC 1267/NRRL Y-1140/WM37) (Yeast) (Candida sphaerica) | ADH4, KLLA0F13530g | P49385 |
| Schizosaccharomyces pombe (strain 972 ATCC 24843) (Fission yeast) | adh4, SPAC5H10.06c | Q09669 |
| Saccharomyces cerevisiae (strain YJM789) (Baker's yeast) | ADH4, ZRG5, SCY_1818 | A6ZTT5 |
| Saccharomyces cerevisiae (strain ATCC 204508/S288c) (Baker's yeast) | ADH4, ZRG5, YGL256W, NRC465 | P10127 |
| Saccharomyces pastorianus (Lager yeast) (Saccharomyces cerevisiae x Saccharomyces eubayanus) | ADH5 | Q6XQ67 |
| Bos taurus (Bovine) | ADH5 | Q3ZC42 |
| Equus caballus (Horse) | ADH5 | P19854 |
| Mus musculus (Mouse) | Adh5, Adh-2, Adh2 | P28474 |
| Rattus norvegicus (Rat) | Adh5, Adh-2, Adh | P12711 |
| Oryctolagus cuniculus (Rabbit) | ADH5, ADH3 | O19053 |
| Homo sapiens (Human) | ADH5, ADHX, FDH | P11766 |
| Dictyostelium discoideum (Slime mold) | adh5, DDB_G0281865 | Q54TC2 |
| Saccharomyces cerevisiae (strain ATCC 204508/S288c) (Baker's yeast) | ADH5, YBR145W YBR1122 | P38113 |
| Homo sapiens (Human) | ADH6 | P28332 |
| Peromyscus manic ulatus North American deer mouse) | ADH6 | P41681 |
| Pongo abelii (Sumatran orangutan) (Pongo pygmaeus abelii) | ADH6 | Q5R7Z8 |
| Rattus norvegicus (Rat) | Adh6 | Q5X195 |
| Homo sapiens (Human) | ADH7 | P40394 |
| Rattus norvegicus (Rat) | Adh7 | P41682 |
| Mus musculus (Mouse) | Adh7, Adh-3 adh-3 | Q64437 |
| Mycobacterium tuberculosis (strain CDC 1551/Oshkosh) | adhA, MT1911 | P9WQC0 |
| Rkizohium meliloti (strain 1021) (Ensifer meliloti) (Sinorhizobium meliloti) | adhA, RA0704 SMa1296 | O31186 |
| Mycobacterium tuberculosis (strain ATCC 25618/H37Rv) | adhA, Rv1862 | P9WQC1 |
| Zymomonas mobilis subsp. mobilis (strain ATCC 31821/ZM4/CP4) | adhA, ZMO1236 | P20368 |
| Mycobacterium bovis (strain ATCC BAA-935/AF2122/97) | adhB, Mb0784c | Q7U1B9 |
| Mycobacterium tuberculosis (strain CDC 1551/Oshkosh) | adhB, MT0786 | P9WQC6 |
| Mycobacterium tuberculosis (strain ATCC 25618/H37Rv) | adhB, Rv0761c, MTCY369.06c | P9WQC7 |
| Zymomonas mobilis subsp. mobilis (strain ATCC 31821/ZM4/CP4) | adhB, ZMO1596 | P0DJA2 |
| Zymomonas mobilis subsp. mobilis (strain ATCC 10988/DSM 424/LMG 404/NCIMB 8938/NRRL B-806/ZM1) | adhB, Zmob_1541 | F8DVL8 |
| Mycobacterium tuberculosis (strain CDC 1551/Oshkosh) | adhD, MT3171 | P9WQB8 |
| Mycobacterium tuberculosis (strain ATCC 25618/H37Rv) | adhD, Rv3086 | P9WQB9 |
| Clostridium acetobutylicum (strain ATCC 824/DSM 792/JCM 1419/LMG 5710/VKM B-1787) | adhE, aad, CA_P0162 | P33744 |
| Escherichia coli (strain K12) | adhE, ana, b1241, JW1228 | P0A9Q7 |
| Escherichia coli O157:H7 | adhE, Z2016, ECs1741 | P0A9Q8 |
| Rhodobacter sphaeroides (strain ATCC 17023/2.4.1/NCIB 8253/DSM 158) | adhI, RHOS4_11650, RSP_2576 | P72324 |
| Oryza sativa subsp. indica (Rice) | ADI-IIII, OsI_0009236 | A2XAZ3 |
| Escherichia coli (strain K12) | adhP, yddN, b1478, JW1474 | P39451 |

TABLE 3-continued

Exemplary alcohol dehydrogenase enzymes.

| Organism | Gene Name | Accession No. |
|---|---|---|
| Geo-bacillus stearothermophilus (Bacillus stearothermophilus) | adhT | P12311 |
| Emericella nidulans (strain FGSC A4/ATCC 38163/CBS 112.46/NRRL 194/M139) (Aspergillus nidulans) | alcA, AN8979 | P08843 |
| Emericella nidulans (strain FGSC A4/ATCC 38163/CBS 112.46/NRRL 194/M139) (Aspergillus nidulans) | alc, AN3741 | P54202 |
| Emericella nidulans (strain FGSC A4/ATCC 38163/CBS 112.46/NRRL 194/M139) (Aspergillus nidulans) | alcC, adh3, AN2286 | P07754 |
| Arabidopsis thaliana (Mouse-ear cress) | At1g22430, F12K8.22 | Q9SK86 |
| Arabidopsis thaliana (Mouse-ear cress) | At1g22440, F12K8.21 | Q9SK87 |
| Arabidopsis thaliana (Mouse-ear cress) | At1g32780, F6N18.16 | A1L4Y2 |
| Arabidopsis thaliana (Mouse-ear cress) | At1g64710, F13O11.3 | Q8VZ49 |
| Arabidopsis thaliana (Mouse-ear cress) | At4g22110 F1N20.210 | Q0V7W6 |
| Arabidopsis thaliana (Mouse-ear cress) | At5g24760, T4C12_30 | Q8LEB2 |
| Arabidopsis thaliana (Mouse-ear cress) | At5g42250, K5.114.5 | Q9FH04 |
| Zea mays (Maize) | FDH | P93629 |
| Drosophila melanogaster (Fruit fly) | Fdh, gfd, ODH CG6598 | P46415 |
| Bacillus subtilis (strain 168) | gbsB, BSU31050 | P71017 |
| Caenorhabditis elegans | H24K24.3 | Q17335 |
| Oryza sativa subsp. japonica (Rice) | Os02g0815500, LOC_Os02g57040, OsJ_008550, P0643F09.4 | Q0DWH1 |
| Mycobacterium tuberculosis (strain ATCC 25618/ H37Rv) | Rv1895 | O07737 |
| Caenorhabditis elegans | sodh-1, K12G11.3 | Q17334 |
| Caenorhabditis elegans | sodh-2, K12G11.4 | O45687 |
| Pseudomonas sp. | terPD | P33010 |
| Escherichia coli (strain K12) | yiaY, b3589, JW5648 | P37686 |
| Moraxella sp. (strain TAE123) | | P81786 |
| Alligator mississippiensis (American alligator) | | P80222 |
| Catharanthus roseus (Madagascar periwinkle) (Vinca rosea) | | P85440 |
| Gadus morhua subsp. callarias (Baltic cod) (Gadus callarias) | | P26325 |
| Naja (Indian cobra) | | P80512 |
| Pisum sativum (Garden pea) | | P12886 |
| Pelophylax perez (Perez's frog) (Rana perezi) | | P22797 |
| Saara hardwickii (Indian spiny-tailedlizard) (Uromastyx hardwickii) | | P25405 |
| Saara hardwickii (Indian spiny-tailed lizard) (Uromastyx hardwickii) | | P25406 |
| Equus caballus (Horse) | | P00327 |
| Equus caballus (Horse) | | P00328 |
| Geobacillus stearothermophilus (Bacillus stearothermophilus) | | P42328 |
| Gadus tnorhua (Atlantic cod) | | P81600 |
| Gad-us morhua (Atlantic cod) | | P81601 |
| Myxine glutinosa (Atlantic hagfish) | | P80360 |
| Octopus vulgaris (Common octopus) | | P81431 |
| Pisum sativum (Garden pea) | | P80572 |
| Saara hardwickii (Indian spiny-tailed lizard) (Uromastryx hardwickii) | | P80467 |
| Scyliorhinus canicula (Small-spotted catshark) (Squalus canicula) | | P86884 |
| Sparus aurata (Gilthead sea bream) | | P79896 |

TABLE 3a

Additional Exemplary alcohol dehydrogenase enzymes

| Organism | Accession No. |
| --- | --- |
| Helicoverpa armigera | A0A0176Q2K7 |
| Helicoverpa armigera | A0A0F6Q2W6 |
| Helicoverpa armigera | AKD01723.1 |
| Helicoverpa amligera | A0A0F6Q4H2 |
| Helicoverpa armigera | A0A0F6Q1E8 |
| Helicoverpa armigera | A0A0F6Q2K3 |
| Helicoverpa armigera | A0A0F6Q4H7 |
| Helicoverpa armigera | A0A0F6Q2J9 |
| Helicoverpa armigera | A0A0F6Q0W0 |
| Helicoverpa armigera | A0A0F6Q0V0 |
| Helicoverpa armigera | A0A0F6Q1F1 |
| Helicoverpa armigera | A0A0F6Q2X2 |
| Helicoverpa armigera | A0A0F6Q4I2 |
| Helicoverpa armigera | A0A0F6Q2X0 |
| Helicoverpa assulta | A0A0F6Q2L9 |
| Helicoverpa assulta | A0A0F6Q4K1 |
| Helicoverpa assulta | A0A0F6Q4J7 |
| Helicoverpa assulta | A0A0F6Q2Y5 |
| Helicoverpa assulta | A0A0F6Q2Y1 |
| Helicoverpa assulta | A0A0F6Q1G6 |
| Helicoverpa assulta | A0A0F6Q2Y9 |
| Helicoverpa assulta | A0A0F6Q0X5 |
| Helicoverpa assulta | A0A0F6Q2M3 |
| Helicoverpa assulta | A0A0F6Q2L1 |
| Helicoverpa assulta | A0A0F6Q1F9 |
| Helicoverpa assulta | A0A0F6Q0W6 |
| Helicoverpa assulta | A0A0F6Q1G9 |
| Fielicoverpa assulta | A0A0F6Q2L4 |
| Helicoverpa assulta | A0A0F6Q2X6 |
| Helicoverpa assulta | A0A0F6Q1H3 |
| Helicoverpa assulta | A0A0F6Q0X1 |
| Bombyx mori | NP_001188510.1 |
| Aedes aegypti | XP001655103 .1 |
| Anopheles darlingi | ETN64198.1 |
| Yarrowia lipolytica | YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), YALI0E07766g (ADH7) |

In some embodiments, the present disclosure teaches a recombinant microorganism comprising a deletion, disruption, mutation, and or reduction in the activity of one or more endogenous (fatty) alcohol dehydrogenase selected from the group consisting of YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), YALI0E07766g (ADH7).

Thus, in some embodiments, the recombinant microorganism of the present disclosure will comprise deletions or other disruptions in endogenous genes encoding proteins exhibiting at least 100%, 99%, 98%, 97%, 95%, 94%, 93%, 92%, 91%, or 90% sequence identity with the proteins encoded by YALI0F09603g (FADH). YALI0D25630g (ADH1). YALI0E17787g (ADH2), YALI0A16379g (ADH3), YALI0E15818g (ADH4), YALI0D02167g (ADH5), YALI0A15147g (ADH6), and YALI0E07766g (ADH7).

Thus, in some embodiments, the recombinant microorganism of the present disclosure will comprise deletions in endogenous genes encoding proteins exhibiting at least 100%, 99%, 98%, 97%, 95%, 94%, 93%, 92%, 91%, or 90% sequence identity with uniprot database IDs Q6C297 (FADH). Q6C7T0 (ADH1), F2Z678 (ADH2), Q6CGT5 (ADH3), Q6C5R5 (ADH4), Q6CAT5 (ADH5), Q6CGX5 (ADH6), and Q6C7K3 (ADH7).

Alcohol Oxidase

The present disclosure describes enzymes that oxidize fatty alcohols to fatty aldehydes.

In some embodiments, an alcohol oxidase (AOX) is used to catalyze the conversion of a fatty alcohol to a fatty aldehyde. Alcohol oxidases catalyze the conversion of alcohols into corresponding aldehydes (or ketones) with electron transfer via the use of molecular oxygen to form hydrogen peroxide as a by-product. AOX enzymes utilize flavin adenine dinucleotide (FAD) as an essential cofactor and regenerate with the help of oxygen in the reaction medium. Catalase enzymes may be coupled with the AOX to avoid accumulation of the hydrogen peroxide via catalytic conversion into water and oxygen.

Based on the substrate specificities, AOXs may be categorized into four groups: (a) short chain alcohol oxidase, (b) long chain alcohol oxidase, (c) aromatic alcohol oxidase, and (d) secondary alcohol oxidase (Goswami et al. 2013). Depending on the chain length of the desired substrate, some members of these four groups are better suited than others as candidates for evaluation.

Short chain alcohol oxidases (including but not limited to those currently classified as EC1.1.3.13, Table 4) catalyze the oxidation of lower chain length alcohol substrates in range of C1-C8 carbons (van der Klei et al. 1991) (Ozimek et al. 2005). Aliphatic alcohol oxidases from methylotrophic yeasts such as *Candida boidinii* and *Komagataella pastoris* (formerly *Pichia pastoris*) catalyze the oxidation of primary alkanols to the corresponding aldehydes with a preference for unbranched short-chain aliphatic alcohols. The most broad substrate specificity is found for alcohol oxidase from the *Pichia pastoris* including propargyl alcohol, 2-chloroethanol, 2-cyanoethanol (Dienys et al. 2003). The major challenge encountered in alcohol oxidation is the high reactivity of the aldehyde product. Utilization of a two liquid phase system (water/solvent) can provide in-situ removal of the aldehyde product from the reaction phase before it is further converted to the acid. For example, hexanal production from hexanol using *Pichia pastoris* alcohol oxidase coupled with bovine liver catalase was achieved in a biphasic system by taking advantage of the presence of a stable alcohol oxidase in aqueous phase (Karra-Chaabouni et al. 2003). For example, alcohol oxidase from *Pichia pastoris* was able to oxidize aliphatic alcohols of C6 to C11 when used biphasic organic reaction system (Murray and Duff 1990). Methods for using alcohol oxidases in a biphasic system according to (Karra-Chaabouni et al. 2003) and (Murray and Duff 1990) are incorporated by reference in their entirety.

Long chain alcohol oxidases (including but not limited to those currently classified as EC 1.1.3.20; Table 5) include fatty alcohol oxidases, long chain fatty acid oxidases, and long chain fatty alcohol oxidases that oxidize alcohol substrates with carbon chain length of greater than six (Goswami et al. 2013). Banthorpe et al. reported a long chain alcohol oxidase purified from the leaves of *Tanacetum vulgare* that was able to oxidize saturated and unsaturated long chain alcohol substrates including hex-trans-2-en-1-ol and octan-1-ol (Banthorpe 1976) (Cardemil 1978). Other plant species, including *Simmondsia chinensis* (Moreau, R. A., Huang 1979). *Arabidopsis thaliana* (Cheng et al. 2004), and *Lotus japonicas* (Zhao et al. 2008) have also been reported as sources of long chain alcohol oxidases. Fatty alcohol oxidases are mostly reported from yeast species (Hommel and Ratledge 1990) (Vanhanen et al. 2000) (Hommel et al. 1994) (Kemp et al. 1990) and these enzymes play an important role in long chain fatty acid metabolism (Cheng et al. 2005). Fatty alcohol oxidases from yeast species that degrade and grow on long chain alkanes and fatty acid catalyze the oxidation of fatty alcohols. Fatty alcohol oxidase from *Candida tropicalis* has been isolated as microsomal cell fractions and characterized for a range of substrates (Eirich et al. 2004) (Kemp et al. 1988) (Kemp et al. 1991) (Mauersberger et al. 1992). Significant activity is observed for primary alcohols of length $C_8$ to $C_{16}$ with reported $K_M$ in the 10-50 µM range (Eirich et al. 2004). Alcohol oxidases described may be used for the conversion of medium chain aliphatic alcohols to aldehydes as described, for example, for whole-cells *Candida boidinii* (Gabelman and Luzio 1997), and *Pichia pastoris* (Duff and Murray 1988) (Murray and Duff 1990). Long chain alcohol oxidases from filamentous fungi were produced during growth on hydrocarbon substrates (Kumar and Goswami 2006) (Savitha and Ratledge 1991). The long chain fatty alcohol oxidase (LjFAO1) from *Lotus japonicas* has been heterologously expressed in *E. coli* and exhibited broad substrate specificity for alcohol oxidation including 1-dodecanol and 1-hexadecanol (Zhao et al. 2008).

TABLE 4

Alcohol oxidase enzymes capable of oxidizing short chain alcohols (EC 1.1.3.13)

| Organism | Gene names | Accession No. |
| --- | --- | --- |
| Komagataella pastoris (strain ATCC 76273/ CBS 7435/CECT 11047/NRRL Y-11430/ Wegner 21-1) (Yeast) (Pichia pastoris) | AOX1 PP7435_Chr4-0130 | F2QY27 |
| Komagataella pastoris (strain GS115/ATCC 20864) (Yeast) (Pichia pastoris) | AOX1 PAS_chr4_0821 | P04842 |
| Komagataella pastoris (strain ATCC 76273/ CBS 7435/CECT 11047/NRRL Y-11430 Wegner 21-1) (Yeast) (Pichia pastoris) | AOX2 PP7435_Chr4-0863 | F2R038 |
| Komagataella pastoris (strain GS115/ATCC 20864) (Yeast) (Pichia pastoris) | AOX2 PAS_chr4_0152 | C4R702 |
| Candida boidinii (Yeast) | AOD1 | Q00922 |
| Pichia angusta (Yeast) (Hansenula polymorpha) | MOX | P04841 |
| Thanatephorus cucumeris (strain AG1-IB/ isolate 7/3/14) (Lettuce bottom rot fungus) (Rhizoctonia solani) | AOD1 BN14_10802 | M5CC52 |
| Thanatephorns cucumeris (strain AG1-IB/ isolate 7/3/14) (Lettuce bottom rot fungus) (Rhizoctonia solani) | MOX BN14_12214 | M5CF32 |
| Thanatephonis cucumeris (strain AG1-IB/ isolate 7/3/14) (Lettuce bottom rot fungus) (Rhizoctonia solani) | AOD1 BN14_10691 | M5CAV1 |
| Thanatephonis cucumeris (strain AG1-IB/ isolate 7/3/14) (Lettuce bottom rot fungus) (Rhizoctonia solani) | AOD1 BN14_09479 | M5C7F4 |
| Thanatephorns cucumeris strain AG1-IB/ isolate 7/3/14) (Lettuce bottom rot fungus) Rhizoctonia solani) | AOD1 BN14_10803 | M5CB66 |
| Thanatephorus cucutneris (strain AGI-IB/ isolate 7/3/14) (Lettuce bottom rot fungus) (Rhizoctonia. solani) | AOD1 BN14_09900 | M5C9N9 |
| Thanatephorus cucumeris (strain AG1-IB/ isolate 7/3/14) (Lettuce bottom rot fungus) (Rhizoctonia solani) | AOD1 BN14_08302 | M5C2L8 |
| Thanatephorus cucumeris (strain AG1-1B/ isolate 7/3/14) (Lettuce bottom rot fungus) Rhizoctonia solani) | MOX BN14_09408 | M5C784 |
| Thanatephorus cucumeris (strain AG1-IB/ isolate 7/3/14) (Lettuce bottom rot fungus) (Rhizoctonia solani) | MOX BN14_09478 | M5C8F8 |
| Thanatephorus cucumeris (strain AG1-IB/ isolate 7/3/14) (Lettuce bottom rot fungus) (Rhizoctonia solani) | AOD1 BN14_11356 | M5CH40 |
| Ogataea henricii | AOD1 | A5LGF0 |
| Candida methanosorbosa | AOD1 | A5LGE5 |
| Candida methanolovescens | AOD1 | A5LGE4 |
| Candida succiphila | AOD1 | A5LGE6 |
| Aspergillus niger (strain CBS 513.88/FGSC A1513) | An18g05480 | A2R501 |
| Aspergillus niger (strain CBS 513.88/FGSC A1513) | An18g05480 | A2RB46 |
| Moniliophthora pemiciosa (Witches'-broom disease fungus) (Marasmius pemiciosus) | | 17CMK2 |
| Candida cariosilignicola | AOD1 | A5LGE3 |
| Candida pignaliae | AOD1 | A5LGE1 |
| Candida pignaliae | AOD2 | A5LGE2 |
| Candida sonorensis | AOD1 | A5LGD9 |
| Candida sonorensis | AOD2 | A5LGE0 |
| Pichia naganishii | AOD1 | A5LGF2 |
| Ogataea minuta | AOD1 | A5LGF1 |
| Ogataea philodendra | AOD1 | A5LGF3 |
| Ogataea wickerhamii | AOD1 | A5LGE8 |
| Kuraishia capsulate | AOD1 | A5LGE8 |

TABLE 4-continued

Alcohol oxidase enzymes capable of oxidizing short chain alcohols (EC 1.1.3.13)

| Organism | Gene names | Accession No. |
|---|---|---|
| Talaromyces stipitatus (strain ATCC 10500/CBS 375.48/QM 6759/NRRL 1006) (Penicillium stipitatum) | TSTA_021940 | B8MHF8 |
| Talaromyces stipitatus (strain ATCC 10500/CBS 375.48/QM 6759/NRRL 1006) (Penicillium stipitatum) | TSTA_065150 | B8LTH7 |
| Talaromyces stipitatus (strain ATCC 10500/CBS 375.48/QM 6759/NRRL 1006) (Penicillium stipitatum) | TSTA_065150 | B8LTH8 |
| Talaromyces stipitatus (strain ATCC 10500/CBS 375.48/QM 6759/NRRL 1006) (Penicillium stipitatum) | TSTA_000410 | B8MSB1 |
| Ogataea glucozyma | AOD1 | A5LGE9 |
| Ogataea parapolymorpha (strain DL-1/ATCC 26012/NRRL Y-7560) (Yeast) (Hansenula polymorpha) | HPODL_03886 | W1QCJ3 |
| Gloeophyllum trabeum (Brown rot fungus) | AOX | A8DPS4 |
| Pichia angusta (Yeast) (Hansenula polymorpha) | mox1 | A6PZG8 |
| Pichia trehalophila | AOD1 | A5LGF4 |
| Pichia angusta (Yeast) (Hansenula polymorpha) | mox1 | A6PZG9 |
| Pichia angusta (Yeast) (Hansenula polymorpha) | mox1 | A6PZG7 |
| Ixodes scapularis (Black-legged tick) (Deer tick) | IscW_ISCW017898 | B7PIZ7 |

TABLE 5

Alcohol oxidase enzymes capable of oxidizing long chain alcohols including fatty alcohols (EC 1.1.3.20)

| Organism | Gene names | Accession No. |
|---|---|---|
| Lotus japonicus (Lotus corniculatus var. japonicus) | FAO1 | B5WWZ8 |
| Arabidopsis thaliana (Mouse-ear cress) | FAO1 At1g03990 F21M11.7 | Q9ZWB9 |
| Lotus japonicus (Lotus corniculatus var. japonicus) | FAO2 | B5WWZ9 |
| Arabidopsis thaliana (Mouse-ear cress) | FAO3 At3g23410 MLM24.14 MLM24.23 | Q9LW56 |
| Arabidopsis thaliana (Mouse-ear cress) | FAO4A At4g19380 T5K18.160 | O65709 |
| Arabidopsis thaliana (Mouse-ear cress) | FAO4B At4g28570 T5F17.20 | Q94BP3 |
| Microbotryum violaceum (strain p1A1 Lamole) (Anther smut fungus) (Ustilago violacea) | MVLG_06864 | U5HIL4 |
| Ajellomyces dermatitidis ATCC 26199 | BIDFG_03507 | T5BNQ0 |
| Gibberella zeae (strain PH-1/ATCC MYA-4620/FGSC 9075/NRRL 31084) (Wheat head blight fungus) (Fusarium graminearum) | FG06918.1 FGSG_06918 | I1RS14 |
| Pichia sorbitophila (strain ATCC MYA-4447/BCRC 22081/CBS 7064/NBRC 10061/NRRLY-195) (Hybrid yeast) | Piso0_004410 GNLVRS01_PISO0K16268a GNLVRS01_PISO0L16269g | G8Y5E1 |
| Emericella nidulans (strain FGSC A4/ATCC 38163/CBS 112.46/NRRL 194/M139) (Aspergillus nidulans) | AN0623.2 AN1A_00623 | Q5BFQ7 |
| Pyrenophora tritici-repentis (strain Pt-IC-BFP) (Wheat tan spot fungus) (Drechslera tritici-repentis) | PTRG_10154 | B2WJW5 |
| Paracoccidioides lutzii (strain ATCC MYA-826/Pb01) (Paracoccidioides brasiliensis) | PAAG_09117 | C1HEC6 |
| Candida parapsilosis (strain CDC 317/ATCC MYA-4646) (Yeast) (Monilia parapsilosis) | CPAR2_204420 | G8BG15 |
| Pseudozyma brasiliensis (strain GHG001) (Yeast) | PSEUBFA_SCAF2a03010 | V5GPS6 |
| Candida parapsilosis (strain CDC 317/ATCC MYA-4646) (Yeast) (Monilia parapsilosis) | CPAR2_204430 | G8BG16 |
| Sclerotinia borealis F-4157 | SBOR_5750 | W9CDE2 |
| Sordaria macrospora (strain ATCC MYA-333/DSM 997/K(L3346)/K-hell) | SMAC_06361 | F7W6K4 |
| Sordaria macrospora (strain ATCC MYA-333/DSM 997/K(L3346)/K-hell) | SMAC_01933 | F7VSA1 |
| Meyerozyma guilliermondii | PGUG_03467 | A5DJL6 |

TABLE 5-continued

Alcohol oxidase enzymes capable of oxidizing long chain alcohols including fatty alcohols (EC 1.1.3.20)

| Organism | Gene names | Accession No. |
|---|---|---|
| (strain ATCC 6260/CBS 566/DSM 6381/ JCM 1539/NBRC 10279/NRRL Y-324) (Yeast) (*Candida guilliermondii*) | | |
| *Trichophyton rubrum* CBS 202.88 | H107_00669 | A0A023ATC5 |
| *Arthrobotrys oligospora* (strain ATCC 24927/CBS 115.81/ DSM 1491) (Nematode-trapping fungus) (*Didymozoophaga oligospora*) | AOL_00097g516 | G1XJI9 |
| *Scheffersomyces stipitis* (strain ATCC 58785/CBS 6054/ NBRC 10063/ NRRL Y-11545) (Yeast) (*Pichia stipitis*) | FAO1 PICST_90828 | A3LYX9 |
| *Scheffersomyces stipitis* (strain ATCC 58785/CBS 6054/ NBRC 10063/ NRRL Y-11545) (Yeast) (*Pichia stipitis*) | FAO2 PICST_32359 | A3LW61 |
| *Aspergillus oryzae* (strain 3.042) (Yellow koji mold) | Ao304_09114 | I8TL25 |
| *Fusarium oxysporum* (strain Fo5176) (*Fusarium* vascular wilt) | FOXB_17532 | F79GFU8 |
| *Rhizopus delemar* (strain RA 99-880/ ATCC MYA-4621/ FGSC 9543/ NRRL 43880) (*Mucormycosis* agent) (*Rhizopus arrhizus* var. *delemar*) | RO3G_08271 | I1C536 |
| *Rhizopus delemar* (strain RA 99-880/ ATCC MYA-4621/ FGSC 9543/ NRRL 43880) (*Mucormycosis* agent) (*Rhizopus arrhizus* var. *delemar*) | RO3G_00154 | I1BGX0 |
| *Fusarium oxysporum* (strain Fo5176) (*Fusarium* vascular wilt) | FOXB_07532 | F9FMA2 |
| *Penicillium roqueforti* | PROQFM164_ S02g001772 | W6QPY1 |
| *Aspergillus clavatus* (strain ATCC 1007/ CBS 513.65/DSM 816/ NCTC 3887/ NRRL 1) | ACLA_018400 | A1CNB5 |
| *Arthrodemia otae* (strain ATCC MYA-4605/CBS 113480) (*Microsporum canis*) | MCYG_08732 | C5G1B0 |
| *Trichophyton tonsurans* (strain CBS 112818) (Scalp ringworm fungus) | TESG_07214 | F2S8I2 |
| *Colletotrichum higginsianum* (strain IMI 349063) (Crucifer anthracnose fungus) | CH063_13441 | H1VUE7 |
| *Ajellomyces capsulatus* (strain H143) (Darling's disease fungus) (*Histoplasma capsulatum*) | HCDG_07658 | C6HN77 |
| *Trichophyton rubnim* (strain ATCC MYA-4607/CBS 118892) (Athlete's foot fungus) | TERG_08235 | F2T096 |
| *Cochliobolus heterostrophus* (strain C5/ ATCC 48332/race O) (Southern corn leaf blight fungus) (*Bipolaris maydis*) | COCHEDRAFT_ 1201414 | M2UMT9 |
| *Candida orthopsilosis* (strain 90-125) (Yeast) | CORT_0D04510 | H8X643 |
| *Candida orthopsilosis* (strain 90-125) (Yeast) | CORT_0D04520 | H8X644 |
| *Candida orthopsilosis* (strain 90-125) (Yeast) | CORT_0D04530 | H8X645 |
| *Pseudozyma aphidis* DSM 70725 | PaG_03027 | W3VP49 |
| *Coccidioides posadasii* (strain C735) (Valley fever fungus) | CPC735_000380 | C5P005 |
| *Magnaporthe oryzae* (strain P131) (Rice blast fungus) (*Pyricularia oryzae*) | OOW_ P131scaffold01214g15 | L7IZ92 |
| *Neurospora tetrasperma* (strain FGSC 2508/ATCC MYA-4615/P0657) | NEUTE1DRAFT_82541 | F8MKD1 |
| *Hypocrea virens* (strain Gv29-8/FGSC 10586) (*Gliocladium virens*) (*Trichoderma virens*) | TRIVIDRAFT_54537 | G9MMY7 |
| *Hypocrea virens* (strain Gv29-8/FGSC 10586) (*Gliocladium virens*) (*Trichoderma virens*) | TRIVIDRAFT_53801 | G9MT89 |
| *Aspergillus niger* (strain CBS 513.88/ FGSC A1513) | An01g09620 | A2Q9Z3 |
| *Verticillium dahliae* (strain VdLs.17/ ATCC MYA-4575/ FGSC 10137) (*Verticillium* wilt) | VDAG_05780 | G2X6J8 |
| *Ustilago maydis* (strain 521/FGSC 9021) (Corn smut fungus) | UM02023.1 | Q4PCZ0 |
| *Fusarium oxysporum f.* sp. *lycopersici* MN25 | FOWG_13006 | W9LNI9 |
| *Fusarium oxysporum f.* sp. *lycopersici* MN25 | FOWG_02542 | W9N9Z1 |
| *Candida tropicalis* (Yeast) | FAO1 | Q6QIR6 |
| *Magnaporthe oryzae* (strain 70-15/ ATCC MYA-4617/ FGSC 8958) (Rice blast fungus) (*Pyricularia oryzae*) | MGG_11317 | G4MVK1 |
| *Candida tropicalis* (Yeast) | faot | Q9P8D9 |
| *Candida tropicalis* (Yeast) | FAO2a | Q6QIR5 |

TABLE 5-continued

Alcohol oxidase enzymes capable of oxidizing long chain alcohols including fatty alcohols (EC 1.1.3.20)

| Organism | Gene names | Accession No. |
|---|---|---|
| *Phaeosphaeria nodorum* (strain SN15/ ATCC MYA-4574/ FGSC 10173) (Glume blotch fungus) (*Septoria nodorum*) | SNOG_02371 | Q0V0U3 |
| *Candida tropicalis* (Yeast) | FAO2b | Q6QIR4 |
| *Pestalotiopsis fici* W106-1 | PFICI_11209 | W3WU04 |
| *Magnaporthe oryzae* (strain Y34) (Rice blast fungus) (*Pyricularia oryzae*) | OOU_Y34scaffold00240g57 | L7IFT5 |
| *Pseudogymnoascus destructans* (strain ATCC MYA-4855/ 20631-21) (Bat white-nose syndrome fungus) (*Geomyces destructans*) | GMDG_01756 | L8G0G6 |
| *Pseudogymnoascus destructans* (strain ATCC MYA-4855/ 20631-21) (Bat white-nose syndrome fungus) (*Geomyces destructans*) | GMDG_04950 | L8GCY2 |
| *Mycosphaerella fijiensis* (strain CIRAD86) (Black leaf streak disease fungus) (*Pseudocercospora fijiensis*) | MYCFIDRAFT_52380 | M2Z831 |
| *Bipolaris oryzae* ATCC 44560 | COCMIDRAFT_84580 | W7A0I8 |
| *Cladophialophora psammophila* CBS 110553 | A1O5_08147 | W9WTM9 |
| *Fusarium oxysporum f.* sp. *melonis* 26406 | FOMG_05173 | X0AEE6 |
| *Fusarium oxysponim f.* sp. *melonis* 26406 | FOMG_17829 | W9ZBB7 |
| *Cyphellophora europaea* CBS 101466 | HMPREF1541_102174 | W2S2S5 |
| *Aspergillus kawachii* (strain NBRC 4308) (White koji mold) (*Aspergillus awamori* var. *kawachi*) | AKAW_00147 | G7X626 |
| *Aspergillus terreus* (strain NIH 2624/ FGSC A1156) | ATEG_05086 | Q0CMJ8 |
| *Coccidioides immitis* (strain RS) (Valley fever fungus) | CIMG_02987 | J3KAI8 |
| *Ajellomyces dermatitidis* (strain ER-3/ ATCC MYA-2586) (*Blastomyces dermatitidis*) | BDCG_04701 | C5GLS5 |
| *Fusarium oxysporum f.* sp. *cubense* strain race 1) (Panama disease fungus) | FOC1_g0013865 | N4U732 |
| *Rhodotorula glutinis* (strain ATCC 204091/IIP 30/MTCC 1151) (Yeast) | RTG_00643 | G0SVU8 |
| *Aspergillus niger* (strain ATCC 1015/ CBS 113.46/FGSC A1144/LSHB Ac4/ NCTC 3858a/NRRL 328/USDA 3528.7) | ASPNIDRAFT_35778 | G3XTM6 |
| *Candida cloacae* | fao1 | Q9P8D8 |
| *Candida cloacae* | fao2 | Q9P8D7 |
| *Fusarium oxysporum f.* sp. *cubense* (strain race 1) (Panama disease fungus) | FOC1_g10006358 | N4TUH3 |
| *Candida albicans* (strain SC5314/ ATCC MYA-2876) (Yeast) | FAO1 CaO19.13562 orf19.13562 | Q59RS8 |
| *Candida albicans* (strain SC5314/ ATCC MYA-2876) (Yeast) | FAO1 CaO19.6143 orf19.6143 | Q59RP0 |
| *Chaetomium thermophilum* (strain DSM 1495/CBS 144.50/IMI 039719) | CTHT_0018560 | G0S2U9 |
| *Mucor circinelloides f. circinelloides* (strain 1006PhL) (*Mucormycosis* agent) (*Calyptromyces circinelloides*) | HMPREF1544_05296 | S2JDN0 |
| *Mucor circinelloides f. circinelloides* (strain 1006PhL) (*Mucormycosis* agent) (*Calyptromyces circinelloides*) | HMPREF1544_05295 | S2JYP5 |
| *Mucor circinelloides f. circinelloides* (strain 1006PhL) (*Mucormycosis* agent) (*Calyptromyces circinelloides*) | HMPREF1544_06348 | S2JVK9 |
| *Botryotinia Fuckeliana* (strain BcDW1) (Noble rot fungus) (*Botrytis cinerea*) | BCDW1_6807 | M7UD26 |
| *Podospora anserina* (strain S/ATCC MYA-4624/DSM 980/ FGSC 10383) (*Pleurage anserina*) | PODANS_5_13040 | B2AFD8 |
| *Neosartorya fumigata* (strain ATCC MYA-4609/Af293/ CBS 101355/ FGSC A1100) (*Aspergillus fumigatus*) | AFUA_1G17110 | Q4WR91 |
| *Fusarium oxysporum f.* sp. *vasinfeetum* 25433 | FOTG_00686 | X0MEE6 |
| *Fusarium oxysporum f.* sp. *vasinfectum* 25433 | FOTG_12485 | X0LE98 |
| *Trichophyton interdigitale* H6 | H101_06625 | A0A022U717 |
| *Beauveria bassiana* (strain ARSEF 2860) (White muscardine disease fungus) (*Tritirachium shiotae*) | BBA_04100 | J4UNY3 |
| *Fusarium oxysporum f.* sp. *radicis-lycopersici* 26381 | FOCG_00843 | X0GQ62 |

TABLE 5-continued

Alcohol oxidase enzymes capable of oxidizing long chain alcohols including fatty alcohols (EC 1.1.3.20)

| Organism | Gene names | Accession No. |
|---|---|---|
| Fusarium oxysporum f. sp. radicis-lycopersici 26381 | FOCG_15170 | X0F4T1 |
| Neurospora tetraspen (strain FGSC 2509/P0656) | NEUTE2DRAFT_88670 | G4UNN6 |
| Pseudozyma hubeiensis (strain SY62) (Yeast) | PHSY_000086 | R9NVU1 |
| Lodderomyces elongisporus (strain ATCC 11503/CBS 2605/JCM 1781/NBRC 1676/NRRL YB-4239) (Yeast) (Saccharomyces elongisporus) | LELG_03289 | A5E102 |
| Malassezia globosa (strain ATCC MYA-4612/CBS 7966) (Dandruff-associated fungus) | MGL_3855 | A8QAY8 |
| Byssochlamys spectabilis (strain No. 5/NBRC 109023) (Paecilomyces variotii) | PVAR5_7014 | V5GBL6 |
| Ajellomyces capsulatus (strain H88) (Darling's disease fungus) (Histoplasma capsulatum) | HCEG_03274 | F0UF47 |
| Trichosporon asahii var. asahii (strain ATCC 90039/CBS 2479/JCM 2466/KCTC 7840/NCYC 2677/UAMH 7654) (Yeast) | A1Q1_03669 | J6FBP4 |
| Penicillium oxalicum (strain 114-2/CGMCC 5302) (Penicillium decumbens) | PDE_00027 | S7Z8U8 |
| Fusarium oxysporum f. sp. conglutinans race 2 54008 | FOPG_02304 | X0IBE3 |
| Fusarium oxysporum f. sp. conglutinans race 2 54008 | FOPG_13066 | X0H540 |
| Fusarium oxysporum f. sp. raphani 54005 | FOQG_00704 | X0D1G8 |
| Fusarium oxysporum f. sp. raphani 54005 | FOQG_10402 | X0C482 |
| Metarhizium acridum (strain CQMa 102) | MAC_03115 | E9DZR7 |
| Arthroderma benhamiae (strain ATCC MYA-4681/CBS 112371) (Trichophyton mentagrophytes) | ARB_02250 | D4B1C1 |
| Fusarium oxysporum f. sp. cubense tropical race 4 54006 | FOIG_12161 | X0JFI6 |
| Fusarium oxysporum f. sp. cubense tropical race 4 54006 | FOIG_12751 | X0JDU5 |
| Cochliobolus heterostrophus (strain C4/ATCC 48331/race T) (Southern corn leaf blight fungus) (Bipolaris maydis) | COCC4DRAFT_52836 | N4WZZ0 |
| Trichosporon asahii var. asahii (strain CBS 8904) (Yeast) | A1Q2_00631 | K1VZW1 |
| Mycosphaerella graminicola (strain CBS 115943/IPO323) (Speckled leaf blotch fungus) (Septoria tritici) | MYCGRDRAFT_37086 | F9X375 |
| Botryotinia fuckeliana (strain T4) (Noble rot fungus) (Botrytis cinerea) | BofuT4_P072020.1 | G2XQ18 |
| Metarhizium anisopliae (strain ARSEF 23/ATCC MYA-3075) | MAA_05783 | E9F0I4 |
| Cladophialophora carrionii CBS 160.54 | G647_J5801 | V9DAR1 |
| Coccidioides posadasii (strain RMSCC 757/Silveira) (Valley fever fungus) | CPSG_09174 | E9DH75 |
| Rhodosporidium toruloides (strain NP11) (Yeast) (Rhodotorula gracilis) | RHTO_06879 | M7X159 |
| Puccinia graminis f. sp. tritici (strain CRL 75-36-700-3/race SCCL) (Black stem rust fungus) | PGTG_10521 | E3KIL8 |
| Trichophyton rubrum CBS 288.86 | H103_00624 | A0A022WG28 |
| Colletotrichum fioriniae PJ7 | CFIO01_08202 | A0A010RKZ4 |
| Trichophyton rubrum CBS 289.86 | H104_00611 | A0A022XB46 |
| Cladophialophora yegresii CBS 114405 | A1O7_02579 | W9WC55 |
| Colletotrichum orbiculare (strain 104-T/ATCC 96160/CBS 514.97/LARS 414/MAFF 240422) (Cucumber anthracnose fungus) (Colletotrichum lagenarium) | Cob_10151 | N4VFP3 |
| Drechslerella stenobrocha 248 | DRE_03459 | W7IDL6 |
| Neosartorya fumigata (strain CEA10/CBS 144.89/FGSC A1163) (Aspergillus fumigatus) | AFUB_016500 | B0XP90 |
| Thielavia terrestris (strain ATCC 38088/NRRL 8126) (Acremonium alabamense) | THITE_2117674 | G2R8H9 |
| Gibberella fujikuroi (strain CBS 19534/IMI 58289/NRRL A-6831) (Bakanae and foot rot disease fungus) (Fusarium fujikuroi) | FFUJ_02948 | S0D7P7 |

TABLE 5-continued

Alcohol oxidase enzymes capable of oxidizing long chain alcohols including fatty alcohols (EC 1.1.3.20)

| Organism | Gene names | Accession No. |
|---|---|---|
| Gibberella fujikuroi (strain CBS 195.34/ IMI 58289/NRRL A-6831) (Bakanae and foot rot disease fungus) (Fusarium fujikuroi) | FFUJ_12030 | S0EMC6 |
| Aspergillus flavus (strain ATCC 200026/ FGSC A1120/NRRL 3357/JCM 12722/SRRC 167) | AFLA_109870 | B8N941 |
| Togninia minima (strain UCR-PA7) (Esca disease fungus) (Phaeoacremonium aleophilum) | UCRPA7_1719 | R8BTZ6 |
| Ajellomyces dermatitidis (strain ATCC 18188/CBS 674.68) (Blastomyces dermatitidis) | BDDG_09783 | F2TUC0 |
| Macrophomina phaseolina (strain MS6) (Charcoal rot fungus) | MPH_10582 | K2RHA5 |
| Neurospora crassa (strain ATCC 24698/ 74-OR23-1A/CBS 708.71/DSM 1257/ FGSC 987) | NCU08977 | Q7S2Z2 |
| Neosartorya fischeri (strain ATCC 1020/ DSM 3700/FGSC A1164/NRRL 181) (Aspergillus fischerianus) | NFIA_008260 | A1D156 |
| Fusarium pseudograminearum (strain CS3096) (Wheat and barley crown-rot fungus) | FPSE_11742 | K3U9J5 |
| Spathaspora passalidarum (strain NRRL Y-27907/11-Y1) | SPAPADRAFT_54193 | G3AJP0 |
| Spathaspora passalidarum (strain NRRL Y-27907/11-Y1) | SPAPADRAFT_67198 | G3ANX7 |
| Trichophyton verrucosum (strain HKI 0517) | TRV_07960 | D4DL86 |
| Arthroderma gypseum (strain ATCC MYA-4604/CBS 118893) (Microsporum gypseum) | MGYG_07264 | E4V2J0 |
| Hypocrea jecorina (strain QM6a) (Trichoderma reesei) | TRIREDRAFT_43893 | G0R7P8 |
| Trichophyton rubrum MR1448 | H110_00629 | A0A022Z1G4 |
| Aspergillus ruber CBS 135680 | EURHEDRAFT_512125 | A0A017SPR0 |
| Glarea lozoyensis (strain ATCC 20868/ MF5171) | GLAREA_04397 | S3D6C1 |
| Setosphaeria turcica (strain 28A) (Northern leaf blight fungus) (Exserohilum turcicum) | SETTUDRAFT_20639 | R0K6H8 |
| Paracoccidioides brasiliensis (strain Pb18) | PADG_0655 | C1GH16 |
| Fusarium oxysporum Fo47 | FOZG_13577 | W9JPG9 |
| Fusarium oxysporum Fo47 | FOZG_05344 | W9KPH3 |
| Trichophyton rubrum MR1459 | H113_00628 | A0A022ZY09 |
| Penicillium marneffei (strain ATCC 18224/CBS 334.59/ QM 7333) | PMAA_075740 | B6QRY3 |
| Sphaerulina musiva (strain SO2202) (Poplar stem canker fungus) (Septoria musiva) | SEPMUDRAFT_154026 | M3DAK6 |
| Gibberella moniliformis (strain M3125/ FGSC 7600) (Maize ear and stalk rot fungus) (Fusarium verticillioides) | FVEG_10526 | W7N4P8 |
| Gibberella moniliformis (strain M3125/ FGSC 7600) (Maize ear and stalk rot fungus) (Fusarium verticillioides) | FVEG_08281 | W7MVR9 |
| Pseudozyma antarctica (strain T-34) Yeast) (Candida amarctica) | PANT_22d00298 | M9MGF2 |
| Paracoccidioides brasiliensis (strain Pb03) | PBG_07795 | C0SJD4 |
| Rhizophagus irregularis (strain DAOM 181602/DAOM 197198/MUCL 43194) (Arbuscular mycorrhizal fungus) (Glomus intraradices) | GLOINDRAFT_82554 | U9TF61 |
| Penicillium chrysogenum (strain ATCC 28089/DSM 1075/ Wisconsin 54-1255) (Penicillium notatum) | Pc21g23700 PCH_Pc21g23700 | B6HJ58 |
| Baudoinia compniacensis (strain UAMH 10762) (Angels' share fungus) | BAUCODRAFT_274597 | M2M6Z5 |
| Hypocrea atroviridis (strain ATCC 20476/IMI 206040) (Trichoderma atroviride) | TRIATDRAFT_280929 | G9NJ32 |
| Colletotrichum gloeosporioides (strain Cg-14) (Anthracnose fungus) (Glomerella cingulata) | CGLO_06642 | T0LPH0 |
| Cordyceps militaris (strain CM01) (Caterpillar fungus) | CCM_02665 | G3JB34 |
| Pyronema omphalodes (strain CBS 100304) (Pyronema confluens) | PCON_13062 | U4LKE9 |

TABLE 5-continued

Alcohol oxidase enzymes capable of oxidizing long chain alcohols including fatty alcohols (EC 1.1.3.20)

| Organism | Gene names | Accession No. |
|---|---|---|
| Colletotrichum graminicola (strain M1.001/M2/FGSC 10212) (Maize anthracnose fungus) (Glomerella graminicola) | GLRG_08499 | E3QR67 |
| Glarea lozoyensis (strain ATCC 74030/MF5533) | M7I_2117 | H0EHX4 |
| Fusarium oxysporum f. sp. cubense (strain race 4) (Panama disease fungus) | FOC4_g10002493 | N1S969 |
| Fusarium oxysporum f. sp. cubense (strain race 4) (Panama disease fungus) | FOC4_g10011461 | N1RT80 |
| Cochliobolus sativus (strain ND90Pr/ATCC 201652) (Common root rot and spot blotch fungus) (Bipolaris sorokiniana) | COCSADRAFT_295770 | M2TBE4 |
| Mixia osmundae (strain CBS 9802/IAM 14324/JCM 22182/KY 12970) | Mo05571 E5Q_05571 | G7E7S3 |
| Mycosphaerella pini (strain NZE10/CBS 128990) (Red band needle blight fungus) (Dothistroma septosporum) | DOTSEDRAFT_69651 | N1PXR0 |
| Grosmannia clavigera (strain kw1407/UAMH 11150) (Blue stain fungus) (Graphiocladiella clavigera) | CMQ_1113 | F0XC64 |
| Fusarium oxysporum FOSC 3-a | FOYG_03004 | W9IUE5 |
| Fusarium oxysporum FOSC 3-a | FOYG_16040 | W9HNP0 |
| Fusarium oxysporum FOSC 3-a | FOYG_17058 | W9HB31 |
| Nectria haematococca (strain 77-13-4/ATCC MYA-4622/FGSC 9596/MPVI) (Fusarium solani subsp. pisi) | NECHADRAFT_37686 | C7YQL1 |
| Nectria haematococca (strain 77-13-4/ATCC MYA-4622/FGSC 9596/MPVI) (Fusarium solani subsp. pisi) | NECHADRAFT_77262 | C7ZJI0 |
| Tuber melanosporum (strain Me128) (Perigord black truffle) | GSTUM_00010376001 | D5GLS0 |
| Ajellomyces dermatitidis (strain SLH14081) (Blastomyces dermatitidis) | BDBG_07633 | C5JYI9 |
| Chaetomium cdobosum (strain ATCC 6205/CBS 148.51/DSM 1962/NBRC 6347/NRRL 1970) (Soil fungus) | CHGG_09885 | Q2GQ69 |
| Candida tenuis (strain ATCC 10573/BCRC 21748/CBS 615/JCM 9827/NBRC 10315/NRRL Y-1498/VKM Y-70) (Yeast) | CANTEDRAF_1108652 | G3B9Z1 |
| Trichophyton rubrum CBS 100081 | H102_00622 | A0A022VKY4 |
| Pyrenophora teres f. teres (strain 0-1) (Barley net blotch fungus) (Drechslera teres f. teres) | PTT_09421 | E3RLZ3 |
| Colletotrichum gloeosporioides (strain Nara gc5) (Anthracnose fungus) (Glomerella cingulata) | CGGC5_4608 | L2GB29 |
| Gibberella zeae (Wheat head blight fungus) (Fusarium graminearum) | FG05_06918 | A0A016PCS4 |
| Trichophyton soudanense CBS 452.61 | H105_00612 | A0A022Y6A6 |
| Sclerotinia sclerotiorum (strain ATCC 18683/1980/Ss-1) (White mold) (Whetzelinia sclerotiorum) | SS1G_07437 | A7EQ37 |
| Fusarium oxysporum f. sp. pisi HDV247 | FOVG_14401 | W9NWU8 |
| Fusarium oxysporum f. sp. pisi HDV247 | FOVQ_02874 | W9Q5V3 |
| Ustilago hordei (strain Uh4875-4) (Barley covered smut fungus) | UHOR_03009 | I2G1Z4 |
| Sporisorium reilianum (strain SRZ2) (Maize head smut fungus) | sr12985 | E6ZYF7 |
| Bipolaris zeicola 26-R-13 | COCCADRAFT_81154 | W6YIP8 |
| Melampsora larici-populina (strain 98AG31/pathotype 3-4-7) (Poplar leaf rust fungus) | MELLADRAFT_78490 | F4RUZ8 |
| Fusarium oxysporum f. sp. lycopersici (strain 4287/CBS 123668/FGSC 9935/NRRL 34936) (Fusarium vascular wilt of tomato) | FOXG_01901 | J9MG95 |
| Fusarium oxysporum f. sp. lycopersici (strain 4287/CBS 123668/FGSC 9935/NRRL 34936) (Fusarium vascular wilt of tomato) | FOXG_11941 | J9N9S4 |
| Bipolaris victoriae FI3 | COCVIDRAFT_39053 | W7EMJ8 |
| Debaryomyces hansenii (strain ATCC 36239/CBS 767/JCM 1990/NBRC 0083/IGC 2968) (Yeast) (Torulaspora hansenii) | DEHA2E04268g | Q6BQL4 |
| Clavispora lusitaniae (strain ATCC 42720) (Yeast) (Candida lusitaniae) | CLUG_01505 | C4XZX3 |
| Candida albicans (strain WO-1) (Yeast) | CAWG_02023 | C4YME4 |

TABLE 5-continued

Alcohol oxidase enzymes capable of oxidizing long chain alcohols including fatty alcohols (EC 1.1.3.20)

| Organism | Gene names | Accession No. |
|---|---|---|
| Trichophyton rubrum MR850 | H100_00625 | A0A022U0Q2 |
| Candida dubliniensis (strain CD36/ATCC MYA-646/CBS 7987/NCPF 3949/NRRL Y-17841) (Yeast) | CD36_32890 | B9WMC7 |
| Starmerella bombicola | AOX1 | A0A024FB95 |
| Thielavia heterothallica (strain ATCC 42464/BCRC 31852/DSM 1799) (Myceliophthora thermophila) | MYCTH_103590 | G2QJL7 |
| Claviceps purpurea (strain 20.1) (Ergot fungus) (Sphacelia segetum) | CPUR_07614 | M1WFI4 |
| Aspergillus oryzae (strain ATCC 42149/RIB 40) (Yellow koji mold) | AO090023000571 | Q2UH61 |
| Dictyostelium discoideum (Slime mold) | DDB_0184181 DDB_G0292042 | Q54DT6 |
| Triticum urartu (Red wild einkorn) (Crithodium urartu) | TRIUR3_22733 | M7YME5 |
| Solanum tuberosum (Potato) | PGSC0003DMG400017211 | M1BG07 |
| Oryza saliva subsp. japonica (Rice) | OSJNBb0044B19.5 LOC_Os10g33540 | Q8W5P8 |
| Oryza sativa subsp. japonica (Rice) | OJ1234_B11.20 Os02g0621800 | Q6K9N5 |
| Oryza sativa subsp. japonica (Rice) | OSJNBa0001K12.5 LOC_Os10g33520 | Q8W5P3 |
| Zea mays (Maize) | ZEAMMTB73_809149 | C0P3J6 |
| Citrus clementina | CICLE_v10011111mg | V4S9P4 |
| Citrus clementina | CICLE_v10018992mg | V4U4C9 |
| Citrus clementina | CICLE_v10004405mg | V4S9D3 |
| Citrus clementina | CICLE_v10004403mg | V4R2Z6 |
| Morus notabilis | L484_011703 | W9RIK0 |
| Morus notabilis | L484_005930 | W9RET7 |
| Medicago truncatula (Barrel medic) (Medicago tribuloides) | MTR_1g075650 | G7I4U3 |
| Arabidopsis thaliana (Mouse-ear cress) | | Q8LDP0 |
| Medicago truncatula (Barrel medic) (Medicago tribuloides) | MTR_4g081080 | G7JF07 |
| Simmondsia chinensis (Jojoba) (Buxus chinensis) | | L7VFV2 |
| Prunus persica (Peach) (Amygdalus persica) | PRUPE_ppa018458mg | M5VXL1 |
| Aphanomyces astaci | H257_07411 | W4GI89 |
| Aphanomyces astaci | H257_07412 | W4GI44 |
| Aphanomyces astaci | H257_07411 | W4GKE3 |
| Aphanomyces astaci | H257_07411 | W4GK29 |
| Aphanomyces astaci | H257_07411 | W4GJ79 |
| Aphanomyces astaci | H257_07411 | W4GI38 |
| Phaeodactylum tricornutum (strain CCAP 1055/1) | PHATRDRAFT_48204 | B7G6C1 |
| Hordeum vulgare var. distichum (Two-rowed barley) | | F2E4R4 |
| Hordeum vulgare var. distichum (Two-rowed barley) | | F2DZG1 |
| Hordeum vulgare var. distichum (Two-rowed barley) | | M0YPG7 |
| Hordeum vulgare var. distichum (Two-rowed barley) | | M0YPG6 |
| Hordeum vulgare var. distichum (Two-rowed barley) | | F2CUY4 |
| Ricinus communis (Castor bean) | RCOM_0867830 | B9S1S3 |
| Brassica rapa subsp. pekinensis (Chinese cabbage) (Brassica pekinensis) | BRA014947 | M4DEM5 |
| Ricinus communis (Castor bean) | RCOM_0258730 | B9SV13 |
| Brassica rapa subsp. pekinensis (Chinese cabbage) (Brassica pekinensis) | BRA001912 | M4CCI2 |
| Brassica rapa subsp. pekinensis (Chinese cabbage) (Brassica pekinensis) | BRA012548 | M4D7T8 |
| Brassica rapa subsp. pekinensis (Chinese cabbage) (Brassica pekinensis) | BRA024190 | M4E5Y6 |
| Brassica rapa subsp. pekinensis (Chinese cabbage) (Brassica pekinensis) | BRA015283 | M4DFL0 |
| Ricinus communis (Castor bean) | RCOM_1168730 | B9SS54 |
| Zea mays (Maize) | | C4J691 |
| Oryza glaberrima (African rice) | | I1P2B7 |
| Zea mays (Maize) | | B6SXM3 |
| Zea mays (Maize) | | C0HFU4 |
| Aegilops tauschii (Tausch's goatgrass) (Aegilops squarrosa) | F775_19577 | R7W4J3 |
| Solanum habrochaites (Wild tomato) (Lycopersicon hirsutum) | | R9R6T0 |
| Physcomitrella patens subsp. patens (Moss) | PHYPADRAFT_124285 | A9S535 |
| Physcomitrella patens subsp. patens (Moss) | PHYPADRAFT_113581 | A9RG13 |
| Physcomitrella patens subsp. patens (Moss) | PHYPADRAFT_182504 | A9S9A5 |
| Solarium pennellii (Tomato) (Lycopersicon pennellii) | | R9R6Q1 |
| Vitis vinifera (Grape) | VIT_02s0087g00630 | F6HJ27 |
| Vitis vinifera (Grape) | VIT_07s0005g03780 | F6HZM3 |
| Vitis vinifera (Grape) | VIT_05s0049g01400 | F6H8T4 |
| Vitis vinifera (Grape) | VITISV_019349 | A5AH38 |
| Capsella rubella | CARUB_v10013046mg | R0HIT3 |
| Capsella rubella | CARUB_v10004212mg | R0GUX4 |
| Capsella rubella | CARUB_v10004208mg | R0F3X6 |
| Capsella rubella | CARUB_v10012453mg | R0ILD0 |
| Capsella rubella | CARUB_v10004208mg | R0GUX1 |
| Eutrema salsugineum (Saltwater cress) (Sisymbrium salsugineum) | EUTSA_v10024496mg | V4MD54 |
| Eutrema salsugineum (Saltwater cress) (Sisymbrium salsugineum) | EUTSA_v10020141mg | V4NM59 |

TABLE 5-continued

Alcohol oxidase enzymes capable of oxidizing long chain alcohols including fatty alcohols (EC 1.1.3.20)

| Organism | Gene names | Accession No. |
|---|---|---|
| Eutrema salsugineum (Saltwater cress) (Sisymbrium salsugineum) | EUTSA_v10024496mg | V4LUR9 |
| Eutrema salsugineum (Saltwater cress) (Sisymbrium salsugineum) | EUTSA_v10024528mg | V4P767 |
| Eutrema salsugineum (Saltwater cress) (Sisymbrium salsugineum) | EUTSA_v10006882mg | V4L2P6 |
| Selaginella moellendorffii (Spikemoss) | SELMODRAFT_87684 | D8R6Z6 |
| Selaginella moellendorffii (Spikemoss) | SELMODRAFT_87621 | D8R6Z5 |
| Selaginella moellendorffii (Spikemoss) | SELMODRAFT_74601 | D8QN81 |
| Selaginella moellendorffii (Spikemoss) | SELMODRAFT_73531 | D8QN82 |
| Sorghum bicolor (Sorghum) (Sorghum vulgare) | Sb04g026390 SORBIDRAFT_04g026390 | C5XXS4 |
| Sorghum bicolor (Sorghum) (Sorghum vulgare) | Sb04g026370 SORBIDRAFT_04g026370 | C5XXS1 |
| Sorghum bicolor (Sorghum) (Sorghum vulgare) | Sb01g019470 SORBIDRAFT_01g019470 | C5WYH6 |
| Sorghum bicolor (Sorghum) (Sorghum vulgare) | Sb01g019480 SORBIDRAFT_01g019480 | C5WYH7 |
| Sorghum bicolor (Sorghum) (Sorghum vulgare) | Sb01g019460 SORBIDRAFT_01g019460 | C5WYH5 |
| Solanum pimpinellifolium (Currant tomato) (Lycopersicon pimpinellifolium) | | R9R6J2 |
| Phaseolus vulgaris (Kidney bean) (French bean) | PHAVU_007G124200g | V7BGM7 |
| Phaseolus vulgaris (Kidney bean) (French bean) | PHAVU_011G136600g | V7AI35 |
| Phaseolus vulgaris (Kidney bean) (French bean) | PHAVU_001G162800g | V7D063 |
| Solanum tuberosum (Potato) | PGSC0003DMG400024294 | M1C923 |
| Solanum tuberosum (Potato) | PGSC0003DMG400018458 | M1BKV4 |
| Solanum tuberosum (Potato) | PGSC0003DMG400018458 | M1BKV3 |
| Glycine max (Soybean) (Glycine hispida) | | K7LK61 |
| Glycine max (Soybean) (Glycine hispida) | | K7KXQ9 |
| Populus trichocarpa (Western balsam poplar) (Populus balsamifera subsp. trichocarpa) | POPTR_0008s16920g | B9HKS3 |
| Picea sitchensis (Sitka spruce) (Pinus sitchensis) | | B8LQ84 |
| Populus trichocarpa (Western balsam poplar) (Populus balsamifera subsp. trichocarpa) | POPTR_0004s24310g | U5GKQ5 |
| Populus trichocarpa (Western balsam poplar) (Populus balsamifera subsp. trichocarpa) | POPTR_0010s07980g | B9HSG9 |
| Glycine max (Soybean) (Glycine hispida) | | I1N9S7 |
| Glycine max (Soybean) (Glycine hispida) | | I1LSK5 |
| Setaria italica (Foxtail millet) (Panicum italicum) | Si034362m.g | K4A658 |
| Solanum lycopersicum (Tomato) (Lycopersicon esculentum) | Solyc09g072610.2 | K4CUT7 |
| Setaria italica (Foxtail millet) (Panicum italicum) | Si016380m.g | K3YQ38 |
| Solanum lycopersicum (Tomato) (Lycopersicon esculentum) | | R9R6I9 |
| Solanum lycopersicum (Tomato) (Lycopersicon esculentum) | Solyc09g090350.2 | K4CW61 |
| Solanum lycopersicum (Tomato) (Lycopersicon esculentum) | Solyc08g005630.2 | K4CI54 |
| Solanum lycopersicum (Tomato) (Lycopersicon esculentum) | Solyc08g075240.2 | K4CMP1 |
| Setaria italica (Foxtail millet) (Panicum italicum) | Si034359m.g | K4A655 |
| Setaria italica (Foxtail millet) (Panicum italicum) | Si034354m.g | K4A650 |
| Mimulus guttatus (Spotted monkey flower) (Yellow monkey flower) | MIMGU_mgv1a001896mg | A0A022PU07 |
| Mimulus guttatus (Spotted monkey flower) (Yellow monkey flower) | MIMGU_mgv1a022390mg | A0A022RAV4 |
| Mimulus guttatus (Spotted monkey flower) (Yellow monkey flower) | MIMGU_mgv1a001868mg | A0A022S2E6 |
| Mimulus guttatus (Spotted monkey flower) (Yellow monkey flower) | MIMGU_mgv1a001883mg | A0A022S275 |
| Mimulus guttatus (Spotted monkey flower) (Yellow monkey flower) | MIMGU_mgv1a001761mg | A0A022QNF0 |
| Musa acuminata subsp. malaccensis (Wild banana) (Musa malaccensis) | | M0SNA8 |
| Musa acuminata subsp. malaccensis (Wild banana) (Musa malaccensis) | | M0RUT7 |
| Musa acuminata subsp. malaccensis (Wild banana) (Musa malaccensis) | | M0RUK3 |
| Saprolegnia diclina VS20 | SDRG_10901 | T0RG89 |
| Brachypodium distachyon (Purple false brome) (Trachynia distachya) | BRADI3G49085 | I1IBP7 |
| Brachypodium distachyon | BRADI3G28677 | I1I4N2 |

TABLE 5-continued

Alcohol oxidase enzymes capable of oxidizing long chain alcohols including fatty alcohols (EC 1.1.3.20)

| Organism | Gene names | Accession No. |
|---|---|---|
| (Purple false brome) (*Trachynia distachya*) Brachypodium distachyon (Purple false brome) (*Trachynia distachya*) | BRADI3G28657 | I1I4N0 |
| *Oryza saliva* subsp. *indica* (Rice) | OsI_34012 | B8BHG0 |
| *Oryza sativa* subsp. *indica* (Rice) | OsI_08118 | B8AFT8 |
| *Orvza saliva* subsp. *indica* (Rice) | OsI_34008 | A2Z8H1 |
| *Oryza sativa* subsp. *indica* (Rice) | OsI_34014 | B8BHG1 |
| *Oryza sativa* subsp. *japonica* (Rice) | LOC_Os10g33460 | Q7XDG3 |
| *Oryza sativa* subsp. *japonica* (Rice) | Os10g0474800 | Q0IX12 |
| *Oryza saliva* subsp. *japonica* (Rice) | 0s10g0474966 | C7J7R1 |
| *Oryza saliva* subsp. *japonica* (Rice) | OSJNBa0001K12.13 | Q8W5N7 |
| *Oryza sativa* subsp. *japonica* (Rice) | OsJ_31873 | B9G683 |
| *Oryza sativa* subsp. *japonica* (Rice) | OsJ_31875 | B9G684 |
| *Oryza sativa* subsp. *japonica* (Rice) | OSJNBa0001K12.3 | Q8W5P5 |
| *Arabidopsis lyrata* subsp. *lyrata* (Lyre-leaved rock-cress) | ARALYDRAFT_470376 | D7KDA3 |
| *Arabidopsis lyrata* subsp. *lyrata* (Lyre-leaved rock-cress) | ARALYDRAFT_479855 | D7L3B6 |
| *Arabidopsis lyrata* subsp. *lyrata* (Lyre-leaved rock-cress) | ARALYDRAFT_491906 | D7MDA9 |
| *Arabidopsis lyrata* subsp. *lyrata* (Lyre-leaved rock-cress) | ARALYDRAFT_914728 | D7MGS9 |

In some embodiments, the present disclosure teaches a recombinant microorganism comprising a deletion, disruption, mutation, and or reduction in the activity of one or more endogenous a (fatty) alcohol oxidase YALI0B14014g (FAO1).

Thus, in some embodiments, the recombinant microorganism of the present disclosure will comprise deletions or other disruptions in endogenous genes encoding proteins exhibiting at least 100%, 99%, 98%, 97%, 95%, 94%, 93%, 92%, 91%, or 90% sequence identity with the proteins encoded by a (fatty) alcohol oxidase YALI0B14014g (FAO1).

Thus, in some embodiments, the recombinant microorganism of the present disclosure will comprise deletions in endogenous genes encoding proteins exhibiting at least 100%, 99%, 98%, 97%, 95%, 94%, 93%, 92%, 91%, or 90% sequence identity with uniprot database IDs Q6CEP8 (FAO1).

Acetyl Transferase

The present disclosure describes enzymes that convert alcohols to fatty acetates.

In some embodiments, an acetyl transferase is used to catalyze the conversion of a fatty alcohol to a fatty acetate. An acetyl transferase is an enzyme that has the ability to produce an acetate ester by transferring the acetyl group from acetyl-CoA to an alcohol. In some embodiments, the acetyl transferase may have an EC number of 2.3.1.84.

The acetyl transferase, or the nucleic acid sequence that encodes it, can be isolated from various organisms, including but not limited to, organisms of the species *Candida glabrata, Saccharomyces cerevisiae, Danaus plexippus, Heliotis virescens, Bombyx mori, Agrotis ipsilon, Agrotis segetum, Euonymus alatus, Homo sapiens, Lachancea thermotolerans* and *Yarrowia lipolytica*. In exemplary embodiments, the acetyl transferase comprises a sequence selected from GenBank Accession Nos. AY242066, AY242065, AY242064, AY242063, AY242062, EHJ65205, ACX53812, NP_001182381, EHJ65977, EHJ68573, KJ579226, GU594061, KTA99184.1, AIN34693.1, AY605053, XP_002552712.1, XP_503024.1, and XP_505595.1, and XP_505513.1. Exemplary acetyl transferase enzymes are listed in Table 5d. Additional exemplary acetyl transferase peptides may be found in US2010/0199548, which is herein incorporated by reference.

TABLE 5d

Exemplary acetyl transferase enzymes

| Organism | Enzyme ID |
|---|---|
| *Candida glabarata* | KTA99184.1 |
| *Agrotis segetum* | AIN34693.1 |
| *Homo sapiens* | AY605053 |
| *Lachancea thermotolerans* | XP_002552712.1 |
| *Yarrowia lipolytica* | XP_503024.1 |
| *Yarrowia lipolytica* | XP_505595.1 |
| *Yarrowia lipolytica* | XP_505513.1 |

Fatty Acyl-ACP Thioesterase

Acyl-ACP thioesterase releases free fatty acids from Acyl-ACPs, synthesized from de novo fatty acid biosynthesis. The reaction terminates fatty acid biosynthesis. In plants, fatty acid biosynthesis occurs in the plastid and thus requires plastid-localized acyl-ACP thioesterases. The main products of acyl-ACP thioesterase are oleate (C18:0) and to a lesser extent palmitate (C16:0) in the vegetative tissues of all plants. The released free fatty acids are re-esterified to coenzyme A in the plastid envelope and exported out of plastid.

There are two isoforms of acyl-ACP thioesterase, FatA and FatB. Substrate specificity of these isoforms determines the chain length and level of saturated fatty acids in plants. The highest activity of FatA is with C18:1-ACP. FatA has very low activities towards other acyl-ACPs when compared with C18:1-ACP. FatB has highest activity with C16:0-ACP. It also has significant high activity with C18:1-ACP, followed by C18:0-ACP and C16:1-ACP. Kinetics studies of FatA and FatB indicate that their substrate specificities with different acyl-ACPs came from the Kcat values, rather than from Km. Km values of the two isoforms with different substrates are similar, in the micromolar order. Domain swapping of FatA and FatB indicates the N-terminus of the isoforms determines their substrate specificities (Salas J J and Ohlrogge J B (2002) Characterization of substrate specificity of plant FatA and FatB acyl-ACP thioesterases. Arch Biochem Biophys 403(1): 25-34). For those plants which predominantly accumulate medium-chain length saturated fatty acids in seeds, they evolved with specialized FatB and/or FatA thioesterases (Voelker T and Kinney A J (2001) Variations in the biosynthesis of seed-storage lipids. Annu Rev Plant Physiol Plant Mol Biol 52: 335-361). For example, laurate (12:0) is the predominant seed oil in coconut. Correspondingly, the medium-chain specific acyl-ACP thioesterase activity was detected in coconut seeds.

In some embodiments, the present disclosure teaches a recombinant microorganism comprising a deletion, disruption, mutation, and or reduction in the activity of YALI0E16016g (FAT1).

Thus, in some embodiments, the recombinant microorganism of the present disclosure will comprise deletions or other disruptions in endogenous genes encoding proteins exhibiting at least 100%, 99%, 98%, 97%, 95%, 94%, 93%, 92%, 91%, or 90% sequence identity with the protein encoded by YALI0E16016g (FAT1).

Thus, in some embodiments, the recombinant microorganism of the present disclosure will comprise deletions in endogenous genes encoding proteins exhibiting at least 100%, 99%, 98%, 97%, 95%, 94%, 93%, 92%, 91%, or 90% sequence identity with uniprot database ID Q6C5Q8 (FAO1).

Acyl-CoA Oxidase

Acyl-CoA oxidase (ACO) acts on CoA derivatives of fatty acids with chain lengths from 8 to 18. They are flavoenzymes containing one noncovalently bound FAD per subunit and belong to the same superfamily as mitochondrial acyl-CoA dehydrogenases. Like mitochondrial fatty acyl-CoA dehydrogenases, peroxisomal acyl-CoA oxidases catalyze the initial and rate-determining step of the peroxisomal fatty acid β-oxidation pathway, i.e. α,β-dehydrogenation of acyl-CoA, yielding trans-2-enoyl-CoA in the reductive half-reaction. In the oxidative half-reaction of peroxisomal acyl-CoA oxidase, the reduced FAD is reoxidized by molecular oxygen, producing hydrogen peroxide.

Acyl-CoA oxidase is a homodimer and the polypeptide chain of the subunit is folded into the N-terminal alpha-domain, beta-domain, and C-terminal alpha-domain. Functional differences between the peroxisomal acyl-CoA oxidases and the mitochondrial acyl-CoA dehydrogenases are attributed to structural differences in the FAD environments.

In some embodiments, recombinant microorganisms and methods are provided for the production of short chain fatty alcohols, fatty aldehydes and/or fatty acetates. In certain embodiments, the short chain fatty alcohols, fatty aldehydes and/or fatty acetates have carbon chain length shorter than or equal to C16. In some embodiments, the short chain fatty alcohols, fatty aldehydes and/or fatty acetates are produced from long chain fatty acids. In some preferred embodiments of methods to produce short chain pheromones, select enzymes capable of shortening fatty acyl-CoAs in the pheromone biosynthetic pathway are co-expressed with pheromone biosynthetic pathway enzymes. Examples of suitable chain shortening enzymes include FAD-dependent acyl-CoA oxidase. In the case of fatty acid molecules with an even number of carbons, chain shortening enzymes produce a molecule of acetyl-CoA, and a fatty acyl-CoA shortened by two carbons. Fatty acid molecules with an odd number of carbons are oxidized in a similar fashion producing acetyl-CoA molecules during every round of oxidation until the chain-length is reduced to 5 carbons. In the final cycle of oxidation, this 5-carbon acyl-CoA is oxidized to produce acetyl-CoA and propionyl-CoA.

Figure 40:
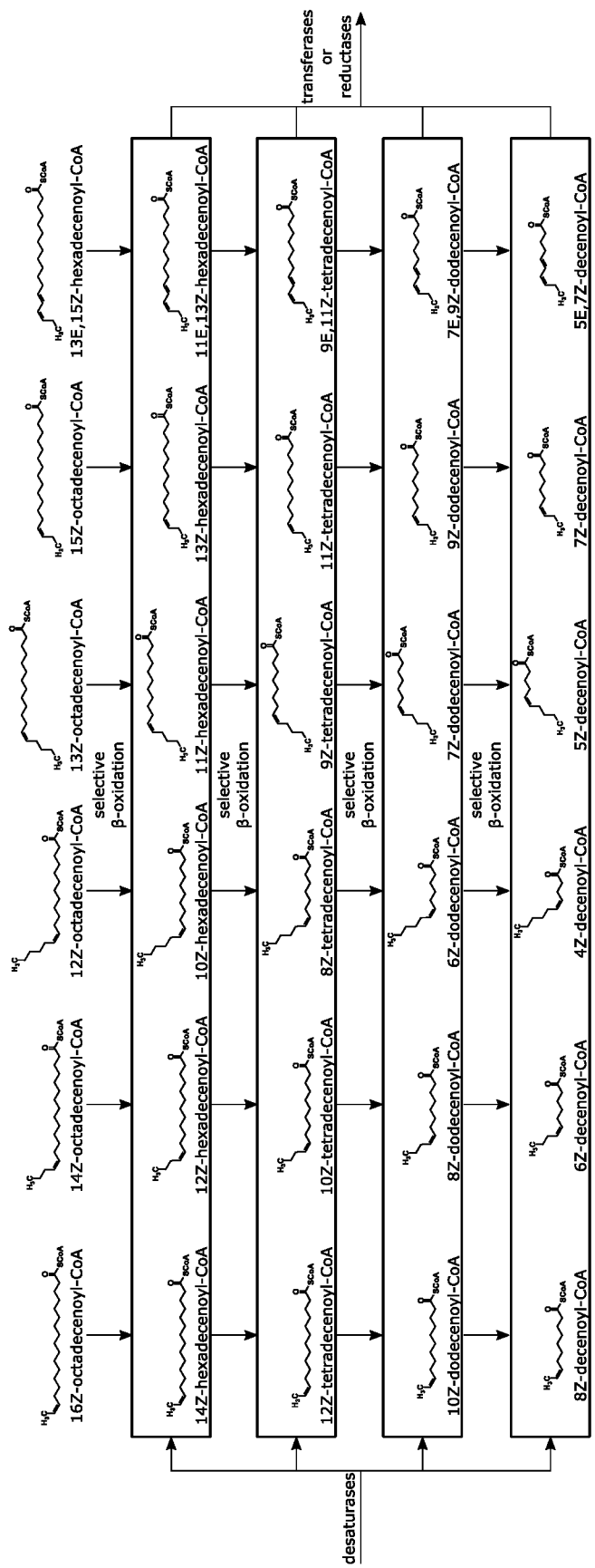
FIG. 40 shows examples of acyl-CoA intermediates generated through selective β-oxidation controlled by acyl-CoA oxidase activity.

It is known that acyl-CoA oxidases exhibit varying specificity towards substrates with different chain-length (FIG. 40). Therefore, controlling the degree of fatty acyl-CoA truncation relies on engineering or selecting the appropriate enzyme variant. Examples of acyl-CoA oxidases that are suitable for this purpose are listed in Table 5a.

In a further embodiment, the disclosure provides a recombinant microorganism capable of producing a mono- or poly-unsaturated ≤$C_{18}$ fatty alcohol from an endogenous or exogenous source of saturated $C_6$-$C_{24}$ fatty acid, wherein the recombinant microorganism comprises: (a) at least one exogenous nucleic acid molecule encoding a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA; (b) at least one exogenous nucleic acid molecule encoding an acyl-CoA oxidase that catalyzes the conversion of the mono- or poly-unsaturated $C_6$-$C_{24}$ fatty acyl-CoA from (a) into a mono- or poly-unsaturated ≤$C_{18}$ fatty acyl-CoA after one or more successive cycle of acyl-CoA oxidase activity, with a given cycle producing a mono- or poly-unsaturated $C_4$-$C_{22}$ fatty acyl-CoA intermediate with a two carbon truncation relative to a starting mono- or poly-unsaturated $C_6$-$C_{24}$ fatty acyl-CoA substrate in that cycle; and (c) at least one exogenous nucleic acid molecule encoding a fatty alcohol forming fatty acyl reductase that catalyzes the conversion of the mono- or poly-unsaturated ≤C18 fatty acyl-CoA from (b) into the corresponding mono- or poly-unsaturated ≤C18 fatty alcohol. In some embodiments, the fatty acyl desaturase is selected from an *Argyrotaenia velutinana*, *Spodoptera litura*, *Sesamia inferens*, *Manduca sexta*, *Ostrinia nubilalis*, *Helicoverpa zea*, *Choristoneura rosaceana*, *Drosophila melanogaster*, *Spodoptera littoralis*, *Lampronia capitella*, *Amyelois transitella*, *Trichoplusia ni*, *Agrotis segetum*, *Ostrinia furnicalis*, and *Thalassiosira pseudonana* derived fatty acyl desaturase. In some embodiments, the fatty acyl desaturase has at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, or 50% sequence identity to a fatty acyl desaturase selected from the group consisting of: SEQ ID NOs: 39, 49-54, 58-63, 78-80 and GenBank Accession nos. AF416738, AGH12217.1, AII21943.1, CAJ43430.2, AF441221, AAF81787.1, AF545481. AJ271414, AY362879, ABX71630.1, NP001299594.1, Q9N9Z8, ABX71630.1 and AIM40221.1. In some embodiments, the acyl-CoA oxidase is selected from Table 5a. In other embodiments, the fatty alcohol forming fatty acyl reductase is selected from an *Agrotis segetum*, *Spodoptera exigua*, *Spodoptera littoralis*, *Euglena gracilis*. *Yponometua evonymellus* and *Helicoverpa armigera* derived fatty alcohol forming fatty acyl reductase. In further embodiments, the fatty alcohol forming fatty acyl reductase has at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, or 50% sequence identity to a fatty alcohol forming fatty acyl reductase selected from the group consisting of: SEQ ID NOs: 1-3, 32, 41-48, 55-57, 73, 75, 77 and 82. In some embodiments, the recombinant microorganism is a yeast selected from the group consisting of *Yarrowia lipolytica*, *Saccharomyces cerevisiae*, *Candida albicans*, *Candida tropicalis* and *Candida viswanathii*.

In some preferred embodiments of methods to produce fatty alcohols, fatty aldehydes and/or fatty acetates, one or more genes of the microbial host encoding acyl-CoA oxidases are deleted or down-regulated to eliminate or reduce the truncation of desired fatty acyl-CoAs beyond a desired chain-length. Such deletion or down-regulation targets include but are not limited to *Y. lipolytica* POX1 (YALI0E32835g), *Y. lipolytica* POX2(YALI0F0857g), *Y.* lipolytica POX3(YALI0D24750g), Y. lipolytica POX4 (YALI0E27654g), Y. lipolytica POX5(YALI0C23859g). Y. lipolytica POX6(YALI0E06567g); S. cerevisiae POX1 (YGL205W); Candida POX2 (CaO19.1655, CaO19.9224. CTRG_02374, M18259), Candida POX4 (CaO19.1652, CaO19.9221, CTRG_02377, M12160), and Candida POX5 (CaO19.5723, CaO19.13146, CTRG_02721, M12161).

In some embodiments, the present disclosure teaches a recombinant microorganism comprising a deletion, disruption, mutation, and or reduction in the activity of one or more acyl-CoA oxidases selected from the group consisting of POX1(YALI0E32835g), Y. lipolytica POX2 (YALI0F10857g), Y. lipolytica POX3(YALI0D24750g), Y. lipolytica POX4(YALI0E27654g), Y. lipolytica POX5 (YALI0C23859g), Y. lipolytica POX6(YALI0E06567g).

Thus, in some embodiments, the recombinant microorganism of the present disclosure will comprise deletions or other disruptions in endogenous genes encoding proteins exhibiting at least 100%, 99%, 98%, 97%, 95%, 94%, 93%, 92%, 91%, or 90% sequence identity with the proteins encoded by POX1 (YALI0E32835g), Y. lipolytica POX2 (YALI0F10857g). Y. lipolytica POX3 (YALI0D24750g), Y. lipolytica POX4 (YALI0E27654g), Y. lipolytica POX5 (YALI0C23859g), Y. lipolytica POX6 (YALI0E06567g).

Thus, in some embodiments, the recombinant microorganism of the present disclosure will comprise deletions in endogenous genes encoding proteins exhibiting at least 100%, 99%, 98%, 97%, 95%, 94%, 93%, 92%, 91%, or 90% sequence identity with uniprot database ID POX1(O74934), Y. lipolytica POX2 (O74935), Y. lipolytica POX3 (O74936), Y. lipolytica POX4 (F2Z627), Y. lipolytica POX5 (F2Z630), K. lipolytica POX6 (Q6C6T0).

In some embodiments, a recombinant microorganism capable of producing a mono- or poly-unsaturated ≤$C_{18}$ fatty alcohol, fatty aldehyde and/or fatty acetate from an endogenous or exogenous source of saturated $C_6$-$C_{24}$ fatty acid is provided, wherein the recombinant microorganism expresses one or more acyl-CoA oxidase enzymes, and wherein the recombinant microorganism is manipulated to delete, disrupt, mutate, and/or reduce the activity of one or more endogenous acyl-CoA oxidase enzymes. In some embodiments, the one or more acyl-CoA oxidase enzymes being expressed are different from the one or more endogenous acyl-CoA oxidase enzymes being deleted or downregulated. In some embodiments, the recombinant microorganism further expresses pheromone biosynthetic pathway enzymes. In further embodiments, the pheromone biosynthetic pathway enzymes comprise one or more fatty acyl desaturase and/or fatty acyl conjugase. In yet further embodiments, the pheromone biosynthetic pathway enzymes comprise one or more fatty alcohol forming fatty acyl reductase. In some embodiments, the one or more acyl-CoA oxidase enzymes that are expressed are selected from Table 5a. In other embodiments, the one or more acyl-CoA oxidase enzymes that are expressed regulate chain length of the mono- or poly-unsaturated ≤$C_{18}$ fatty alcohol, fatty aldehyde and/or fatty acetate. In some embodiments, the one or more endogenous acyl-CoA oxidase enzymes that are deleted, disrupted, mutated, or downregulated are selected from Y. lipolytica POX1(YALI0E32835g), Y. lipolytica POX2(YALI0F10857g), Y. lipolytica POX3 (YALI0D24750g), Y. lipolytica POX4(YALI0E27654g), Y. lipolytica POX5(YALI0C23859g), Y. lipolytica POX6 (YALI0E06567g); S. cerevisiae POX1(YGL205W): Candida POX2 (CaO19.1655, CaO19.9224, CTRG_02374, M18259), Candida POX4 (CaO19.1652, CaO19.9221, CTRG_02377, M12160), and Candida POX5 (CaO19.5723, CaO19.13146, CTRG_02721, M12161). In other embodiments, the one or more endogenous acyl-CoA oxidase enzymes that are deleted, disrupted, mutated, or downregulated control chain length of the mono- or poly-unsaturated ≤$C_{18}$ fatty alcohol, fatty aldehyde and/or fatty acetate.

In some embodiments, a method of producing a mono- or poly-unsaturated ≤$C_{18}$ fatty alcohol, fatty aldehyde and/or fatty acetate from an endogenous or exogenous source of saturated $C_6$-$C_{24}$ fatty acid are provided, wherein the method comprises introducing into or expressing in a recombinant microorganism at least one endogenous or exogenous nucleic acid molecule encoding an acyl-CoA oxidase and introducing a deletion, insertion, or loss of function mutation in one or more gene encoding an acyl-CoA oxidase, wherein the at least one endogenous or exogenous nucleic acid molecule encoding an acyl-CoA oxidase being introduced or expressed is different from the one or more gene encoding an acyl-CoA oxidase being deleted or downregulated. In some embodiments, the method further comprises introducing into or expressing in the recombinant microorganism at least one endogenous or exogenous nucleic acid molecule encoding a fatty acyl desaturase and/or fatty acyl conjugase. In further embodiments, the method further comprises introducing into or expressing in the recombinant microorganism at least one endogenous or exogenous nucleic acid molecule encoding a fatty alcohol forming fatty acyl reductase. In some embodiments, the least one endogenous or exogenous nucleic acid molecule encodes an acyl-CoA oxidase selected from Table 5a. In other embodiments, the least one endogenous or exogenous nucleic acid molecule encodes an acyl-CoA oxidase that regulates chain length of the mono- or poly-unsaturated $C_6$-$C_{24}$ fatty alcohol, fatty aldehyde and/or fatty acetate. In some embodiments, the one or more gene being deleted or downregulated encodes an acyl-CoA oxidase selected from Y. lipolytica POX1(YALI0E32835g), Y. lipolytica POX2(YALI0F10857g), Y. lipolytica POX3 (YALI0D24750g), Y. lipolytica POX4(YALI0E27654g), Y. lipolytica POX5(YALI0C23859g), Y. lipolytica POX6 (YALI0E06567g); S. cerevisiae POX1(YGL205W): Candida POX2 (CaO19.1655, CaO19.9224, CTRG_02374, M18259), Candida POX4 (CaO19.1652, CaO19.9221, CTRG_02377, M12160), and Candida POX5 (CaO19.5723, CaO19.13146, CTRG_02721, M12161). In other embodiments, the one or more gene being deleted or downregulated encodes an acyl-CoA oxidase that regulates chain length of the mono- or poly-unsaturated $C_6$-$C_{24}$ fatty alcohol, fatty aldehyde and/or fatty acetate.

TABLE 5a

Exemplary acyl-CoA oxidases

| Accession No. | Source Organism |
| --- | --- |
| P07877 | Rama norvegicus |
| A0A178WDE4 | Arabidopsis thaliana |
| P0CZ23 | Arabidopsis thaliana |
| D7KG20 | Arabidopsis lyrata |
| R0I9Z2 | Capsella rubella |
| V4KEW0 | Eutrema salsugineum |
| M4DG68 | Brassica rapa |
| A0A078IZG1 | Brassica napus |
| A0A087HLF00 | Arabis alpina |
| A0A0D3C825 | Brassica oleracea |
| A0A078FAW4 | Brassica napus |
| A0A178W833 | Arabidopsis thaliana |
| Q9LMI7 | Arabidopsis thaliana |
| D7KG21 | Arabidopsis lyrata |
| A0A0D3C827 | Brassica oleracea |
| M4DG69 | Brassica rapa |

TABLE 5a-continued

Exemplary acyl-CoA oxidases

| Accession No. | Source Organism |
|---|---|
| A0A078J4V6 | Brassica napus |
| A0A078FAY6 | Brassica napus |
| V4KY71 | Eutrema salsugineum |
| A0A061E5C2 | Theobroma cacao |
| A0A061E4K0 | Theobroma cacao |
| M1APJ5 | Solanum tuberosum |
| J7KB16 | Prunus persica |
| K4CXY8 | Solanum lycopersicum |
| V4W234 | Citrus clementina |
| G8XNW7 | Malus domestica |
| F6H4X3 | Vitis vinifera |
| A0A068V5Q3 | Coffea canephora |
| M1APJ6 | Solanum tuberosum |
| A0A067KHP0 | Jatropha curcas |
| A0A0D2PZG8 | Gossypium raimondii |
| B9IQS0 | Populus trichocarpa |
| W9RG01 | Morus notabilis |
| A0A0S3SB10 | Vigna angularis var. angularis |
| A0A0L9V573 | Phaseolus angularis |
| A0A0B0PPT6 | Gossypium arboreum |
| A0A0D2T164 | Gossypium raimondii |
| I1KEV4 | Glycine max |
| I1LS94 | Glycine max |
| G7JUZ2 | Medicago truncatula |
| U5FVP5 | Populus trichocarpa |
| V7AGL5 | Phaseolus vulgaris |
| A0A059A0G8 | Eucalyptus grandis |
| A0A059A0N3 | Eucalyptus grandis |
| A0A166AUM6 | Daucus carota subsp. sativus |
| A0A061EB81 | Theobroma cacao |
| A0A0A0LQY1 | Cucumis sativus |
| A0A022QRB0 | Erythranthe guttata |
| A0A0S3SB01 | Vigna angularis var. angularis |
| A0A0D2Q6S9 | Gossypium raimondii |
| B9SGN6 | Ricinus communis |
| A0A0B2PER8 | Glycine soja |
| A0A0B0NGI2 | Gossypium arboreum |
| A0A0D2SKF2 | Gossypium raimondii |
| A0A0B0NRR7 | Gossypium arboreum |
| A0A0J8EFZ4 | Beta vulgaris subsp. vulgaris |
| A0A0J8BLD2 | Beta vulgaris subsp. vulgaris |
| M4DG71 | Brassica rapa |
| W1Q1I1 | Amborella trichopoda |
| M0S864 | Musa acuminata |
| A0A166ABS1 | Daucus carota subsp. sativus |
| A0A1D6CA75 | Triticum aestivum |
| A0A0A9CN11 | Arundo donax |
| A0A1D6CKJ3 | Triticum aestivum |
| A0A164W703 | Daucus carota subsp. sativus |
| A0A1D1YDC5 | Anthurium amnicola |
| I1Q2B7 | Oryza glaberrima |
| A0A0D9WQH3 | Leersia perrieri |
| Q69XR7 | Oryza sativa subsp. japonica |
| A0A1D6CA73 | Triticum aestivum |
| A0A0E0A9E1 | Oryza glumipatula |
| A0A199W504 | Ananas comosus |
| A0A0E0HQR9 | Oryza nivara |
| M0T4I4 | Musa acuminata subsp. malacc. |
| C0PTG5 | Picea sitchensis |
| I1I3F1 | Brachypodium distachyon |
| K3XV57 | Setaria italica |
| A0A0D3GGF4 | Oryza barthii |
| A2YCR4 | Oryza sativa subsp. indica |
| A0A0K9RYF5 | Spinacia oleracea |
| A0A0D3GGF3 | Oryza barthii |
| A0A0D3GGF2 | Oryza barthii |
| A0A0E0HQR8 | Oryza nivara |
| A0A1D6CA72 | Triticum aestivum |
| A3BBK8 | Oryza sativa subsp. japonica |
| A0A199V6E4 | Ananas comosus |
| C5XPR4 | Sorghum bicolor |
| A0A0E0PXN1 | Oryza rufipogon |
| B6U7U8 | Zea mays |
| A0A1D6N7A4 | Zea mays |
| A0A0E0E1N7 | Oryza meridionalis |
| A0A0K9NPK9 | Zostera marina |
| A0A059Q1I9 | Saccharum hybrid cultivar R570 |
| J3MDZ2 | Oryza brachyantha |
| A0A0K9RYH2 | Spinacia oleracea |
| A0A103YIT3 | Cynara cardunculus |
| A0A0E0PXN2 | Otyza rufipogon |
| A9RZ70 | Physcomitrella patens |
| D8TES8 | Selaginella moellendorffii |
| D8SQF1 | Selaginella moellendorffii |
| M5X7E6 | Prunus persica |
| A9T150 | Physcomitrella patens |
| A0A176WTU5 | Marchantia polymorpha |
| A0A0D2QZ34 | Gossypium raimondii |
| A0A1D6N7A2 | Zea mays |
| A0A1D1Z3C0 | Anthurium amnicola |
| A0A067DSI1 | Citrus sinensis |
| A0A1D6CA74 | Triticum aestivum |
| M8CMI0 | Aegilops tauschii |
| A0A0S3SB72 | Vigna angularis var. angularis |
| M0UX36 | Hordeum Vulgare subsp. vulgare |
| A0A1D6CA76 | Triticum aestivum |
| A0A151SDZ7 | Cajanus cajan |
| Q9LNB8 | Arabidopsis thaliana |
| A0A1D6CKJ4 | Triticum aestivum |
| F2EGJ0 | Hordeum vulgare subsp. vulgare |
| A0A0D2U3V1 | Gossypium raimondii |
| M0UX35 | Hordeum vulgare subsp. vulgare |
| M2Y3U7 | Galdieria sulphuraria |
| S8CGJ3 | Genlisea aurea |
| A0A0E0HQS2 | Oryza nivara |
| A0A199VU62 | Ananas comosus |
| M2WTY9 | Galdieria sulphuraria |
| A0A1D6N7A3 | Zea mays |
| A0A0E0HQS0 | Oryza nivara |
| A0A1E5VL23 | Dichanthelium oligosanthes |
| R7Q711 | Chondrus crispus |
| S0F2R6 | Chondrus crispus |
| S0F2T2 | Chondrus crispus |
| A0A0E0HQS1 | Oryza nivara |
| D3BSZ9 | Polysphondylium pallidum |
| A0A0D2WJ11 | Capsaspora owczarzaki strai. |
| R7QDC3 | Chondrus crispus |
| M1VCW4 | Cyanidioschyzon merolae str. |
| F1A2F0 | Dictyostelium purpureum |
| F4PI57 | Dictyostelium fasciculatum |
| Q54II1 | Dictyostelium discoideum |
| A0A0ELBG6 | Oryza punctata |
| A0A151ZK0 | Dictyostelium lacteum |
| M1BZ65 | Solanum tuberosum |
| H8MFT9 | Corralococcus corralloides s. |
| F8CEB4 | Myxococcus fulvus |
| A0A0H4WJP1 | Myxococcus hansupus |
| Q1CYG7 | Myxococcus xanthus |
| F1A3A8 | Dictyostelium purpureum |
| L7UK64 | Myxococcus stipitatus |
| A0A0F7BPX0 | Myxococcus fulvus 124B02 |
| A0A0G4J3N5 | Plasmodiophora brassicae |
| D5H9X3 | Salinibacter ruber strain M8 |
| Q2S1W1 | Salinibacter ruber strain D. |
| A0A085WN59 | Hyalangium minutum |
| A0A0G2ZRH9 | Archangium gephyra |
| A0A0S8HAC5 | Gemmatimonas sp. SM23_52 |
| A0A177Q5I1 | Verrucomicrobia bacterium SC |
| D8TVM2 | Volvox carter f. nagariensis |
| A0A084SWJ9 | Cystobacter violaceus Cb vi76 |
| Q096A6 | Stigmatella aurantiaca stra. |
| R7QMZ0 | Chondrus crispus |
| A0A0G4J5Q9 | Plasmodiophora brassicae |
| A0A0Q9RNC6 | Nocardioides sp. Soil797 |
| A0A010GYG34 | Cryptosporangium arvum DSM 4 |
| A0A098BJC6 | Putative Rhodococcus ruber |
| A0A059ML28 | Rhodococcus aetherivorans |
| N1M744 | Rhodococcus sp. EsD8 |
| W3ZXB8 | Rhodococcus rhodochrous ATCC |
| A0A0A9CKJ6 | 2 Arundo donax |
| F4PQH3 | Distyostelium fasciculatum |
| I0Z1P9 | Coccomyxa subellipsoidea St. |

TABLE 5a-continued

Exemplary acyl-CoA oxidases

| Accession No. | Source Organism |
|---|---|
| A0A076ESS0 | Rhodococcus opacus |
| D3BKV2 | Polysphondylium pallidum |
| X0Q4M3 | Putative Rhodococcus wratislaviensis |
| A0A1D6BHN7 | Triticum aestivum |
| C1AZ37 | Putative Rhodococcus opacus strain B4 |
| M7ZG40 | Triticum urartu |
| W8HEJ3 | Rhodococcus opacus PD630 |
| A0A135GJ74 | Rhodococcus sp. SC4 |
| A0A149ZW75 | Rhodococcus sp. LB1 |
| Q0SF32 | Rhodococcus jostii strain R. |
| J2JJ09 | Rhodococcus sp. JVH1 |
| K8XW36 | Rhodococcus opacus M213 |
| A0A152A546 | Dictyostelium lacteum |
| A0A0Q8ZY28 | Flavobacterium sp. Root901 |
| L2TJT8 | Rhodococcus wratislaviensis |
| I0WB64 | Rhodococcus imtechensis |
| A0A1B1KC92 | Rhodococcus opacus |
| I3C521 | Joostella marina DSM 19592 |
| A0A0F6W8X8 | Sandaracimus amylolyticus |
| I3Z8X9 | Belliella baltica strain DS |
| A0A0J6W3K0 | Mycobacterium obuense |
| A0A0Q7GA13 | Flavobacterium sp. Root420 |
| D3BUR8 | Polysphondylium pallidum |
| A0A098SD35 | Phaeodactylibcicter xiamenensis |
| A0A0D1LF86 | Mycobacterium llatzerense |
| A0A0Q5QHB8 | Williamsia sp. Leaf354 |
| A0A139VJG5 | Mycobacterium phlei DSM 4323 |
| F4PMW9 | Dictyostelium fasciculatum |
| A0A180ERQ3 | Lewinella sp. 4G2 |
| Q8MMS1 | Dictyostelium discoideum |
| A0A101CR99 | Pavobacteriaceae bacterium |
| A0A0Q9TDE2 | Nocardioides sp. Soil805 |
| A0A0Q9DX23 | Flavobacterium sp. Root935 |
| A0A0C1XE41 | Hassallia byssoidea VB512170 |
| A0A0J6W7K0 | Mycobacterium chubuense |
| A0A0H4PGA5 | Cyclobacterium amurskyense |
| A0A1B1WLB8 | Mycobacterium sp. djl-10 |
| A0A0Q8NET9 | Flavobacterium sp. Root186 |
| A0A0J6ZGS8 | Mycobacterium chlorophenolicum |
| A0A085ZIW1 | Flavobacterium reichenbachii |
| J3BZ97 | Flavobacteriuin sp. strain C. |
| A0A066WRY7 | Flavobacterium seoulense |
| K2PYQ1 | Galbibacter marinus |
| A0A0G4IN41 | Plasmodiophora brassicae |
| A0A1B5ZW29 | Arenibacter sp. C-21 |
| A0A1B9DW83 | Flavobacterium piscis |
| A0A099CMP1 | Mycobacterium rufum |
| A0A1B2U6C7 | Pavobacterium johnsoniae |
| A0A0M8YPK7 | Saccharothrix sp. NRRL B-16348 |
| A0A0T1WAX5 | Mycobacterium sp. Root135 |
| K0VAQ4 | Mycobacterium vaccae |
| A0A0Q9JG60 | Mycobacterium sp. Soil538 |
| A0A0M0TLE5 | Flavobacterium sp. VMW |
| A0A151ZK81 | Dictyostelium lacteum |
| K6WMK4 | Putative Gordonia rhizosphera NBRC 16 |
| L8GZJ4 | Acanthamoeba castellanii |
| I4BLB8 | Mycobacterium chubuense |
| H0RLL0 | Putative Gordonia polyisoprenivorans |
| A0A0C1LEQ5 | Prauserella sp. Am3 |
| A0A1E4NXS4 | Pseudonocardia sp. SCN 73-27 |
| A0A1A1YGK6 | Mycobacterium sp. ACS4331 |
| A0A0G3ILT8 | Mycobacterium sp. EPa45 |
| G7GR35 | Putative Gordonia amarae NBRC 15530 |
| A0A1A2LUF7 | Mycobacterium sp. E136 |
| A0A1A3GTN2 | Mycobacterium Mucogenicum |
| A0A1A0RZ49 | Mycobacterium sp. 852002-519.. |
| A0A101AHK0 | Mycobacterium sp. IS-1496 |
| A0A126YBZ9 | Streptomyces albus |
| A0A0X3WJ69 | Streptomyces griseus subsp. |
| A0A1C4KUQ6 | Streptomyces sp. BvitLS-983 |
| A0A1C4T5K2 | Streptomyces sp. OspMP-M43 |
| A0A1A3C0V1 | Mycobacterium sp. E740 |
| A0A0G4IKE4 | Plosmodiophora brassicae |
| K1VUE5 | Streptomyces sp. SM8 |
| D6B5U8 | Streptomyces albus J1074 |
| A0A1C4NBH5 | Streptomyces sp. ScaeMP-6W |
| A0A1C4Q3W7 | Streptomyces sp. IgraMP-1 |
| R7WSQ4 | Rhodococcus rhodnii LMG 5362 |
| A0A0K2YP95 | Rhodococcus sp. RD6.2 |
| XP_011566937 | Plutella xylostella peroxisomal acyl-coenzyme A oxidase 1-like |
| XP_011568279 | Plutella xylostella probable peroxisomal acyl-coenzyme A oxidase 1 |
| XP_011568389.1 | Plutella xylostella probable peroxisomal acyl-coenzyme A oxidase 1 |
| XP_011554180.1 | Plutella xylostella probable peroxisomal acyl-coenzyme A oxidase 1 |
| XP_011549583.1 | Plutella xylostella probable peroxisomal acyl-coenzyme A oxidase 3 |
| XP_011548846.1 | Plutella xylostella probable peroxisomal acyl-coenzyme A oxidase 3 |
| AAP37772 | A. thaliana_Acyl-CoA oxidase-3 (ACX3) |
| XP_011548846.1 | Plutella_xylostella_dbmfjv1x1_core_32_85_1_protein_XP_011548846.1 predicted peroxisomal acyl-coenzyme A oxidase 3 |

Acyl Transferases

In some embodiments, recombinant microorganisms and methods are provided for the production of short chain fatty alcohols, fatty aldehydes and/or fatty acetates. In certain embodiments, the short chain fatty alcohols, fatty aldehydes and/or fatty acetates have carbon chain length shorter than or equal to C18. In some preferred embodiments of methods to produce short chain pheromones, select enzymes which prefer to store short-chain fatty acyl-CoAs are co-expressed with one or more fatty acyl desaturase. Such suitable acyltransferase enzymes are exemplified by heterologous or engineered glycerol-3-phosphate acyl transferases (GPATs), lysophosphatidic acid acyltransferases (LPAATs), glycerolphospholipid acyltransferase (GPLATs) and/or diacylglycerol acyltransferases (DGATs). Examples of acyl transferases that are suitable for this purpose are listed in Table 5b.

In some preferred embodiments of methods to produce fatty alcohols, fatty aldehydes and/or fatty acetates, one or more genes of the microbial host encoding glycerol-3-phosphate acyl transferases (GPATs), lysophosphatidic acid acyltransferases (LPAATs), glycerolphospholipid acyltransferase (GPLATs) and/or diacylglycerol acyltransferases (DGATs) are deleted or downregulated, and replaced with one or more GPATs, LPAATs, GPLATs, or DGATs which prefer to store short-chain fatty acyl-CoAs. Such deletion or downregulation targets include but are not limited to *Y. lipolytica* YALI0C00209g, *Y. lipolytica* YALI0E18964g, *Y. lipolytica* YALI0F19514g, *Y. lipolytica* *Y. lipolytica* YALI0C14014g, *Y. lipolytica* YALI0E16797g, *Y. lipolytica* YALI0E32769g, *Y. lipolytica* YALI0D07986g, *S. cerevisiae* YBL011w, *S. cerevisiae* YDL052c, *S. cerevisiae* YOR175C, *S. cerevisiae* YPR139C, *S. cerevisiae* YNR008w, *S. cerevisiae* YOR245c, *Candida* I503_02577, *Candida* CTRG_02630, *Candida* CaO19.250, *Candida* CaO19.7881. *Candida* CTRG_02437, *Candida* CaO19.1881, *Candida* CaO19.9437, *Candida* CTRG_01687, *Candida* CaO19.1043, *Candida* CaO19.8645, *Candida* CTRG_04750, *Candida* CaO19.13439, *Candida* CTRG_04390, *Candida* CaO19.6941, *Candida* CaO19.14203, and *Candida* CTRG_06209. In other embodiments, the acyltransferase is inserted at the AXP Acid extracellular protease locus (YALI0B05654g).

Thus, in some embodiments, the present disclosure teaches a recombinant microorganism comprising an acyltransferase exhibiting at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 700%, 69%, 68%, 67%, 66%, 65%, 64%, 63%, 62%, 61%, 60%, 59%, 58%, 57%, 56%, 55%, 54%, 53%, 52%, 51%, or 50% sequence identity with any one of SEQ ID Nos. selected from the group consisting of 92.

Thus, in some embodiments, the present disclosure teaches a recombinant microorganism comprising a nucleic acid molecule encoding for an acyltransferase, wherein said nucleic acid molecule exhibits at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50% sequence identity with any one of SEQ ID Nos. selected from the group consisting of 91.

In some embodiments, the present disclosure teaches a recombinant microorganism comprising at least one nucleic acid molecule encoding an acyltransferase having at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50% sequence identity to an acyltransferase selected from the group consisting of SEQ ID NO: 92.

In some embodiments, the present disclosure teaches a recombinant microorganism comprising a deletion, disruption, mutation, and or reduction in the activity of one or more acyltransferases selected from the group consisting of YALI0E32791g (DGA1) and/or YALI0D07986g (DGA2).

Thus, in some embodiments, the recombinant microorganism of the present disclosure will comprise deletions or other disruptions in endogenous genes encoding proteins exhibiting at least 100%, 99%, 98%, 97%, 95%, 94%, 93%, 92%, 91%, or 90% sequence identity with the proteins encoded by YALI0E32791g (DGA1) and YALI0D07986g (DGA2).

Thus, in some embodiments, the recombinant microorganism of the present disclosure will comprise deletions in endogenous genes encoding proteins exhibiting at least 100%, 99%, 98%, 97%, 95%, 94%, 93%, 92%, 91%, or 90% sequence identity with uniprot database ID Q6C3R1 (DGA1) and/or Q6C9V5 (DGA2).

Glycerol-3-phosphate acyltransferase (GPAT)

The present disclosure describes enzymes that catalyze the acylation reaction at the sn-1 position of glycerol 3-phosphate shown as follows:

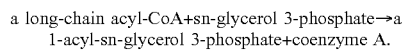

a long-chain acyl-CoA+sn-glycerol 3-phosphate→a 1-acyl-sn-glycerol 3-phosphate+coenzyme A.

Glycerol-3-phosphate acyltransferase (GPAT) catalyzes the acylation reaction at the sn-1 position of glycerol 3-phosphate. The plant cell contains three types of GPAT, which are located in the chloroplasts, mitochondria and cytoplasm. The enzyme in chloroplasts is soluble and uses acyl-(acyl-carrier protein) as the acyl donor, whereas the enzymes in the mitochondria and the cytoplasm are bound to membranes and use acyl-CoA as the acyl donor (Nishida I et al. (1993) The gene and the RNA for the precursor to the plastid-located glycerol-3-phosphate acyltransferase of *Arabidopsis thaliana*. Plant Mol Biol. 21(2): 267-77; Murata N and Tasaka Y (1997) Glycerol-3-phosphate acyltransferase in plants. Biochim Biophys Acta. 1348(1-2):10-16).

Eight GPAT genes have been identified in *Arabidopsis* (Zheng Z et al. (2003) *Arabidopsis* AtGPAT1, a member of the membrane-bound glycerol-3-phosphate acyltransferase gene family, is essential for tapetum differentiation and male fertility. Plant Cell 15(8):1872-87). GPAT1 was shown to encode a mitochondrial enzyme (Zheng et al. 2003). GPAT4, GPAT5 and GPAT8 were shown to be essential for cutin biosynthesis (Beisson F et al. (2007) The acyltransferase GPAT5 is required for the synthesis of suberin in seed coat and root of *Arabidopsis*. Plant Cell 19(1): 351-368: Li, Y et al. (2007) Identification of acyltransferases required for cutin biosynthesis and production of cutin with suberin-like monomers. Proc Natl Acad Sci USA 104(46): 18339-18344). GPAT2, GPAT3, GPAT6 and GPAT7 have not been characterized yet.

The cytoplasmic GPAT is responsible for the synthesis of triacylglycerol and non-chloroplast membrane phospholipids. It is expected to have a substrate preference for palmitate (C16:0) and oleate (C18:1) since these two fatty acids are the most common ones found at the sn-1 position of plant triacylglycerols. The cytoplasmic GPAT was partially purified from avocado (Eccleston V S and Harwood J L (1995) Solubilisation, partial purification and properties of acyl-CoA; glycerol-3-phosphate acyltransferase from avocado (*Persea americana*) fruit mesocarp. Biochim Biophys Acta 1257(1): 1-10).

Membrane-bound glycerol-3-phosphate acyltransferase (PlsB) from *E. coli* catalyzes the first committed step in phospholipid biosynthesis and is thought to function in close proximity to the succeeding enzyme 1-acylglycerol-3-phosphate O-acyltransferase (PlsC) (Kessels J M et al. (1983) Facilitated utilization of endogenously synthesized lysophosphatidic acid by 1-acylglycerophosphate acyltransferase from *Escherichia coli*. Biochim Biophys Acta 753(2): 227-235). It is specific for acylation at position 1 of sn-glycerol 3-phosphate and can utilize either fatty acyl-acyl carrier protein (acyl-ACP) or fatty acyl-coenzyme A (acyl-CoA) thioesters as acyl donors to form a 1-acyl-sn-glycerol 3-phosphate. Fatty acids that are endogenously synthesized are attached to ACP and exogenously added fatty acids are attached to CoA. In *E. coli* phospholipids, the sn 1 position is occupied mainly by either palmitate, or cis-vaccenate, whereas the sn 2 position is predominantly palmitoleate, or cis-vaccenate. This is thought to result from the substrate preferences of the PlsB and PlsC enzymes.

The plsB gene has been shown to be regulated by stress response regulators such as RNA polymerase, sigma 24 (sigma E) factor and ppGpp (Wahl A et al. (2011) Antagonistic regulation of dgkA and plsB genes of phospholipid synthesis by multiple stress responses in *Escherichia coli*. Mol Microbiol 80(5): 1260-75. PlsB is part of a protein network for phospholipid synthesis and interacts with a holo-[acyl-carrier protein] (ACP), esterase/thiocsterase (YbgC) and phosphatidylserine synthase (PssA) to form a complex at the cytoplasmic side of the inner membrane.

plsB is essential for growth (Baba T et al. (2006) Construction of *Escherichia coli* K-12 in-frame, single-gene knockout mutants: the Keio collection. Mol Syst Biol. 2:2006-2008; Yoshimura M et al. (2007) Involvement of the YneS/YgiH and PlsX proteins in phospholipid biosynthesis in both *Bacillus subtilis* and *Escherichia coli*. BMC Microbiol 7: 69).

Site-directed mutagenesis and chemical modification studies have demonstrated catalytically important amino acid residues in PlsB, including an invariant histidine residue that is essential for catalysis (Lewin T M et al. (1999) Analysis of amino acid motifs diagnostic for the sn-glycerol-3-phosphate acyltransferase reaction. Biochemistry 38(18): 5764-5771). Genetic studies have identified the plsB locus as involved in the formation of multidrug tolerant persister cells.

The properties of the E. coli B enzyme were studied in earlier work (Kito M et al. (1972) Inhibition of L-glycerol 3-phosphate acyltransferase from Escherichia coli by cis-9, 10-methylenehexadecanoic acid. J Biochem 71(1): 99-105; Okuyama H and Wakil S J (1973) Positional specificities of acyl coenzyme A: glycerophosphate and acyl coenzyme A: monoacylglycerophosphate acyltransferases in Escherichia coli. J Biol Chem 248(14): 5197-5205; Kito M et al. (1978) Function of phospholipids on the regulatory properties of solubilized and membrane-bound sn-glycerol-3-phosphate acyltransferase of Escherichia coli. Biochim Biophys Acta 529(2): 237-249).

A glycerol-3-phosphate/dihydroxyacetone phosphate dual substrate-specific sn-1 acyltransferase is located in lipid particles and the ER and is involved in the stepwise acylation of glycerol-3-phosphate and dihydroxyacetone in lipid biosynthesis. The most conserved motifs and functionally relevant residues are oriented towards the ER lumen.

A gene (SCT1) encoding a dual glycerol-3-phosphate O-acyltransferase (GAT)/dihydroxyacetone phosphate acyltransferase (DHAT) was identified, cloned and biochemically characterized from Saccharomyces cerevisiae. In the yeast Δgpt1 mutant which exhibits very low GAT/DHAT activity, the overexpression of SCT1 through a plasmid vector showed increased GAT/DHAT activity underlining the proposed molecular function as glycerol-3-phosphate O-acyltransferase/dihydroxyacetone phosphate acyltransferase. The GAT/DHAT activity towards acyl-donors was highest with palmitoleoyl-CoA followed by palmitoyl-CoA, oleoyl-CoA and stearoyl-CoA. The SCT1p was localized to membranes in the cytosol, most probably to the endoplasmic reticulum. In vivo studies of Δsct1 mutants did reveal an impact on all four phospholipids but the observed decrease of 16:0 fatty acids in the phosphatidylethanolamine class was balanced out by an increase in other fatty acids, particularly 18:0 molecular species. The null mutants of SCT1 and GPT2 were synthetically lethal in yeast (Zheng Z and Zou J (2001) The initial step of the glycerolipid pathway: identification of glycerol 3-phosphate/dihydroxyacetone phosphate dual substrate acyltransferases in Saccharomyces cerevisiae. J Biol Chem 276(45): 417104-41716).

The gene (GPT2) encoding a dual glycerol-3-phosphate O-acyltransferase (GAT)/dihydroxyacetone phosphate acyltransferase (DHAT) from Saccharomyces cerevisiae was identified, cloned and biochemically characterized. GPT2 was recombinantly expressed in E. coli in the ΔplsB background devoid of GAT/DHAT activity and showed an increased GAT activity but could not rescue the mutant probably because of the incorrect embedding of GPT2 in the membrane. In the yeast Δgpt1 mutant which exhibits very low GAT/DHAT activity, the overexpression of GPT2 from a plasmid vector showed increased GAT/DHAT activity, underlining the proposed molecular function as glycerol-3-phosphate O-acyltransferase/dihydroxyacetone phosphate acyltransferase. The GAT/DHAT activity towards acyl-donors was highest with oleoyl-CoA followed by palmitoleoyl-CoA, palmitoyl-CoA and stearoyl-CoA.

The GPT2p was localized to membranes in the cytosol. In vivo studies of Δgpt2 mutants did not reveal any significant impact on the total fatty acid profile but a decrease of 16:1 fatty acids in the phosphatidylethanolamine class was observed which was compensated by an increase in 16:0 and 18:1 molecular species. Analysis of a known yeast mutant TTA1 deficient in GAT activity showed that the TTA1 GPT2 gene had a missense mutation with one nucleotide change in the conserved motif III for acyltransferases. The null mutants of SCT1 and GPT2 were synthetically lethal in yeast (Zheng and Zou 2001).

In some embodiments, the glycerol-3-phosphate acyltransferase is a GPAT from Arabidopsis thaliana (At1g02390). In some embodiments, the glycerol-3-phosphate acyltransferase is PlsB from E. coli (Gene ID EG10740). In some embodiments, the glycerol-3-phosphate acyltransferase is the dual glycerol-3-phosphate O-acyltransferase (GAT)/dihydroxyacetone phosphate acyltransferase (DHAT) SCT1 from S. cerevisiae (YBL011w). In some embodiments, the glycerol-3-phosphate acyltransferase is YALI0C00209g from Yarrowia lipolytica. In some embodiments, the glycerol-3-phosphate acyltransferase is I503_02577 from Candida albicans. In some embodiments, the glycerol-3-phosphate acyltransferase is CTRG_02630 from Candida tropicalis. In some embodiments, the glycerol-3-phosphate acyltransferase is the dual glycerol-3-phosphate O-acyltransferase (GAT)/dihydroxyacetone phosphate acyltransferase (DHAT) GPT2 from S. cerevisiae (YKR067w). In some embodiments, the glycerol-3-phosphate acyltransferase is CaO19.5815 from Candida albicans. In some embodiments, the glycerol-3-phosphate acyltransferase is CaO19.13237 from Candida albicans. In some embodiments, the glycerol-3-phosphate acyltransferase is CTRG_02630 from Candida tropicalis.

Lysophosphatidic Acid Acyltransferase (LPAAT)

The present disclosure describes enzymes that catalyze acylation of the sn-2 position of triacylglycerol.

Membrane-bound 1-acylglycerol-3-phosphate O-acyltransferase encoded by gene plsC catalyzes the second step in phospholipid biosynthesis and is thought to function in close proximity to the preceding enzyme glycerol-3-phosphate acyltransferase encoded by gene plsB (Kessels J M et al. 1983). It is specific for acylation at the sn-2 position of a 1-acyl-sn-glycerol 3-phosphate and can utilize either acyl-acyl carrier protein (acyl-ACP), or acyl-coenzyme A (acyl-CoA) as the fatty acyl donor to form a 1,2-diacyl-sn-glycerol 3-phosphate (a phosphatidate, a phosphatidic acid). Fatty acids that are endogenously synthesized are attached to ACP and exogenously added fatty acids are attached to CoA (Greenway D L and Silbert D F (1983) Altered acyltransferase activity in Escherichia coli associated with mutations in acyl coenzyme A synthetase. J Biol Chem 258(21): 13034-13042). In E. coli phospholipids at the sn 1 position is occupied mainly by either palmitate, or cis-vaccenate, whereas the sn 2 position is predominantly palmitoleate, or cis-vaccenate. This is thought to result from the substrate preferences of the PlsB and PlsC enzymes (Rock C O et al. (1981) Phospholipid synthesis in Escherichia coli. Characteristics of fatty acid transfer from acyl-acyl carrier protein to sn-glycerol 3-phosphate. J Biol Chem 256(2): 736-742; Goelz S E and Cronan J E (1980) The positional distribution of fatty acids in Escherichia coli phospholipids is not regulated by sn-glycerol 3-phosphate levels. J Bacteriol 144(1): 462-464).

Site directed mutagenesis studies showed that changing threonine-122 to alanine or leucine resulted in changes in acyl-CoA substrate specificity (Morand L Z et al. (1998)

Alteration of the fatty acid substrate specificity of lysophosphatidate acyltransferase by site-directed mutagenesis. Biochem Biophys Res Commun 244(1): 79-84).

In an engineered strain of *E. coli*, overexpression of PlsC and GalU resulted in increased production of glycoglycerolipids (Mora-Buye N et al. (2012). An engineered *E. coli* strain for the production of glycoglycerolipids. Metab Eng 14(5): 551-559).

The plsC gene of *Streptococcus pneumoniae* encodes a 1-acylglycerol-3-phosphate acyltransferase homologous to the *E. coli* enzyme. The gene was cloned and expressed in *E. coli*, and membranes expressing it were shown to catalyze the predicted function (Lu Y J et al. (2006) Acyl-phosphates initiate membrane phospholipid synthesis in Gram-positive pathogens. Mol Cell 23(5): 765-772).

Plant lysophosphatidate acyltransferase (LPAAT) catalyzes acylation of the sn-2 position of triacylglycerol. The substrate specificity of LPAAT in a given plant species generally determines what fatty acid species are incorporated at the sn-2 position. LPAAT has been cloned from maize and meadow foam. There are two LPAAT genes in meadow foam, whereas only one in maize. The enzyme activity of both LAT1 and LAT2 in meadow foam was confirmed by in vitro assay. In addition, LAT2 was shown to functional complement the *E. coli* LPAAT deficient strain (Brown A P et al. (2002) *Limnanthes douglasii* lysophosphatidic acid acyltransferases: immunological quantification, acyl selectivity and functional replacement of the *Escherichia coli* plsC gene. Biochem J 364(Pt 3):795-805).

LAT1 is a highly selective acyltransferase that only uses 18:1-CoA as a substrate. LAT2 is less selective. The highest activity was shown towards 22:1-CoA, followed by 16:0- and 18:1-CoA. The substrate specificities of LAT1 and LAT2 are consistent with their proposed roles, for LAT1 in membrane lipid biosynthesis and LAT2 in storage lipid biosynthesis. Plant cell membranes predominantly contain C16 and C18 unsaturated fatty acids, whereas storage lipids contain a wide range of fatty acids including saturated fatty acids and very long-chain unsaturated fatty acids. The protein level of LAT1 and LAT2 in different plant tissues was detected by antibodies. LAT1 is present in both leaves and developing seeds, whereas LAT2 is only detected in developing seeds. This again is consistent with their proposed roles. The role of LAT2 in triacylglycerol biosynthesis was further shown by transformation of LAT2 in oil seed rape which does not normally contain 22:1-CoA at the sn-2 position. The transformation of the meadow foam LAT2 inserted 22:1-CoA at the sn-2 position (Lassner M W et al. (1995) Lysophosphatidic acid acyltransferase from meadowfoam mediates insertion of erucic acid at the sn-2 position of triacylglycerol in transgenic rapeseed oil. Plant Physiol 109(4): 1389-1394).

Utilizing viable mutant *Saccharomyces cerevisiae* strains lacking sphingolipid biosynthesis, the gene SLC1 was isolated and demonstrated to encode an acyl-CoA; lysophosphatidate acyltransferase. Sequence homology with the PLSC protein of *E. coli* which is classified as 1-acyl-sn-glycerol-3-phosphate acyltransferase indicated a similar function. This presumed molecular function of SLC1p was corroborated by the ability to rescue the ΔplsC mutant of *E. coli*. It could be shown that a single nucleotide alteration changing an L-glutamine to an L-leucine at position 131 transformed the substrate preference from C16 and C18 fatty acids to C26 fatty acids which was reflected in vivo in the corresponding fatty acid composition of wild type (SLC1) versus mutant (SLC1-1) (Nagiec M M et al. (1993) A suppressor gene that enables *Saccharomyces cerevisiae* to grow without making sphingolipids encodes a protein that resembles an *Escherichia coli* fatty acyltransferase. J Biol Chem 268(29): 22156-22163).

In vitro assays with the recombinantly expressed and purified SLC1p in *E. coli* revealed a substrate preference towards lyso-phosphatidate and oleoyl-CoA but also accepted 1-palmitoylglycerol 3-phosphate and 1-stearoyl-sn-glycerol 3-phosphate. In vivo studies of mutants such as Δslc1, Δslc4 (another potential acyl-CoA:phosphatidyl acyltransferase) and double mutants of Δslc1 Δslc4 bearing a plasmid with either the SLC1 or SLC4 gene referred to as 2.ΔSLC1 (or 2.ΔSLC4) showed that SLC1 promoted the biosyntheses of phosphatidate and also phosphatidylinositol and diacylglycerol. It was suggested that SLC1 is involved in phospholipid remodeling by exchanging fatty acids on glycerophospholipids in vive (Benghezal M et al. (2007) SLC1 and SLC4 encode partially redundant acyl-coenzyme A 1-acylglycerol-3-phosphate O-acyltransferases of budding yeast. J Biol Chem 282(42): 30845-30855).

Screening the yeast genome with candidate open reading frames (ORFs) of known acyltransferase enzymes and testing the associated deletion strains, the gene encoding an acyl-CoA dependent lyso-phospholipid acyltransferase (ALE1) was identified. In the Δale1 strain a dramatic decrease of lyso-phosphatidylethanolamine acyltransferase (LPEAT) activity was observed but it could also be demonstrated that ALE1p may provide redundant lyso-phosphatidate acyltransferase (LPAAT) activity when the main LPAAT in *Saccharomyces cerevisiae*, i.e. SLC1p, is absent or rendered inactive. ALE1p preferably attaches unsaturated acyl chains of varying length to the sn-2 position of lyso-phospholipids. The enzyme was localized to both microsomal and mitochondrial membranes utilizing high purity cell fractionation. It has been proposed that ALE1 may be the major LPEAT in the exogenous lysolipid metabolism (ELM) pathway in yeast but it is also required for efficient functioning of the endogenous Kennedy pathway (Riekhof W R et al. (2007) Identification and characterization of the major lysophosphatidylethanolamine acyltransferase in *Saccharomyces cerevisiae*. J Biol Chem 282 (39): 28344-28352).

In a simultaneous study, LPT1 (synonymous to ALE1) was identified by applying a synthetic genetic array analysis and shown to have lyso-phospholipid acyltransferase activity. In this study the best substrate for LPT1 (=ALE1) was lyso-phosphatidylcholine, hence acting as a lyso-phosphatidylcholine acyltransferase (LPCAT) and the residual activity as LPAAT reported earlier was also demonstrated utilizing single Δlpt1 and double Δscl1Δlpt1 mutants, the latter being inviable. The ratio of incorporating oleate into phosphatidylcholine was determined as 70% towards the de novo synthesis and 30% towards remodeling (Jain S et al. (2007) Identification of a novel lysophospholipid acyltransferase in *Saccharomyces cerevisiae*. J Biol Chem 282(42): 30562-30569).

The molecular function of ALE1 (also referred to as LCA1 or SLC4) as a lyso-phosphatidylcholine acyltransferase (LPCAT) was corroborated in another simultaneous study monitoring the incorporation of radioactive labeled lyso-phosphatidylcholine and/or palmitoyl-CoA into phosphatidylcholine (PC). The study confirmed that ALE1p (=LCA1p in this study) was accepting a variety of acyl-donors but showed highest activity as LPCAT regardless of the acyl-chain of lyso-phosphatidylcholine species (16:0 or 18:1). In addition, a high sensitivity towards Zn2+ was observed which was inhibitory at concentrations above 0.1 mM and activating at lower concentrations (10 to 25 μM).

The high PC turnover-rate measured for ALE1p (=LCA1p) emphasized the enzyme as a key catalyst involved in the re-acylation of PC (Chen Q et al. (2007) The yeast acylglycerol acyltransferase LCA1 is a key component of Lands cycle for phosphatidylcholine turnover." FEBS Lett 581 (28): 5511-5516).

The search for genes causing aberrations in the formation of lipid droplets (LD) in *Saccharomyces cerevisiae* identified the gene LOA1 (formerly VPS66) encoding for an acyl-CoA dependent lysophosphatidate acyltransferase. The in vivo molecular function of LOA1p was determined using the comparison of the lipidome of wild type and Δloa1 yeast strains. The analysis showed that in the LOA1 deficient mutant (Δloa1) the percentage of oleate containing phosphatidate molecular species was considerably reduced and the content of triacylglycerols (TGA) was lowered by 20 percent. The protein was recombinantly expressed in *E. coli* and partially purified by obtaining the highly enriched lipid droplet fraction and by affinity chromatography with LOA1p still attached to the matrix beads. The purified LOA1p was characterized in in vitro assays demonstrating that LOA1p was specific for lysophosphatidate and oleoyl-CoA, thus acting as a oleoyl-CoA; lysophosphatidate acyltransferase in yeast. Based upon the results, LOA1p was proposed to be significantly involved in channeling excess oleate—containing phosphatidate species into TAG biosynthesis and the proper development of lipid droplets (LD's). Utilizing a genomic-tagging construct, subcellular fractionation, immunohistochemistry and fluorescence microscopy LOA1 could be localized to both endoplasmic reticulum (ER) and lipid droplets (LD's) (Ayciriex S et al. (2012) YPR139c/LOA encodes a novel lysophosphatidic acid acyltransferase associated with lipid droplets and involved in TAG homeostasis. Mol Biol Cell 23(2): 233-246).

In some embodiments, the lysophosphatidic acid acyltransferase is plsC from *E. coli* (MetaCyc Accession ID EG11377). In other embodiments, the lysophosphatidic acid acyltransferase is plsC from *S. pneumoniae* (MetaCyc Accession ID G-10763). In some embodiments, the lysophosphatidic acid acyltransferase is LAT1 from *Limnanthes douglasii*. In some embodiments, the lysophosphatidic acid acyltransferase is LAT2 from *Limnanthes douglasii* (MetaCyc Accession ID G-9398). In some embodiments, the lysophosphatidic acid acyltransferase is SLC1 from *Saccharomyces cerevisiae* (YDL052c). In some embodiments, the lysophosphatidic acid acyltransferase is YALI0E18964g from *Yarrowia lipolytica*. In some embodiments, the lysophosphatidic acid acyltransferase is CaO19.250 from *Candida albicans*. In some embodiments, the lysophosphatidic acid acyltransferase is CaO19.7881 from *Candida albicans*. In some embodiments, the lysophosphatidic acid acyltransferase is CTRG_02437 from *Candida tropicalis*. In some embodiments, the lysophosphatidic acid acyltransferase is ALE1 from *Saccharomyces cerevisiae* (YOR175C). In some embodiments, the lysophosphatidic acid acyltransferase is YALI0F19514g from *Yarrowia lipolytica*. In some embodiments, the lysophosphatidic acid acyltransferase is CaO19.1881 from *Candida albicans*. In some embodiments, the lysophosphatidic acid acyltransferase is CaO19.9437 from *Candida albicans*. In some embodiments, the lysophosphatidic acid acyltransferase is CTRG_01687 from *Candida tropicalis*. In some embodiments, the lysophosphatidic acid acyltransferase is LOA1 from *Saccharomyces cerevisiae* (YPR139C). In some embodiments, the lysophosphatidic acid acyltransferase is YALI0C14014g from *Yarrowia lipolytica*. In some embodiments, the lysophosphatidic acid acyltransferase is CaO19.1043 from *Candida albicans*. In some embodiments, the lysophosphatidic acid acyltransferase is CaO19.8645 from *Candida albicans*. In some embodiments, the lysophosphatidic acid acyltransferase is CTRG_04750 from *Candida tropicalis*.

Glycerolphospholipid Acyltranserase (GPLAT)

The present disclosure describes enzymes that catalyze the following reaction:

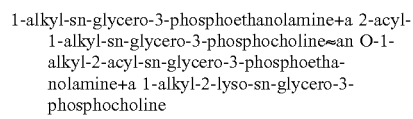

GPLAT enzymes catalyze the transfer of fatty acids from intact choline- or ethanolamine-containing glycerolphospholipids to the sn-2 position of a lyso-glycerolphospholipid. The organyl group on sn-1 of the donor or acceptor molecule can be alkyl, acyl or alk-1-enyl. The term 'radyl' has sometimes been used to refer to such substituting groups. The enzyme requires Coenzyme A and does not favor the transfer of polyunsaturated acyl groups.

Diacylglycerol Acyltransferase (DGAT)

The present disclosure describes enzymes that add an acyl group to the sn-3 position of diacylglycerol (DAG) to form triacylglycerol (TAG).

Diacylglycerol acyltransferase (DGAT) catalyzes the only unique reaction in triacylglycerol biosynthesis. It adds an acyl group to the sn-3 position of diacylglycerol (DAG) and forms triacylglycerol (TAG), shown as follows:

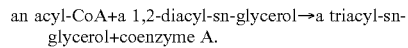

DGAT accepts a broad range of acyl-CoA as acyl donor including C18:1, C18:2, and C20:1 acyl-CoA as demonstrated for the *Arabidopsis* DGAT (Jako C et al. (2001) Seed-specific over-expression of an *Arabidopsis* cDNA encoding a diacylglycerol acyltransferase enhances seed oil content and seed weight. Plant Physiol 126(2): 861-874). Expressing the *Arabidopsis* cDNA of DGAT in an insect cell culture and in yeast, as well as over-expressing the cDNA in wild type *Arabidopsis*, demonstrated the DGAT activity in transferring an acyl group to the sn-3 position of DAG (Hobbs D H et al. (1999) Cloning of a cDNA encoding diacylglycerol acyltransferase from *Arabidopsis thaliana* and its functional expression. FEBS Lett 452(3): 145-149; Zou J et al. (1999) The *Arabidopsis thaliana* TAG1 mutant has a mutation in a diacylglycerol acyltransferase gene. Plant J 19(6): 645-653). Over-expression of the *Arabidopsis* cDNA in wild type *Arabidopsis* increased oil deposition in seeds and this increase is correlated to the increased mRNA expression level of DGAT. This indicates that DGAT is a regulatory point of the triacylglycerol biosynthesis pathway.

The gene encoding the bifunctional acyl-CoA:acylglycerol acyltransferase (DGAT) has been identified in *Saccharomyces cerevisiae* as a major contributor to triacylglycerol biosynthesis (Sandager L et al. (2002) Storage lipid synthesis is non-essential in yeast. J Biol Chem 277(8): 6478-6482). The gene (DGA1) belongs in the DGAT2 family which members are characterized as acyl-CoA dependent acyltransferases (Lardizabal K D et al. (2001) DGAT2 is a new diacylglycerol acyltransferase gene family: purification, cloning, and expression in insect cells of two polypeptides from *Mortierella ramanniana* with diacylglycerol acyltransferase activity." J Biol Chem 276(42): 38862-38869). It has been demonstrated that DGA1p is the only acyl-CoA dependent acyltransferase catalyzing the esterification of diacylglycerol (DAG) to triacylglycerol (TAG) in the yeast genome. This has been shown in deletion mutants of DGA1

(Δdga1) and in combination with the deletion of the other diacylglycerol acyltransferase of importance in yeast, i.e. LRO1 which esterifies DAG utilizing a phospholipid acyl donor (Δlro1). In the Δdga1Δlro1 double mutant almost all of the diacylglycerol acyltransferase has been lost and TAG synthesis was abolished. A plasmid carrying the DGA1 gene could rescue the TAG synthetic deficiency in the mutant indicating that in vivo DGA1 was prominently involved in the TAG biosynthetic route (Sorger D, Daum G (2002). Synthesis of triacylglycerols by the acyl-coenzyme A:diacylglycerol acyltransferase Dga1p in lipid particles of the yeast Saccharomyces cerevisiae. J Bacteriol 184(2): 519-524: Oelkers P et al. (2002) The DGA1 gene determines a second triglyceride synthetic pathway in yeast. J Biol Chem 277(11): 8877-8881). In vitro a preference of DGA1p towards oleoyl-CoA and palmitoyl-CoA was observed which is inverted for the phospholipid dependent acyltransferase LRO1p (Oelkers et al. 2002).

In addition, the function of DGA1p as an acyl-CoA dependent monoacylglycerol acyltransferase (MGAT) was demonstrated in vivo utilizing Δdga1 mutants which had lost more than 60% of the MGAT activity. The in vitro MGAT activity of DGA1 was shown by the oleoyl-CoA dependent esterification of 2-oleoylglycerol yielding 1,2-dioleoylglycerol in the process (Heier C et al. (2010) Identification of Yju3p as functional orthologue of mammalian monoglyceride lipase in the yeast Saccharomyces cerevisiae. Biochim Biophys Acta 1801(9): 1063-1071).

More insights into the functional importance and topological orientation of sequence motifs in the primary sequence of DGA1p has been gained by in silico analyses, site-directed mutagenesis of signature motifs and deletion mutations of the C- and N-termini. It could be demonstrated that besides the signature motifs found in other DGAT2 family members Saccharomyces possesses a unique hydrophilic stretch which was shown to significantly modulate enzyme activity. Also, the histidine residue 195 in the second of the four determined transmembrane domains was proven to be essential for enzyme activity. The topology of DGA1 revealed that both C- and N-termini face the cytoplasm and that the C-terminus was more important for DGA1 activity than the N-terminus (Liu Q et al. (2011) Functional and topological analysis of yeast acyl-CoA: diacylglycerol acyltransferase 2, an endoplasmic reticulum enzyme essential for triacylglycerol biosynthesis. J Biol Chem 286(15): 13115-13126).

Using highly purified cell fragments and immunoblotting, Sorger et al. (2002) and Liu et al. (2011) demonstrated that DGA1 was localized to lipid droplets and microsomal membranes, most probably the endoplasmic reticulum.

Acinetobacter sp. ADP1 expresses a bifunctional enzyme that exhibits both wax ester synthase (WS) and acyl-coA: diacylglycerol acyltransferase (DGAT) activities (Kalscheuer R and Steinbuchel A (2003) A novel bifunctional wax ester synthase/acyl-CoA:diacylglycerol acyltransferase mediates wax ester and triacylglycerol biosynthesis in Acinetobacter calcoaceticus ADP1. J Biol Chem 278(10): 8075-8082). This homodimer catalyzes the final steps in TAG and WE biosynthesis (Stoveken T et al. (2005) The wax ester synthase/acyl coenzyme A:diacylglycerol acyltransferase from Acinetobacter sp. strain ADP1: characterization of a novel type of acyltransferase. J Bacteriol 187(4): 1369-1376). It mediates both oxo ester and thio ester bond formation and has a broad substrate range, accepting medium chain fatty alcohols and acyl-CoA esters as well as monoacylglycerols (MAGs) (Uthoff S et al. (2005) Thio wax ester biosynthesis utilizing the unspecific bifunctional wax ester synthase/acyl coenzyme A:diacylglycerol acyltransferase of Acinetobacter sp. strain ADP1. Appl Environ Microbiol 71(2): 790-796).

In some embodiments, the diacylglycerol acyltransferase is TAG1 from Arabidopsis thaliana (Gene ID AT2G19450). In some embodiments, the diacylglycerol acyltransferase is DGA1 from S. cerevisiae (YOR245c). In some embodiments, the diacylglycerol acyltransferase is atfA from Acinetobacter sp. ADP1 (MetaCyc Accession ID ACIAD0832). In some embodiments, the diacylglycerol acyltransferase is YALI0E32769g from Yarrowia lipolytica. In some embodiments, the diacylglycerol acyltransferase is CaO19.6941 from Candida albicans. In some embodiments, the diacylglycerol acyltransferase is CaO19.14203 from Candida albicans. In some embodiments, the diacylglycerol acyltransferase is CTRG_06209 from Candida tropicalis.

Phospholipid: diacylglycerol acyltransferase (PDAT) catalyzes the following reaction:

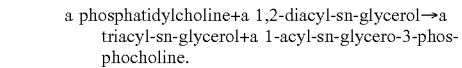

The Arabidopsis PDAT can use different phospholipids as acyl donor, with acyl groups of 10-22 carbon chain length at either sn-positions (Stahl U et al. (2004) Cloning and functional characterization of a phospholipid:diacylglycerol acyltransferase from Arabidopsis. Plant Physiol 135(3): 1324-1335). Acyl group at the sn-2 position of phosphatidylcholine is however used three times greater than at the sn-1 position. The highest activity is with acyl groups having multiple double bonds, epoxy or hydroxy groups. Among the tested, the enzyme activity was highest with ricinoleoyl, 18:0- and 22:1-acyl groups gave the lowest enzyme activity. Among different phospholipid species, higher activity is with phosphatidylethanolamine than with phosphatidate or phosphatidylcholine.

A PDAT activity was detected in castor bean seed microsome fraction. Radio-labeled ricinoleoyl and vernoloyl groups are effectively transferred from phosphatidylcholine to DAG forming triacylglycerol (Dahlqvist A et al. (2000) Phospholipid: diacylglycerol acyltransferase: an enzyme that catalyzes the acyl-CoA-independent formation of triacylglycerol in yeast and plants. Proc Natl Acad Sci USA 97(12): 6487-6492).

In other embodiments, the diacylglycerol acyltransferase is a phospholipid: diacylglycerol acyltransferase (PDAT). In some embodiments, the PDAT is from Arabidopsis thaliana (Gene ID AT5G13640). In some embodiments, the PDAT is from Ricinus communis. In some embodiments, the PDAT is LRO1 from Saccharomyces cerevisiae (YNR008w). In some embodiments, the PDAT is YALI0E6797g from Yarrowia lipolytica. In some embodiments, the PDAT is CaO19.13439 from Candida albicans. In some embodiments, the PDAT is CTRG_04390 from Candida tropicalis.

In some embodiments, a recombinant microorganism capable of producing a mono- or poly-unsaturated ≤$C_{18}$ fatty alcohol, fatty aldehyde and/or fatty acetate from an endogenous or exogenous source of saturated $C_6$-$C_{24}$ fatty acid is provided, wherein the recombinant microorganism expresses one or more acyltransferase enzymes, and wherein the recombinant microorganism is manipulated to delete, disrupt, mutate, and/or reduce the activity of one or more endogenous acyltransferase enzymes. In some embodiments, the one or more acyltransferase enzymes being expressed are different from the one or more endogenous acyltransferase enzymes being deleted or downregulated. In some embodiments, the one or more endogenous or exogenous acyltransferase enzymes comprise glycerol-3-phosphate acyl transferases (GPATs), lysophosphatidic acid acyltransferases (LPAATs), glycerolphospholipid acyltransferase (GPLATs) and/or diacylglycerol acyltransferases (DGATs). In some embodiments, the one or more acyltransferase enzymes being expressed prefer to store short-chain fatty acyl-CoAs. In other embodiments, the one or more acyltransferase enzymes being expressed are selected from Table 5b. In some embodiments, the one or more endogenous acyltransferase enzymes being deleted or downregulated are selected from *Y. lipolytica* YALI0C00209g, *Y. lipolytica* YALI0E18964g, *Y. lipolytica* YALI0F19514g, *Y. lipolytica* YALI0C14014g, *Y. lipolytica* YALI0E16797g, *Y. lipolytica* YALI0E32769g, *Y. lipolytica* YALI0D07986g, *S. cerevisiae* YBL011w, *S. cerevisiae* YDL052c, *S. cerevisiae* YOR175C, *S. cerevisiae* YPR139C, *S. cerevisiae* YNR008w, *S. cerevisiae* YOR245c, *Candida* I503_02577, *Candida* CTRG_02630, *Candida* CaO19.250, *Candida* CaO19.7881, *Candida* CTRG_02437, *Candida* CaO19.1881, *Candida* CaO19.9437, *Candida* CTRG_01687, *Candida* CaO19.1043, *Candida* CaO19.8645, *Candida* CTRG_04750, *Candida* CaO19.13439, *Candida* CTRG_04390, *Candida* CaO19.6941, *Candida* CaO19.14203, and *Candida* CTRG_06209. In some embodiments, the recombinant microorganism further expresses pheromone biosynthetic pathway enzymes. In further embodiments, the pheromone biosynthetic pathway enzymes comprise one or more fatty acyl desaturase and/or fatty acyl conjugase. In yet further embodiments, the pheromone biosynthetic pathway enzymes comprise one or more fatty alcohol forming fatty acyl reductase.

In some embodiments, a method of producing a mono- or poly-unsaturated $\leq C_{18}$ fatty alcohol, fatty aldehyde and/or fatty acetate from an endogenous or exogenous source of saturated $C_6$-$C_{24}$ fatty acid are provided, wherein the method comprises introducing into or expressing in a recombinant microorganism at least one endogenous or exogenous nucleic acid molecule encoding an acyltransferase and introducing a deletion, insertion, or loss of function mutation in one or more gene encoding an acyltransferase, wherein the at least one endogenous or exogenous nucleic acid molecule encoding an acyltransferase being introduced or expressed is different from the one or more gene encoding an acyltransferase being deleted or downregulated. In some embodiments, the at least one endogenous or exogenous nucleic acid molecule encoding an acyltransferase being introduced or expressed or the one or more gene encoding an acyltransferase being deleted or downregulated comprise glycerol-3-phosphate acyl transferases (GPATs), lysophosphatidic acid acyltransferases (LPAATs), glycerolphospholipid acyltransferase (GPLATs) and/or diacylglycerol acyltransferases (DGATs). In some embodiments, the at least one endogenous or exogenous nucleic acid molecule encodes an acyltransferase that prefers to store short-chain fatty acyl-CoAs. In some embodiments, the at least one endogenous or exogenous nucleic acid molecule encodes an acyltransferase selected from Table 5b. In some embodiments, the one or more endogenous acyltransferase enzymes being deleted or downregulated are selected from *Y. lipolytica* YALI0C00209g, *Y. lipolytica* YALI0E18964g, *Y. lipolytica* YALI0F19514g, *Y. lipolytica* YALI0C14014g, *Y. lipolytica* YALI0E16797g, *Y. lipolytica* YALI0E32769g, *Y. lipolytica* YALI0D07986g, *S. cerevisiae* YBL011w, *S. cerevisiae* YDL052c, *S. cerevisiae* YOR175C. *S. cerevisiae* YPR139C, *S. cerevisiae* YNR008w, *S. cerevisiae* YOR245c, *Candida* I503_02577, *Candida* CTRG_02630, *Candida* CaO19.250, *Candida* CaO19.7881, *Candida* CTRG_02437, *Candida* CaO19.1881, *Candida* CaO19.9437, *Candida* CTRG_01687, *Candida* CaO19.1043, *Candida* CaO19.8645, *Candida* CTRG_04750, *Candida* CaO19.13439, *Candida* CTRG_04390, *Candida* CaO19.6941, *Candida* CaO19.14203, and *Candida* CTRG_06209. In some embodiments, the method further comprises introducing into or expressing in the recombinant microorganism at least one endogenous or exogenous nucleic acid molecule encoding a fatty acyl desaturase and/or fatty acyl conjugase. In further embodiments, the method further comprises introducing into or expressing in the recombinant microorganism at least one endogenous or exogenous nucleic acid molecule encoding a fatty alcohol forming fatty acyl reductase.

TABLE 5B

Exemplary acyltransferases

| Accession No. | Source Organism |
| --- | --- |
| AALA9962.1 | *Bos taurus* |
| BAC43739.1 | *Rattus norvegicus* |
| AAH89846.1 | *Rattus norvegicus* |
| F6TMU0 | *Equus caballus* |
| F6PXX7 | *Equus caballus* |
| F7B020 | *Equus caballus* |
| ALT83519.1 | *Macadamia tetraphylla* |
| ANN46862.1 | *Cuphea avigera* |
| ANN46863.1 | *Cuphea avigera* |
| ANN46864.1 | *Cuphea avigera* |
| ANN46865.1 | *Cuphea avigera* |
| AAC49119.1 | *Cocos mucifera* |
| JAT48335.1 | *Anthurium amnicola* |
| XP_008793203.1 | *Phoenix dactylifera* |
| XP_008806896.1 | *Phoenix dactylifera* |
| XP_008806740.1 | *Phoenix dactylifera* |
| XP_010908895.1 | *Elaeis guineensis* |
| XP_010908896.1 | *Elaeis guineensis* |
| Q96UY2 | *Umbelopsis ramanniana* |
| A0A077WEU5 | *Lichtheimia ramosa* |
| A0A068SDP4 | *Lichtheimia corymbifera* JMRC |
| A0A068RXA2 | *Lichtheimia corymbifera* JMRC |
| A0A197JCE2 | *Mortierella elongata* AG-77 |
| A0A1C7N060 | *Choanephora cucurbitarum* |
| I1BLC3 | *Rhizopus delemar* |
| A0A1C7NC56 | *Choanephora cucurbitarum* |
| A0A077X3B5 | *Lichtheimia ramosa* |
| Q96UY1 | *Umbelopsis ramanniana* |
| A0A077WVD4 | *Lichtheimia ramosa* |
| A0A163K8G3 | *Absidia glauca* |
| S2J8P3 | *Mucor circinelioides* |
| A0A168J818 | *Mucor circinelloides* |
| A0A0C9MR10 | *Mucor ambiguus* |
| A0A162PN39 | *Phycomyces blakesleeanus* |
| A0A167QXD0 | *Phycomyces blakesleeanus* |
| A0A0C9M4C3 | *Mucor ambiguus* |
| A0A0R7NDT1 | *Parasitella parasitica* |
| A0A015LM78 | *Rhizophagus irregularis* |
| A0A0B7NHQ3 | *Parasitella parasitica* |
| A0A0A1NVK5 | *Rhizopus microsporus* |
| A0A0A1P436 | *Rhizopus microsporus* |
| A0A0D7BI48 | *Cylindrobasidium torrendii* |
| A0A1B9HZT8 | *Kwoniella pini* |
| A0A1D1XN50 | *Anthurium amnicola* |
| A0A1B9ILF0 | *Kwoniella mangroviensis* |
| S2JU94 | *Mucor circineiloides* |
| A0A1B9GCB0 | *Kwoniella bestiolae* CBS 10118 |
| A0A068RKT0 | *Lichtheimia corymbifera* |
| Q5KFU4 | *Cryptococcus neoformans* |
| Q55QC2 | *Cryptococcus neoformans* |
| U5GY58 | *Microbotryum lychnidis* |
| A0A197KA94 | *Mortierella elongata* AG-77 |
| A0A088FR92 | *Rhodotorula diobovata* |
| A0A194SBY3 | *Rhodotorula graminis* |
| E6R8N8 | *Cryptococcus gattii* |
| M7WKS9 | *Rhodosporidium toruloides* |

TABLE 5B-continued

Exemplary acyltransferases

| Accession No. | Source Organism |
|---|---|
| A0A191UMW0 | *Rhodosporidium toruloides* |
| C6KZS6 | *Rhodosporidium toruloides* |
| J9VS50 | *Cryptococcus neoformans* |
| A0A109FM23 | *Rhodotorula* sp. JG-1b |
| I4YE91 | *Wallemia mellicola* |
| A0A066WAJ3 | *Tilletiaria anomala* UBC 951 |
| A0A151VHJ4 | *Hypsizygus marmoreus* |
| A0A168LDJ3 | *Absidia glauca* |
| A0A0A1ULK8 | *Rhizoctonia solani* AG-3 Rhs1AP |
| A0A074RWU7 | *Rhizoctonia solani* 123E |
| A0A0K6FWT6 | *Rhizoctonia solani* |
| R9AL76 | *Wallemia ichthyophaga* |
| E6ZMU5 | *Sporisorium reilianum* |
| A0A0K3CJX4 | *Rhodosporidium toruloides* |
| A0A162Y103 | *Phycomyces blakesleeanus* |
| A0A0B7FYU9 | *Thanatephorus cucumeris* |
| A0A1A5ZUI2 | *Kwoniella dejecticola* |
| A0A1B9GXE9 | *Kwoniella heveanensis* BCC8398 |
| V5EIP7 | *Kalmanozyma brasiliensis* |
| A0A127ZHG0 | *Sporisorium scitamineum* |
| M5FTN9 | *Dacryopinax primogenitus* |
| A0A166HX72 | *Sistotremastrum suecicun* |
| A0A067QH80 | *Jaapia argillacea* MUCL 33604 |
| A0A165PFB6 | *Neolentinus lepideus* |
| G7DXE4 | *Mixia osmundae* |
| A0A165KJK5 | *Exidia glandulosa* HHB12029 |
| A0A0F7TLQ7 | *Penicillium brasilianum* |
| S8FI87 | *Fomitopsis pinicola* |
| S7ZL04 | *Penicillium oxalicum* |
| I2FMX3 | *Ustilago hordei* |
| F8P370 | *Serpula lacrymans* |
| V2WTH2 | *Moniliophthora roreri* |
| S7Q9H4 | *Gloeophyllum trabeum* |
| W3VTZ4 | *Pseudozyma aphidis* |
| B8M0V7 | *Talaromyces stipitatus* |
| A0A0D7B6H5 | *Cylindrobasidium torrendii* |
| R7SCW4 | *Tremella mesenterica* |
| A0A093UWD0 | *Talaromyces marneffei* PM1 |
| B6Q8Q9 | *Talaromyces marneffei* |
| A0A093VC12 | *Talaromyces marneffei* PM1 |
| A0A167SF58 | *Calocera viscosa* TUFC12733 |
| A0A180GQ68 | *Puccinia triticina* |
| E3KWZ5 | *Puccinia graminis f.* sp. |
| F4S978 | *Melampsora larici-populina* |
| A0A0U5GN87 | *Aspergillus calidoustus* |
| W9WBT1 | *Clacdophialophora yegresii* |
| A0A0D2A9G0 | *Verruconis gallopava* |
| S3DKQ1 | *Glarea lozoyensis* |
| A0A167S691 | *Penicillin-in chrysogenum* |
| A0A0C3G1P8 | *Piloderma croceum* F 1598 |
| A0A117NM34 | *Penicillium freii* |
| A0A0M8NPT1 | *Penicillium nordicum* |
| M2R3J5 | *Ceriporiopsis subvermispora* |
| A0A1E3JS60 | *Cryptococcus depauperatus* |
| V9DJY4 | *Cladophialophora carrionii* |
| A0A1C1D128 | *Cladophialophora carrionii* |
| A0A194XRZ1 | *Phialocephala scopiformis* |
| A0A135LQY4 | *Penicillium patulum* |
| F2S034 | *Trichophyton tonsurans* |
| A0A059J710 | *Trichophyton interdigitale* |
| R7YTC1 | *Coniosporium apollinis* |
| A0A0G4PR11 | *Penicillium camemberti* FM 013 |
| F2SHG6 | *Trichophyton rubrum* |
| A0A022VWY8 | *Trichophyton rubrum* CBS 288.86 |
| A0A178F1Q9 | *Trichophyton rubrum* |
| A0A022XM67 | *Trichophyton soudanense* |
| F2PHM1 | *Trichophyton equinum* |
| A0A178FDV0 | *Trichophyton violaceum* |
| A0A0F8UUV5 | *Aspergillus ochraceoroseus* |
| A0A0F8XD12 | *Aspergillus rambellii* |
| D8Q1Z6 | *Schizophyllum commune* |
| A0A0L0VQ99 | *Puccinia striiformis* |
| W6QE33 | *Penicillium roqueforti* |
| A0A0J0XU39 | *Cutaneotrichosporon* |
| K2RIY7 | *Macrophomina phaseolina* |
| A0A1B9HIE8 | *Kwoniella heveanensis* CBS 569 |
| A0A0A2KLE4 | *Penicillium italicum* |
| A0A177FP94 | *Fonsecaea monophora* |
| Q0CU51 | *Aspergillus terreus* |
| A0A0D2C195 | *Exophiala spinifera* |
| K9GS70 | *Penicillium digitatum* |
| K9H4T7 | *Penicillium digitatum* |
| A0A0A2IRX2 | *Penicillium expansum* |
| A0A165XA55 | *Fibulorhizoctonia* sp. |
| A0A1E3HS30 | *Cryptococcus depauperatus* |
| R0JHT6 | *Setosphaeria turcica* |
| W6XT38 | *Bipolaris zeicola* 26-R-13 |
| K1WNS8 | *Marssonina brunnea f.* sp. |
| A0A077R6Q5 | *Melanopsichium pennsylvanicum* |
| A0A0G2F2K4 | *Phaeomoniella chlamydospora* |
| M2UB23 | *Cochliobolus heterostrophus* |
| N4WZB4 | *Cochliobolus heterostrophus* |
| A0A0D2ECJ4 | *Capronia semi-immersa* |
| K5ULK6 | *Phanerochaete carnosa* |
| A0A081CNS6 | *Pseudozyma Antarctica* |
| W7E3D1 | *Bipolaris victoriae* FI3 |
| A0A0D1YAT0 | *Exophiala sideris* |
| V5FVB4 | *Byssochlamys spectabilis* |
| A0A150V2J4 | *Acidomyces richmondensis* BFW |
| A0A0D2P224 | *Hypholoma sublateritium* |
| C5FY83 | *Arthroderma otae* |
| A0A0E9NND3 | *Saitoella complicata* |
| A0A163JYI7 | *Absidia glauca* |
| M2SYN8 | *Cochliobolus sativus* |
| A0A0D2A9Y8 | *Exophiala oligosperma* |
| B2WFQ5 | *Pyrenophora tritici* |
| A0A178Z686 | *Fonsecaea erecta* |
| R1GYF1 | *Botryosphaeria parva* |
| A0A0D2AM77 | *Cladophialophora immunda* |
| A0A067TPJ7 | *Galerina marginata* CBS 339.88 |
| A0A0G2DT71 | *Diplodia seriata* |
| A0A0S6XG57 | fungal sp. No. 11243 |
| A1CD57 | *Aspergillus clavatus* strain |
| W6ZE59 | *Bipolaris oryzae* ATCC 44560 |
| W9X299 | *Cladophialophora psammophila* |
| A0A0L1HS74 | *Stemphylium lycopersici* |
| E3RYE6 | *Pyrenophora teres* |
| A0A178C491 | *Fonsecaea multimorphosa* |
| A0A0D2JW30 | *Fonsecaea multimorphosa* |
| A0A100ISZ7 | *Aspergillus niger* |
| G7XRR4 | *Aspergillus kawachii* |
| E4ZGH1 | *Leptosphaeria maculans* |
| A0A0C3AU69 | *Serendipita vermifera* |
| A0A0U1M481 | *Talaromyces islandicus* |
| A0A179UDB8 | *Ajellomyces dermatitidis* |
| A0A177DML0 | *Alternaria alternata* |
| A0A074XTA2 | *Aureobasidium namibiae* |
| R8BK00 | *Togninia minima* |
| A0A178E1M9 | *Pyrenochaeta* sp. DS3sAY3a |
| A0A074XCF2 | *Aureobasidium pullulans* |
| A0A178CVL7 | *Fonsecaea nubica* |
| J4R349 | *Fibroporia radiculosa* |
| F2T2H3 | *Ajellomyces dermatitidis* |
| T5C9R0 | *Blastomyces dermatitidis* |
| C5GGF5 | *Ajellomyces dermatitidis* |
| F8Q4F5 | *Serpula lacrymans* |
| A0A074YHW3 | *Aureobasidium subglaciale* |
| A0A0D2E953 | *Exophiala xenobiotica* |
| A0A0D2ETM7 | *Exophiala xenobiotica* |
| A0A163ADJ9 | *Didymella rabiei* |
| U7PLY5 | *Sporothrix schenckii* |
| A0A0F2MF45 | *Sporothrix schenckii* 1099-18 |
| A0A0C2J820 | *Sporothrix brasiliensis* 5110 |
| A0A1E3B843 | *Aspergillus cristatus* |
| A0A01L6WTD3 | *Termitomyces* sp. J132 |
| G2YTS7 | *Botryotinia fuckeliana* |
| W9XGA9 | *Capronia epimyces* CBS 606.96 |
| A0A0F4YS69 | *Rasamsonia emersonii* |
| M9LWR9 | *Pseudozyma antarctica* |
| A0A074WDM7 | *Aureobasidium melanogenum* |
| M3CBZ0 | *Sphaerulina musiva* |
| A0A0C7C2J7 | *Rhizopus microsporus* |

TABLE 5B-continued

Exemplary acyltransferases

| Accession No. | Source Organism |
| --- | --- |
| W9YU83 | *Capronia coronata* CBS 617.96 |
| I8IUH8 | *Aspergillus oryzae* |
| A0A139HZI0 | *Pseudocercospora musae* |
| E9DGY4 | *Coccidioides posadasii* |
| A0A0J6F9P8 | *Coccidioides posadasii* |
| H6BM52 | *Exophiala dermatitidis* |
| Q2UDX3 | *Aspergillus oryzae* |
| M3ASJ4 | *Pseudocercospora fijiensis* |
| A0A177BZU0 | *Paraphaeosphaeria sporulosa* |
| A0A017S910 | *Aspergillus ruber* CBS 135680 |
| A0A175VVF2 | *Madurella mycetomatis* |
| A0A0J8UWI6 | *Coccidioides immitis* |
| A0A0J6YFS7 | *Coccidioides immitis* RMSCC |
| J3K3F7 | *Coccidioides immitis* |
| A0A0D2FX82 | *Rhinocladiella mackenziei* |
| A0A072PSS5 | *Exophiala aquamarina* |
| A0A0A1MWE2 | *Rhizopus microsporus* |
| W2RSU8 | *cyphellophora europaea* |
| C0S1D5 | *Paracoccidioides brasiliensiensis* |
| C1G9R2 | *Paracoccidioides brasiliensiensis* |
| A0A1D2JGH6 | *Paracoccidioides brasiliensis* |
| A0A166PXN0 | *Cordyceps brongniartii* |
| Q54GC1 | *Dictyostelium discoideum* |
| A0A0H1B9A9 | *Emmonsia parva* UAMH 139 |
| R4XEF3 | *Taphrina deformans* |
| D3B2U8 | *Polysphondylium pallidum* |
| U1HHT8 | *Endocarpon pusillum* |
| A0A1E3JYY5 | *Tsuchiyaea wingfieldii* |
| A0A0C3JN41 | *Pisolithus tinctorius* Marx 270 |
| B6HF05 | *Penicillium rubens* |
| A0A060S368 | *Pycnoporus cinnabarinus* |
| K5W449 | *Agaricus bisporus* |
| B0CTA0 | *Laccaria bicolor* |
| F0XD96 | *Grosmannia clavigera* |
| A0A165EP91 | *Calocera cornea* HHB12733 |

Acylglycerol Lipases and Sterol Esterases

In some embodiments, recombinant microorganisms and methods are provided for the production of short chain fatty alcohols, fatty aldehydes and/or fatty acetates. In certain embodiments, the short chain fatty alcohols, fatty aldehydes and/or fatty acetates have carbon chain length shorter than or equal to C18. In some preferred embodiments of methods to produce short chain pheromones, select enzymes which prefer to hydrolyze ester bonds of long-chain acylglycerols are co-expressed with one or more fatty acyl desaturases. Such suitable enzymes are exemplified by heterologous or engineered acylglycerol lipases. Examples of acylglycerol lipases that are suitable for this purpose are listed in Table 5c.

In some preferred embodiments of methods to produce fatty alcohols, fatty aldehydes and/or fatty acetates, one or more genes of the microbial host encoding acylglycerol lipases (mono-, di-, or triacylglycerol lipases) and sterol ester esterases are deleted or downregulated and replaced with one or more acylglycerol lipases which prefer long chain acylglycerol substrates. Such deletion or down-regulation targets include, but are not limited to *Y. lipolytica* YALI0E32035g, *Y. lipolytica* YALI0D17534g, *Y. lipolytica* YALI0F10010g, *Y. lipolytica* YALI0C14520g, *Y. lipolytica* YALI0E00528g, *S. cerevisiae* YKL140w, *S. cerevisiae* YMR313c, *S. cerevisiae* YKR089c, *S. cerevisiae* YOR081c, *S. cerevisiae* YKL094W, *S. cerevisiae* YLL012W, *S. cerevisiae* YLR020C, *Candida* CaO19.2050, *Candida* CaO19.9598, *Candida* CTRG_01138, *Candida* W5Q_03398, *Candida* CTRG_00057, *Candida* CaO19.5426, *Candida* CaO19.12881, *Candida* CTRG_06185, *Candida* CaO19.4864, *Candida* CaO19.12328, *Candida* CTRG_03360, *Candida* CaO19.6501, *Candida* CaO19.13854, *Candida* CTRG_05049, *Candida* CaO19.1887, *Candida* CaO19.9443, *Candida* CTRG_01683, and *Candida* CTRG_04630.

Carboxylic ester hydrolases (EC 3.1.1) are a large class of enzymes catalyzing the hydrolysis or synthesis of ester bonds. They have been described in all life domains, prokaryotic and eukaryotic. Most of them belong to the α/β-hydrolase superfamily and have a conserved "catalytic triad" formed by His, an acidic amino acid and a Ser residue that is located in a highly conserved GXSXG sequence. During hydrolysis, the catalytic Ser will start the nucleophilic attack of the substrate helped by the other two residues from the triad, which are in close spatial vicinity. These are presumed to facilitate the hydrolysis of esters by a mechanism similar to that of chymotrypsin-like serine proteases. Another characteristic feature is the presence of an amino acidic region whose sequence is not as conserved as that of the catalytic triad, the oxyanion hole, which serves to stabilize a transition state generated during catalysis. In addition, these enzymes generally do not require cofactors. Acylglycerol lipases and sterol esterases belong to the carboxylic ester hydrolase family.

An acylglycerol lipase enzyme catalyzes a chemical reaction that uses water molecules to break the glycerol monoesters of long-chain fatty acids. The systematic name of this enzyme class is glycerol-ester acylhydrolase. Other names in common use include monoacylglycerol lipase, monoacylglycerolipase, monoglyceride lipase, monoglyceride hydrolase, fatty acyl monoester lipase, monoacylglycerol hydrolase, monoglyceridyllipase, and monoglyceridase. This enzyme participates in glycerolipid metabolism.

A sterol esterase enzyme catalyzes the chemical reaction:

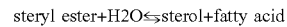
steryl ester+H2O⇌sterol+fatty acid

Thus, the two substrates of this enzyme are steryl ester and H2O, whereas its two products are sterol and fatty acid.

The systematic name of this enzyme class is steryl-ester acylhydrolase. Other names in common use include cholesterol esterase, cholesteryl ester synthase, triterpenol esterase, cholesteryl esterase, cholesteryl ester hydrolase, sterol ester hydrolase, cholesterol ester hydrolase, cholesterase, and acylcholesterol lipase. This enzyme participates in bile acid biosynthesis. Sterol esterases are widespread in nature and have been identified from mammals' tissues such as the pancreas, intestinal mucosa, liver, placenta, aorta, and brain, to filamentous fungi, yeast, and bacteria.

In terms of substrate specificity, many sterol esterases are able to catalyze the hydrolysis or synthesis of a rather broad range of other substrates containing ester linkages, such as acylglycerols, aryl esters, and in some cases alcohol esters, cinnamyl esters, xhantophyl esters, or synthetic polymers.

In some embodiments, a recombinant microorganism capable of producing a mono- or poly-unsaturated ≤$C_{18}$ fatty alcohol, fatty aldehyde and/or fatty acetate from an endogenous or exogenous source of saturated $C_6$-$C_{24}$ fatty acid is provided, wherein the recombinant microorganism expresses one or more acylglycerol lipase and/or sterol ester esterase enzymes, and wherein the recombinant microorganism is manipulated to delete, disrupt, mutate, and/or reduce the activity of one or more endogenous acylglycerol lipase and/or sterol ester esterase enzymes. In some embodiments, the one or more acylglycerol lipase and/or sterol ester esterase enzymes being expressed are different from the one or more endogenous acylglycerol lipase and/or sterol ester esterase enzymes being deleted or downregulated. In some embodiments, the one or more endogenous or exogenous acylglycerol lipase and/or sterol ester esterase enzymes being expressed prefer to hydrolyze ester bonds of long-chain acylglycerols. In other embodiments, the one or more acylglycerol lipase and/or sterol ester esterase enzymes being expressed are selected from Table 5c. In some embodiments, the one or more endogenous acylglycerol lipase and/or sterol ester esterase enzymes being deleted or downregulated are selected from *Y. lipolytica* YALI0E32035g, *Y. lipolytica* YALI0D17534g, *Y. lipolytica* YALI0F10010g, *Y. lipolytica* YALI0C14520g, *Y. lipolytica* YALI0E00528g, *S. cerevisiae* YKL140w, *S. cerevisiae* YMR313c, *S. cerevisiae* YKR089c, *S. cerevisiae* YOR081c, *S. cerevisiae* YKL094W, *S. cerevisiae* YLL012W, *S. cerevisiae* YLR020C, *Candida* CaO19.2050, *Candida* CaO19.9598, *Candida* CTRG_01138, *Candida* W5Q_03398, *Candida* CTRG_00057, *Candida* CaO19.5426. *Candida* CaO19.12881, *Candida* CTRG_06185, *Candida* CaO19.4864, *Candida* CaO19.12328, *Candida* CTRG_03360, *Candida* CaO19.6501, *Candida* CaO19.13854, *Candida* CTRG_05049, *Candida* CaO19.1887, *Candida* CaO19.9443, *Candida* CTRG_01683, and *Candida* CTRG_04630. In some embodiments, the recombinant microorganism further expresses pheromone biosynthetic pathway enzymes. In further embodiments, the pheromone biosynthetic pathway enzymes comprise one or more fatty acyl desaturase and/or fatty acyl conjugase. In yet further embodiments, the pheromone biosynthetic pathway enzymes comprise one or more fatty alcohol forming fatty acyl reductase.

In some embodiments, a method of producing a mono- or poly-unsaturated ≤$C_{18}$ fatty alcohol, fatty aldehyde and/or fatty acetate from an endogenous or exogenous source of saturated $C_6$-$C_{24}$ fatty acyl-CoA are provided, wherein the method comprises introducing into or expressing in a recombinant microorganism at least one endogenous or exogenous nucleic acid molecule encoding an acylglycerol lipase or sterol ester esterase and introducing a deletion, insertion, or loss of function mutation in one or more gene encoding an acylglycerol lipase or sterol ester esterase, wherein the at least one endogenous or exogenous nucleic acid molecule encoding an acylglycerol lipase or sterol ester esterase being introduced or expressed is different from the one or more gene encoding an acylglycerol lipase or sterol ester esterase being deleted or downregulated. In some embodiments, the at least one endogenous or exogenous nucleic acid molecule encoding an acylglycerol lipase or sterol ester esterase being introduced or expressed prefers to hydrolyze ester bonds of long-chain acylglycerols. In some embodiments, the at least one endogenous or exogenous nucleic acid molecule encoding an acylglycerol lipase or sterol ester esterase being introduced or expressed is selected from Table 5c. In some embodiments, the one or more gene being deleted or downregulated encodes an acylglycerol lipase or sterol ester esterase selected from *Y. lipolytica* YALI0E32035g. *Y. lipolytica* YALI0D17534g, *Y. lipolytica* YALI0F10010g, *Y. lipolytica* YALI0C4520g. *Y. lipolytica* YALI0E00528g, *S. cerevisiae* YKL140w, *S. cerevisiae* YMR313c, *S. cerevisiae* YKR089c, *S. cerevisiae* YOR081c, *S. cerevisiae* YKL094W, *S. cerevisiae* YLL012W, *S. cerevisiae* YLR020C, *Candida* CaO19.2050, *Candida* CaO19.9598, *Candida* CTRG_01138, *Candida* W5Q03398, *Candida* CTRG_00057, *Candida* CaO19.5426, *Candida* CaO19.12881, *Candida* CTRG_06185, *Candida* CaO19.4864, *Candida* CaO19.12328, *Candida* CTRG_03360, *Candida* CaO19.6501, *Candida* CaO19.13854, *Candida* CTRG_05049, *Candida* CaO19.1887, *Candida* CaO19.9443, *Candida* CTRG_01683, and *Candida* CTRG_04630. In some embodiments, the method further comprises introducing into or expressing in the recombinant microorganism at least one endogenous or exogenous nucleic acid molecule encoding a fatty acyl desaturase and/or fatty acyl conjugase. In further embodiments, the method further comprises introducing into or expressing in the recombinant microorganism at least one endogenous or exogenous nucleic acid molecule encoding a fatty alcohol forming fatty acyl reductase.

TABLE 5c

Exemplary acylglycerol lipases

| Accession No. | Source Organism |
|---|---|
| EAY76846.1 | *Oryza sativa* |
| OEL29276.1 | *Dichanthelium oligosanthes* |
| ONM35522.1 | *Zea mays* |
| AFW56472.1 | *Zea mays* |
| AFW60230.1 | *Zea mays* |
| ACG33769.1 | *Zea mays* |
| ACG30143.1 | *Zea mays* |
| ACG39100.1 | *Zea mays* |
| ACG48810.1 | *Zea mays* |
| KQK11040.1 | *Brachypodium distachyon* |
| CAA64004.1 | *Saccharomyces cerevisiae* |
| CAA81640.1 | *Saccharomyces cerevisiae* |
| CAG78037.1 | *Yarrowia lipolytica* |
| EEF47288.1 | *Ricinus communis* |
| EEF45491.1 | *Ricinus communis* |
| EEF52390.1 | *Ricinus communis* |
| EEF38788.1 | *Ricinus communis* |
| EER38789.1 | *Ricinus communis* |
| EEF28563.1 | *Ricinus communis* |
| EEF46013.1 | *Ricinus communis* |
| AFQ93681.1 | *Ricinus communis* |
| EEF45592.1 | *Ricinus communis* |
| EEF43592.1 | *Ricinus communis* |
| EEF50924.1 | *Ricinus communis* |
| EEF33440.1 | *Ricinus communis* |

Expression of Toxic Proteins or Polypeptides

The present disclosure describes a toxic protein, peptide, or small molecule that can be encoded by a recombinant microorganism. In some embodiments, the toxic protein, peptide, or small molecule is biosynthetically produced along with an insect pheromone.

In some embodiments, the recombinant microorganism expresses one or more nucleic acid molecules encoding a protein or polypeptide which is toxic to an insect. In some embodiments, the toxic protein or polypeptide is from an entomopathogenic organism. In some embodiments, the entomopathogenic organism is selected from *Bacillus thuringiensis, Pseudomonas aenruginosa,* and *Serratia marcescens*. In a particular embodiment, the nucleic acid molecule encodes a *Bacillus thuringiensis* toxin.

In some embodiments, a recombinant microorganism is engineered to express a metabolic pathway which, when expressed, produces a small molecule that is toxic to an insect.

In exemplary embodiments, an insect pheromone produced by a recombinant microorganism described herein may be used to attract a pest insect, and subsequently, the pest insect is eradicated with a toxic substance, such as a toxic protein, peptide, or small molecule, which has been co-produced by a recombinant microorganism described herein.

Biosynthesis of Pheromones Using a Recombinant Microorganism

Figure 1:
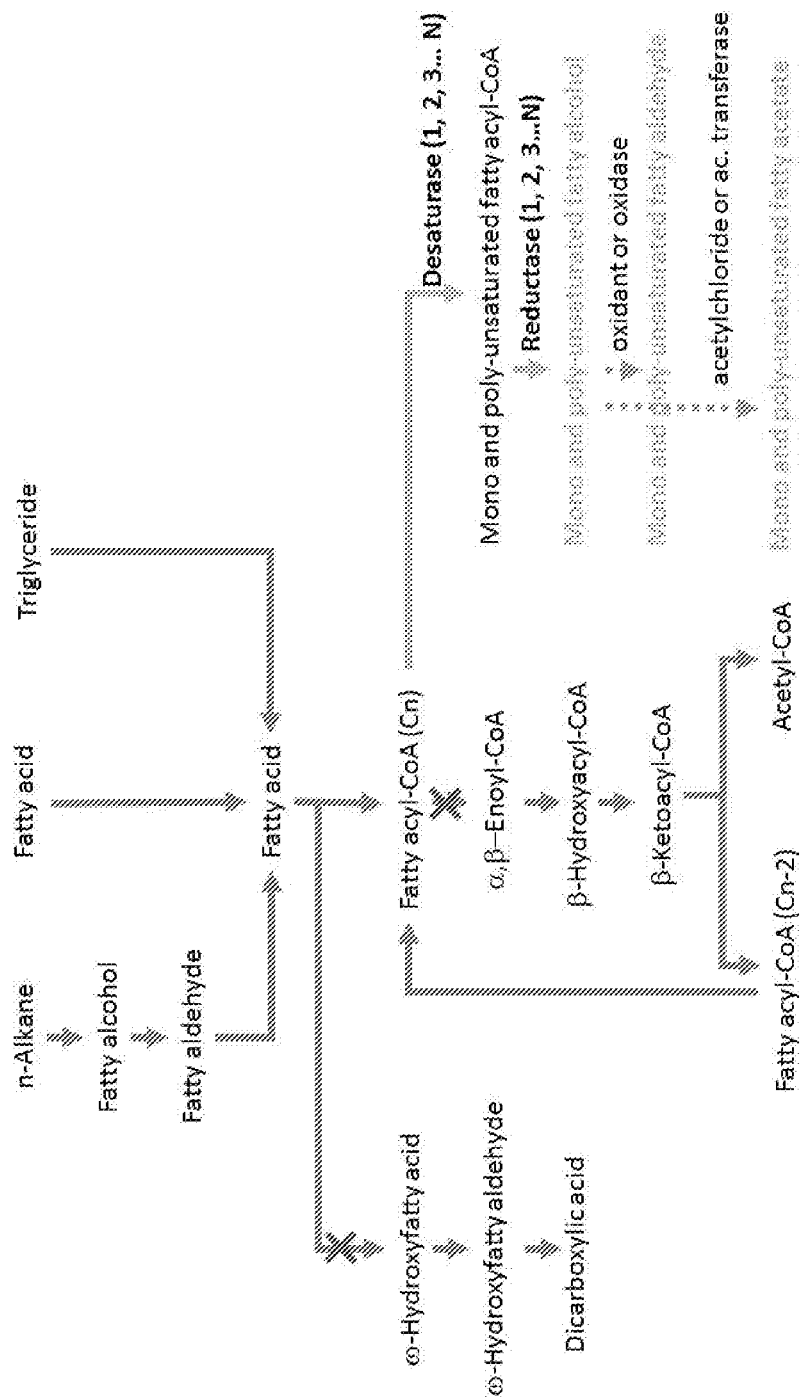
FIG. 1 illustrates the conversion of a saturated fatty acyl-CoA to an unsaturated fatty alcohol.

As discussed above, in a first aspect, the present disclosure relates to a recombinant microorganism capable of producing a mono- or poly-unsaturated $C_6$-$C_{24}$ fatty alcohol from an endogenous or exogenous source of saturated $C_6$-$C_{24}$ fatty acyl-CoA. An illustrative embodiment of the first aspect is shown in FIG. 1. The blue lines designate biochemical pathways used to produce a saturated acyl-CoA, which acts as a substrate for unsaturated fatty-acyl CoA conversion. The substrate to unsaturated fatty acyl-CoA conversion can be performed by endogenous or exogenous enzymes in a host. Green lines indicate conversions catalyzed by an exogenous nucleic acid molecule encoding for an enzyme. Accordingly, in some embodiments, the conversion of a saturated fatty acyl-CoA to a mono- or poly-unsaturated fatty acyl-CoA is catalyzed by at least one desaturase, which is encoded by an exogenous nucleic acid molecule. In further embodiments, the conversion of the mono- or poly-unsaturated fatty acyl-CoA to a mono- or poly-unsaturated fatty alcohol is catalyzed by at least one reductase, which is encoded by an exogenous nucleic acid molecule. The dashed grey lines indicate downstream steps for the synthesis of pheromones, fragrances, flavors, and polymer intermediates, such as using an alcohol oxidase or oxidant to produce a mono- or poly-unsaturated fatty aldehyde, and an acetyl transferase or a chemical such as acetylchloride to produce a mono- or poly-unsaturated fatty acetate. The red crosses indicate deleted or down regulated pathways native to the host, which increase flux towards the engineered pathway.

Accordingly, in one embodiment, the recombinant microorganism expresses: (a) at least one exogenous nucleic acid molecule encoding a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA; and (b) at least one exogenous nucleic acid molecule encoding a fatty alcohol forming fatty-acyl reductase that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol. In some embodiments, the saturated $C_6$-$C_{24}$ fatty acyl-CoA can be produced using endogenous enzymes in the host microorganism. In other embodiments, the saturated $C_6$-$C_{24}$ fatty acyl-CoA can be produced using one or more exogenous enzymes in the host microorganism.

As described above, a fatty acyl desaturase catalyzes the desaturation of the hydrocarbon chain on, e.g., a saturated fatty acyl-CoA molecule to generate a corresponding unsaturated fatty acyl CoA molecule. In some embodiments, an exogenous fatty acyl desaturase can be selected and expressed in a recombinant microorganism to catalyze the formation of at least one double bond in fatty acyl-CoA molecule having from 6 to 24 carbons in the hydrocarbon chain. Accordingly, in some embodiments, the fatty-acyl desaturase is a desaturase capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms.

An exogenous fatty acyl desaturase described herein can be selected to catalyze the desaturation at a desired position on the hydrocarbon chain. Accordingly, in some embodiments, the fatty-acyl desaturase is capable of generating a double bond at position C5, C6, C7, C8, C9, C10, C11, C12, or C13, in the fatty acid or its derivatives, such as, for example, fatty acid CoA esters.

One or more than one fatty acyl-CoA desaturase can be expressed in the host to catalyze desaturation at multiple positions on the hydrocarbon chain. In some embodiments, the fatty acyl-CoA desaturase is heterologous to the host microorganism. Accordingly, various embodiments provide for recombinant microorganism comprised of at least one exogenous nucleic acid molecule, which encodes a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA.

In one exemplary embodiment, the fatty-acyl desaturase is a Z11 desaturase. The Z11 fatty-acyl desaturase catalyze double bond formation between the $11^{th}$ and $12^{th}$ carbons in the substrate relative to the carbonyl group. In various embodiments described herein, the Z11 desaturase, or the nucleic acid sequence that encodes it, can be isolated from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana*. Further Z11-desaturases, or the nucleic acid sequences encoding them, can be isolated from *Bombjx mori, Manduca sexta, Diatraea grandiosella, Earias insulana, Earias vittella, Plutella xylostella, Bombyx mori* or *Diaphania nitidalis*. In exemplary embodiments, the Z11 desaturase comprises a sequence selected from GenBank Accession Nos. JX679209, JX964774, AF416738, AF545481, EU152335, AAD03775, AAF81787, and AY493438. In some embodiments, a nucleic acid sequence encoding a Z11 desaturase from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana* is codon optimized. In some embodiments, the Z11 desaturase comprises a sequence selected from SEQ ID NOs: 9, 18, 24 and 26 from *Trichoplusia ni*. In some embodiments, the Z11 desaturase comprises an amino acid sequence set forth in SEQ ID NO: 49 from *Trichoplusia ni*. In other embodiments, the Z11 desaturase comprises a sequence selected from SEQ ID NOs: 10 and 16 from *Agrotis segetum*. In some embodiments, the Z11 desaturase comprises an amino acid sequence set forth in SEQ ID NO: 53 from *Agrotis segetum*. In some embodiments, the Z11 desaturase comprises a sequence selected from SEQ ID NOs: 11 and 23 from *Thalassiosira pseudonana*. In some embodiments, the Z11 desaturase comprises an amino acid sequence selected from SEQ ID NOs: 50 and 51 from *Thalassiosira pseudonana*. In certain embodiments, the Z11 desaturase comprises a sequence selected from SEQ ID NOs: 12, 17 and 30 from *Amyelois transitella*. In some embodiments, the Z11 desaturase comprises an amino acid sequence set forth in SEQ ID NO: 52 from *Amyelois transitella*. In further embodiments, the Z11 desaturase comprises a sequence selected from SEQ ID NOs: 13, 19, 25, 27 and 31 from *Helicoverpa zea*. In some embodiments, the Z11 desaturase comprises an amino acid sequence set forth in SEQ ID NO: 54 from *Helicoverpa zea*. In some embodiments, the Z11 desaturase comprises an amino acid sequence set forth in SEQ ID NO: 39 from *S. inferens*. In some embodiments, the Z11 desaturase comprises an amino acid sequence set forth in GenBank Accession nos. AF416738, AGH12217.1, AII21943.1, CAJ43430.2, AF441221, AAF81787.1, AF545481, AJ271414, AY362879, ABX71630.1, NP001299594.1, Q9N9Z8, ABX71630.1 and AIM40221.1. In some embodiments, the Z11 desaturase comprises a chimeric polypeptide. In some embodiments, a complete or partial Z11 desaturase is fused to another polypeptide. In certain embodiments, the N-terminal native leader sequence of a Z11 desaturase is replaced by an oleosin leader sequence from another species. In certain embodiments, the Z11 desaturase comprises a sequence selected from SEQ ID NOs: 15, 28 and 29. In some embodiments, the Z11 desaturase comprises an amino acid sequence selected from SEQ ID NOs: 61, 62, 63, 78, 79 and 80.

In certain embodiments, the Z11 desaturase catalyzes the conversion of a fatty acyl-CoA into a mono- or polyunsaturated product selected from Z11-13:Acyl-CoA, E11-13:Acyl-CoA, (Z,Z)-7,11-13:Acyl-CoA, Z11-14:Acyl-CoA, E11-14:Acyl-CoA, (E,E)-9,11-14:Acyl-CoA, (E,Z)-9,11-14:Acyl-CoA, (Z,E)-9.11-14:Acyl-CoA, (Z,Z)-9,11-14:Acyl-CoA, (E,Z)-9,11-15:Acyl-CoA, (Z,Z)-9,11-15:Acyl-CoA, Z11-16:Acyl-CoA, E11-16:Acyl-CoA, (E,Z)-6,11-16:Acyl-CoA, (E,Z)-7,11-16:Acyl-CoA, (E,Z)-8,11-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA, (E,E)-11,13-16:Acyl-CoA, (E,Z)-11,13-16:Acyl-CoA, (Z,E)-11,13-16:Acyl-CoA, (Z,Z)-11,13-16:Acyl-CoA, (Z,E)-11,14-16:Acyl-CoA, (E,E,Z)-4,6,11-16:Acyl-CoA, (Z,Z,E)-7,11,13-16:Acyl-CoA, (E,E,Z,Z)-4,6,11,13-16:Acyl-CoA, Z11-17:Acyl-CoA, (Z,Z)-8,11-17:Acyl-CoA, Z11-18:Acyl-CoA, E11-18:Acyl-CoA, (Z,Z)-11,13-18:Acyl-CoA, (E,E)-11,14-18:Acyl-CoA, or combinations thereof.

In another exemplary embodiment, the fatty-acyl desaturase is a Z9 desaturase. The Z9 fatty-acyl desaturase catalyze double bond formation between the $9^{th}$ and $10^{th}$ carbons in the substrate relative to the carbonyl group. In various embodiments described herein, the Z9 desaturase, or the nucleic acid sequence that encodes it, can be isolated from organisms of the species *Ostrinia furnacalis, Ostrinia nobilalis, Choristoneura rosaceana, Lampronia capitella, Helicoverpa assulta,* or *Helicoverpa zea.* In exemplary embodiments, the Z9 desaturase comprises a sequence selected from GenBank Accession Nos. AY057862, AF243047, AF518017, EU152332, AF482906, and AAF81788. In some embodiments, a nucleic acid sequence encoding a Z9 desaturase is codon optimized. In some embodiments, the Z9 desaturase comprises a nucleotide sequence set forth in SEQ ID NO: 20 from *Ostrinia furnacalis*. In some embodiments, the Z9 desaturase comprises an amino acid sequence set forth in SEQ ID NO: 58 from *Ostrinia furnacalis*. In other embodiments, the Z9 desaturase comprises a nucleotide sequence set forth in SEQ ID NO: 21 from *Lampronia capitella*. In some embodiments, the Z9 desaturase comprises an amino acid sequence set forth in SEQ ID NO: 59 from *Lampronia capitella*. In some embodiments, the Z9 desaturase comprises a nucleotide sequence set forth in SEQ ID NO: 22 from *Helicoverpa zea*. In some embodiments, the Z9 desaturase comprises an amino acid sequence set forth in SEQ ID NO: 60 from *Helicoverpa zea*.

In certain embodiments, the Z9 desaturase catalyzes the conversion of a fatty acyl-CoA into a monounsaturated or polyunsaturated product selected from Z9-11:Acyl-CoA, Z9-12:Acyl-CoA, E9-12:Acyl-CoA, (E,E)-7,9-12:Acyl-CoA, (E,Z)-7,9-12:Acyl-CoA, (Z,E)-7,9-12:Acyl-CoA, (Z,Z)-7,9-12:Acyl-CoA, Z9-13:Acyl-CoA, E9-13:Acyl-CoA, (E,Z)-5,9-13:Acyl-CoA, (Z,E)-5,9-13:Acyl-CoA, (Z,Z)-5,9-13:Acyl-CoA, Z9-14:Acyl-CoA, E9-14:Acyl-CoA, (E,Z)-4,9-14:Acyl-CoA, (E,E)-9.11-14:Acyl-CoA, (E,Z)-9,11-14:Acyl-CoA, (Z,E)-9,11-14:Acyl-CoA, (Z,Z)-9,11-14:Acyl-CoA, (E,E)-9,12-14:Acyl-CoA, (Z,E)-9,12-14:Acyl-CoA, (Z,Z)-9,12-14:Acyl-CoA, Z9-15:Acyl-CoA, E9-15:Acyl-CoA, (Z,Z)-6,9-15:Acyl-CoA, Z9-16:Acyl-CoA. E9-16:Acyl-CoA, (E,E)-9,11-16:Acyl-CoA, (E,Z)-9,11-16:Acyl-CoA, (Z,E)-9,11-16:Acyl-CoA, (Z,Z)-9.11-16: Acyl-CoA, Z9-17:Acyl-CoA, E9-18:Acyl-CoA, Z9-18:Acyl-CoA, (E,E)-5,9-18:Acyl-CoA, (E,E)-9,12-18:Acyl-CoA, (Z,Z)-9,12-18:Acyl-CoA, (Z,Z,Z)-3,6,9-18:Acyl-CoA, (E,E,E)-9,12,15-18:Acyl-CoA, (Z,Z,Z)-9,12,15-18:Acyl-CoA, or combinations thereof.

Desaturation of a saturated $C_6$-$C_{24}$ fatty acyl-CoA can proceed through a plurality of reactions to produce a polyunsaturated $C_6$-$C_{24}$ fatty acyl-CoA. In some embodiments, the recombinant microorganism may express a bifunctional desaturase capable of catalyzing the formation at least two double bonds. In some embodiments, the recombinant microorganism may express more than one exogenous nucleic acid molecule encoding more than one fatty-acyl desaturase that catalyzes the conversion of a saturated $C_6$-$C_{24}$ fatty acyl-CoA to a corresponding poly-unsaturated $C_6$-$C_{24}$ fatty acyl-CoA. For example, the recombinant microorganism may express an exogenous nucleic acid molecule encoding a Z11 desaturase and another exogenous nucleic acid molecule encoding a Z9 desaturase. Thus, the resultant poly-unsaturated fatty acyl-CoA would have a double bond between the $9^{th}$ and $10^{th}$ carbon and another double bond between the $11^{th}$ and $12^{th}$ carbon.

In some embodiments, the recombinant microorganism may express a fatty-acyl conjugase that acts independently or together with a fatty-acyl desaturase to catalyze the conversion of a saturated or monounsaturated fatty acyl-CoA to a conjugated polyunsaturated fatty acyl-CoA.

In one embodiment, the disclosure provides a recombinant microorganism capable of producing a polyunsaturated $C_6$-$C_{24}$ fatty alcohol from an endogenous or exogenous source of saturated or monounsaturated $C_6$-$C_{24}$ fatty acyl-CoA, wherein the recombinant microorganism expresses: (a) at least one exogenous nucleic acid molecule encoding a fatty acyl conjugase that catalyzes the conversion of a saturated or monounsaturated $C_6$-$C_{24}$ fatty acyl-CoA to a corresponding polyunsaturated $C_6$-$C_{24}$ fatty acyl-CoA; and (b) at least one exogenous nucleic acid molecule encoding a fatty alcohol forming fatty-acyl reductase that catalyzes the conversion of the polyunsaturated $C_6$-$C_{24}$ fatty acyl-CoA from (a) into the corresponding polyunsaturated $C_6$-$C_{24}$ fatty alcohol.

In another embodiment, the recombinant microorganism expresses at least two exogenous nucleic acid molecules encoding fatty-acyl conjugases that catalyze the conversion of a saturated or monounsaturated $C_6$-$C_{24}$ fatty acyl-CoA to a corresponding polyunsaturated $C_6$-$C_{24}$ fatty acyl-CoA.

In a further embodiment, the disclosure provides a recombinant microorganism capable of producing a polyunsaturated $C_6$-$C_{24}$ fatty alcohol from an endogenous or exogenous source of saturated or monounsaturated $C_6$-$C_{24}$ fatty acyl-CoA, wherein the recombinant microorganism expresses: (a) at least one exogenous nucleic acid molecule encoding a fatty-acyl desaturase and at least one exogenous nucleic acid molecule encoding a fatty acyl conjugase that catalyze the conversion of a saturated or monounsaturated $C_6$-$C_{24}$ fatty acyl-CoA to a corresponding polyunsaturated $C_6$-$C_{24}$ fatty acyl-CoA; and (b) at least one exogenous nucleic acid molecule encoding a fatty alcohol forming fatty-acyl reductase that catalyzes the conversion of the polyunsaturated $C_6$-$C_{24}$ fatty acyl-CoA from (a) into the corresponding polyunsaturated $C_6$-$C_{24}$ fatty alcohol.

In another embodiment, the recombinant microorganism expresses at least two exogenous nucleic acid molecules encoding fatty-acyl desaturases and at least two exogenous nucleic acid molecules encoding fatty-acyl conjugases that catalyze the conversion of a saturated or monounsaturated $C_4$-$C_{24}$ fatty acyl-CoA to a corresponding polyunsaturated $C_6$-$C_{24}$ fatty acyl-CoA.

In yet a further embodiment, the fatty-acyl conjugase is a conjugase capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms.

In certain embodiments, the conjugase, or the nucleic acid sequence that encodes it, can be isolated from organisms of the species *Cydia pomonella, Cydia nigricana, Lobesia botrana, Myelois cribrella, Plodia interpunctella, Dendrolimus punctatus, Lampronia capitella, Spodoptera litura, Amyelois transitella, Manduca sexta, Bombyx mori, Calendula officinalis, Trichosanthes kirilowii, Punica granatum, Momordica charantia, Impatiens balsamina,* and *Epiphyas postvittana*. In exemplary embodiments, the conjugase comprises a sequence selected from GenBank Accession No. or Uniprot database: A0A059TBF5, A0A0M3L9E8, A0A0M3L9S4, A0A0M3LAH8, A0A0M3LAS8, A0A0M3LAH8, B6CBS4, XP_013183656.1, XP_004923568.2, ALA65425.1, NP_001296494.1, NP_001274330.1, Q4A181, Q75PL7. Q9FPP8, AY178444, AY178446, AF182521, AF182520, Q95UJ3.

As described above, a fatty acyl reductase catalyzes the reduction of a carbonyl group, e.g., on an unsaturated fatty acyl-CoA molecule to generate a corresponding unsaturated fatty acid molecule. In some embodiments, the fatty alcohol forming fatty acyl CoA reductase is heterologous to the microorganism. Accordingly, various embodiments provide for recombinant microorganism comprised of at least one exogenous nucleic acid molecule, which encodes a fatty alcohol forming fatty acyl reductase that catalyzes the reduction of a carbonyl group on an unsaturated fatty acyl-CoA molecule to generate a corresponding unsaturated fatty acid molecule.

In some embodiments, the fatty acyl reductase is from an organism of the species *Agrotis segetum, Spodoptera exigua, Spodoptera littoralis, Euglena gracilis, Yponomeuta evonymellus* and *Helicoverpa armigera*. In some embodiments, a nucleic acid sequence encoding a fatty-acyl reductase is codon optimized. In some embodiments, the fatty acyl reductase comprises a sequence set forth in SEQ ID NO: 1 from *Agrotis segetum*. In some embodiments, the fatty acyl reductase comprises an amino acid sequence set forth in SEQ ID NO: 55 from *Agrotis segetum*. In other embodiments, the fatty acyl reductase comprises a sequence set forth in SEQ ID NO: 2 from *Spodoptera littoralis*. In other embodiments, the fatty acyl reductase comprises an amino acid sequence set forth in SEQ ID NO: 56 from *Spodoptera littoralis*. In some embodiments, the fatty acyl reductase comprises a sequence selected from SEQ ID NOs: SEQ ID NOs: 3, 32, 40, 72, 74, 76 and 81. In some embodiments, the fatty acyl reductase comprises an amino acid sequence set forth in SEQ ID NO: 55 from *Agrotis segetum*. In other embodiments, the fatty acyl reductase comprises an amino acid sequence set forth in SEQ ID NO: 56 from *Spodoptera littoralis*. In some embodiments, the fatty acyl reductase comprises an amino acid sequence selected from SEQ ID NOs: 41 and 57 from *Helicoverpa armigera*. In some embodiments, the fatty acyl reductase comprises an amino acid sequence selected from SEQ ID NOs: 73 and 82 from *Spodoptera exigua*. In some embodiments, the fatty acyl reductase comprises an amino acid sequence set forth in SEQ ID NO: 75 from *Euglena gracilis*. In some embodiments, the fatty acyl reductase comprises an amino acid sequence set forth in SEQ ID NO: 77 from *Yponomeuta evonymellus*.

In some embodiments, the production of unsaturated fatty alcohols in a recombinant microorganism comprises the expression of one or more mutant FARs. In certain embodiments, *Helicoverpa amigera* fatty acyl-CoA reductase (HaFAR) variants are provided which show a net increase in fatty alcohol produced compared to the wild type *Helicoverpa amigera* fatty acyl-CoA reductase encoded by an amino acid sequence set forth in SEQ ID NO: 41. In some embodiments, the increased enzymatic activity is a net activity increase in amount of fatty alcohol produced relative to the amount of fatty alcohol produced by a wild type enzymatic activity of HaFAR encoded by an amino acid sequence set forth in SEQ ID NO: 41. In some embodiments, a wild type HaFAR comprises a nucleotide sequence set forth in SEQ ID NO: 90. In some embodiments, a variant of a wild type HaFAR encoded by an amino acid sequence set forth in SEQ ID NO: 41 comprises point mutations at the following positions: S60X, S195X, S298X. S378X. S394X, S418X, and S453X, wherein X comprises the amino acids F, L, M, I, V, P, T, A, Y, K, H, N, Q, K, D, E, C, W, R. In some embodiments, a variant of a wild type HaFAR encoded by an amino acid sequence set forth in SEQ ID NO: 41 comprises a combination of point mutations selected from mutations at the following amino acid positions: S60X, S195X, S298X, S378X, S394X, S418X, and S453X, wherein X comprises the amino acids F, L, M, I, V, P, T, A, Y, K, H, N, Q, K, D, E, C, W, R. In some embodiments, the fatty acyl reductase is a mutated fatty acyl reductase and comprises an amino acid sequence selected from SEQ ID NOs: 42-48. In some embodiments, the fatty acyl reductase is a mutated fatty acyl reductase and comprises nucleotide sequence selected from SEQ ID NOs: 83-89.

In exemplary embodiments, the fatty-acyl reductase catalyzes the conversion of a mono- or poly-unsaturated fatty acyl-CoA into a fatty alcohol product selected from (Z)-3-hexenol, (Z)-3-nonenol, (Z)-5-decenol, (E)-5-decenol. (Z)-7-dodecenol, (E)-8-dodecenol, (Z)-8-dodecenol, (Z)-9-dodecenol, (Z)-9-tetradecenol, (Z)-9-hexadcenol, (Z)-11-tetradecenol, (Z)-7-hexadecenol, (Z)-11-hexadecenol, (E)-11-tetradecenol, or (Z,Z)-11,13-hexadecadienol, (11Z,13E)-hexadecadienol, (E,E)-8,10-dodecadienol, (E,Z)-7,9-dodecadienol, (Z)-13-octadecenol, or combinations thereof.

In some embodiments, a recombinant microorganism described herein can include a plurality of fatty acyl reductases. Accordingly, in such embodiments, the recombinant microorganism expresses at least two exogenous nucleic acid molecules, which encode fatty-acyl reductases that catalyze the conversion of the mono- or poly-unsaturated $C_6$-$C_{24}$ fatty acyl-CoA into the corresponding mono- or poly-unsaturated $C_6$-$C_{24}$ fatty alcohol.

In a further embodiment, the disclosure provides a recombinant microorganism capable of producing a mono- or poly-unsaturated ≤$C_{18}$ fatty alcohol from an endogenous or exogenous source of saturated $C_6$-$C_{24}$ fatty acid, wherein the recombinant microorganism comprises: (a) at least one exogenous nucleic acid molecule encoding a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA; (b) at least one exogenous nucleic acid molecule encoding an acyl-CoA oxidase that catalyzes the conversion of the mono- or poly-unsaturated $C_6$-$C_{24}$ fatty acyl-CoA from (a) into a mono- or poly-unsaturated ≤$C_{18}$ fatty acyl-CoA after one or more successive cycle of acyl-CoA oxidase activity, with a given cycle producing a mono- or poly-unsaturated $C_4$-$C_{22}$ fatty acyl-CoA intermediate with a two carbon truncation relative to a starting mono- or poly-unsaturated $C_6$-$C_{24}$ fatty acyl- CoA substrate in that cycle, and (c) at least one exogenous nucleic acid molecule encoding a fatty alcohol forming fatty acyl reductase that catalyzes the conversion of the mono- or poly-unsaturated ≤C18 fatty acyl-CoA from (b) into the corresponding mono- or poly-unsaturated ≤C18 fatty alcohol. In some embodiments, the fatty acyl desaturase is selected from an *Argyrotaenia velutinana, Spodoptera litura, Sesamia inferens, Manduca sexta, Ostrinia nubilalis, Helicoverpa zea, Choristoneura rosaceana, Drosophila melanogaster, Spodoptera littoralis, Lampronia capitella, Amyelois transitella, Trichoplusia ni, Agrotis segetum, Ostrinia furnicalis*, and *Thalassiosira pseudonana* derived fatty acyl desaturase. In some embodiments, the fatty acyl desaturase has 95% sequence identity to a fatty acyl desaturase selected from the group consisting of: SEQ ID NOs: 39, 49-54, 58-63, 78-80 and GenBank Accession nos. AF416738, AGH12217.1, AII21943.1, CAJ43430.2, AF441221, AAF81787.1, AF545481, AJ271414, AY362879. ABX71630.1, NP001299594.1, Q9N9Z8, ABX71630.1 and AIM40221.1. In some embodiments, the acyl-CoA oxidase is selected from Table 5a. In other embodiments, the fatty alcohol forming fatty acyl reductase is selected from an *Agrotis segetum, Spodoptera exigua, Spodoptera littoralis, Euglena gracilis, Yponomeuta evonymellus* and *Helicoverpa armigera* derived fatty alcohol forming fatty acyl reductase. In further embodiments, the fatty alcohol forming fatty acyl reductase has 95% sequence identity to a fatty alcohol forming fatty acyl reductase selected from the group consisting of: SEQ ID NOs: 1-3, 32, 41-48, 55-57, 73, 75, 77 and 82. In some embodiments, the recombinant microorganism is a yeast selected from the group consisting of *Yarrowia lipolytica, Saccharomyces cerevisiae, Candida albicans, Candida tropicalis* and *Candida viswanathii*.

In some embodiments, the recombinant microorganism further comprises at least one endogenous or exogenous nucleic acid molecule encoding an acyltransferase that preferably stores ≤$C_{18}$ fatty acyl-CoA. In some embodiments, the acyltransferase is selected from the group consisting of glycerol-3-phosphate acyl transferase (GPAT), lysophosphatidic acid acyltransferase (LPAAT), glycerolphospholipid acyltransferase (GPLAT) and diacylglycerol acyltransferases (DGAT). In some preferred embodiments, the acyltransferase is selected from Table 5b.

In some embodiments, the coexpression of a wax esterase would allow the storage of fatty alcohols and fatty acids in a 1:1 ratio. In combination with TAG storage that could lead to interesting ratios of TAG and fatty alcohols which could subsequently be used for different product streams. Examples for waxester synthases: *Homo sapiens* AWAT2 (XM_011530876.2), *Mus musculus* (AAT68766.1) *Euglena gracilis* WS (ADI60058.1), *Euglena gracilis* WSD2 (BAV82975.1), *Euglena gracilis* WSD5 (BAV82978.1).

In some embodiments, the recombinant microorganism further comprises at least one endogenous or exogenous nucleic acid molecule encoding an acylglycerol lipase that preferably hydrolyzes ester bonds of >C16, of >C14, of >C12 or of >C10 acylglycerol substrates. In some embodiments, the acylglycerol lipase is selected from Table 5c.

In some embodiments, the recombinant microorganism comprises a deletion, disruption, mutation, and/or reduction in the activity of one or more endogenous enzymes that catalyzes a reaction in a pathway that competes with the biosynthesis pathway for the production of a mono- or poly-unsaturated ≤$C_{18}$ fatty alcohol. In further embodiments, the recombinant microorganism comprises a deletion, disruption, mutation, and/or reduction in the activity of one or more endogenous enzyme selected from: (i) one or more acyl-CoA oxidase; (ii) one or more acyltransferase; (iii) one or more acylglycerol lipase and/or sterol ester esterase; (iv) one or more (fatty) alcohol dehydrogenase; (v) one or more (fatty) alcohol oxidase; and (vi) one or more cytochrome P450 monooxygenase.

In some preferred embodiments, one or more genes of the microbial host encoding acyl-CoA oxidases are deleted or down-regulated to eliminate or reduce the truncation of desired fatty acyl-CoAs beyond a desired chain-length. In some embodiments, the recombinant microorganism comprises a deletion, disruption, mutation, and/or reduction in the activity of one or more endogenous acyl-CoA oxidase enzyme selected from the group consisting of *Y. lipolytica* POX1 (YALI0E32835g), *Y. lipolytica* POX2 (YALI0F10857g), *Y. lipolytica* POX3 (YALI0D24750g), *Y. lipolytica* POX4 (YALI0E27654g), *Y. lipolytica* POX5 (YALI0C23859g), *Y. lipolytica* POX6 (YALI0E06567g); *S. cerevisiae* POX1 (YGL205W); *Candida* POX2 (CaO19.1655, CaO19.9224, CTRG_02374, M18259), *Candida* POX4 (CaO19.1652, CaO19.9221, CTRG_02377, M12160), and *Candida* POX5 (CaO19.5723, CaO19.13146. CTRG_02721, M12161).

In some embodiments, a recombinant microorganism capable of producing a mono- or poly-unsaturated $C_6$-$C_{24}$ fatty alcohol, fatty aldehyde and/or fatty acetate from an endogenous or exogenous source of saturated $C_6$-$C_{24}$ fatty acid is provided, wherein the recombinant microorganism expresses one or more acyl-CoA oxidase enzymes, and wherein the recombinant microorganism is manipulated to delete, disrupt, mutate, and/or reduce the activity of one or more endogenous acyl-CoA oxidase enzymes. In some embodiments, the one or more acyl-CoA oxidase enzymes being expressed are different from the one or more endogenous acyl-CoA oxidase enzymes being deleted or down-regulated. In other embodiments, the one or more acyl-CoA oxidase enzymes that are expressed regulate chain length of the mono- or poly-unsaturated $C_6$-$C_{24}$ fatty alcohol, fatty aldehyde and/or fatty acetate. In other embodiments, the one or more acyl-CoA oxidase enzymes being expressed are selected from Table 5a.

In some embodiments, the recombinant microorganism comprises a deletion, disruption, mutation, and/or reduction in the activity of one or more endogenous acyltransferase enzyme selected from the group consisting of *Y. lipolytica* YALI0C00209g, *Y. lipolytica* YALI0E18964g, *Y. lipolytica* YALI0F19514g, *Y. lipolytica* YALI0C14014g, *Y. lipolytica* YALI0E16797g, *Y. lipolytica* YALI0E32769g, and *Y. lipolytica* YALI0D07986g. *S. cerevisiae* YBL011w, *S. cerevisiae* YDL052c, *S. cerevisiae* YOR175C, *S. cerevisiae* YPR139C, *S. cerevisiae* YNR008w, and *S. cerevisiae* YOR245c, and *Candida* I503_02577, *Candida* CTRG_02630, *Candida* CaO19.250, *Candida* CaO19.7881, *Candida* CTRG_02437, *Candida* CaO19.1881, *Candida* CaO19.9437, *Candida* CTRG_01687, *Candida* CaO19.1043, *Candida* CaO19.8645. *Candida* CTRG_04750, *Candida* CaO19.13439, *Candida* CTRG_04390, *Candida* CaO19.6941, *Candida* CaO19.14203, and *Candida* CTRG_06209.

In some embodiments, a recombinant microorganism capable of producing a mono- or poly-unsaturated ≤$C_{18}$ fatty alcohol, fatty aldehyde and/or fatty acetate from an endogenous or exogenous source of saturated $C_6$-$C_{24}$ fatty acid is provided, wherein the recombinant microorganism expresses one or more acyltransferase enzymes, and wherein the recombinant microorganism is manipulated to delete, disrupt, mutate, and/or reduce the activity of one or more endogenous acyltransferase enzymes. In some preferred embodiments, one or more genes of the microbial host encoding GPATs, LPAATs, GPLATs and/or DGATs are deleted or downregulated, and replaced with one or more GPATs. LPAATs, GPLATs, or DGATs which prefer to store short-chain fatty acyl-CoAs. In some embodiments, the one or more acyltransferase enzymes being expressed are different from the one or more endogenous acyltransferase enzymes being deleted or downregulated. In other embodiments, the one or more acyltransferase enzymes being expressed are selected from Table 5b.

In some preferred embodiments, one or more genes of the microbial host encoding acylglycerol lipases (mono-, di-, or triacylglycerol lipases) and sterol ester esterases are deleted or downregulated and replaced with one or more acylglycerol lipases which prefer long chain acylglycerol substrates. In some embodiments, the recombinant microorganism comprises a deletion, disruption, mutation, and/or reduction in the activity of one or more endogenous acylglycerol lipase and/or sterol ester esterase enzyme selected from the group consisting of *Y. lipolytica* YALI0E32035g, *Y. lipolytica* YALI0D17534g, *Y. lipolytica* YALI0F10010g, *Y. lipolytica* YALI0C14520g, and *Y. lipolytica* YALI0E00528g, *S. cerevisiae* YKL140w, *S. cerevisiae* YMR313c, *S. cerevisiae* YKR089c, *S. cerevisiae* YOR081c, *S. cerevisiae* YKL094W, *S. cerevisiae* YLL012W, and *S. cerevisiae* YLR020C, and *Candida* CaO19.2050, *Candida* CaO19.9598. *Candida* CTRG_01138. *Candida* W5Q_03398, *Candida* CTRG_00057, *Candida* CaO19.5426. *Candida* CaO19.12881, *Candida* CTRG_06185, *Candida* CaO19.4864, *Candida* CaO19.12328, *Candida* CTRG_03360, *Candida* CaO19.6501, *Candida* CaO19.13854, *Candida* CTRG_05049. *Candida* CaO19.1887, *Candida* CaO19.9443, *Candida* CTRG_01683, and *Candida* CTRG_04630.

In some embodiments, the recombinant microorganism comprises a deletion, disruption, mutation, and/or reduction in the activity of one or more endogenous cytochrome P450 monooxygenases selected from the group consisting of *Y. lipolytica* YALI0E25982g (ALK1), *Y. lipolytica* YALI0F01320g (ALK2), *Y. lipolytica* YALI0E23474g (ALK3), *Y. lipolytica* YALI0B13816g (ALK4), *Y. lipolytica* YALI0B13838g (ALK5), *Y. lipolytica* YALI0B01848g (ALK6). *Y. lipolytica* YALI0A15488g (ALK7), *Y. lipolytica* YALI0C12122g (ALK5), *Y. lipolytica* YALI0B06248g (ALK9), *Y. lipolytica* YALI0B20702g (ALK10), *Y. lipolytica* YALI0C10054g (ALK11) and *Y. lipolytica* YALI0A20130g (ALK12).

In some embodiments, a recombinant microorganism capable of producing a mono- or poly-unsaturated ≤$C_{18}$ fatty alcohol, fatty aldehyde and/or fatty acetate from an endogenous or exogenous source of saturated $C_6$-$C_{24}$ fatty acid is provided, wherein the recombinant microorganism expresses one or more acylglycerol lipase and/or sterol ester esterase enzymes, and wherein the recombinant microorganism is manipulated to delete, disrupt, mutate, and/or reduce the activity of one or more endogenous acylglycerol lipase and/or sterol ester esterase enzymes. In some embodiments, the one or more acylglycerol lipase and/or sterol ester esterase enzymes being expressed are different from the one or more endogenous acylglycerol lipase and/or sterol ester esterase enzymes being deleted or downregulated. In some embodiments, the one or more endogenous or exogenous acylglycerol lipase and/or sterol ester esterase enzymes being expressed prefer to hydrolyze ester bonds of long-chain acylglycerols. In other embodiments, the one or more acylglycerol lipase and/or sterol ester esterase enzymes being expressed are selected from Table 5c.

In some embodiments, the fatty acyl desaturase catalyzes the conversion of a fatty acyl-CoA into a mono- or poly-unsaturated intermediate selected from E5-10:Acyl-CoA, E7-12:Acyl-CoA, E9-14:Acyl-CoA, E11-16:Acyl-CoA, E13-18:Acyl-CoA, Z7-12:Acyl-CoA, Z9-14:Acyl-CoA, Z11-16:Acyl-CoA, Z13-18:Acyl-CoA, Z8-12:Acyl-CoA, Z10-14:Acyl-CoA, Z12-16:Acyl-CoA, Z14-18:Acyl-CoA, Z7-10:Acyl-coA, Z9-12:Acyl-CoA, Z11-14:Acyl-CoA, Z13-16:Acyl-CoA, Z15-18:Acyl-CoA, E7-10:Acyl-CoA, E9-12:Acyl-CoA, E11-14:Acyl-CoA, E13-16:Acyl-CoA, E15-18:Acyl-CoA, E5Z7-12:Acyl-CoA, E7Z9-12:Acyl-CoA, E9Z11-14:Acyl-CoA, E11Z13-16:Acyl-CoA, E13Z15-18:Acyl-CoA, E6E8-10:Acyl-CoA, E8E10-12:Acyl-CoA, E10E12-14:Acyl-CoA, E12E14-16:Acyl-CoA, Z5E8-10:Acyl-CoA, Z7E10-12:Acyl-CoA, Z9E12-14:Acyl-CoA, Z11E14-16:Acyl-CoA, Z13E16-18:Acyl-CoA, Z3-10:Acyl-CoA, Z5-12:Acyl-CoA, Z7-14:Acyl-CoA, Z9-16:Acyl-CoA, Z11-18:Acyl-CoA, Z3Z5-10:Acyl-CoA, Z5Z7-12:Acyl-CoA, Z7Z9-14:Acyl-CoA, Z9Z11-16:Acyl-CoA, Z1Z13-16:Acyl-CoA, and Z13Z15-18:Acyl-CoA. In further embodiments, the mono- or poly-unsaturated ≤$C_{18}$ fatty alcohol is selected from the group consisting of E5-10: OH, Z8-12:OH, Z9-12:OH, Z11-14:OH, Z11-16:OH, E11-14:OH, E8E10-12:OH, E7Z9-12:OH, Z11Z13-16OH, Z9-14:OH, Z9-16:OH, and Z13-18:OH.

In some embodiments, the recombinant microorganism further comprises at least one endogenous or exogenous nucleic acid molecule encoding an aldehyde forming fatty acyl-CoA reductase capable of catalyzing the conversion of the mono- or poly-unsaturated ≤$C_{18}$8 fatty alcohol into a corresponding ≤$C_{18}$ fatty aldehyde. In some preferred embodiments, the aldehyde forming fatty acyl-CoA reductase is selected from the group consisting of *Acinetobacter calcoaceticus* A0A1C4HN78, *A. calcoaceticus* N9DA85. *A. calcoaceticus* R8XW24, *A. calcoaceticus* A0A1A0GGM5, *A. calcoaceticus* A0A1117N158, and *Nostoc punctiforme* YP_001865324. In some embodiments, the recombinant microorganism further comprises at least one endogenous or exogenous nucleic acid molecule encoding an alcohol oxidase or an alcohol dehydrogenase capable of catalyzing the conversion of the mono- or poly-unsaturated ≤$C_{18}$ fatty alcohol into a corresponding ≤$C_{18}$ fatty aldehyde. In some preferred embodiments, the ≤$C_{18}$ fatty aldehyde is selected from the group consisting of Z9-16:Ald, Z11-16: Ald, Z11Z13-16:Ald, and Z13-18:Ald.

In some embodiments, the recombinant microorganism further comprises at least one endogenous or exogenous nucleic acid molecule encoding an acetyl transferase capable of catalyzing the conversion of the mono- or poly-unsaturated ≤$C_{18}$ fatty alcohol into a corresponding ≤$C_{18}$ fatty acetate. In some embodiments, the acetyl transferase is selected from Table 5d. In some preferred embodiments, the ≤C18 fatty acetate is selected from the group consisting of E5-10:Ac, Z7-12:Ac, Z8-12:Ac, Z9-12:Ac, E7Z9-12:Ac, Z9-14:Ac, Z9E12-14:Ac, Z11-14:Ac, E11-14:Ac, Z9-16: Ac, and Z11-16:Ac.

In some embodiments, the recombinant microorganism further comprises: at least one endogenous or exogenous nucleic acid molecule encoding an enzyme selected from an alcohol oxidase, an alcohol dehydrogenase, and an aldehyde forming fatty acyl-CoA reductase capable of catalyzing the conversion of the mono- or poly-unsaturated ≤$C_{18}$ fatty alcohol into a corresponding ≤$C_{18}$ fatty aldehyde; and at least one endogenous or exogenous nucleic acid molecule encoding an acetyl transferase capable of catalyzing the conversion of the mono- or poly-unsaturated ≤$C_{18}$ fatty alcohol into a corresponding ≤$C_{18}$ fatty acetate. In some preferred embodiments, the mono- or poly-unsaturated ≤C18 fatty aldehyde and ≤$C_{18}$ fatty acetate is selected from the group consisting of E5-10:Ac, Z7-12:Ac, Z8-12:Ac, Z9-12:Ac, E7Z9-12:Ac, Z9-14:Ac, Z9E12-14:Ac, E11-14:Ac, Z11-14:Ac, Z11-16:Ac, Z9-16:Ac, Z9-16:Ald, Z11-16:Ald, Z11Z13-16:Ald, and Z13-18:Ald.

In a further embodiment, the disclosure provides a recombinant Yarrowia lipolytica microorganism capable of producing a mono- or poly-unsaturated $C_6$-$C_{24}$ fatty alcohol from an endogenous or exogenous source of saturated $C_6$-$C_{24}$ fatty acid, wherein the recombinant Yarrowia lipolytica microorganism comprises: (a) at least one nucleic acid molecule encoding a fatty acyl desaturase having 95% sequence identity to a fatty acyl desaturase selected from the group consisting of SEQ ID NOs: 54, 60, 62, 78, 79, 80, 95, 97, 99, 101, 103, and 105 that catalyzes the conversion of a saturated $C_6$-$C_{24}$ fatty acyl-CoA to a corresponding mono- or poly-unsaturated $C_6$-$C_{24}$ fatty acyl-CoA; and (b) at least one nucleic acid molecule encoding a fatty alcohol forming fatty acyl reductase having 95% sequence identity to a fatty alcohol forming fatty acyl reductase selected from the group consisting of SEQ ID NOs: 41-48, 57, 73, 75 and 77 that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol.

In some embodiments, the recombinant Yarrowia lipolytica microorganism comprises a deletion, disruption, mutation, and/or reduction in the activity of one or more endogenous enzymes that catalyzes a reaction in a pathway that competes with the biosynthesis pathway for the production of a mono- or poly-unsaturated $C_6$-$C_{24}$ fatty alcohol. In some preferred embodiments, the recombinant Yarrowia lipolytica microorganism comprises a deletion, disruption, mutation, and/or reduction in the activity of one or more endogenous enzyme selected from the following: (i) one or more acyl-CoA oxidase selected from the group consisting of YALI0E32835g (POX1), YALI0F10857g (POX2), YALI0D24750g (POX3), YALI0E27654g (POX4), YALI0C23859g (POX5), YALI0E06567g (POX6); (ii) one or more (fatty) alcohol dehydrogenase selected from the group consisting of YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), YALI0E07766g (ADH7); (iii) a (fatty) alcohol oxidase YALI0B14014g (FAO1); (iv) one or more cytochrome P450 enzyme selected from the group consisting of YALI0E25982g (ALK1), YALI0F01320g (ALK2), YALI0E23474g (ALK3). YALI0B13816g (ALK4), YALI0B13838g (ALK5), YALI0B01848g (ALK6), YALI0A15488g (ALK7), (YALI0C12122g (ALK8), YALI0B06248g (ALK9), YALI0B20702g (ALK10), YALI0C10054g (ALK1) and YALI0A20130g (Alk12); and (v) one or more diacylglycerol acyltransferase selected from the group consisting of YALI0E32791g (DGA1) and YALI0D07986g (DGA2). In other preferred embodiments, the recombinant Yarrowia lipolytica microorganism comprises a deletion of one or more endogenous enzyme selected from the following: (i) one or more acyl-CoA oxidase selected from the group consisting of YALI0E32835g (POX1). YALI0F10857g (POX2). YALI0D24750g (POX3), YALI0E27654g (POX4), YALI0C23859g (POX5), YALI0E06567g (POX6); (ii) one or more (fatty) alcohol dehydrogenase selected from the group consisting of YALI0F09603g (FADH). YALI0D25630g (ADH1), YALI0E17787g (ADH2), YALI0A16379g (ADH3). YALI0E15818g (ADH4), YALI0D02167g (ADH5), YALI0A15147g (ADH6), YALI0E07766g (ADH7); (iii) a (fatty) alcohol oxidase YALI0B14014g (FAO1); (iv) one or more cytochrome P450 enzyme selected from the group consisting of YALI0E25982g (ALK1), YALI0F01320g (ALK2), YALI0E23474g (ALK3), YALI0B13816g (ALK4), YALI0B3838g (ALK5), YALI0B01848g (ALK6), YALI0A15488g (ALK7), (YALI0C12122g (ALK8).YALI0B06248g (ALK9), YALI0B20702g (ALK10), YALI0C10054g (ALK1) and YALI0A20130g (Alk12), and (v) one or more diacylglycerol acyltransferase selected from the group consisting of YALI0E32791g (DGA1) and YALI0D07986g (DGA2).

In some embodiments, the fatty acyl desaturase catalyzes the conversion of a saturated fatty acyl-CoA into a mono- or poly-unsaturated intermediate selected from Z9-14:Acyl-CoA, Z11-14:Acyl-CoA, E11-14:Acyl-CoA, Z9-16:Acyl-CoA, and Z11-16:Acyl-CoA. In other embodiments, the mono- or poly-unsaturated $C_6$-$C_{24}$ fatty alcohol is selected from the group consisting of Z9-14:OH, Z11-14:OH, E11-14:OH, Z9-16:OH, Z11-16:OH, Z11Z13-16:OH, and Z13-18:OH.

In some embodiments, the recombinant Yarrowia lipolytica microorganism further comprises at least one endogenous or exogenous nucleic acid molecule encoding an alcohol oxidase or an alcohol dehydrogenase capable of catalyzing the conversion of the mono- or poly-unsaturated $C_6$-$C_{24}$ fatty alcohol into a corresponding $C_6$-$C_{24}$ fatty aldehyde. In some embodiments, the alcohol dehydrogenase is selected from Table 3a. In some embodiments, the $C_6$-$C_{24}$ fatty aldehyde is selected from the group consisting of Z9-14:Ald, Z11-14:Ald, E11-14:Ald, Z9-16:Ald. Z11-16:Ald, Z1Z13-16:Ald and Z13-18:Ald.

In some embodiments, the recombinant Yarrowia lipolytica microorganism further comprises at least one endogenous or exogenous nucleic acid molecule encoding an acetyl transferase capable of catalyzing the conversion of the mono- or poly-unsaturated $C_6$-$C_{24}$ fatty alcohol into a corresponding $C_6$-$C_{24}$ fatty acetate. In some embodiments, the acetyl transferase is selected from Table 5d. In some embodiments, the $C_6$-$C_{24}$ fatty acetate is selected from the group consisting of Z9-14:Ac, Z11-14:Ac, E11-14:Ac, Z9-16:Ac, Z11-16:Ac, Z11Z13-16:Ac, and Z13-18:Ac.

In some embodiments, the recombinant Yarrowia lipolytica microorganism further comprises: at least one endogenous or exogenous nucleic acid molecule encoding an alcohol oxidase or an alcohol dehydrogenase capable of catalyzing the conversion of the mono- or poly-unsaturated $C_6$-$C_{24}$ fatty alcohol into a corresponding $C_6$-$C_{24}$ fatty aldehyde; and at least one endogenous or exogenous nucleic acid molecule encoding an acetyl transferase capable of catalyzing the conversion of the mono- or poly-unsaturated $C_6$-$C_{24}$ fatty alcohol into a corresponding $C_6$-$C_{24}$ fatty acetate. In some embodiments, the mono- or poly-unsaturated $C_6$-$C_{24}$ fatty aldehyde and $C_6$-$C_{24}$ fatty acetate is selected from the group consisting of Z9-14:Ac, Z11-14:Ac. E11-14:Ac, Z9-16:Ac, Z11-16:Ac, Z1Z13-16:Ac, Z13-18:Ac, Z9-14:Ald, Z11-14:Ald, E11-14:Ald, Z9-16:Ald, Z11-16:Ald, Z11Z13-16:Ald and Z13-18:Ald.

In some embodiments, the fatty acyl desaturase does not comprise a fatty acyl desaturase comprising an amino acid sequence selected from the group consisting of SEQ ID NOs: 64, 65, 66 and 67. In other embodiments, the fatty acyl desaturase does not comprise a fatty acyl desaturase selected from an *Amyelois transitella*, *Spodoptera littoralis*, *Agrotis segetum*, or *Trichoplusia ni* derived desaturase.

In some embodiments, the disclosure provides a method of engineering a *Yarrowia lipolytica* microorganism that is capable of producing a mono- or poly-unsaturated $C_6$-$C_{24}$ fatty alcohol from an endogenous or exogenous source of saturated $C_6$-$C_{24}$ fatty acid, wherein the method comprises introducing into the *Yarrowia lipolytica* microorganism the following: (a) at least one nucleic acid molecule encoding a fatty acyl desaturase having 95% sequence identity to a fatty acyl desaturase selected from the group consisting of SEQ ID NOs: 39, 54, 60, 62, 78, 79, 80, 95, 97, 99, 101, 103, and 105 that catalyzes the conversion of a saturated $C_6$-$C_{24}$ fatty acyl-CoA to a corresponding mono- or poly-unsaturated $C_6$-$C_{24}$ fatty acyl-CoA; and (b) at least one nucleic acid molecule encoding a fatty alcohol forming fatty acyl reductase having 95% sequence identity to a fatty alcohol forming fatty acyl reductase selected from the group consisting of SEQ ID NOs: 41-48, 57, 73, 75 and 77 that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol. In some embodiments, the microorganism is MATA ura3-302::SUC2 Δpox1 Δpox2 Δpox3 Δpox4 Δpox5 Δpox6 Δfadh Δadh1 Δadh2 Δadh3 Δadh4 Δadh5 Δadh6 Δadh7 Δfao1::URA3.

In some embodiments, the disclosure provides a method of producing a mono- or poly-unsaturated $C_6$-$C_{24}$ fatty alcohol, fatty aldehyde or fatty acetate from an endogenous or exogenous source of saturated $C_6$-$C_{24}$ fatty acid, comprising: cultivating a recombinant microorganism described herein in a culture medium containing a feedstock that provides a carbon source adequate for the production of the mono- or poly-unsaturated $C_6$-$C_{24}$ fatty alcohol, fatty aldehyde or fatty acetate. In some embodiments, the method further comprises a step of recovering the mono- or poly-unsaturated $C_6$-$C_{24}$ fatty alcohol, fatty aldehyde or fatty acetate. In further embodiments, the recovery step comprises distillation. In yet further embodiments, the recovery step comprises membrane-based separation.

In some embodiments, the mono- or poly-unsaturated $C_6$-$C_{24}$ fatty alcohol is converted into a corresponding $C_6$-$C_{24}$ fatty aldehyde using chemical methods. In further embodiments, the chemical methods are selected from TEMPO-bleach, TEMPO-copper-air, TEMPO-PhI(OAc)$_2$, Swern oxidation and noble metal-air. In some embodiments, the mono- or poly-unsaturated $C_6$-$C_{24}$ fatty alcohol is converted into a corresponding $C_6$-$C_{24}$ fatty acetate using chemical methods. In further embodiments, the chemical methods utilize a chemical agent selected from the group consisting of acetyl chloride, acetic anhydride, butyryl chloride, butyric anhydride, propanoyl chloride and propionic anhydride in the presence of 4-N. N-dimethylaminopyridine (DMAP) or sodium acetate to esterify the mono- or poly-unsaturated $C_6$-$C_{24}$ fatty alcohol to the corresponding $C_6$-$C_{24}$ fatty acetate.

Figure 2:
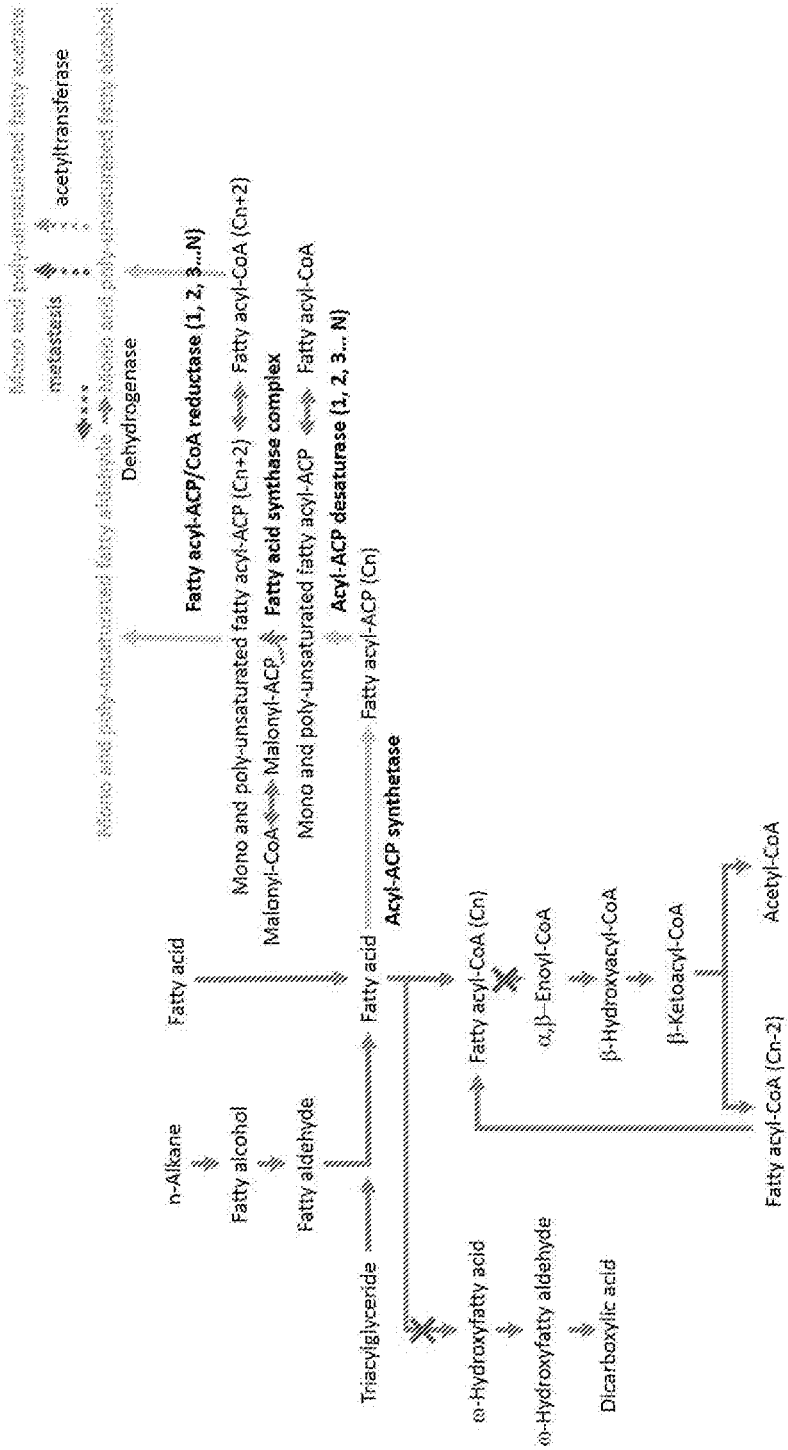
FIG. 2 illustrates the conversion of a saturated fatty acid to a mono- or poly-unsaturated fatty aldehyde, alcohol, or acetate.

As discussed above, in a second aspect, the application relates to a recombinant microorganism capable of producing an unsaturated $C_6$-$C_{24}$ fatty alcohol from an endogenous or exogenous source of $C_6$-$C_{24}$ fatty acid. An illustrative embodiment of the second aspect is shown in FIG. 2. The blue lines designate biochemical pathways endogenous to the host, e.g., pathways for converting an n-alkane, fatty alcohol, or fatty aldehyde to a fatty acid, or the conversion of a fatty acid to fatty-acyl-CoA, acetyl-CoA, or dicarboxylic acid. The substrate to unsaturated fatty acid conversion can be performed by endogenous or exogenous enzymes in a host. Yellow lines indicate conversions catalyzed by an exogenous nucleic acid molecule encoding for an enzyme. Accordingly, in some embodiments, the conversion of a saturated fatty acid to a saturated fatty acyl-ACP can be catalyzed by at least one saturated fatty acyl-ACP synthetase, wherein the fatty acyl-ACP synthetase is encoded by an exogenous nucleic acid molecule. In further embodiments, the conversion of the saturated fatty acyl-ACP to a mono- or poly-unsaturated fatty acyl-ACP can be catalyzed by at least one fatty acyl-ACP desaturase, wherein the fatty acyl-ACP desaturase is encoded by an exogenous nucleic acid molecule. In still further embodiments, the mono- or poly-unsaturated fatty acyl-ACP can be elongated by at least 2 carbons relative using a fatty acid synthase complex and a carbon source, e.g., malonyl-ACP. In one such embodiment, the conversion of the mono- or poly-unsaturated fatty acyl-ACP to a corresponding two carbon elongated mono- or poly-unsaturated fatty acyl-ACP can be catalyzed by at least one fatty acid synthase complex, wherein the fatty acid synthase complex is encoded by one or more exogenous nucleic acid molecules. In yet further embodiments, the conversion of the elongated mono- or poly-unsaturated fatty acyl-ACP to a mono- or poly-unsaturated fatty aldehyde can be catalyzed by a fatty aldehyde forming fatty acyl reductase, wherein the fatty aldehyde forming fatty acyl reductase is encoded by an exogenous nucleic acid molecule. In some embodiments, the mono- or poly-unsaturated fatty aldehyde can be converted to a corresponding mono- or poly-unsaturated fatty alcohol, wherein the substrate to product conversion is catalyzed by a dehydrogenase, wherein the dehydrogenase is encoded by an endogenous or exogenous nucleic acid molecule. The dashed lines indicate downstream steps of the disclosure, such as utilizing an acetyl transferase or metathesis, or subsequent chemical transformations to produce functionalized pheromones. The red crosses indicate deleted or down regulated pathways native to the host, which increase flux towards the engineered pathway.

In one embodiment, the recombinant microorganism expresses (a): at least one exogenous nucleic acid molecule encoding an acyl-ACP synthetase that catalyzes the conversion of a $C_6$-$C_{24}$ fatty acid to a corresponding saturated $C_6$-$C_{24}$ fatty acyl-ACP; (b) at least one exogenous nucleic acid molecule encoding a fatty-acyl-ACP desaturase that catalyzes the conversion of a saturated $C_6$-$C_{24}$ fatty acyl-ACP to a corresponding mono- or poly-unsaturated $C_6$-$C_{24}$ fatty acyl-ACP; (c) one or more endogenous or exogenous nucleic acid molecules encoding a fatty acid synthase complex that catalyzes the conversion of the mono- or poly-unsaturated $C_6$-$C_{24}$ fatty acyl-ACP from (b) to a corresponding mono- or poly-unsaturated $C_6$-$C_{24}$ fatty acyl-ACP with a two carbon elongation relative to the product of (b); (d): at least one exogenous nucleic acid molecule encoding a fatty aldehyde forming fatty-acyl reductase that catalyzes the conversion of the mono- or poly-unsaturated $C_6$-$C_{24}$ fatty acyl-ACP from (c) into a corresponding mono- or poly-unsaturated $C_6$-$C_{24}$ fatty aldehyde; and (e) at least one endogenous or exogenous nucleic acid molecule encoding a dehydrogenase that catalyzes the conversion of the mono- or poly-unsaturated $C_6$-$C_{24}$ fatty aldehyde $C_6$-$C_{24}$ from (d) into a corresponding mono- or poly-unsaturated $C_6$-$C_{24}$ fatty alcohol. In some embodiments, the $C_6$-$C_{24}$ fatty acid can be produced using endogenous enzymes in the host microorganism. In other embodiments, the saturated $C_6$-$C_{24}$ fatty acid can be produced by one or more exogenous enzymes in the host microorganism.

In some embodiments, the recombinant microorganism disclosed herein includes an acyl-ACP synthetase to catalyze the conversion of a $C_6$-$C_{24}$ fatty acid to a corresponding saturated $C_6$-$C_{24}$ fatty acyl-ACP. In some embodiments the acyl-ACP synthetase is a synthetase capable of utilizing a fatty acid as a substrate that has a chain length of 6, 7, 8, 9, 10, 11, 12, 13, 14, 15, 16, 17, 18, 19, 20, 21, 22, 23, or 24 carbon atoms. In exemplary embodiments, the recombinant microorganism can include a heterologous the acyl-ACP synthetase from an organism of the species *Vibrio harveyi, Rhodotorula glutinis*, or *Yarrowia lipolytica*.

In some embodiments, the recombinant microorganism includes a fatty acyl-ACP desaturase. In some embodiments, the fatty acyl-ACP desaturase is a soluble desaturase. In other embodiments, the fatty-acyl-ACP desaturase is from an organism of the species *Pelargonium hortorum, Asclepias syriaca*, or *Uncaria tomentosa*.

In some embodiments, the recombinant microorganism includes a fatty acid synthase complex. In some embodiments, the one or more nucleic acid molecules encoding the fatty acid synthase complex are endogenous nucleic acid molecules. In other embodiments, the one or more nucleic acid molecules encoding a fatty acid synthase complex are exogenous nucleic acid molecules.

In some embodiments, the recombinant microorganism disclosed herein includes a fatty aldehyde forming fatty-acyl reductase which catalyzes the conversion of a $C_6$-$C_{24}$ fatty acyl-ACP to the corresponding $C_6$-$C_{24}$ fatty aldehyde. In exemplary embodiments, the fatty aldehyde forming fatty-acyl reductase is from an organism of the species *Pelargonium hortorum, Asclepias syriaca*, and *Uncaria tomentosa*. In some embodiments, the recombinant microorganism includes a dehydrogenase to convert the unsaturated fatty aldehyde to a corresponding unsaturated fatty alcohol. In some embodiments, the nucleic acid molecule encoding the dehydrogenase is endogenous to the recombinant microorganism. In other embodiments, the nucleic acid molecule encoding a dehydrogenase is exogenous to the recombinant microorganism. In exemplary embodiments, the endogenous or exogenous nucleic acid molecule encoding a dehydrogenase is isolated from organisms of the species *Saccharomyces cerevisiae, Escherichia coli, Yarrowia lipolytica*, or *Candida tropicalis*.

Figure 3:
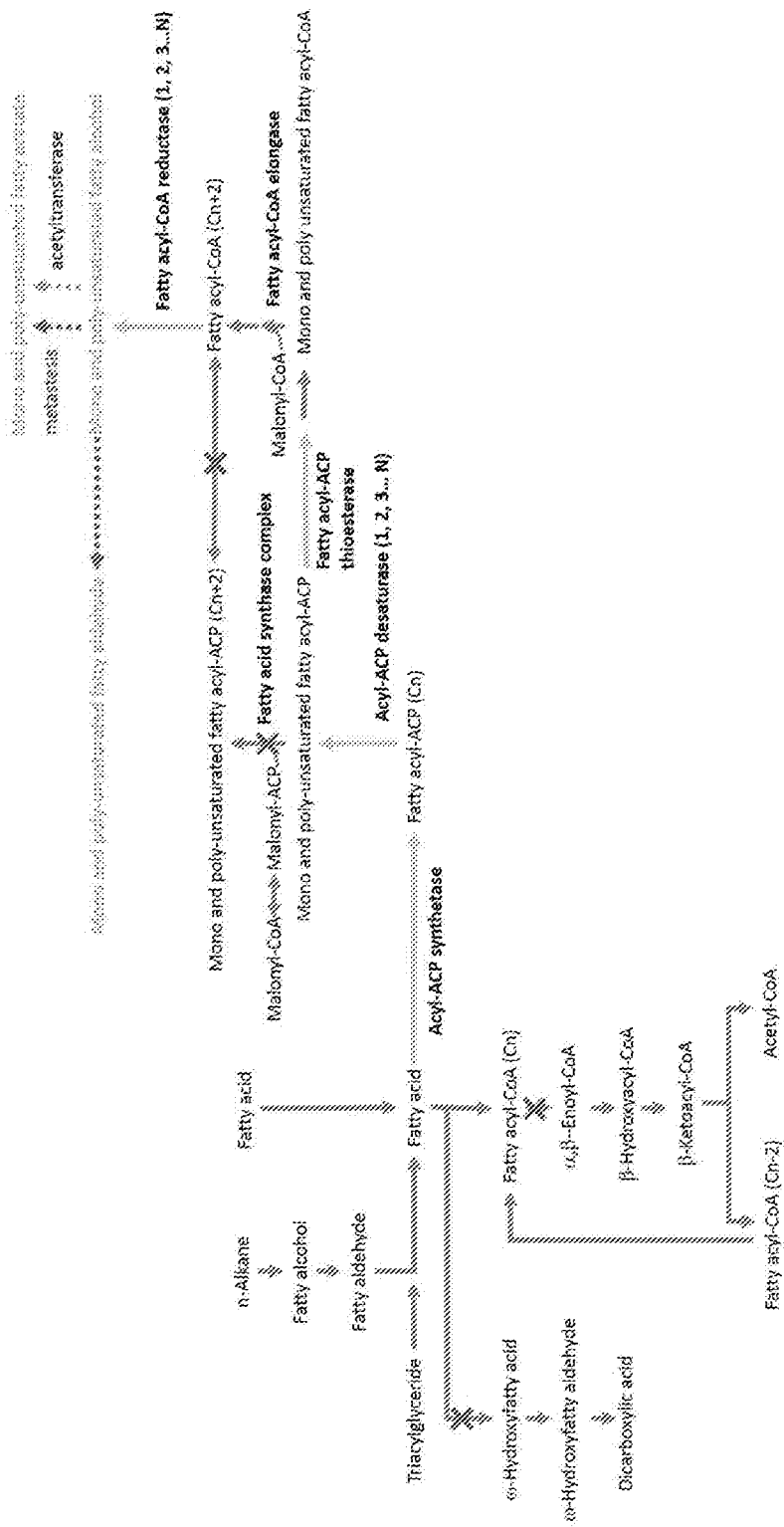
FIG. 3 illustrates an additional pathway for the conversion of a saturated fatty acid to a mono- or poly-unsaturated fatty aldehyde, alcohol, or acetate.
Figure 4:
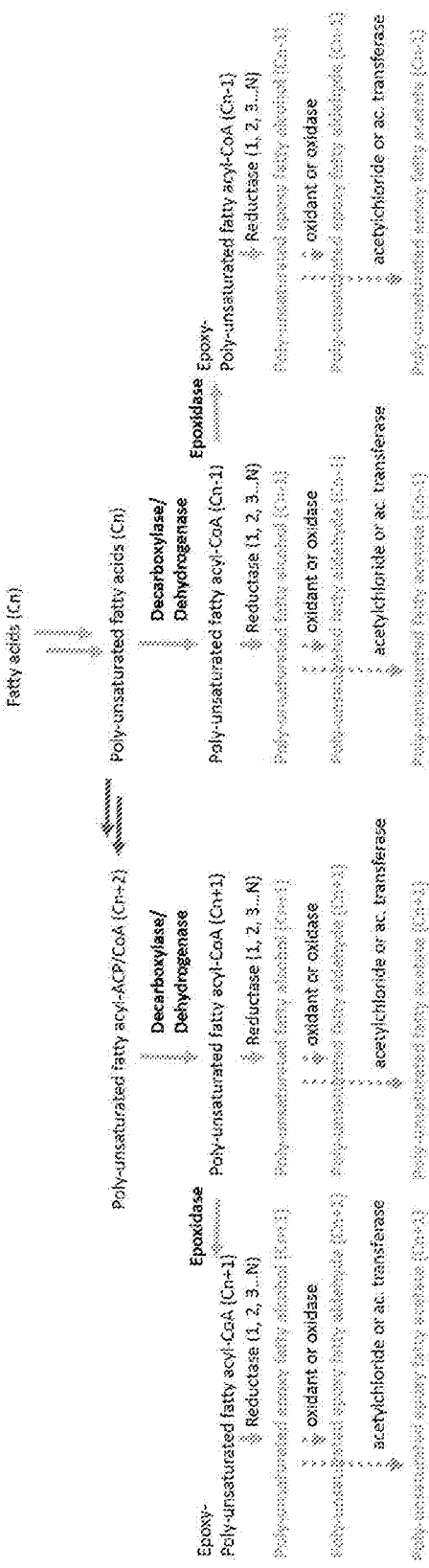
FIG. 4 illustrates a pathway for the conversion of a saturated fatty acid to various trienes, dienes, epoxides, and odd-numbered pheromones.

As discussed above, in a third aspect, the application relates to a recombinant microorganism capable of producing an unsaturated $C_6$-$C_{24}$ fatty alcohol from an endogenous or exogenous source of $C_6$-$C_{24}$ fatty acid. An illustrative embodiment of the second aspect is shown in FIG. 3. The blue lines designate biochemical pathways endogenous to the host, e.g., pathways for converting an n-alkane, fatty alcohol, or fatty aldehyde to a fatty acid, or the conversion of a fatty acid to fatty-acyl-CoA, acetyl-CoA, or dicarboxylic acid. The substrate to unsaturated fatty acid conversion can be performed by endogenous or exogenous enzymes in a host. Yellow lines indicate conversions catalyzed by an exogenous nucleic acid molecule encoding for an enzyme. Accordingly, in some embodiments, the conversion of a saturated fatty acid to a saturated fatty acyl-ACP can be catalyzed by at least one saturated fatty acyl-ACP synthetase, wherein the fatty acyl-ACP synthetase is encoded by an exogenous nucleic acid molecule. The non-native saturated fatty acyl-ACP thioesters create a substrate suitable for desaturation and distinct from CoA-thioesters used for beta-oxidation or fatty acid elongation. In further embodiments, the conversion of the saturated fatty acyl-ACP to a mono- or poly-unsaturated fatty acyl-ACP can be catalyzed by at least one fatty acyl-ACP desaturase, wherein the fatty acyl-ACP desaturase is encoded by an exogenous nucleic acid molecule. In still further embodiments, the mono- or poly-unsaturated fatty acyl-ACP can be converted to a corresponding mono- or poly-unsaturated fatty acid by a fatty-acyl-ACP thioesterase. In a particular embodiment, soluble fatty acyl-ACP thioesterases can be used to release free fatty acids for reactivation to a CoA thioester. Fatty acyl-ACP thioesterases including Q41635, Q39473, P05521.2, AEM72519. AEM72520, AEM72521, AEM72523, AAC49784, CAB60830, EER87824, EER96252, ABN54268, AAO77182, CAH09236, ACL08376, and homologs thereof may be used. In an additional embodiment, the mono- or poly-unsaturated fatty acyl-CoA can be elongated by at least 2 carbons relative using an elongase and a carbon source, e.g., malonyl-ACP. In yet further embodiments, the conversion of the elongated mono- or poly-unsaturated fatty acyl-CoA to a mono- or poly-unsaturated fatty alcohol can be catalyzed by a fatty alcohol forming fatty acyl reductase, wherein the fatty alcohol forming fatty acyl reductase is encoded by an exogenous nucleic acid molecule. The dashed lines indicate downstream steps of the disclosure, such as utilizing an acetyl transferase or metathesis, or subsequent chemical transformations to produce functionalized pheromones. The red crosses indicate deleted or down regulated pathways native to the host, which increase flux towards the engineered pathway.

The fatty alcohols produced as taught herein can be further converted to produce downstream products such as insect pheromones, fragrances, flavors, and polymer intermediates, which utilize aldehydes or acetate functional groups. Thus, in some embodiments, the recombinant microorganism further comprises at least one endogenous or exogenous nucleic acid molecule encoding an alcohol oxidase or an alcohol dehydrogenase, wherein the alcohol oxidase or alcohol dehydrogenase is capable of catalyzing the conversion of a $C_6$-$C_{24}$ fatty alcohol into a corresponding $C_6$-$C_{24}$ fatty aldehyde. In other embodiments, the recombinant microorganism can further comprise at least one endogenous or exogenous nucleic acid molecule encoding an acetyl transferase capable of catalyzing the conversion of a $C_6$-$C_{24}$ fatty alcohol into a corresponding $C_6$-$C_{24}$ fatty acetate. In certain embodiments, the acetyl transferase, or the nucleic acid sequence that encodes it, can be isolated from organisms of the species *Candida glabrata, Saccharomyces cerevisiae, Danaus plexippus, Heliotis virescens, Bombyx mori, Agrotis ipsilon, Agrotis segetum, Euonymus alatus. Homo sapiens, Lachancea thermotolerans* and *Yarrowia lipolytica*. In exemplary embodiments, the acetyl transferase comprises a sequence selected from GenBank Accession Nos. AY242066, AY242065, AY242064, AY242063, AY242062, EHJ65205, ACX53812, NP_001182381, EHJ65977, EHJ68573, KJ579226, GU594061 KTA99184.1, AIN34693.1, AY605053, XP_002552712.1, XP_503024.1, and XP_505595.1.

Recombinant Microorganism

The disclosure provides microorganisms that can be engineered to express various exogenous enzymes.

In various embodiments described herein, the recombinant microorganism is a eukaryotic microorganism. In some embodiments, the eukaryotic microorganism is a yeast. In exemplary embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*.

The present inventors have discovered that oleaginous yeast, such as *Candida* and *Yarrowia*, have a surprisingly high tolerance to the $C_6$-$C_{24}$ fatty alcohol substrates and products. Accordingly, in one such exemplary embodiment, the recombinant microorganism of the invention is an oleaginous yeast. In further embodiments, the oleaginous yeast is a member of a genus selected from the group consisting of *Yarrowia, Candida, Rhodotorula, Rhodosporidium. Cryptococcus, Trichosporon,* and *Lipomyces.* In even further embodiments, the oleaginous yeast is a member of a species selected from *Yarrowia lipolytica, Candida tropicalis, Rhodosporidium toruloides, Lipomyces starkey, L. lipoferus, C. revkaufi. C. pulcherrima, C. utilis, Rhodotorula minuta, Trichosporon pullans, T. culaneum, Cryptococcus curvatus, R. glutinis,* and *R. graminis.*

In some embodiments, the recombinant microorganism is a prokaryotic microorganism. In exemplary embodiments, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium,* and *Brevibacterium.*

In some embodiments, the recombinant microorganism is used to produce a mono- or poly-unsaturated $C_6$-$C_{24}$ fatty alcohol, aldehyde, or acetate disclosed herein.

Accordingly, in another aspect, the present inventions provide a method of producing a mono- or poly-unsaturated $C_6$-$C_{24}$ fatty alcohol, aldehyde, or acetate using a recombinant microorganism described herein. In one embodiment, the method comprises cultivating the recombinant microorganism in a culture medium containing a feedstock providing a carbon source until the mono- or poly-unsaturated $C_6$-$C_{24}$ fatty alcohol, aldehyde, or acetate is produced. In some embodiments, the method comprises cultivating the recombinant microorganism described herein in a culture medium containing a feedstock that provides a carbon source adequate for the production of a mono- or poly-unsaturated ≤$C_{18}$ fatty alcohol, fatty aldehyde or fatty acetate. In a further embodiment, the mono- or poly-unsaturated ≤$C_{18}$ fatty alcohol, aldehyde, or acetate is recovered. Recovery can be by methods known in the art, such as distillation, membrane-based separation gas stripping, solvent extraction, and expanded bed adsorption.

In some embodiments, the feedstock comprises a carbon source. In various embodiments described herein, the carbon source may be selected from sugars, glycerol, alcohols, organic acids, alkanes, fatty acids, lignocellulose, proteins, carbon dioxide, and carbon monoxide. In a further embodiment, the sugar is selected from the group consisting of glucose, fructose, and sucrose.

Methods of engineering microorganisms that are capable of producing mono- or poly-unsaturated $C_6$-$C_{24}$ fatty alcohols, fatty aldehydes and/or fatty acetates In one aspect, the present disclosure provides a method of engineering a microorganism that is capable of producing a mono- or poly-unsaturated ≤$C_{18}$ fatty alcohol from an endogenous or exogenous source of saturated $C_6$-$C_{24}$ fatty acid, wherein the method comprises introducing into a microorganism the following: (a) at least one exogenous nucleic acid molecule encoding a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA; (b) at least one exogenous nucleic acid molecule encoding an acyl-CoA oxidase that catalyzes the conversion of the mono- or poly-unsaturated $C_6$-$C_{24}$ fatty acyl-CoA from (a) into a mono- or poly-unsaturated ≤$C_{18}$ fatty acyl-CoA after one or more successive cycle of acyl-CoA oxidase activity, with a given cycle producing a mono- or poly-unsaturated $C_4$-$C_{22}$ fatty acyl-CoA intermediate with a two carbon truncation relative to a starting mono- or poly-unsaturated $C_6$-$C_{24}$ fatty acyl-CoA substrate in that cycle; and (c) at least one exogenous nucleic acid molecule encoding a fatty alcohol forming fatty acyl reductase that catalyzes the conversion of the mono- or poly-unsaturated ≤$C_{18}$ fatty acyl-CoA from (b) into the corresponding mono- or poly-unsaturated ≤$C_{18}$ fatty alcohol. In some embodiments, the microorganism is MATA ura3-302::SUC2 Δpox1 Δpox2 Δpox3 Δpox4 Δpox5 Δpox6 Δfadh Δadh1 Δadh2 Δadh3 Δadh4 Δadh5 Δadh6 Δadh7 Δfao1::URA3.

In some embodiments, the fatty acyl desaturase is selected from an *Argyrotaenia velutinana, Spodoptera litura, Sesamia inferens, Manduca sexta, Ostrinia nubilalis, Helicoverpa zea, Choristoneura rosaceana, Drosophila melanogaster, Spodoptera littoralis, Lampronia capitella, Amyelois transitella, Trichoplusia ni, Agrotis segetum, Ostrinia furnicalis,* and *Thalassiosira pseudonana* derived fatty acyl desaturase. In some preferred embodiments, the fatty acyl desaturase has 95% sequence identity to a fatty acyl desaturase selected from the group consisting of: SEQ ID NOs: 39, 49-54, 58-63, 78-80 and GenBank Accession nos. AF416738, AGH12217.1, AII21943.1, CAJ43430.2, AF441221, AAF81787.1, AF545481, AJ271414, AY362879, ABX71630.1 and NP001299594.1, Q9N9Z8, ABX71630.1 and AIM40221.1. In further embodiments, the acyl-CoA oxidase is selected from Table 5a. In yet further embodiments, the fatty alcohol forming fatty acyl reductase is selected from an *Agrotis segetum, Spodoptera exigua. Spodoptera littoralis, Euglena gracilis, Yponomeuta evonymellus* and *Helicoverpa armigera* derived fatty alcohol forming fatty acyl reductase. In further embodiments, the fatty alcohol forming fatty acyl reductase has 90% sequence identity to a fatty alcohol forming fatty acyl reductase selected from the group consisting of: SEQ ID NOs: 1-3, 32, 41-48, 55-57, 73, 75, 77 and 82. In some embodiments, the recombinant microorganism is a yeast selected from the group consisting of *Yarrowia lipolytica. Saccharomyces cerevisiae, Candida albicans, Candida tropicalis* and *Candida viswanathii.*

In some embodiments, the fatty acyl desaturase catalyzes the conversion of a fatty acyl-CoA into a mono- or poly-unsaturated intermediate selected from E5-10:Acyl-CoA, E7-12:Acyl-CoA, E9-14:Acyl-CoA, E11-16:Acyl-CoA, E13-18:Acyl-CoA, Z7-12:Acyl-CoA, Z9-14:Acyl-CoA, Z11-16:Acyl-CoA, Z13-18:Acyl-CoA, Z8-12:Acyl-CoA, Z10-14:Acyl-CoA, Z2-16:Acyl-CoA, Z4-18:Acyl-CoA, Z7-10:Acyl-coA, Z9-12:Acyl-CoA, Z11-14:Acyl-CoA, Z13-16:Acyl-CoA, Z15-18:Acyl-CoA, E7-10:Acyl-CoA, E9-12:Acyl-CoA, E11-14:Acyl-CoA. E13-16:Acyl-CoA, E15-18:Acyl-CoA, E5Z7-12:Acyl-CoA, E7Z9-12:Acyl-CoA, E9Z11-14:Acyl-CoA, E11Z13-16:Acyl-CoA, E13Z15-18:Acyl-CoA, E6E8-10:Acyl-CoA, E8E10-12:Acyl-CoA, E10E12-14:Acyl-CoA, E12E14-16:Acyl-CoA, Z5E8-10:Acyl-CoA, Z7E10-12:Acyl-CoA, Z9E12-14:Acyl-CoA, Z11E14-16:Acyl-CoA, Z13E16-18:Acyl-CoA, Z3-10:Acyl-CoA, Z5-12:Acyl-CoA, Z7-14:Acyl-CoA, Z9-16:Acyl-CoA, Z11-18:Acyl-CoA, Z3Z5-10:Acyl-CoA, Z5Z7-12:Acyl-CoA, Z7Z9-14:Acyl-CoA, Z9Z11-16:Acyl-CoA, Z11Z13-16:Acyl-CoA, and Z13Z15-18:Acyl-CoA. In further embodiments, the mono- or poly-unsaturated ≤$C_{18}$ fatty alcohol is selected from the group consisting of E5-10:OH, Z8-12:OH, Z9-12:OH, Z11-14:OH, Z11-16:OH, E11-14:OH, E8E10-12:OH, E7Z9-12:OH, Z11Z13-16OH, Z9-14:OH. Z9-16:OH, and Z13-18:OH.

In some embodiments, the method further comprises introducing into the microorganism at least one endogenous or exogenous nucleic acid molecule encoding an acyltransferase that preferably stores ≤$C_{18}$ fatty acyl-CoA. In some embodiments, the acyltransferase is selected from the group consisting of glycerol-3-phosphate acyl transferase (GPAT), lysophosphatidic acid acyltransferase (LPAAT), glycerolphospholipid acyltransferase (GPLAT) and diacylglycerol acyltransferases (DGAT). In some preferred embodiments, the acyltransferase is selected from Table 5b.

In some embodiments, the method further comprises introducing into the microorganism at least one endogenous or exogenous nucleic acid molecule encoding an acylglycerol lipase that preferably hydrolyzes ester bonds of >C16, of >C14, of >C12 or of >C10 acylglycerol substrates. In some embodiments, the acylglycerol lipase is selected from Table 5c.

In some embodiments, the method further comprises introducing into the microorganism one or more modifications comprising a deletion, disruption, mutation, and/or reduction in the activity of one or more endogenous enzyme that catalyzes a reaction in a pathway that competes with the biosynthesis pathway for the production of a mono- or poly-unsaturated ≤$C_{18}$ fatty alcohol. In further embodiments, the recombinant microorganism comprises a deletion, disruption, mutation, and/or reduction in the activity of one or more endogenous enzyme selected from: (i) one or more acyl-CoA oxidase; (ii) one or more acyltransferase; (iii) one or more acylglycerol lipase and/or sterol ester esterase; (iv) one or more (fatty) alcohol dehydrogenase; (v) one or more (fatty) alcohol oxidase; and (vi) one or more cytochrome P450 monooxygenase.

In some embodiments, the method further comprises introducing into the microorganism one or more modifications comprising a deletion, disruption, mutation, and/or reduction in the activity of one or more endogenous acyl-CoA oxidase enzyme selected from the group consisting of *Y. lipolytica* POX1(YALI0E32835g), *Y. lipolytica* POX2 (YALI0F10857g), *Y. lipolytica* POX3(YALI0D24750g), *Y. lipolytica* POX4(YALI0E27654g), *Y. lipolytica* POX5 (YALI0C23859g), *Y. lipolytica* POX6(YALI0E06567g); *S. cerevisiae* POX1(YGL205W); *Candida* POX2 (CaO19.1655, CaO19.9224. CTRG_02374. M18259), *Candida* POX4 (CaO19.1652, CaO19.9221, CTRG_02377, M12160), and *Candida* POX5 (CaO19.5723, CaO19.13146, CTRG_02721, M12161).

In some embodiments, the method further comprises introducing into the microorganism one or more modifications comprising a deletion, disruption, mutation, and/or reduction in the activity of one or more endogenous acyltransferase enzyme selected from the group consisting of *Y. lipolytica* YALI0C00209g, *Y. lipolytica* YALI0E18964g, *Y. lipolytica* YALI0F19514g, *Y. lipolytica* YALI0C14014g, *Y. lipolytica* YALI0E16797g, *Y. lipolytica* YALI0E32769g, and *Y lipolytica* YALI0D07986g, *S. cerevisiae* YBL011w, *S. cerevisiae* YDL052c, *S. cerevisiae* YOR175C, *S. cerevisiae* YPR139C, *S. cerevisiae* YNR008w, and *S. cerevisiae* YOR245c, and *Candida* I503_02577, *Candida* CTRG_02630, *Candida* CaO19.250, *Candida* CaO19.7881, *Candida* CTRG_02437, *Candida* CaO19.1881, *Candida* CaO19.9437, *Candida* CTRG_01687, *Candida* CaO19.1043, *Candida* CaO19.8645, *Candida* CTRG_04750, *Candida* CaO19.13439, *Candida* CTRG_04390, *Candida* CaO19.6941, *Candida* CaO19.14203, and *Candida* CTRG_06209.

In some embodiments, the method further comprises introducing into the microorganism one or more modifications comprising a deletion, disruption, mutation, and/or reduction in the activity of one or more endogenous acylglycerol lipase and/or sterol ester esterase enzyme selected from the group consisting of *Y. lipolytica* YALI0E32035g, *Y. lipolytica* YALI0D17534g, *Y. lipolytica* YALI0F10010g, *Y. lipolytica* YALI0C4520g, and *Y. lipolytica* YALI0E00528g, *S. cerevisiae* YKL140w, *S. cerevisiae* YMR313c, *S. cerevisiae* YKR089c, *S. cerevisiae* YOR08c, *S. cerevisiae* YKL094W. *S. cerevisiae* YLL012W, and *S. cerevisiae* YLR020C, and *Candida* CaO19.2050, *Candida* CaO19.9598, *Candida* CTRG_01138, *Candida* W5Q_03398, *Candida* CTRG_00057, Candid CaO19.5426, *Candida* CaO19.12881, *Candida* CTRG_06185, *Candida* CaO19.4864, *Candida* CaO19.12328, *Candida* CTRG_03360, *Candida* CaO19.6501, *Candida* CaO19.13854, *Candida* CTRG_05049, *Candida* CaO19.1887, *Candida* CaO19.9443. *Candida* CTRG_01683, and *Candida* CTRG_04630.

In some embodiments, the method further comprises introducing into the microorganism one or more modifications comprising a deletion, disruption, mutation, and/or reduction in the activity of one or more endogenous cytochrome P450 monooxygenases selected from the group consisting of *Y. lipolytica* YALI0E25982g (ALK1), *Y. lipolytica* YALI0F01320g (ALK2), *Y. lipolytica* YALI0E23474g (ALK3), *Y. lipolytica* YALI0B13816g (ALK4), *Y. lipolytica* YALI0B13838g (ALK5), *Y. lipolytica* YALI0B01848g (ALK6), *Y. lipolytica* YALI0A15488g (ALK7), *Y. lipolytica* YALI0C12122g (ALK8), *Y. lipolytica* YALI0B06248g (ALK9), *Y. lipolytica* YALI0B20702g (ALK10), *Y. lipolytica* YALI0C10054g (ALK11) and *K. lipolytica* YALI0A20130g (ALK12).

In some embodiments, the method further comprises introducing into the microorganism at least one endogenous or exogenous nucleic acid molecule encoding an aldehyde forming fatty acyl-CoA reductase capable of catalyzing the conversion of the mono- or poly-unsaturated ≤$C_{18}$ fatty alcohol into a corresponding ≤$C_{18}$ fatty aldehyde. In some preferred embodiments, the aldehyde forming fatty acyl-CoA reductase is selected from the group consisting of *Acinetobacter calcoaceticus* A0A1C4HN78, *A. calcoaceticus* N9DA85, *A. calcoaceticus* R8XW24, *A. calcoaceticus* A0A1A0GGM5, *A. calcoaceticus* A0A117N158, and *Nostoc punctiforme* YP_001865324. In some embodiments, the method further comprises introducing into the microorganism at least one endogenous or exogenous nucleic acid molecule encoding an alcohol oxidase or an alcohol dehydrogenase capable of catalyzing the conversion of the mono- or poly-unsaturated ≤$C_{18}$ fatty alcohol into a corresponding ≤$C_{18}$ fatty aldehyde. In some preferred embodiments, the ≤$C_{18}$ fatty aldehyde is selected from the group consisting of Z9-16:Ald, Z11-16:Ald, Z11Z13-16:Ald, and Z13-18:Ald.

In some embodiments, the method further comprises introducing into the microorganism at least one endogenous or exogenous nucleic acid molecule encoding an acetyl transferase capable of catalyzing the conversion of the mono- or poly-unsaturated ≤$C_{18}$ fatty alcohol into a corresponding ≤$C_{18}$ fatty acetate. In some embodiments, the acetyl transferase is selected from Table 5d. In some preferred embodiments, the ≤$C_{18}$ fatty acetate is selected from the group consisting of E5-10:Ac, Z7-12:Ac, Z8-12:Ac, Z9-12:Ac, E7Z9-12:Ac, Z9-14:Ac, Z9E12-14:Ac, Z11-14:Ac, E11-14:Ac, Z9-16:Ac, and Z11-16:Ac.

In some embodiments, the method further comprises introducing into the microorganism: at least one endogenous or exogenous nucleic acid molecule encoding an enzyme selected from an alcohol oxidase, an alcohol dehydrogenase, and an aldehyde forming fatty acyl-CoA reductase capable of catalyzing the conversion of the mono- or poly-unsaturated ≤$C_{18}$ fatty alcohol into a corresponding ≤$C_{18}$ fatty aldehyde; and at least one endogenous or exogenous nucleic acid molecule encoding an acetyl transferase capable of catalyzing the conversion of the mono- or poly-unsaturated ≤$C_{18}$ fatty alcohol into a corresponding ≤$C_{18}$ fatty acetate. In some preferred embodiments, the mono- or poly-unsaturated ≤$C_{18}$ fatty aldehyde and ≤$C_{18}$ fatty acetate is selected from the group consisting of E5-10:Ac, Z7-12:Ac, Z8-12:Ac, Z9-12:Ac, E7Z9-12:Ac, Z9-14:Ac, Z9E12-14:Ac, E11-14:Ac, Z11-14:Ac, Z11-16:Ac, Z9-16:Ac, Z9-16:Ald, Z11-16:Ald, Z11Z13-16:Ald, and Z13-18:Ald.

In some embodiments, the disclosure provides a method of producing a mono- or poly-unsaturated ≤$C_{18}$ fatty alcohol, fatty aldehyde or fatty acetate from an endogenous or exogenous source of saturated $C_6$-$C_{24}$ fatty acid, comprising: cultivating a recombinant microorganism described herein in a culture medium containing a feedstock that provides a carbon source adequate for the production of the mono- or poly-unsaturated ≤$C_{18}$ fatty alcohol, fatty aldehyde or fatty acetate. In some embodiments, the method further comprises a step of recovering the mono- or poly-unsaturated ≤$C_{18}$ fatty alcohol, fatty aldehyde or fatty acetate. In further embodiments, the recovery step comprises distillation. In yet further embodiments, the recovery step comprises membrane-based separation.

In some embodiments, the mono- or poly-unsaturated ≤$C_{18}$ fatty alcohol is converted into a corresponding ≤$C_{18}$ fatty aldehyde using chemical methods. In further embodiments, the chemical methods are selected from TEMPO-bleach. TEMPO-copper-air, TEMPO-PhI(OAc), Swern oxidation and noble metal-air. In some embodiments, the mono- or poly-unsaturated ≤$C_{18}$ fatty alcohol is converted into a corresponding ≤$C_{18}$ fatty acetate using chemical methods. In further embodiments, the chemical methods utilize a chemical agent selected from the group consisting of acetyl chloride, acetic anhydride, butyryl chloride, butyric anhydride, propanoyl chloride and propionic anhydride in the presence of 4-N,N-dimethylaminopyridine (DMAP) or sodium acetate to esterify the mono- or poly-unsaturated ≤$C_{18}$ fatty alcohol to the corresponding ≤$C_{18}$ fatty acetate.

In another aspect, the present disclosure provides methods of engineering a *Yarrowia lipolytica* microorganism capable of producing a mono- or poly-unsaturated $C_6$-$C_{24}$ fatty alcohol from an endogenous or exogenous source of saturated $C_6$-$C_{24}$ fatty acid, wherein the recombinant *Yarrowia lipolytica* microorganism comprises: (a) at least one nucleic acid molecule encoding a fatty acyl desaturase having 95% sequence identity to a fatty acyl desaturase selected from the group consisting of SEQ ID NOs: 54, 60, 62, 78, 79, 80, 95, 97, 99, 101, 103, and 105 that catalyzes the conversion of a saturated $C_6$-$C_{24}$ fatty acyl-CoA to a corresponding mono- or poly-unsaturated $C_6$-$C_{24}$ fatty acyl-CoA; and (b) at least one nucleic acid molecule encoding a fatty alcohol forming fatty acyl reductase having 95% sequence identity to a fatty alcohol forming fatty acyl reductase selected from the group consisting of SEQ ID NOs: 41-48, 57, 73, 75 and 77 that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol.

In some embodiments, the method further comprises introducing into the *Yarrowia lipolytica* microorganism one or more modifications comprising a deletion, disruption, mutation, and/or reduction in the activity of one or more endogenous enzymes that catalyzes a reaction in a pathway that competes with the biosynthesis pathway for the production of a mono- or poly-unsaturated $C_6$-$C_{24}$ fatty alcohol. In some preferred embodiments, the recombinant *Yarrowia lipolytica* microorganism comprises a deletion, disruption, mutation, and/or reduction in the activity of one or more endogenous enzyme selected from the following: (i) one or more acyl-CoA oxidase selected from the group consisting of YALI0E32835g (POX1), YALI0F0857g (POX2), YALI0D24750g (POX3), YALI0E27654g (POX4), YALI0C23859g (POX5), YALI0E06567g (POX6); (ii) one or more (fatty) alcohol dehydrogenase selected from the group consisting of YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), YALI0E07766g (ADH7); (iii) a (fatty) alcohol oxidase YALI0B14014g (FAO1); (iv) one or more cytochrome P450 enzyme selected from the group consisting of YALI0E25982g (ALK1), YALI0F01320g (ALK2), YALI0E23474g (ALK3), YALI0B13816g (ALK4), YALI0B13838g (ALK5), YALI0B01848g (ALK6), YALI0A15488g (ALK7), (YALI0C12122g (ALK8), YALI0B06248g (ALK9), YALI0B20702g (ALK10), YALI0C10054g (ALK11) and YALI0A20130g (Alk12); and (v) one or more diacylglycerol acyltransferase selected from the group consisting of YALI0E32791g (DGA1) and YALI0D07986g (DGA2). In other preferred embodiments, the recombinant *Yarrowia lipolytica* microorganism comprises a deletion of one or more endogenous enzyme selected from the following: (i) one or more acyl-CoA oxidase selected from the group consisting of YALI0E32835g (POX1), YALI0F10857g (POX2), YALI0D24750g (POX3), YALI0E27654g (POX4), YALI0C23859g (POX5), YALI0E06567g (POX6); (ii) one or more (fatty) alcohol dehydrogenase selected from the group consisting of YALI0F09603g (FADH), YALI0D25630g (ADH1), YALI0E17787g (ADH2). YALI0A16379g (ADH3), YALI0E15818g (ADH4), YALI0D02167g (ADH5), YALI0A15147g (ADH6). YALI0E07766g (ADH7); (iii) a (fatty) alcohol oxidase YALI0B14014g (FAO1); (iv) one or more cytochrome P450 enzyme selected from the group consisting of YALI0E25982g (ALK1), YALI0F01320g (ALK2), YALI0E23474g (ALK3), YALI0B13816g (ALK4), YALI0B13838g (ALK5), YALI0B01848g (ALK6), YALI0A15488g (ALK7), (YALI0C12122g (ALK8), YALI0B06248g (ALK9), YALI0B20702g (ALK10), YALI0C10054g (ALK11) and YALI0A20130g (Alk12); and (v) one or more diacylglycerol acyltransferase selected from the group consisting of YALI0E32791g (DGA1) and YALI0D07986g (DGA2).

In some embodiments, the fatty acyl desaturase catalyzes the conversion of a saturated fatty acyl-CoA into a mono- or poly-unsaturated intermediate selected from Z9-14:Acyl-CoA, Z11-14:Acyl-CoA, E11-14:Acyl-CoA, Z9-16:Acyl-CoA, and Z11-16:Acyl-CoA. In other embodiments, the mono- or poly-unsaturated $C_6$-$C_{24}$ fatty alcohol is selected from the group consisting of Z9-14:OH, Z11-14:OH, E11-14:OH, Z9-16:OH, Z11-16:OH, Z11Z13-16:OH, and Z13-18:OH.

In some embodiments, the method further comprises introducing into the *Yarrowia lipolytica* microorganism at least one endogenous or exogenous nucleic acid molecule encoding an alcohol oxidase or an alcohol dehydrogenase capable of catalyzing the conversion of the mono- or poly-unsaturated $C_6$-$C_{24}$ fatty alcohol into a corresponding $C_6$-$C_{24}$ fatty aldehyde. In some embodiments, the alcohol dehydrogenase is selected from Table 3a. In some embodiments, the $C_6$-$C_{24}$ fatty aldehyde is selected from the group consisting of Z9-14:Ald, Z11-14:Ald, E11-14:Ald, Z9-16: Ald, Z11-16:Ald, Z11Z13-16:Ald and Z13-18:Ald.

In some embodiments, the method further comprises introducing into the *Yarrowia lipolytica* microorganism at least one endogenous or exogenous nucleic acid molecule encoding an acetyl transferase capable of catalyzing the conversion of the mono- or poly-unsaturated $C_6$-$C_{24}$ fatty alcohol into a corresponding $C_6$-$C_{24}$ fatty acetate. In some embodiments, the acetyl transferase is selected from Table 5d. In some embodiments, the $C_6$-$C_{24}$ fatty acetate is selected from the group consisting of Z9-14:Ac, Z11-14:Ac, E11-14:Ac, Z9-16:Ac, Z11-16:Ac, Z11Z3-16:Ac, and Z13-18:Ac.

In some embodiments, the method further comprises introducing into the *Yarrowia lipolytica* microorganism: at least one endogenous or exogenous nucleic acid molecule encoding an alcohol oxidase or an alcohol dehydrogenase capable of catalyzing the conversion of the mono- or poly-unsaturated $C_6$-$C_{24}$ fatty alcohol into a corresponding $C_6$-$C_{24}$ fatty aldehyde; and at least one endogenous or exogenous nucleic acid molecule encoding an acetyl transferase capable of catalyzing the conversion of the mono- or poly-unsaturated $C_6$-$C_{24}$ fatty alcohol into a corresponding $C_6$-$C_{24}$ fatty acetate. In some embodiments, the mono- or poly-unsaturated $C_6$-$C_{24}$ fatty aldehyde and $C_6$-$C_{24}$ fatty acetate is selected from the group consisting of Z9-14:Ac, Z11-14:Ac, E11-14:Ac, Z9-16:Ac, Z11-16:Ac, Z11Z13-16: Ac, Z13-18:Ac, Z9-14:Ald, Z11-14:Ald, E11-14:Ald, Z9-16:Ald, Z11-16:Ald, Z11Z13-16:Ald and Z13-18:Ald.

In some embodiments, the fatty acyl desaturase does not comprise a fatty acyl desaturase comprising an amino acid sequence selected from the group consisting of SEQ ID NOs: 64, 65, 66 and 67. In other embodiments, the fatty acyl desaturase does not comprise a fatty acyl desaturase selected from an *Amyelois transitella, Spodoptera littoralis, Agrotis segetum*, or *Trichoplusia ni* derived desaturase.

In some embodiments, the disclosure provides a method of producing a mono- or poly-unsaturated $C_6$-$C_{24}$ fatty alcohol, fatty aldehyde or fatty acetate from an endogenous or exogenous source of saturated $C_6$-$C_{24}$ fatty acid, comprising: cultivating a recombinant microorganism described herein in a culture medium containing a feedstock that provides a carbon source adequate for the production of the mono- or poly-unsaturated $C_6$-$C_{24}$ fatty alcohol, fatty aldehyde or fatty acetate. In some embodiments, the method further comprises a step of recovering the mono- or poly-unsaturated $C_6$-$C_{24}$ fatty alcohol, fatty aldehyde or fatty acetate. In further embodiments, the recovery step comprises distillation. In yet further embodiments, the recovery step comprises membrane-based separation.

In some embodiments, the mono- or poly-unsaturated $C_6$-$C_{24}$ fatty alcohol is converted into a corresponding $C_6$-$C_{24}$ fatty aldehyde using chemical methods. In further embodiments, the chemical methods are selected from TEMPO-bleach, TEMPO-copper-air. TEMPO-PhI(OAc)$_2$. Swern oxidation and noble metal-air. In some embodiments, the mono- or poly-unsaturated $C_6$-$C_{24}$ fatty alcohol is converted into a corresponding $C_6$-$C_{24}$ fatty acetate using chemical methods. In further embodiments, the chemical methods utilize a chemical agent selected from the group consisting of acetyl chloride, acetic anhydride, butyryl chloride, butyric anhydride, propanoyl chloride and propionic anhydride in the presence of 4-N, N-dimethylaminopyridine (DMAP) or sodium acetate to esterify the mono- or poly-unsaturated $C_6$-$C_{24}$ fatty alcohol to the corresponding $C_6$-$C_{24}$ fatty acetate.

Enzyme Engineering

The enzymes in the recombinant microorganism can be engineered to improve one or more aspects of the substrate to product conversion. Non-limiting examples of enzymes that can be further engineered for use in methods of the disclosure include a desaturase (e.g., a fatty acyl-CoA desaturase or fatty acyl-ACP desaturase), a fatty alcohol forming fatty acyl reductase, an acyl-ACP synthetase, a fatty acid synthetase, a fatty acid synthase complex, an acetyl transferase, dehydrogenase, and an alcohol oxidase, and combinations thereof. These enzymes can be engineered for improved catalytic activity, improved selectivity, improved stability, improved tolerance to various fermentations conditions (temperature, pH, etc.), or improved tolerance to various metabolic substrates, products, by-products, intermediates, etc.

Desaturase enzymes can be engineered for improved catalytic activity in the desaturation of an unsaturated substrate, for improved hydrocarbon selectivity, for improved selectivity of a Z product over an E product, or an E product over a Z product. For example, the Z9 fatty-acyl desaturase can be engineered to improve the yield in the substrate to product conversion of a saturated fatty acyl-CoA to the corresponding unsaturated fatty acyl-CoA, and, in addition or in the alternative, to improve selectivity of the desaturation at the 9 position to produce a corresponding Z-9 fatty acyl-CoA. In further non-limiting examples, the fatty acyl-ACP synthetase can be engineered for improved ACP ligation activity; a fatty acid synthase complex enzyme can be engineered for improved catalytic activity of elongation of a fatty acid substrate; a fatty alcohol forming fatty acyl-reductase can be engineered for improved catalytic activity in the reduction of a fatty acyl-CoA to a corresponding fatty alcohol: a fatty aldehyde forming fatty acyl-reductase can be engineered for improved catalytic activity in the reduction of a fatty acyl-ACP to a corresponding fatty aldehyde: a dehydrogenase can be engineered for improved catalytic activity in the conversion of a fatty acyl-ACP to a corresponding fatty alcohol; an alcohol oxidase can be engineered for improved catalytic activity in the conversion of a fatty alcohol into a corresponding fatty aldehyde; and an acetyl transferase can be engineered for improved catalytic activity in the conversion of a fatty alcohol into a corresponding fatty acetate.

The term "improved catalytic activity" as used herein with respect to a particular enzymatic activity refers to a higher level of enzymatic activity than that measured relative to a comparable non-engineered enzyme, such as a non-engineered desaturase (e.g. fatty acyl-CoA desaturase or fatty acyl-ACP desaturase), fatty alcohol or aldehyde forming fatty-acyl reductase, acyl-ACP synthetase, fatty acid synthetase, fatty acid synthase complex, acyl transferase, dehydrogenase, or an alcohol oxidase enzyme. For example, overexpression of a specific enzyme can lead to an increased level of activity in the cells for that enzyme. Mutations can be introduced into a desaturase (e.g. fatty acyl-CoA desaturase or fatty acyl-ACP desaturase), a fatty alcohol or aldehyde forming fatty-acyl reductase, a acyl-ACP synthetase, a fatty acid synthetase, a fatty acid synthase complex, a acyl transferase, a dehydrogenase, or an alcohol oxidase enzyme resulting in engineered enzymes with improved catalytic activity. Methods to increase enzymatic activity are known to those skilled in the art. Such techniques can include increasing the expression of the enzyme by increasing plasmid copy number and/or use of a stronger promoter and/or use of activating riboswitches, introduction of mutations to relieve negative regulation of the enzyme, introduction of specific mutations to increase specific activity and/or decrease the $K_M$ for the substrate, or by directed evolution. See. e.g., *Methods in Molecular Biology* (vol. 231), ed. Arnold and Georgiou, Humana Press (2003).

Metabolic Engineering—Enzyme Overexpression and Gene Deletion/Downregulation for Increased Pathway Flux In various embodiments described herein, the exogenous and endogenous enzymes in the recombinant microorganism participating in the biosynthesis pathways described herein may be overexpressed.

The terms "overexpressed" or "overexpression" refers to an elevated level (e.g., aberrant level) of mRNAs encoding for a protein(s), and/or to elevated levels of protein(s) in cells as compared to similar corresponding unmodified cells expressing basal levels of mRNAs or having basal levels of proteins. In particular embodiments, mRNA(s) or protein(s) may be overexpressed by at least 2-fold, 3-fold, 4-fold, 5-fold, 6-fold, 8-fold, 10-fold, 12-fold, 15-fold or more in microorganisms engineered to exhibit increased gene mRNA, protein, and/or activity.

In some embodiments, a recombinant microorganism of the disclosure is generated from a host that contains the enzymatic capability to synthesize a substrate fatty acid. In this specific embodiment it can be useful to increase the synthesis or accumulation of a fatty acid to, for example, increase the amount of fatty acid available to an engineered fatty alcohol production pathway.

In some embodiments, it may be useful to increase the expression of endogenous or exogenous enzymes involved in the fatty alcohol, aldehyde, or acetate production pathway to increase flux from the fatty acid to the fatty alcohol, aldehyde, or acetate, thereby resulting in increased synthesis or accumulation of the fatty alcohol, aldehyde, or acetate.

In some embodiments, it may be useful to increase the expression of endogenous or exogenous enzymes to increase intracellular levels of a coenzyme. In one embodiment, the coenzyme is NADH. In another embodiment, the coenzyme is NADPH. In one embodiment, the expression of proteins in the pentose phosphate pathway is increased to increase the intracellular levels of NADPH. The pentose phosphate pathway is an important catabolic pathway for supplying reduction equivalents and an important anabolic pathway for biosynthesis reactions. In one embodiment, a glucose-6-phosphate dehydrogenase that converts glucose-6-phosphate to 6-phospho D-glucono-1,5-lactone is overexpressed. In some embodiments, the glucose-6-phosphate dehydrogenase is ZWF1 from yeast. In another embodiment, the glucose-6-phosphate dehydrogenase is ZWF1 (YNL241C) from *Saccharomyces cerevisiae*. In one embodiment, a glucose-6-phosphate-1-dehydrogenase that converts D-glucopyranose-6-phosphate to 6-phospho D-glucono-1,5-lactone is overexpressed. In another embodiment, the glucose-6-phosphate-1-dehydrogenase is zwf from bacteria. In certain embodiments, the glucose-6-phosphate-1-dehydrogenase is zwf (NP_416366) from *E. coli*. In one embodiment, a 6-phosphogluconolactonase that converts 6-phospho D-glucono-1,5-lactone to D-gluconate 6-phosphate is overexpressed. In some embodiments, the 6-phosphogluconolactonase is SOL3 of yeast. In certain embodiments, the 6-phosphogluconolactonase is SOL3 (NP_012033) of *Saccharomyces cerevisiae*. In some embodiments, the 6-phosphogluconolactonase is SOL4 of yeast. In certain embodiments, the 6-phosphogluconolactonase is SOL4 (NP_011764) of *Saccharomyces cerevisiae*. In some embodiments, the 6-phosphogluconolactonase is pgl of bacteria. In certain embodiments, the 6-phosphogluconolactonase is pgl (NP_415288) of *E. coli*. In one embodiment, a 6-phosphogluconate dehydrogenase that converts D-gluconate 6-phosphate to D-ribulose 5-phosphate is overexpressed. In some embodiments, the 6-phosphogluconate dehydrogenase is GND1 from yeast. In certain embodiments, the 6-phosphogluconate dehydrogenase is GND1 (YHR183W) from *Saccharomyces cerevisiae*. In some embodiments, the 6-phosphogluconate dehydrogenase is GND2 from yeast. In certain embodiments, the 6-phosphogluconate dehydrogenase is GND2 (YGR256W) from *Saccharomyces cerevisiae*. In some embodiments, the 6-phosphogluconate dehydrogenase is gnd from bacteria. In certain embodiments, the 6-phosphogluconate dehydrogenase is gnd (NP_416533) from *E. coli*. In one embodiment, a transaldolase that interconverts D-glyceraldehyde 3-phosphate and D-sedoheptulose 7-phosphate to β-D-fructofuranose 6-phosphate and D-erythrose 4-phosphate is overexpressed. In some embodiments, the transaldolase is TAL1 of yeast. In certain embodiments, the transaldolase is TAL1 (NP_013458) of *Saccharomyces cerevisiae*. In some embodiments, the transaldolase is NQM1 of yeast. In certain embodiments, the transaldolase is NQM1 (NP_011557) of *Saccharomyces cerevisiae*. In some embodiments, the transaldolase is tal of bacteria. In certain embodiments, the transaldolase is talB (NP_414549) of *E. coli*. In certain embodiments, the transaldolase is talA (NP_416959) of *E. coli*. In one embodiment, a transketolase that interconverts D-erythrose 4-phosphate and D-xylulose 5-phosphate to β-D-fructofuranose 6-phosphate and D-glyceraldehyde 3-phosphate and/or interconverts D-sedoheptulose 7-phosphate and D-glyceraldehyde 3-phosphate to D-ribose 5-phosphate and D-xylulose 5-phosphate is overexpressed. In some embodiments, the transketolase is TKL1 of yeast. In certain embodiments, the transketolase is TKL1 (NP_015399) of *Saccharomyces cerevisiae*. In some embodiments, the transketolase is TKL2 of yeast. In certain embodiments, the transketolase is TKL2 (NP_009675) of *Saccharomyces cerevisiae*. In some embodiments, the transketolase is tkt of bacteria. In certain embodiments, the transketolase is tktA (YP_026188) of *E. coli*. In certain embodiments, the transketolase is tktB (NP_416960) of *E. coli*. In one embodiment, a ribose-5-phosphate ketol-isomerase that interconverts D-ribose 5-phosphate and D-ribulose 5-phosphate is overexpressed. In some embodiments, the ribose-5-phosphate ketol-isomerase is RKI1 of yeast. In certain embodiments, the ribose-5-phosphate ketol-isomerase is RKI1 (NP_014738) of *Saccharomyces cerevisiae*. In some embodiments, the ribose-5-phosphate isomerase is rpi of bacteria. In certain embodiments, the ribose-5-phosphate isomerase is rpiA (NP_417389) of *E. coli*. In certain embodiments, the ribose-5-phosphate isomerase is rpiB (NP_418514) of *E. coli*. In one embodiment, a D-ribulose-5-phosphate 3-epimerase that interconverts D-ribulose 5-phosphate and D-xylulose 5-phosphate is overexpressed. In some embodiments, the D-ribulose-5-phosphate 3-epimerase is RPE1 of yeast. In certain embodiments, the D-ribulose-5-phosphate 3-epimerase is RPE1 (NP_012414) of *Saccharomyces cerevisiae*. In some embodiments, the D-ribulose-5-phosphate 3-epimerase is rpe of bacteria. In certain embodiments, the D-ribulose-5-phosphate 3-epimerase is rpe (NP_417845) of *E. coli*.

In one embodiment, the expression of an NADP+-dependent isocitrate dehydrogenase is increased to increase intracellular levels of a coenzyme. In one embodiment, an NADP+ dependent isocitrate dehydrogenase oxidizes D-threo-isocitrate to 2-oxoglutarate with concomitant generation of NADPH. In another embodiment, an NADP+ dependent isocitrate dehydrogenase oxidizes D-threo-isocitrate to 2-oxalosuccinate with concomitant generation of NADPH. In some embodiments, the NADP+-dependent isocitrate dehydrogenase is IDP from yeast. In certain embodiments, the NADP+-dependent isocitrate dehydrogenase is IDP2 (YLR174W) from *Saccharomyces cerevisiae*. In some embodiments, the NADP+-dependent isocitrate dehydrogenase is icd from bacteria. In certain embodiments, the NADP+-dependent isocitrate dehydrogenase is icd (NP_415654) from *E. coli*.

In some embodiments, the expression of a malic enzyme that decarboxylates malate to pyruvate with concomitant generation of NADH or NADPH is increased to increase intracellular levels of a coenzyme. In one embodiment, the malic enzyme is NAD+ dependent. In another embodiment, the malic enzyme is NADP+ dependent. In one embodiment, the malic enzyme is an NAD+ dependent malate dehydrogenase from bacteria. In some embodiments, the NAD+ dependent malate dehydrogenase is maeA (NP_415996) from *E. coli*. In some embodiments, the NAD+ dependent malate dehydrogenase is macE (CAQ68119) from *Lactobacillus casei*. In another embodiment, the malic enzyme is a mitochondrial NAD+ dependent malate dehydrogenase from yeast. In some embodiments, the NAD+ dependent malate dehydrogenase is MAE1 (YKL029C) from *S. cerevisiae*. In another embodiment, the malic enzyme is a mitochondrial NAD+ dependent malate dehydrogenase from a parasitic nematode. In some embodiments, the NAD+ dependent malate dehydrogenase is M81055 from *Ascaris suum*. In one embodiment, the malic enzyme is an NADP+ dependent malate dehydrogenase from bacteria. In some embodiments, the NADP+ dependent malate dehydrogenase is macB (NP_416958) from *E. coli*. In one embodiment, the malic enzyme is an NADP+ dependent malate dehydrogenase from corn. In some embodiments, the NADP+ dependent malate dehydrogenase is me 1 from *Zea mays*.

In some embodiments, the expression of an aldehyde dehydrogenase that oxidizes an aldehyde to a carboxylic acid with concomitant generation of NADH or NADPH is increased to increase intracellular levels of a coenzyme. In one embodiment, the aldehyde dehydrogenase is NAD+ dependent. In another embodiment, the aldehyde dehydrogenase is NADP+ dependent. In one embodiment, the aldehyde dehydrogenase is an NAD+ dependent aldehyde dehydrogenase from bacteria. In some embodiments, the NAD+ dependent aldehyde dehydrogenase is aldA (NP_415933) from *E. coli*. In another embodiment, the aldehyde dehydrogenase is a cytosolic NADP+ dependent aldehyde dehydrogenase from yeast. In some embodiments, the NADP+ dependent aldehyde dehydrogenase is ALD6 (YPL061W) from *S. cerevisiae*. In another embodiment, the aldehyde dehydrogenase is a cytosolic NADP+ dependent aldehyde dehydrogenase from bacteria. In some embodiments, the NADP+ dependent aldehyde dehydrogenase is aldB (NP_418045) from *E. coli*.

In one embodiment, overexpression of an enzyme to increase intracellular levels of a coenzyme comprises coupling supplementation of a co-substrate and overexpression of the enzyme. In one embodiment, the overexpression of an enzyme coupled with supplementation of a co-substrate of that enzyme increase flux through a biochemical pathway. In one embodiment, an NAD+ or NADP+ dependent alcohol dehydrogenase is expressed with a co-substrate. In certain embodiments, an alcohol dehydrogenase is expressed with an isopropanol co-substrate. In one embodiment, an NAD+ or NADP+ dependent glucose dehydrogenase is expressed with a co-substrate. In certain embodiments, a glucose dehydrogenase is expressed with a glucose co-substrate.

In one embodiment, the expression of a transhydrogenase is increased to interconvert NADH and NADPH. In some embodiments, the transhydrogenase is a pyridine nucleotide transhydrogenase. In some embodiments, the pyridine nucleotide transhydrogenase is from bacteria. In certain embodiments, the pyridine nucleotide transhydrogenase is pntAB (beta subunit: NP_416119 alpha subunit: NP_416120) from *E. coli*. In some embodiments, the pyridine nucleotide transhydrogenase is from human. In certain embodiments, the pyridine nucleotide transhydrogenase is NNT (NP_036475) from *Homo sapiens*. In certain embodiments, the pyridine nucleotide transhydrogenase is from *Solanum tuberosum*. In certain embodiments, the pyridine nucleotide transhydrogenase is from *Spinacea oleracea*.

In some embodiments, it may be useful to increase the expression of endogenous or exogenous proteins to induce endoplasmic reticulum (ER) membrane proliferation. In some embodiments, the induction of endoplasmic reticulum membrane proliferation can improve production of fatty alcohols, aldehydes, or acetates. In one embodiment, the expression of an inactivated HMG-CoA reductase (hydroxymethylglutaryl-CoA reductase) containing one or more ER facing loops is increased. In certain embodiments, the one or more loops is between transmembrane domains 6 and 7 of an inactivated HMG-CoA reductase. In some embodiments, the inactivated HMG-CoA reductase comprises an inactivated protein or chimera which codes for the first 500 amino acids or a subsequence of the first 500 amino acids of *Yarrowia lipolytica* YALI0E04807p. In other embodiments, the inactivated HMG-CoA reductase comprises an inactivated protein or chimera which codes for the first 522 amino acids or a subsequence of the first 522 amino acids of HMG1 from *Saccharomyces cerevisiae* (NP_013636.1). In other embodiments, the inactivated HMG-CoA reductase comprises an inactivated protein or chimera which codes for the first 522 amino acids or a subsequence of the first 522 amino acids of HMG2 from *Saccharomyces cerevisiae* (NP_013555.1). In some embodiments, the expression of one or more regulatory proteins is increased to improve production of fatty alcohols, aldehydes, or acetates. In certain embodiments, the regulatory protein comprises HAC transcription factor from *Saccharomyces cerevisiae* (NP_116622.1). In certain embodiments, the regulatory protein comprises HAC1 transcription factor from *Yarrowia lipolytica* (YALI0B2716p).

Increased synthesis or accumulation can be accomplished by, for example, overexpression of nucleic acids encoding one or more of the above-described a fatty alcohol pathway enzymes. Overexpression of a fatty alcohol pathway enzyme or enzymes can occur, for example, through increased expression of an endogenous gene or genes, or through the expression, or increased expression, of an exogenous gene or genes. Therefore, naturally occurring organisms can be readily modified to generate non-natural, fatty alcohol producing microorganisms through overexpression of one or more nucleic acid molecules encoding a fatty alcohol biosynthetic pathway enzyme. In addition, a non-naturally occurring organism can be generated by mutagenesis of an endogenous gene that results in an increase in activity of an enzyme in the fatty alcohol biosynthetic pathways.

Equipped with the present disclosure, the skilled artisan will be able to readily construct the recombinant microorganisms described herein, as the recombinant microorganisms of the disclosure can be constructed using methods well known in the art as exemplified above to exogenously express at least one nucleic acid encoding a fatty alcohol pathway enzyme in sufficient amounts to produce a fatty alcohol.

Methods for constructing and testing the expression levels of a non-naturally occurring fatty alcohol-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); Ausubo et al., *Current Protocols in Molecular Biology*, John Wiley and Sons, Baltimore, Md. (1999).

A variety of mechanisms known in the art can be used to express, or overexpress, exogenous or endogenous genes. For example, an expression vector or vectors can be constructed to harbor one or more fatty alcohol biosynthetic pathway enzyme encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome.

Selectable marker genes also can be included that, for example, provide resistance to antibiotics or toxins, complement auxotrophic deficiencies, or supply critical nutrients not in the culture media. In some embodiments, the present disclosure teaches the use of the bla (bacterial ampR resistance marker). In some embodiments, the present disclosure teaches use of the URA3 marker. In some embodiments, the present disclosure teaches microorganisms comprising the SUC2 gene to permit fermentation in sucrose media.

Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art.

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., *Science*, 236: 1237-1245 (1987)). Exemplary expression control sequences are described in, for example, Goeddel, *Gene Expression Technology: Methods in Enzymology*, Vol. 185, Academic Press, San Diego, Calif. (1990).

In various embodiments, an expression control sequence may be operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

In some embodiments, the recombinant microorganism is manipulated to delete, disrupt, mutate, and/or reduce the activity of one or more endogenous enzymes that catalyzes a reaction in a pathway that competes with the biosynthesis pathway for the production of a mono- or poly-unsaturated $C_6$-$C_{24}$ fatty alcohol, aldehyde, or acetate.

In some embodiments, the recombinant microorganism is manipulated to delete, disrupt, mutate, and/or reduce the activity of one or more endogenous enzymes that catalyzes the conversion of a fatty acid into a ω-hydroxyfatty acid. In some such embodiments, the enzymes that catalyze the conversion of a fatty acid into a ω-hydroxyfatty acid are selected from the group consisting of XP_504406, XP_504857, XP_504311, XP_500855, XP_500856, XP500402, XP_500097, XP_501748, XP_500560, XP_501148, XP_501667, XP_500273, BAA02041, CAA39366, CAA39367, BAA02210, BAA02211, BAA02212, BAA02213, BAA02214, AAO73952, AAO73953, AAO73954, AAO73955, AAO73956, AAO73958, AAO73959, AAO73960, AAO73961, AAO73957, XP_002546278, BAM49649, AAB80867, AAB17462, ADL27534, AAU24352, AAA87602, CAA34612, ABM17701, AAA25760, CAB51047, AAC82967, WP_011027348, or homologs thereof.

In some embodiments, the recombinant microorganism is manipulated to delete, disrupt, mutate, and/or reduce the activity of one or more endogenous cytochrome P450 monooxygenases selected from the group consisting of *Y. lipolytica* YALI0E25982g (ALK1), *Y. lipolytica* YALI0F01320g (ALK2), *Y. lipolytica* YALI0E23474g (ALK3), *Y. lipolytica* YALI0B13816g (ALK4), *Y. lipolytica* YALI0B13838g (ALK5), *Y. lipolytica* YALI0B01848g (ALK6), *Y. lipolytica* YALI0A15488g (ALK7), *Y. lipolytica* YALI0C12122g (ALK8), *Y. lipolytica* YALI0B06248g (ALK9), *Y. lipolytica* YALI0B20702g (ALK10), *Y. lipolytica* YALI0C10054g (ALK11) and *Y. lipolytica* YALI0A2130g (ALK12).

In other embodiments, the recombinant microorganism is manipulated to delete, disrupt, mutate, and/or reduce the activity of one or more endogenous enzymes that catalyzes the conversion of a fatty acyl-CoA into α,β-enoyl-CoA. In some such embodiments, the enzymes that catalyze the conversion of a fatty acyl-CoA into α,β-enoyl-CoA are selected from the group consisting of CAA04659, CAA04660, CAA04661, CAA04662, CAA04663, CAG79214, AAA34322, AAA34361, AAA34363, CAA29901, BAA04761, AAA34891, AAB08643, CAB15271, BAN55749, CAC44516, ADK16968, AEI37634, WP_000973047, WP_025433422, WP_035184107, WP_026484842, CEL80920, WP_026818657. WP_005293707, WP_005883960, or homologs thereof.

In some embodiments, one or more genes of the microbial host encoding acyl-CoA oxidases are deleted or down-regulated to eliminate or reduce the truncation of desired fatty acyl-CoAs beyond a desired chain-length. Such deletion or down-regulation targets include but are not limited to *Y. lipolytica* POX1(YALI0E32835g). *Y. lipolytica* POX2 (YALI0F10857g), *Y. lipolytica* POX3(YALI0D24750g), *Y. lipolytica* POX4(YALI0E27654g), *Y. lipolytica* POX5 (YALI0C23859g), *Y. lipolytica* POX6(YALI0E06567g): *S. cerevisiae* POX1(YGL205W); *Candida* POX2 (CaO19.1655. CaO19.9224, CTRG_02374, M18259), *Can-* dida POX4 (CaO19.1652, CaO19.9221, CTRG_02377, M12160), and Candida POX5 (CaO19.5723, CaO19.13146, CTRG_02721, M12161).

In some embodiments, the recombinant microorganism is manipulated to delete, disrupt, mutate, and/or reduce the activity of one or more proteins involved in peroxisome biogenesis. In such embodiments, the one or more proteins involved in peroxisome biogenesis are selected from the group consisting of XP_505754, XP_501986, XP_501311, XP_504845, XP_503326, XP_504029, XP_002549868, XP_002547156, XP_002545227, XP_002547350, XP_002546990, EIW11539, EIW08094, EIW11472, EIW09743, EIW0828, or homologs thereof.

In some embodiments, the recombinant microorganism is manipulated to delete, disrupt, mutate, and/or reduce the activity of one or more endogenous enzymes that catalyzes a reaction in a pathway that competes with the biosynthesis pathway for one or more unsaturated fatty acyl-CoA intermediates. In one embodiment, the one or more endogenous enzymes comprise one or more diacylglycerol acyltransferases. In the context of a recombinant yeast microorganism, the recombinant yeast microorganism is engineered to delete, disrupt, mutate, and/or reduce the activity of one or more diacylglycerol acyltransferases selected from the group consisting of YALI0E32769g, YALI0D07986g and CTRG_06209, or homolog thereof. In another embodiment, the one or more endogenous enzymes comprise one or more glycerolphospholipid acyltransferases. In the context of a recombinant yeast microorganism, the recombinant yeast microorganism is engineered to delete, disrupt, mutate, and/or reduce the activity of one or more glycerolphospholipid acyltransferases selected from the group consisting of YALI0E16797g and CTG_04390, or homolog thereof. In another embodiment, the one or more endogenous enzymes comprise one or more acyl-CoA/sterol acyltransferases. In the context of a recombinant yeast microorganism, the recombinant yeast microorganism is engineered to delete, disrupt, mutate, and/or reduce the activity of one or more acyl-CoA/sterol acyltransferases selected from the group consisting of YALI0F06578g, CTRG_01764 and CTRG_01765, or homolog thereof.

In some embodiments, one or more genes of the microbial host encoding glycerol-3-phosphate acyl transferases (GPATs), lysophosphatidic acid acyltransferases (LPAATs), glycerolphospholipid acyltransferase (GPLATs) and/or diacylglycerol acyltransferases (DGATs) are deleted or downregulated, and replaced with one or more GPATs, LPAATs, GPLATs, or DGATs which prefer to store short-chain fatty acyl-CoAs. Such deletion or downregulation targets include but are not limited to Y. lipolytica YALI0C00209g, Y. lipolytica YALI0E18964g, Y. lipolytica YALI0F19514g, Y. lipolytica Y. lipolytica YALI0C14014g, Y. lipolytica YALI0E16797g, Y. lipolytica YALI0E32769g, Y. lipolytica YALI0D07986g, S. cerevisiae YBL011w, S. cerevisiae YDL052c, S. cerevisiae YOR175C, S. cerevisiae YPR139C, S. cerevisiae YNR008w, S. cerevisiae YOR245c, Candida I503_02577, Candida CTRG_02630, Candida CaO19.250, Candida CaO19.7881, Candida CTRG_02437, Candida CaO19.1881, Candida CaO19.9437, Candida CTRG_01687, Candida CaO19.1043, Candida CaO19.8645, Candida CTRG_04750, Candida CaO19.13439, Candida CTRG_04390, Candida CaO19.6941, Candida CaO19.14203, and Candida CTRG_06209.

In some preferred embodiments, one or more genes of the microbial host encoding acylglycerol lipases (mono-, di-, or triacylglycerol lipases) and sterol ester esterases are deleted or downregulated and replaced with one or more acylglycerol lipases which prefer long chain acylglycerol substrates. In some embodiments, the one or more endogenous acylglycerol lipase and/or sterol ester esterase enzymes being deleted or downregulated are selected from Y. lipolytica YALI0E32035g, Y. lipolytica YALI0D17534g, Y. lipolytica YALI0F0010g, Y. lipolytica YALI0C14520g, Y. lipolytica YALI0E00528g, S. cerevisiae YKL140w, S. cerevisiae YMR313c, S. cerevisiae YKR089c, S. cerevisiae YOR081c, S. cerevsiae YKL094W. S. cerevisiae YLL012W, S. cerevisiae YLR020C, Candida CaO19.2050, Candida CaO19.9598, Candida CTRG_01138, Candida W5Q03398, Candida CTRG_00057, Candida CaO19.5426, Candida CaO19.12881, Candida CTRG_06185, Candida CaO19.4864, Candida CaO19.12328. Candida CTRG_03360, Candida CaO19.6501, Candida CaO19.13854, Candida CTRG_05049. Candida CaO19.1887, Candida CaO19.9443, Candida CTRG_01683, and Candida CTRG_04630.

In another embodiment, the recombinant microorganism is manipulated to delete, disrupt, mutate, and/or reduce the activity of one or more endogenous enzymes that catalyzes a reaction in a pathway that oxidizes fatty aldehyde intermediates. In one embodiment, the one or more endogenous enzymes comprise one or more fatty aldehyde dehydrogenases. In the context of a recombinant yeast microorganism, the recombinant yeast microorganism is engineered to delete, disrupt, mutate, and/or reduce the activity of one or more fatty aldehyde dehydrogenases selected from the group consisting of YALI0A17875g, YALI0E15400g, YALI0B01298g, YALI0F23793g, CTRG_05010 and CTRG_04471, or homolog thereof.

In another embodiment, the recombinant microorganism is manipulated to delete, disrupt, mutate, and/or reduce the activity of one or more endogenous enzymes that catalyzes a reaction in a pathway that consumes fatty acetate products. In one embodiment, the one or more endogenous enzymes comprise one or more sterol esterases. In the context of a recombinant yeast microorganism, the recombinant yeast microorganism is engineered to delete, disrupt, mutate, and/or reduce the activity of one or more sterol esterases selected from the group consisting of YALI0E32035g, YALI0E00528g, CTRG_01138, CTRG_01683 and CTRG_04630, or homolog thereof. In another embodiment, the one or more endogenous enzymes comprise one or more triacylglycerol lipases. In the context of a recombinant yeast microorganism, the recombinant yeast microorganism is engineered to delete, disrupt, mutate, and/or reduce the activity of one or more triacylglycerol lipases selected from the group consisting of YALI0D17534g, YALI0F10010g, CTRG_00057 and CTRG_06185, or homolog thereof. In another embodiment, the one or more endogenous enzymes comprise one or more monoacylglycerol lipases. In the context of a recombinant yeast microorganism, the recombinant yeast microorganism is engineered to delete, disrupt, mutate, and/or reduce the activity of one or more monoacylglycerol lipases selected from the group consisting of YALI0C14520g, CTRG_03360 and CTRG_05049, or homolog thereof. In another embodiment, the one or more endogenous enzymes comprise one or more extracellular lipases. In the context of a recombinant yeast microorganism, the recombinant yeast microorganism is engineered to delete, disrupt, mutate, and/or reduce the activity of one or more extracellular lipases selected from the group consisting of YALI0A20350g, YALI0D19184g, YALI0B09361g, CTRG_05930, CTRG_04188, CTRG_02799, CTRG_03052 and CTRG_03885, or homolog thereof.

In some embodiments, the recombinant microorganism is manipulated to delete, disrupt, mutate, and/or reduce the activity of one or more endogenous enzymes that (1) break down fatty acids in the course of beta-oxidation and/or (2) oxidize ω-hydroxy fatty acids to fatty acid aldehyde or to dicarboxylic acid in the course of ω-oxidation. In some embodiments, the recombinant microorganism comprises a deletion, disruption, mutation, and/or reduction in the activity of: (i) one or more endogenous acyl-CoA oxidase selected from the group consisting of YALI0E32835g (POX1), YALI0F10857g (POX2), YALI0D24750g (POX3), YALI0E27654g (POX4), YALI0C23859g (POX5), YALI0E06567g (POX6); (ii) one or more endogenous (fatty) alcohol dehydrogenase selected from the group consisting of YALI0F09603g (FADH), YALI0D25630g (ADH1), YALI0E17787g (ADH2), YALI0A16379g (ADH3), YALI0E15818g (ADH4). YALI0D02167g (ADH5), YALI0A15147g (ADH6), YALI0E07766g (ADH7); and (iii) an endogenous (fatty) alcohol oxidase YALI0B14014g (FAO1).

In some embodiments, the *Y. lipolytica* microorganism into which biosynthesis pathways for the production of $C_6$-$C_{24}$ fatty alcohol, fatty aldehyde and/or fatty acetate are introduced is H222 ΔP ΔA ΔF ΔURA3. AP denotes deletion of the acyl-CoA oxidase genes (POX1-6) in *Y. lipolytica*. AA denotes deletion of the (fatty) alcohol dehydrogenase genes (FADH, ADH1-7) in *Y. lipolytica*. AF denotes deletion of the (fatty) alcohol oxidase gene (FAO1) in *Y. lipolytica*. ΔURA3 denotes deletion of the URA3 gene in *Y. lipolytica*, rendering the yeast a uracil auxotroph. In some embodiments, the *Y. lipolytica* microorganism into which biosynthesis pathways for the production of $C_6$-$C_{24}$ fatty alcohol, fatty aldehyde and/or fatty acetate are introduced is H222 ΔP ΔA ΔF. In some embodiments, the *Y. lipolytica* microorganism into which biosynthesis pathways for the production of $C_6$-$C_{24}$ fatty alcohol, fatty aldehyde and/or fatty acetate are introduced is MATA ura3-302::SUC2 Δpox1 Δpox2 Δpox3 Δpox4 Δpox5 Δpox6 Δfadh Δadh1 Δadh2 Δadh3 Δadh4 Δadh5 Δadh6 Δadh7 Δfao1::URA3.

A wild type isolate of the yeast *Y. lipolytica*, preferably of the strain H222, can be used as the starting strain for the construction of strains according to the disclosure. The strain H222 was deposited on 29 Apr. 2013 at the DSMZ (Deutsche Sammlung fur Mikroorganismen and Zellkulturen GmbH, D-38142 Braunschweig) under the number DSM 27185 according to the Budapest Treaty on the International Recognition of the Deposit of Microorganisms for the Purposes of Patent Procedure. A selection marker is required for the use of a strain for further genetic processing. This selection marker can be introduced into the strain in a manner known per se, e.g. in the form of the uracil auxotroph. Alternatively, already known uracil auxotrophic strains can be used, preferably the strain H222-S4 (Mauersberger S, Wang H J, Gaillard in C, Barth G & Nicaud J M (2001) J Bacteriol 183: 5102-5109). The respective deletion cassette (e.g. POX1-6, FADH, ADH1-7, FAO1) is obtained by PCR or restriction and transformed into *Y. lipolytica* H222-S4, which can be produced from *Y. lipolytica* H222 (Mauers-berger et al. (2001)), according to Barth and Gaillardin (Barth G & Gaillardin C (1996) *Yarrowia lipolytica*. Springer-Verlag, Berlin, Heidelberg, New York). The creation of H222 ΔP ΔA ΔF ΔURA3 is described in WO 2015/086684, which is herein incorporated by reference in its entirety. *Y. lipolytica* strain H222 ΔP ΔA ΔF ΔURA3 is used as the starting microorganism for introduction of desaturases and reductases in the present disclosure (see, for example, Examples 7, 9 and 10).

In another embodiment, the recombinant microorganism is manipulated to delete, disrupt, mutate, and/or reduce the activity of one or more endogenous reductase or desaturase enzymes that interferes with the unsaturated $C_6$-$C_{24}$ fatty alcohol, aldehyde, or acetate, i.e., catalyzes the conversion of a pathway substrate or product into an unwanted by-product.

Chemical Conversion of Product from Microorganism Synthesis

The present disclosure describes chemical conversions that can be used to convert a product synthesized by recombinant microorganism into a down-stream product.

In some embodiments, an unsaturated fatty alcohol, aldehyde, acetate, or carboxylic acid produced by a microorganism can undergo subsequent chemical conversion to produce a pheromone, fragrance, flavor, polymer, or polymer intermediate. Non-limiting examples of chemical transformations include esterification, metathesis, and polymerization.

Unsaturated fatty carboxylic acids can be esterified by methods known in the art. For example, Fischer esterification can be used to covert a fatty carboxylic acid to a corresponding fatty ester. See, e.g., Komura, K. et al., *Synthesis* 2008, 3407-3410.

Elongation of the carbon chain can be performed by known methods to covert an unsaturated fatty alcohol into an elongated derivative thereof. Olefin metastasis catalysts can be performed to increase the number of carbons on the fatty carbon chain and impart Z or E stereochemistry on the corresponding unsaturated product.

In some embodiments, the metathesis catalyst is a tungsten metathesis catalyst, a molybdenum metathesis catalyst, or a ruthenium metathesis catalyst. In certain embodiments, the metathesis catalyst is a tungsten catalyst or a molybdenum catalyst. The catalysts employed in the present invention generally employ metals which can mediate a particular desired chemical reaction. In general, any transition metal (e.g., having d electrons) can be used to form the catalyst, e.g., a metal selected from one of Groups 3-12 of the periodic table or from the lanthanide series. In some embodiments, the metal is selected from Groups 3-8, or, in some cases, from Groups 4-7. In some embodiments, the metal is selected from Group 6. The term "Group 6" refers to the transition metal group comprising chromium, molybdenum, and tungsten. Additionally, the present invention may also include the formation of heterogeneous catalysts containing forms of these elements (e.g., by immobilizing a metal complex on an insoluble substrate, for example, silica).

In general, any metathesis catalyst stable under the reaction conditions and nonreactive with functional groups on the fatty substrate (e.g., alcohol, ester, carboxylic acid, aldehyde, or acetate) can be used with the present disclosure. Such catalysts are, for example, those described by Grubbs (Grubbs, R. H., "Synthesis of large and small molecules using olefin metathesis catalysts." *PMSE Prepr.*, 2012), herein incorporated by reference in its entirety. Depending on the desired isomer of the olefin, as cis-selective metathesis catalyst may be used, for example one of those described by Shahane et al. (Shahane, S., et al. *ChemCatChem*, 2013, 5(12): p. 3436-3459), herein incorporated by reference in its entirety. Catalysts exhibiting cis-selectivity have been described previously (Khan, R K., et al. *J. Am. Chem. Soc.*, 2013, 135(28): p. 10258-61; Hartung, J. et al. *J. Am. Chem. Soc.*, 2013, 135(28): p. 10183-5; Rosebrugh, L. E., et al. *J. Am. Chem. Soc.*, 2013, 135(4): p. 1276-9; Marx, V. M., et al. *J. Am. Chem. Soc.*, 2013, 135(1): p. 94-7.; Herbert, M. B., et al. *Angew. Chem. Int. Ed. Engl.*, 2013, 52(1): p. 310-4; Keitz, B. K., et al. *J. Am. Chem. Soc.*, 2012, 134(4): p. 2040-3: Keitz, B. K., et al. *J. Am. Chem. Soc.,* 2012, 134(1): p. 693-9; Endo, K. et al. *J. Am. Chem. Soc.,* 2011, 133(22): p. 8525-7).

Additional Z-selective catalysts are described in (Cannon and Grubbs 2013: Bronner et al. 2014; Hartung et al. 2014; Pribisko et al. 2014: Quigley and Grubbs 2014) and are herein incorporated by reference in their entirety. Due to their excellent stability and functional group tolerance, in some embodiments metathesis catalysts include, but are not limited to, neutral ruthenium or osmium metal carbene complexes that possess metal centers that are formally in the +2 oxidation state, have an electron count of 16, are pentacoordinated, and are of the general formula LL'AA'M=CRbRc or LL'AA'M=(C=)nCRbRc (Pederson and Grubbs 2002); wherein M is ruthenium or osmium;

L and L' are each independently any neutral electron donor ligand and selected from phosphine, sulfonated phosphine, phosphite, phosphinite, phosphonite, arsine, stibnite, ether, amine, amide, imine, sulfoxide, carboxyl, nitrosyl, pyridine, thioether, or heterocyclic carbenes; and A and A' are anionic ligands independently selected from halogen, hydrogen, C1-C20 alkyl, aryl, C1-C20 alkoxide, aryloxide, C2-C20 alkoxycarbonyl, arylcarboxylate, C1-C20 carboxylate, arylsulfonyl, C1-C20 alkylsulfonyl, C1-C20 alkylsulfinyl; each ligand optionally being substituted with C1-C5 alkyl, halogen, C1-C5 alkoxy; or with a phenyl group that is optionally substituted with halogen, C1-C5 alkyl, or C1-C5 alkoxy; and A and A' together may optionally comprise a bidentate ligand; and Rb and Rc are independently selected from hydrogen, C1-C20 alkyl, aryl, C1-C20 carboxylate, C1-C20 alkoxy, aryloxy, C1-C20 alkoxycarbonyl, C1-C20 alkylthio, C1-C20 alkylsulfonyl and C1-C20 alkylsulfinyl, each of Rb and Rc optionally substituted with C1-C5 alkyl, halogen, C1-C5 alkoxy or with a phenyl group that is optionally substituted with halogen, C1-C5 alkyl, or C1-C5 alkoxy.

Other metathesis catalysts such as "well defined catalysts" can also be used. Such catalysts include, but are not limited to, Schrock's molybdenum metathesis catalyst, 2,6-diisopropylphenylimido neophylidenemolybdenum (VI) bis (hexafluoro-t-butoxide), described by Grubbs et al. (*Tetrahedron* 1998, 54: 4413-4450) and Basset's tungsten metathesis catalyst described by Couturier, J. L. et al. (*Angew. Chem. Int. Ed. Engl.* 1992, 31: 628).

Catalysts useful in the methods of the disclosure also include those described by U.S. Pat. No. 9,776,179, Peryshkov, et al. *J. Am. Chem. Soc.* 2011, 133: 20754-20757; Wang, et al. *Angewandte Chemie,* 2013, 52: 1939-1943; Yu, et al. *J. Am. Chem. Soc.,* 2012, 134: 2788-2799; Halford. Chem. *Eng. News.* 2011, 89 (45): 11; Yu, et al. *Nature,* 2011, 479: 88-93; Lee. *Nature.* 2011, 471: 452-453; Meek, et al. *Nature,* 2011: 471, 461-466; Flook, et al. *J. Am. Chem. Soc.* 2011, 133: 1784-1786; Zhao, et al. *Org Lett.,* 2011, 13(4): 784-787; Ondi, et al. "High activity, stabilized formulations, efficient synthesis and industrial use of Mo- and W-based metathesis catalysts" *XiMo Technology Updates.* 2015: http://www.ximo-inc.com/files/ximo/uploads/download/Summary_3.11.15.pdf; Schrock, et al. *Macromolecules,* 2010: 43, 7515-7522; Peryshkov, et al. *Organometallics* 2013: 32, 5256-5259; Gerber, et al. *Organometallics* 2013: 32, 5573-5580; Marinescu, et al. *Organometallics* 2012: 31, 6336-6343; Wang, et al. *Angew. Chem. Int. Ed.* 2013: 52, 1939-1943; Wang, et al. *Chem. Eur. J.* 2013: 19, 2726-2740; and Townsend et al. *J. Am. Chem. Soc.* 2012: 134, 11334-11337.

Catalysts useful in the methods of the disclosure also include those described in International Pub. No. WO 2014/155185; International Pub. No. WO 2014/172534; U.S. Pat. Appl. Pub. No. 2014/0330018; International Pub. No. WO 2015/003815; and International Pub. No. WO 2015/003814.

Catalysts useful in the methods of the disclosure also include those described in U.S. Pat. Nos. 4,231,947; 4,245,131; 4,427,595; 4,681,956; 4,727,215; International Pub. No. WO 1991/009825; U.S. Pat. Nos. 5,087,710; 5,142,073; 5,146,033; International Pub. No. WO 1992/019631; U.S. Pat. Nos. 6,121,473; 6,346,652; 8,987,531: U.S. Pat. Appl. Pub. No. 2008/0119678; International Pub. No. WO 2008/066754; International Pub. No. WO 2009/094201: U.S. Pat. Appl. Pub. No. 2011/0015430: U.S. Pat. Appl. Pub. No. 2011/0065915; U.S. Pat. Appl. Pub. No. 2011/0077421; International Pub. No. WO 2011/040963; International Pub. No. WO 2011/097642; U.S. Pat. Appl. Pub. No. 2011/0237815; U.S. Pat. Appl. Pub. No. 2012/0302710; International Pub. No. WO 2012/167171: U.S. Pat. Appl. Pub. No. 2012/0323000: U.S. Pat. Appl. Pub. No. 2013/0116434; International Pub. No. WO 2013/070725; U.S. Pat. Appl. Pub. No. 2013/0274482; U.S. Pat. Appl. Pub. No. 2013/0281706; International Pub. No. WO 2014/139679; International Pub. No. WO 2014/169014; U.S. Pat. Appl. Pub. No. 2014/0330018; and U.S. Pat. Appl. Pub. No. 2014/0378637.

Catalysts useful in the methods of the disclosure also include those described in International Pub. No. WO 2007/075427; U.S. Pat. Appl. Pub. No. 2007/0282148; International Pub. No. WO 2009/126831; International Pub. No. WO 2011/069134; U.S. Pat. Appl. Pub. No. 2012/0123133; U.S. Pat. Appl. Pub. No. 2013/0261312: U.S. Pat. Appl. Pub. No. 2013/0296511; International Pub. No. WO 2014/134333; and U.S. Pat. Appl. Pub. No. 2015/0018557.

Catalysts useful in the methods of the disclosure also include those described in U.S. Pat. Appl. Pub. No. 2008/0009598: U.S. Pat. Appl. Pub. No. 2008/0207911: U.S. Pat. Appl. Pub. No. 2008/0275247; U.S. Pat. Appl. Pub. No. 2011/0040099; U.S. Pat. Appl. Pub. No. 2011/0282068; and U.S. Pat. Appl. Pub. No. 2015/0038723.

Catalysts useful in the methods of the disclosure include those described in International Pub. No. WO 2007/140954: U.S. Pat. Appl. Pub. No. 2008/0221345; International Pub. No. WO 2010/037550: U.S. Pat. Appl. Pub. No. 2010/0087644; U.S. Pat. Appl. Pub. No. 2010/0113795; U.S. Pat. Appl. Pub. No. 2010/0174068; International Pub. No. WO 2011/091980; International Pub. No. WO 2012/168183: U.S. Pat. Appl. Pub. No. 2013/0079515; U.S. Pat. Appl. Pub. No. 2013/0144060: U.S. Pat. Appl. Pub. No. 2013/0211096; International Pub. No. WO 2013/135776; International Pub. No. WO 2014/001291; International Pub. No. WO 2014/067767; U.S. Pat. Appl. Pub. No. 2014/0171607; and U.S. Pat. Appl. Pub. No. 2015/0045558.

The catalyst is typically provided in the reaction mixture in a sub-stoichiometric amount (e.g., catalytic amount). In certain embodiments, that amount is in the range of about 0.001 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, less than about 0.1 mol %, less than about 0.015 mol %, less than about 0.01 mol %, less than about 0.0015 mol %, or less, relative to the limiting reagent. In some embodiments, the catalyst is present in the range of about 2.5 mol % to about 5 mol %, relative to the limiting reagent. In some embodiments, the reaction mixture contains about 0.5 mol % catalyst. In the case where the molecular formula of the catalyst complex includes more than one metal, the amount of the catalyst complex used in the reaction may be adjusted accordingly.

In some cases, the methods described herein can be performed in the absence of solvent (e.g., neat). In some cases, the methods can include the use of one or more solvents. Examples of solvents that may be suitable for use in the disclosure include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the method is performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the method is performed at a pressure of about less than 760 torr. In some embodiments, the method is performed at a pressure of about less than 700 torr. In some embodiments, the method is performed at a pressure of about less than 650 torr. In some embodiments, the method is performed at a pressure of about less than 600 torr. In some embodiments, the method is performed at a pressure of about less than 550 torr. In some embodiments, the method is performed at a pressure of about less than 500 torr. In some embodiments, the method is performed at a pressure of about less than 450 torr. In some embodiments, the method is performed at a pressure of about less than 400 torr. In some embodiments, the method is performed at a pressure of about less than 350 torr. In some embodiments, the method is performed at a pressure of about less than 300 torr. In some embodiments, the method is performed at a pressure of about less than 250 torr. In some embodiments, the method is performed at a pressure of about less than 200 torr. In some embodiments, the method is performed at a pressure of about less than 150 torr. In some embodiments, the method is performed at a pressure of about less than 100 torr. In some embodiments, the method is performed at a pressure of about less than 90 torr. In some embodiments, the method is performed at a pressure of about less than 80 torr. In some embodiments, the method is performed at a pressure of about less than 70 torr. In some embodiments, the method is performed at a pressure of about less than 60 torr. In some embodiments, the method is performed at a pressure of about less than 50 torr. In some embodiments, the method is performed at a pressure of about less than 40 torr. In some embodiments, the method is performed at a pressure of about less than 30 torr. In some embodiments, the method is performed at a pressure of about less than 20 torr. In some embodiments, the method is performed at a pressure of about 20 torr. In some embodiments, the method is performed at a pressure of about 10 torr. In some embodiments, the method is performed at a pressure of about 10 torr. In some embodiments, the method is performed at a pressure of about 1 torr. In some embodiments, the method is performed at a pressure of less than about 1 torr.

In some embodiments, the two metathesis reactants are present in equimolar amounts. In some embodiments, the two metathesis reactants are not present in equimolar amounts. In certain embodiments, the two reactants are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the two reactants are present in a molar ratio of about 10:1. In certain embodiments, the two reactants are present in a molar ratio of about 7:1. In certain embodiments, the two reactants are present in a molar ratio of about 5:1. In certain embodiments, the two reactants are present in a molar ratio of about 2:1. In certain embodiments, the two reactants are present in a molar ratio of about 1:10. In certain embodiments, the two reactants are present in a molar ratio of about 1:7. In certain embodiments, the two reactants are present in a molar ratio of about 1:5. In certain embodiments, the two reactants are present in a molar ratio of about 1:2.

In general, the reactions with many of the metathesis catalysts disclosed herein provide yields better than 15%, better than 50%, better than 75%, or better than 90%. In addition, the reactants and products are chosen to provide at least a 5° C. difference, a greater than 20° C. difference, or a greater than 40° C. difference in boiling points. Additionally, the use of metathesis catalysts allows for much faster product formation than byproduct, it is desirable to run these reactions as quickly as practical. In particular, the reactions are performed in less than about 24 hours, less than 12 hours, less than 8 hours, or less than 4 hours.

One of skill in the art will appreciate that the time, temperature and solvent can depend on each other, and that changing one can require changing the others to prepare the pyrethroid products and intermediates in the methods of the disclosure. The metathesis steps can proceed at a variety of temperatures and times. In general, reactions in the methods of the disclosure are conducted using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, reactions in the methods of the disclosure are conducted at a temperature of from about 0° C. to about 200° C. For example, reactions can be conducted at 15-100° C. In some embodiments, reaction can be conducted at 20-80° C. In some embodiments, reactions can be conducted at 100-150° C.

Unsaturated fatty esters can be reduced using a suitable reducing agent which selectively reduces the ester to the corresponding aldehyde or alcohol but does not reduce the double bond. An unsaturated fatty ester can be reduced to the corresponding unsaturated fatty aldehyde using di-isobutyl aluminum halide (DIBAL) or Vitride®. The unsaturated fatty aldehyde can be reduced to the corresponding fatty alcohol with, e.g., DIBAL or Vitride®. In some embodiments, the unsaturated fatty ester can be reduced to the corresponding fatty alcohol using $AlH_3$ or 9-Borabicyclo (3.3.1)nonane (9-BBN). (See Galatis, P. *Encyclopedia of Reagents for Organic Synthesis.* 2001. New York: John Wiley & Sons; and Carey & Sunderburg. *Organic Chemistry. Part B: Reactions and Synthesis,* $5^{th}$ edition, 2007. New York. Springer Sciences)

Pheromone Compositions and Uses Thereof

As described above, products made via the methods described herein are pheromones. Pheromones prepared according to the methods of the invention can be formulated for use as insect control compositions. The pheromone compositions can include a carrier, and/or be contained in a dispenser. The carrier can be, but is not limited to, an inert liquid or solid.

Examples of solid carriers include but are not limited to fillers such as kaolin, bentonite, dolomite, calcium carbonate, talc, powdered magnesia. Fuller's earth, wax, gypsum, diatomaceous earth, rubber, plastic, China clay, mineral earths such as silicas, silica gels, silicates, attaclay, limestone, chalk, loess, clay, dolomite, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or compositions of these.

Examples of liquid carriers include, but are not limited to, water; alcohols, such as ethanol, butanol or glycol, as well as their ethers or esters, such as methylglycol acetate; ketones, such as acetone, cyclohexanone, methylethyl ketone, methylisobutylketone, or isophorone: alkanes such as hexane, pentane, or heptanes; aromatic hydrocarbons, such as xylenes or alkyl naphthalenes: mineral or vegetable oils; aliphatic chlorinated hydrocarbons, such as trichloroethane or methylene chloride: aromatic chlorinated hydrocarbons, such as chlorobenzenes; water-soluble or strongly polar solvents such as dimethylformamide, dimethyl sulfoxide, or N-methylpyrrolidone; liquefied gases: waxes, such as beeswax, lanolin, shellac wax, carnauba wax, fruit wax (such as bayberry or sugar cane wax) candelilla wax, other waxes such as microcrystalline, ozocerite, ceresin, or montan; salts such as monoethanolamine salt, sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate and mixtures thereof. Baits or feeding stimulants can also be added to the carrier.

Synergist

In some embodiments, the pheromone composition is combined with an active chemical agent such that a synergistic effect results. The synergistic effect obtained by the taught methods can be quantified according to Colby's formula (i.e. $(E)=X+Y-(X*Y/100)$. See Colby, R. S., "Calculating Synergistic and Antagonistic Responses of Herbicide Combinations", 1967 Weeds, vol. 15, pp. 20-22, incorporated herein by reference in its entirety. Thus, by "synergistic" is intended a component which, by virtue of its presence, increases the desired effect by more than an additive amount. The pheromone compositions and adjuvants of the present methods can synergistically increase the effectiveness of agricultural active compounds and also agricultural auxiliary compounds.

Thus, in some embodiments, a pheromone composition can be formulated with a synergist. The term, "synergist," as used herein, refers to a substance that can be used with a pheromone for reducing the amount of the pheromone dose or enhancing the effectiveness of the pheromone for attracting at least one species of insect. The synergist may or may not be an independent attractant of an insect in the absence of a pheromone.

In some embodiments, the synergist is a volatile phytochemical that attracts at least one species of Lepidoptera. The term, "phytochemical," as used herein, means a compound occurring naturally in a plant species. In a particular embodiment, the synergist is selected from the group comprising β-caryophyllene, iso-caryophyllene, α-humulene, inalool, Z3-hexenol/yl acetate, β-farnesene, benzaldehyde, phenylacetaldehyde, and combinations thereof.

The pheromone composition can contain the pheromone and the synergist in a mixed or otherwise combined form, or it may contain the pheromone and the synergist independently in a non-mixed form.

Insecticide

The pheromone composition can include one or more insecticides. In one embodiment, the insecticides are chemical insecticides known to one skilled in the art. Examples of the chemical insecticides include one or more of pyrethoroid or organophosphorus insecticides, including but are not limited to, cyfluthrin, permethrin, cypermethrin, bifinthrin, fenvalerate, flucythrinate, azinphosmethyl, methyl parathion, buprofezin, pyriproxyfen, flonicamid, acetamiprid, dinotefuran, clothianidin, acephate, malathion, quinolphos, chloropyriphos, profenophos, bendiocarb, bifenthrin, chlorpyrifos, cyfluthrin, diazinon, pyrethrum, fenpropathrin, kinoprene, insecticidal soap or oil, neonicotinoids, diamides, avermectin and derivatives, spinosad and derivatives, azadirachtin, pyridalyl, and mixtures thereof.

In another embodiment, the insecticides are one or more biological insecticides known to one skilled in the art. Examples of the biological insecticides include, but are not limited to, azadirachtin (neem oil), toxins from natural pyrethrins, *Bacillus thuringiencis* and *Beauveria bassiana*, viruses (e.g., CYD-X™, CYD-X HP™, Germstar™, Madex HP™ and Spod-X™), peptides (Spear-™, Spear-P™, and Spear-C™).

In another embodiment, the insecticides are insecticides that target the nerve and muscle. Examples include acetylcholinesterase (AChE) inhibitors, such as carbamates (e.g., methomyl and thiodicarb) and organophosphates (e.g., chlorpyrifos) GABA-gated chloride channel antagonists, such as cyclodiene organochlorines (e.g., endosulfan) and phenylpyrazoles (e.g., fipronil), sodium channel modulators, such as pyrethrins and pyrethroids (e.g., cypermethrin and λ-cyhalothrin), nicotinic acetylcholine receptor (nAChR) agonists, such as neonicotinoids (e.g., acetamiprid, tiacloprid, thiamethoxam), nicotinic acetylcholine receptor (nAChR) allosteric modulators, such as spinosyns (e.g., spinose and spinetoram), chloride channel activators, such as avermectins and milbemycins (e.g., abamectin, emamectin benzoate), Nicotinic acetylcholine receptor (nAChR) blockers, such as bensultap and cartap, voltage dependent sodium channel blockers, such as indoxacarb and metaflumizone, ryanodine receptor modulator, such as diamides (e.g. dhlorantraniliprole and flubendiamide). In another embodiment, the insecticides are insecticides that target respiration. Examples include chemicals that uncouple oxidative phosphorylation via disruption of the proton gradient, such as chlorfenapyr, and mitochondrial complex I electron transport inhibitors.

In another embodiment, the insecticides are insecticides that target midgut. Examples include microbial disruptors of insect midgut membranes, such as *Bacillus thuringiensis* and *Bacillus sphaericus*.

In another embodiment, the insecticides are insecticides that target growth and development. Examples include juvenile hormone mimics, such as juvenile hormone analogues (e.g. fenoxycarb), inhibitors of chitin biosynthesis, Type 0, such as benzoylureas (e.g., flufenoxuron, lufenuron, and novaluron), and ecdysone receptor agonists, such as diacylhydrazines (e.g., methoxyfenozide and tebufenozide)

Stabilizer

According to another embodiment of the disclosure, the pheromone composition may include one or more additives that enhance the stability of the composition. Examples of additives include, but are not limited to, fatty acids and vegetable oils, such as for example olive oil, soybean oil, corn oil, safflower oil, canola oil, and combinations thereof.

Filler

According to another embodiment of the disclosure, the pheromone composition may include one or more fillers. Examples of fillers include, but are not limited to, one or more mineral clays (e.g., attapulgite). In some embodiments, the attractant-composition may include one or more organic thickeners. Examples of such thickeners include, but are not limited to, methyl cellulose, ethyl cellulose, and any combinations thereof.

Solvent

According to another embodiment, the pheromone compositions of the present disclosure can include one or more solvents. Compositions containing solvents are desirable when a user is to employ liquid compositions which may be applied by brushing, dipping, rolling, spraying, or otherwise applying the liquid compositions to substrates on which the user wishes to provide a pheromone coating (e.g., a lure). In some embodiments, the solvent(s) to be used is/are selected so as to solubilize, or substantially solubilize, the one or more ingredients of the pheromone composition. Examples of solvents include, but are not limited to, water, aqueous solvent (e.g., mixture of water and ethanol), ethanol, methanol, chlorinated hydrocarbons, petroleum solvents, turpentine, xvylene, and any combinations thereof.

In some embodiments, the pheromone compositions of the present disclosure comprise organic solvents. Organic solvents are used mainly in the formulation of emulsifiable concentrates, ULV formulations, and to a lesser extent granular formulations. Sometimes mixtures of solvents are used. In some embodiments, the present disclosure teaches the use of solvents including aliphatic paraffinic oils such as kerosene or refined paraffins. In other embodiments, the present disclosure teaches the use of aromatic solvents such as xylene and higher molecular weight fractions of C9 and C10 aromatic solvents. In some embodiments, chlorinated hydrocarbons are useful as co-solvents to prevent crystallization when the formulation is emulsified into water. Alcohols are sometimes used as co-solvents to increase solvent power.

Solubilizing Agent

In some embodiments, the pheromone compositions of the present disclosure comprise solubilizing agents. A solubilizing agent is a surfactant, which will form micelles in water at concentrations above the critical micelle concentration. The micelles are then able to dissolve or solubilize water-insoluble materials inside the hydrophobic part of the micelle. The types of surfactants usually used for solubilization are non-ionics: sorbitan monooleates; sorbitan monooleate ethoxylates; and methyl oleate esters.

Binder

According to another embodiment of the disclosure, the pheromone composition may include one or more binders. Binders can be used to promote association of the pheromone composition with the surface of the material on which said composition is coated. In some embodiments, the binder can be used to promote association of another additive (e.g., insecticide, insect growth regulators, and the like) to the pheromone composition and/or the surface of a material. For example, a binder can include a synthetic or natural resin typically used in paints and coatings. These may be modified to cause the coated surface to be friable enough to allow insects to bite off and ingest the components of the composition (e.g., insecticide, insect growth regulators, and the like), while still maintaining the structural integrity of the coating.

Non-limiting examples of binders include polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or compositions of these; lubricants such as magnesium stearate, sodium stearate, talc or polyethylene glycol, or compositions of these; antifoams such as silicone emulsions, long-chain alcohols, phosphoric esters, acetylene diols, fatty acids or organofluorine compounds, and complexing agents such as: salts of ethylenediaminetetraacetic acid (EDTA), salts of trinitrilotriacetic acid or salts of polyphosphoric acids, or compositions of these.

In some embodiments, the binder also acts a filler and/or a thickener. Examples of such binders include, but are not limited to, one or more of shellac, acrylics, epoxies, alkyds, polyurethanes, linseed oil, tung oil, and any combinations thereof.

Surface-Active Agents

In some embodiments, the pheromone compositions comprise surface-active agents. In some embodiments, the surface-active agents are added to liquid agricultural compositions. In other embodiments, the surface-active agents are added to solid formulations, especially those designed to be diluted with a carrier before application. Thus, in some embodiments, the pheromone compositions comprise surfactants. Surfactants are sometimes used, either alone or with other additives, such as mineral or vegetable oils as adjuvants to spray-tank mixes to improve the biological performance of the pheromone on the target. The surface-active agents can be anionic, cationic, or nonionic in character, and can be employed as emulsifying agents, wetting agents, suspending agents, or for other purposes. In some embodiments, the surfactants are non-ionics such as: alkyl ethoxylates, linear aliphatic alcohol ethoxylates, and aliphatic amine ethoxylates. Surfactants conventionally used in the art of formulation and which may also be used in the present formulations are described, in *McCutcheon's Detergents and Emulsifiers Annual*, MC Publishing Corp., Ridgewood, N.J., 1998, and in *Encyclopedia of* Surfactants, Vol. I-III. Chemical Publishing Co., New York, 1980-81. In some embodiments, the present disclosure teaches the use of surfactants including alkali metal, alkaline earth metal or ammonium salts of aromatic sulfonic acids, for example, ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or compositions of these.

In some embodiments, the present disclosure teaches other suitable surface-active agents, including salts of alkyl sulfates, such as diethanolammonium lauryl sulfate; alkylarylsulfonate salts, such as calcium dodecylbenzenesulfonate; alkylphenol-alkylene oxide addition products, such as nonylphenol-C18 ethoxylate; alcohol-alkylene oxide addition products, such as tridecyl alcohol-C16 ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Wetting Agents

In some embodiments, the pheromone compositions comprise wetting agents. A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank or other vessel to reduce the wetting time of wettable powders and to improve the penetration of water into water-dispersible granules. In some embodiments, examples of wetting agents used in the pheromone compositions of the present disclosure, including wettable powders, suspension concentrates, and water-dispersible granule formulations are: sodium lauryl sulphate; sodium dioctyl sulphosuccinate; alkyl phenol ethoxylates; and aliphatic alcohol ethoxylates.

Dispersing Agent

In some embodiments, the pheromone compositions of the present disclosure comprise dispersing agents. A dispersing agent is a substance which adsorbs onto the surface of particles and helps to preserve the state of dispersion of the particles and prevents them from reaggregating. In some embodiments, dispersing agents are added to pheromone compositions of the present disclosure to facilitate dispersion and suspension during manufacture, and to ensure the particles redisperse into water in a spray tank. In some embodiments, dispersing agents are used in wettable powders, suspension concentrates, and water-dispersible granules. Surfactants that are used as dispersing agents have the ability to adsorb strongly onto a particle surface and provide a charged or steric barrier to re-aggregation of particles. In some embodiments, the most commonly used surfactants are anionic, non-ionic, or mixtures of the two types.

In some embodiments, for wettable powder formulations, the most common dispersing agents are sodium lignosulphonates. In some embodiments, suspension concentrates provide very good adsorption and stabilization using polyelectrolytes, such as sodium naphthalene sulphonate formaldehyde condensates. In some embodiments, tristyrylphenol ethoxylated phosphate esters are also used. In some embodiments, such as alkylarylethylene oxide condensates and EO-PO block copolymers are sometimes combined with anionics as dispersing agents for suspension concentrates.

Polymeric Surfactant

In some embodiments, the pheromone compositions of the present disclosure comprise polymeric surfactants. In some embodiments, the polymeric surfactants have very long hydrophobic 'backbones' and a large number of ethylene oxide chains forming the 'teeth' of a 'comb' surfactant. In some embodiments, these high molecular weight polymers can give very good long-term stability to suspension concentrates, because the hydrophobic backbones have many anchoring points onto the particle surfaces. In some embodiments, examples of dispersing agents used in pheromone compositions of the present disclosure are: sodium lignosulphonates; sodium naphthalene sulphonate formaldehyde condensates; tristyrylphenol ethoxylate phosphate esters; aliphatic alcohol ethoxylates; alkyl ethoxylates; EO-PO block copolymers; and graft copolymers.

Emulsifying Agent

In some embodiments, the pheromone compositions of the present disclosure comprise emulsifying agents. An emulsifying agent is a substance, which stabilizes a suspension of droplets of one liquid phase in another liquid phase. Without the emulsifying agent the two liquids would separate into two immiscible liquid phases. In some embodiments, the most commonly used emulsifier blends include alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. In some embodiments, emulsion stability can sometimes be improved by the addition of a small amount of an EO-PO block copolymer surfactant.

Gelling Agent

In some embodiments, the pheromone compositions comprise gelling agents. Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. In some embodiments, the pheromone compositions comprise one or more thickeners including, but not limited to: montmorillonite, e.g. bentonite; magnesium aluminum silicate; and attapulgite. In some embodiments, the present disclosure teaches the use of polysaccharides as thickening agents. The types of polysaccharides most commonly used are natural extracts of seeds and seaweeds or synthetic derivatives of cellulose. Some embodiments utilize xanthan and some embodiments utilize cellulose. In some embodiments, the present disclosure teaches the use of thickening agents including, but are not limited to: guar gum; locust bean gum; carrageenan; alginates: methyl cellulose: sodium carboxymethyl cellulose (SCMC); hydroxyethyl cellulose (HEC). In some embodiments, the present disclosure teaches the use of other types of anti-settling agents such as modified starches, polyacrylates, polyvinyl alcohol, and polyethylene oxide. Another good anti-settling agent is xanthan gum.

Anti-Foam Agent

In some embodiments, the presence of surfactants, which lower interfacial tension, can cause water-based formulations to foam during mixing operations in production and in application through a spray tank. Thus, in some embodiments, in order to reduce the tendency to foam, anti-foam agents are often added either during the production stage or before filling into bottles/spray tanks. Generally, there are two types of anti-foam agents, namely silicones and nonsilicones. Silicones are usually aqueous emulsions of dimethyl polysiloxane, while the nonsilicone anti-foam agents are water-insoluble oils, such as octanol and nonanol, or silica. In both cases, the function of the anti-foam agent is to displace the surfactant from the air-water interface.

Preservative

In some embodiments, the pheromone compositions comprise a preservative.

Additional Active Agent

According to another embodiment of the disclosure, the pheromone composition may include one or more insect feeding stimulants. Examples of insect feeding stimulants include, but are not limited to, crude cottonseed oil, fatty acid esters of phytol, fatty acid esters of geranyl geraniol, fatty acid esters of other plant alcohols, plant extracts, and combinations thereof.

According to another embodiment of the disclosure, the pheromone composition may include one or more insect growth regulators ("IGRs"). IGRs may be used to alter the growth of the insect and produce deformed insects. Examples of insect growth regulators include, for example, dimilin.

According to another embodiment of the disclosure, the attractant-composition may include one or more insect sterilants that sterilize the trapped insects or otherwise block their reproductive capacity, thereby reducing the population in the following generation. In some situations allowing the sterilized insects to survive and compete with non-trapped insects for mates is more effective than killing them outright.

Sprayable Compositions

In some embodiments, the pheromone compositions disclosed herein can be formulated as a sprayable composition (i.e., a sprayable pheromone composition). An aqueous solvent can be used in the sprayable composition, e.g., water or a mixture of water and an alcohol, glycol, ketone, or other water-miscible solvent. In some embodiments, the water content of such mixture is at least about 10%, at least about 20%, at least about 30%, at least about 40%, 50%, at least about 60%, at least about 70%, at least about 80%, or at least about 90%. In some embodiments, the sprayable composition is concentrate, i.e. a concentrated suspension of the pheromone, and other additives (e.g., a waxy substance, a stabilizer, and the like) in the aqueous solvent, and can be diluted to the final use concentration by addition of solvent (e.g., water).

In some embodiments, a waxy substance can be used as a carrier for the pheromone and its positional isomer in the sprayable composition. The waxy substance can be, e.g., a biodegradable wax, such as bees wax, carnauba wax and the like, candelilla wax (hydrocarbon wax), montan wax, shellac and similar waxes, saturated or unsaturated fatty acids, such as lauric, palmitic, oleic or stearic acid, fatty acid amides and esters, hydroxylic fatty acid esters, such as hydroxyethyl or hydroxypropyl fatty acid esters, fatty alcohols, and low molecular weight polyesters such as polyalkylene succinates.

In some embodiments, a stabilizer can be used with the sprayable pheromone compositions. The stabilizer can be used to regulate the particle size of concentrate and/or to allow the preparation of a stable suspension of the pheromone composition. In some embodiments, the stabilizer is selected from hydroxylic and/or ethoxylated polymers. Examples include ethylene oxide and propylene oxide copolymer, polyalcohols, including starch, maltodextrin and other soluble carbohydrates or their ethers or esters, cellulose ethers, gelatin, polyacrylic acid and salts and partial esters thereof and the like. In other embodiments, the stabilizer can include polyvinyl alcohols and copolymers thereof, such as partly hydrolyzed polyvinyl acetate. The stabilizer may be used at a level sufficient to regulate particle size and/or to prepare a stable suspension, e.g., between 0.1% and 15% of the aqueous solution.

In some embodiments, a binder can be used with the sprayable pheromone compositions. In some embodiments, the binder can act to further stabilize the dispersion and/or improve the adhesion of the sprayed dispersion to the target locus (e.g., trap, lure, plant, and the like). The binder can be polysaccharide, such as an alginate, cellulose derivative (acetate, alkyl, carboxymethyl, hydroxyalkyl), starch or starch derivative, dextrin, gum (arabic, guar, locust bean, tragacanth, carrageenan, and the like), sucrose, and the like. The binder can also be a non-carbohydrate, water-soluble polymer such as polyvinyl pyrrolidone, or an acidic polymer such as polyacrylic acid or polymethacrylic acid, in acid and/or salt form, or mixtures of such polymers.

Microencapsulated Pheromones

In some embodiments, the pheromone compositions disclosed herein can be formulated as a microencapsulated pheromone, such as disclosed in Ill'lchev, A L et al., *J Econ. Entomol.* 2006:99(6):2048-54; and Stelinki, L L et al., *J. Econ. Entomol.* 2007; 100(4):1360-9. Microencapsulated pheromones (MECs) are small droplets of pheromone enclosed within polymer capsules. The capsules control the release rate of the pheromone into the surrounding environment, and are small enough to be applied in the same method as used to spray insecticides. The effective field longevity of the microencapsulated pheromone formulations can range from a few days to slightly more than a week, depending on inter alia climatic conditions, capsule size and chemical properties.

Slow-Release Formulation

Pheromone compositions can be formulated so as to provide slow release into the atmosphere, and/or so as to be protected from degradation following release. For example, the pheromone compositions can be included in carriers such as microcapsules, biodegradable flakes and paraffin wax-based matrices. Alternatively, the pheromone composition can be formulated as a slow release sprayable.

In certain embodiments, the pheromone composition may include one or more polymeric agents known to one skilled in the art. The polymeric agents may control the rate of release of the composition to the environment. In some embodiments, the polymeric attractant-composition is impervious to environmental conditions. The polymeric agent may also be a sustained-release agent that enables the composition to be released to the environment in a sustained manner.

Examples of polymeric agents include, but are not limited to, celluloses, proteins such as casein, fluorocarbon-based polymers, hydrogenated rosins, lignins, melamine, polyurethanes, vinyl polymers such as polyvinyl acetate (PVAC), polycarbonates, polyvinylidene dinitrile, polyamides, polyvinyl alcohol (PVA), polyamide-aldehyde, polyvinyl aldehyde, polyesters, polyvinyl chloride (PVC), polyethylenes, polystyrenes, polyvinylidene, silicones, and combinations thereof. Examples of celluloses include, but are not limited to, methylcellulose, ethyl cellulose, cellulose acetate, cellulose acetate-butyrate, cellulose acetate-propionate, cellulose propionate, and combinations thereof.

Other agents which can be used in slow-release or sustained-release formulations include fatty acid esters (such as a sebacate, laurate, palmitate, stearate or arachidate ester) or a fatty alcohols (such as undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol).

Pheromones prepared according to the methods of the invention, as well as compositions containing the pheromones, can be used to control the behavior and/or growth of insects in various environments. The pheromones can be used, for example, to attract or repel male or female insects to or from a particular target area. The pheromones can be used to attract insects away from vulnerable crop areas. The pheromones can also be used example to attract insects as part of a strategy for insect monitoring, mass trapping, lure/attract-and-kill or mating disruption.

Lures

The pheromone compositions of the present disclosure may be coated on or sprayed on a lure, or the lure may be otherwise impregnated with a pheromone composition.

Traps

The pheromone compositions of the disclosure may be used in traps, such as those commonly used to attract any insect species, e.g., insects of the order Lepidoptera. Such traps are well known to one skilled in the art, and are commonly used in many states and countries in insect eradication programs. In one embodiment, the trap includes one or more septa, containers, or storage receptacles for holding the pheromone composition. Thus, in some embodiments, the present disclosure provides a trap loaded with at least one pheromone composition. Thus, the pheromone compositions of the present disclosure can be used in traps for example to attract insects as part of a strategy for insect monitoring, mass trapping, mating disruption, or lure/attract and kill for example by incorporating a toxic substance into the trap to kill insects caught.

Mass trapping involves placing a high density of traps in a crop to be protected so that a high proportion of the insects are removed before the crop is damaged. Lure/attract-and-kill techniques are similar except once the insect is attracted to a lure, it is subjected to a killing agent. Where the killing agent is an insecticide, a dispenser can also contain a bait or feeding stimulant that will entice the insects to ingest an effective amount of an insecticide. The insecticide may be an insecticide known to one skilled in the art. The insecticide may be mixed with the attractant-composition or may be separately present in a trap. Mixtures may perform the dual function of attracting and killing the insect.

Such traps may take any suitable form, and killing traps need not necessarily incorporate toxic substances, the insects being optionally killed by other means, such as drowning or electrocution. Alternatively, the traps can contaminate the insect with a fungus or virus that kills the insect later. Even where the insects are not killed, the trap can serve to remove the male insects from the locale of the female insects, to prevent breeding.

It will be appreciated by a person skilled in the art that a variety of different traps are possible. Suitable examples of such traps include water traps, sticky traps, and one-way traps. Sticky traps come in many varieties. One example of a sticky trap is of cardboard construction, triangular or wedge-shaped in cross-section, where the interior surfaces are coated with a non-drying sticky substance. The insects contact the sticky surface and are caught. Water traps include pans of water and detergent that are used to trap insects. The detergent destroys the surface tension of the water, causing insects that are attracted to the pan, to drown in the water. One-way traps allow an insect to enter the trap but prevent it from exiting. The traps of the disclosure can be colored brightly, to provide additional attraction for the insects.

In some embodiments, the pheromone traps containing the composition may be combined with other kinds of trapping mechanisms. For example, in addition to the pheromone composition, the trap may include one or more florescent lights, one or more sticky substrates and/or one or more colored surfaces for attracting moths. In other embodiments, the pheromone trap containing the composition may not have other kinds of trapping mechanisms.

The trap may be set at any time of the year in a field. Those of skill in the art can readily determine an appropriate amount of the compositions to use in a particular trap, and can also determine an appropriate density of traps/acre of crop field to be protected.

The trap can be positioned in an area infested (or potentially infested) with insects. Generally, the trap is placed on or close to a tree or plant. The aroma of the pheromone attracts the insects to the trap. The insects can then be caught, immobilized and/or killed within the trap, for example, by the killing agent present in the trap.

Traps may also be placed within an orchard to overwhelm the pheromones emitted by the females, so that the males simply cannot locate the females. In this respect, a trap need be nothing more than a simple apparatus, for example, a protected wickable to dispense pheromone.

The traps of the present disclosure may be provided in made-up form, where the compound of the disclosure has already been applied. In such an instance, depending on the half-life of the compound, the compound may be exposed, or may be sealed in conventional manner, such as is standard with other aromatic dispensers, the seal only being removed once the trap is in place.

Alternatively, the traps may be sold separately, and the compound of the disclosure provided in dispensable format so that an amount may be applied to trap, once the trap is in place. Thus, the present disclosure may provide the compound in a sachet or other dispenser.

Dispenser

Pheromone compositions can be used in conjunction with a dispenser for release of the composition in a particular environment. Any suitable dispenser known in the art can be used. Examples of such dispensers include but are not limited to, aerosol emitters, hand-applied dispensers, bubble caps comprising a reservoir with a permeable barrier through which pheromones are slowly released, pads, beads, tubes rods, spirals or balls composed of rubber, plastic, leather, cotton, cotton wool, wood or wood products that are impregnated with the pheromone composition. For example, polyvinyl chloride laminates, pellets, granules, ropes or spirals from which the pheromone composition evaporates, or rubber septa. One of skill in the art will be able to select suitable carriers and/or dispensers for the desired mode of application, storage, transport or handling.

In another embodiment, a device may be used that contaminates the male insects with a powder containing the pheromone substance itself. The contaminated males then fly off and provide a source of mating disruption by permeating the atmosphere with the pheromone substance, or by attracting other males to the contaminated males, rather than to real females.

Behavior Modification

Pheromone compositions prepared according to the methods disclosed herein can be used to control or modulate the behavior of insects. In some embodiments, the behavior of the target insect can be modulated in a tunable manner inter alia by varying the ratio of the pheromone to the positional isomer in the composition such that the insect is attracted to a particular locus but does not contact said locus or such the insect in fact contacts said locus. Thus, in some embodiments, the pheromones can be used to attract insects away from vulnerable crop areas. Accordingly, the disclosure also provides a method for attracting insects to a locus. The method includes administering to a locus an effective amount of the pheromone composition.

The method of mating disruption may include periodically monitoring the total number or quantity of the trapped insects. The monitoring may be performed by counting the number of insects trapped for a predetermined period of time such as, for example, daily, Weekly, bi-Weekly, monthly, once-in-three months, or any other time periods selected by the monitor. Such monitoring of the trapped insects may help estimate the population of insects for that particular period, and thereby help determine a particular type and/or dosage of pest control in an integrated pest management system. For example, a discovery of a high insect population can necessitate the use of methods for removal of the insect. Early warning of an infestation in a new habitat can allow action to be taken before the population becomes unmanageable. Conversely, a discovery of a low insect population can lead to a decision that it is sufficient to continue monitoring the population. Insect populations can be monitored regularly so that the insects are only controlled when they reach a certain threshold. This provides cost-effective control of the insects and reduces the environmental impact of the use of insecticides.

Mating Disruption

Pheromones prepared according to the methods of the disclosure can also be used to disrupt mating. Mating disruption is a pest management technique designed to control insect pests by introducing artificial stimuli (e.g., a pheromone composition as disclosed herein) that confuses the insects and disrupts mating localization and/or courtship, thereby preventing mating and blocking the reproductive cycle.

In many insect species of interest to agriculture, such as those in the order Lepidoptera, females emit an airborne trail of a specific chemical blend constituting that species' sex pheromone. This aerial trail is referred to as a pheromone plume. Males of that species use the information contained in the pheromone plume to locate the emitting female (known as a "calling" female). Mating disruption exploits the male insects' natural response to follow the plume by introducing a synthetic pheromone into the insects' habitat, which is designed to mimic the sex pheromone produced by the female insect. Thus, in some embodiments, the synthetic pheromone utilized in mating disruption is a synthetically derived pheromone composition comprising a pheromone having a chemical structure of a sex pheromone and a positional isomer thereof which is not produced by the target insect.

The general effect of mating disruption is to confuse the male insects by masking the natural pheromone plumes, causing the males to follow "false pheromone trails" at the expense of finding mates, and affecting the males' ability to respond to "calling" females. Consequently, the male population experiences a reduced probability of successfully locating and mating with females, which leads to the eventual cessation of breeding and collapse of the insect infestation.

Strategies of mating disruption include confusion, trail-masking and false-trail following. Constant exposure of insects to a high concentration of a pheromone can prevent male insects from responding to normal levels of the pheromone released by female insects. Trail-masking uses a pheromone to destroy the trail of pheromones released by females. False-trail following is carried out by laying numerous spots of a pheromone in high concentration to present the male with many false trails to follow. When released in sufficiently high quantities, the male insects are unable to find the natural source of the sex pheromones (the female insects) so that mating cannot occur.

In some embodiments, a wick or trap may be adapted to emit a pheromone for a period at least equivalent to the breeding season(s) of the midge, thus causing mating disruption. If the midge has an extended breeding season, or repeated breeding season, the present disclosure provides a wick or trap capable of emitting pheromone for a period of time, especially about two weeks, and generally between about 1 and 4 weeks and up to 6 weeks, which may be rotated or replaced by subsequent similar traps. A plurality of traps containing the pheromone composition may be placed in a locus, e.g., adjacent to a crop field. The locations of the traps, and the height of the traps from ground may be selected in accordance with methods known to one skilled in the art.

Alternatively, the pheromone composition may be dispensed from formulations such as microcapsules or twist-ties, such as are commonly used for disruption of the mating of insect pests.

Attract and Kill

The attract and kill method utilizes an attractant, such as a sex pheromone, to lure insects of the target species to an insecticidal chemical, surface, device, etc., for mass-killing and ultimate population suppression, and can have the same effect as mass-trapping. For instance, when a synthetic female sex pheromone is used to lure male pests, e.g., moths, in an attract-and-kill strategy, a large number of male moths must be killed over extended periods of time to reduce matings and reproduction, and ultimately suppress the pest population. The attract-and-kill approach may be a favorable alternative to mass-trapping because no trap-servicing or other frequent maintenance is required. In various embodiments described herein, a recombinant microorganism can co-express (i) a pathway for production of an insect pheromone and (ii) a protein, peptide, oligonucleotide, or small molecule which is toxic to the insect. In this way, the recombinant microorganism can co-produce substances suitable for use in an attract-and-kill approach.

As will be apparent to one of skill in the art, the amount of a pheromone or pheromone composition used for a particular application can vary depending on several factors such as the type and level of infestation; the type of composition used: the concentration of the active components; how the composition is provided, for example, the type of dispenser used; the type of location to be treated; the length of time the method is to be used for; and environmental factors such as temperature, wind speed and direction, rainfall and humidity. Those of skill in the art will be able to determine an effective amount of a pheromone or pheromone composition for use in a given application.

As used herein, an "effective amount" means that amount of the disclosed pheromone composition that is sufficient to affect desired results. An effective amount can be administered in one or more administrations. For example, an effective amount of the composition may refer to an amount of the pheromone composition that is sufficient to attract a given insect to a given locus. Further, an effective amount of the composition may refer to an amount of the pheromone composition that is sufficient to disrupt mating of a particular insect population of interest in a given locality.

EXAMPLES

Example 1. Production of Pheromones Products from Enzymatically-Derived Gondoic Acid through Metathesis and Chemical Conversion This example illustrates that different fatty acids can be used as a starting material for the biosynthetic production of a pheromone or pheromone precursor. The product obtained from the biosynthetic process disclosed herein can be subject to further chemical conversions to generate different products.

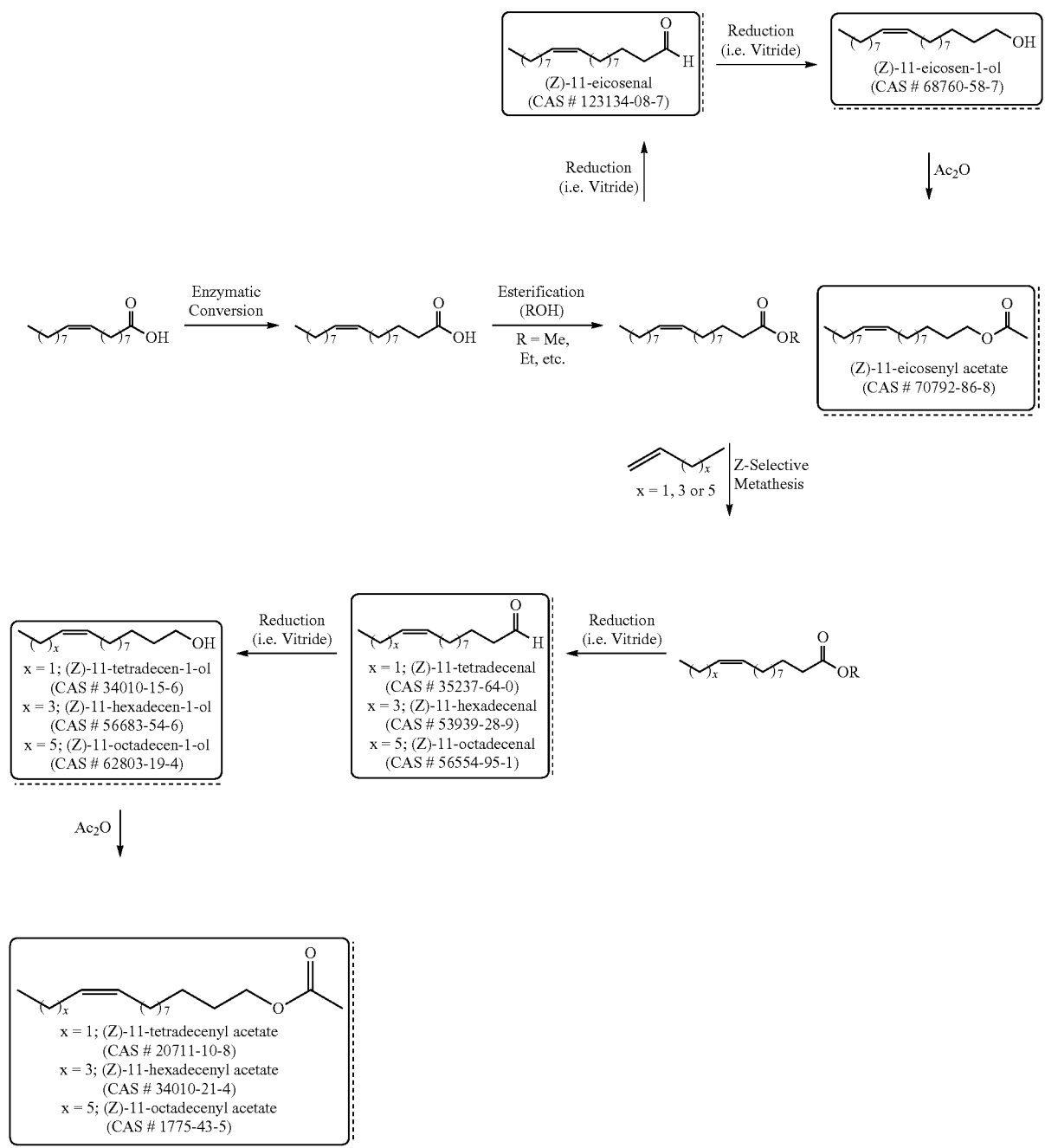

Enzymatic two carbon elongation of oleic acid yields gondoic acid. After esterification, gondoic fatty acid methyl ester (FAME) can then converted via Z-selective olefin metathesis into C16 and C18 FAME products containing a C11 unsaturation. Upon reduction of the ester, aldehyde and fatty alcohol pheromone materials can be produced. Acetylation of the fatty alcohol product can generate the corresponding fatty acetate pheromones. Additionally, gondoic acid can be directly converted into C20 fatty aldehyde, alcohol and acetate pheromones through application of the same chemical transformation of enzymatically modified oleic acid.

Prophetic Example 2: Tailored Synthetic Blends

This prophetic example illustrates that the recombinant microorganisms disclosed herein can be used to create synthetic blends of insect pheromones.

As shown in the scheme depicted in FIG. 54, using tetradecyl-ACP (14:ACP), a blend of E- and Z-tetradecenyl acetate (E11-14:OAc and Z11-14:OAC) pheromones can be produced with the recombinant microorganism. This blend is produced by a variety of insects, e.g., *Chonstoneura roseceana* (a moth of the Tortricidae family).

Similarly, using hexadecyl-ACP (16:ACP), a blend of Z- and E hexadecenyl acetate pheromones (E11-16:OAc and Z11-16:OAc) can be produced with the recombinant microorganism.

The microorganism can be engineered with different desaturases, or other enzymes such as reductases, etc. to produce the desired blend of pheromones. One blend of particular relevance capable of being produced using the recombinant microorganisms and methods of the instant invention is a 97:3 ratio of (Z)-11-hexadecenal (Z11-16:Ald) and (Z)-9-hexadecenal (Z9-16:Ald).

Example 3: Expression of Transmembrane Alcohol-Forming Reductases in *S. cerevisiae*

Background and Rationale

Engineering microbial production of insect fatty alcohols from fatty acids entails the functional expression of a synthetic pathway. One such pathway comprises a transmembrane desaturase, and an alcohol-forming reductase to mediate the conversion of fatty acyl-CoA into regio- and stereospecific unsaturated fatty acyl-CoA, and subsequently into fatty alcohols. A number of genes encoding these enzymes are found in some insects (as well as some microalgae in the case of fatty alcohol reductase) and can be used to construct the synthetic pathway in yeasts, which are preferred production hosts. A number of transmembrane desaturases and alcohol-forming reductase variants will be screened to identify ensembles which allow high level synthesis of a single insect fatty alcohol or a blend of fatty alcohols. Additionally, these enzymes will be screened across multiple hosts (*Saccharomyces cerevisiae, Candida tropicalis*, and *Yarrowia lipolytica*) to optimize the search toward finding a suitable host for optimum expression of these transmembrane proteins.

Summary of Approach

Three alcohol-forming reductases of insect origin were selected.

Nucleic acids encoding the reductases were synthesized (synthons) with codon optimization for expression in *S. cerevisiae*.

Each nucleic acid encoding a given reductase was subcloned into an episomal expression cassette under the Gall promoter.

*S. cerevisiae* wild-type and beta-oxidation deletion mutant were transformed with expression constructs.

Heterologous protein was induced by galactose, and functional expression of the reductases was assessed in vivo via bioconversion of Z11-hexadecenoic acid into Z11-hexedecenol.

GC-MS analysis was used to identify and quantify metabolites.

Results

Figure 5:
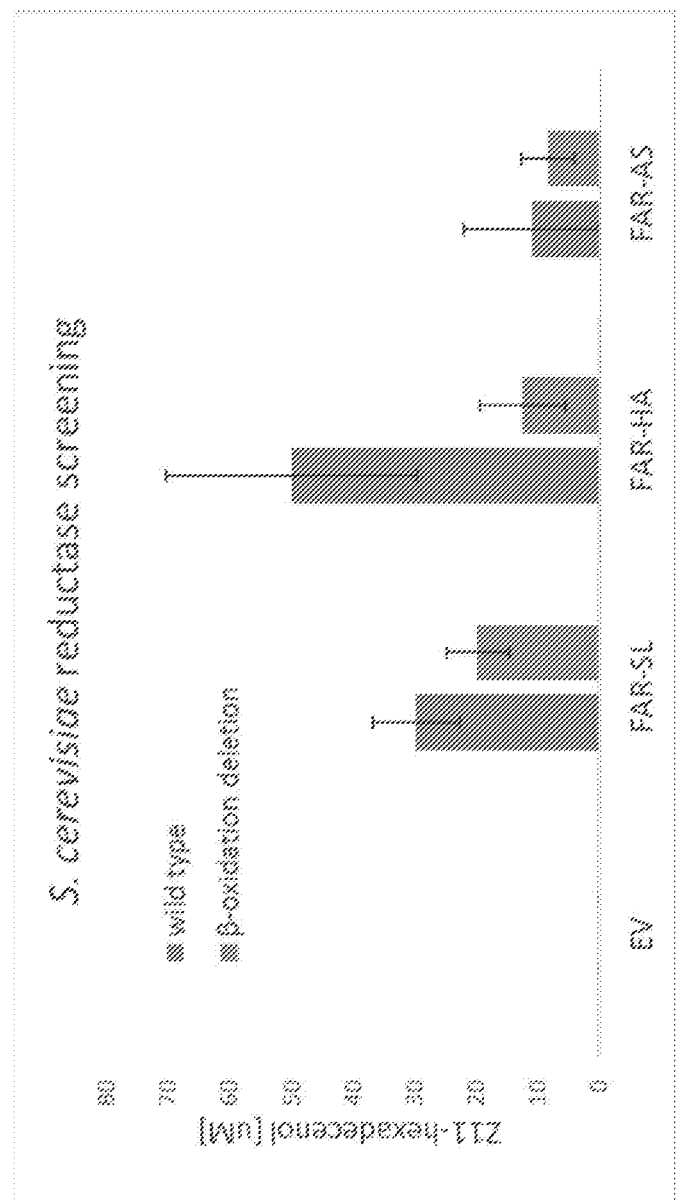
FIG. 5 shows Z11-hexadecenol production from W303A and BY4742 ΔPOX1. Strain expressing empty vector (EV), *S. littoralis* reductase (FAR-SL), *H. armigera* reductase (FAR-HA), *A. segetum* reductase (FAR-AS). Error bars represent standard deviation derived from N=2 biologically independent samples.
Figure 6:
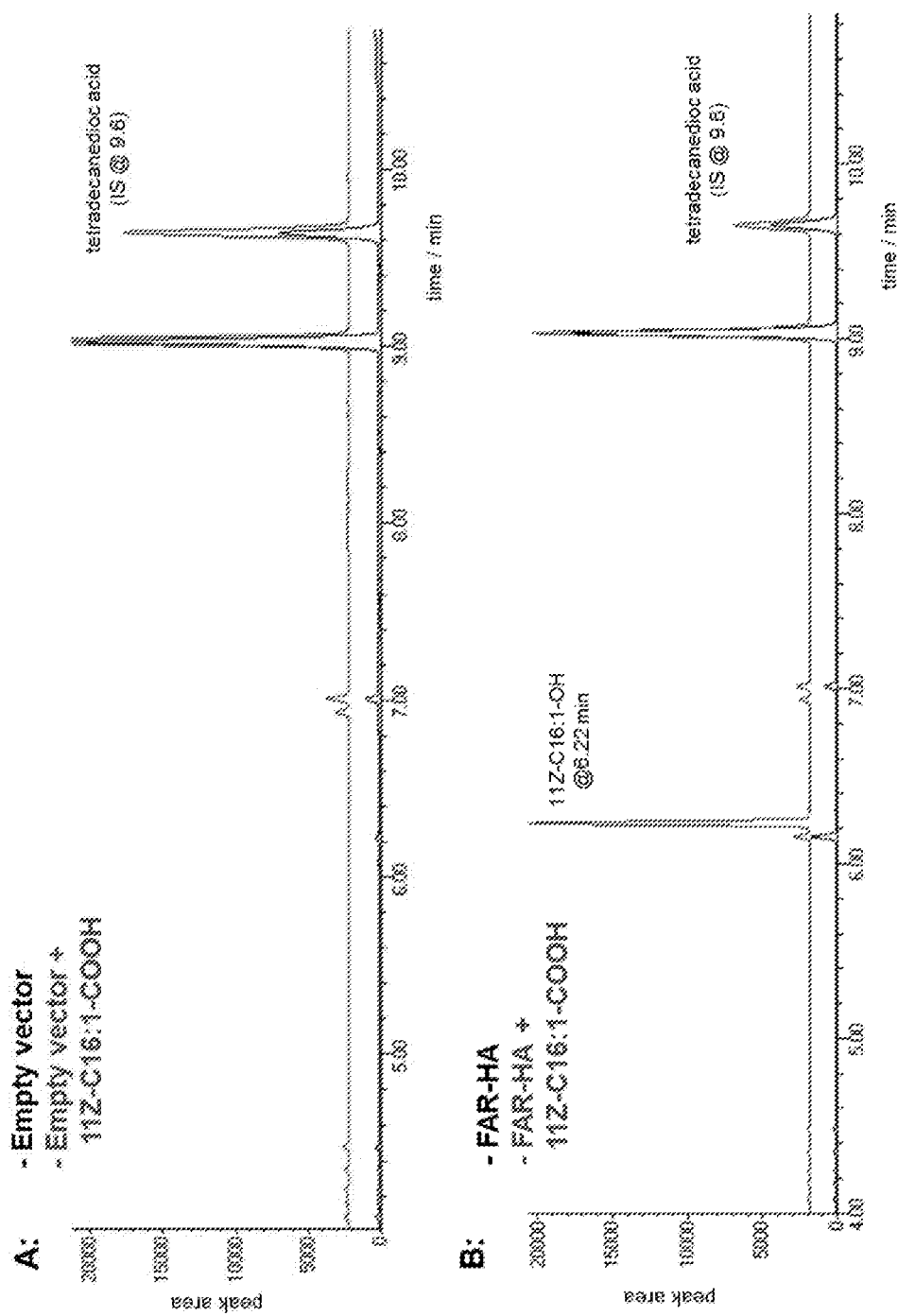
FIG. 6A-FIG. 6B shows sample chromatograms of biotransformation product of Z11-hexadecenoic acid using *S. cerevisiae* expressing either an empty vector (FIG. 6A), or *Helicoverpa armigera* alcohol-forming reductase (FIG. 6B). Black lines: no substrate added. Purple line: Z11-hexadecenoic acid was added as substrate.
Figure 7:
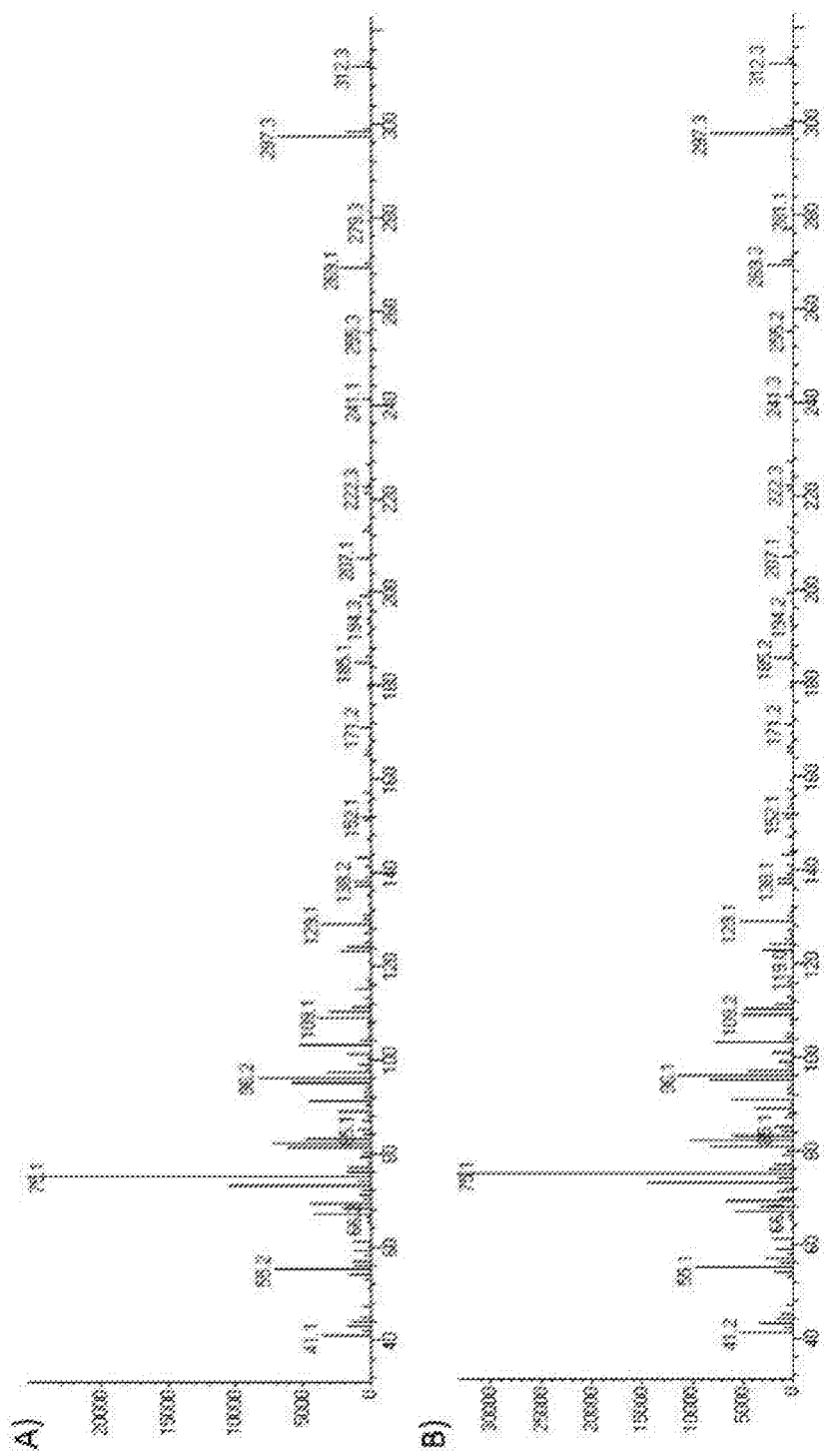
FIG. 7A-FIG. 7B shows a comparison of GC-MS fragmentation pattern of Z11-hexadecenol authentic compound (FIG. 7A), and Z11-hexadecenol biologically derived (FIG. 7B).
Figure 8:
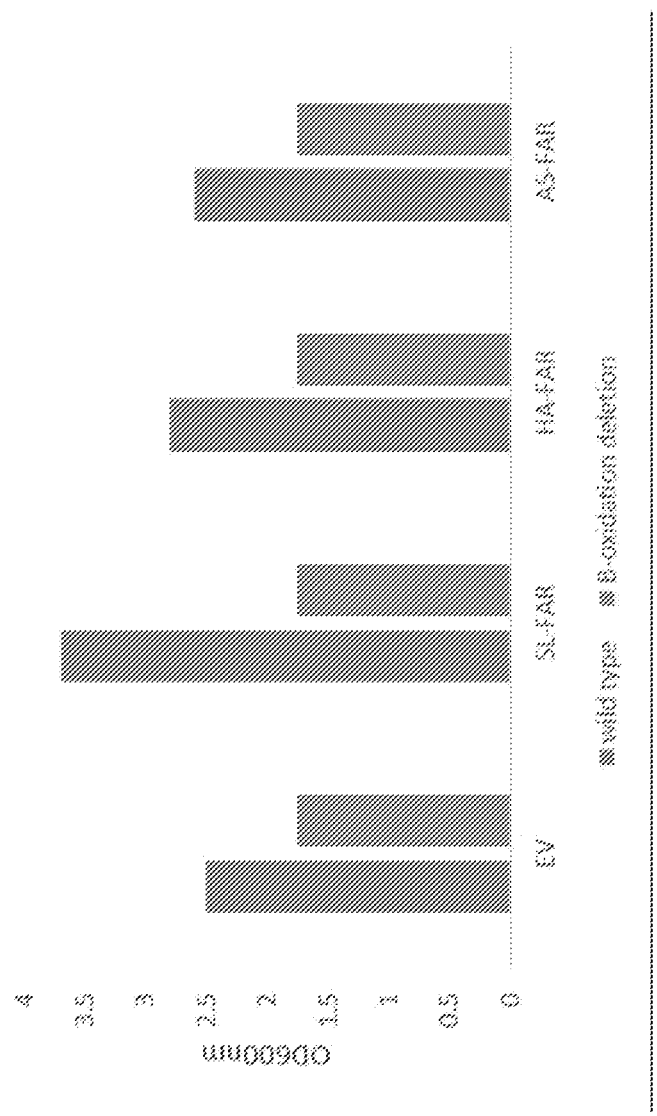
FIG. 8 shows biomass at the time of harvesting for product analysis of W303A (wild type) and BY4742 ΔPOX1 (beta-oxidation deletion mutant). Strain expressing empty vector (EV), *S. littoralis* reductase (FAR-SL), *H. armigera* reductase (FAR-HA), *A. segetum* reductase (FAR-AS). Error bars represent standard deviation derived from N=2 biologically independent samples.

Alcohol-forming reductase variants were screened for activity in *S. cerevisiae* W303 (wild type) and BY4742 ΔPOX1 (beta-oxidation deletion mutant). Z11-hexadecenoic acid was chosen as a substrate in assessing enzyme activity. The in vivo bioconversion assay showed that the expression of enzyme variants derived from *Spodoptera littoralis, Helicoverpa armigera*, and *Agrotis segetum* (Ding, B-J., Löfstedt, C. Analysis of the *Agrotis segetum* pheromone gland transcriptome in the light of sex pheromone biosynthesis. BMC Genomics 16:711 (2015)) in W303A conferred Z11-hexadecenol production, and reached up-to ~37 µM (8 mg/L), ~70 µM (~16 mg/L), and 11 µM (~3 mg/L), respectively, within 48h of protein induction (FIG. 5 and FIG. 6). Biologically-produced Z11-hexadecenol matched authentic Z11-hexadecenol standard (Bedoukian) as determined via GC-MS (FIG. 7). BY4742 ΔPOX1 was also explored as an expression host since deletion in the key beta-oxidation pathway enzyme could limit the degradation of Z11-hexadecenoic acid. Expressing the reductase variants in the beta-oxidation deletion mutant, however, reduced the product titer when compared to expression in the wild-type host (FIG. 5). One contributing factor of titer reduction when using BY4742 ΔPOX1 as a host was the reduction of biomass when compared to W303 (FIG. 8).

Therefore, functional expression of at least two alcohol-forming reductases in *S. cerevisiae* conferred bioconversion of Z11-hexadecenoic acid into Z11-hexadecenol.

Conclusions

Functional expression of insect transmembrane alcohol-forming reductase in *S. cerevisiae* was demonstrated. Among the reductases tested, the variant derived from *Helicoverpa armigera* is most active toward Z11-hexadecenoic acid.

The bioconversion of other fatty acid substrates can be explored to assess enzyme plasticity.

Materials & Methods

Strain Construction and Functional Expression Assay

*S. cerevisiae* W303 (MATA ura3-1 trp1-1 leu2-3_112 his3-11_15 ade2-1 can1-100) and BY4742 (MATa POX1::kanMX his3Δ1 leu2Δ0 lys2Δ0 ura3Δ0) were used as expression hosts. DNA sequences which encode fatty alcohol reductase variants were redesigned to optimize expression in *S. cerevisiae* (SEQ ID NOs: 1-3). Generated synthons (Genscript) were cloned into pESC-URA vector using BamHI-XhoI sites to facilitate protein expression utilizing the Gall promoter. The resulting plasmid constructs were used to transform W303, and positive transformants were selected on CM agar medium (with 2% glucose, and lacking uracil) (Teknova). To assess functional expression, two positive transformation clones that have been patched on CM agar medium (with 2% glucose, and lacking uracil) were used to seed CM liquid medium using a 24 deep-well plate format. To induce protein expression, the overnight cultures that had been grown at 28° C. were then supplemented with galactose, raffinose, and YNB to a final concentration of 2%, 1%, and 6.7 g/L, respectively. Post 24h of protein induction, the bioconversion substrate Z11-hexadecenoic acid (in ethanol) or heptadecanoic acid (in ethanol) was added to a final concentration of 300 mg/L. Bioconversion assay proceeded for 48 h at 28° C. prior to GC-MS analysis.

Metabolite Extraction and GC-MS Detection

Figure 9:
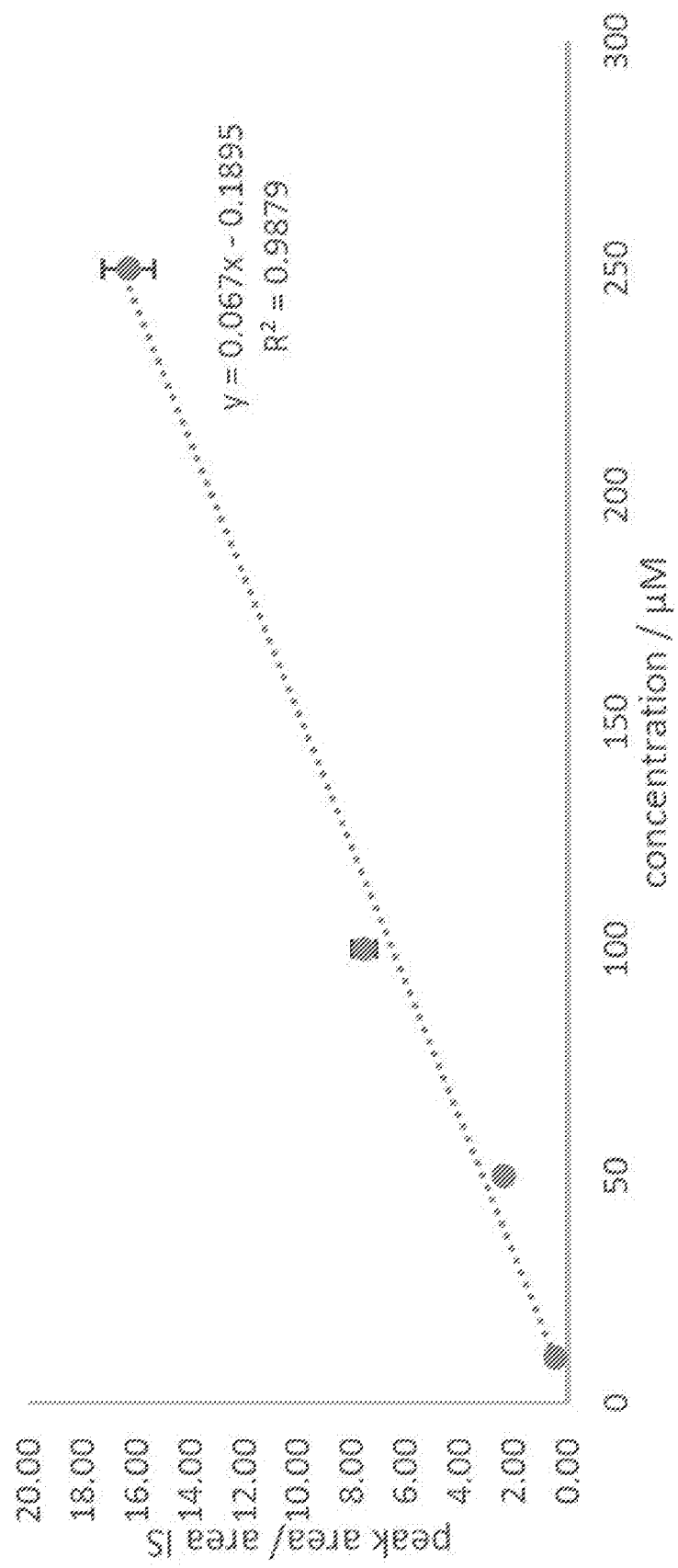
FIG. 9 shows a Z11-hexedecenol calibration curve constructed using an authentic standard. The samples were generated with the extraction and analysis method described in Materials and Methods of Example 3. Error bars represent standard deviation derived from N=3 samples.

The lipids were extracted according to a modified procedure of Hagström et al. (2012) (Hagström, Å. K., Liénard, M. A., Groot, A. T., Hedenström, E. & Löfstedt, C. Semi-Selective Fatty Acyl Reductases from Four Heliothine Moths Influence the Specific Pheromone Composition. *PLoS One* 7: e37230 (2012)), 1.5 mL-cell culture was transferred to a 15 mL falcon tube. The cell suspension was acidified with 1 mL 5 N HCl, 5 µL tetradecanedioic acid (10 mM in ethanol) was added as internal standard. The mixture was extracted by adding 1.5 mL hexane, then shaken for 1 h at 37° C., 250 rpm. To facilitate phase separation, the sample was centrifuged for 10 min at 2000 g, 1 mL of the organic hexane phase was then transferred to a 1.5 mL plastic tube. The solvent was removed by heating the sample 30 min at 90° C. After the sample was evaporated to dryness, 50 µL of BSTFA (N,O-bis(trimethylsilyl) trifluoroacetamide containing 1% of trimethylchlorosilane) was added. The 1.5 mL plastic tubes were shaken vigorously two times for 10 s. Prior to the transfer into a screw cap GC glass vial containing a glass insert, the sample was centrifuged for 1 min (13000 rpm). The vials were capped and heated for 30 min at 90° C. The trimethylsilyl-esters, which were generated by this method were subsequently analyzed by GC-MS analysis. GC-MS parameters are specified in Table 6. The use of SIM mode (characteristic product and IS ions) increases detection sensitivity by reducing background noise, allowing detection of the product as low as 2.4 µM (0.6 mg/L). A further reduction in the split ratio offers the possibility to further increase the sensitivity for future applications. A Z11-hexadecenol calibration curve shown in FIG. 9 was used to quantify the Z11-hexadecenol produced from yeasts. The bioconversion of heptadecanoic acid was also tested since the easily distinguished heptadecanol product could be used to benchmark successful GC-MS runs. However, none of the reductase tested showed any activity toward heptadecanoic acid.

TABLE 6

GC-MS parameters

| | |
|---|---|
| System | Agilent 6890 N GC, ChemStation G1701EA E.02.01.1177 |
| Column | Rtx-5 30 m × 320 µm × 25 µm |
| | Pressure = 11.74 psi; Flow = 7.1 mL/min |
| Inlet | Heater = 250° C.; Pressure = 11.74 psi; |
| | Total Flow {He} = 19.5 mL/min |
| Carrier | He @ 147 cm/sec, 11.74 psi |
| Signal | Data rate = 2 Hz/0.1 min |
| Oven | 150° C. for 1 min |
| | Ramp 12° C./min to 220° C., hold 3 min |
| | Ramp 35° C./min to 300° C., hold 4 min |
| Injection | Split, 250° C. |
| | Split ratio −20:1 |
| Detector | HP 5973 MSD in SIM mode (m/z: 297.3 and 387.3), |
| | 100 msec Dwell, EMV mode: Gain factor 1, |
| | 3 min solvent delay, 8.33 cycles/sec| |
| Sample | Injection volume = 1 uL |

Example 4: Expression of Transmembrane Desaturases in *S. cerevisiae*

Background and Rationale

Engineering microbial production of insect fatty alcohols from fatty acids requires the functional expression of a synthetic pathway. One such pathway comprises a transmembrane desaturase, and an alcohol-forming reductase to mediate the conversion of fatty acyl-CoA into regio- and stereospecific unsaturated fatty acyl-CoA, and subsequently into fatty alcohols. A number of genes encoding these enzymes are found in some insects as well as some microalgae. A number of transmembrane desaturases and alcohol-forming reductase variants will be screened to identify ensembles which allow high level synthesis of a single insect fatty alcohol or a blend of fatty alcohols. Additionally, these enzymes will be screened across multiple hosts (*Saccharomyces cerevisiae, Candida tropicalis,* and *Yarrowia lipolytica*) to optimize the search toward finding a suitable host for optimum expression of these transmembrane proteins.

Summary of Approach

A small set of desaturases (insect origin: *Agrotis segetum, Trichoplusia ni, Amyelois transitella, Helicoverpa zea,* and marine diatom: *Thalassiosira pseudonana*) were selected as a test case to explore and establish functional expression assays, metabolite extraction methods, and analytical chemistry.

A synthetic cassette for expression of the desaturases in *S. cerevisiae* was constructed. The cassette consists of the OLE1 promoter region, OLE1 N-terminal leader sequence, and VSP13 terminator.

The expression cassette was tested for functionality via expression of a GFP variant. Validation of the cassette allowed its utilization for exploring expression of insect desaturase.

*S. cerevisiae* ΔOLE1 was transformed with expression constructs containing heterologous desaturases. Functionality of the desaturases was assessed via the ability to rescue growth of ΔOLE1 without exogenous supplementation of unsaturated fatty acid (UFA). *S. cerevisiae* desaturase (OLE1) was used as a positive control of successful complementation.

Functionality of the desaturase was validated via an in vive bioconversion of hexadecanoic acid (palmitic acid) into (Z)-11-hexadecenoic acid (palmitvaccenic acid).

GC-MS analysis was used to identify and quantify metabolites.

Results

Figure 10:
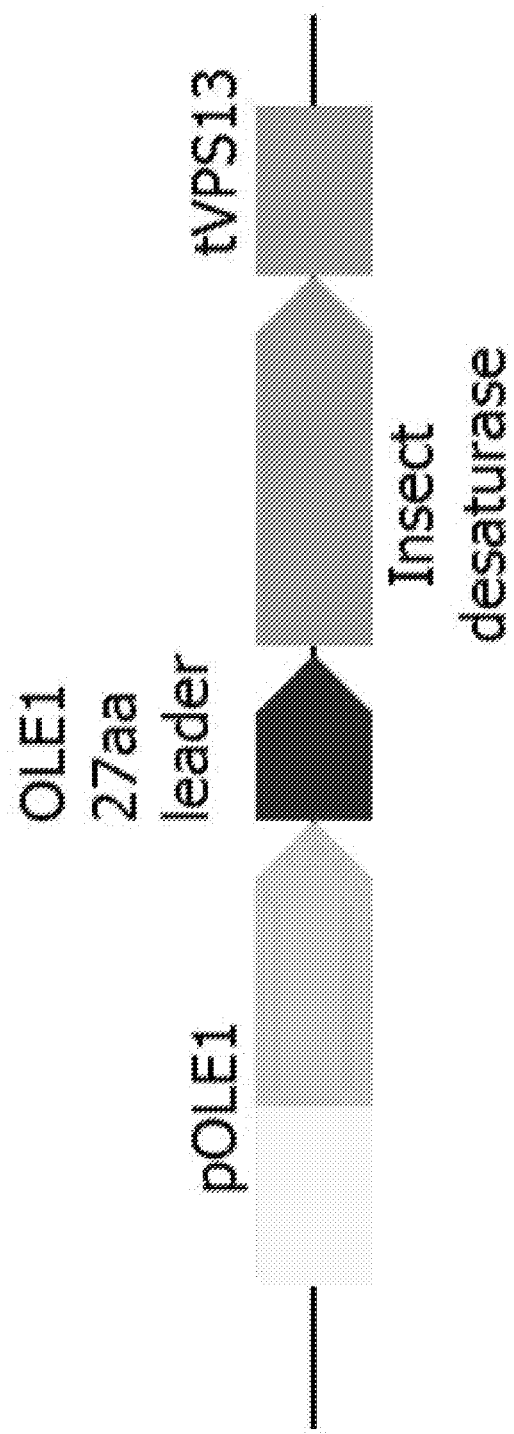
FIG. 10 shows a pOLE1 cassette comprising an extended OLE1 promoter sequence (light yellow), OLE1 promoter (orange), OLE1 leader sequence (dark grey), a synthon such as an insect desaturase sequence (light grey), and the VSP13 terminator sequence (blue).
Figure 11:
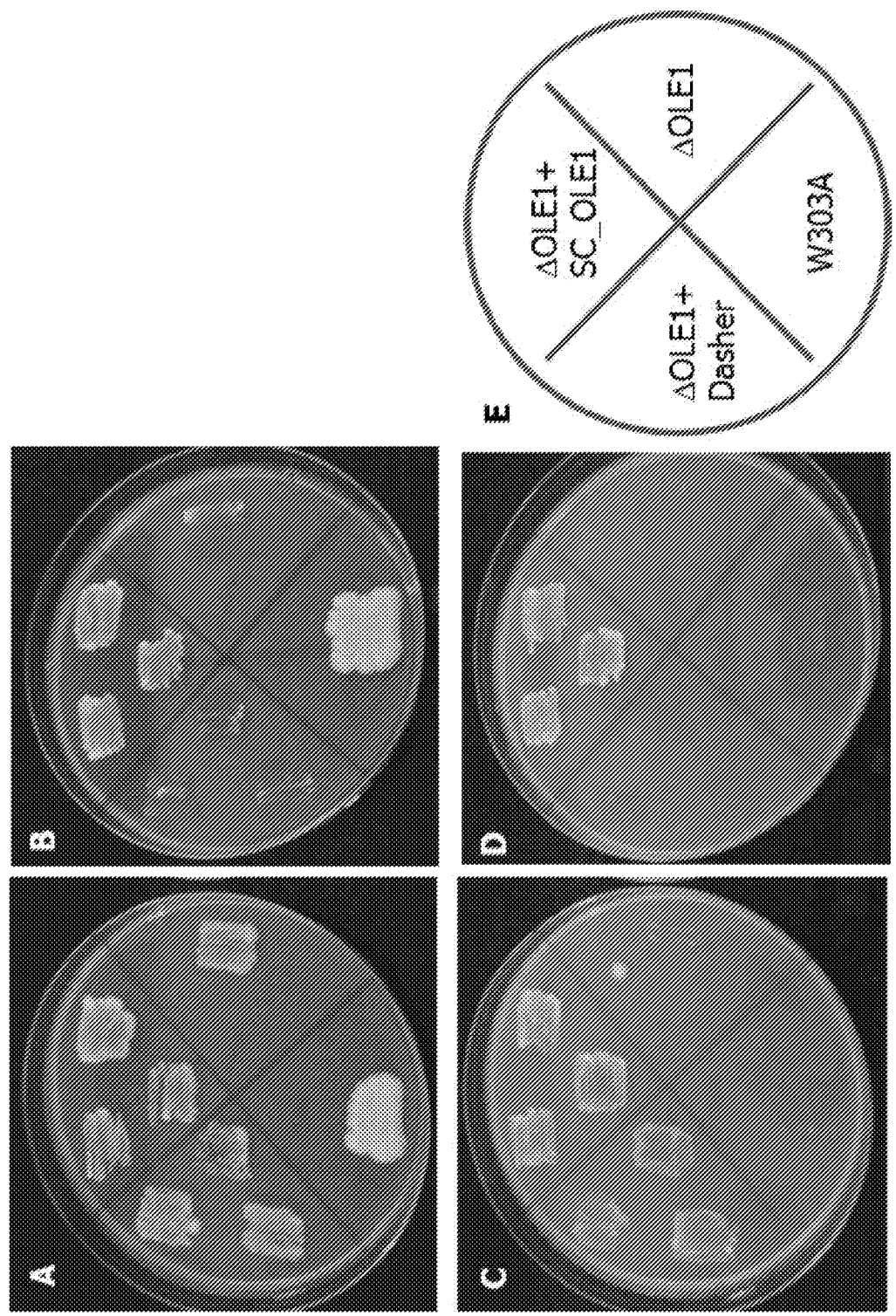
FIG. 11A-FIG. 11E shows validation of the pOLE1 cassette, and complementation assay.
Figure 12:
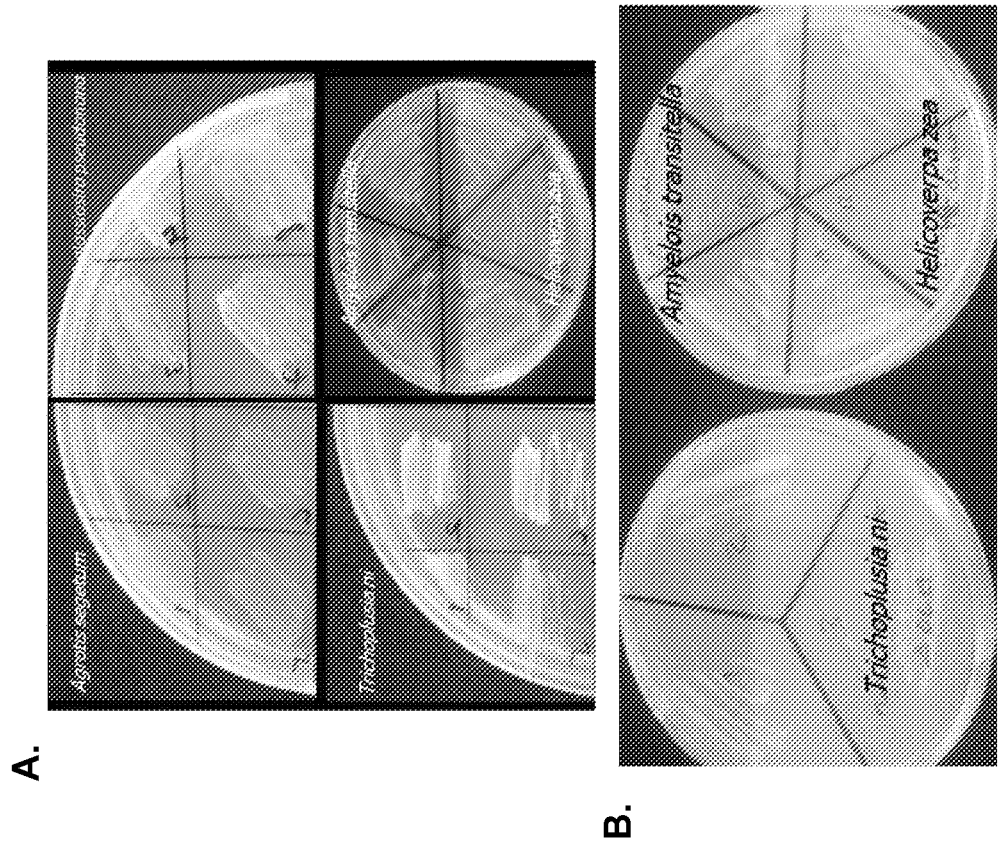
FIG. 12A shows complementation of ΔOLE1 growth without UFA on YPD.
FIG. 12B shows complementation of ΔOLE1 growth without UFA on CM-Ura glucose.

Transmembrane desaturase variants were screened in *S. cerevisiae*. Three variants were initially tested to explore and establish functional expression assays, metabolite extraction methods, and analytical chemistry. To allow functional expression of these desaturases in *S. cerevisiae*, an episomal synthetic expression cassette termed pOLE1 cassette (FIG. 10) was constructed, which consisted of an OLE1 promoter region, an N-terminal leader sequence encoding for the first 27 amino acids of *S. cerevisiae* OLE1, and a terminator region of VPS13 (a protein involved in the protospore membrane formation, the terminator of which has been previously characterized to increase heterologous protein expression potentially by extending mRNA half-life). The functionality of the pOLE1 cassette was validated via its ability to express a GFP (FIG. 11A-FIG. 11E). Subsequently, insect desaturase synthons, and yeast OLE synthon were cloned into the pOLE1 cassette, and expressed in *S. cerevisiae* ΔOLE1 strain. This strain was chosen since deletion of the OLE1 allele (which encodes for palmitoyl:CoA/ stearoyl:CoA (z)-9-desaturase) allows its utilization as a tool to screen for functional insect desaturase. Specifically, an active desaturase would allow complementation of growth without requiring exogenous supplementation of UFAs. Expression of OLE1 using pOLE1 cassette complemented growth of ΔOLE1 growth without UFA (FIG. 11A-FIG. 11E); therefore, it serves as a positive control in the complementation assays. When insect desaturases were expressed, we observed that they rescued ΔOLE1 growth without UFA at varying degree. On rich medium (YPD) agar plate, expression of S. cerevisiae OLE1 conferred the highest level of growth, followed by T. ni desaturase (FIG. 12A). The latter indicated that production of unsaturated fatty acyl:CoA by T. ni desaturase could act as a surrogate to the missing (Z)-9-hexadecenoyl:CoA biosynthesis in ΔOLE1. Expression of T. pseudonana and A. segetum desaturases did not appear to rescue growth on YPD very well (FIG. 12A). When patched on minimal medium (CM-Ura glucose) agar plate, only expression of S. cerevisiae OLE1 and T. ni desaturase rescued ΔOLE1 growth without exogenous UFA (FIG. 12B). Expression of T. pseudonana and A. segetum desaturases did not confer growth of ΔOLE1 on minimal medium agar, suggesting their limited activity in producing UFA (results not shown). Screening a desaturase library in Candida tropicalis identified functional expression of A. transitella and H. zea desaturases. When these desaturases were expressed in ΔOLE1, they conferred growth without UFA on both YPD and CM-Ura glucose media similar to expression of T. ni desaturase (FIG. 12B).

Figure 13:
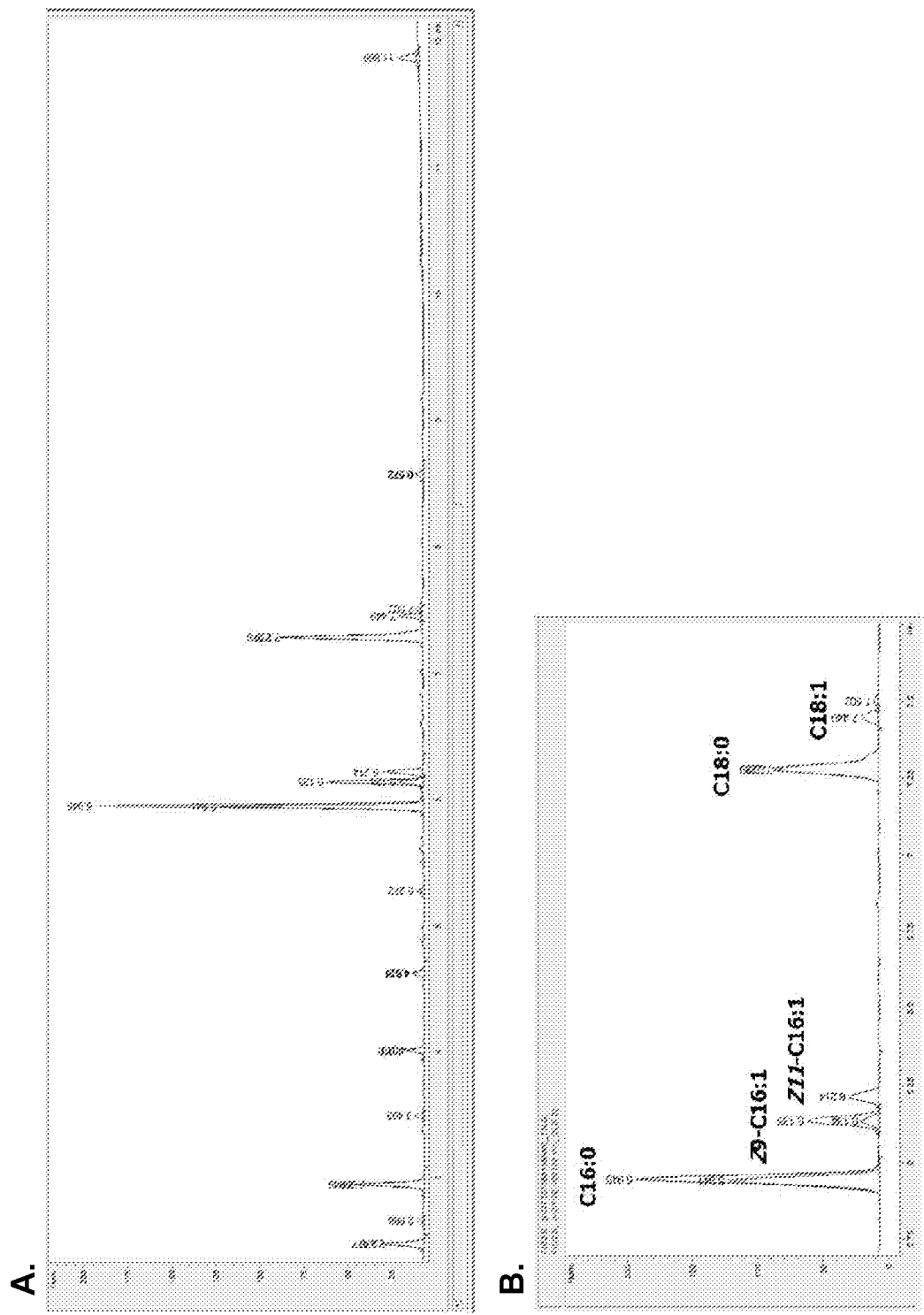
FIG. 13A shows the full fatty acid spectrum of a ΔOLE1 strain expressing: *S. cerevisiae* OLE desaturase (blue), chimeric *T. ni* desaturase (red).
FIG. 13B shows a focused fatty acid spectrum within 5.5-min-8-min retention time of *S. cerevisiae* ΔOLE1 strain expressing *S. cerevisiae* OLE1 desaturase (red) and chimeric *T. ni* desaturase (blue).
Figure 14:
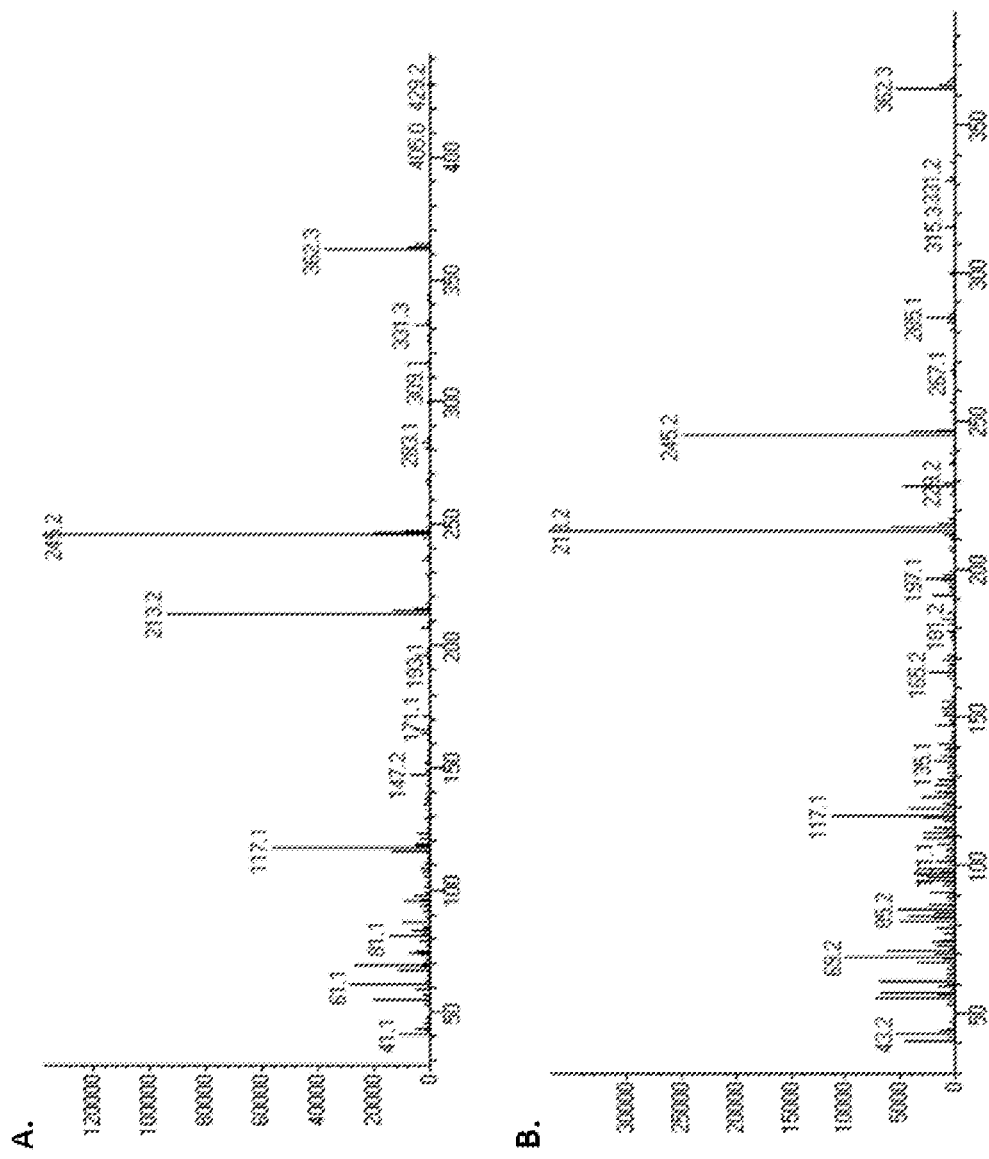
FIG. 14A-FIG. 14B shows a comparison of GC-MS fragmentation pattern of (Z)-11-hexadecenoic acid from an authentic compound (FIG. 14A) and biologically derived (FIG. 14B).

Functional expression of the heterologous desaturases was further characterized via in vivo bioconversion of palmitic acid into insect-specific UFA. Post ~96h-cultivation in minimal medium containing palmitic acid, total fatty acid analysis of S. cerevisiae ΔOLE1 expressing T. ni desaturase revealed production of a new fatty acid species (Z)-11-hexadecenoic acid that is not present in the control strain which expresses native yeast OLE1 desaturase (FIG. 13A-FIG. 13B). (Z)-11-hexadecenoic acid is not detected in strains expressing A. segetum, or T. pseudonana desaturase (results not shown). In addition to (Z)-11-hexadecenoic acid, (Z)-9-hexadecenoic acid was also detected in ΔOLE1 strain expressing T. ni desaturase (FIG. 13A-FIG. 13B). Under the cultivation condition, C16-fatty acid in the ΔOLE1 expressing T. ni desaturase is composed of approximately 84.7% hexadecanoic acid, 5.6% (Z)-9-hexadecenoic acid and 9.8% (Z)-11-hexadecenoic acid. In comparison, the C16 fatty acid fraction of ΔOLE1 expressing OLE1 desaturase is composed of approximately 68.6% hexadecanoic acid and 31.4% (Z)-9-hexadecenoic acid. (Z)-1 I1-hexadecenoic acid biosynthesis in ΔOLE1 expressing T. ni desaturase account for 1.5 mg/L. The amount of total fatty acids and each fatty acid within this mixture can be quantified. The biologically produced (Z)-11-hexadecenoic acid also match the retention time and fragmentation pattern of authentic standard (Z)-11-hexadecenoic acid (Larodan) as determined by GC-MS (FIG. 14A-FIG. 14B). Therefore, the regio- and stereoisomer of the biologically produced (Z)-11-hexadecenoic acid was confirmed. In vivo characterization of A. transitella and H. zea desaturase can also be done.

In summary, at least three insect desaturases capable of rescuing growth of S. cerevisiae ΔOLE1 without exogenous supplementation of UFA, i.e. (Z)-9-hexadecenoic acid (palmitoleic acid), were identified.

The extent of growth on rich medium (YPD) of S. cerevisiae ΔOLE1 bearing the expression construct was in the following order of desaturase content: OLE1, T. ni. T, pseudonana, and A. segetum.

The extent of growth on minimal medium (CM Glucose w/out uracil) of S. cerevisiae ΔOLE1 bearing the expression construct was in the following order of desaturase content: OLE1. T. ni.

Complementation assays using A. transitella and H. zea desaturases were also done, demonstrating functional expression in Candida tropicalis shown via in vivo bioconversion assay. These desaturases also complemented S. cerevisiae ΔOLE1 growth on rich and minimal media at least as well as T. ni desaturase.

Expression of T. pseudonana and A. segetum desaturases did not confer growth of S. cerevisiae ΔOLE1 on minimal medium without UFAs even after an extended incubation period up to 14 days. No (Z)-11-hexadecenoic acid was observed in strains harboring T. pseudonana or A. segetum desaturase.

Conclusions

Functional expression of transmembrane desaturases of insect origin in S. cerevisiae has been achieved.

The activity of a given heterologous desaturase can be assessed from its ability to complement growth of S. cerevisiae ΔOLE1 without exogenous palmitoleic supplementation, and its ability to convert palmitic acid into insect pheromone precursors (Z)-11-hexadecenoic acid.

Functional expression and/or activity of insect desaturase in S. cerevisiae varies widely depending on sequence origin. Variants derived from T. ni exhibited the best activity compared to A. segetum and T. pseudonana, as measured by the above criteria.

Desaturases derived from A. transitella and H. zea complemented ΔOLE1 as well as T. ni desaturase. Bioconversion assays using these desaturases can be done.

The bioconversion of other fatty acid substrates can be explored to assess enzyme plasticity.

Materials & Methods

Strain Construction and Functional Expression Assay

S. cerevisiae ΔOLE1 (MATA OLE::LEU2 ura3-52 his4) was used as an expression host. A synthetic expression cassette termed pOLE1 (FIG. 10. SEQ ID NO: 4) which comprises the OLE1 promoter region (SEQ ID NOs: 5 and 6), nucleotides encoding for 27 N-terminal amino acids of the OLE1 leader sequence (SEQ ID NO: 7), and a VPS13 terminator sequence (SEQ ID NO: 8) was created, and cloned into pESC-URA vector in between SacI and EcoRI sites. To test the functionality of the pOLE1 cassette, Dasher GFP synthon was inserted in between SpeI and NotI sites to create pOLE1-GFP plasmid. Competent ΔOLE1 was transformed with pOLE1-GFP, and plated on CM-Ura glucose agar plate (Teknova) containing UFA (20 mm CM-URA glucose agar plate was coated with 100 μL CM-Ura glucose medium containing 1% tergitol, and 3 μL palmitoleic acid). After incubation at 30° C. for 5 days, Dasher GFP expression was apparent as displayed by green coloration of ΔOLE1 transformants. This result showed that the pOLE1 cassette was capable of driving heterologous protein expression. Validation of ΔOLE1 complementation was performed by restoring OLE1 activity. Specifically, native S. cerevisiae OLE1 synthon was inserted into pOLE1 cassette devoid of the leader sequence to create pOLE1-OLE1 plasmid. After transformation of ΔOLE1, and selection on CM-Ura glucose agar containing UFA, single colonies were patched onto YPD and CM-Ura glucose without UFA. After incubation at 30° C. for 5 days, growth was observed (FIG. 11A-FIG.

11E). As expected, Dasher GFP expression could not complement ΔOLE1 growth without UFA (FIG. 11A-FIG. 11E). DNA sequences which encode for desaturase variants were synthesized (to include nucleotide changes which remove restriction sites used for cloning purposes), and cloned into pOLE1 using SpeI-NotI sites (Genscript, SEQ ID NOs: 9-13). Complementation assay of ΔOLE1 with insect desaturases were performed in the same way as with OLE1 desaturase.

To assess functional expression, two positive transformation clones that had been patched on CM-Ura glucose agar medium containing UFA were inoculated in 1.5 mL CM-Ura glucose liquid medium containing palmitic acid (in ethanol) at a final concentration of 300 mg/L, and with 6.7 g/L of YNB. For (z)-11-hexadecenoic isomer confirmation, a 20 mL culture was generated. Bioconversion assay proceeded for 96 h at 28° C. prior to GC-MS analysis.

Metabolite Extraction and GC-MS Detection

Total lipid composition as well as the (Z)-11-hexadecenoic acid quantification was based on modified procedures by Moss et al. (1982) (Moss, C. W., Shinoda, T. & Samuels, J. W. Determination of cellular fatty acid compositions of various yeasts by gas-liquid chromatography. *J. Clin. Microbiol.* 16: 1073-1079 (1982)) and Yousuf et al (2010) (Yousuf, A., Sannino, F., Addorisio, V. & Pirozzi, D. Microbial Conversion of Olive Oil Mill Wastewaters into Lipids Suitable for Biodiesel Production. *J. Agric. Food Chem.* 58: 8630-8635 (2010)). The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL screw-cap GC-vial. The mixture was heated for 1 h in the heat block at 90° C. Prior to acidification with 400 2.5 N HCl the vial was allowed to cool to room temperature. 500 μL chloroform containing 1 mM heptadecanoic were added and the mixture was shaken vigorously, then both aqueous and organic phase were transferred into a 1.5 mL plastic tube. The mixture was centrifuged at 13.000 rpm, afterwards 450 μL of the organic phase were transferred into a new 1.5 mL plastic tube. The aqueous phase was extracted a second time with 500 μL chloroform, this time without heptadecanoic acid. The combined organic phases were evaporated at 90° C. After cooling to room temperature, residual fatty acid methyl esters and free fatty acids were dissolved and derivatized in methanol containing 0.2 M TMSH (trimethylsulfonium hydroxide).

The regioselectivity of biologically produced (Z)-11-hexadecenoic acid was determined by comparing the fragmentation patterns of the dimethyl disulfide (DMDS) derivative with the DMDS derivative of an authentic standard. A yeast culture was split into 12 aliquots (to not change any parameters in the developed procedure). The cells were pelleted, which yielded 63 mg cells (ccw) on average (755 mg from 18 mL culture). The pellets were subjected to base methanolysis as described above. However, after acidification the samples were combined in a 50 mL Falcon tube. The combined sample was extracted two times with 10 mL chloroform. The mixture was centrifuged 10 min at 3000 rpm to achieve a better phase separation. The combined organic phases, which were combined in a new 50 mL Falcon and were washed consecutively with 10 mL brine and 10 mL water. The organic phase was dried with anhydrous sodium sulfate and concentrated in vacuo. The concentrated oil was dissolved in 1.5 mL chloroform and transferred to a 1.5 mL plastic tube. The chloroform was evaporated at 90° C. The remaining sample was the dissolved in 50 μL methyl tert-butyl ether (MTBE). The 50 μL were split into 1, 5, 10 and 20 μL and transferred into GC-vials without insert. To each vial 200 μL DMDS (dimethyl disulfide) and 50 μL MTBE (containing 60 mg/mL iodine) were added. After the mixture was heated 48 h at 50° C., excess iodine was removed by the addition of 100 μL saturated sodium thiosulfate solution. The samples were transferred to plastic vials and extracted to times with 500 μL dichloromethane. The combined organic phases were transferred to a new 1.5 mL plastic vial and evaporated at 90° C. The samples were taken up in 50 μL DCM and transferred to a GC-vial. The sample was analyzed by GC-MS (Table 7) using the method of Hagström et al. (2013) (Hagström, A. K. et al. A moth pheromone brewery: production of (Z)-11-hexadecenol by heterologous co-expression of two biosynthetic genes from a noctuid moth in a yeast cell factory. *Microb. Cell Fact.* 12: 125 (2013)).

TABLE 7

Analytical parameters used for GC-MS analysis of DMDS-derivatives

| | |
|---|---|
| System | Agilent 6890 N GC, ChemStation G1701EA E.02.01.1177 |
| Column | Rtx-5 30 m × 320 μm × 25 μm |
| | Pressure = 11.74 psi; Flow = 7.1 mL/min |
| Inlet | Heater = 250° C.; Pressure = 11.74 psi; |
| | Total Flow {He} = 19.5 mL/min |
| Carrier | He @ 147 cm/sec, 11.74 psi |
| Signal | Data rate = 2 Hz/0.1 min |
| Oven | 150° C. for 2 min |
| | Ramp 10° C./min to 180° C. |
| | Ramp 3° C./min to 260° C. |
| | Ramp 20° C./min to 280° C., hold 10 min |
| Injection | Split, 250° C. |
| | Split ratio −1:1 |
| Detector | HP 5973 MSD in SCAN mode (mass range: 41 to 550 amu) |
| | 100 msec Dwell, EMV mode: Gain factor 1, |
| | 3 min solvent delay, 8.33 cycles/sec |
| Sample | Injection volume = 1 uL |

Example 5: *S. cerevisiae* as a Production Platform for Insect Fatty Alcohol Synthesis Background and Rationale Engineering microbial production of insect fatty alcohols from fatty acids requires the functional expression of a synthetic pathway. One such pathway comprises a transmembrane desaturase, and an alcohol-forming reductase to mediate the conversion of fatty acyl-CoA into regio- and stereospecific unsaturated fatty acyl-CoA, and subsequently into fatty alcohols. A number of genes encoding these enzymes are found in some insects as well as some microalgae. A number of gene variants were screened to identify enzyme activities that allow the creation of pathways capable of high level synthesis of a single or a blend of insect fatty alcohols. Additionally, these enzymes were screened across multiple hosts (*Saccharomyces cerevisiae*, *Candida tropicalis*, and *Yarrowia lipolytica*) in order to find a suitable host for optimum expression of these transmembrane proteins.

Summary of Approach

*S. cerevisiae* was engineered previously to express select functional transmembrane desaturase variants to allow synthesis of (Z)-11-hexadecenoic acid from palmitic acid. This allowed the identification and rank-ordering of the variants based on their bioconversion performance (see Example 4).

*S. cerevisiae* was engineered previously to express select functional transmembrane reductase variants to allow synthesis of (Z)-11-hexadecenol (Z11-16OH) from (Z)-11-hexadecenoic acid. This allowed the identification and rank-ordering of the variants based on their bioconversion performance (see Example 3).

Several fatty alcohol pathways comprised of the most active variant desaturases and reductases identified in the previous screens were assembled.

S. cerevisiae W303A and ΔOLE1 were transformed with the pathway constructs. Functionality of the pathway was assessed via the ability of the recombinant yeasts to synthesize Z11-16OH from palmitic acid.

GC-MS analysis was used to identify and quantify metabolites.

Results

The goal was to engineer one or more insect fatty alcohol biosynthetic pathways in S. cerevisiae. Previously, the functional expression of several transmembrane desaturases of insect origin in S. cerevisiae was demonstrated (see Example 4). Briefly, heterologous desaturase expression was enabled by designing an expression cassette which consists of an OLE1 promoter region, an N-terminal leader sequence encoding the first 27 amino acids of S. cerevisiae OLE1, and a terminator region of VPS13. Screening for active desaturases was done by using two approaches. First, active desaturases were screened for their ability to rescue ΔOLE1 growth without exogenous addition of unsaturated fatty acid (UFA), and second, active desaturases were screened via an in vivo screen for bioconversion of palmitic acid into (Z)-11-hexadecenoic acid. These screening strategies allowed the identification of several active variants, and the rank ordering of their relative activity. Based on these screening results, desaturases from Trichoplusia ni (TN_desat) and S. cerevisiae (SC_desat) were selected for combinatorial expression in fatty alcohol pathways. S. cerevisiae desaturase is known to form palmitoleic acid and oleic acid.

The functional expression of several transmembrane alcohol forming reductases of insect origin in S. cerevisiae had also been previously demonstrated (see Example 3). An expression cassette comprising the GAL1 promoter and CYC terminator was used to enable the functional expression of the reductases in S. cerevisiae. Screening several reductases via in vivo bioconversion of (Z)-11-hexadecenoic acid into Z11-16OH allowed the identification of active variants and rank ordering of their relative activity. Based on this screen, reductases from Helicoverpa armigera (HA_reduc), and Spodoptera littoralis (SL_reduc) were chosen for assembly of the fatty alcohol pathways.

Figure 15:
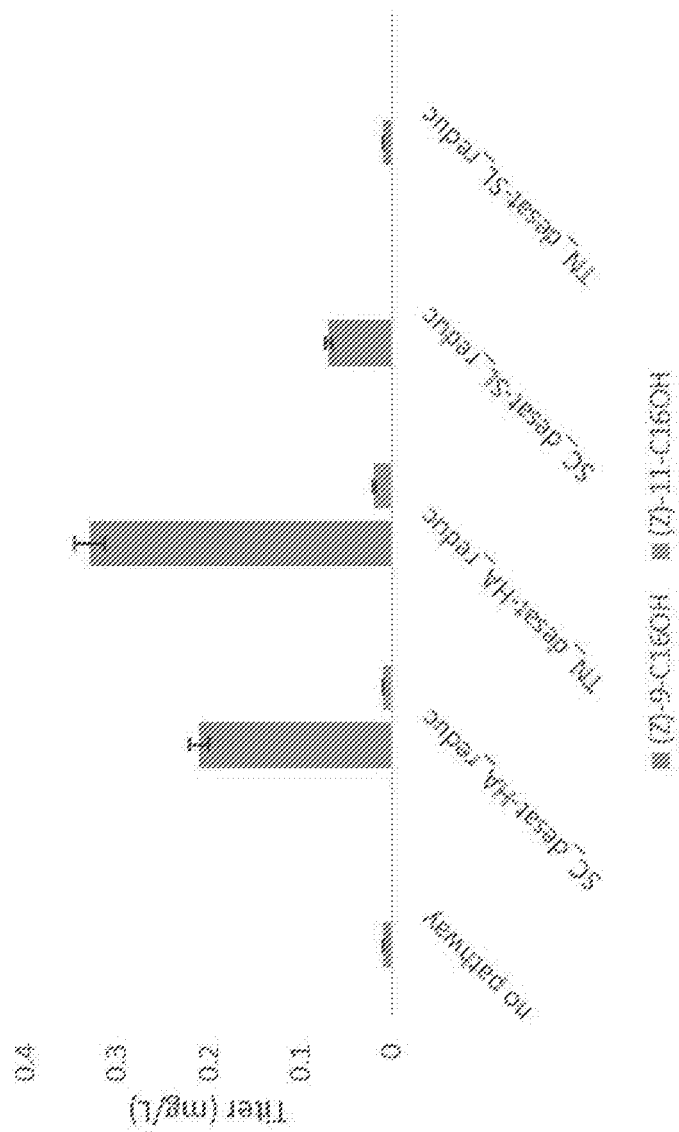
FIG. 15 shows C16 fatty alcohol production from ΔOLE1 expressing various fatty alcohol pathway variants in culture supplemented with palmitic and palmitoleic acid. Error bars represent 5% uncertainty of metabolite quantification accuracy.
Figure 16:
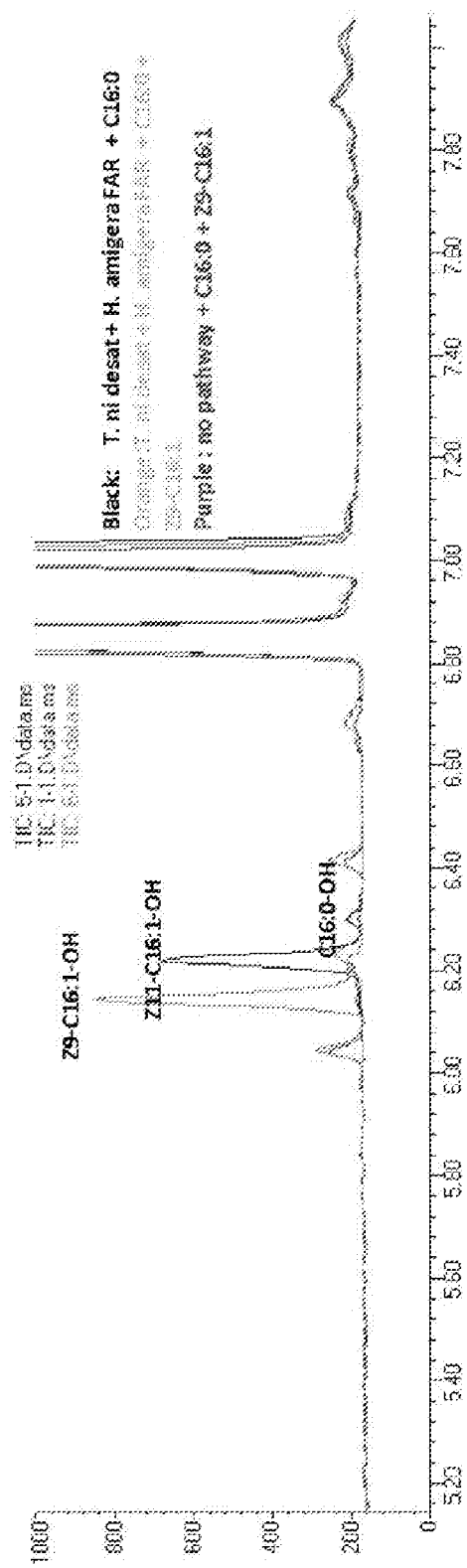
FIG. 16 shows representative chromatograms of biotransformation product C16 fatty acids using *S. cerevisiae* expressing fatty alcohol pathways TN_desat-HA_reduc when fed with palmitic acid (black) and when fed with palmitic and palmitoleic acids (orange). Profile of a negative control strain (harboring an empty vector) fed with palmitic acid (purple).
Figure 17:
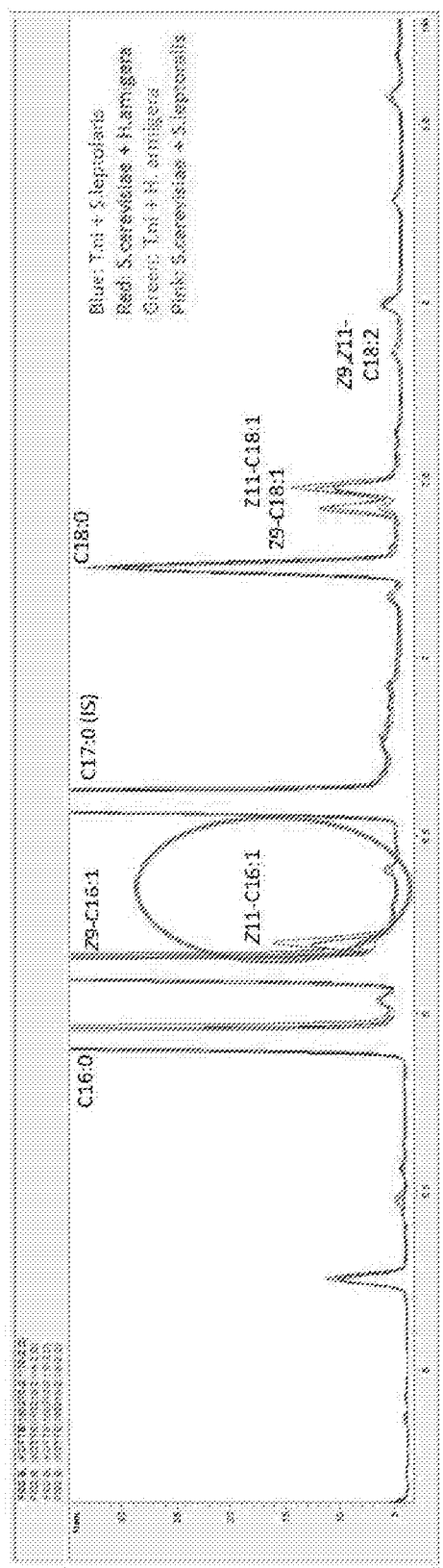
FIG. 17 shows that (Z)-11-hexadecenoic acid was detected in the cell pellets of *S. cerevisiae* expressing fatty alcohol pathways TN_desat-SL_reduc (blue), SC_desat-HA_reduc (red), TN_desat-HA_reduc (green). SC_desat-SL_reduc (pink).

Combinatorial assembly created four fatty alcohol pathways, i.e. TN_desat-HA_reduc, TN_desat-SL_reduc, SC_desat-HA_reduc, and SC_desat-SL_reduc. Pathways with SC_desat served as negative control for insect Z11-16OH synthesis. S. cerevisiae ΔOLE1 and W303A were transformed with constructs harboring these pathways, and transformants that grew on CM-Ura with 2% glucose and coated with palmitoleic acid were isolated. To test for fatty alcohol production, individual clones were inoculated into CM-Ura medium containing 2% glucose, 1% raffinose, 2% galactose, 300 mg/L palmitic acid, and 360 mg/L palmitoleic acid were added as bioconversion substrates. Bioconversion using palmitic acid without palmitoleic was also tested. Post ~96h-cultivation in the presence of palmitic and palmitoleic acid, culture broth analysis revealed synthesis of Z11-9OH as a major $C_{16}$ alcohol product at ~0.2 mg/L, and ~0.3 mg/L in cultivation of ΔOLE1 strains harboring SC_desat-HA_reduc, and TN_desat-HA_reduc, respectively (FIG. 15, FIG. 16). A minute amount of Z11-16OH was also detected in pathways with T. ni or S. cerevisiae desaturase, and H. armigera reductase. In general, it was expected that in the presence of palmitic acid and palmitoleic acid, Z9-16OH synthesis was more favorable than Z11-16OH synthesis because (Z)-11-hexadecenoic acid must be biosynthesized from T. ni desaturase, whereas exogenous addition of palmitoleic acid resulted in a more readily available substrate for synthesis of Z9-16OH. Fatty acid analysis was also performed. The results showed higher accumulation of (Z)-11-hexadecenoic acid (FIG. 17) in pathways containing insect desaturase than in pathways expressing S. cerevisiae desaturase. Albeit at minute quantities, detection of Z11-16OH, and (Z)-11-hexadecenoic acid from pathways harboring S. cerevisiae desaturase (which was unexpected) opens the possibility of a minor Δ11 desaturation activity by S. cerevisiae desaturase. Low level synthesis of Z11-16COOH fatty acid moieties can also be derived from elongation of Z9-14COOH fatty acyl intermediate. The data shown in FIG. 15 also showed that in comparison to pathways with H. armigera reductase, the inclusion of S. littoralis reductase resulted in the reduction of (up-to ~30 fold) in Z9-16OH titer. No Z11-16OH could be detected in pathways employing S. littoralis reductase. These results are consistent with the reductase screening assay, which showed superior bioconversion of (Z)-11-hexadecenoic acid using H. armigera reductase in comparison to S. littoralis reductase.

Figure 18:
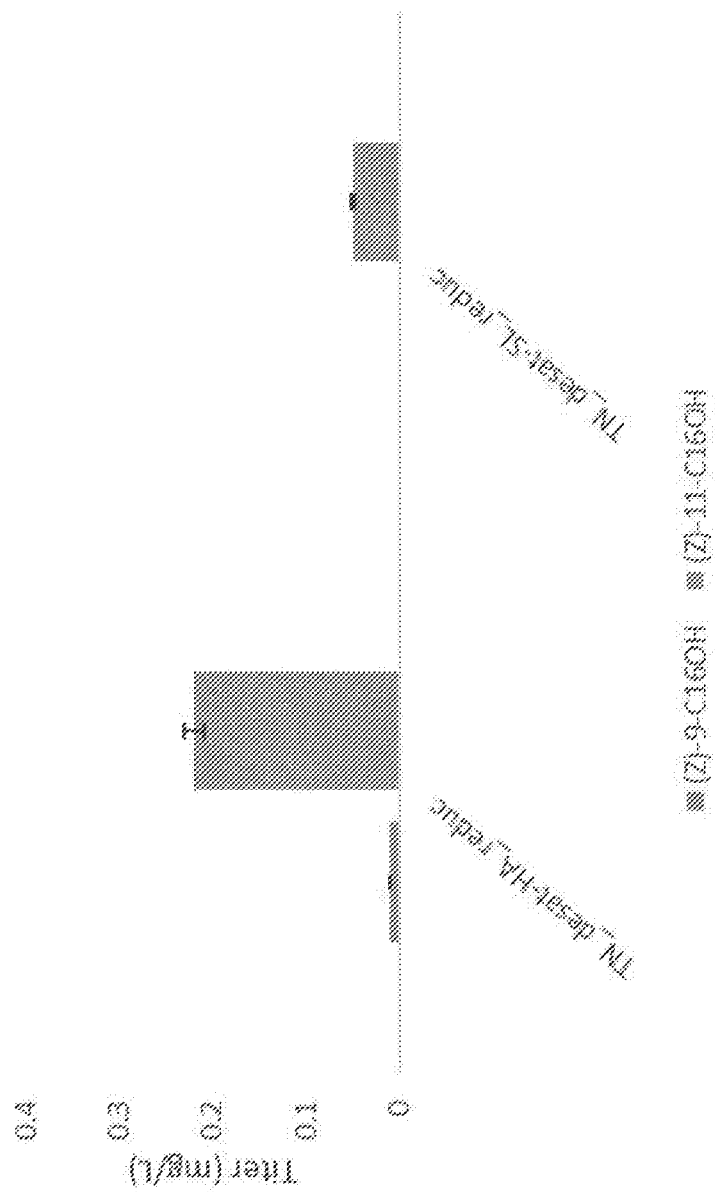
FIG. 18 shows C16 fatty alcohol production from ΔOLE1 expressing various fatty alcohol pathway variants in culture supplemented with palmitic acid only. Error bars represent 5% uncertainty of metabolite quantification accuracy.
Figure 19:
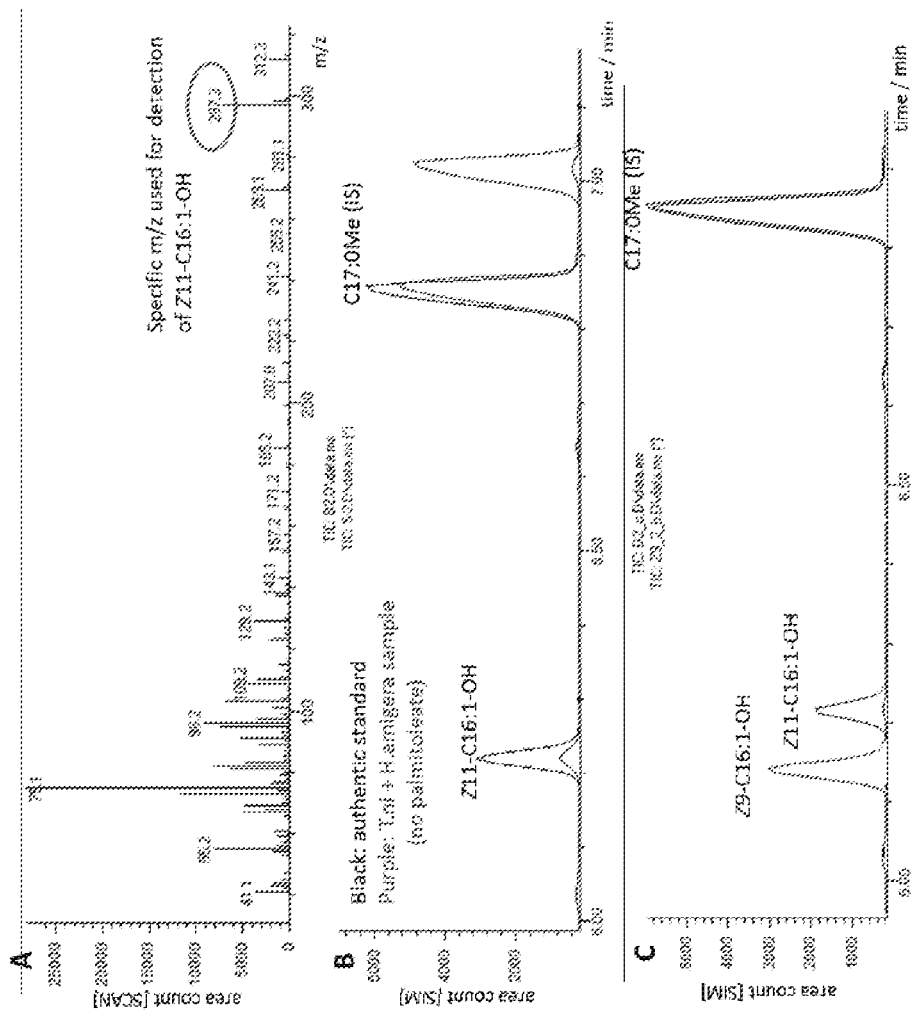
FIG. 19A-FIG. 19C shows detection of (Z)-11-hexadecenol.

The bioconversion of palmitic acid was also tested alone (without exogenous addition of palmitoleic acid) by ΔOLE1 strains expressing TN_desat-HA_reduc and TN_desat-SL_reduc (FIG. 18). Culture broth analysis determined the synthesis of Z11-16OH as the dominant unsaturated C16 fatty acid product (FIG. 16). In this assay, up to 0.22 mg/L, and 0.05 mg/L Z11-16OH was synthesized by a pathway harboring H. armigera reductase and S. littoralis reductase, respectively. The biologically produced Z11-16OH also matched the retention time and exhibited the characteristic 297.3 m/z peak like the authentic standard Z11-16OH as determined by GC-MS (SIM). Therefore, the regio- and stereoisomer of the biologically produced Z11-16OH was confirmed (FIG. 19). Furthermore, Z9-16OH (0.01 mg/L) was also observed in the cultivation of strain co-expressing T. ni desaturase and H. armigera reductase. This suggested that T. ni desaturase may also possess Δ9 desaturation activity.

OLE1 deletion impairs growth. Therefore, pathway expression was also explored in W303A, a host with intact OLE allele. However, despite growth improvement, pathway expression in this host resulted in more than two-fold reduction of Z11-16OH titers. This result was likely due to the repression of OLE1 promoter (which drove heterologous desaturase expression) by endogenous unsaturated fatty acyl:CoAs, the products of OLE1. The S. cerevisiae OLE1 promoter has been previously characterized with structural regions found to be positively and negatively regulated by saturated and unsaturated fatty acid, respectively (Choi, J-Y. et al. Regulatory Elements That Control Transcription Activation and Unsaturated Fatty Acid-mediated Repression of the Saccharomyces cerevisiae OLE1 Gene. J. Biol. Chem. 271: 3581-3589 (1996)). In addition to cis-transcriptional regulation, unsaturated fatty acids also interact with OLE1 promoter elements to regulate mRNA stability (Gonzales, C. I. et al. Fatty acid-responsive control of mRNA stability. Unsaturated fatty acid-induced degradation of the Saccharomyces OLE transcript. J. Biol. Chem. 271: 25801-25809 (1996)). Due to this inherent complexity of the OLE1 promoter, the utilization of unregulated orthogonal promoters, such as the OLE1 promoter from S. kluyveri (Kajihara, S. Molecular cloning and characterization of the v9 fatty acid desaturase gene and its promoter region from Saccharomyces kluyveri. FEMS Yeast. Res. 2: 333-339 (2002)) to drive insect desaturase expression can be explored to enhance fatty alcohol production.

In summary, functional expression of synthetic pheromone pathway variants in S. cerevisiae ΔOLE1 resulted in the synthesis of Z11-16OH and Z9-16OH from palm oil fatty acids (palmitic acid and palmitoleic acid) up to approximately 0.2 mg/L and 0.3 mg/L, respectively.

The engineered pathway that resulted in the highest fatty alcohols is comprised of T. ni desaturase and H. armigera reductase.

Accumulation of (Z)-1-hexadecenoic acid, an intermediate of the pathway, was also observed in strains that produced Z11-16OH.

No Z11-16OH was produced and only trace Z9-16OH was detected in the negative control strain (harboring vector only).

The regio- and stereochemistry of the biologically produced Z11-16OH were confirmed by comparing the retention time and fragmentation pattern to the authentic standard compound via GC-MS.

Conclusions

The engineering of Baker's yeast for synthesis of Z11-16OH and Z9-16OH, fatty alcohol precursors of insect pheromones, was demonstrated.

Fatty alcohol production varies depending on the selection of the desaturase and reductase variants.

Accumulation of (Z)-11-hexadecenoic acid suggested the possibility of further fatty alcohol improvement by increasing the performance of alcohol forming reductase. However, it is also possible that detection of (Z)-11 1-hexadecenoic acid was due to its incorporation as phospholipid into any membrane other than the endoplasmic reticulum membrane (such as mitochondrial membranes, peroxisome, nuclear envelope, etc), therefore inaccessible to alcohol forming reductase (presumably translocated into the endoplasmic reticulum) which must utilize (Z)-11-hexadecenoic acid in its CoA thioester moiety as its substrate.

Culture conditions can be explored to increase fatty alcohol titers. The T. ni desaturase can be replaced in the pathway by A. transitella desaturase, another variant that also showed high activity and rescued ΔOLE1 growth faster than T. ni desaturase. The synthetic pathway can be imported into Candida tropicalis and Yarrowia lipolytica, which are yeasts with high adhesion property to hydrophobic substrates such as palmitic and palmitoleic acid. By increasing substrate accessibility to the microbial production platform, it is foreseeable that product titer and yield can be improved.

Materials & Methods

Strain Construction and Functional Expression Assay

S. cerevisiae ΔOLE1 (MATA OLE1::LEU2 ura3-52 his4), and W303A (MATA ura3-1 trp1-1 leu2-3_112 his3-11_15 ade2-1 can1-100) were used as expression hosts. Modular design allows combinatorial pathway assembly utilizing BamHI and XhoI to excise reductase synthons (see Example 3) and subcloning into plasmids containing pOLE1-desaturase constructs (see Example 4). Competent yeasts were transformed with pathway constructs and plated on CM-Ura glucose agar plate (Teknova). In the case of ΔOLE1 transformation, colony plating utilized 20 mM CM-Ura glucose agar plates that were coated with 100 μL CM-Ura glucose medium containing 1% tergitol and 3 μL palmitoleic acid.

To assess functional expression, transformants were inoculated in ~20 mL CM-Ura liquid medium containing 6.7 g/L of YNB, 2% glucose, 1% raffinose, and 2% galactose. Fatty acid substrates, i.e. palmitic acid (in ethanol), was added at a final concentration of 300 mg/L. Palmitoleic acid was added at a final concentration of 360 mg/L. Bioconversion assay proceeded for 96 h at 28° C. prior to GC-MS analysis.

Metabolite Extraction and GC-MS Detection

Fatty acid analysis was as described in Example 4, except that instead of extracting the sample two times, the sample was only extracted once with chloroform containing 1 mM methyl heptadecanoate (C17:0Me). Fatty alcohol analysis was as described in Example 3, except that instead of hexane (containing tetradecanedioic acid), chloroform (containing 1 mM methyl heptadecanoate) was used. The extraction time was reduced from 1 h to 20 s. Afterwards the samples were collected in a 1.8 mL GC vial and not in a 1.5 mL plastic tube. The mass spectrometer was used in SIM mode (m/z 208, 297.3 and 387.3).

Example 6: Expression of Transmembrane Desaturases in Candida tropicalis

Background and Rationale

Engineering microbial production of insect fatty alcohols from fatty acids requires the functional expression of a synthetic pathway. One such pathway comprises a transmembrane desaturase, and an alcohol-forming reductase to mediate the conversion of fatty acyl-CoA into regio- and stereospecific unsaturated fatty acyl-CoA, and subsequently into fatty alcohols. A number of genes encoding these enzymes are found in some insects as well as some microalgae. A number of gene variants were screened to identify enzyme activities that allow the creation of pathways capable of high level synthesis of a single or a blend of insect fatty alcohols. Additionally, these enzymes can be screened across multiple hosts (Saccharomyces cerevisiae, Candida tropicalis, and Yarrowia lipolytica) to optimize the search toward finding a suitable host for optimum expression of these transmembrane proteins.

Summary of Approach

A small set of desaturases (insect origin: Agrotis segetum, Amyelois transitella, Helicoverpa zea, Trichoplusia ni, Ostrinia furnacalis, and Lampronia capitella and marine diatom: Thalassiosira pseudonana) were selected as a test case to explore and establish functional expression assays, metabolite extraction methods, and analytical chemistry.

Successful integration and functional expression of mCherry control from pXICL expression cassette in SPV053 were confirmed.

Figure 20:
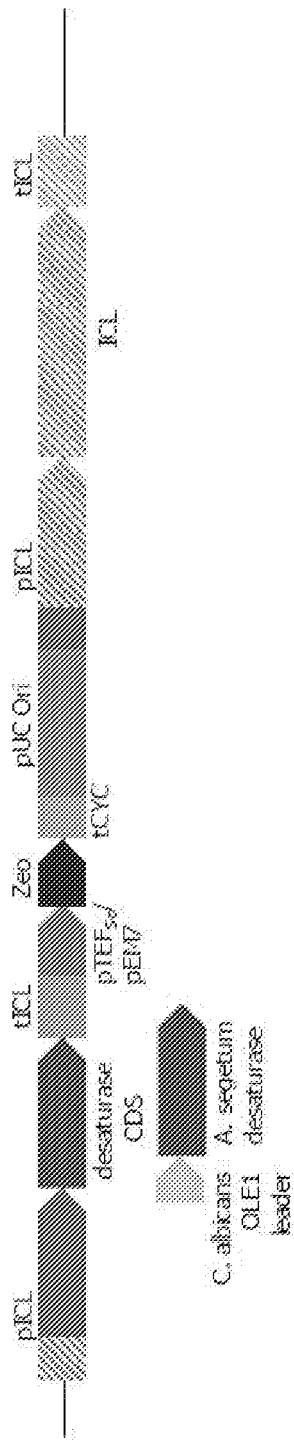
FIG. 20 shows pXICL expression cassette architecture. The *C. albicans* OLE1 leader-*A. segetum* desaturase fusion is also shown.
Figure 21:
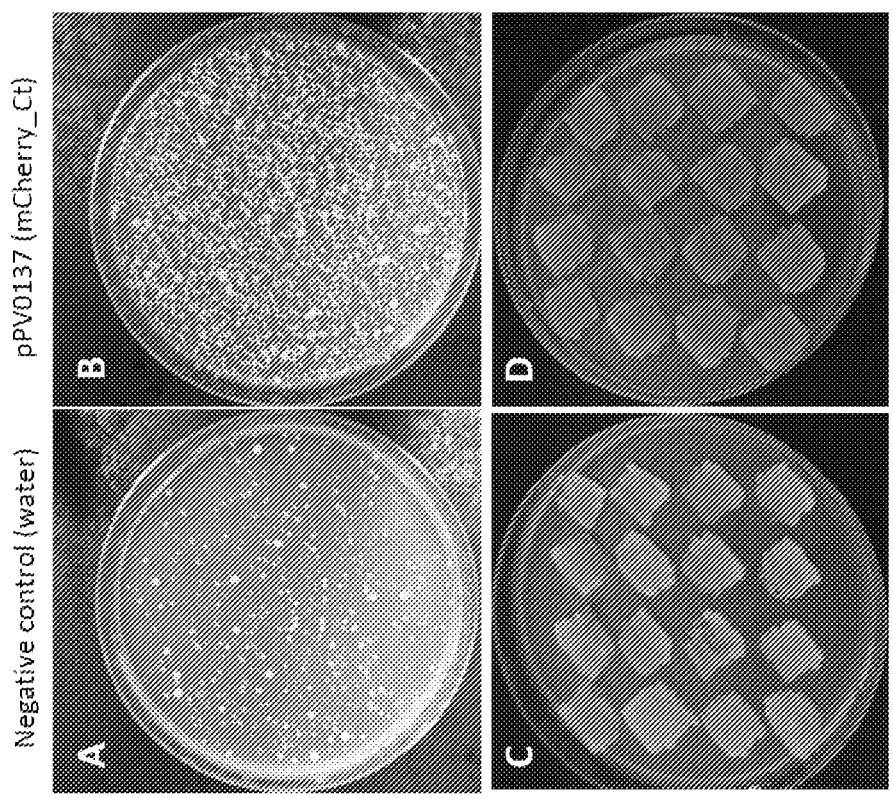
FIG. 21A-FIG. 21D shows mCherry control integration.

A recombinant desaturase library using the same pXICL vector in SPV053 background was integrated (FIG. 20). One variant, the Z11 desaturase of Agrotis segetum, was also cloned to produce a protein product with the first 27 amino acids of Candida albicans Ole1p fused to the N-terminus of the insect desaturase (SEQ ID NO: 15).

Functionality of the desaturase was validated via an in vivo bioconversion of hexadecanoic acid (palmitic acid) into (Z)-11-hexadecenoic acid (palmitvaccenic acid).

GC-FID and GC-MS analyses were used to identify and quantify metabolites.

Results

Library Construction

This study focused on the screening for transmembrane desaturase variants in C. tropicalis (SPV053). Five insect desaturases with reported Z11 desaturase activity on palmitoyl-CoA (C16:0) (SEQ ID NOs: 16-19, 23) and three insect desaturases with reported Z9 desaturase activity (SEQ ID NOs: 20-22) were included in the screen. One variant, the Z11 desaturase from A. segetum (SEQ ID NO: 16), was also cloned with 27 amino acids of the Candida albicans OLE1 N-terminus fused upstream of the insect sequence (FIG. 20, SEQ ID NO: 15). At the time of construction, the *A. segetum* Z11 desaturase was believed to be a positive control and the *C. albicans* OLE1 fusion was constructed to test if inclusion of a *Candida* leader sequence would improve functional expression. The construct was designed to mimic those used in *Saccharomyces cerevisiae* desaturase screening (See Example 4). Finally, a control construct expressing mCherry red fluorescent protein (SEQ ID NO: 14) was included to act as a positive control for integration and expression and a negative control for recombinant desaturase activity (FIG. 21A-FIG. 21D).

Figure 22:
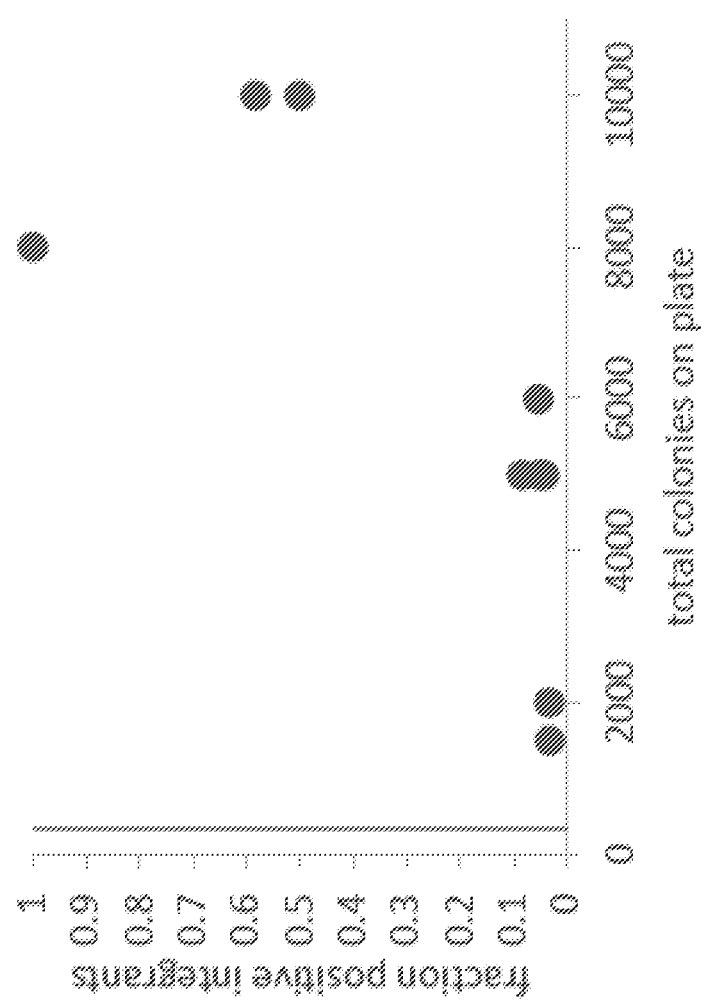
FIG. 22 shows integration efficiency as a function of total observed colonies. A control plate with no DNA added to the transformation was observed to have 350 colonies (indicated by orange line). The fraction of clones confirmed to be positive integrants is positively correlated with total colony count. A sharp increase is observed above 6,000 total colonies. The data suggests that the presence of positive integrants increases the observed background growth. For some transformations the efficiency was high enough that the background population was small relative to the positive integrant population.
Figure 23:
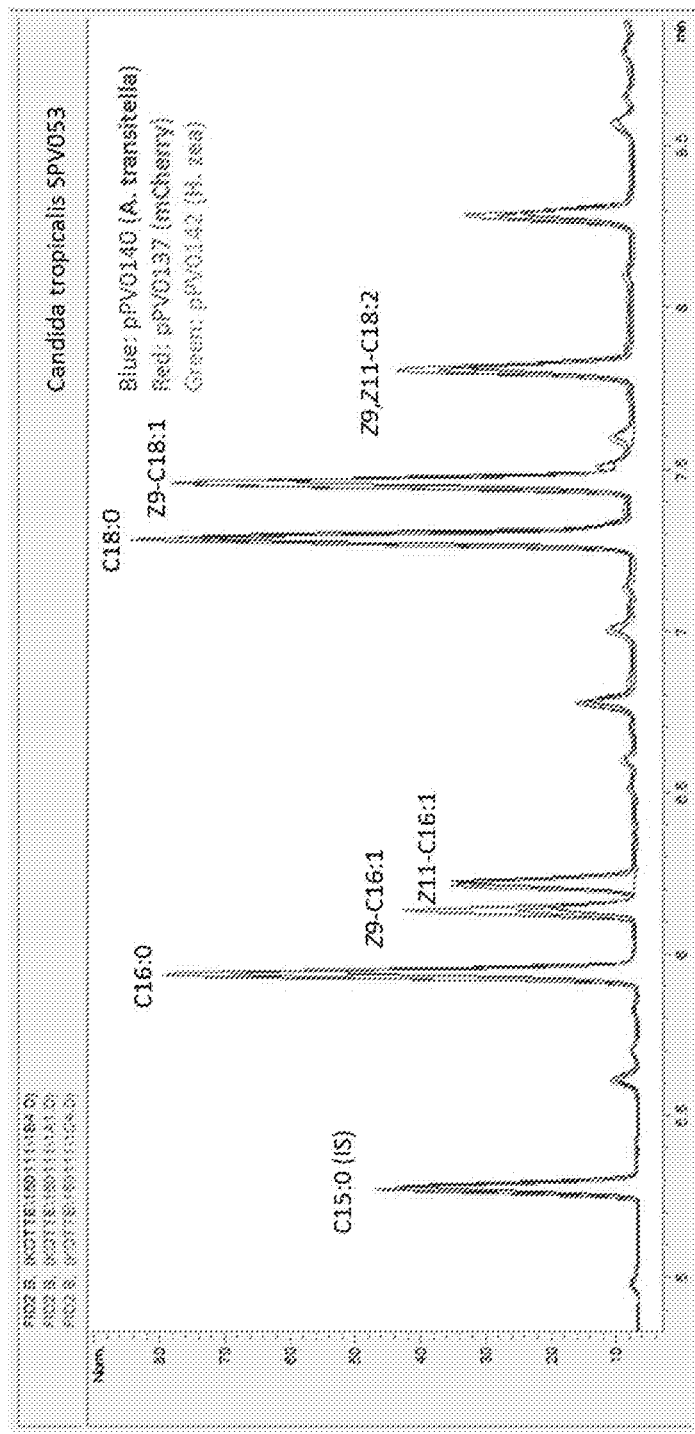
FIG. 23 shows a chromatogram overlay of *Candida tropicalis* SPV053 strains. Compared to the mCherry (red) control experiment a clear peak at 6.22 min is observable for the *A. transitella* (blue) and *H. zea* (green) desaturase. Therefore, the formation of Z-11-hexadecenoic acid is only observable in strains expressing an active Z11-desaturase.
Figure 24:
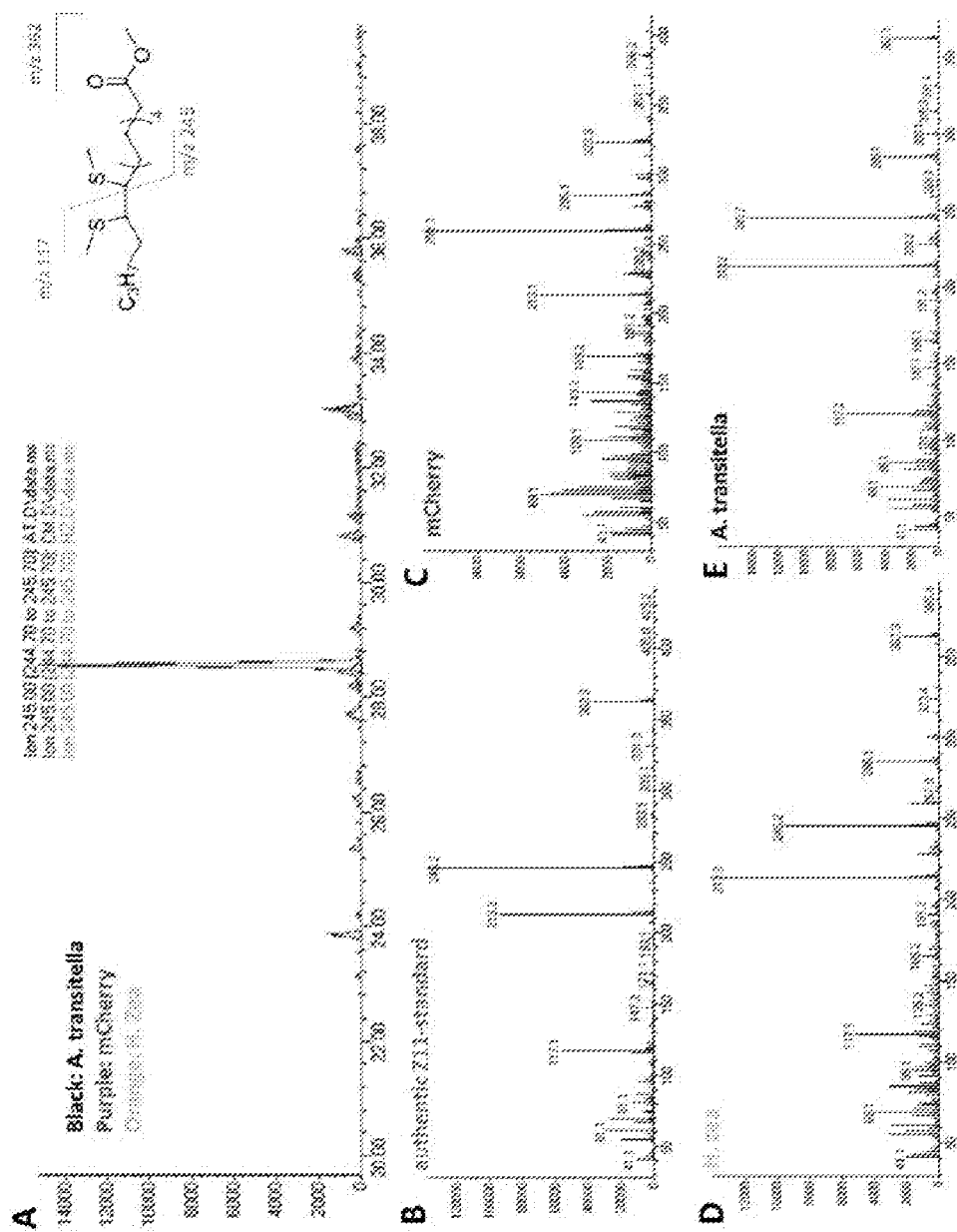
FIG. 24A-FIG. 24E shows confirmation of the 11Z-regioisomer.

Transformation efficiencies of linearized plasmids into SPV053 varied greatly across constructs. Despite low efficiencies, at least 3 clonal isolates were identified for each variant (Tables 8 and 9). It had been hypothesized that larger colonies on transformation plates were more likely to be positive integrants because the presence of the Zeocin resistance marker should increase growth rate under Zeocin selection. Analysis of the screening results suggested that the number of large colonies is not correlated to transformation efficiency. Instead total colony (small and large) count correlated best with observed efficiency (FIG. 22). In addition, in some cases positive clones were found among the small colonies. It is possible that at lower plating density growth rate may be correlated with integration events (i.e. positive integrants grow faster). A secondary screen of repatching colonies on YPD+Zeocin proved effective in enriching for positive integrants. Fast growing patches were more likely to be positive integrants than the general population of colonies on transformation plates.

TABLE 8

Desaturase transformations in SPV053. Efficiency of transformation varied across constructs with a relatively high degree of background under Zeocin selection.

| specificity | source species | pXICL plasmid | DNA ug | large colonies (control plate) | total colonies (control plate) |
|---|---|---|---|---|---|
| control | mCherry_Ct | pPV0137 | 1.1 | 60 (60) | 2,000 (600) |
| Z11 | Agrotis segetum-OEL1_Ca | pPV0138 | 1.2 | 120 (78) | >10,000 (320) |
|  | Agrotis segetum | pPV0139 | 1.3 | 115 (78) | 8,000 (320) |
|  | Amyelois transitella | pPV0140 | 1.1 | 220 (78) | 5,000 (320) |
|  | Trichoplusia nl | pPV0141 | 1.1 | 100 (78) | >10,000 (320) |
|  | Helicoverpa zea | pPV0142 | 1.0 | 350 (78) | 5,000 (320) |
|  | Thalassiorira pseudonana | pPV0146 | 1.1 | 140 (78) | 1,500 (320) |
| Z9 | Ostrinia furnacalis | pPV0143 | 0.9 | 220 (78) | 6,000 (320) |
|  | Lampronia capitella | pPV0144 | 1.2 | 230 (78) | 5,000 (320) |
|  | Helicoverpa zea | pPV0145 | 1.2 | 72 (78) | 2,000 (320) |

TABLE 9

Desaturase SPV053 library construction. Five insect desaturases with putative Z11 desaturation activity and 3 insect desaturases with putative Z9 desaturation activity were integrated into the SPV053 background using the pXICL vector. In addition, a control strain expressing mCherry was constructed with the same vector.

| specificity | source species | pXICL plasmid | Total positives | Total screened | Fraction positive |
|---|---|---|---|---|---|
| control | mCherry_Ct | pPV0137 | 16 | 16 | 1.00 |
| Z11 | *Agrotis segetum-OEL1_Ca* | pPV0138 | 7 | 12 | 0.58 |
| | *Agrotis segetum* | pPV0139 | 12 | 12 | 1.00 |
| | *Amyelois transitella* | pPV0140 | 5 | 60 | 0.08 |

TABLE 9-continued

Desaturase SPV053 library construction. Five insect desaturases with putative Z11 desaturation activity and 3 insect desaturases with putative Z9 desaturation activity were integrated into the SPV053 background using the pXICL vector. In addition, a control strain expressing mCherry was constructed with the same vector.

| specificity | source species | pXICL plasmid | Total positives | Total screened | Fraction positive |
|---|---|---|---|---|---|
| | *Trichoplusia nl* | pPV0141 | 6 | 12 | 0.50 |
| | *Helicoverpa zea* | pPV0142 | 5 | 120 | 0.04 |
| | *Thalassiorira pseudonana* | pPV0146 | 3 | 96 | 0.03 |
| Z9 | *Ostrinia furnacalis* | pPV0143 | 3 | 57 | 0.05 |
| | *Lampronia capitella* | pPV0144 | 3 | 58 | 0.05 |
| | *Helicoverpa zea* | pPV0145 | 3 | 94 | 0.03 |

Functional Expression Assay

Functional expression of the heterologous desaturases was characterized by a series of in vivo bioconversion experiments. *C. tropicalis* SPV053 derived stains expressing insect desaturases were cultured in rich (YPD) or defined (CM glucose) media supplemented with ethanol (for induction) and saturated acid substrates (palmitic acid, methyl palmitate, methyl myristate). Small scale (2 ml) cultures were cultivated for a total of 72 hours in 24 deep well plates with substrate added after the initial 24 hours.

The first screen examined multiple bioconversion media with supplementation of a palmitic acid substrate. Two functional palmitoyl-CoA (Z)-11 desaturases were identified by fatty acid methyl ester (FAME) analysis of the cellular lipid content. Strains expressing *A. transitella* or *H. zea* Z1 desaturases (SPV0305-SPV0310) produced a fatty acid species not observed in the mCherry control strains (SPV0302-SPV0304) which eluted with the (Z)-11-hexadecenoic acid standard (FIG. 23). No other tested strains produced non-native fatty acid species (data not shown). Approximate fatty acid composition of the C16-fraction is listed in Table 10. The native palmitoyl-CoA (Z)-9 desaturase is still present in the SPV053 background which means the (Z)-9/(Z)-11 specificity of the desaturases cannot be rigorously determined. Supplementation of palmitic acid in the media increased the (Z)-11/(Z)-9 hexadecenoic acid ratio from 0.6 to 1.4 for *H. zea* desaturase expressing strains. (Z)-11-hexadecenoic acid titers were observed to be approximately 5.62 mg/L for strains expressing *A. transitella* desaturase and 5.96 mg/L for strains expressing *H. zea* desaturase. Similar performance was observed with methyl palmitate supplementation (data not shown).

TABLE 10

Composition of the C16-fatty acid fraction in different *C. tropicalis* SPV053 expressing different desaturases. *NS = no substrate (hexadecanoic acid) was added.

| | C16:0 [%] | Z9-C16:1 [%] | Z11-C16:1 [%] | Z11/Z9 ratio |
|---|---|---|---|---|
| mCherry | 72.9 | 27.1 | 0.0 | 0.0 |
| Hzea-YPD_NS | 50.0 | 30.9 | 19.1 | 0.6 |
| Hzea-YPD | 58.1 | 17.5 | 24.4 | 1.4 |
| AT-YPD | 55.5 | 14.5 | 30.0 | 2.1 |

The bioconversion assay was scaled-up to 20 ml in shake flasks in order to generate enough biomass for additional characterization of the putative (Z)-11-hexadecenoic acid species. While the observed species eluted with the (Z)-11-hexadecenoic acid standard and independently of the (Z)-

9-hexadecenoic acid standard, it was possible that a different fatty acid isomer (e.g. (E)-9-hexadecenoic acid) could have a similar retention time to (Z)-1-hexadecenoic acid. As different stereoisomers elute differently on the DB-23 the occurrence of (E)-11-hexadecenoic could be excluded. Final confirmation of (Z)-11-hexadecenoic acid production was completed by using mass spectroscopy detection of DMDS derivatized fatty acids to confirm the 11-regioselectivity. Using this derivatization technique (Z)-11 and (E)-11 isomers could in principle also be resolved. The fragmentation pattern of experimental samples could be matched to the (Z)-11-hexadecenoic acid standard (FIG. 24A-24E). Using this technique, production of the specific (Z)-11-hexadecenoic acid regio- and stereoisomer was confirmed for both A. transitella and H. zea desaturase expressing strains.

Figure 25:
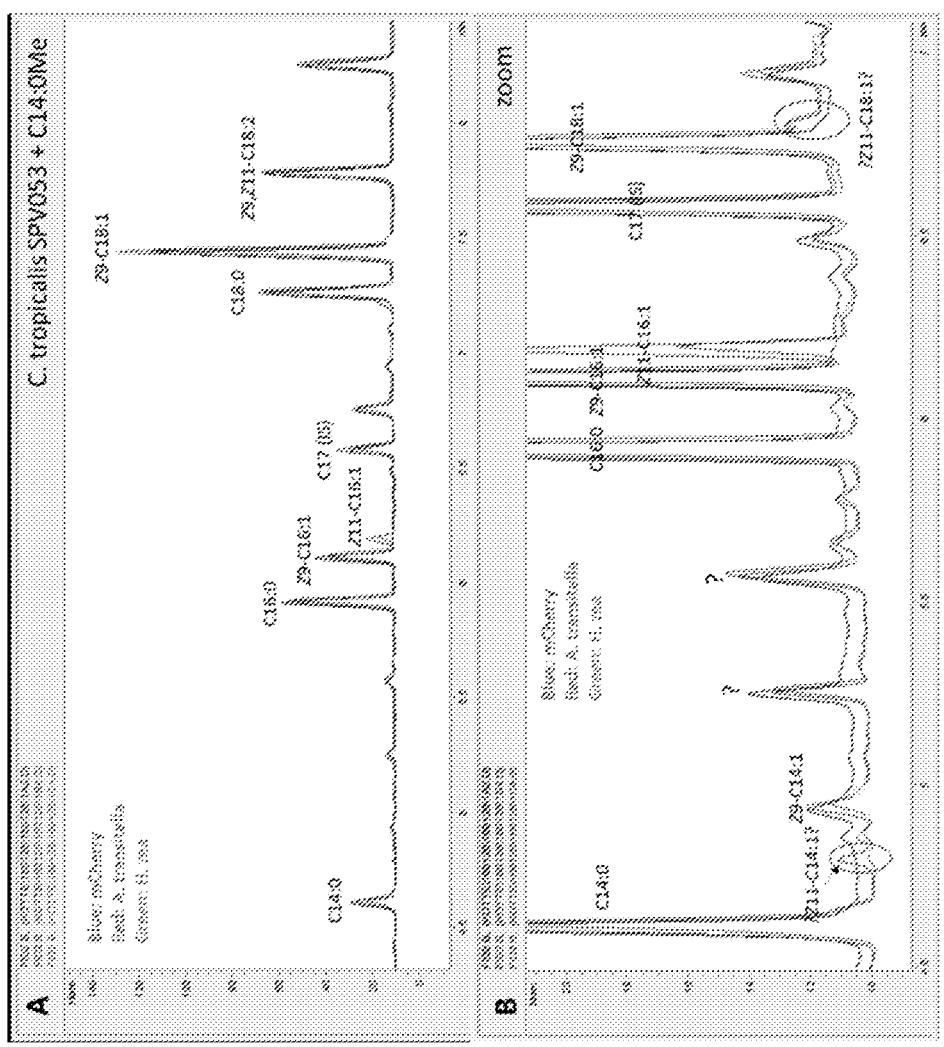
FIG. 25A-FIG. 25B shows a GC-FID chromatogram of different *C. tropicalis* SPV053 strains incubated with methyl tretradecanoate.

Finally, methyl myristate (C14:0) was tested as substrate for the entire desaturase library. A non-native fatty acid species which elutes between myristate (C14:0) and (Z)-9-tetradecenoic acid (Z9-C14:1) was observed in strains expressing either A. transitella or H. zea Z1 desaturases (FIG. 25A). It is hypothesized that this non-native species is (Z)-11-tetradecenoic acid, and this can be confirmed with an authentic standard. In addition, A. segetum Z11 desaturase, T. furnacalis Z9 desaturase, and H. zea Z9 desaturase all produced a shoulder peak which eluted just after the myristate (C14:0) peak (FIG. 25B). Other C14 derived species (e.g. tetradecanedioic acid) were observed in all strains. These results suggest that A. transitella and H. zea desaturases have some activity on myristoyl-CoA. Confirmation of unknown species and quantification is required to draw further conclusions about desaturase substrate specificity in vivo.

In summary, two desaturases from Helicoverpa zea (AAF81787) and from Amyelois transitella (JX964774), were expressed in SPV053 and conferred synthesis of (Z)-1-hexadecenoic acid from either endogenously produced or supplemented palmitic acid.

Functional expression of H. zea and A. transitella desaturases in C. tropicalis SPV053 was confirmed using an in vivo bioconversion assay in both rich (YPD) and defined (CM glucose) media. The active desaturases generated intracellular (Z)-11-hexadecenoic acid which was not observed in mCherry expressing control strains. C16-fatty acid composition of SPV053 expressing H. zea desaturase is approximately 50.0% hexadecanoic acid, 30.91% (Z)-9-hexadecenoic acid and 19.1% (Z)-11-hexadeceneoic acid. With palmitic acid supplementation the composition is 58.1% hexadecanoic acid, 17.5% (Z)-9-hexadecenoic acid and 24.4% (Z)-11-hexadeceneoic acid. The C16-fatty acid composition of SPV053 expressing A. transitella desaturase is 55.5% hexadecanoic acid, 14.5% (Z)-9-hexadecenoic acid and 30.0% (Z)-11-hexadeceneoic acid. In comparison, SPV053 expressing mCherry produced a C16-fatty acid composition of approximately 72.9% hexadecanoic acid, 27.1% (Z)-9-hexadecenoic acid and no (Z)-11-hexadeceneoic acid. (Z)-11-hexadecenoic acid was produced at approximately 5.5 mg/L in both strains expressing functional Z11 desaturases.

No (Z)-11-hexadecenoic acid was observed in strains harboring T. ni. T. pseudonana, or A. segetum desaturase.

No difference in fatty acid composition was observed for strains expressing Z9 insect desaturases from H. zea. O. furnacalis, or L. capitella.

The regio- and stereoisomer of the biologically produced (Z)-11-hexadecenoic acid were confirmed by comparing the retention time and fragmentation pattern of the authentic standard compound via GC-MS after DMDS derivatization.

Bioconversions of SPV053 expressing A. transitella and H. zea desaturases with supplementation of methyl myristate produced an unidentified metabolite not observed in the mCherry expressing negative control strain. The GC retention time of this metabolite is found between myristate (C14:0) and (Z)-9-tetradecenoic acid.

Conclusions

Functional expression of transmembrane desaturase of insect origin in C. tropicalis SPV053 has been achieved.

The active desaturases identified via screening in C. tropicalis also complemented OLE function when expressed in S. cerevisiae ΔOLE1 (See Example 4).

An in vivo assay can be used to assay desaturase activity in C. tropicalis for non-native fatty acid isomers (e.g. (Z)-11-hexadecenoic acid). Enhanced ratios of non-native fatty acids can be produced with supplementation of saturated acid substrates such as palmitic acid or methyl myristate.

Functional expression and/or activity of insect desaturases varies widely in C. tropicalis SPV053 depending on sequence origin. Similar to results observed in the S. cerevisiae screen (See Example 4), A. segetum and T. pseudonana variants did not produce detectable (Z)-11-hexadecenoic acid. Interestingly, T. ni desaturase also failed to produce detectable (Z)-11-hexadecenoic acid under assay conditions. Unlike in the S. cerevisiae assay, the T. ni expression construct did not include a chimeric OLE1 leader sequence.

The inclusion of the C. albicans OLE1 leader sequence on the functional H. zea variant and non-functional T. ni variant can be tested.

The functional expression of additional desaturase variants to identify C14-specific desaturases can be explored.

Expression of functional desaturase with reductase variants can be done and subsequent screen for unsaturated fatty alcohol production can be performed.

Materials & Methods

Strain Construction

A conservative approach was used for recoding of genes. Native sequences were unaltered except for replacement of CTG leucine codons with TTA. All genes were cloned into pPV0053 using NcoI and NotI restriction sites by Genscript. After transformation into E. coli NEB10β, plasmids were miniprepped using the Zyppy Plasmid Miniprep Kit (Zymo Research, Irvine, Calif.). Plasmids were linearized by digestion with BsiWI (New England Biolabs, Ipswich, Mass.) before transformation into SPV053. After digestion, DNA was isolated using Clean and Concentrator Kit (Zymo Research, Irvine. Calif.). Approximately 1 µg of DNA was transformed by electroporation. Instead of incubation with TE+100 mM lithium acetate+DTT, cells were incubated in only TE+100 mM lithium acetate for 2 hours. Positive integrants were found to be site-specific and genotyping was conducted by check PCR. A two-stage approach was adopted for further screening of low efficiency transformations. Approximately 60 colonies were re-patched on YPD+ 300 µg/ml Zeocin and grown overnight. The subset of patches which grew quickly (dense growth within 24 hours) were screened by colony PCR. The vast majority of rapid growing patches were identified as positive integrants.

Functional Expression Assay

Palmitic Acid Supplementation in YPD and CM Glucose

Positive isolates were re-patched onto YPD+300 pig/ml Zeocin and grown overnight and then stored at 4° C. Strains were inoculated from patch plates into 2 ml of YPD in 24 deep well plates (square well, pyramid bottom). Three positive clones were inoculated for each desaturase variant and the mCherry expressing control strain. Deep well plates were incubated at 30° C., 1000 rpm, and 80% humidity in the Infors HT Multitron Pro plate shaker for 24 hrs. After 24 hrs of incubation, cultures were split into equal 1 ml volumes to make two sets of identical plates. Both sets of plates were pelleted by centrifugation at 500×g. One set of plates was resuspended in 2 ml of YPD+0.3% (v/v) ethanol and the second set was resuspended in 2 ml of CM glucose+ 0.3% ethanol. Ethanol was added at this stage to induce recombinant enzyme expression from the ICL promoter. Cultures were incubated for another 24 hours under the same conditions before 300 mg/L palmitic acid was added to cultures from a 90 g/L stock solution in ethanol. The result was the addition of a fresh 0.3% ethanol in conjunction with the palmitic acid. A subset of strains was also cultured without palmitic acid addition. These cultures had 0.3% ethanol added instead. All cultures were incubated for an additional 24 hrs before a final addition of 0.3% ethanol. After another 24 hr period of incubation, 1.5 ml of each culture was harvested in 1.7 ml microcentrifuge tubes and pelleted. Supernatant was saved in fresh tubes and pellets were processed as described below. A subset of supernatant samples was also extracted to look for free acid in the extracellular medium.

Repeated Screening with Alternate Substrates

The mCherry control and confirmed positive variants were rescreened using both palmitic acid and methyl palmitate as substrates. The culturing was conducted as described above with equimolar (1.17 mM) amounts of substrate added from ethanol stock solutions (methyl palmitate 94 g/L stock, 313 mg/L final concentration). The same protocol was also repeated with the full panel of strains using an 84 g/L stock of methyl myristate (C14:0). The final concentration of substrate was again 1.17 mM.

Confirmation of (Z)-11-Hexadecenoic Acid Isomer

The in vivo bioconversion assay was scaled up for confirmation of (Z)-11-hexadecenoic acid synthesis, 2 ml YPD seed cultures of strains SPV0302, SPV0303, and SPV0304 (mCherry), SPV0304, SPV0305, and SPV0306 (*A. transitella* Z11 desaturase), and SPV0307, SPV0308, and SPV0309 (*H. zea* Z11 desaturase) were grown overnight at 30° C., 1000 rpm, 80% humidity in the Infors HT Multitron plate shaker, 200 µl of overnight culture from each of the three clonal isolates was pooled and inoculated into a single 125 ml baffled flask containing 20 ml YPD. The resulting three flasks were grown for 24 hrs at 30° C. and 250 rpm (Infors Flask shaker). Cultures were pelleted by centrifugation at 500×g and resuspended in 20 ml of YPD+0.3% (v/v) ethanol and returned to 125 ml baffled shake flasks. Cultures were incubated for an additional 24 hours before addition of 300 mg/L palmitic acid in a 90 g/L stock in ethanol (221 µl per flask). After 24 hours of incubation another 0.3% (v/v) ethanol (221 µl) was added to each flask for sustained induction. Flasks were incubated for an additional 24 hours before cells were harvested for FAME analysis and DMDS derivatization.

Metabolite Extraction and GC-MS Detection

Total lipid composition as well as the (Z)-11-hexadecenoic acid quantification was based on modified procedures by Moss et al. (1982) and Yousuf et al (2010). The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL screw-cap GC-vial. The mixture was heated for 1 h in the heat block at 90° C. Prior to acidification with 400 2.5 N HCl the vial was allowed to cool to room temperature. 500 µL chloroform containing 1 mM heptadecanoic were added and the mixture was shaken vigorously, then both aqueous and organic phase were transferred into a 1.5 mL plastic tube. The mixture was centrifuged at 13,000 rpm, afterwards 450 µL of the organic phase were transferred into a new 1.5 mL plastic tube. The aqueous phase was extracted a second time with 500 µL chloroform, this time without heptadecanoic acid. The combined organic phases were evaporated at 90° C. After cooling to room temperature, residual fatty acid methyl esters and free fatty acids were dissolved and derivatized in methanol containing 0.2 M TMSH (trimethylsulfonium hydroxide).

The regioselectivity of biologically produced (Z)-11-hexadecenoic acid was determined by comparing the fragmentation patterns of the dimethyl disulfide (DMDS) derivative with the DMDS derivative of an authentic standard. A yeast culture was split into 12 aliquots (to not change any parameters in the developed procedure). The cells were pelleted, which yielded 63 mg cells (ccw) on average (755 mg from 18 mL culture). The pellets were subjected to base methanolysis as described above. However, after acidification the samples were combined in a 50 mL falcon tube. The combined sample was extracted two times with 10 mL chloroform. The mixture was centrifuged 10 min at 3000 rpm to achieve a better phase separation. The combined organic phases were combined in a new 50 mL falcon and were washed consecutively with 10 mL brine and 10 mL water. The organic phase was dried with anhydrous sodium sulfate and concentrated in vacuo. The concentrated oil was dissolved in 1.5 mL chloroform and transferred to a 1.5 mL plastic tube. The chloroform was evaporated at 90° C. The remaining sample was the dissolved in 50 µL methyl tert-butyl ether (MTBE). The 50 µL were split into 1, 5, 10 and 20 µL and transferred into GC-vials without insert. To each vial 200 µL DMDS (dimethyl disulfide) and 50 µL MTBE (containing 60 mg/mL iodine) were added. After the mixture was heated 48 h at 50° C., excess iodine was removed by the addition of 100 µL saturated sodium thiosulfate solution, however, due to excessive formation of detergents from the *Candida* strain, the layer did not mix properly. The samples were therefore diluted in a 15 mL falcon tube to a final sample composition of 200 µL, 3.55 mL MTBE (containing iodine and analyte), 500 µL dichloromethane, 1.5 mL water and 1 mL ethanol. The organic phase was evaporated stepwise at 85° C. in a 1.8 mL glass vial. The samples were taken up in 500 µL dichloromethane and the sample was analyzed by GC-MS using the method of Hagström et al. (2013) as in Example 4.

Example 7: Expression of Transmembrane Desaturases in *Yarrowia lipolytica*

Background and Rationale

Engineering microbial production of insect fatty alcohols from fatty acids requires the functional expression of a synthetic pathway. One such pathway comprises a transmembrane desaturase, and an alcohol-forming reductase to mediate the conversion of fatty acyl-CoA into regio- and stereospecific unsaturated fatty acyl-CoA, and subsequently into fatty alcohols. A number of genes encoding these enzymes are found in some insects as well as some microalgae. Alternatively, regio- and stereospecific desaturases can be used to produce a microbial oil rich in fatty acid precursors. The microbial oil can then be derivatized and reduced to active ingredients. A number of gene variants were screened to identify enzyme activities that allow the creation of pathways capable of high level synthesis of a single or a blend of insect fatty acids and alcohols. Additionally, these enzymes were screened across multiple hosts (*Saccharomyces cerevisiae, Candida viswanathii (tropicalis)*, and *Yarrowia lipolytica*) to optimize the search toward finding a suitable host for optimum expression of these transmembrane proteins.

Initial screening of desaturases in *S. cerevisiae* and *C. viswanathii (tropicalis)* identified three active Z11-C16:1 desaturase variants from *Amyelois transitella, Helicoverpa zea*, and *Trichoplusia ni*. The *S. cerevisiae* screening used coding sequences with an N-terminal leader sequence of the *S. cerevisiae* Ole1p Z9 desaturase fused to the full length insect Z11 desaturase sequence. This strategy has been used previously in the scientific literature to express eukaryotic desaturases in *S. cerevisiae*. All three of the above desaturases displayed Z11 desaturase activity with the Ole1p leader fusion when expressed in a OLE1 deletion background. An analogous design with a *C. albicans* Ole1p leader sequence was used with the Z11 desaturase from *H. zea*. While active, this Ole1p-*H. zea* desaturase fusion did not significantly increase Z11-hexadecenoic acid titer. Additionally, a conservatively optimized *A. transitella* Z11 desaturase was active in both *S. cerevisiae* and *C. viswanathii*. The following study focused on testing the functional expression of the *H. zea, T. ni,* and *A. transitella* Z11 desaturases in two different *Y. lipolytica* strains, SPV140 and SPV300. Both native and *Homo sapiens* codon optimized sequences were used for the *H. zea* and *T. ni* desaturases while only the native sequence was used for *A. transitella*. Finally, the N-terminus of the *Y. lipolytica* Ole1p Z9 stearoly-CoA desaturase aligns more closely with insect desaturases than the N-terminus of Ole1p from either *S. cerevisiae* or *C. albicans*. Based on this alignment two additional desaturase versions were created. A putative leader sequence was swapped from the *Y. lipolytica* Ole1p onto the *T. ni* and *H. zea* desaturases.

Summary of Approach

A focused library of Z11 desaturases (insect origin: *Amyelois transitella. Helicoverpa zea. Trichoplusia ni*), which had observed activity in either *S. cerevisiae* or *C. vswanathii* were cloned into a double crossover cassette targeting the XPR2 locus with a URA3 selection marker. Protein coding sequences use either the native insect sequence (SEQ ID NOs: 24, 25), *Homo sapiens* optimized coding sequence (SEQ ID NOs: 26, 27), or the *Homo sapiens* optimized sequence with the N-terminal 84 bases (*H. zea*, SEQ ID NO: 29) or 81 bases (*T. ni*. SEQ ID NO: 28) swapped for the N-terminal 96 bases of the *Y. lipolytica* OLE1 (YALI0C05951) gene. Unlike in the *S. cerevisiae* and *C. viswanathii* screens, the leader sequence chimeras test a direct swap of leader sequences instead of concatenating a host leader sequence to the N-terminus of the full length desaturase coding sequence. Only the native coding sequence was used for the *A. transitella* desaturase (SEQ ID NO: 30).

Each of the 7 desaturase constructs was transformed into SPV140 (PO1f) and SPV300 (H222 ΔP ΔA ΔF ΔURA3) and site-specific integrants were confirmed.

Desaturase activity was tested via an in vivo bioconversion of hexadecanoic acid (palmitic acid) into (Z)-11-hexadecenoic acid (palmitvaccenic acid) in YPD medium.

GC-FID Analyses were Used to Identify and Quantify Metabolites.

Results

Strain Construction

Desaturase variants were cloned into the pPV101 vector which contains a *Y. lipolytica* expression cassette targeting integration into the XPR2 locus (YALI0F31889g).

The T: ni and *H. zea* desaturases were each synthesized with the native insect sequence (SEQ ID NOs: 24, 25), full length insect sequence codon optimized for *Homo sapiens* (SEQ ID NOs: 26, 27), or with the putative leader sequence replaced by the leader sequence from *Y. lipolytica* OLE desaturase (SEQ ID NOs: 28, 29). The *A. transitella* desaturase was also synthesized using the native insect coding sequence (SEQ ID NO: 30). All seven desaturase variants were transformed into SPV140. Based on previous activity results, only the *H. zea* and *A. transitella* desaturase variants were transformed into SPV300.

Functional Expression Assay

Functional activity was assessed by a modification of the protocol used for transmembrane desaturase expression in *C. viswanathii* SPV053 (See Example 6). Briefly, *Y. lipolytica* SPV140 and SPV300 derived stains expressing insect desaturases were cultured in rich (YPD) to generate biomass. Using the YPD generated biomass, small scale (2 ml) cultures were cultivated with palmitic acid for a total of 48 hours in 24 deep well plates (See Materials & Methods for detail).

Figure 26:
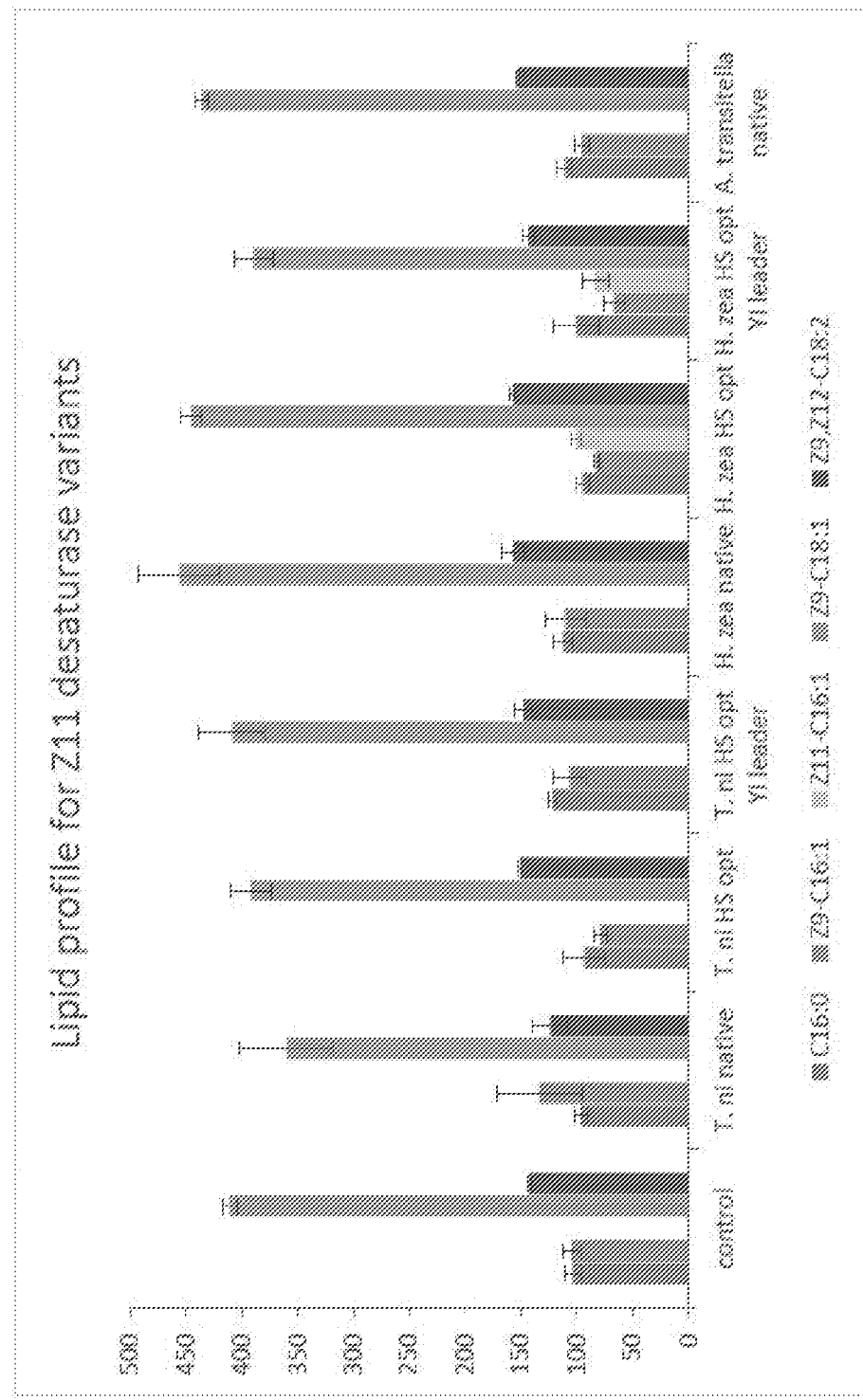
FIG. 26 shows only codon optimized *H. zea* desaturase variants produce detectable Z11-hexadecenoic acid in SPV140 screen, control=pPV101 integrants of SPV140, *T. ni* native=*T. ni* Z11 desaturase with native codon usage (pPV195), *T. ni* HS opt=*T. ni* Z11 desaturase with *Homo sapiens* codon optimization (pPV196), *T. ni* HS opt Y1 leader=*T. ni* Z11 desaturase with *Homo sapiens* codon optimization and swapped *Y. lipolytica* OLE1 leader sequence (pPV197), *H. zea* native=*H. zea* Z11 desaturase with native codon usage (pPV198), *H. zea* HS opt=*H. zea* Z11 desaturase with *Homo sapiens* codon optimization (pPV199), *H. zea* HS opt Y1 leader=*H. zea* Z11 desaturase with *Homo sapiens* codon optimization and swapped *Y. lipolytica* OLE1 leader sequence (pPV200). *A. transitella* native=*A. transitella* Z11 desaturase with native codon usage (pPV201). All data average of 3 biological replicates. Error bars represent standard deviation.

In the initial screen of *T. ni, H. zea,* and *A. transitella* variants, only *H. zea* desaturase variants that were codon optimized for *Homo sapiens* produced detectable Z11-hexadecenoic acid (FIG. 26). Expression of native *H. zea* desaturase conferred production of 100+5 mg/L Z11-hexadecenoic acid and the version with a *Y. lipolytica* OLE leader sequence produced 83±11 mg/L. As seen in FIG. 26, the distribution of the other major fatty acid species was relatively unaffected by functional desaturase expression. In the active strains, Z11-hexadecenoic acid made up ~10% (g/g) of the fatty acid species (including palmitic acid substrate which may be adsorbed to the outer cell surface).

Figure 27:
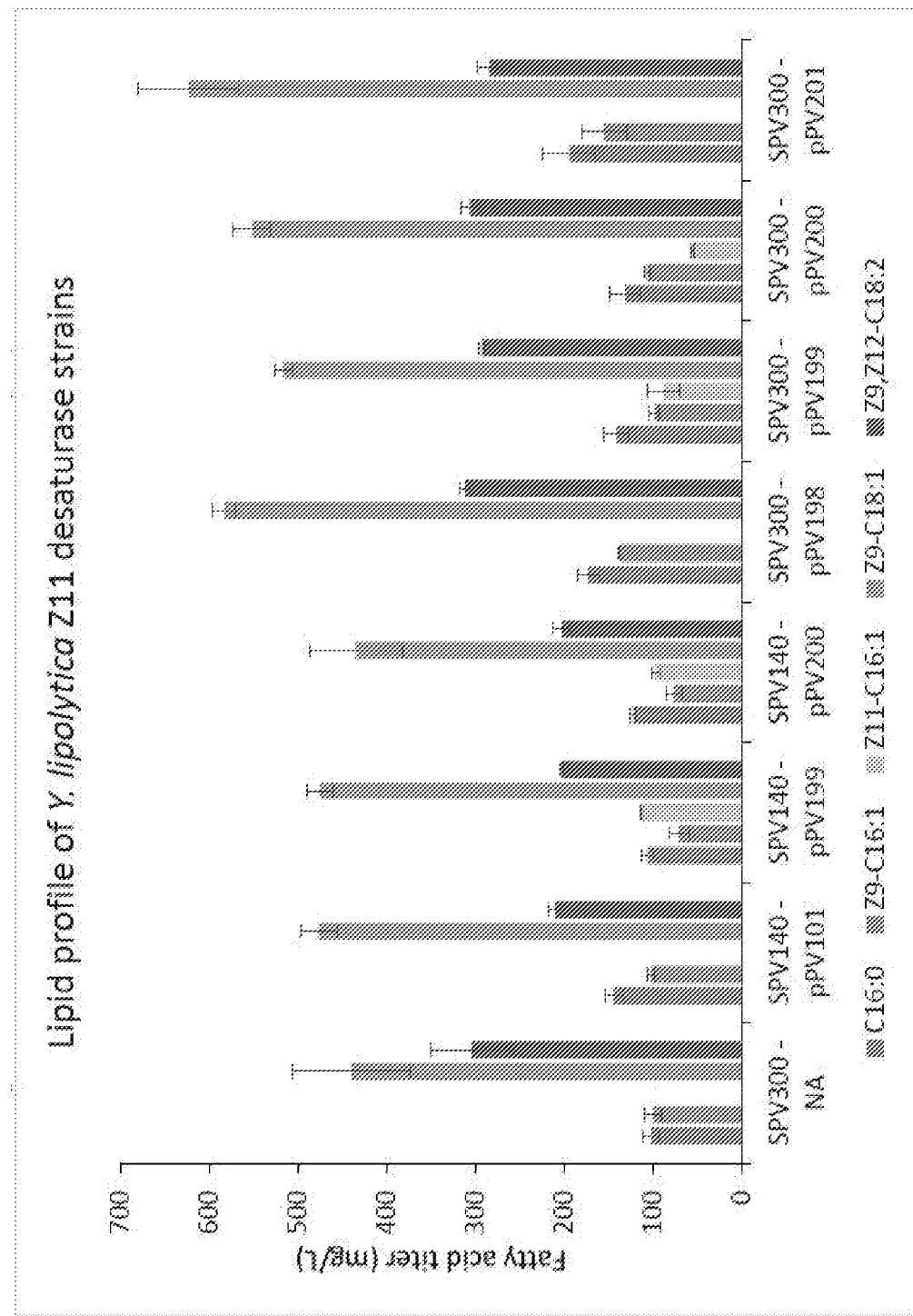
FIG. 27 shows only codon optimized *H. zea* desaturase variants produce detectable Z11-hexadecenoic acid in SPV300 screen. Labels indicate parent strain and plasmid of desaturase expression cassette, pPV101=hrGFP control, pPV198=*H. zea* Z11 desaturase with native codon usage, pPV199=*H. zea* Z11 desaturase with *Homo sapiens* codon optimization, pPV200=*H. zea* Z11 desaturase with *Homo sapiens* codon optimization and swapped *Y. lipolytica* OLE1 leader sequence, pPV201=*A. transitella* Z11 desaturase with native codon usage.
Figure 28:
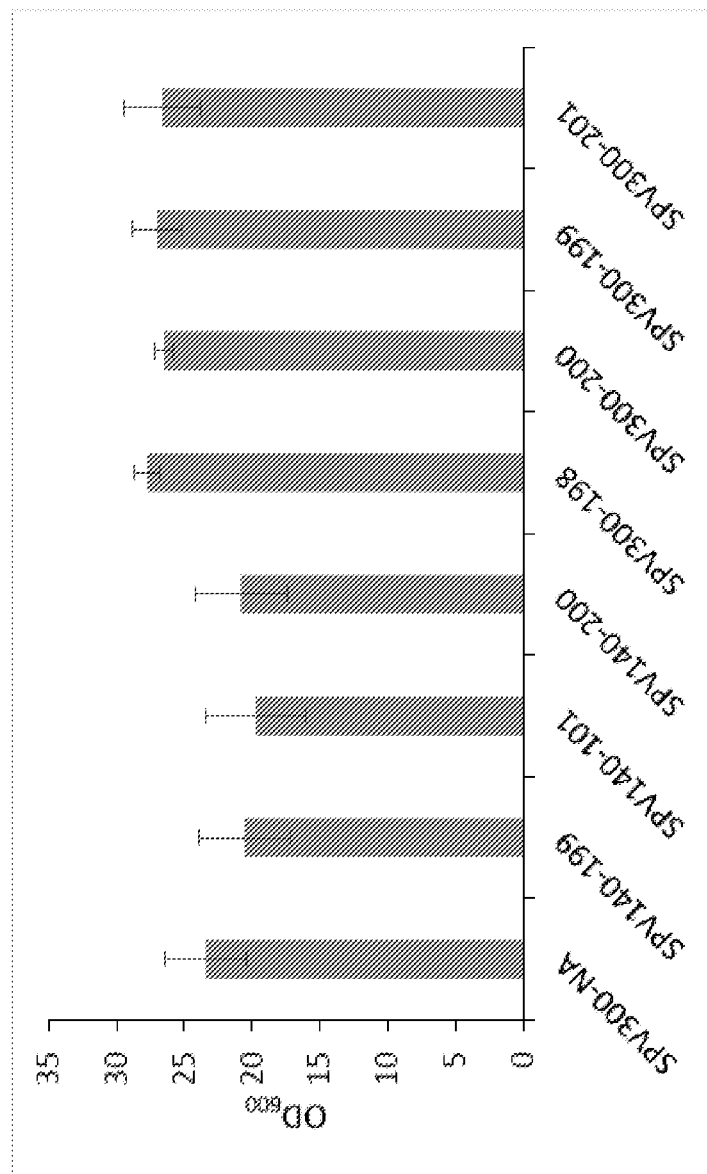
FIG. 28 shows final cell densities for desaturase screen in SPV140 and SPV300 backgrounds. SPV300 strains with integrated desaturase cassettes grew to higher cell densities.
Figure 29:
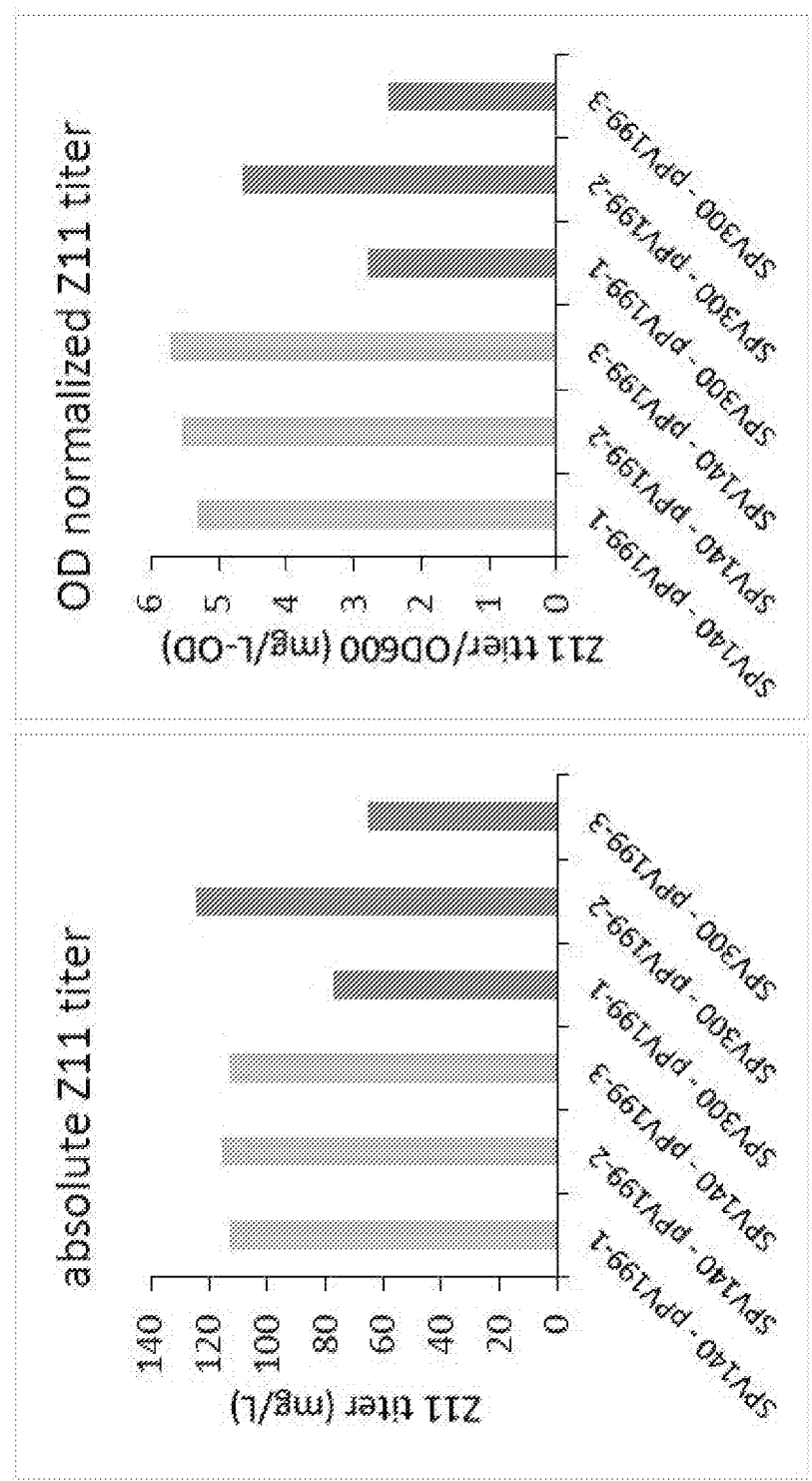
FIG. 29 shows individual isolate Z11-hexadecenoic acid titers for SPV140 and SPV300 strains expressing *H. zea* Z11 desaturase with *H. sapiens* codon optimization.

A follow up experiment was conducted comparing active variants in the SPV140 background to SPV300 derived desaturase strains. The parent SPV300 and SPV140 expressing hrGFP were used as negative controls. The same bioconversion assay protocol was used. As in SPV140, only *H. sapiens* optimized variants produced detectable activity (FIG. 27). SPV300 strains grew to higher final cell densities (SPV300 OD600=26-28, SPV140 OD600=19-22) (FIG. 28). The highest titers were observed for strains expressing the native *H. zea* Z11-desaturase with *H. sapiens* codon optimization (pPV199). The retested SPV140 strains produced 113±1 mg/L (5.5±0.2 mg/L/OD) Z11-hexadecenoic acid which is 13% higher than titers observed in the first experiment (FIG. 29). SPV300 strains expressing the same desaturase generated a wider range of productivity. On average they produced 89±18 mg/L (3.3±1.2 mg/L/OD) Z11-hexadecenoic acid, but one clone produced 124 mg/L (4.6 mg/L/OD) Z11-hexadecenoic acid.

In summary, only the *H. zea* Z11 desaturase variants with *Homo sapiens* codon optimization produced detectable Z11-hexadecenoic acid. Under the current assay condition, marginally higher titers were observed in the SPV140 background over SPV300. Table 11 summarizes the Z11-hexadecenoic acid titers.

TABLE 11

Z11-hexadecenoic acid titers obtained from expression of exemplary desaturases in *Yarrowia lipolytica*

| Desaturase | Codon optimization | Parent Strain | Z11-hexadecenoic acid titer (mg/L) |
| --- | --- | --- | --- |
| Z11 T. ni | Native | SPV140 | ND (no detection) |
| Z11 T. ni | Homo sapiens | SPV140 | ND |
| Yl OLE1-Z11 T. ni | Homo sapiens | SPV140 | ND |
| Z11 H. zea | Native | SPV140 | ND |
|  |  | SPV300 | ND |
| Z11 H. zea | Homo sapiens | SPV140 | 100 ± 5 |
|  |  | SPV300 | 87 ± 18 |
| Yl OLE1-Z11 H. zea | Homo sapiens | SPV140 | 83 ± 11 |
|  |  | SPV300 | 55 ± 1 |
| Z11 A. transitella | Native | SPV140 | ND |
|  |  | SPV300 | ND |

In SPV300, one non-site-specific integrant of pPV200 (*Y. lipolytica* OLE1-*H. zea* Z1 desaturase with *Homo sapiens* codon optimization) was tested. This integrant did not produce detectable Z11-hexadecenoic acid, while the two site-specific integrants produced 55+1 mg/L.

No major hydroxy or diacid peaks were observed from pellets of SPV140 or SPV300 derived strains, and deletion of β-oxidation/ω-oxidation genes in SPV300 did not increase Z11-hexadecenoic acid accumulation under the current assay condition (relatively low substrate concentration, rich medium).

Conclusions

The *H. zea* Z11 desaturase is active and confers production of ~100 mg/L Z11-hexadecenoic acid, from ~500 mg/L palmitic acid substrate. The functional expression was demonstrated across three positive integrants and replicate experiments in a 24 well plate assay.

*H. zea* desaturase required codon optimization (*Homo sapiens* or potentially *Y. lipolytica*) for activity in *Y. lipolytica*.

The *T. ni* Z11 desaturase, while active in *S. cerevisiae*, does not produce detectable Z11-hexadecenoic acid in *Y. lipolytica*.

The reproducibility of the assay for *Y. lipolytica* strains can be confirmed starting from glycerol stock.

*A. transitella* desaturase can be codon optimized for expression in *Y. lipolytica*.

Since *Y. lipolytica* is a candidate production host, additional copies of active desaturases can be integrated in *Y. lipolytica*, culture conditions to improve bioconversion can be identified, and substrate conversion can be quantified.

Materials & Methods

Strain Construction

All desaturase genes were synthesized (Genscript). Either native sequences or *Homo sapiens* codon optimization was used. Synthesized genes were subcloned into pPV101. Plasmids were transformed and prepped from *E. coli* EPI400 using the Zyppy Plasmid Miniprep Kit (Zymo Research, Irvine, Calif.). Approximately ~1-2 μg of linearized DNA was transformed using Frozen-EZ Yeast Transformation II Kit (Zymo Research. Irvine, Calif.). The entire transformation mixture was plated on CM glucose-ura agar plates. Positive integrants were found to be site-specific and genotyping was conducted by check PCR.

Functional Expression Assay

Palmitic Acid Supplementation in YPD

Positive isolates were re-patched onto YPD, grown overnight, and then stored at 4° C. Strains were inoculated from patch plates into 2 ml of YPD in 24 deep well plates (square well, pyramid bottom). Three positive clones were inoculated for each desaturase variant. Three isolates of pPV101 in SPV140 and the parent SPV300 were used as negative controls. Deep well plates were incubated at 28° C. and 250 rpm in the Infors Multitron refrigerated flask shaker for 24 hrs. After 24 hrs of incubation, a 1 ml volume of each culture was pelleted by centrifugation at 500×g. Each pellet was resuspended in 2 ml of YPD, 500 mg/L palmitic acid was added to cultures from a 90 g/L stock solution in ethanol. The result was the addition of 0.5% ethanol with the palmitic acid substrate. All cultures were incubated for 48 hours before endpoint sampling. Final cell densities were measured with the Tecan Infinite 200pro plate reader, 0.75 or 0.8 ml of each culture was harvested in 1.7 ml microcentrifuge tubes and pelleted. Supernatant was removed and pellets were processed as described below.

Metabolite Extraction and GC-FID Analysis

Total lipid composition as well as the (Z)-11-hexadecenoic acid quantification was based on modified procedures by Moss et al. (1982) and Yousuf et al (2010). The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL crimp vial. The mixture was heated for 1 h in the heat block at 90° C. Prior to acidification with 400 2.5 N HCl the vial was allowed to cool to room temperature. 500 μL chloroform containing 1 mM methyl heptadecanoate were added and the mixture was shaken vigorously, then both aqueous and organic phase were transferred into a 1.5 mL plastic tube. The mixture was centrifuged at 13,000 rpm, afterwards 450 μL of the organic phase were transferred into a GC vial. For the analysis of lipids and the quantification of fatty acids 50 L of 0.2 M TMSH (trimethylsulfonium hydroxide in methanol) was added and the sample analyzed by GC-FID.

Example 8: *Candida viswanathii* (*Tropicalis*) as a Production Platform for Insect Fatty Alcohol Synthesis Background and Rationale Variants of insect transmembrane desaturases and reductases were previously screened and rank-ordered based on their functional expression in either *Candida viswanathii* or *Saccharomyces cerevisiae* (see Examples 3, 4 and 6). *Helicoverpa zea* desaturase and *Helicoverpa armigera* reductase were selected to assemble a synthetic insect fatty alcohol pathway in *C. viswanathii*. Simultaneous expression of codon optimized *H. zea* desaturase under *Candida* isocitrate lyase (ICL) promoter, and codon optimized *H. armigera* reductase under *Candida* transcription elongation factor (TEF) promoter was achieved via genomic integration of the full fatty alcohol pathway. Accumulation of Z11-16OH was achieved in cultures of the recombinant strain (SPV0490) using simple carbon sources and palmitic acid.

Summary of Approach

Integration plasmids were designed containing a functional *Helicoverpa zea* desaturase (See Example 6) paired with a *Helicoverpa armigera* reductase driven by a putatively constitutive *C. tropicalis* promoter (pTEF).

Functionality of the full pathway was assessed via an in vivo bioconversion of hexadecanoic acid (palmitic acid) into Z11-16OH.

GC-FID and GC-MS analyses were used to identify and quantify metabolites.

Results

Figure 30:
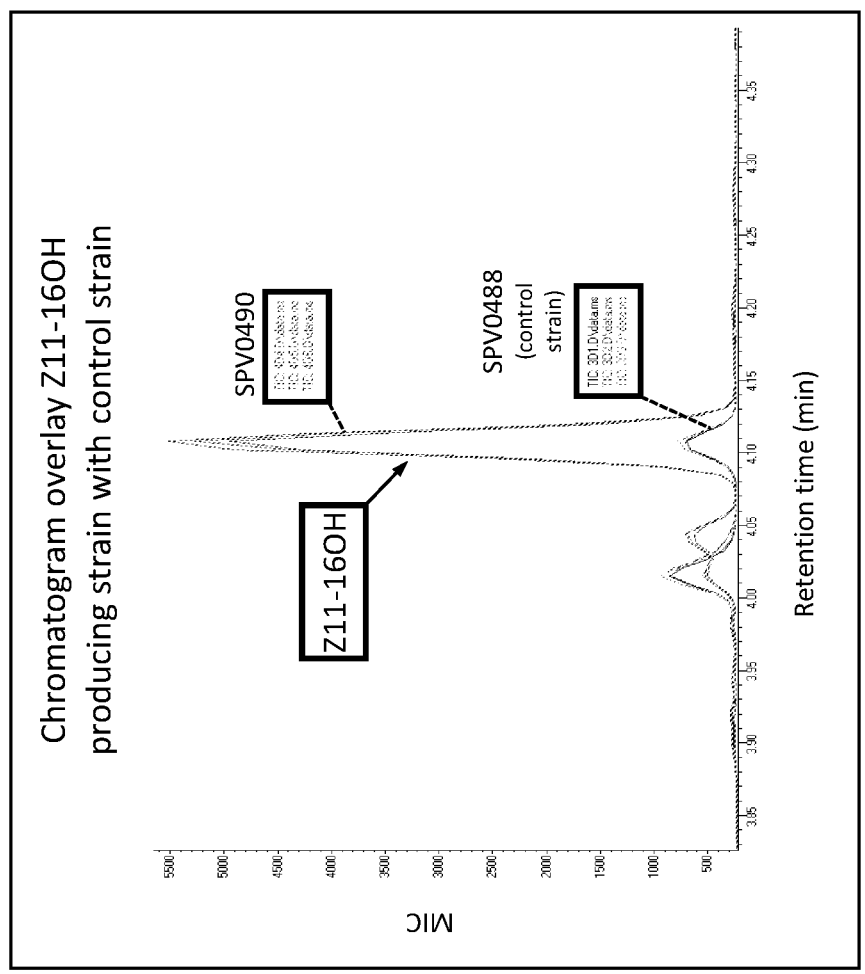
FIG. 30 shows a chromatogram overlay of extracted metabolites for Z11-16OH producing strain (SPV0490) versus control strain (SPV0488) of *Candida viswanathii* (*tropicalis*).
Figure 31:
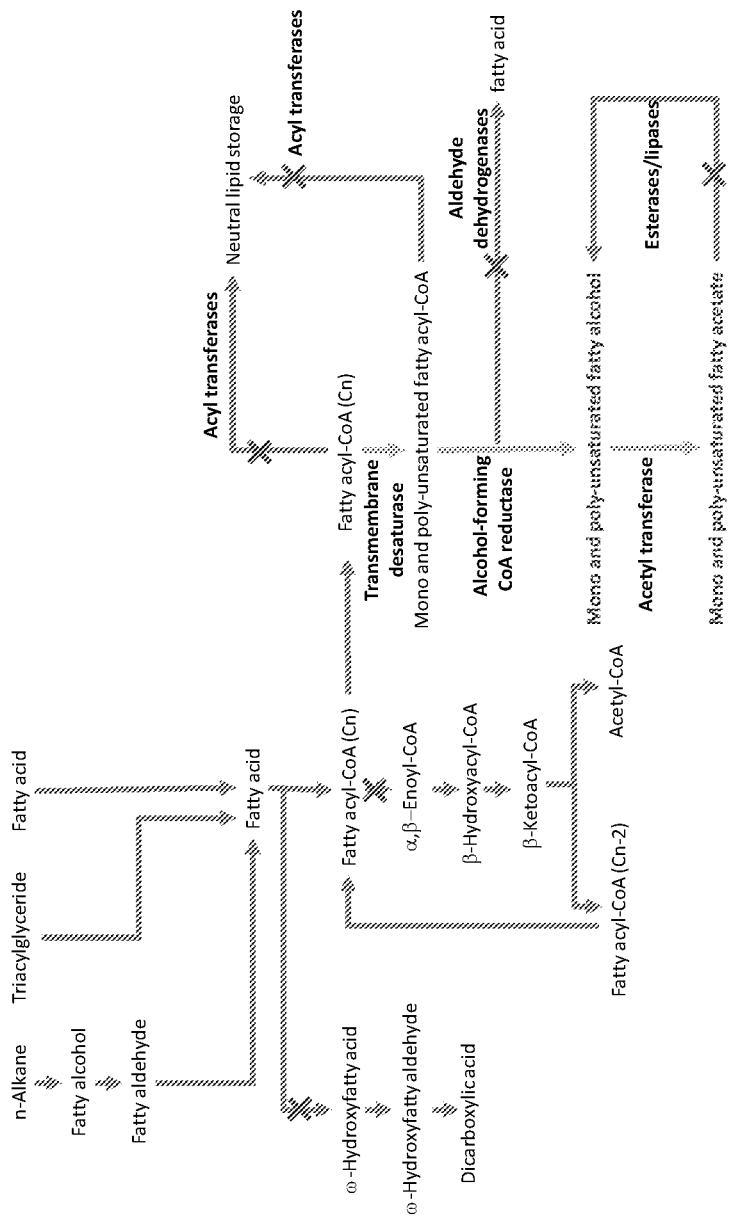
FIG. 31 illustrates pathways that can be deleted or disrupted to reduce or eliminate competition with the biosynthesis pathway for the production of a mono- or poly-unsaturated $C_6$-$C_{24}$ fatty alcohol, aldehyde, or acetate.

Accumulation of Z11-16OH was detected in cultures of *Candida* engineered to express *H. zea* desaturase under an ICL promoter and *H. armigera* reductase under a TEF promoter (Table 12 and FIG. 30).

TABLE 12

Tabulated Z11-16OH titers from *Candida viswanathii* bioconversion assay. SPV088 is *C. viswanathii* which was engineered to express mCherry (negative control).
SPV0490 is *C. viswanathii* which was engineered to express the insect fatty alcohol pathway.
Z11-16OH titers (mg/L)

|  | SPV0488 (negative control) | SPV0490 |
|---|---|---|
| Sample 1 | 0.08 | 1.03 |
| Sample 2 | 0.07 | 0.93 |
| Sample 3 | 0.06 | 0.88 |
| Average | 0.07 | 0.95 |
| StDev | 0.01 | 0.06 |

Materials & Methods

Strain Construction

The integration plasmid (ppV0228) was designed to contain two expression cassettes. The first cassette contains *H. zea* codon-optimized desaturase (SEQ ID NO: 31) that was driven by the *C. viswanathii* ICL promoter (SEQ ID NO: 33). The second cassette contains codon-optimized *H. armigera* reductase (SEQ ID NO: 32) driven by the *C. tropicalis* TEF promoter (SEQ ID NO: 34). Gene expression in the ICL promoter cassette is terminated by the ICL terminator sequence (SEQ ID NO: 35). Gene expression in the TEF promoter cassette is terminated by the TEF terminator sequence (SEQ ID NO: 36). A conservative approach was used for recoding of genes. Native gene sequences were unaltered except for replacement of CTG leucine codons with TTA. After transformation into *E. coli* NEB10β, plasmids were miniprepped using the Zyppy Plasmid Miniprep Kit (Zymo Research, Irvine, Calif.). Plasmids were linearized by digestion with BsiWI (New England Biolabs, Ipswich, Mass.) before transformation into SPV053. After digestion, DNA was isolated using Clean and Concentrator Kit (Zymo Research, Irvine, Calif.). Approximately 3-5 μg of DNA was transformed by electroporation. Positive integrants were found to be site-specific and genotyping was conducted by check PCR. A two-stage approach was adopted for further screening of low efficiency transformations. Approximately 100 colonies were re-patched on YPD+250 μg/ml Zeocin and grown overnight. The subset of patches which grew quickly (dense growth within 24 hours) were screened by colony PCR.

Functional Expression Assay

Palmitic Acid Supplementation in YPD

Positive isolates were re-patched onto YPD+300 μg/ml Zeocin, grown overnight and then stored at 4° C. Strains were inoculated from patch plates into 2 ml of YPD in 24 deep well plates (square well, pyramid bottom). Four positive clones were inoculated for each desaturase and reductase variant and three positive clones were inoculated for each desaturase and mCherry expressing control strain. Deep well plates were incubated at 30° C., 1000 rpm, and 80% humidity in the Infors HT Multitron Pro plate shaker for 24 hrs. After 24 hrs of incubation, a 1 ml volume of each culture was pelleted by centrifugation at 500×g. Each pellet was resuspended in 2 ml of YPD+0.3% (v/v) ethanol. Ethanol was added at this stage to induce recombinant enzyme expression from the ICL promoter. Cultures were incubated for another 24 hours under the same conditions before 300 mg/L palmitic acid was added to cultures from a 90 g/L stock solution in ethanol. The result was the addition of a fresh 0.3% ethanol in conjunction with the palmitic acid. All cultures were incubated for an additional 24 hrs before a final addition of 0.3% ethanol. After another 24 hr period of incubation, 1.5 ml of each culture was harvested in 1.7 ml microcentrifuge tubes and pelleted. Supernatant was removed and pellets were processed as described below.

Metabolite Extraction and GC-MS Detection

The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL crimp vial. The mixture was heated for 1 h in a heat block at 90° C. Prior to acidification with 400 μL 2.5 N HCl the vial was allowed to cool to room temperature. 500 μL chloroform containing 1 mM methyl heptadecanoate were added and the mixture was shaken vigorously, then both aqueous and organic phase were transferred into a 1.5 mL plastic tube. The mixture was centrifuged at 13,000 rpm, afterwards 450 μL of the organic phase were transferred into a GC vial. The organic phase was evaporated in a heat block at 90° C. for 30 min. The residue was dissolved in 50 μL N,O-Bis(trimethylsilyl) trifluoroacetamide containing 10/trimethylchlorosilane. Prior to transfer into glass inserts the mixture was heated 5 min at 90° C. The samples were analyzed by GC-MS (Table 13).

TABLE 13

Analytical parameters used for GC-MS analysis of metabolites

| System | Agilent 6890 N GC, ChemStation G1701EA E.02.01.1177 |
|---|---|
| Column | DB23 30 m × 25 μm × 25 μm |
| | Pressure = 11.60 psi; Flow = 0.6 mL/min |
| Inlet | Heater = 250° C.; Pressure = 11.74 psi; |
| | Total Flow {He} = 111 mL/min |
| Carrier | He @ 29 cm/sec, 11.60 psi |
| Signal | Data rate = 2 Hz/0.1 min |
| Oven | 150° C. for 1 min |
| | Ramp 12° C./min to 220° C., hold 3 min |
| | Ramp 35° C./min to 300° C., hold 4 min |
| Injection | Splitless, 250° C. |
| Detector | HP 5973 MSD in SIM mode (m/z: 208.0, 297.3 and 387.3), |
| | 100 msec Dwell, EMV mode: Gain factor 1, |
| | 2.4 min solvent delay, 3.09 cycles/sec |
| Sample | Injection volume = 1 μL |

Example 9: Insect Fatty Alcohol Production from *Yarrowia lipolytica*

Background and Rationale

*Yarrowia lipolytica* was engineered as a production platform for insect fatty alcohol (Z11-16OH and Z9-16OH) synthesis from palmitic acid.

After individually confirming functional expression of a Z11 desaturase (Example 7) and fatty acyl-CoA reductase (FAR), the full Z11-16OH and Z9-16OH pathways (Bdr) were engineered in *Y. lipolytica*. For the purpose of improving fatty alcohol titers, cultivations designed for promoting growth vs. for eliciting lipid storage were also explored. A growth condition favors high biomass production, but limits fatty acyl-CoA pool size used by the engineered pathway and directs fatty acyl-CoA intermediates to membrane synthesis. Conversely, a lipid storage condition creates a strong sink for production of fatty acyl-CoAs which is desirable. However, fatty acyl-CoA transport towards lipid bodies creates a strong competition for FAR activity. Under this second scenario, even though Z11-16Acid or Z9-16Acid accumulates in the cell, most of it is inaccessible to the FAR.

On the other hand, there may be a continual flux of lipid remobilization under lipid storage conditions which leads to a sustained pool of Z11-16CoA or Z9-16CoA which is available to the FAR.

Summary of Approach

Two biodesaturation-reduction (Be) pathway variants were tested in the H222 ΔPΔAΔF (SPV300) background. The first combined recombinant expression of *Helicoverpa zea* Z11 desaturase paired with a *Helicoverpa armigera* fatty acyl-CoA reductase (FAR amino acid sequence set forth in SEQ ID NO: 41) creating a Z11-16OH synthesis pathway. The second combined native *Y. lipolytica* Z9 desaturase activity with *H. armigera* fatty acyl-CoA reductase (FAR) expression creating a Z9-16OH pathway.

Two integration plasmids were constructed to express the *H. zea* desaturase and the *H. armigera* FAR. The TEF promoter was used for desaturase expression and the EXP1 (export protein) or the TAL (transaldolase) promoter was used for reductase expression.

Successful integration of the Z11-16OH pathway cassette into the H222 ΔPΔAΔF (SPV300) background was confirmed by colony PCR.

Functionality of the full Z11-16OH pathway was assessed via an in vivo bioconversion of 16Acid (palmitic acid) into Z11-16OH (Z-11-hexadecenol).

Functionality of a full Z9-16OH pathway was assessed via an in vivo bioconversion of 16Acid (palmitic acid) using previously constructed SPV471 (H222 ΔPΔAΔF derived) which expresses the *H. armigera* FAR driven by the TEF promoter.

GC-MS analysis was used to identify and quantify Z9-16OH and Z11-16OH. GC-FID analysis was used to identify and quantify fatty acids.

Summary

Ten isolates expressing the *H. zea* desaturase (pTEF) and *H. armigera* reductase (pEXP1) were screened. The in vivo bioconversion assay confirmed Z11-16OH production from all isolates.

Relatively low, detectable Z11-16OH titers (0.26±0.09 mg/L) were observed in a YPD medium supplemented with 10 g/L methyl palmitate. The Z11-16Acid precursor was measured at 220±11 mg/L (across clones 2, 4, 9, 17, 23).

Higher Z11-16OH titers were observed in a semi-defined medium with C:N ratio of ~80. Across all 10 isolates Z11-16OH was produced at 2.65±0.36 mg/L. The Z11-16Acid precursor titer was 900±30 mg/L. One isolate (SPV578) produced 3.68±0.31 mg/L Z11-16OH (Z11-16Acid 840±14 mg/L).

Nine isolates expressing the *H. zea* desaturase (pTEF) and *H. armigera* reductase (pTAL1) were screened. The in vivo bioconversion assay confirmed Z11-16OH production from all isolates.

One isolate (SPV603) produced 6.82±1.11 mg/L Z-16OH in a semi-defined medium (Z11-16Acid 1.36 g/L).

The previously tested reductase strain, SPV471 (H222 ΔPΔAΔF expressing *H. armigera* FAR), produced 4.30±2.33 mg/L Z9-16OH and 450±80 mg/L Z9-16Acid using a semi-defined medium (C:N ratio of ~80).

TABLE 14

Summary table of Z11/Z9-16OH titers from $B_{dr}$ pathway strains in in vivo bioconversion assay.

| Strain | Medium | Z11-16OH (mg/L) | Z9-16OH (mg/L) |
|---|---|---|---|
| pTEF-*H. zea* Z11 desaturase pEXP-*H. armigera* FAR Clone 17 (SPV578) | Semi-Defined C:N = 80 | 3.99 ± 0.37 (n = 4) | 0.22 ± 0.03 (n = 4) |
| pTEF-*H. zea* Z11 desaturase pEXP-*H. armigera* FAR Clone 9 (SPV603) | Semi-Defined C:N = 80 | 6.82 ± 1.11 (n = 2) | 0.22 ± 0.01 (n = 2) |
| pOLE1-*Y. lipolytica* OLE1 (native) pTEF-*H. armigera* FAR (SPV471) | Semi-Defined C:N = 80 | 0.22 ± 0.03 (n = 2) | 4.30 ± 2.23 (n = 2) |

Results

Strain Construction

Evidence in the literature suggests both insect desaturases and FARs are localized in the membrane of the endoplasmic reticulum with active sites oriented towards the cytoplasm. Of the functional variants, the Z11 desaturase from *H. zea* and the FAR from *H. armigera* (FAR amino acid sequence set forth in SEQ ID NO: 41) were selected, one hypothesis being that using enzymes from the same genus (*Helicoverpa*) could better conserve protein-protein interactions that may occur in the ER membrane.

Two new constructs were ordered from Genscript and cloned into the previously assembled *H. zea* desaturase plasmid, pPV0199. Two FAR synthons with either the EXP1 or TAL1 promoter from *Y. lipolytica* were cloned into this expression cassette.

One dual expression plasmid (with EXP1 promoter) was transformed into the parent strain SPV300 (H222 Δpox1 Δpox2 Δpox3 Δpox4 Δpox5 Δpox6 Δadh1 Δadh2 Δadh3 Δadh4 Δadh5 Δadh6 Δadh7 Δfao1 Δura3). Two different competent cell preparations of the same parent strain were transformed to study variability in strain performance resulting from competent cell preparation. Approximately 25% of URA+ clones were confirmed to be targeted integrants at the XPR2 locus (20% for preparation 1, 33% for preparation 2). Two clones from Comp. Cell Preparation 1 and all eight targeted clones from Comp. Cell Preparation 2 were selected for screening in the functional expression assay.

The second dual expression plasmid (with TAL1 promoter) was integrated into the same parent strain (SPV300). Twenty-three colonies were screened by check PCR and 11 were found to be targeted integrants (48%). Nine integrants were selected for screening in the functional expression assay.

The construct of SPV471 (H222 ΔPΔAΔF expressing *H. armigera* FAR) was described previously.

Z11-16OH Functional Expression Assay

An in vivo, 24-well plate assay was used to evaluate production of Z11-16OH. The assay was based on designs used for screening desaturase and reductase variants as well as conditions used to increase fatty acid accumulation. A rich medium (YPD) and a semi-defined medium were used with 10 g/L methyl palmitate supplemented as bioconversion substrate. The semi-defined medium had a C:N ratio of ~80 and included 5 g/L glycerol and 60 g/L glucose (See Materials & Methods for further details).

Figure 32:
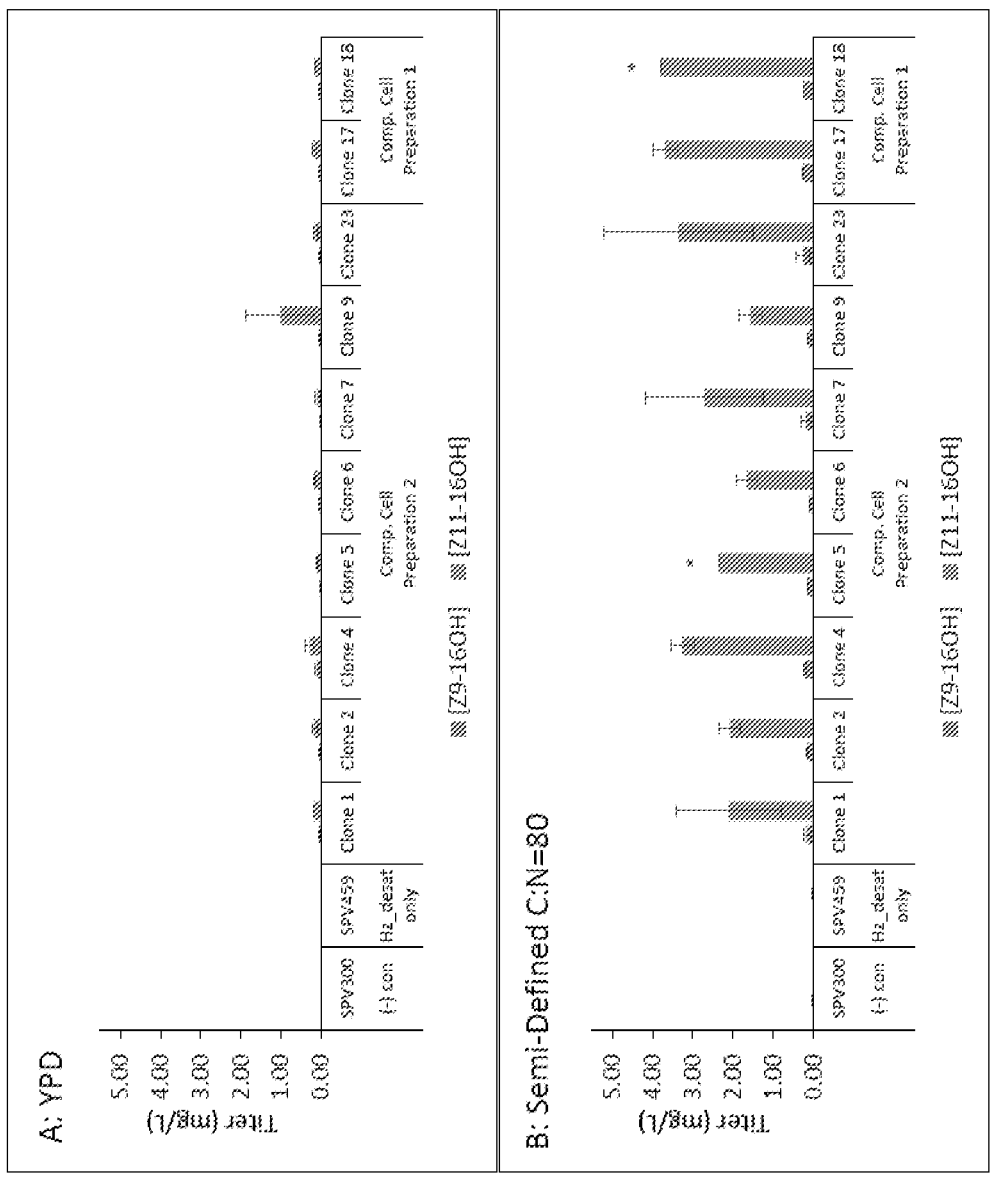
FIG. 32A-FIG. 32B shows Z9-16OH and Z11-16OH titers in YPD (FIG. 32A) and Semi-Defined C:N=80 (FIG. 32B) media for pEXP clones. Ten isolates expressing the *H. zea* desaturase under the TEF promoter and *H. armigera* reductase under the EXP promoter from two independent competent cell preparations (Comp. Cell Preparation 1, Comp. Cell Preparation 2) were compared to a parental negative control (SPV300) and a desaturase only negative control (SPV459 Hz_desat only). Error bars represent the SEM (standard error of the mean) measured from technical replicates for each strain and condition (N=2). *One replicate from Clone 5 and Clone 18 under the Semi-Defined C:N=80 condition was lost during sample work-up so the titers for that condition are from a single data point (N=1, Comp. Cell Preparation 1 Clone 18 and Comp. Cell Preparation 2 Clone 5).

The initial screen of strains harboring the *H. zea* desaturase driven by the TEF promoter and the *H. armigera* FAR (FAR amino acid sequence set forth in SEQ ID NO: 41)

driven by the EXP1 promoter confirmed that the presence of FAR was required to produce Z11-16OH. No hexadecenol was observed from both the parent and desaturase-only control strains under any condition. Under both media conditions Z11-16OH and to a lesser extent Z9-16OH were detected from clones expressing the full desaturase-reductase pathway. When the conversion was completed in rich medium, 0.26±0.09 mg/L Z11-16OH and 0.06±0.01 mg/L Z9-16OH were produced (FIG. 32A). A10-fold increase in Z11-16OH titer and 3-fold increase in Z9-16OH titer was observed when the Semi-Defined medium was used (FIG. 32B). Across all pathway clones 2.65±0.29 mg/L Z11-16OH and 0.18±0.02 mg/L Z9-16OH were produced. The enrichment of Z11-16OH over Z9-16OH supports the potential for engineering a regiospecific Bdr pathway. Consistency between technical replicates varied across clones under the Semi-Defined medium condition. Titers for Clones 2, 4, 6, 9, and 17 were consistent with CVs <20. Clones 1, 7, and 23 have CVs >40%. The highest consistent Z11-16OH titer was observed for Clone 17, 3.68±31 mg/L (Table 15).

TABLE 15

Summary table of Z11/Z9-16OH tilers for pEXP1 clones. A population of ten isolates expressing the H. zea desaturase driven by pTEF and H. armigera reductase driven by pEXP1, from two independent competent cell preparations, were assayed for Z11-16OH and Z9-16OH production under two different media conditions. Alcohol production across isolates and from select clones are presented.

| pTEF-Hz_desat pEXP-Ha_FAR Clone(s) | Medium | Z11-16OH (mg/L) | Z9-16OH (mg/L) | Z11-16OH fold increase (relative to YPD) | Z9-16OH fold increase (relative to YPD) |
|---|---|---|---|---|---|
| All clones | YPD | 0.26 ± 0.09 | 0.06 ± 0.01 | — | — |
| All clones | Semi-Defined | 2.65 ± 0.29 | 0.18 ± 0.02 | 10 | 3 |
| Clone 2 (SPV574) | YPD | 0.18 ± 0.09 | 0.05 ± 0.03 | — | — |
| Clone 2 (SPV574) | Semi-Defined | 2.08 ± 0.26 | 0.14 ± 0.04 | 12 | 3 |
| Clone 4 (SPV575) | YPD | 0.28 ± 0.01 | 0.11 ± 0.01 | — | — |
| Clone 4 (SPV575) | Semi-Defined | 3.24 ± 0.28 | 0.21 ± 0.03 | 12 | 2 |
| Clone 9 (SPV576) | YPD | 1.03 ± 0.84 | 0.05 ± 0.01 | — | — |
| Clone 9 (SPV576) | Semi-Defined | 1.56 ± 0.28 | 0.11 ± 0.02 | 1.5 | 2 |
| Clone 23 (SPV577) | YPD | 0.16 ± 0.14 | 0.05 ± 0.05 | — | — |
| Clone 23 (SPV577) | Semi-Defined | 3.35 ± 1.85 | 0.26 ± 0.15 | 21 | 5 |
| Clone 17 (SPV578) | YPD | 0.19 ± 0.01 | 0.06 ± 0.01 | — | — |
| Clone 17 (SPV578) | Semi-Defined | 3.68 ± 0.31 | 0.26 ± 0.02 | 14 | 4 |

Figure 33:
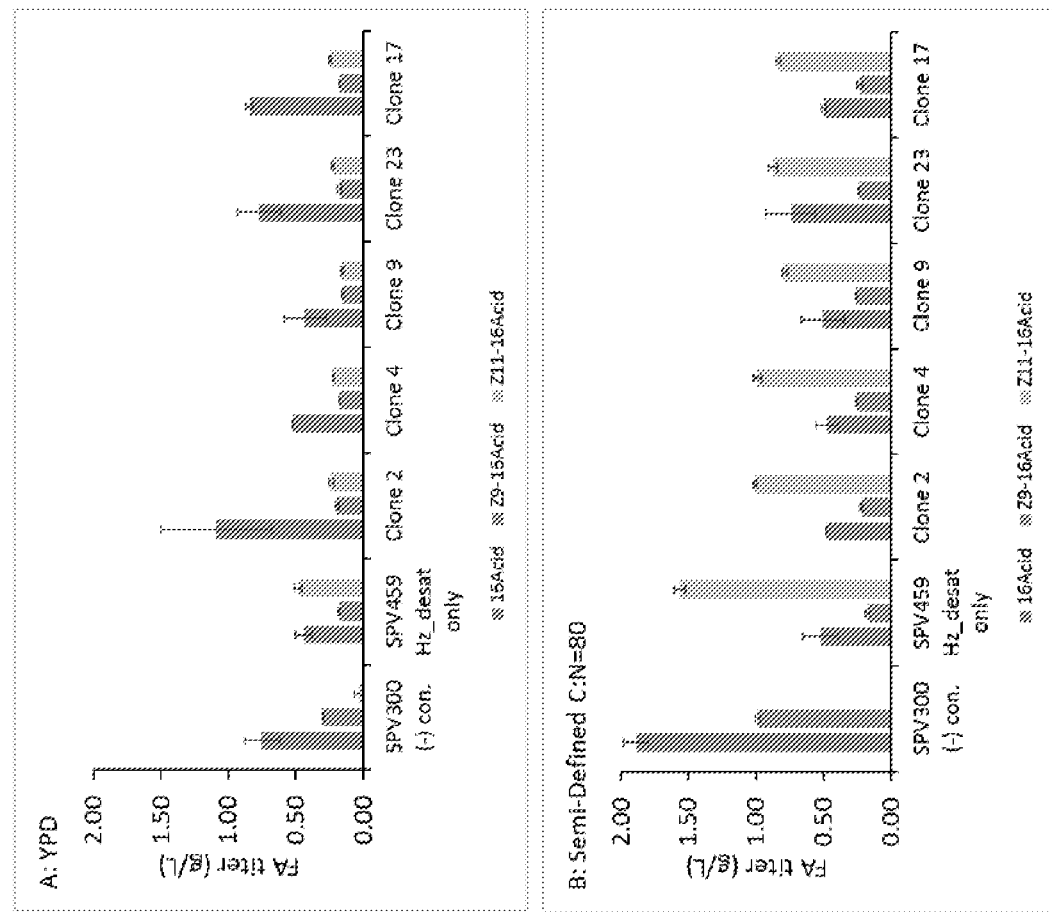
FIG. 33A-FIG. 33B shows profiles of 16-carbon fatty acid species in YPD (FIG. 33A) and Semi-Defined C:N=80 (FIG. 33B) media for pEXP1 clones. The 16-carbon lipid profiles of 5 select clones expressing the *H. zea* desaturase under the TEF promoter and *H. armigera* reductase under the EXP promoter are compared to a parental negative control (SPV300) and a desaturase only negative control (SPV459 Hz_desat only). Error bars represent the SEM (standard error of the mean) measured from technical replicates for each strain and condition (N=2).

The lipid profiles of the full pathway clones were also quantified. For simplicity the 16 carbon fatty acid species are plotted for select clones in FIG. 33A-33B. In general, the full Bdr pathway clones accumulated less Z11-16Acid than the desaturase only control (0.25<0.5 g/L in YPD, 0.8-1.0<1.5 g/L in Semi-Defined). Lower Z11-16Acid titers in full Bdr pathway clones may result from reduced desaturase expression in the dual expression cassette or potentially from Z11-16Acid consumption by FAR and subsequent byproduct pathways. No trend in 16Acid titer was observed in YPD, while 16Acid titers were similar for desaturase only and full pathway strains in the Semi-Defined medium.

Figure 34:
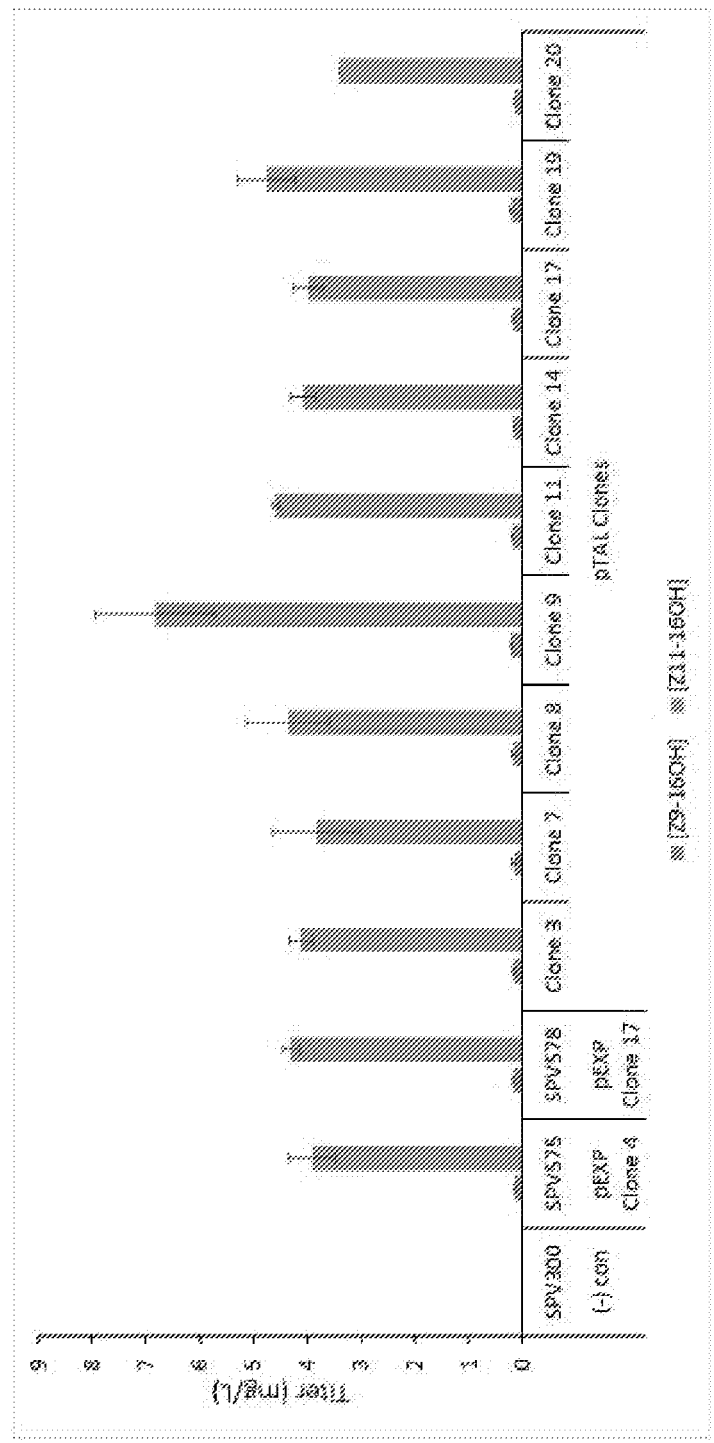
FIG. 34 shows Z9-16OH and Z11-16OH titers in Semi-Defined C:N=80 media for pTAL1 clones. Nine isolates expressing the *H. zea* desaturase under the TEF promoter and *H. armigera* reductase under the TAL promoter were compared to a parental negative control (SPV300) and positive Bdr pathway controls using the EXP promoter to drive *H. armigera* FAR expression (SPV575, SPV578). Error bars represent the SEM (standard error of the mean) measured from technical replicates for each strain and condition (N=2).

Strains using the second dual expression cassette (pTAL-Ha_FAR) were assayed under the same Semi-Defined medium condition used to evaluate the pEXP clones. Nine pTAL clones were assayed against SPV300 (parent), SPV575 (pEXP-Ha_FAR Clone 4), and SPV578 (pEXP-Ha_FAR Clone 17) controls. As expected, no alcohol products were observed from the negative control. Alcohol titers from pEXP positive control strains replicated results observed in the initial assay of pEXP clones (FIG. 34, Table 16). Excluding one outlier clone, Clone 9. Z11-16OH titer was equivalent from pTAL clones (4.19±0.16 mg/L) and pEXP clones (4.10±0.22 mg/L). Clone 9 produced Z11-16OH at 6.82±1.11 mg/L. As in the first assay with pEXP clones, low but detectable titers of Z9-16OH were observed (FIG. 34, Table 16).

TABLE 16

Summary table of Z11/Z9-16OH titers for pTAL1 clones. A population of nine isolates expressing the H. zea desaturase under the TEF promoter and H. armigera reductase under the TAL promoter were assayed for Z11-16OH and Z9-16OH production under a Semi-Defined medium condition. Clones were compared to positive controls expressing the H. zea desaturase under the TEF promoter and H. armigera reductase under the EXP promoter. Alcohol production across isolates and from select clones are presented.

| pTEF-Hz-desat pEXP-Ha-FAR Clone(s) | Medium | Z11-16OH (mg/L) | Z9-16OH (mg/L) |
|---|---|---|---|
| EXP Clone 4 (SPV575) | Semi-Defined | 3.91 ± 0.44 | 0.15 ± 0.01 |
| EXP Clone 17 (SPV578) | Semi-Defined | 4.30 ± 0.16 | 0.17 ± 0.02 |
| pTAL clones excluding Clone 9 | Semi-Defined | 4.19 ± 0.16 | 0.18 ± 0.01 |
| pTAL Clone 9 (SPV603) | Semi-Defined | 6.82 ± 1.11 | 0.22 ± 0.01 |

Figure 35:
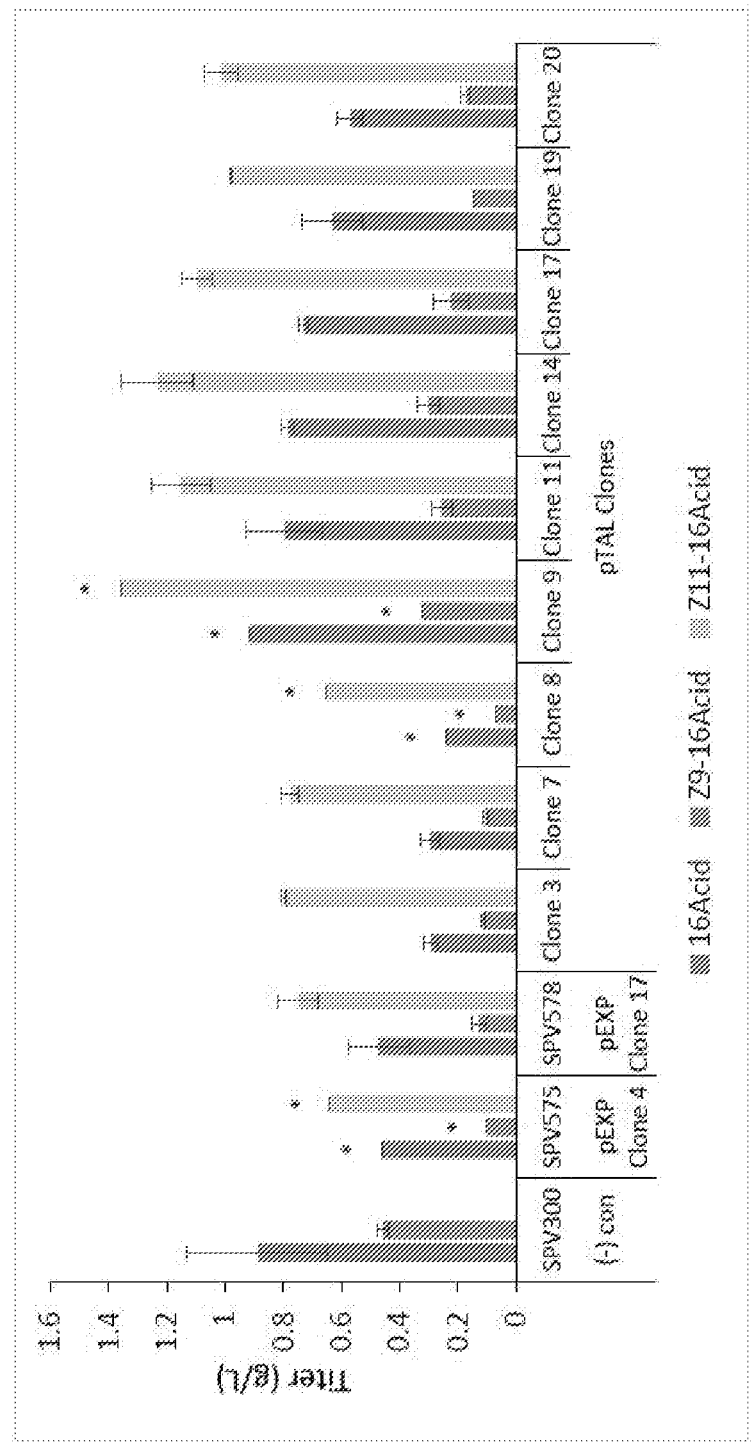
FIG. 35 shows profiles of 16-carbon fatty acid species in Semi-Defined C:N=80 medium for pTAL1 clones. The 16-carbon lipid profiles of 5 select clones expressing the *H. zea* desaturase under the TEF promoter and *H. armigera* reductase under the EXP promoter are compared to a parental negative control (SPV300) and positive Bdr pathway controls using the EXP promoter to drive *H. armigera* FAR expression (SPV575, SPV578). Error bars represent the SEM (standard error of the mean) measured from technical replicates for each strain and condition (N=2). * indicates clones for which one of the replicates was lost during sample processing, N=1.
Figure 36:
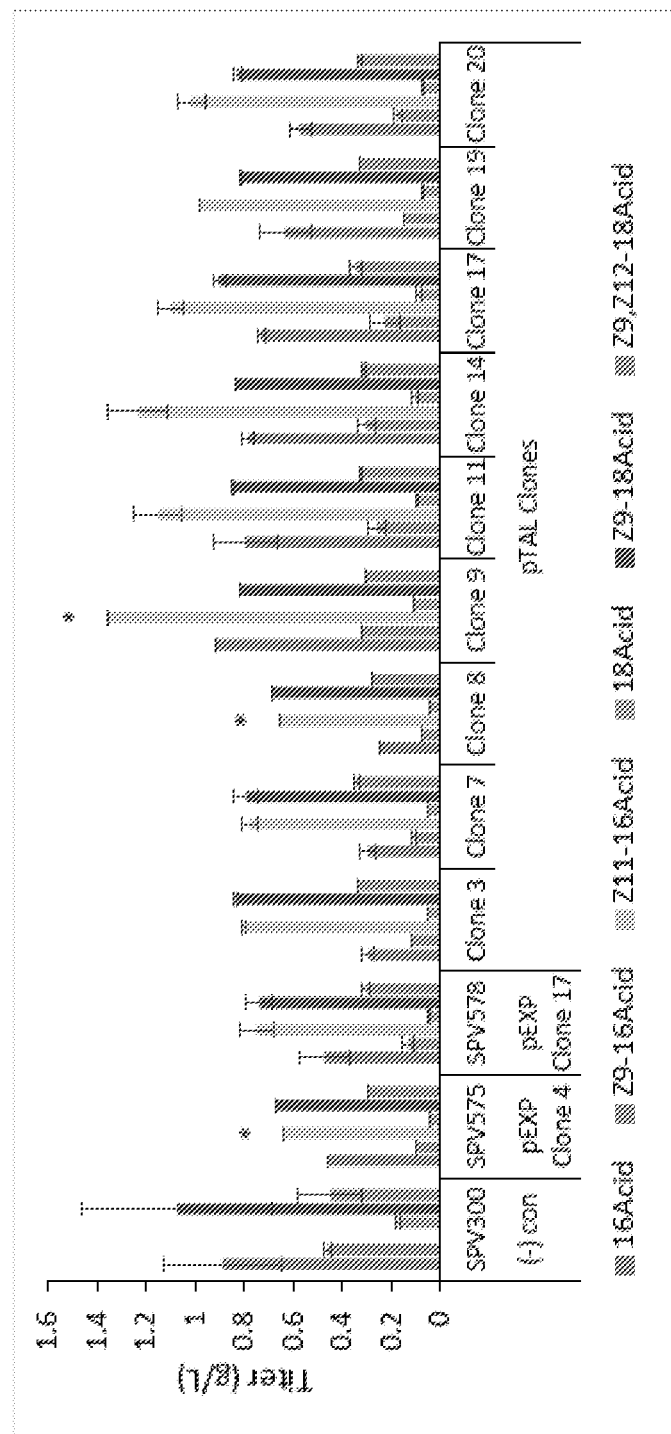
FIG. 36 shows full Bdr pathway pTAL1 screen (strains expressing *H. zea* Z11 desaturase (pTEF) and *H. armigera* FAR) full lipid profiles in Semi-Defined C:N=80 medium after 48 hours of bioconversion. Error bars represent the SEM (standard error of the mean) measured from technical replicates for each strain and condition (N=2). * indicates clones for which one of the replicates was lost during sample processing, N=1.

The lipid profiles of all strains in the second (pTAL) full pathway screen were also quantified. For simplicity the 16 carbon fatty acid species are plotted in FIG. 35. As expected, Z11-16Acid is present only for strains expressing the desaturase. Complete lipid profiles were similar to those observed previously (FIG. 36). Z9-18Acid (oleic acid) was the second most abundant fatty acid species after Z11-16Acid.

Z9-16OH Functional Expression Assay

Figure 37:
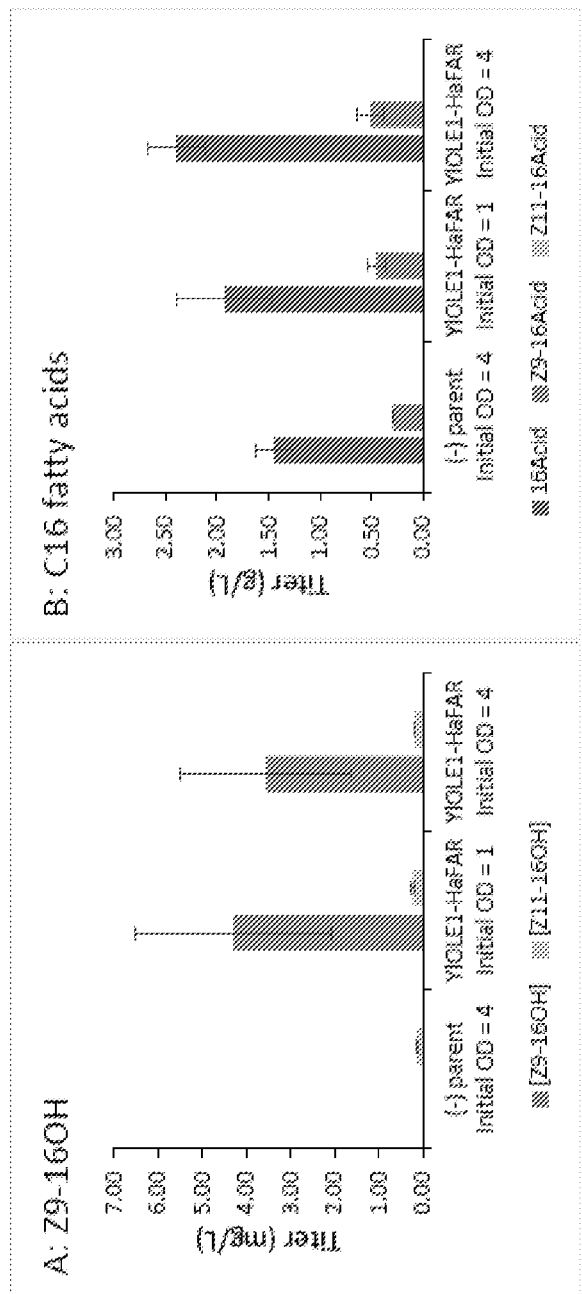
FIG. 37A-FIG. 37B shows SPV471 (H222 ΔPΔAΔF expressing native *Y. lipolytica* OLE1 and *H. armigera* FAR) Z9-16OH (FIG. 37A) and fatty acid (FIG. 37B) titers in Semi-Defined C:N=80 medium after 24 hours of bioconversion. Error bars represent the SEM (standard error of the mean) measured from technical replicates for each strain and condition (N=2).
Figure 38:
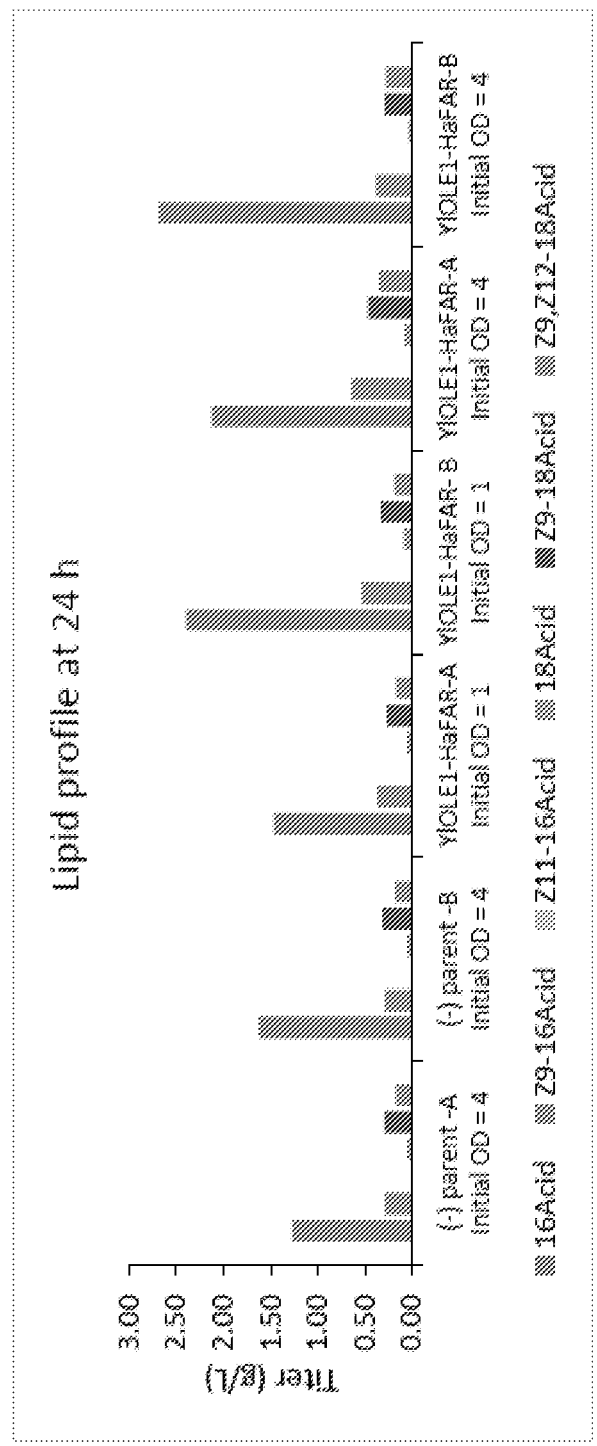
FIG. 38 shows SPV471 (H222 ΔPΔAΔF expressing native *Y. lipolytica* OLE1 and *H. armigera* FAR) full lipid profiles in Semi-Defined C:N=80 medium after 24 hours of bioconversion.
Figure 39:
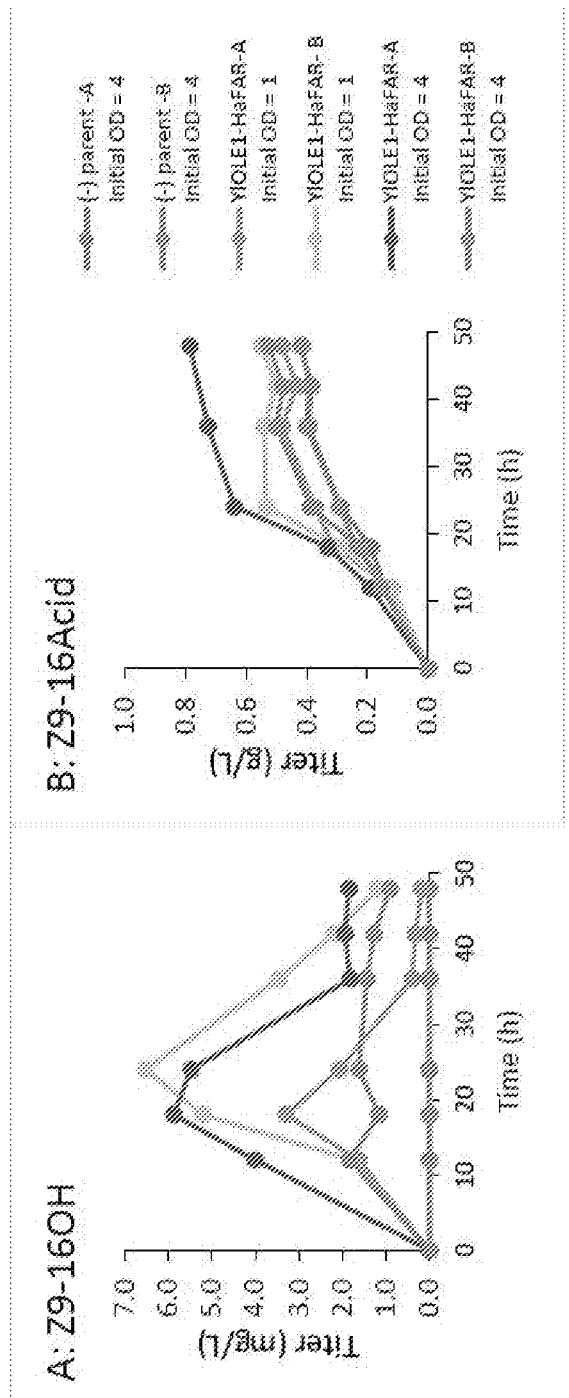
FIG. 39A-FIG. 39B shows SPV471 (H222 ΔPΔAΔF expressing native *Y. lipolytica* OLE1 and *H. armigera* FAR) Z9-16OH (FIG. 39A) and Z9-16 Acid (FIG. 39B) titer time courses. Bioconversion of 16Acid was conducted in Semi-Defined C:N=80 medium using a methyl palmitate (16Acid) substrate.

An in vivo, flask scale assay was used to test for Z9-16OH production. The parent control strain, H222 ΔPΔAΔF (SPV300), was compared to a strain expressing H. armigera FAR which relied on native Z9 desaturase activity to synthesize the Z9-16CoA precursor (SPV471). Biomass was generated through a YPD seed culture, mimicking the plate assay. Bioconversion flasks were inoculated at an initial OD600=1 or OD600=4 into the same Semi-Defined C:N=80 medium used in the Z11-16OH plate assay (See Materials & Methods for details). As expected, control flasks did not produce detectable Z9-16OH while SPV471 flasks produced up to 4.30±2.23 mg/L after 24 hours of incubation (FIG. 37A-FIG. 37B). While there was large variability between replicates, all SPV471 (H. armigera FAR) replicates exceeded 1 mg/L titer. Increased seeding density did not increase Z9-16Acid or Z9-16OH titer. The precursor Z9-16Acid titer at 24 hours was significantly less (<0.5 g/L) than the Z11-16Acid precursor observed for dual expression cassette strains used to produce Z11-16OH. The relative abundance of other fatty acid species was similar to previously observed profiles, with Z9-18Acid as the next most abundant species (FIG. 38). Both lipid and alcohol samples were taken over the course of 48 hours to produce a time course of Z9-16OH and lipid titers. Z9-16OH titer peaked at 24 hours before decreasing over the second day (FIG. 39A). Z9-16Acid increased rapidly over the first 24 hours before stabilizing or increasing slowly over the second 24 hours (FIG. 39B). Since the employed analytical method utilizes only the cell pellet, the decrease in Z9-16OH titer supports the hypothesis of downstream consumption or secretion of the alcohol products. They may be oxidized (co-oxidation), secreted as free alcohol, or derivatized and secreted as an ester. Analysis of supernatant samples using FID and MS SCAN detection revealed no detectable Z9-16OH or Z9-16OH derivatives supporting the hypothesis of consumption via oxidation pathways.

Conclusions

Combining expression of *Helicoverpa* Z11 desaturase and fatty acyl-CoA reductase led to production of Z11-16OH in *Y. lipolytica* H222 ΔPΔAΔF (SPV300) at titers >1 mg/L.

High C:N ratio conditions improved Z11-16OH titer relative to a rich medium condition.

Under lipid accumulating conditions the combination of native Z9 desaturase and *H. armigera* FAR activities are sufficient for synthesis of >1 mg/L Z9-16OH.

Titers are increased, for example, by deleting pathways consuming fatty alcohol products and/or fatty acid precursors; identifying FAR variants which exhibit higher turnover rate than *H. armigera* FAR; and/or increasing pathway copy number.

Key undesired byproducts are identified.

The possibility that some of the fatty alcohol product is converted into fatty acetate by the activity of one or more endogenous acetyltransferases is explored.

Improved host strains are engineered to eliminate the ω-oxidation pathway and components of the lipid storage pathway.

Materials & Methods

Strain Construction

All desaturase and reductase genes were ordered from Genscript. *Homo sapiens* codon optimization was used (Genscript algorithm). The newly synthesized expression cassette was subcloned into pPV199 by Genscript using the SapI restriction site. Plasmids were transformed and prepped from *E. coli* EPI400 using the Zyppy Plamsid Miniprep Kit (Zymo Research, Irvine, Calif.). Plasmids were digested with PmeI (New England Biolabs, Ipswich, Mass.) and purified by gel extraction using Zymoclean Gel DNA recovery Kit (Zymo Research, Irvine, Calif.). DNA was further concentrated using Clean and Concentrator Kit (Zymo Research, Irvine. Calif.). Approximately ~1-2 µg of DNA was transformed using Frozen-EZ Yeast Transformation II Kit (Zymo Research, Irvine, Calif.). The manufacturer's protocol was modified as follows: A 2 ml YPD seed culture was inoculated at 9 am the day before competent cell preparation. The seed was grown 8 hours (until 5 µm) before 40 ml of YPD in a 250 ml baffled shake flask (or 20 ml in a 125 ml baffled flask) was inoculated to an initial OD600 of 0.0005. The culture was incubated at 28° C. and 250 rpm ~24 hours. Cells were harvested at an OD600=0.5-1. Instead of resuspending 10 ml of culture in 1 ml of Solution 2 as in the manufacturer's instructions (OD600-10), 10 ml of SPV140 culture was resuspended in 0.5 ml (OD600-20-30). All Solution 2 aliquots were slowly frozen to −80° C. by placing the tubes in a closed Styrofoam box before putting in the −80° C. freezer, 50 µl aliquots of competent cells in 1.7 ml Eppendorf tubes were thawed on ice, DNA eluted in water was added directly to the cells, and 500 µl of Solution 3 was used to suspend the cells with gentle pipetting. Tubes were incubated at 28° C. for 3 hours with gentle vortexing every 30 minutes. The entire transformation mixture was plated on CM glucose-ura agar plates. Positive integrants were found to be site-specific and genotyping was conducted by check PCR.

Z11-16OH Functional Expression Assay

Positive isolates were repatched onto YPD, grown overnight, and then stored at 4° C. Strains were inoculated from patch plates into 2 ml of YPD in 24 deepwell plates (square well, pyramid bottom). Replicate inoculations were made from each patch. Negative control strains were struck out on YPD from glycerol stocks and individual colonies were used to inoculate. Deepwell plates were incubated at 28° C. and 250 rpm in the Infors Multitron refrigerated flask shaker for 24 hrs. After 24 hrs of incubation, a 0.85 ml volume of each culture was pelleted by centrifugation at 800×g. Each pellet was resuspended in either 2 ml of YPD or Semi-defined medium (described in Table 17 below), 10 g/L methyl palmitate (pre-warmed to ~50° C.) was added to cultures. All cultures were incubated for 48 hours before endpoint sampling. Final cell densities were measured with the Tecan Infinite 200pro plate reader, 1.5 ml (alcohol analysis) or 500 µl (lipid analysis) was transferred to 1.7 ml microcentrifuge tubes and pelleted. Supernatant was transferred to clean tubes and samples were processed as described below.

TABLE 17

Semi-defined (C:N = 80) medium composition. Components of the semi-defined base medium used to induce lipid storage are described.

| Media Components | Conc. | Units |
|---|---|---|
| Yeast Extract | 2 | g/L |
| Peptone | 1 | g/L |
| Potassium phosphate buffer pH7 | 0.1 | M |
| YNB w/o aa, NH4 | 1.7 | g/L |
| Glucose | 60 | g/L |
| Glycerol | 5 | g/L |

Z9-16OH Functional Expression Assay

SPV300 (negative control) and SPV471 were struck out onto YPD agar plates, grown overnight, and then stored at 4° C. Strains were inoculated from colonies into 2 ml of YPD and incubated at 28° C. and 250 rpm in 14 ml round bottom culture tubes for ~8 hours. After incubation, 2 ml of culture was used to inoculate 20 ml of YPD in a 125 ml baffled shake flask. Shake flasks were incubated 24 hrs at 28° C. and 250 rpm. After incubation, cell density in shake flasks was measured using a Tecan Infinite 200pro plate reader. An appropriate volume of culture was pelleted in order to resuspend cells in 25 ml of Semi-defined C:N=80 medium (see Table 17 above) at an initial OD600=1 (~1 gDCW/L) or 4 (~4gDCW/L). The resuspended culture was added to 250 ml baffled shake flasks. Neat methyl palmitate was added at 10 g/L final concentration after pre-heating to 50° C. After substrate addition, flasks were incubated at 28° C. and 250 rpm for two days. At 12, 18, 24, 36, 42, and 48 hours 500 µl (lipid analysis) and 1.5 ml (alcohol analysis) samples were taken in 1.7 ml microcentrifuge tubes. Samples were pelleted and the supernatant was transferred to a clean microcentrifuge tube.

Metabolite Extraction and GC-MS Detection

Alcohol Analysis

The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL crimp vial. The mixture was heated for 1 h in the heat block at 90° C. Prior to acidification with 400 µL 2.5 N HCl the vial was allowed to cool to room temperature. 500 µL chloroform containing 1 mM methyl heptadecanoate were added and the mixture was shaken vigorously, then both aqueous and organic phase were transferred into a 1.5 mL plastic tube. The mixture was centrifuged at 13,000 rpm, afterwards 450 µL of the organic phase were transferred into a GC vial. The organic phase was evaporated in a heat block at 90° C. for 30 min. The residue was dissolved in 50 µL N,O-Bis(trimethylsilyl) trifluoroacetamide containing 1% trimethylchlorosilane. Prior to transfer into glass inserts the mixture was heated 5 min at 90° C. The samples were analyzed by GC-MS (Table 18).

TABLE 18

| GC-MS parameters | |
|---|---|
| System | Agilent 6890 N GC, ChemStation G1701EA E.02.01.1177 |
| Column | DB23 30 m × 25 µm × 25 µm |
| | Pressure = 11.60 psi; Flow = 0.6 mL/min |
| Inlet | Heater = 250° C.; Pressure = 11.74 psi; |
| | Total Flow {He} = 111 mL/min |
| Carrier | He @ 29 cm/sec, 11.60 psi |
| Signal | Data rate = 2 Hz/0.1 min |
| Oven | 150° C. for 1 min |
| | Ramp 12° C./min to 220° C., hold 3 min |
| | Ramp 35° C./min to 300° C., hold 4 min |
| Injection | Splitless, 250° C. |
| Detector | Initial strain screening and first technical triplicate: HP 5973 MSD in SIM mode (m/z: 208.0, 297.3 and 387.3), |
| | SPV488/SPV490 alcohol quantification: HP 5973 MSD in SIM mode (m/z: 284.0 and 297.3), |
| | 100 msec Dwell, EMV mode: Gain factor 1, |
| | 2.4 min solvent delay, 3.09 cycles/sec |
| Sample | Injection volume = 1 uL |

Lipid Analysis

Total lipid composition was based on modified procedures by Moss et al. (1982) and Yousuf et al (2010). The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL glass crimp GC-vial. The mixture was heated for 1 h in the heat block at 90° C. Prior to acidification with 400 µL 2.5 N HCl, the vial was allowed to cool to room temperature. 500 µL chloroform containing 1 mM methyl heptadecanoate were added and the mixture was shaken vigorously, then both aqueous and organic phase were transferred into a 1.5 mL plastic tube. The mixture was centrifuged at 13,000 rpm, afterwards 450 µL of the organic phase was transferred into a new 1.8 mL glass screw-cap GC-vial. After cooling to room temperature residual fatty acid methyl esters and free fatty acids were dissolved and derivatized in methanol containing 0.2 M TMSH (trimethylsulfonium hydroxide)(Table 19).

TABLE 19

| GC-MS parameters | |
|---|---|
| System | Agilent 6890 GC, ChemStation Rev. B.03.02 (341) |
| Column | J&W DR-23 30 m × 25 mm × 25 µm |
| | Pressure = 16 psi; Flow = 0.9 mL/min; Run Time = 14.4 min |
| Inlet | Heater = 240° C.; Pressure = 16 psi; Total Flow {He} = 31.4 mL/min |
| Carrier | $H_2$ @ 1 mL/min, 9 psi, 35 cm/sec |
| Signal | Data rate = 2 Hz/0.1 min |
| Oven | 150° C. for 1 min |
| | Ramp 12° C./min to 220° C., hold 3 min |
| | Ramp 35° C./min to 240° C., hold 6 min |
| | Equilibration Time: 2 min |

TABLE 19-continued

| GC-MS parameters | |
|---|---|
| Injection | Split, 240° C. |
| | Split ratio - 30:1, 29.1 mL/min |
| Detector | FID, 240° C. |
| | $H_2$ @ 35.0 mL/min, Air @ 350 mL/min;; Electrometer {Lit Offset} @ 2.0 pA |
| Sample | Injection volume = 1 uL |

Example 10: Production of Z11-14Acid in *Yarrowia lipolytica*

Background and Rationale

*Yarrowia lipolytica* was engineered to produce Z11-14Acid, the precursor to target Lepidoptera pheromone Z11-14Ac.

A library of 73 desaturases was chosen to target potential pheromones including Z11-14Ac, Z7-12Ac, Z9E12-14Ac, E8E10-C12OH and Z9E11-14Ac. All desaturases were tested in the H222 ΔPΔAΔF (SPV300) background.

Eleven desaturases were identified from literature to have Δ11 activity (DST001-DST009, DST030, and DST039, Table 20). All desaturases were screened by feeding either methyl palmitate (C16), methyl myristate (C14), or methyl laurate (C12) as substrate, and full product profiles were determined by GC analysis.

The resulting activity of the purported Δ11 desaturase library, and other desaturases shown to produce Δ11 compounds, specifically Z11-14Acid, is discussed.

TABLE 20

Desaturases discussed in Example 10

| Enzyme Code | Organism of origin | GenBank Accession |
|---|---|---|
| DST001 | *Argyrotaenia velutinana* | AF416738 |
| DST002 | *Spodoptera litura* | AGH12217.1 |
| DST003 | *Sesamia inferens* | AII21943.1 |
| DST004 | *Manduca sexta* | CAJ43430.2 |
| DST005 | *Ostrinia nubilalis* | AF441221 |
| DST006 | *Helicoverpa zea* | AAF81787.1 |
| DST007 | *Choristoneura rosaceana* | AF545481 |
| DST008 | *Drosophila melanogaster* | AJ271414 |
| DST009 | *Spodoptera littoralis* | AY362879 |
| DST030 | *Lampronia capitella* | ABX71630.1 |
| DST039 | *Amyelois transitella* | NP001299594.1 |

Results

Figure 41:
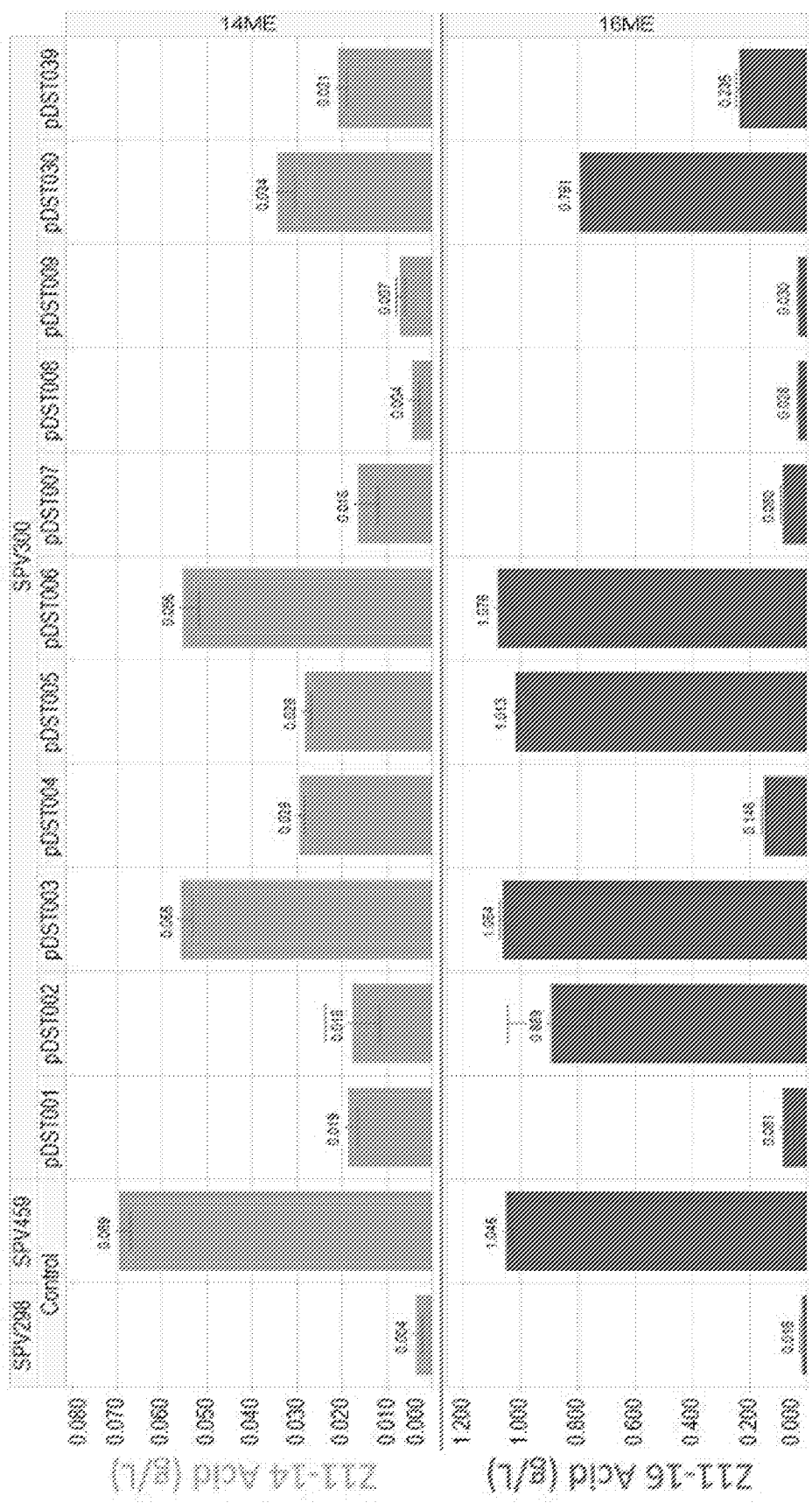
FIG. 41 shows Z11-14Acid (methyl myristate fed—14ME) and Z11-16Acid (methyl palmitate fed—16ME) titers of characterized Δ11 desaturases. SPV300=desaturase library integration parent. SPV298=prototrophic parent of SPV300, negative control. SPV459=SPV300 with current best desaturase (*Helicoverpa zea*, SEQ ID NO: 54), positive control. The desaturase in DST006 is genetically equivalent to the *H. zea* desaturase expressed in SPV459 and served as an internal library control.
Figure 42:
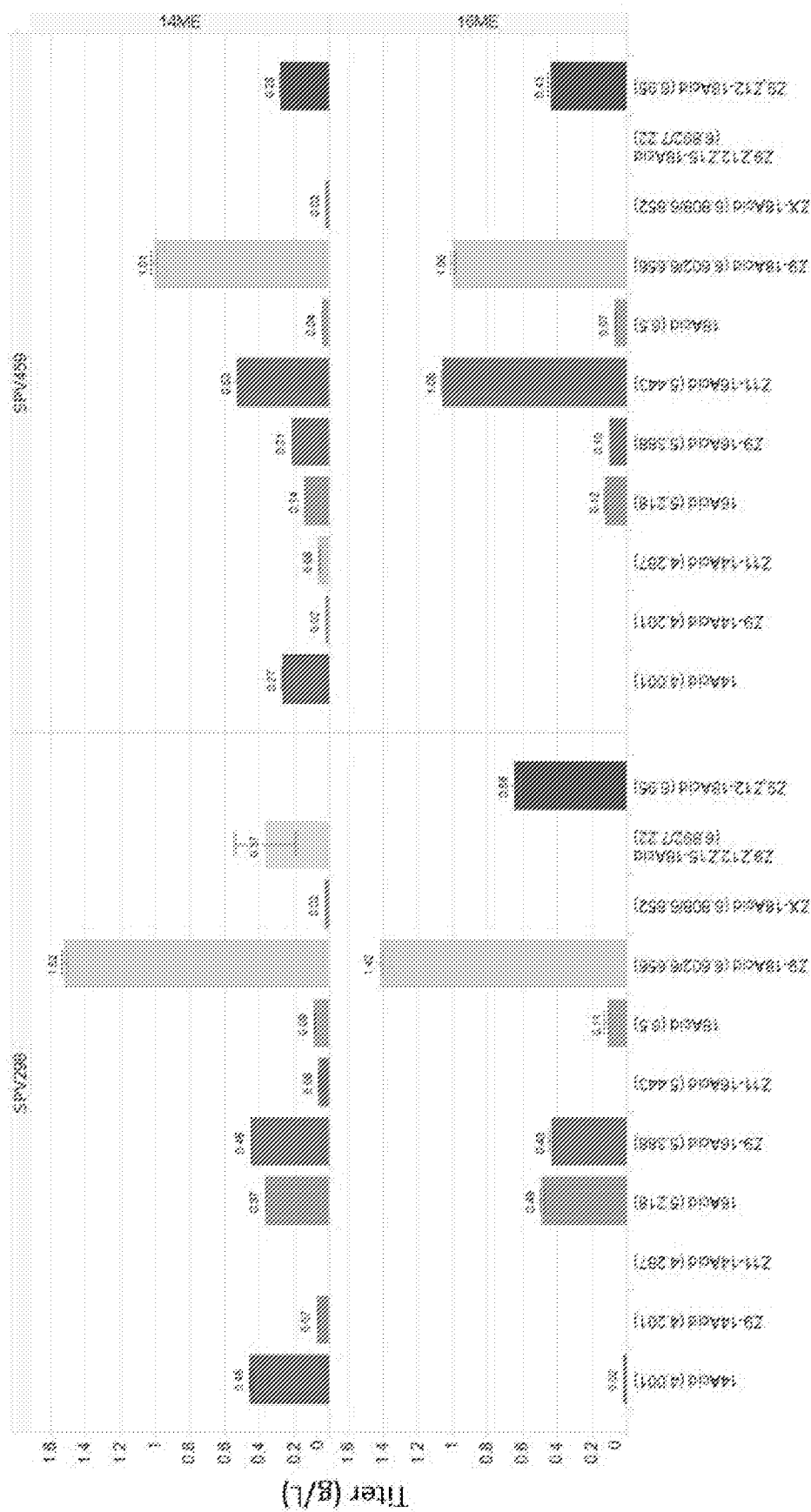
FIG. 42 shows C14 and C18 product profiles of SPV298 (negative control, parent strain) and SPV459 (SPV298 lineage with *H. zea* desaturase, SEQ ID NO: 54) fed on either methyl palmitate (16ME) or methyl myristate (14ME).

Up to 69 mg/L Z11-14Acid production was observed when feeding 2 g/L methyl myristate to the desaturase library (FIG. 41). The current best desaturase, *Helicoverpa zea* (Hz) DST (SPV459, encoded by SEQ ID NO: 54), in addition to desaturases DST001 through DST007, DST030 and DST039, produce some amount of Z11-14Acid ranging from 16 mg/L to 69 mg/L. DST001 (*A. velutinana*), DST004 (*A. sexta*), and DST039 (*A. transitella*) are more specific for Z11-14Acid production than Z11-16Acid production, although these desaturases produce ~20 mg/L Z11-14Acid. Strains producing higher Z11-14Acid titer also produced Z9-14Acid from the methyl myristate substrate at 20-30 mg/L, which was reduced compared to the negative control SPV298. The C14-C18 product profile of Hz DST (SPV459) compared to SPV298 is shown in FIG. 42.

Proof-of-concept of Z11-14Acid synthesis is shown. Attempts were made to identify enzymes that had improved Z11-16Acid titer or product specificity over *Helicoverpa zea* DST (1.05 g/L Z11-16Acid; 69 mg/L Z11-14Acid). While there were no desaturases that had higher production than Hz DST (SPV459), DST003 (SEQ ID NO: 39) had similar production phenotypes to the HzDesat strain, and DST002 and DST005 had similar Z11-16Acid production with reduced Z11-14Acid. The desaturase in DST006 is genetically equivalent to the *H. zea* desaturase expressed in SPV459 and served as a library control. DST006 produced equivalent levels of Z11-16Acid when fed methyl palmitate; however this strain produced a lower titer of Z11-14Acid on methyl myristate. Genetic variation in strain background may account for the observed difference.

DST039 (*A. transitella*) was previously screened under different conditions. In rich media, Z11-16Acid production with the native *A. transitella* coding sequence was not observed. The *H. sapiens* optimized sequence was tested and still no activity was observed with the rich medium condition. In this screen, DST039 was tested in nitrogen limited condition with Hs optimized sequence and resulted in 235 mg/L production of Z11-16Acid and 21 mg/L Z11-14Acid on the relevant substrates.

Δ11 products from DST008 (*Drosophila melanogaster*) or DST009 (*Spodoptera littoralis*) in the SPV300 background were not observed.

Summary

Z11-14Acid production was observed in ten desaturases with titers ranging from 16 mg/L to 69 mg/L (2 g/L methyl myristate fed).

*H. zea* DST (SEQ ID NO: 54) remained the best Z11-16Acid producer (>1 g/L when fed with methyl palmitate).

DST003 (*S. inferens*, SEQ ID NO: 39) has the most similar phenotype to *H. zea* DST.

DST002 (*S. litura*) and DST005 (*O. nubialis*) are more specific than *H. zea* DST for Z11-16Acid production (reduced Z11-14Acid production).

DST001 (*A. velutinana*). DST004 (*M. sexta*), and DST039 (*A. transitella*) are more specific than *H. zea* DST for Z11-14Acid production.

Conclusions

Z11-14Acid can be produced with the heterologous expression of specific desaturases in *Yarrowia lipolytica* when feeding methyl myristate.

Multiple copies of desaturase (identical or combination of sequences) are integrated in improved strain backgrounds for increased Z11-14Acid titer, product specificity, and genetic stability.

Materials & Methods

Library Generation

Desaturase sequences were provided to Genscript for codon optimization (*Homo sapiens* expression organism) cloning into pPV266 (XPR2 locus integration vector with TEF promoter and terminator) using PacI/SapI restriction digestion. Lyophilized DNA was provided as well as EPI400 agar stabs. Desaturase constructs are listed in Table 21.

Constructs were linearized using PmeI restriction enzyme and directly transformed into host strain SPV300. Transformants were verified by check PCR using primers outside of the XPR2 integration junction and within the pTEF promoter.

TABLE 21

Desaturase constructs

| Enzyme Code | Species | GenBank Accession | E. coli SPV | Plasmid pPV |
|---|---|---|---|---|
| DST001 | Argyrotaenia valutinana | AF416738 | SPV0609 | pPV0300 |
| DST002 | Spodoptera litura | AGH12217.1 | SPV0610 | pPV0301 |
| DST003 | Sesamia inferens | AII21943.1 | SPV0611 | pPV0302 |
| DST004 | Manduca sexta | CAJ43430.2 | SPV0612 | pPV0303 |
| DST005 | Ostrinia nubilialis | AF441221 | SPV0613 | pPV0304 |
| DST006 | Helicoverpa zea | AAF81787.1 | SPV0614 | pPV0305 |
| DST007 | Choristoneura rosaceana | AF545481 | SPV0615 | pPV0306 |
| DST008 | Drosophila melanogaster | AJ271414 | SPV0616 | pPV0307 |
| DST009 | Spodoptera littoralis | AY362879 | SPV0617 | pPV0308 |
| DST030 | Lampronia capitella | ABX71630.1 | SPV0638 | pPV0329 |
| DST039 | Amyelois transitella | NP_001299594.1 | SPV0647 | pPV0338 |

Plasmid Digest

~10 μg of lyophilized DNA was ordered from Genscript. DNA was resuspended in 50 μL water for a final concentration of ~200 ng/L, 10 μL of DNA was mixed with 1.25 μL 10× CutSmart Buffer and 1.25 μL PmeI restriction enzyme (12.5 μL reaction volume). The reaction was incubated in the PCR machine for 1.5 hours at 37° C. and heat inactivated at 65° C. for 30 minutes.

Transformation

SPV300 competent cells were grown by inoculating a YPD culture at 0.001 OD in a baffled flask and growing until 0.5-1.0 OD. Cells were harvested at 800×g and washed with 0.25× volume of Solution 1 from the Zymo Frozen-EZ Transformation II Kit for Yeast. Cells were resuspended in Solution 2 at 1000× concentration of the original culture volume and slowly frozen at −80° C. while insulated in a styrofoam container (frozen cells may have better transformation efficiency over fresh), 50 μL of cells were first mixed with the 12.5 μL digestion reaction (no cleanup necessary), and then with 500 μL Solution 3. Transformations were incubated for 3 hours at 28° C. without shaking, after which the full transformation mixture was plated to appropriate selective agar media. Petri dishes were incubated for 3-4 days before the appearance of colonies.

Check PCR

Transformation colonies were picked to 7 μL water in a PCR plate, 5 μL of cells were patched by multichannel to selective omni trays and grown overnight. The remaining 2 μL of cells were microwaved for 2 minutes before adding 15 μL of PCR master mix.

| PCR Master Mix | 1× reaction |
|---|---|
| 2× Phusion Master Mix (HF Buffer) | 7.5 μL |
| 100 μM oPV204 (XPR2 locus F) | 0.1 μL |
| 100 μM oPV195 (pTER R) | 0.1 μL |
| Water | 7.3 μL |

PCR Cycle:

| Temp. | Time | Cycles |
|---|---|---|
| 98° C. | 2 min | 1× |
| 98° C. | 15 sec | 30× |
| 64° C. | 30 sec | |
| 72° C. | 60 sec | |
| 72° C. | 5 min | 1× |
| 4° C. | ∞ | 1× |

Colony Patching

Positive clones were re-patched to YPD omni trays in 24-well format including assay controls. Omni trays were grown overnight at 28° C. and used to inoculate bioassay cultures.

Bioassay

Positive transformants (N=4 clones per construct) were inoculated into 1 mL YPD in a 24-well culture plate and incubated for 24 hours in the Infors HT Mulitron Pro at 28° C. with 1000 rpm shaking. Cells were pelleted at 800×g and resuspended in S2 media with 5 µL substrate (~2 g/L concentration), 250 µL of culture was sampled into glass crimp top vials after 48 hours of bioconversion.

S2 Media 2 g/L Yeast Extract, 1 g/L Peptone, 0.1M Phosphate buffer, 1.7 g/L YNB w/o aa, NH4, 60 g/L Glucose, 5 g/L Glycerol GC Sample Processing Front Inlet/Detector:

| | |
|---|---|
| System | 6890 GC, ChemStation Rev. B.03.02 (341) |
| Column | J&W DB-23 30 m × 25 mm × 25 um Run Time = 14.4 min |
| Inlet | Heater = 240° C.; Pressure = 9.0 psi; Total Flow {H2} = 36.2 mL/min |
| Carrier | H2 @ 1.0 mL/min, 9.0 psi, 35 cm/sec |
| Signal | Data rate = 2 Hz/0.1 min |
| Oven | 150° C. for 1 min<br>Ramp 12° C./min to 220° C., hold 3 min<br>Ramp 35° C./min to 240° C., hold 4 min<br>Equilibration Time: 2 mim |
| Injection | Split, 240° C.<br>Split ratio - 30:1; 29.1 mL/min |
| Detector | FID, 240° C.<br>H2 @ 35.0 mL/min, Air @ 350 mL/min<br>Electrometer {Lit Offset} @ 2.0 pA |
| Sample | Injection volume = 1 µL |

Back Inlet/Detector:

| | |
|---|---|
| System | 6890 GC, ChemStation Rev. B.03.02 (341) |
| Column | J&W DR-23 30 m × 25 mm × 25 um Run Time = 14.4 min |
| Inlet | Heater = 240° C.; Pressure = 9.8 psi; Total Flow {H2} = 40.1 mL/min |
| Carrier | H2 @ 1.1 mL/min, 9.8 psi, 38 cm/sec |
| Signal | Data rate = 2 Hz/0.1 min |
| Oven | 150° C. for 1 min<br>Ramp 12° C./min to 220° C., hold 3 min<br>Ramp 35° C./min to 240° C., hold 4 min<br>Equilibration Time: 2 min |
| Injection | Split, 240° C.<br>Split ratio - 30:1; 32.3 mL/min |
| Detector | FID, 240° C.<br>H2 @ 35.0 mL/min, Air @ 350 mL/min<br>Electrometer {Lit Offset} @ 2.0 pA |
| Sample | Injection volume = 1 µL |

TMSH: Trimethylsulfonium Hydroxide (0.2 mol/L in Methanol)—VWR TCT1576-025ML

Example 11: Production of Z11-16OH in *Yarrowia lipolytica* Using Increased Copy Number of or Engineered Variant Fatty Alcohol Forming Fatty Acyl-CoA Reductases (FARs)

Background and Rationale

Engineering the microbial production of unsaturated insect fatty alcohols requires the functional expression of a synthetic pathway. One such pathway comprises a transmembrane desaturase to mediate the conversion of fatty acyl-CoA into regio- and stereospecific unsaturated fatty acyl-CoA. An alcohol-forming reductase (FAR) complements the synthetic pathway to produce the respective fatty alcohol.

In some insects species the respective FAR enzymes are activated via site specific dephosphorylation (Jurenka, R. & Rafaeli, A. Regulatory Role of PBAN in Sex Pheromone Biosynthesis of Heliothine Moths. Front. Endocrinol. (Lausanne), 2, 46 (2011); Gilbert, L. I. Insect Endocrinology. (Academic Press)). Phosphorylation of heterologously expressed FAR enzymes in *Y. lipolytica* may lead to inactivation, and result in low fatty alcohol titers. A bioinformatic approach was used to predict phosphorylated residues within HaFAR.

Alanine substitution of serine and threonine residues has been shown to abolish phosphorylation (Shi, S., Chen, Y., Siewers, V. & Nielsen, J. Improving Production of Malonyl Coenzyme A-Derived Metabolites by Abolishing Snf1-Dependent Regulation of Acc1, mBio 5, (2014)). Thus, in addition to increasing FAR gene copy number, the impact of alanine substitutions of several serine residues of an HaFAR enzyme (HaFAR amino acid sequence set forth in SEQ ID NO: 41 and HaFAR nucleotide sequence set forth in SEQ ID NO: 90) on Z11-16OH titer was tested.

Approach

A second copy of human codon-optimized *H. armigera* FAR gene (HaFAR) was introduced into the chromosome of the Z11-16OH producer parent strain. In parallel, the effects of introducing a copy of a mutated *H. armigera* FAR gene variant towards Z11-16OH production improvement were also explored. Seven mutated variants were designed with the aim to increase FAR activity by potentially relieving the requirement for dephosphorylation (as observed in some insect species). To this end, several potential phosphorylation sites within the amino acid sequence of the *H. armigera* FAR were identified, and replaced with alanine.

Results

Determination of Phosphorylated Sites in HaFAR

The server at world wide web address: cbs.dtu.dk/services/NetPhos/( ) predicts potential phosphorylation sites based on a database (world wide web address: phospho.elm.eu.org/about.htmL) of experimentally verified phosphoproteins based on 17 kinases: ATM, CKI, CKII, CaMII, DNAPK, EGFR, GSK3, INSR, PKA, PKB, PKC, RSK, SRC, cdc2, cdk5 and p38MAPK.

Figure 43:
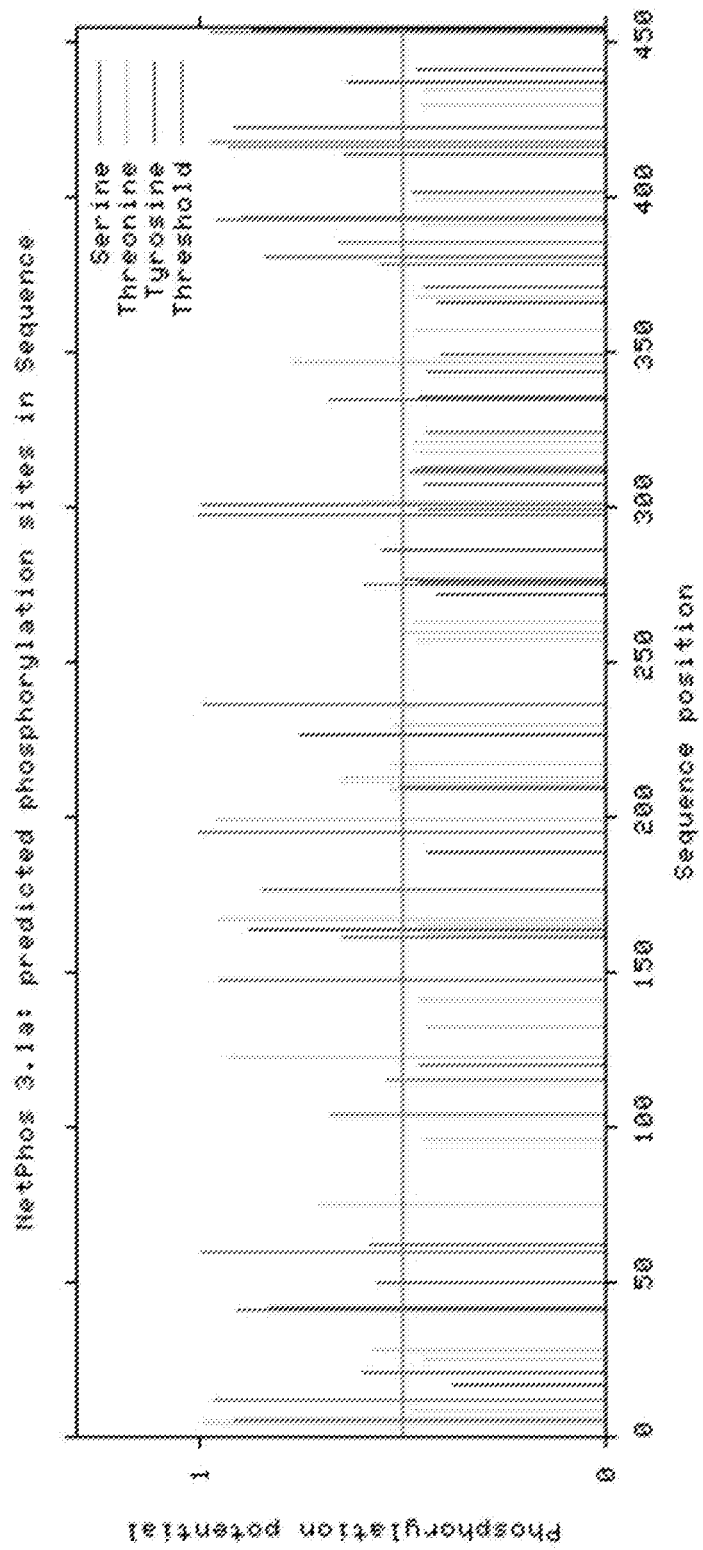
FIG. 43 shows bioinformatic analysis of potential serine, threonine and tyrosine phosphorylation sites of the *H. amigera* FAR enzyme (SEQ ID NO: 41). The horizontal line resembles the threshold for potential phosphorylation.

The software program predicted 22 serine, 11 threonine and 10 tyrosine as potential phosphorylation sites in *H. armigera* FAR (FIG. 43).

Figure 44:
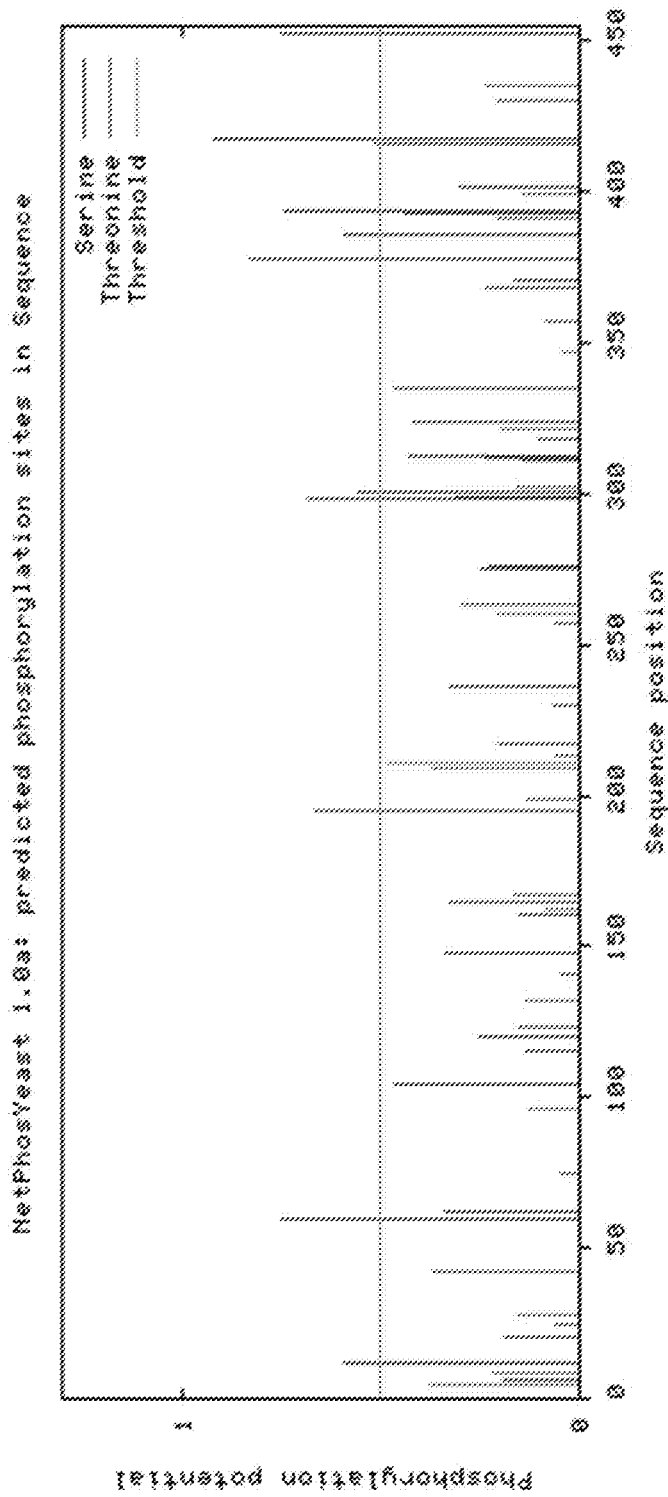
FIG. 44 shows bioinformatic analysis of potential serine and threonine phosphorylation sites of the *Helicoverpa*

Next, a tailored prediction program to determine phosphorylation sites of the *H. armigera* FAR upon expression in yeasts was applied (world wide web address: cbs.dtu.dk/services/NetPhosYeast/, Blom, N., Gammeltoft, S. & Brunak, S. Sequence and structure-based prediction of eukaryotic protein phosphorylation sites1. J. Mol. Biol. 294, 1351-1362 (1999)). Since in yeast no tyrosine kinases have been identified yet (Ingrell, C. R., Miller. M. L., Jensen. O. N. & Blom. N. NetPhosYeast: prediction of protein phosphorylation sites in yeast. Bioinforma. 23, 895-897 (2007)), the yeast-specific software only considers serine and threonine as potential phosphorylation sites. It was striking that both programs predicted the same 11 serine residues to be phosphorylated. In contrast, the yeast specific analysis tool did not predict any phosphorylated threonine residues (FIG. 44).

In a first experiment a small library consisting of 7 Ser to Ala point mutants was tested (Table 22). Three predicted phosphorylation sites were not considered for mutagenesis (position Ser301, Ser386. Ser416 scored barely above the threshold). For the remaining 7 serine residues, alanine substitutions were introduced.

TABLE 22

Serine to alanine mutant library

| Parent strain | Additional Enzyme | Strain # |
|---|---|---|
| Y. lipolytica H222ΔPΔAΔF xpr2::pTEF-HZ_Z11_desat_ Hs-tLIP2-pTAL1-HA_FAR-tXPR2_loxP | HaFAR | SPV916 |
| Y. lipolytica H222ΔPΔAΔF xpr2::pTEF-HZ_Z11_desat_ Hs-tLIP2-pTAL1-HA_FAR-tXPR2_loxP | HaFAR S60A | SPV909 |
| Y. lipolytica H222ΔPΔAΔF xpr2::pTEF-HZ_Z11_desat_ Hs-tLIP2-pTAL1-HA_FAR-tXPR2_loxP | HaFAR S195A | SPV910 |
| Y. lipolytica H222ΔPΔAΔF xpr2::pTEF-HZ_Z11_desat_ Hs-tLIP2-pTAL1-HA_FAR-tXPR2_loxP | HaFAR S298A | SPV911 |
| Y. lipolytica H222ΔPΔAΔF xpr2::pTEF-HZ_Z11_desat_ | HaFAR S378A | SPV912 |

TABLE 22-continued

Serine to alanine mutant library

| Parent strain | Additional Enzyme | Strain # |
|---|---|---|
| Hs-tLIP2-pTAL1-HA_FAR-tXPR2_loxP Y. lipolytica H222ΔPΔAΔF xpr2::pTEF-HZ_Z11_desat_ Hs-tLIP2-pTAL1-HA_FAR-tXPR2_loxP | HaFAR S394A | SPV913 |
| Y. lipolytica H222ΔPΔAΔF xpr2::pTEF-HZ_Z11_desat_ Hs-tLIP2-pTAL1-HA_FAR-tXPR2_loxP | HaFAR S418A | SPV914 |
| Y. lipolytica H222ΔPΔAΔF xpr2::pTEF-HZ_Z11_desat_ Hs-tLIP2-pTAL1-HA_FAR-tXPR2_loxP | HaFAR S453A | SPV915 |

The HaFAR library was custom synthesized, and subcloned into plasmid pPV234 for expression under TEF promoter, and XPR2 terminator at the AXP locus. Linearized constructs were transformed into strain Y. lipolytica H222ΔPΔAΔF SPV603 which expresses H. zea Z11 desaturase (SEQ ID NO: 54) combined with the H. armigera FAR (SEQ ID NO: 41). This approach determined the impact of a second copy e.g. protein expression in addition to the impact of the individual point mutations.

Four individual clones of positive integrants were tested. Cultivation was performed in 24 well plates. Briefly, 2 mL YPD was inoculated from patches of individual clones and incubated for 24h at 28° C. 1000 rpm. After 24h OD600 was measured and the cells were centrifuged at 1000 rpm (Table 23). The cell pellets were resuspended in 1 mL S2 media and 10 g/L methyl palmitate was added. The cells were incubated for 18h at 28° C., 1000 rpm. Cultivations were stored at −20° C. until analyzed. Extraction and analysis was performed according to previously established standard protocols using GC-FID.

TABLE 23

OD600 measurement of the 24 well plate cultivations (two plates were cultivated in parallel). Each individual well was measured as duplicates upon 1:10 dilution after 24 h cultivation in YPD. Calculated OD600 values are given.

| OD600 | HaFAR-GFP 1 | HaFAR-GFP 2 | HaFAR-GFP 3 | HaFAR S60A 4 | HaFAR S195A Clone 2 5 | HaFAR S195A Clone 2 6 | HaFAR S195A Clone 3 7 | HaFAR S195A Clone 3 8 | HaFAR S298A 9 | HaFAR S298A 10 | SPV603 11 | SPV603 12 | |
|---|---|---|---|---|---|---|---|---|---|---|---|---|---|
| A | 15.392 | 16.16 | 17.376 | 17.976 | 17.56 | 18.272 | 14.188 | 14.774 | 14.774 | 15.708 | 17.14 | 17.24 | plate2 |
| B | 16.62 | 17.172 | 18.632 | 18.596 | 18.894 | 18.088 | 16.082 | 15.38 | 16.04 | 16.03 | 16.572 | 16.584 | plate2 |
| C | 16.978 | 16.952 | 18.154 | 18.224 | 18.678 | 19.384 | 16.062 | 14.858 | 15.498 | 15.58 | 18.14 | 17.528 | plate2 |
| D | 16.596 | 17.23 | 17.668 | 18.842 | 18.39 | 18.792 | 20.678 | 16.566 | 16.094 | 15.904 | 1.262 | 1.152 | plate2 |
| E | 17.53 | 17.156 | 16.78 | 15.776 | 17.398 | 16.736 | 16.154 | 15.514 | 16.748 | 16.792 | 18.26 | 17.322 | plate1 |
| F | 18.336 | 17.928 | 16.392 | 15.33 | 20.018 | 19.37 | 15.06 | 14.266 | 17.522 | 17.076 | 16.724 | 16.522 | plate1 |
| G | 17.16 | 17.224 | 15.984 | 16.194 | 17.878 | 17.626 | 15.372 | 15.15 | 16.688 | 17.022 | 17.742 | 16.942 | plate1 |
| H | 16.258 | 16.12 | 16.134 | 16.236 | 16.808 | 16.176 | 15.382 | 14.51 | 15.456 | 15.394 | 7.664 | 7.956 | plate1 |

| OD600 | HaFAR S378A 1 | HaFAR S378A 2 | HaFAR S394A 3 | HaFAR S394A 4 | HaFAR S418A 5 | HaFAR S418A 6 | HaFAR S453A 7 | HaFAR S453A 8 | HaFAR 9 | HaFAR 10 | SPV603 11 | SPV603 12 | |
|---|---|---|---|---|---|---|---|---|---|---|---|---|---|
| A | 15.842 | 15.97 | 15.31 | 16.278 | 16.088 | 16.302 | 16.074 | 15.502 | 15.34 | 15.742 | 16.89 | 16.062 | plate 2 |
| B | 16.3 | 17.306 | 16.064 | 16.5 | 16.64 | 16.344 | 15.69 | 15.598 | 15.434 | 15.248 | 16.674 | 16.476 | plate 2 |
| C | 17.088 | 17.146 | 15.966 | 15.472 | 16.508 | 16.548 | 15.82 | 15.216 | 15.796 | 16.098 | 16.81 | 17.246 | plate 2 |
| D | 17.512 | 17.198 | 15.15 | 14.168 | 16.094 | 13.93 | 15.642 | 15.078 | 16.77 | 16.242 | 0.9 | 0.864 | plate 2 |
| E | 16.446 | 17.014 | 15.762 | 16.536 | 17.188 | 17.372 | 16.164 | 15.892 | 15.8 | 16.422 | 17.998 | 17.814 | plate 1 |
| F | 16.982 | 11.196 | 16.098 | 13.148 | 16.1 | 12.348 | 16.688 | 10.232 | 15.596 | 13.068 | 18.456 | 16.098 | plate 1 |
| G | 15.4 | 15.568 | 15.236 | 16.348 | 15.504 | 15.824 | 14.922 | 15.622 | 15.11 | 15.576 | 17.142 | 17.672 | plate 1 |
| H | 17.088 | 16.63 | 0.968 | 1.006 | 13.82 | 12.49 | 15.826 | 15.27 | 17.132 | 16.166 | 1.082 | 0.932 | plate 1 |

As shown in FIG. 45, strains expressing a second HaFAR copy encoding a point mutation, HaFAR-GFP or HaFAR* (where * indicates a second copy of the parental HaFAR enzyme in addition to the existing copy of the parental strain). The copy increased fatty alcohol titers when compared to the parental strain (SPV603). The introduction of HaFAR (S60A), HaFAR (S298A), HaFAR (S394A), HaFAR (S453A) was neutral or showed slight increases when compared to the HaFAR double copy strain. In contrast, expression of HaFAR (S418A), and HaFAR (S195A) resulted in a distinct increase of Z11-16OH titers.

Overall, these results suggest that residue 195 and 418 are important for increasing HaFAR activity in *Y. lipolytica*. Their substitutions to alanine may inhibit phosphorylation; therefore, a dephosphorylation mechanism was not required for their enhanced activity. Among other explanations, the activating effect of the serine to alanine mutation could be from improved protein folding, increased stability or higher protein expression.

In addition, several fatty acid species were quantified to determine whether the increased Z11-16OH production led to Z11-16Acid depletion. The standard deviations for some samples were very high (FIG. 46). In all samples saturated and Z11-16Acid was detected. Quantification of the respective product intermediate Z11-16Acid showed increased consumption for the mutant strains SPV910 and SPV914 expressing HaFAR S195A and HaFAR S418A.

Chromosomal integration of an additional HaFAR into the parent strain increased the Z11-16OH titer from ~20 mg/L to 40 mg/L in shake flask experiments.

When HaFAR (Ser195Ala) or HaFAR (Ser418Ala) was introduced, Z11-16OH titer increased from ~40 mg/L to ~120 mg/L or ~80 mg/L, respectively in shake flask experiments.

The pathway intermediate Z11-16Acid for mutant strains SPV910 harboring HaFAR (Ser195Ala), and SPV914 harboring HaFAR (Ser418Ala) accumulated at ~100 mg/L less than the parent strain SPV603.

Conclusions

The addition of another *H. armigera* FAR gene into Z11-16OH producer strain marginally increased titer. Introduction of mutated FARs, however, significantly improved Z11-16OH by up to ~7×. This suggests that *Y. lipolytica* phosphorylates FAR enzymes, and that FAR dephosphorylation is a bottleneck for its full activity. The designed mutations in HaFAR may relieve its requirement for dephosphorylation to convert Z11-16Acid into Z11-16OH. It is also possible that the designed mutations improved FAR activity through a dephosphorylation-independent mechanism. Shake flask experiments suggest a direct correlation between biomass, time and fatty alcohol titers.

Second generation strains are created for further improvement in Z11-16OH by, for example, eliminating lipid storage pathways (e.g. diacylglycerol acetyltransferase (DGAT) gene deletions), and/or eliminating byproduct (hydroxyacid, diacid) pathways.

Materials & Methods

Marker rescue of SPV603

30 mL of CM minus uracil were inoculated with SPV603 in a 250 mL baffled shake flask. The culture was incubated in a bench top shaker at 250-300 rpm and 28° C. The following morning the OD600 of the culture was measured. Cells were harvested at OD600: 0.6. Cells were pelleted in a falcon tube (800×g, 5 min). Supernatant was removed and wash in ½ volume (15 mL) of Solution 1 from the Zymo kit. Cells were pelleted again (800×g, 5 min) and resuspended in 200 μl of Solution 2. A 50 μl aliquot was used directly in a 1.7 mL Eppendorf tube. Remaining aliquots were stored at −80° C. 10 μl of DNA (1-2 μg) was added and gently mixed with cells. 500 μl of Solution 3 was added and mixed gently. Transformation mix was incubated for ≥3 hours in 28° C. plate incubator subsequently washed with 2 mL deionized water (autoclaved). Recovery was performed in 2 mL YPD o/n at 28° C. The transformation mix was plated directly on selection plate. Clones were picked and repatched on URA minus FOA 0.1% and YPD plates. URA removal was confirmed using standard PCR protocols.

Construction of HaFAR Integration Cassette

The HaFAR library was custom synthesized with human codons (Genscript), and subcloned into plasmid pPV234 using the restriction site SpeI and NotI for expression under TEF promoter, and XPR2 terminator at the AXP locus. Linearized constructs were transformed into strain *Y. lipolytica* H222ΔPΔΔF SPV603 which expresses *H. zea* Z11 desaturase (SEQ ID NO: 54) combined with the *H. armigera* FAR (SEQ ID NO: 41). Amino acid sequences for the variant FARs are set forth in SEQ ID NOs: 42-48. Nucleotide sequences for the variant FARs are set forth in SEQ ID NOs: 83-89.

Cultivation of HaFAR Mutant Library in 24 Well Plates

In a first round four individual isolate from each transformation was tested. Cultivation was performed in 24 well plates. 2 mL YPD was inoculated from patches of individual clones and incubated for 24h at 28° C., 1000 rpm. After 24h OD600 was measured and the cells were centrifuged at 1000 rpm. The cell pellets were resuspended in 1 mL S2 media and 10 g/L methyl palmitate was added. The cells were incubated for 24h at 28° C., 1000 rpm. Cultivations were stored at −20° C. until analyzed. Next, four clones of the best performing positive integrant were tested. Cultivation was performed in 24 well plates. 2 mL YPD was inoculated from patches of individual clones and incubated for ~28h at 28° C. 1000 rpm. After 28h OD600 was measured and the cells were centrifuged at 1000 rpm. The cell pellets were resuspended in 1 mL S2 media and 10 g/L methyl palmitate was added. The cells were incubated for 18h at 28° C., 1000 rpm. Cultivations were stored at −20° C. until analyzed.

Cultivation of HaFAR Mutant Library in Shake Flasks

Shake Flask Experiment 1: Time-Course Analysis of Fatty Alcohol and Fatty Acid Titers During Shake Flask Cultivation In a first step a shake flask experiment of the respective strains was performed to analyze fatty alcohol and fatty acid formation over time. The best performing clone of the strains expressing HaFAR. HaFAR S195A and HaFAR S418A were tested. 10 mL YPD was inoculated from patches of individual clones and incubated for 24h at 28° C., 250 rpm in a 125 mL shake flask. Next, 25 mL YPD were inoculated with 5 mL starter culture in 500 mL shake flasks and incubated for 24h at 28° C., 250 rpm. The cells were harvested and the pellets were resuspended in 15 mL S2 media and 10 g/L methyl palmitate was added. OD600 was measured and subsequently methyl palmitate was added. The cells were incubated for 72h at 28° C., 1000 rpm. 4×0.5 mL samples were taken every 24h and stored at −20° C. until analyzed according to a previously established standard protocol (FIG. 47 and FIG. 48). To improve sampling and reduce the standard deviation, samples were transferred directly into GC crimp vials and stored until analyzed.

The OD600 for the strains were: SPV910-10.2, SPV914-11.5 and SPV916-12.3.

Shake Flask Experiment 2: Impact of Increased Biomass on Bioconversion

The time-course experiment revealed a decrease in fatty alcohols over time. Thus, sampling was reduced to 20h. In previous 24 well plate bioconversion experiments the measured biomass was ~2× higher compared to the shake flask experiment. Next a shake flask experiment of the respective strains was performed to analyze the impact of biomass on fatty alcohol titers. The overall incubation time was reduced and the biomass was increased during bioconversion phase. The best performing clone of the strains expressing HaFAR S195A and HaFAR S418A were tested. 20 mL YPD was inoculated from patches of individual clones and incubated for 28h at 28° C., 250 rpm in a 500 mL shake flask. The cells were harvested and the pellets were resuspended in 10 mL S2 media and 10 g/L, OD600 was measured and subsequently methyl palmitate was added. The cells were incubated for 20h at 28° C., 1000 rpm. 4×0.5 mL samples were taken and analyzed according to a previously established standard protocol (FIG. 49).

The OD600 for the strains were: SPV910-24.9 and SPV914-24.7.

Metabolite Extraction

Cell pellets were resuspended with 500 µL 5% NaOH (in methanol) then heated for 1 hour at 85° C. Samples were cooled down and then acidified by adding 400 µL 5N HCl. Next, 500 µL chloroform (containing 1 mM C17:0 heptadecanoate internal standard) were added to samples. Samples were mixed vigorously then spun down for 2 minutes at 13,000 RPM using a table top centrifuge. 450 µL chloroform were transferred to a new vial then evaporated at 85° C. for ~15 minutes. Samples were then resuspended in 50 µL BSTFA (and were now ready for GC analysis). After analysis of the fatty alcohols samples were diluted ~1:10 and rerun on the GC to improve peak separation of the fatty acid peaks.

Quantification

All quantifications were based on the concentration of the internal standard. The concentration of the internal standard $C_{17}ME$ is 1 mM. The final concentration of fatty alcohols as well as fatty acids were calculated based on the effective carbon number compared to the internal standard.

Example 12: Production of Fatty Alcohol and Fatty Acid in *Yarrowia lipolytica* Using Second Generation Strains Engineered to Eliminate Lipid Storage Pathways or Using Additional Variant Fatty Alcohol Forming Fatty Acyl-CoA Reductases (FARs)

The impact of an endogenous diacyl glycerol acyltransferase deletion selected from the group consisting of YALI0E32791g (DGA1) and YALI0D07986g (DGA2) was tested. Each dga gene was deleted individually in the strain SPV735 (ΔURA, ΔLeu, leu2::pTEF-HZ_Z11_desat_Hs-tXPR2_loxP). Subsequently, the individual selection marker in each deletion strain SPV957 (Δdga1, ΔLeu, leu2::pTEF-HZ_Z11_desat_Hs-tXPR2_loxP) and SPV959 (Δdga2 ΔURA, leu2::pTEF-HZ_Z11_desat_Hs-tXPR2_loxP) according to standard procedures was performed. The resulting strain SPV1053 (Δdga1 ΔURA, ΔLeu, leu2::pTEF-HZ_Z11_desat_Hs-tXPR2_loxP) and SPV1054 (Δdga2 ΔURA, ΔLeu, leu2::pTEF-HZ_Z11_desat_Hs-tXPR2_loxP) were used to transform HaFAR and HaFARS195A. The formation of fatty alcohols compared to the strain SPV603 was tested in shake flasks (FIG. 50 and FIG. 51). The results in shake flasks over time suggest that the deletion of each individual dga gene improves fatty alcohol formation and decreases fatty acid storage.

Time-Course Analysis of Fatty Alcohol and Fatty Acid Titers During Shake Flask Cultivation A copy of the enzyme HAFAR (SEQ ID NO: 41) or HaS195A (SEQ ID NO: 43) was introduced into the strain SPV1053 (Δdga1 ΔURA, ΔLeu, leu2::pTEF-HZ_Z11_desat_Hs-tXPR2_loxP) and SPV1054 (Δdga2 ΔURA, ΔLeu, leu2::pTEF-HZ_Z11_desat_Hs-tXPR2_loxP), each of which expresses *H. zea* Z11 desaturase (SEQ ID NO: 54) and is deleted for either DGA1 or DGA2 diacylglycerol acyltransferase.

Cultivation was performed as biological triplicates in shake flasks. The starting culture for each strain was grown in 50 mL YPD in 250 mL shake flask for 28h at 250 rpm, 28° C. Cells were harvested via centrifugation at 800 g for 5 min at room temperature and resuspended in 30 mL S2 media. Cell suspensions were normalized to OD600: ~8. Each starting culture was split in three individual 125 mL shake flasks. 10 g/L methyl palmitate was added. Cultures were incubated for 72h. Sampling was performed every 24h and OD600 for each shake flask was measured. FIG. 50 and FIG. 51 show fatty alcohol titers and fatty acid titers, respectively, for the time course experiments.

Extraction of cultivation samples. 0.5 mL of each sample were harvested directly into crimp vials. The crimp vials were centrifuged at 800 g for 5 min. The supernatant was removed and the samples were sealed and stored at −20° C. until analysis. Samples were resuspended in 500 µL methanol containing 5% KOH and incubated for 60 min at 65° C. to 85° C. 200 µL 5N HCL was added to each crimp vial after cool down step. 600 µL chloroform containing 1 mM C17Me were added and sealed again. Samples were mixed and centrifuged. 500 uL of the chloroform was transferred to a new GC vial and dried to completeness at 85° C. for 30 min. Samples were resuspend in 100 uL BSTFA and incubated at room temperature for 1 h. Samples were analyzed according to standard protocol using gas chromatography.

Fatty Alcohol Forming Fatty Acyl-CoA Reductase Library Screening of New Strains in 24 Well Plates A single copy of each respective FAR enzyme from Table 24 was introduced into the strain SPV1054 (Δdga2 ΔURA, ΔLeu, leu2::pTEF-HZ_Z11_desat_Hs-tXPR2_loxP) expressing *H. zea* Z1 desaturase (SEQ ID NO: 54) and deleted for DGA2 diacylglycerol acyltransferase.

Cultivation was performed as biological quadruplicates in 24 well plates. 2 mL YPD were inoculated from a patch of each individual transformant. 24 well plates were incubated for 28h at 250 rpm, 28° C. Cells were harvested via centrifugation at 800 g for 5 min at room temperature. Cells were resuspended in 1 mL S2+60 g/L glycerol and 10 g/L methyl palmitate was added. Cell were incubated for 96h at 1000 rpm, 28° C. FIG. 52 and FIG. 53 show fatty alcohol titers and fatty acid titers, respectively, for the 24 well plate screening experiments.

Extraction of cultivation samples. 0.5 mL of each sample were harvested directly into crimp vials. The crimp vials were centrifuged at 800 g for 5 min. The supernatant was removed, and the samples were sealed and stored at −20° C. until analysis. Samples were resuspended in 500 µL methanol containing 5% KOH and incubated for 60 min at 65° C. to 85° C. 200 µL 5N HCL was added to each crimp vial after cool down step. 600 µL chloroform containing 1 mM C17Me were added and sealed again. Samples were mixed and centrifuged. 500 µL of the chloroform was transferred to a new GC vial and dried to completeness at 85° C. for 30 min. Samples were resuspend in 100 μL BSTFA and incubated at room temperature for 1 h. Samples were analyzed according to standard protocol using gas chromatography.

These FAR enzymes are tested as described above for fatty alcohol and fatty acid production.

TABLE 24

New FAR enzyme library

| Organism | Enzyme ID | Gen ID |
|---|---|---|
| *Agrotis segetum* | FAR027 | AID66655.1 |
| *Euglena gracilis* | FAR028 | GU733919 |
| *Ostrinia palustralis* | FAR029 | MIQSS3 |
| *Ostrinia latipennis* | FAR030 | MIRG73 |
| *Ostrinia nubilalis* | FAR031 | FJ807735 |
| *Ostrinia nubilalis* | FAR032 | FJ807736 |
| *Ostrinia zealis* | FAR033 | MIQSS9 |
| *Yponomeuta evonymellus* | FAR034 | GQ907232 |
| *Yponomeuta padellus* | FAR035 | GQ907235 |
| *Yponomeuta rorrellus* | FAR036 | GQ907234 |
| *Tyto alba* | FAR037 | JN638549 |
| *Ostrinia scapulalis* | FAR038 | EU817405 |
| *Spodoptera exigua* | FAR039 | KR781121.1 |
| *Spodoptera littoralis* | FAR040 | KR781120 |
| *H. virescens* | FAR041 | EZ407233 |
| *H. subflexa* | FAR042 | AFD04726.1 |
| *H. amigera* | FAR043 | AKD01773.1 |
| *H. assaulta* | FAR044 | AFD04727.1 |

Additional FAR variants and additional bacterial FAR enzymes are listed in Table 25 and Table 26, respectively.

TABLE 25

New FAR Enzyme library with phosphorylation point mutants

| Amino acid mutations | Enzyme ID |
|---|---|
| HaFAR S12A | pFAR055 |
| SlFAR S10A | pFAR056 |
| SlFAR S13A | pFAR057 |
| SlFAR S61A | pFAR058 |
| SlFAR S104A | pFAR059 |
| SlFAR S310A | pFAR060 |
| SlFAR S314A | pFAR061 |
| SlFAR S419A | pFAR062 |

TABLE 26

Additional bacterial FAR enzyme library

| Organism | Gen ID |
|---|---|
| *Spongiibacter tropicus* | WP_022959477.1 |
| *Oleiphilus* sp. HI0086 | KZY30886.1 |
| *Marinobacter lipolyticus* | WP_012138772.1 |
| *Marinobacter antarcticus* | WP_072799080.1 |

SEQUENCE LISTING

SEQ ID NO: 1    *Agrotis segetum* FAR_*S. cerevisiae* codon opt
```
ATGCCAGTTTTGACTTCTAGAGAAGATGAAAAGTTGTCAGTTCCAGAATTTTACGCTGGTA
AATCTATCTTCGTTACAGGTGGTACTGGTTTCTTGGGTAAAGTTTTTATTGAAAAGTTGTT
GTACTGTTGTCCAGATATTGATAAAATCTATATGTTAATTAGAGAAAAGAAAAATTTGTCT
ATTGATGAAAGAATGTCAAAGTTCTTGGATGATCCATTATTTTCTAGATTGAAGGAAGAAA
GACCTGGTGACTTGGAAAAGATTGTTTTGATTCCAGGTGACATTACAGCTCCAAATTTGGG
TTTATCAGCAGAAAACGAAAGAATTTTGTTAGAAAAAGTTTCTGTTATTATTAATTCAGCT
GCAACTGTTAAGTTTAATGAACCATTGCCAATCGCTTGGAAGATTAATGTTGAAGGTACAA
GAATGTTGTTGGCATTGTCTAGAAGAATGAAGAGAATCGAAGTTTTTATTCATATTTCTAC
TGCTTACTCAAATGCATCTTCAGATAGAATCGTTGTTGATGAAATCTTGTATCCAGCTCCA
GCAGATATGGATCAAGTTTACCAATTGGTTAAAGATGGTGTTACAGAAGAAGAAACTGAAA
GATTGTTGAACGGTTTGCCAAACACTTACACTTTTACTAAGGCTTTGACAGAACATTTGGT
TGCAGAACATCAAACATACGTTCCAACTATCATCATCAGACCATCTGTTGTTGCTTCAATT
AAAGATGAACCAATCAGAGGTTGGTTATGTAATTGGTTTGGTGCTACAGGTATCTCTGTTT
TTACTGGAAAGGGTTTGAACAGAGTTTTGTTGGGTAAAGCTTCAAACATCGTTGATGTTAT
CCCAGTTGATTACGTTGCAAATTTGGTTATTGTTGCTGGTGCAAAATCTGGTGGTGAAAAA
TCAGATGAATTAAAGATCTATAACTGTTGTTCTTCAGATTGTAACCCAGTTACTTTGAAGA
AAATTATTAAAGAGTTTAGTGAAGATAGTATTAAAAATAAGTCTCATATTATGCCATTGCC
AGGTTGGTTCGTTTTTACTAAGTACAAGTGGTTGTTGACATTGTTAACTATTATTTTTCAA
ATGTTACCAATGTATTTGGCTGATGTTTACAGAGTTTTGACAGGTAAAATCCCAAGATACA
TGAAGTTGCATCATTTGGTTATTCAAACAAGATTGGGTATCGATTTCTTTACTTCTCATTC
ATGGGTTATGAAGACAGATAGAGTTAGAGAATTATTCGGTTCTTTGTCATTGGGAGAAAAG
CATATGTTTCCATGTGATCCATCTTCAATCGATTGGACAGATTATTTGCAATCATACTGTT
ACGGTGTTAGAAGATTTTTGGAAAAGAAGAAATAA
```

SEQ ID NO: 2    *Spodoptera littoralis* FAR1_*S. cerevisiae* codon opt
```
ATGGTTGTTTTGACTTCAAAGGAAAAATCAAACATGTCTGTTGCTGATTTCTACGCTGGTA
AATCTGTTTTTATTACAGGTGGTACTGGTTTCTTGGGTAAAGTTTTTATTGAAAAGTTGTT
GTACTCATGTCCAGATATTGATAAAATCTATATGTTGATCAGAGAAAAGAAAGGTCAATCT
ATCAGAGAAAGATTAACTAAAATTGTTGATGATCCATTGTTTAATAGATTGAAGGATAAGA
GACCAGATGATTTGGGTAAAATCGTTTTGATCCCAGGTGACATCACAGTTCCAGGTTTGGG
TATTTCTGAAGAAACGAAACAATCTTGACTGAAAAAGTTTCAGTTGTTATTCATTCTGCT
GCAACTGTTAAGTTTAATGAACCATTGGCTACTGCATGGAACGTTAACGTTGAAGGTACAA
GAATGATCATGGCATTATCAAGAAGAATGAAGAGAATCGAAGTTTTTATTCATATTTCTAC
TGCTTACACTAACACAAACAGAGGAGTTATTGATGAAGTTTTGTATCCACCACCAGCTGAT
ATCAACGATGTTCATCAACATGTTAAAAATGGTGTTACAGAAGAAGAAACTGAAAAGATTT
TGAACGGTAGACCAAACACTTACACTTTTACTAAGGCTTTGACTGAACATTTGGTTGCAGA
AAACCAATCATACATGCCAACAATCATTGTTAGACCATCTATTGTTGGTGCTATTAAAGAT
GATCCAATTAGAGGTTGGTTGGCTAATTGGTATGGTGCAACAGGTTTGTCAGTTTTTACTG
CAAAGGGTTTGAACAGAGTTTATATATGGTCATTCTAACCATGTTGTTGATTTGATTCCAGT
TGATTACGTTGCTAATTTGGTTATTGTTGCTGGTGCAAAGACATACCATTCAAACGAAGTT
ACTATCTATAACTCTTGTTCTTCATCTTGTAACCCAATCACTATGAAGAGATTGGTTGGTT
TGTTTATTGATTACACAGTTAAGCATAAGTCATACGTTATGCCATTGCCAGGTTGGTATGT
TTACTCTAACTACAAGTGGTTGGTTTTCTTGGTTACTGTTATTTTCCAAGTTATTCCAGCT
TACTTAGGTGACATTGGTAGAAGATTGTTAGGTAAAAATCCAAGATACTACAAGTTGCAAA
```

| | SEQUENCE LISTING |
|---|---|
| | ATTTGGTTGCTCAAACACAAGAAGCAGTTCATTTCTTTACATCACATACTTGGGAAATTAA<br>ATCAAAGAGAACTTCTGAATTGTTTTCATCTTTGTCTTTGACAGATCAAAGAATGTTTCCA<br>TGTGATGCTAACAGAATCGATTGGACAGATTACATCACTGATTAGTGTTCTGGTGTTAGAC<br>AATTTTTGGAAAAGATTAAATAA |
| SEQ ID NO: 3 | Helicoverpa armigera FAR3_S. cerevisiae codon opt<br>ATGGTTGTTTTGACTTCAAAGGAAACAAAGCCATCTGTTGCTGAATTTTACGCTGGTAAAT<br>CAGTTTTTATTACAGGTGTACTGGTTTCTTGGGTAAAGTTTTTATTGAAAAGTTGTTGTAC<br>TCTTGTCCAGATATTGAAAATATCTATATGTTGATCAGAGAAAGAAAGGTTTGTCAGTTT<br>CTGAAAGAATTAAACAATTTTTAGATGATCCATTGTTTACAAGATTGAAGGATAAGAGACC<br>AGCTGATTTGGAAAAGATTGTTTTGATCCCAGGTGACATCACTGCACCAGATTTGGGTATT<br>AATTCTGAAAACGAAAAGATGTTGATTGAAAAAGTTTCAGTTATTATTCATTCTGCTGCAA<br>CTGTTAAGTTTAATGAACCATTACCAACAGCTTGGAAGATTAATGTTGAAGGTACTAGAAT<br>GATGTTGGCATTGTCAAGAAGAATGAAGAGAATCGAAGTTTTTATTCATATTTCTACAGCT<br>TACACTAACACAAACAGAGAAGTTGTTGATGAAATCTTGTATCCAGCTCCAGCAGATATCG<br>ATCAAGTTCATCAATACGTTAAGGATGGTATCTCAGAAGAAGATACTGAAAAGATTTTGAA<br>CGGTAGACCAAACACTTACACTTTTACTAAGGCTTTGACAGAACATTTGGTTGCTGAAAAT<br>CAAGCATACGTTCCAACTATTATTGTTAGACCATCTGTTGTTGCTGCAATTAAAGATGAAC<br>CATTGAAAGGTTGGTTGGGTAATTGGTTTGGTGCTACAGGTTTGACTGTTTTTACAGCAAA<br>GGGTTTGAACAGAGTTATATATGGTCATTCTTCATACATCGTTGATTTGATCCCAGTTGAT<br>TACGTTGCTAATTTGGTTATTGCTGCAGGTGCAAAATCTTCAAAGTCAACAGAATTGAAGG<br>TTTACAACTGTTGTTCTTCATCTTGTAACCCAGTTACTATCGGTACATTGATGTCAATGTT<br>CGCTGATGATGCAATTAAACAAAATCTTACGCTATGCCATTGCCAGGTTGGTACATTTTT<br>ACAAAGTACAAGTGGTTGGTTTTGTTGTTGACATTTTTGTTCCAAGTTATTCCAGCATACG<br>TTACTGATTTGTCAAGACATTTGATCGGTAAATCTCCAAGATACATCAAGTTGCAATCATT<br>GGTTAACCAAACTAGATCATCTATCGATTTCTTTACAAACCATTCTTGGGTTATGAAAGCT<br>GATAGAGTTAGAGAATTGTACGCTTCATTGTCTCCAGCTGATAAGTACTTATTCCCATGTG<br>ATCCAACTGATATCAACTGGACACATTACATCCAAGATTACTGTTGGGGTGTTAGACATTT<br>CTTGGAAAAGAAATCTTACGAATAA |
| SEQ ID NO: 4 | pOLE1 cassette<br>CTTGCTGAAAAGATGATGTTCTGAGGTATTCGTATCGCTAGCTTGATACGCTTTTAACAAA<br>AGTAAGCTTTTCGTTTGCAGGTTTGGTTACTTTTCTGTACGAGATGATATCGCTAAGTTTA<br>TAGTCATCTGTGAAATTTCTCAAAAACCTCATGGTTTCTCCATCACCCATTTTTCATTTCA<br>TTTGCCGGGCGGAAAAAAAAAGGAAAAAAAAAAAAAAAAAAAATAAATGACACATGGAAA<br>TAAGTCAAGGATTAGCGGATATGTAGTTCCAGTCCGGGTTATACCATCACGTGATAATAAA<br>TCCAAATGAGAATGAGGGTGTCATATCTAATCATTATGCACGTCAAGATTCTCCGTGACTA<br>TGGCTCTTTTCTGAAGCATTTTTCGGGCGCCCGGTGGCCAAAAACTAACTCCGAGCCCGGG<br>CATGTCCCGGGGTTAGCGGGCGCAACAAAGGCGCTTATCTGGTGGGCTTCCGTAGAAGAAA<br>AAAAGCTGTTGAGCGAGCTATTTCGGGTATCCCAGCCTTCTCTGCAGACCGCCCCAGTTGG<br>CTTGGCTCTGGTGCTGTTCGTTAGCATCACATCGCCTGTGACAGGCAGAGGTAATAACGGC<br>TTAAGGTTCTCTTCGCATAGTCGGCAGCTTTCTTTCGGACGTTGAACACTCAACAAACCTT<br>ATCCTAGTGCCCAACCAGGTGTGCTTCTACGAGTCTTGCTCACTCAGACACACCTATCCCTA<br>TTGTTACGGCTATGGGGATGGCACACAAAGGTGGAAATAATAGTAGTTAACAATATATGCA<br>GCAAATCATCGGCTCCTGGCTCATCGAGTCTTGCAAATCAGCATATACATATATATATGGG<br>GGCAGATCTTGATTCATTTATTGTTCTATTTCCATCTTTCCTAGTTCTGTTTCCGTTTATA<br>TTTTGTATTACGTAGAATAGAACATCATAGTAATAGATAGTTGTGGTGATCATATTATAAA<br>CAGCACTAAAACATTACAACAAAGAATGCCAACTTCTGGAACTACTATTGAATTGATTGAC<br>GACCAATTTCCAAAGGATGACTCTGCCAGCAGTGGCATTGTCGACACTAGTGCGGCCGCTC<br>ACATATGAAAGTATATACCCGCTTTTGTACACTATGTAGCTATAATTCAATCGTATTATTG<br>TAGCTCCGCACGACCATGCCTTAGAAATATCCGCAGCGCG |
| SEQ ID NO: 5 | Extended OLE1 promoter region<br>CTTGCTGAAAAGATGATGTTCTGAGGTATTCGTATCGCTAGCTTGATACGCTTTTAACAAA<br>AGTAAGCTTTTCGTTTGCAGGTTTGGTTACTTTTCTGTACGAGATGATATCGCTAAGTTTA<br>TAGTCATCTGTGAAATTTCTCAAAAACCTCATGGTTTCTCCATCACCCATTTTTCATTTCA<br>TTTGCCGGGCGGAAAAAAAAAGGAAAAAAAAAAAAAAAAAAAATAAATGACACATGGAAA<br>TAAGTCAAGGATTAGCGGATATGTAGTTCCAGTCCGGGTTATACCATCACGTGATAATAAA<br>TCCAAATGAGAATGAGGGTGTCATATCTAATCATTATGCACGTCAAGATTCTCCGTGACTA<br>TGGCTCTTTTCTGAAGCATTTTTCGGGCGCCCGGTGGCCAAAAACTAACTCCGAGCCCGGG<br>CATGTCCCGGGGTTAGCGGGCCCAACAAAGGCGCTTATCTGGTGGGCTTCCGTAGAAGAAA<br>AAAAGCTGTTGAGCGAGCTATTTCGGGTATCCCAGCCTTCTCTGCAGACCGCCCCAGTTGG<br>CTTGGCTCTGGTGCTGTTCGTTAGGATCACATCGCCTGTGACAGGCAGAGGTAATAACGGC<br>TTAAGGTTCTCTTCGCATAGTCGGCAGCTTTCTTTCGGACGTTGA |
| SEQ ID NO: 6 | OLE1 promoter region<br>ACACTCAACAAACCTTATCCTAGTGCCCAACCAGGTGTGCTTCTACGAGTCTTGCTCACTCA<br>GACACACCTATCCCTATTGTTACGGCTATGGGGATGGCACACAAAGGTGGAAATAATAGTA<br>GTTAACAATATATGCAGCAAATCATCGGCTCCTGGCTCATCGAGTCTTGCAAATCAGCATA<br>TACATATATATATGGGGGCAGATCTTGATTCATTTATTGTTCTATTTCCATCTTTCCTACT<br>TCTGTTTCCGTTTATATTTTGTATTACGTAGAATAGAACATCATAGTAATAGATAGTTGTG<br>GTGATCATATTATAAACAGCACTAAAACATTACAACAAAGA |
| SEQ ID NO: 7 | OLE1 27 aa leader<br>ATGCCAACTTCTGGAACTACTATTGAATTGATTGACGACCAATTTCCAAAGGATGACTCTG<br>CCAGCAGTGGCATTGTCGAC |

| | SEQUENCE LISTING |
|---|---|
| SEQ ID NO: 8 | Vsp13 terminator region<br>TCACATATGAAAGTATATACCCGCTTTTGTACACTATGTAGCTATAATTCAATCGTATTAT<br>TGTAGCTCCGCACGACCATGCCTTAGAAATATCCGCAGCGCG |
| SEQ ID NO: 9 | T. ni desaturase<br>ATGGCTGTGATGGCTCAAACAGTACAAGAAACGGCTACAGTGTTGGAAGAGGAAGCTCGCA<br>CAGTGACTCTTGTGGCTCCAAAGACAACGCCAAGGAAATATAAATATATATACACCAACTT<br>TCTTACATTTTCATATGCGCATTTAGCTGCATTATACGGACTTTATTTGTGCTTCACCTCT<br>GCGAAATGGGAAACATTGCTATTCTCTTTCGTACTCTTCCACATGTCAAATATAGGCATCA<br>CCGCAGGGGCTCACCGACTCTGGACTCACAAGACTTTCAAAGCCAAATTGCCTTTGGAAAT<br>TGTCCTCATGATATTCAACTCTTTTAGCCTTTCAAAAACACGGCTATTAGATGGGCTAGAGAA<br>CATCGGCTACATCACAAATACAGCGATACTGATGCTGATCCCCACAATGCGTCAAGAGGGT<br>TCTTCTACTCGCATGTTGGCTGGCTATTAGTAAAAAAACATCCCGATGTCCTGAAATATGG<br>AAAAACTATAGACATGTCGGATGTATACAATAATCCTGTGTTAAAATTTCAGAAAAAGTAC<br>GCAGTACCCTTAATTGGAACAGTTTGTTTTGCTCTGCCAACTTTGATTCCAGTCTACTGTT<br>GGGGCGAATCGTGGAACAACGCTTGGCACATAGCCTTATTTCGATACATATTCAATCTTAA<br>CGTGACTTTCCTAGTCAACAGTGCTGCGCATATCTGGGGGAATAAGCCTTATGATAAAAGC<br>ATCTTGCCCGCTCAAAACCTGCTGGTTTCCTTCCTAGCAAGTGGAGAAGGCTTCCATAATT<br>ACCATCACGTCTTTCCATGGGATTACCGCACAGCAGAATTAGGGAATAACTTCCTGAATTT<br>GACGACGCTGTTCATTGATTTTTGTGCCTGGTTTGGATGGGCTTATGACTTGAAGTCTGTA<br>TCAGAGGATATTATAAAACAGAGAGCTAAACGAACAGGTGACGGTTCTTCAGGGGTCATTT<br>GGGGATGGGACGACAAAGACATGGACCGCGATATAAAATCTAAAGCTAACATTTTTTATGC<br>TAAAAAGGAATGA |
| SEQ ID NO: 10 | A. segetum desaturase<br>ATGGCTCAAGGTGTCCAAACAACTACGATATTGAGGGAGGAGGAGCCGTCATTGACTTTCG<br>TGGTACCTCAAGAACCGAGAAAGTATCAAATCGTGTACCCAAACCTTATCACATTTGGGTA<br>CTGGCATATAGCTGGTTTATACGGGCTATATTTGTGCTTTACTTCGGCAAAATGGCAAACA<br>ATTTTATTCAGTTTCATGCTCGTTGTGTTAGCAGAGTTGGGAATAACAGCCGGCGCTCACA<br>GGTTATGGGCCCACAAAACATATAAAGCGAAGCTTCCCTTACAAATTATCCTGATGATACT<br>GAACTCCATTGCCTTCCAAAATTCCGCCATTGATTGGGTGAGGGACCACCGTCTCCATCAT<br>AAGTACAGTGACACTGATGCAGACCCTCACAATGCTACTCGTGGTTTCTTCTATTCTCATG<br>TTGGATGGTTGCTCGTAAGAAAACATCCAGAAGTCAAGAGACGTGGAAAGGAACTTGACAT<br>GTCTGATATTTACAACAATCCAGTGCTGAGATTTCAAAAGAAGTATGCTATACCCTTCATC<br>GGGGCAATGTGCTTCGGATTACCAACTTTTATCCCTGTTTACTTCTGGGGAGAAACCTGGA<br>GTAATGCTTGGCATATCACCATGCTTCGGTACATCCTCAACCTAAACATTACTTTCCTGGT<br>CAACAGTGCTGCTCATATCTGGGGATACAAACCTTATGACATCAAAATATTGCCTGCCCAA<br>AATATAGCAGTTTCCATAGTAACCGGCGGCGAAGTTTCCATAACTACCACCACGTTTTTTC<br>CTTGGGATTATCGTGCAGCAGAATTGGGGAACAATTATCTTAATTTGACGACTAAGTTCAT<br>AGATTTCTTCGCTTGGATCGGATGGGCTTACGATCTTAAGACGGTGTCCAGTGATGTTATA<br>AAAAGTAAGGCGAAAGAACTGGTGATGGGACGAATCTTTGGGGTTTAGAAGACAAAGGTG<br>AAGAAGATTTTTTGAAAATCTGGAAAGAGAATTAA |
| SEQ ID NO: 11 | T. pseudonana desaturase<br>ACTAGTATGGACTTTCTCTCCGGCGATCCTTTCCGGACACTCGTCCTTGCAGCACTTGTTG<br>TCATCGGATTTGCTGCGGCGTGGCAATGCTTCTACCCGCCGAGCATCGTCGGCAAGCCTCG<br>TACATTAAGCAATGGTAAACTCAATACCAGAATCCATGGCAAATTGTACGACCTCTCATCG<br>TTTCAGCATCCAGGAGGCCCCGTGGCTCTTTCTCTTGTTCAAGGTCGCGACGGAACAGCTC<br>TATTTGAGTCACACCATCCCTTCATACCTCGAAAGAATCTACTTTCAGATCCTCTCCAAGTA<br>CGAGGTTCCGTCGACTGAAGACTCTGTTTCCTTCATCGCCACCCTAGACGAACTCAATGGT<br>GAATCTCCGTACGATTGGAAGGACATTGAAAATGATGATTTCGTATCTGACCTACGAGCTC<br>TCGTAATTGAGCACTTTTCTCCTCTCGCCAAGGAAAGGGGAGTTTCACTCGTTGAGTCGTC<br>GAAGGCAACACCTCAGCGGTGGATGGTGGTTCTACTGCTCCTTGCGTCGTTCTTCCTGAGC<br>ATCCCATTATATTTGAGTGGTTCGTGGACTTTCGTTGTCGTCACTCCCATCCTCGCTTGGC<br>TGGCGGTTGTCAATTACTGGCACGATGCTACTCACTTTGCATTGAGCAGCAACTGGATTTT<br>GAATGCTGCGCTCCCATATCTCCTCCCTCTCCTATCGAGTCCGTCAATGTGGTATCATCAT<br>CACGTCATTGGACATCACGCATACACCAACATTTCCAAAAGAGATCCAGATCTTGCTCACG<br>CTCCACAACTCATGAGAGAACACAAGAGTATCAAATGGAGACCATCTCACTTAAATCAAAC<br>ACAGCTTCCGCGGATTCTCTTCATCTGGTCGATTGCAGTCGGTATTGGGTTGAACTTACTG<br>AACGACGTGAGAGCACTAACCAAGCTTTCATACAACAACGTTGTTCGGGTGGAGAAGATGT<br>CATCGTCGCGAACATTACTCCATTTCCTTGGACGTATGTTGCACATCTTTGTGACTACACT<br>TTGGCCCTTTTTGGCGTTTCCGGTGTGGAAGGCCATCGTTGGGCGACTGTACCGAATGCC<br>ATACTGAGTTTGTGCTTCATGCTGAATACGCAAATCAATCACCTCATCAACACGTGTGCAC<br>ATGCTTCCGATAACAACTTTTACAAGCATCAAGTTGTAACTGCTCAGAACTTTGGCCGATC<br>AAGTGCCTTTTGCTTCATCTTCTCGGGAGGTCTCAACTACCAAATTGAACATCATTTGTTG<br>CCGACGGTGAACCATTGCCATTTGCCAGCTTTGGCCCCGGGTGTAGAGCGTTTGTGTAAGA<br>AACACGGGGTGACATACAACTCTGTTGAAGGATACAGAGAGGCCATCATTGCACACTTTGC<br>ACATACCAAAGATATGTCGACGAAGCCTACTGATTGA |
| SEQ ID NO: 12 | A. transitella desaturase<br>ATGGTCCCTAACAAGGGTTCCAGTGACGTTTTGTCTGAACATTCTGAGCCCCAGTTCACTA<br>AACTCATAGCTCCACAAGCAGGGCCGAGGAAATACAAGATAGTGTATCGAAATTTGCTCAC<br>ATTCGGCTATTGGCACTTATCAGCTGTTTATGGGCTCTACTTGTGCTTTACTTGTGCGAAA<br>TGGCTACCATCTTATTTGCATTTTCTTATACGTGATCGCGAAATCGGTATAACAGGTG<br>GCGCTCATAGGCTATGGGCACATCGGACTTATAAAGCCAAGTTGCCTTTAGAGATTTTGTT<br>ACTCATAATGAACTCTATTGCCTTCCAAGACACTGCTTTCACCTGGGCTCGTGATCACCGC<br>CTTCATCACAAATATTCGGATACTGACGCTGATCCCCACAATGCTACCAGAGGGTTTTTCT |

| SEQUENCE LISTING | |
|---|---|
| | ATTCACATGTAGGCTGGCTTTTGGTGAAGAAACACCCTGAAGTCAAAGCAAGAGGAAAATA<br>CTTGTCGTTAGATGATCTTAAGAATAATCCATTGCTTAAATTCCAAAAGAAATACGCTATT<br>CTAGTTATAGGCACGTTATGCTTCCTTATGCCAACATTTGTGCCCGTATACTTCTGGGGCG<br>AGGGCATCAGCACGGCCTGGAACATCAATCTATTGCGATACGTCATGAATCTTAACATGAC<br>TTTCTTAGTTAACAGTGCAGCGCATATCTTTGGCAACAAACCATACGATAAGAGCATAGCC<br>TCAGTCCAAAATATTTCAGTTAGCTTAGCTACTTTTGGCGAAGGATTCCATAATTACCATC<br>ACACTTACCCCTGGGATTATCGTGCGGCAGAATTAGGAAATAATAGGCTAAATATGACTAC<br>TGCTTTCATAGATTTCTTCGCTTGGATCGGCTGGGCTTATGACTTGAAGTCTGTGCCACAA<br>GAGGCCATTGCAAAAAGGTGTGCGAAAACTGGCGATGGAACGGATATGTGGGGTCGAAAAA<br>GATAA |
| SEQ ID NO: 13 | *H. zea* desaturase<br>ATGGCCCAAAGCTATCAATCAACTACGGTTTTGAGTGAGGAGAAAGAACTAACACTGCAAC<br>ATTTGGTGCCCCAAGCATCGCCCAGGAAGTATCAAATAGTGTATCCGAACCTCATTACGTT<br>TGGTTACTGGCACATAGCCGGACTTTATGGCCTTTACTTGTGCTTCACTTCTGCTAAATGG<br>GCTACGATTTTATTCAGCTACATCCTCTTCGTGTTAGCAGAAATAGGAATCACGGCTGGCG<br>CTCACAGACTCTGGGCCCACAAAACTTACAAAGCGAAACTACCATTAGAAATACTCTTAAT<br>GGTATTCAACTCCATCGCTTTTCAAAACTCAGCCATTGACTGGGTGAGGGACCACCGACTC<br>CACCATAAGTATAGCGATACAGATGCTGATCCCCACAATGCCAGCCGAGGGTTCTTTTATT<br>CCCATGTAGGATGGCTACTTGTGAGAAAACATCCTGAAGTCAAAAGCGAGGGAAAGAACT<br>CAATATGTCCGATATTTACAACAATCCTGTCCTGCGGTTTCAGAAAAAATACGCCATACCC<br>TTCATTGGGGCTGTTTGTTTCGCCTTACCTACAATGATACCTGTTTACTTCTGGGGAGAAA<br>CCTGGTCCAATGCTTGGCATATCACCATGCTTCGCTACATCATGAACCTCAATGTCACCTT<br>TTTGGTAAACAGCGCTGCTCATATATGGGGAAACAAGCCTTATGACGCAAAAATATTACCT<br>GCACAAAATGTAGCTGTGTCGGTCGCCACTGGTGGAGAAGGTTTCCATAATTACCACCATG<br>TCTTCCCCTGGGATTATCGAGCAGCGGAACTCGGTAACAATAGCCTCAATCTGACGACTAA<br>ATTCATAGATTTATTCGCAGCAATCGGATGGGCATATGATCTGAAGACGGTTTCGGAGGAT<br>ATGATAAAACAAAGGATTAAACGCACTGGAGATGGAACGGATCTTTGGGGACACGAACAAA<br>ACTGTGATGAAGTGTGGGATGTAAAAGATAAATCAAGTTAA |
| SEQ ID NO: 14 | mCherry *C. tropicalis* optimized<br>ATGGTTTCTAACGGTGAAGAAGACAACATGGCAATCATCAAGGAATTTATGCGTTTTAAGG<br>TCCATATGGAAGGCTCCGTTAACGGCCACGAGTTCGAGATCGAGGGAGAAGGTGAGGGTAG<br>ACCATACGAAGGTACTCAAACCGCCAAGTTGAAAGTTACAAAGGGTGGTCCATTGCCATTT<br>GCTTGGGATATCTTGTCCCCACAATTTATGTACGGATCAAAGGCATATGTCAAGCATCCTG<br>CCGACATCCCAGATTACTTGAAGTTATCCTTTCCAGAAGGTTTTAAGTGGGAGAGAGTTAT<br>GAACTTTGAAGATGGCGGAGTTGTTACTGTTACTCAGGACTCTTCCTTGCAAGATGGTGAA<br>TTTATCTATAAAGTGAAATTGAGAGGTACTAACTTTCCATCCGACGGTCCAGTCATGCAAA<br>AGAAGAGAATGGGTTGGGAGGCTTCTTCCGAAAGAATGTACCCAGAAGACGGTGCATTGAA<br>AGGTGAAATCAAGCAACGTTTAAAGTTGAAGGACGGTGGTCACTACGATGCCGAGGTCAAG<br>ACCACTTATAAGGCTAAGAAGCCAGTCCAATTGCCAGGTGCTTATAACGTTAACATCAAGT<br>TAGATATTACTTCACACAACGAAGACTACACAATCGTTGAACAATATGAAAGAGCCGAAGG<br>TAGACATTCTACCGGCGGCATGGACGAGTTATATAAGTAG |
| SEQ ID NO: 15 | CaOLE1-*A. segetum* Z11 desaturase<br>ATGACTACAGTTGAACAACTTGAAACTGTTGATATCACTAAATTGAATGCCATTGCTGCTG<br>GTACTAATAAGAAGGTGCCAATGGCTCAAGGTGTCCAAACAACTACGATATTGAGGGAGGA<br>AGAGCCGTCATTGACTTTCGTGGTACCTCAAGAACCGAGAAAGTATCAAATCGTGTACCCA<br>AACCTTATCACATTTGGGTACTGGCATATAGCTGGTTTATACGGGCTATATTTGTGCTTTA<br>CTTCGGCAAAATGGCAAACAATTTTATTCAGTTTCATGCTCGTTGTGTTAGCAGAGTTGGG<br>AATAACAGCCGGCGCTCACAGGTTATGGGCCCACAAACATATAAAGCGAAGCTTCCCTTA<br>CAAATTATCTTAATGATATTAAACTCCATTGCCTTCCAAAATTCCGCCATTGATTGGGTGA<br>GGGACCACCGTCTCCATCATAAGTACAGTGACACTGATGCAGACCCTCACAATGCTACTCG<br>TGGTTTCTTCTATTCTCATGTTGGATGGTTGCTCGTAAGAAAACATCCAGAAGTCAAGAGA<br>CGTGGAAAGGAACTTGACATGTCTGATATTTACAACAATCCAGTGTTAAGATTTCAAAAGA<br>AGTATGCTATACCCTTCATCGGGGCAATGTGCTTCGGATTACCAACTTTTATCCCTGTTTA<br>CTTCTGGGGAGAAACCTGGAGTAATGCTTGGCATATCACCATGCTTCGGTACATCCTCAAC<br>CTAAACATTACTTTCTTAGTCAACAGTGCTGCTCATATCTGGGGATACAAACCTTATGACA<br>TCAAAATATTGCCTGCCCAAAATATAGCAGTTTCCATAGTAACCGGCGGCGAACTTTCCAT<br>AACTACCACCACGTTTTTCCTTGGGATTATCGTGCAGCAGAATTGGGGAACAATTATCTT<br>AATTTGACGACTAAGTTCATAGATTTCTTCGCTTGGATCGGATGGGCTTACGATCTTAAGA<br>CGGTGTCCAGTGATGTTATAAAAAGTAAGGCGGAAAGAACTGGTGATGGGACGAATCTTTG<br>GGGTTTAGAAGACAAAGGTGAAGAAGATTTTTTGAAAATCTGGAAAGACAATTAA |
| SEQ ID NO: 16 | *A. segetum* Z11 desaturase<br>ATGGCTCAAGGTGTCCAAACAACTACGATATTGAGGGAGGAAGAGCCGTCATTGACTTTCG<br>TGGTACCTCAAGAACCGAGAAAGTATCAAATCGTGTACCCAAACCTTATCACATTTGGGTA<br>CTGGCATATAGCTGGTTTATACGGGCTATATTTGTGCTTTACTTCGGCAAAATGGCAAACA<br>ATTTTATTCAGTTTCATGCTCGTTGTGTTAGCAGAGTTGGGAATAACAGCCGGCGCTCACA<br>GGTTATGGGCCCACAAACATATAAAGCGAAGCTTCCCTTACAAATTATCTTAATGATATT<br>AAACTCCATTGCCTTCCAAAATTCCGCCATTGATTGGGTGAGGGACCACCGTCTCCATCAT<br>AAGTACAGTGACACT<br>GATGCAGACCCTCACAATGCTACTCGTGGTTTCTTCTATTCTCATGTTGGATGGTTGCTCG<br>TAAGAAAACATCCAGAAGTCAAGAGACGTGGAAAGGAACTTGACATGTCTGATATTTACAA<br>CAATCCAGTGTTAAGATTTCAAAAGAAGTATGCTATACCCTTCATCGGGGCAATGTGCTTC<br>GGATTACCAACTTTTATCCCTGTTTACTTCTGGGGAGAAACCTGGAGTAATGCTTGGCATA<br>TCACCATGCTTCGGTACATCCTCAACCTAAACATTACTTTCTTAGTCAACAGTGCTGCTCA |

| | SEQUENCE LISTING |
|---|---|
| | TATCTGGGGATACAAACCTTATGACATCAAAATATTGCCTGCCCAAAATATAGCAGTTTCC<br>ATAGTAACCGGCGGCGAAGTTTCCATAACTACCACCACGTTTTTTCCTTGGGATTATCGTG<br>CAGCAGAATTGGGGAACAATTATCTTAATTTGACGACTAAGTTCATAGATTTCTTCGCTTG<br>GATCGGATGGGCTTACGATCTTAAGACGGTGTCCAGTGATGTTATAAAAAGTAAGGCGGAA<br>AGAACTGGTGATGGGACGAATCTTTGGGGTTTAGAAGACAAAGGTGAAGAAGATTTTTTGA<br>AAATCTGGAAAGACAATTAA |
| SEQ ID NO: 17 | A. transitella Z11 desaturase<br>ATGGTCCCTAACAAGGGTTCCAGTGACGTTTTGTCTGAACATTCTGAGCCCCAGTTCACTA<br>AACTCATAGCTCCACAAGCAGGGCCGAGGAAATACAAGATAGTGTATCGAAATTTGCTCAC<br>ATTCGGCTATTGGCACTTATCAGCTGTTTATGGGCTCTACTTGTGCTTTACTTGTGCGAAA<br>TGGGCTAGCATCTTATTTGCATTTTTCTTATACGTGATCGCGGAAATCGGTATAACAGGTG<br>GCGCTCATAGGCTATGGGCACATCGGACTTATAAAGCCAAGTTGCCTTTAGAGATTTTGTT<br>ACTCATAATGAATTCTATTGCCTTCCAAGACACTGCTTTCACCTGGGCTCGAGATCACCGC<br>CTTCATCACAAATATTCGGATACTGACGCTGATCCCCACAATGCTACCAGAGGGTTTTCT<br>ATTCACATGTAGGCTGGCTTTTGGTGAAGAAACACCCTGAAGTCAAAGCAAGAGGAAAATA<br>CTTGTCGTTAGATGATCTTAAGAATAATCCATTGCTTAAATTCCAAAAGAAATACGCTATT<br>CTAGTTATAGGCACGTTATGCTTCCTTATGCCAACATTTGTGCCCGTATACTTCTGGGGCG<br>AGGGCATCAGCACGGCCTGGAACATCAATCTATTGCGATACGTCATGAATCTTAACATGAC<br>TTTCTTAGTTAACAGTGCAGCGCATATCTTTGGCAACAAACCATACGATAAGAGCATAGCC<br>TCAGTCCAAAATATTTCAGTTAGCTTAGCTACTTTTGGCGAAGGATTCCATTATTACCATC<br>ACACTTACCCCTGGGATTATCGTGCGGCAGAATTAGGGAATAATAGGCTAAATATGACTAG<br>TGCTTTCATAGATTTCTTCGCTTGGATCGGCTGGGCTTATGACTTGAAGTCTGTGCCACAA<br>GAGGCCATTGCAAAAAGGTGTGCGAAAACTGGCGATGGAACGGATATGTGGGGTCGAAAAA<br>GATAA |
| SEQ ID NO: 18 | T. ni Z11 desaturase<br>ATGGCTGTGATGGCTCAAACAGTACAAGAAACGGCTACAGTGTTGGAAGAGGAAGCTCGCA<br>CAGTGACTCTTGTGGCTCCAAAGACAACGCCAAGGAAATATAAATATATATACACCAACTT<br>TCTTACATTTTCATATGCGCATTTAGCTGCATTATACGGACTTTATTTGTGCTTCACCTCT<br>GCGAAATGGGAAACATTGCTATTCTCTTTCGTACTCTTCCACATGTCAAATATAGGCATCA<br>CCGCAGGGGCTCACCGACTCTGGACTCACAAGACTTTCAAAGCCAAATTGCCTTTGGAAAT<br>TGTCCTCATGATATTCAACTCTTTAGCCTTTCAAAACACGGCTATTACATGGGCTAGAGAA<br>CATCGGCTACATCACAAATACAGCGATACTGATGCTGATCCCCACAATGCGTCAAGAGGGT<br>TCTTCTACTCGCATGTTGGCTGGCTATTAGTAAAAAAACATCCCGATGTCTTAAAATATGG<br>AAAAACTATAGACATGTCGGATGTATACAATAATCCTGTGTTAAAATTTCAGAAAAAGTAC<br>GCAGTACCCTTAATTGGAACAGTTTGTTTTGCTCTTCCAACTTTGATTCCAGTCTACTGTT<br>GGGGCGAATCGTGGAACAACGCTTGGCACATAGCCTTATTTCGATACATATTCAATCTTAA<br>CGTGACTTTCCTAGTCAACAGTGCTGCGCATATCTGGGGGAATAAGCCTTATGATAAAAGC<br>ATCTTGCCCGCTCAAAACTTATTAGTTTCCTTCCTAGCAAGTGGAGAAGGCTTCGATAATT<br>ACCATCACGTCTTTCCATGGGATTACCGCACAGCAGAATTAGGGAATAACTTCTTAAATTT<br>GACGACGTTATTCATTGATTTTTGTGCCTGGTTTGGATGGGCTTATGACTTGAAGTCTGTA<br>TCAGAGGATATTATAAAACAGAGAGCTAAACCAACAGGTGACGGTTCTTCAGGGGTCATTT<br>GGGGATGGGACGACAAAGACATGGACCGCGATATAAAATCTAAAGCTAACATTTTTTATGC<br>TAAAAAGGAATGA |
| SEQ ID NO: 19 | H. zea Z11 desaturase<br>ATGGCCCAAAGCTATCAATCAACTACGGTTTTGAGTGAGGAGAAAGAACTAACATTACAAC<br>ATTTGGTGCCCCAAGCATCGCCCAGGAAGTATCAAATAGTGTATCCGAACCTCATTCAGTT<br>TGGTTACTGGCACATAGCCGGACTTTATGGCCTTTACTTGTGCTTCACTTCTGCTAAATGG<br>GCTAGGATTTTATTCAGCTACATCCTCTTCGTGTTAGCAGAAATAGGAATCACGGCTGGCG<br>CTCACAGACTCTGGGCCCACAAAACTTACAAAGCGAAACTAGCATTAGAAATACTCTTAAT<br>GGTATTCAACTCCATCGCTTTTCAAAACTCAGCCATTGACTGGGTGAGGGACCACCGACTC<br>CACCATAAGTATAGCGATACAGATGCTGATCCCCACAATGCCAGCCGAGGGTTCTTTTATT<br>CCCATGTAGGATGGCTACTTGTGAGAAAACATCCTGAAGTCAAAAAGCGAGGGAAAGAACT<br>CAATATGTCCGATATTTAGAACAATCCTGTCTTACGGTTTCAGAAAAAATACGCCATACCC<br>TTCATTGGGGCTGTTTGTTTCGCCTTACCTACAATGATACCTGTTTACTTCTGGGGAGAAA<br>CCTGGTCCAATGCTTGGCATATCACCATGCTTCGCTACATCATGAACCTCAATGTCACCTT<br>TTTGGTAAACAGCGCTGCTCATATATGGGGAAACAAGCCTTATGACGAAAAATATTACCT<br>GCACAAAATGTAGCTGTGTCGGTCGCCACTGGTGGAGAAGGTTTCCATAATTACCACCATG<br>TCTTCCCCTGGGATTATCGAGCAGCGGAACTCGGTAACAATAGCCTCAATTTAACGACTAA<br>ATTCATAGATTTATTCGCAGCAATCGGATGGGCATATGATTTAAAGACGGTTTCGGAGGAT<br>ATGATAAAACAAAGGATTAAACGCACTGGAGATGGAACGGATCTTTGGGGACACGAACAAA<br>ACTGTGATGAAGTGTGGGATGTAAAAGATAAATCAAGTTAA |
| SEQ ID NO: 20 | O. furnacalis Z9 desaturase<br>ATGGCTCCTAATATTAAGGACGGAGCTGATTTGAACGGAGTTTTATTTGAAGATGACGCTA<br>GCACCCCGATTATGCCCTTGCCACGGCCCAGTCCAGAAAGCAGACAACTATCCCAGAAA<br>ACTAGTGTGGAGAAACATCATCTCTTTGCATACCTTCACCTTGCCGCTGTGTATGGAGCA<br>TACCTATTCTTATTTTCAGCGAAATGGCAGACAGATATTTTTGCCTACATTCTTTACGTGA<br>TCTCAGGACTCGGCATCACAGCGGGAGCCCACCGCCTTTGGGCGCACAAGTCATACAAGGC<br>TAAGTGGCCACTTAGACTCATTCTTATTATCTTCAACACTGTATCATTCCAGGACTCTGCT<br>CTCGACTGGTCACGTGACCACCGCATGCACCACAAATACTCGGAGACCGACGCCGACCCGC<br>ACAACGCGACTCGAGGGTTCTTCTTCTCATATCGGCTGGTTATTAGTCCGCAAGCACCC<br>GGAATTAAAGAGAAAGGGCAAGGGATTAGACTTAAGCGACTTGTATGCTGATCCCATCCTC<br>CGTTTCCAGAAGAAGTACTATTTACTATTAATGCCTCTTGGCTGCTTCATCATGCCGACGG<br>TGGTCCCGGTGTACTTCTGGGGTGAGACTTGGACTAACGCTTTCTTCGTCGCCGCGCTCTT |

| SEQUENCE LISTING |
| --- |

```
                CCGATACACCTTCATCCTCAATGTCACCTGGTTGGTCAACTCCGCCGCGCACAAGTGGGGC
                CACAAGCCCTATGACAGCAGCATCAAGCCTTCCGAGAACCTCTCAGTCTCCTTATTCGCGT
                TGGGCGAAGGATTCCACAACTACCACCACACATTCCCCTGGGACTACAAAACTGCCGAGCT
                CGGCAACAACAGACTCAATTTCACAACAAACTTCATCAACTTCTTCGCTAAAATCGGATGG
                GCTTACGACTTGAAAACGGTCTCCGACGAGATTATTCAGAATAGAGTCAAGCGCACAGGAC
                ATGGCTCCCACCACTTATGGGGTTGGGGCGACAAGGATCAACCTAAAGAGGAGGTAAACGC
                AGCCATTAGAATTAATCCTAAAGACGAGTAA
```

SEQ ID NO: 21   L. capitella Z9 desaturase
```
                ATGCCGCCGAACGTGACAGAGGCGAACGGAGTGTTATTTGAGAATGACGTGCAGACTCCTG
                ACATGGGGCTACAAGTGGCCCCTGTGCAGAAGGCTGACGAGCGTAAGATCCAGCTCGTTTG
                GAGGAACATCATCGCTTTTGCATGTCTTCATTTAGCAGCTGTGTATGGAGCTTATTTATTC
                TTCACCTCGGCTATATGGCAGACAGACATATTTGCATACATCCTTTACGTTATGTCTGGAT
                TAGGAATCACGGCGGGAGCGCACAGATTATGGGCTCATAAGTCATACAAGGCGAAGTGGCC
                GTTAAGATTAATCCTCGTCGCATTCAACACTTTGGCATTCCAGGATTCGGCAATCGACTGG
                GCGCGCGACCACCGCATGCACCACAAGTACTCGGAGACGGATCGGACCCACATAACGCCA
                CTCGCGGCTTCTTCTTTTCGCACATTGGTTGGTTACTCTGCCGAAAACACCCGGAGCTAAA
                GCGCAAGGGCCAGGGCCTCGACTTAAGTGACCTCTACGCAGATCCTATTATTCGCTTCCAA
                AAGAAGTACTACTTATTGTTAATGCCGTTAGCCTGCTTTGTTCTTCCCACCATAATTCCGG
                TCTACCTCTGGGGCGAGTCCTGGAAAAACGCGTTCTTCGTAGCTGCAATGTTCCGTTACAC
                GTTCATCCTCAACGTAACATGGCTCGTCAACTCCGCCGCCCACAAATGGGGAGGCAAGCCC
                TATGATAAGAACATCCAGCCCGCTCAGAACATCTCTGTAGCTATCTTCGCATTAGGCGAGG
                GCTTCCACAACTACCACCACACGTTCCCCTGGGACTAGAAGACCGCTGAATTAGGAAACAA
                CAGGTTAAATTTCACAACTTCGTTTATCAATTTCTTCGCAAGCTTCGGATGGCCTACGAC
                TTAAAGACCGTGTCGGACGAGATTATACAACAGCGCGTTAAGAGGACGGGAGATGGGACGCC
                ATCACTTACGGGGCTGGGGCGACCAGGACATACCGGCCGAAGAAGCTCAAGCTGCTTTACG
                CATTAACCGTAAAGATGATTAG
```

SEQ ID NO: 22   H. zea Z9 desaturase
```
                ATGGCTCCAAATATATCGGAGGATGTGAACGGGGTGCTCTTCGAGAGTGATGCAGCGACGC
                CGGACTTAGCGTTATCCACGCCGCCTGTGCAGAAGGCTGACAACAGGCCCAAGCAATTAGT
                GTGGAGGAACATACTATTATTCGCGTATCTTCACTTAGCGGCTCTTTACGGAGGTTATTTA
                TTCCTCTTCTCAGCTAAATGGCAGACAGACATATTTGCCTACATCTTATATGTGATCTCCG
                GCTTGGTATCACGGCTGGAGCACATCGCTTATGGGCCCACAAGTCCTACAAAGCTAAATG
                GCCTCTCCGAGTTATCTTAGTCATCTTTAACACAGTGGCATTCCAGGATGCCGCTATGGAC
                TGGGCGCGCGACCACCGCATGCATCACAAGTACTCGGAAACCGATGCTGATCCTCATAATG
                CGACCCGAGGATTCTTCTTCTCTCACATTGGCTGGTTACTTGTCAGGAAACATCCCGACCT
                TAAGGAGAAGGGCAAGGGACTCGACATGAGCGACTTACTTGCTGACCCCATTCTCAGGTTC
                CAGAAAAAATACTACTTAATCTTAATGCCCTTGGCTTGCTTCGTGATGCCTACCGTGATTC
                CTGTGTACTTCTGGGGTGAAACCTGGACCAACGCATTCTTTTGTGGCGGCCATGTTCCGCTA
                CGCGTTCATCCTAAATGTGACGTGGCTCGTCAACTCTGCCGCTCACAAGTGGGGAGACAAG
                CCCTACGACAAAAGCATTAAGCCTTCCGAAAACTTGTCGGTCGCCATGTTCGCTCTCGGAG
                AAGGATTCCACAACTACCACCACACTTTCCCTTGGGACTACAAAACTGCTGAGTTAGGCAA
                CAACAAACTCAACTTCACTACCACCTTTATTAACTTCTTCGCTAAAATTGGCTGGGCTTAC
                GACTTAAAGACAGTGTCTGATGATATCGTCAAGACAGGGTGAAGCGCACTGGTGACGGCT
                CCCACCACTTATGGGGCTGGGGAGACGAAAATCAATCCAAAGAAGAAATTGATGCCGCTAT
                CAGAATCAATCCTAAGGACGATTAA
```

SEQ ID NO: 23   T. pseudonana Z11 desaturase
```
                ATGGACTTTCTCTCCGGCGATCCTTTCCGGACACTCGTCCTTGCAGCACTTGTTGTCATCG
                GATTTGCTGCGGCGTGGCAATGCTTCTACCCGCCGAGCATCGTCGGCAAGCCTCGTACATT
                AAGCAATGGTAAACTCAATACCAGAATCCATGGCAAATTGTACGACCTCTCATCGTTTCAG
                CATCCAGGAGGCCCCGTGGCTCTTTCTCTTGTTCAAGGTCGCGACGGAACAGCTCTATTTG
                AGTCACACCATCCCTTCATACCTCGAAAGAATCTACTTCAGATCCTCTCCAAGTACGAGGT
                TCCGTCGACTGAAGACTCTGTTTCCTTCATCGCCACCCTAGACGAACTCAATGGTGAATCT
                CCGTACGATTGGAAGGAGATTGAAAATGATGATTTCGTATCTGAGCTAGGAGCTCTCGTAA
                TTGAGCACTTTTCTCCTCTCGCCAAGGAAAGGGGAGTTTCACTCGTTGAGTCGTCGAAGGC
                AACACCTCAGCGGTGGATGGTGGTTCTATTACTCCTTGCGTCGTTCTTCCTCAGCATCCCA
                TTATATTTGAGTGGTTCGTGGACTTTCGTTGTCGTCACTCCCATCCTCGCTTGGTTAGCGG
                TTGTCAATTACTGGCACGATGCTACTCACTTTGCATTGAGCAGCAACTGGATTTTGAATGC
                TGCGCTCCCATATCTCCTCCCTCTCCTATCGAGTCCGTCAATGTGGTATCATCATCACGTC
                ATTGGACATCACGCATACACCAACATTTCCAAAAGAGATCCAGATCTTGCTCACGCTCCAC
                AACTCATGAGAGAACACAAGAGTATCAAATGGAGACCATCTCACTTAAATCAAACACAGCT
                TCCGCGGATTCTCTTCATCTGGTCGATTGCAGTCGGTATTGGGTTGAACTTATTAAACGAC
                GTGAGAGCACTAACCAAGCTTTCATACAACAACGTTGTTCGGGTGGAGAAGATGTCATCGT
                CGCGAACATTACTCCATTTCCTTGGACGTATGTTGCACATCTTTGTGACTACACTTTGGCC
                CTTTTTGGCGTTTCCGGTGTGGAAGGCCATCGTTTGGGCGACTGTACCGAATGCCATATTA
                AGTTTGTGCTTCATGTTAAATACGCAAATCAATCACCTCATCAACACGTGTGCACATGCTT
                CCGATAACAACTTTTACAAGCATCAAGTTGTAACTGCTCAGAACTTTGGCCGATCAAGTGC
                CTTTTGCTTCATCTTCTCGGGAGGTCTCAACTACCAAATTGAACATCATTTGTTGCCGACG
                GTGAACCATTGCCATTTGCCAGCTTTGGCCCCGGGTGTAGAGCGTTTGTGTAAGAAACACG
                GGGTGACATACAACTCTGTTGAAGGATACAGAGAGGCCATCATTGCACACTTTGCACATAC
                CAAAGATATGTCGACGAAGCCTACTGATTGA
```

SEQ ID NO: 24   Native T. ni Z11 desaturase
```
                ATGGCTGTGATGGCTCAAACAGTACAAGAAACGGCTACAGTGTTGGAAGAGGAAGCTCGCA
                CAGTGACTCTTGTGGCTCCAAAGACAACGCCAAGGAAATATAAATATATATACACCAACTT
```

| | SEQUENCE LISTING |
|---|---|
| | TCTTACATTTTCATATGCGCATTTAGCTGCATTATACGGACTTTATTTGTGCTTCACCTCT<br>GCGAAATGGGAAACATTGCTATTCTCTTTCGTACTCTTCCACATGTGAAATATAGGCATCA<br>CCGCAGGGGCTCACCGACTCTGGACTCACAAGACTTTCAAAGCCAAATTGCCTTTGGAAAT<br>TGTCCTCATGATATTCAACTCTTTAGCCTTTCAAAACACGGCTATTAGATGGGCTAGAGAA<br>CATCGGCTACATCACAAATACAGCGATACTGATGCTGATCCCCACAATGCGTCAAGAGGGT<br>TCTTCTACTCGCATGTTGGCTGGCTATTAGTAAAAAAACATCCCGATGTCCTGAAATATGG<br>AAAAACTATAGACATGTCGGATGTATACAATAATCCTGTGTTAAAATTTCAGAAAAAGTAC<br>GCAGTACCCTTAATTGGAACAGTTTGTTTTGCTCTGCCAACTTTGATTCCAGTCTACTGTT<br>GGGGCGAATCGTGGAACAACGCTTGGCACATAGCCTTATTTCGATACATATTCAATCTTAA<br>CGTGACTTTCCTAGTCAACAGTGCTGCGCATATCTGGGGGAATAAGCCTTATGATAAAAGC<br>ATCTTGCCGGCTCAAAACCTGCTGGTTTCCTTCCTAGCAAGTGGAGAAGGCTTCCATAATT<br>ACCATCACGTCTTTCCATGGGATTACCGCACAGCAGAATTAGGGAATAACTTCCTGAATTT<br>GACGACGCTGTTCATTGATTTTTGTGCCTGGTTTGGATGGGCTTATGACTTGAAGTCTGTA<br>TCAGAGGATATTATAAAACAGAGAGCTAAACGAACAGGTGACGGTTCTTCAGGGGTCATTT<br>GGGGATGGGACGACAAAGACATGGACCGCGATATAAAATCTAAAGCTAACATTTTTTATGC<br>TAAAAAGGAATGA |
| SEQ ID NO: 25 | H. zea Z11 desaturase<br>ATGGCCCAAAGCTATCAATCAACTACGGTTTTGAGTGAGGAGAAAGAACTAACACTGCAAC<br>ATTTGGTGCCCCAAGCATCGCCCAGGAAGTATCAAATAGTGTATCCGAACCTCATTACGTT<br>TGGTTACTGGCACATAGCCGGACTTTATGGCCTTTACTTGTGCTTCACTTCTGCTAAATGG<br>GCTACGATTTTATTCAGCTACATCCTCTTCGTGTTAGCAGAAATAGGAATCACGGCTGGCG<br>CTCACAGACTCTGGGCCCACAAAACTTACAAAGCGAAACTACCATTAGAAATACTCTTAAT<br>GGTATTCAACTCCATCGCTTTTCAAAACTCAGCCATTGACTGGGTGAGGGACCACCGACTC<br>CACCATAAGTATAGCGATACAGATGCTGATCCCCACAATGCCAGCCGAGGGTTCTTTTATT<br>CCCATGTAGGATGGCTACTTGTGAGAAAACATCCTGAAGTCAAAAAGCGAGGGAAAGAACT<br>CAATATGTCCGATATTTAGAACAATCCTGTCCTGCGGTTTCAGAAAAAATACGCCATACCC<br>TTCATTGGGGCTGTTTGTTTCGCCTTACCTACAATGATACCTGTTTACTTCTGGGGAGAAA<br>CCTGGTCCAATGCTTGGCATATCACCATGCTTCGCTACATCATGAACCTCAATGTCACCTT<br>TTTGGTAAACAGCGCTGCTCATATATGGGGAAACAAGCCTTATGACGCAAAAATATTACCT<br>GCACAAAATGTAGCTGTGTCGGTCGCCACTGGTGGAGAAGGTTTCCATAATTACCACCATG<br>TCTTCCCCTGGGATTATCGAGCAGCGGAACTCGGTAACAATAGCCTCAATCTGACGACTAA<br>ATTCATAGATTTATTCGCAGCAATCGGATGGGCATATGATCTGAAGACGGTTTCGGAGGAT<br>ATGATAAAACAAAGGATTAAACGCACTGGAGATGGAACGGATCTTTGGGGACACGAACAAA<br>ACTGTGATGAAGTGTGGGATGTAAAAGATAAATCAAGTTAA |
| SEQ ID NO: 26 | T. ni Z11 desaturase Homo sapiens optimized<br>ATGGCCGTGATGGCCCAGACCGTGCAGGAGACCGCAACAGTGCTGGAGGAGGAGGCAAGGA<br>CCGTGACACTGGTGGCACCCAAGACCACACCTAGAAAGTACAAGTATATCTACACCAACTT<br>CCTGACCTTCAGCTACGCACACCTGGCCCCCCTGTATGGACTCTACCTGTGCTTTACCTCC<br>GCCAAGTGGGAGACACTGCTGTTCTCTTTTGTGCTGTTCCACATGAGCAATATCGGAATCA<br>CCGCAGGAGCACACAGGCTGTGGACCCACAAGACATTCAAGGCCAAGCTGCCTCTGGAGAT<br>CGTGCTGATGATCTTCAACTCTCTGGCCTTTCAGAATACCGCCATCACATGGGCCCGGGAG<br>CACAGACTGCACCACAAGTATAGCGACACCGATGCAGACCCACACAACGCAAGCAGGGGCT<br>TCTTTTACTCCCACGTGGGCTGGCTGCTGGTGAAGAAGCACCCCGACGTGCTGAAGTATGG<br>CAAGACAATCGACATGTCCGACGTGTACAACAATCCCGTGCTGAAGTTTCAGAAGAAGTAT<br>GCCGTGCCTCTGATCGGCACCGTGTGCTTCGCCCTGCCAACACTGATCCCCGTGTATTGTT<br>GGGGCGAGTCTTGGAACAATGCCTGGCACATCGCCCTGTTCCGGTACATCTTTAACCTGAA<br>TGTGACCTTTCTGGTGAACTCCGCCGCCCACATCTGGGGCAATAAGCCTTACGACAAGTCT<br>ATCCTGCCAGCCCAGAACCTGCTGGTGTCCTTCCTGGCCTCTGGCGAGGGCTTTCACAATT<br>ATCACCACGTGTTCCCATGGGACTACAGGACCGCAGAGCTGGGCAACAATTTTCTGAACCT<br>GACCACACTGTTCATCGATTTTTGTGCCTGGTTCGGCTGGGCCTATGACCTGAAGTCTGTG<br>AGCGAGGATATCATCAAGCAGAGGGCAAAGAGGACAGGCGATGGCAGCTCCGGCGTGATCT<br>GGGGATGGGACGATAAGGATATGGACAGAGATATCAAGAGCAAGGCCAATATCTTCTACGC<br>CAAGAAGGAGTGA |
| SEQ ID NO: 27 | H. zea Z11 desaturase Homo sapiens optimized<br>ATGGCACAGTCATATCAGAGCACTACCGTCCTGAGCGAAGAGAAGGAACTGACACTGCAGC<br>ACCTGGTCCCACAGGCATCACCTAGAAAGTACCAGATCGTGTATCCAAACCTGATCACCTT<br>CGGCTACTGGCACATCGCCGGCCTGTACGGCCTGTATCTGTGCTTTAGCTCCGCCAAGTGG<br>GCCACAATCCTGTTCTCTTACATCCTGTTTGTGCTGGCAGAGATCGGAATCACCGCAGGAG<br>CACACAGACTGTGGGCACACAAGACATATAAGGCCAAGCTGCCCCTGGAGATCCTGCTGAT<br>GGTGTTCAACAGCATCGCCTTTCAGAATTCCGCCATCGATTGGGTGCGGGACCACAGACTG<br>CACCACAAGTACTCCGACACCGATGCCGACCCCCACAACGCCTCTAGGGGCTTCTTTTATA<br>GCCACGTGGGATGGCTGCTGGTGCGGAAGCACCCTGAGGTGAAGAAGAGAGGCAAGGAGCT<br>GAATATGTCTGATATCTACAACAATCCTGTGCTGCGCTTCCAGAAGAAGTATGCCATCCCA<br>TTCATCGGCGCCGTGTGCTTTGCCCTGCCCACCATGATCCCCGTGTACTTTGGGGCGAGA<br>CATGGAGCAACGCCTGGCACATTCACAATGCTGCGGTATATCATGAACCTGAATGTGACATT<br>CCTGGTGAACTCCGCCGCCCACATCTGGGGCAATAAGCCATACGACGCCAAGATCCTGCCC<br>GCCCAGAACGTGGCCGTGAGCGTGGCAACCGGAGGAGAGGGCTTCCACAATTACCACCACG<br>TGTTTCCTTGGGATTATCGGGCCGCCGAGCTGGGCAACAATTCTCTGAATCTGACCACAAA<br>GTTCATCGACCTGTTTGCCGCCATCGGCTGGGCCTATGATCTGAAGACAGTGAGCGAGGAC<br>ATGATCAAGCAGAGGATCAAGCGCACCGGCGATGGCACAGACCTGTGGGGCACGAGCAGA<br>ACTGTGATGAAGTGTGGGATGTGAAAGACAAGTCCTCCTAA |

SEQUENCE LISTING

SEQ ID NO: 28    Y. lipolytica OLE1 leader - T. ni Z11 desaturase Homo sapiens
                 optimized
                 ATGGTGAAGAACGTGGACCAGGTGGATCTGTCTCAGGTGGACACCATCGCAAGCGGAAGGG
                 ATGTGAATTATAAGGTGAAGTACACATCTGGCGTGAAGACCACACCAAGAAAGTACAAGTA
                 TATCTACACCAACTTCCTGACATTTTCTTACGCCCACCTGGCCGCCCTGTATGGCCTGTAC
                 CTGTGCTTTACCAGCGCCAAGTGGGAGACACTGCTGTTCTCCTTTGTGCTGTTCCACATGT
                 CTAATATCGGAATCACCGCAGGAGCACACAGGCTGTGGACCCACAAGACATTCAAGGCCAA
                 GCTGCCCCTGGAGATCGTGCTGATGATCTTCAACTCCCTGGCCTTTCAGAATACCGCCATC
                 ACATGGGCCCGGGAGCACAGACTGCACCACAAGTATTCTGACACCGATGCAGACCCACACA
                 ACGCAAGCAGGGGCTTCTTTTACTCCCACGTGGGCTGGCTGCTGGTGAAGAAGCACCCTGA
                 CGTGCTGAAGTATGGCAAGACAATCGACATGAGCGACGTGTACAACAATCCTGTGCTGAAG
                 TTTCAGAAGAAGTATGCCGTGCCACTGATCGGCACCGTGTGCTTCGCCCTGCCCACACTGA
                 TCCCCGTGTACTGTTGGGGCGAGTCCTGGAACAATGCCTGGCACATCGCCCTGTTCCGGTA
                 CATCTTTAACCTGAATGTGACCTTTCTGGTGAACAGCGCCGCCCACATCTGGGGCAATAAG
                 CCATACGACAAGTCCATCCTGCCCGCCCAGAACCTGCTGGTGTCCTTCCTGGCCTCTGGCG
                 AGGGCTTTCACAATTATCACCACGTGTTCCCTTGGGACTACAGGACCGCAGAGCTGGGCAA
                 CAATTTTCTGAACCTGACCACACTGTTCATCGATTTTTGTGCCTGGTTCGGCTGGGCCTAT
                 GACCTGAAGTCTGTGAGCGAGGATATCATCAAGCAGAGGGCAAAGAGGACAGGCGATGGCA
                 GCTCCGGCGTGATCTGGGGATGGGACGATAAGGATATGGACAGAGATATCAAGTCCAAGGC
                 CAATATCTTCTACGCCAAGAAGGAGTGA SEQ ID NO: 29    Y. lipolytica OLE1 leader - H. zea Z11 desaturase Homo
                 sapiens optimized
                 ATGGTGAAAAACGTGGACCAAGTGGATCTCTCGCAGGTCGACACCATTGCCTCCGGCCGAG
                 ATGTCAACTACAAGGTCAAGTACACCTCCGGCGTTCGCAAGTATCAGATCGTGTATCCTAA
                 CCTGATCACCTTCGGCTACTGGCATATCGCTGGACTGTACGGACTGTATCTGTGCTTCACT
                 TCCGCCAAGTGGGCCACCATCCTGTTCTCTTACATCCTGTTTGTGCTGGCAGAGATCGGAA
                 TCACCGCAGGAGCACACAGACTGTGGGCACACAAGACATATAAGGCCAAGCTGCCACTGGA
                 GATCCTGCTGATGGTGTTCAACAGCATCGCCTTTCAGAATTCCGCCATCGATTGGGTGCGG
                 GACCACAGACTGCACCACAAGTACTCCGACACAGATGCCGACCCCCACAACGCCTCTAGGG
                 GCTTCTTTTATAGCCACGTGGGATGGCTGCTGGTGCGGAAGCACCCTGAGGTGAAGAAGAG
                 AGGCAAGGAGCTGAATATGTCTGATATCTACAACAATCCTGTGCTGCGCTTCCAGAAGAAG
                 TATGCCATCCCATTCATCGGCGCCGTGTGCTTTGCCCTGCCCACCATGATCCCCGTGTACT
                 TTTGGGGCGAGACATGGAGCAACGCCTGGCACATCACAATGCTGCGGTATATCATGAACCT
                 GAATGTGACATTCCTGGTGAACTCCGCCGCCCACATCTGGGGCAATAAGCCATACGACGCC
                 AAGATCCTGCCCGCCCAGAACGTGGCCGTGAGCGTGGCAACCGGAGGAGAGGGCTTCCACA
                 ATTACCACCACGTGTTTCCATGGGATTATAGGGCAGCAGAGCTGGGAAACAATTCTCTGAA
                 TCTGACCACAAAGTTCATCGACCTGTTTGCCGCCATCGGCTGGGCCTATGATCTGAAGACA
                 GTGAGCGAGGACATGATCAAGCAGAGGATCAAGCGCACCGGCGATGGCACAGACCTGTGGG
                 GGCACGAGCAGAATTGTGATGAAGTGTGGGATGTGAAGGATAAAAGCAGTTGA SEQ ID NO: 30    Native A. transitella Z11 desaturase
                 ATGGTCCCTAACAAGGGGTTCCAGTGACGTTTTGTCTGAACATTCTGAGCCCCAGTTCACTA
                 AACTCATAGCTCCACAAGCAGGGCCGAGGAAATACAAGATAGTGTATCGAAATTTGCTCAC
                 ATTCGGCTATTGGCACTTATCAGCTGTTTATGGGCTCTACTTGTGCTTTACTTGTGCGAAA
                 TGGGCTACCATCTTATTTGCATTTTTCTTATACGTGATCGCGGAAATCGGTATAACAGGTG
                 GCGCTCATAGGCTATGGGCACATCGGACTTATAAAGCCAAGTTGCCTTTAGAGATTTTGTT
                 ACTCATAATGAATTCTATTGCCTTCCAAGACACTGCTTTCACCTGGGCTCGAGATCACCGC
                 CTTCATCACAAATATTCGGATACTGACGCTGATCCCCACAATGCTAGCAGAGGGTTTTTCT
                 ATTCACATGTAGGCTGGCTTTTGGTGAAGAAACACCCTGAAGTCAAAGCAAGAGGAAAATA
                 CTTGTCGTTAGATGATCTTAAGAATAATCCATTGCTTAAATTCCAAAAGAAATACGCTATT
                 CTAGTTATAGGCACGTTATGCTTCCTTATGCCAACATTTGTGCCCGTATACTTCTGGGGCG
                 AGGGCATCAGCACGGCCTGGAACATCAATCTATTGCGATACGTCATGAATCTTAACATGAC
                 TTTCTTAGTTAACAGTGCAGCGCATATCTTTGGCAACAAACCATACGATAAGAGCATAGCC
                 TCAGTCCAAAATATTTCAGTTAGCTTAGCTACTTTTGGCGAAGGATTCCATAATTACCATC
                 ACACTTACCCCTGGGATTATCGTGCGGCAGAATTAGGAAATAATAGGCTAAATATGACTAC
                 TGCTTTCATAGATTTCTTCGCTTGGATCGGCTGGGCTTATGACTTGAAGTCTGTGCCACAA
                 GAGGCGATTGCAAAAAGGTGTGCGAAAACTGGCGATGGAACGGATATGTGGGGTCGAAAAA
                 GATAA SEQ ID NO: 31    pPV0228_-_Z11_Helicoverpa zea_desaturase
                 ATGGCCCAAAGCTATAATCAACTACGGTTTTGAGTGAGGAGAAAGAACTAACATTACAAC
                 ATTTGGTGCCCCAAGCATCGCCCAGGAAGTATCAAATAGTGTATCCGAACCTCATTACGTT
                 TGGTTACTGGCACATAGCCGGACTTTATGGCCTTTACTTGTGCTTCACTTCTGCTAAATGG
                 GCTACGATTTTATTCAGCTACATCCTCTTCGTGTTAGCAGAAATAGGAATCACGGCTGGCG
                 CTCACAGACTCTGGGCCACAAAAACTTACAAAGCGAAACTACCATTAGAAATACTCTTAAT
                 GGTATTCAACTCCATCGCTTTTCAAAACTCAGCCATTGACTGGGTGAGGGACCACCGACTC
                 CACCATAAGTATAGCGATACAGATGCTGATCCCCACAATGCCAGCCGAGGGTTCTTTTATT
                 CCCATGTAGGATGGCTACTTGTGAGAAAACATCCTGAAGTCAAAAAGCGAGGGAAAGAACT
                 CAATATGTCCGATATTTACAACAATCCTGTCTTACGGTTTCAGAAAAAATACGCCATACCC
                 TTCATTGGGGCTGTTTGTTTCGCCTTACCTACAATGATACCTGTTTAGTTCTGGGGAGAAA
                 CCTGGTCCAATGCTTGGCATATCACCATGCTTCGCTACATCATGAACCTCAATGTCACCTT
                 TTTGGTAAACAGCGCTGCTCATATATGGGGAAACAAGCCTTATGACGCAAAAATATTCCCT
                 GCACAAAATGTAGCTGTGTCGGTCGCCACTGGTGGAGAAGGTTTCCATAATTACCACCATG
                 TCTTCCCCTGGGATTATCGAGCAGCGGAACTCGGTAACAATAGCCTCAATTTAACGACTAA
                 ATTCATAGATTATTCGCAGCAATCGGATGGGCATATGATTTAAAGACGGTTTCGGAGGAT

|  | SEQUENCE LISTING |
| --- | --- |
|  | ATGATAAAACAAAGGATTAAACGCACTGGAGATGGAACGGATCTTTGGGGACACGAACAAA<br>ACTGTGATGAAGTGTGGGATGTAAAAGATAAATCAAGTTAA |
| SEQ ID NO: 32 | pPV0228_-_Helicoverpa armigera reductase codon optimized<br>ATGGTCGTTTTAACTTCTAAAGAGACAAAACCTTCAGTAGCTGAGTTTTATGCGGGAAAAT<br>CTGTTTTTATTACGGGTGGCACTGGATTCCTTGGAAAGGTATTCATAGAGAAACTTTTATA<br>TAGCTGTCCAGATATCGAGAATATCTACATGCTCATACGAGAGAAGAAAGGTCTTTCTGTT<br>AGCGAAAGAATAAAACAGTTCCTTGATGACCCGCTCTTTACCAGACTAAAAGACAAAAGAC<br>CAGCTGACTTAGAGAAGATTGTATTAATACCAGGAGATATTACTGCTCCTGACTTAGGCAT<br>TAATTCTGAAAACGAGAAGATGCTTATAGAGAAGGTATCGGTGATTATTCATTCGGCTGCT<br>ACGGTGAAGTTTAATGAGCCTCTCCCTACGGCTTGGAAGATCAACGTGGAAGGAACCAGAA<br>TGATGTTAGCTTTGAGTCGAAGAATGAAGCGGATTGAGGTTTTCATTCACATATCGACAGC<br>ATACACGAACACAAACAGGGAAGTGGTTGACGAGATCTTATACCCAGCTCCTGCTGATATC<br>GACCAAGTTCATCAGTATGTCAAAGATGGAATCTCTGAGGAAGACACTGAGAAAATATTAA<br>ATGGTCGTCCAAATACGTACACGTTTACGAAAGCGTTAACTGAGCATTTAGTTGCTGAGAA<br>CCAAGCCTACGTACCCACTATTATCGTCAGGCCGTCAGTCGTGGCAGCAATAAAAGATGAG<br>CCATTAAAAGGTTGGTTAGGCAACTGGTTTGGAGCGACTGGTCTCACCGTGTTCACCGCTA<br>AGGGTCTCAACCGAGTCATCTACGGTCATTCTAGCTACATCGTAGACTTAATTCCTGTGGA<br>TTATGTCGCTAATTTAGTGATTGCTGCTGGGGCTAAGAGTAGCAAGTCAACTGAGTTGAAG<br>GTATAGAACTGCTGCAGCAGCTCCTGCAATCCCGTCACTATTGGCACGTTAATGAGCATGT<br>TTGCTGACGATGCCATCAAACAGAAGTCGTATGCTATGCCGCTACCGGGGTGGTACATATT<br>CACGAAATATAAGTGGTTAGTTCTTCTTTTAACATTTCTCTTCCAAGTTATACCGGCGTAT<br>GTCACAGATCTCTCCAGGCACTTGATTGGGAAGAGTCCACGGTACATAAAACTCCAATCAC<br>TAGTAAATCAAACGCGCTCTTCAATCGACTTCTTCACGAATCACTCCTGGGTGATGAAGGC<br>AGACAGAGTGAGAGAGTTATATGCGTCTCTTTCCCCCGCAGACAAGTACTTATTTCCCTGT<br>GATCCTACGGACATTAACTGGACACATTACATACAAGACTACTGTTGGGGAGTCCGACATT<br>TTTTGGAGAAAAAAAGCTACGAATAA |
| SEQ ID NO: 33 | pPV0228_-_ICL_promoter<br>TATTAGGCGAAGAGGCATCTAGTAGTAGTGGCAGTGGTGAGAACGTGGGCGCTGCTATAGT<br>GAACAATCTCCAGTCGATGGTTAAGAAGAAGAGTGACAAACCAGCAGTGAATGACTTGTCT<br>GGGTCCGTGAGGAAAAGAAAGAAGCCCGACACAAAGGACAGTAACGTCAAGAAACCCAAGA<br>AATAGGGGGGACCTGTTTAGATGTATAGGAATAAAAACTCCGAGATGATCTCAATGTGTAA<br>TGGAGTTGTAATATTGCAAAGGGGGAAAATCAAGACTCAAACGTGTGTATGAGTGAGCGTA<br>CGTATATCTCCGAGAGTAGTATGACATAATGATGACTGTGAATCATCGTAATCTCACACAA<br>AAACCCCATTGTCGGCCATATACCACACCAAGCAACACCACATATCCCCCGGAAAAAAAAA<br>CGTGAAAAAAGAAACAATCAAAACTACAACCTACTCCTTGATCACACAGTCATTGATCAA<br>GTTACAGTTCCTGCTAGGGAATGACCAAGGTACAAATCAGCACCTTAATGGTTAGCACGCT<br>CTCTTACTCTCTCACAGTCTTCCGGCCCTATTCAAATTCTGCACTTCCATTTGACCC<br>CAGGGTTGGGAAACAGGGCCACAAAAGAAAAACCCGACGTGAATGAAAAAACTAAGAAAAG<br>AAAAAAAATTATCACACCAGAAATTTACCTAATTGGGTAATTCCCATCGGTGTTTTTCCTG<br>GATTGTCGCACGCACGCATGCTGAAAAAAGTGTTCGAGTTTTGCTTTTGCCTCGGAGTTTC<br>ACGCAAGTTTTTCGATCTCGGAACCGGAGGGCGGTCGCCTTGTTGTTTGTGATGTCGTGCT<br>TTGGGTGTTCTAATGTGCTGTTATTGTGCTCTTTTTTTTCTTCTTTTTTTGGTGATCATA<br>TGATATTGCTCGGTAGATTACTTTCGTGTGTAGGTATTCTTTTAGACGTTTGGTTATTGGG<br>TAGATATGAGAGAGAGAGAGTGGGTGGGGGAGGAGTTGGTTGTAGGAGGGACCCCTGGGAG<br>GAAGTGTAGTTGAGTTTTCCCTGACGAATGAAAATACGTTTTTGAGAAGATAATACAGGAA<br>AGGTGTGTCGGTGAATTTCCATCTATCCGAGGATATGAGTGGAGGAGAGTCGTGTGCGTGT<br>GGTTAATTTAGGATCAGTGGAACACACAAAGTAACTAAGACAGAGGACAGAGAGAAAAAT<br>CTGGGGAAGAGACAAAGAGTCAGAGTGTGTGAGTTATTCTGTATTGTGAAATTTTTTTGCC<br>CAACTACATAATATTGCTGAAACTAATTTTACTTAAAAAGAAAAGCCAACAACGTCCCCAG<br>TAAAACTTTTCTATAAATATCAGCAGTTTTCCCTTTCCTCCATTCCTCTTCTTGTCTTTTT<br>TCTTACTTTCCCTTTTTTATACCTTTTCATTATCATCCTTTATAATTGTCTAACCAACAAC<br>TATATATCTATCAA |
| SEQ ID NO: 34 | pPV0228_-_TEF_Candida tropicalis_promoter_region<br>AGGAAGACAACCAAAAGAAAGATCAAATTGACTAAATGTTGAACAGACCAAAAAAAAAGAA<br>CAACAAATAGATAAATTACAACATATTAATCTTTTGATATGTTGTTGAATATTCTAGTAAA<br>TCTAATGATCTCAATAGTGGTTATCATTCACTCTCTTCGTCCTCCTCTCTCCCCTCCTCCT<br>CTTGCAGTATATTAAAAGCAATAAAAAAAAAAAAAAAAAAGAAAATCTGCCAACACACACAA<br>AAAAAACTTACATAGTCGTGTACCAGTGTCAATATTTCACCAGCGCAGAGAAAAGAAGATG<br>AACAGAAAAATTTTCTCTTTGGTTTTGTCTTTGGTTTTGTATTAATCTCATTGAAAAATTT<br>TTTCTCTCTCTCTCTCTCTCTCACTCACACACTCACTCGCATTTCGTTTGGGTTACA<br>GCAGAAGTCAGACAGAAAAAAAAATCGTATATAACTCTCATCAAATGCCCTAGAGAAAAA<br>TTTTTCTTCTATCCTTTTTTTTTCTTCTTCTTCTTTTCCTTTTTTCTTTTAGAAGAT<br>CTTTTTGAATTCATCAAAGATATATATTTAATCAATC |
| SEQ ID NO: 35 | pPV0228_-_ICL_terminator<br>AAGAAAAAACAAAGGTAAAGAACTTCATTTGAGATGAACTTTTGTATATGACTTTTAGTT<br>TCTAGTTTTTTTTTATTTATTGCTTAATTTTCTTTATTTCAATCCCCCATAGTTTGTGTA<br>GAATATATTTATTCATTCTGGTAACTCAAACACGTAGCAAGCTCGTTGCATCTCGCCTCGT<br>CACGGGTACAGCTCTGGAACCAAAGACAAAAAAAAAGTTGATCCGAACCCTCTCGCTATT<br>CCTTGCTATGCTATCCACGAGATGGGGTTTATCAGCCCAGGCAAGTCACTAAA |
| SEQ ID NO: 36 | pPV0228_-_TEF_terminator<br>GCTGATTAATGAATAATTAATAAGTATTGTTTTTTTTGTTTTTAATATATATATATCTTGA<br>AATTAGTATAAAAAAAATCTTTTTTTTTTCTTTTTTATTTATTTTATCAATAGTTTATATA |

| | |
|---|---|
| SEQ ID NO: 37 | SapI-tLIP2-pEXP1-HA_FAR-SapI (insert into pPV199 creating pPV247)<br>GCCTGAAGAGCGCTATTTATCACTCTTTACAACTTCTACCTCAACTATCTACTTTAATAAA<br>TGAATATCGTTTATTCTCTATGATTACTGTATATGCGTTCCTCCATGGGAGTTTGGCGCCC<br>GTTTTTTCGAGCCCCACACGTTTCGGTGAGTATGAGCGGCGGCAGATTCGAGCGTTTCCGG<br>TTTCCGCGGCTGGACGAGAGCCCATGATGGGGGCTCCCACCACCAGCAATCAGGGCCCTGA<br>TTACACACCCACCTGTAATGTCATGCTGTTCATCGTGGTTAATGCTGCTGTGTGCTGTGTG<br>TGTGTGTTGTTTGGCGCTCATTGTTGCGTTATGCAGCGTAGACCACAATATTGGAAGCTTA<br>TTAGCCTTTCTATTTTTTCGTTTGCAAGGCTTAACAACATTGCTGTGGAGAGGGATGGGGA<br>TATGGAGGCCGCTGGAGGGAGTCGGAGAGGCGTTTTGGAGCGGCTTGGCCTGGCGCCCAGC<br>TCGCGAAACGCACCTAGGACCCTTTGGCACGCCGAAATGTGCCACTTTTCAGTCTAGTAAC<br>GCCTTACCTACGTCATTCCATGCATGCATGTTTGCGCCTTTTTTCCCTTGCCCTTGATCGC<br>CACACAGTACAGTGCACTGTACAGTGGAGGTTTTGGGGGGGTCTTAGATGGGAGCTAAAAG<br>CGGCCTAGCGGTACACTAGTGGGATTGTATGGAGTGGCATGGAGCCTAGGTGGAGCCTGAC<br>AGGACGCACGACCGGCTAGCCCGTGACAGACGATGGGTGGCTCCTGTTGTCCACCGCGTAC<br>AAATGTTTGGGCCAAAGTCTTGTCAGCCTTGCTTGCGAACCTAATTCCCAATTTTGTCACT<br>TCGCACCCCCATTGATCGAGCCCTAACCCCTGCCCATCAGGCAATCCAATTAAGCTCGCAT<br>TGTCTGCCTTGTTTAGTTTGGCTCCTGCCCGTTTCGGCGTCCACTTGCACAAACACAAACA<br>AGCATTATATATAAGGCTCGTCTCTCCCTCCCAACCACACTCACTTTTTTGCCCGTCTTCC<br>CTTGCTAACACAAAAGTCAAGAACACAAACAACCACCCCAACCCCCTTACACACAAGACAT<br>ATCTACAGCAATGGTGGTGCTGACCAGCAAGGAGACAAAGCCTTCCGTGGCCGAGTTCTAC<br>GCCGGCAAGTCCGTGTTTATCACAGGCGGCACCGGCTTCCTGGGCAAGGTGTTTATCGAGA<br>AGCTGCTGTACTCTTGCCCAGACATCGAGAACATCTATATGCTGATCGGGAGAAGAAGGG<br>CCTGAGCGTGTCCGAGAGAATCAAGCAGTTCCTGGACGATCCCCTGTTTACACGGCTGAAG<br>GACAAGAGACCTGCCGATCTGGAGAAGATCGTGCTGATCCCGGGCGACATCACCGCACCAG<br>ATCTGGGCATCAACTCCGAGAATGAGAAGATGCTGATCCAGAAGGTGTCCGTGATCATCCA<br>CTCTGCCGCCACCGTGAAGTTCAACGAGCCCCTGCCTACAGCCTGGAAGATCAATGTGGAG<br>GGCACCAGGATGATGCTGGCCCTGAGCCGGAGAATGAAGCGCATCGAGGTGTTTATCCACA<br>TCTCCACAGCCTACACCAACACAAATCGGGAGGTGGTGGACGAGATCCTGTACCCAGCCCC<br>CGCCGACATCGATCAGGTGCACCAGTATGTGAAGGACGGCATCAGCGAGGAGGATACCGAG<br>AAGATCCTGAACGGCCGGCCAAATACCTACACATTCACCAAGGCCCTGACAGAGCACCTGG<br>TGGCCGAGAACCAGGCCTATGTGCCTACCATCATCGTGAGACCATCCGTGGTGGCCGCCAT<br>CAAGGATGAGCCCCTGAAGGGATGGCTGGGAAACTGGTTCGGAGCAACAGGACTGACCGTG<br>TTTACAGCCAAGGGCCTGAATAGAGTGATCTACGGCCACAGCTCCTATATCGTGGACCTGA<br>TCCCCGTGGATTACGTGGCAAACCTGGTCATCGCAGCAGGAGCCAAGTCTAGCAAGTCTAC<br>CGAGCTGAAGGTGTATAACTGCTGTTCCTCTAGCTGTAATCCTGTGACCATCGGCACACTG<br>ATGTCCATGTTCGCCGACGATGCCATCAAGCAGAAGTCTTACGCCATGCCTCTGCCAGGCT<br>GGTACATCTTTACAAAGTATAAGTGGCTGGTGCTGCTGACCTTCCTGTTTCAGGTCAT<br>CCCAGCCTACGTGACCGATCTGTCTAGGCACCTGATCGGCAAGAGCCCCCGCTATATCAAG<br>CTGCAGTCTCTGGTGAACCAGACGAGGTCCTCTATCGACTTCTTTACAAATGACAGCTGGG<br>TCATGAAGGCCGATAGGGTGCGCGAGCTGTACGCCTCTCTGAGCCCTGCCGACAAGTATCT<br>GTTCCCCTGCGACCCTACCGATATCAATTGGACACACTACATCCAGGATTATTGTTGGGGC<br>GTGCGCCACTTCCTGGAAGAAGTCCTATGAGTGAGCCTGAAGAGC |
| SEQ ID NO: 38 | NcoI-pTAL-AleI (insert into pPV247 creating pPV248)<br>CCATGGGTAAGCAGGTGGCTCCGTTTGTGTCTTTGTGTTTTTCCCCTCCTTTTTGGACCAT<br>TTGTCAGCATGTTGCGTAGGTCTGGGTGTTTGACTGTTCAGGTGGTGGATGACGGATGCAT<br>CATCTGACGGCAGAGTGGGTACCTGGCAGTGGCAGGCTCGCAGACGAGGTAGAGAGATTCT<br>GAAAGGAGCCATTGACAGATGGAGAATTGGATACTCCTGGTATGTCCTCCGTTTCCACTTT<br>TGACGTTGGTGACGTGCTCTGGAACGACTTTTTTCTTTTTCTTTAAAACAAAAAAAAGAAA<br>GAAAAAAAAAACATTTACTACTACCAGTAGTACACCTCAACATTGGGTCCAGAACGTCCCA<br>ACTGCATGAGTCACTGGAGTCATGCCGAGGTCGCTAAGGTGCTGTAAAATACAACGTCAAT<br>TGAGAGAGACACAGGCGCAGCGCGCCGAGGGAGAAACGAGGCATTTATCTTCTGACCCTCC<br>TTTTTACTCGTAATCTGTATCCCGGAACCGCGTCGCATCCATGTTAATTAAATCAACACTT<br>ACACTTGCTTGCTTCGTATGATGAAGATTTCTGACTGGCAACCCAGTCAGCAGCAGATTGG<br>GGCAGATGTAGTAATGAAAACACTGCAAGGTGTGACGTTTGAGACACTCCAATTGGTTAG<br>AAAGCGACAAAGAAGACGTCGGAAAAATACCGGAAAAATCGAGTCTTTTTCTTTCTGCGTA<br>TTGGGCCCTTCTGCCTCCTTTGCCGCCCTTTCCACGCTCTTTCCACACCCTCACACTCCCT<br>GAGCACTATGATCTCATTGCGCAATAAGATATACATGCACGTGCATTTGGTGAGCACGCAG<br>AACCTTGTTGGGGAAGATGCCCTAACCCTAAGGGCGTTCCATACGGTTCGACAGAGTAAC<br>CTTGCTGTCGATTATAACGCATATATAGCCCCCCCCTTCGGACCCTCCTTCTGATTTCTGT<br>TTCTGTATCAACATTACACACAAACACACAATGGTG |
| SEQ ID NO: 39 | pDST003_Sesamia inferens desaturase<br>MLSQEEPTDTSLVPRAAPRKYQIVYPNLITFGYWHLAGLYGLYLCFTSAKWTTILFSFILC<br>VIAEIGVTAGAHRLWAHKTYKANLPLQILLMVMNSIAFQNSAIDWVPDHRLHHKYSDTDAD<br>PHNASRGFFYSHVGWLLVKKHPEVKKRGKELDMSDIYSNPVLRFQKQYAIPFIGAVCFILP<br>TVIPVYCWGETWTNAWHITMLRYITNLNVTFLVNSAAHIWGYKPYDENILPAQNIAVSIAT<br>CGEGFHNYHHVFPWDYRAAELGNNNLNLTTKFIDFFAWLGWAYDLKTVSSDMIKLRAKRTG<br>DGTNLWGEHNDELKEGKED |
| SEQ ID NO: 40 | H. armigera FAR from SEQ ID NO: 37<br>ATGGTGGTGCTGACCAGCAAGGAGACAAAGCCTTCCGTGGCCGAGTTCTAGGCCGGCAAGT<br>CCGTGTTTATCACAGGCGGCACCGGCTTCCTGGGCAAGGTGTTTATCGAGAAGCTGCTGTA |

```
CTCTTGCCCAGACATCGAGAACATCTATATGCTGATCCGGGAGAAGAAGGGCCTGAGCGTC
TCCGAGAGAATCAAGCAGTTCCTGGACGATCCCCTGTTTACACGGCTGAAGGACAAGAGAC
CTGCCGATCTGGAGAAGATCGTGCTGATCCCAGGCGACATCACCGCACCAGATCTGGGCAT
CAACTCCGAGAATGAGAAGATGCTGATCGAGAAGGTGTCCGTGATCATCCACTCTGCCGCC
ACCGTGAAGTTCAACGAGCCCCTGCCTACAGCCTGGAAGATCAATGTGGAGGGCACCAGGA
TGATGCTGGCCCTGAGCCGGAGAATGAAGCGCATCGAGGTCTTTATCCACATCTCCACAGC
CTACACCAACACAAATCGGGAGGTGGTGGACGAGATCCTGTACCCAGCCCCCGCCGACATC
GATCAGGTGCACCAGTATGTGAAGGACGGCATCAGCGAGGAGGATACCGAGAAGATCCTGA
ACGGCCGGCCAAATACCTACACATTCACCAAGGCCCTGACAGAGCACCTGGTGGCCGAGAA
CCAGGCCTATGTGCCTACCATCATCGTGAGACCATCCGTGGTGGCCGCCATCAAGGATGAG
CCCCTGAAGGGATGGCTGGGAAACTGGTTCGGAGCAACAGGACTGACCGTGTTTACAGCCA
AGGGCCTGAATAGAGTGATCTACGGCCACAGCTCCTATATCGTGGACCTGATCCCCGTGGA
TTACGTGGCAAACCTGGTCATCGCAGCAGGAGCCAAGTCTAGCAAGTCTACCGAGCTGAAG
GTGTATAACTGCTGTTCCTCTAGCTGTAATCCTGTGACCATCGGCACACTGATGTCCATGT
TCGCCGACGATGCCATGAAGCAGAAGTCTTACGCCATGCCTCTGCCAGGCTGGTACATCTT
TACAAAGTATAAGTGGCTGGTGCTGCTGACCTTCCTGTTTCAGGTCATCCCAGCCTAC
GTGACCGATCTGTCTAGGCACCTGATCGGCAAGAGCCCCCGCTATATCAAGCTGCAGTCTC
TGGTGAACCAGACCAGGTCCTCTATCGACTTCTTTACAAATCACAGCTGGGTCATGAAGGC
CGATAGGGTGCGCGAGCTGTACGCCTCTCTGAGCCCTGCCGACAAGTATCTGTTCCCCTGC
GACCCTACCGATATCAATTGGACACACTACATCCAGGATTATTGTTGGGGCGTGCGCCACT
TCCTGGAGAAGAAGTCCTATGAGTGA
```

SEQ ID NO: 41  *H. armigera* alcohol forming reductase (HaFAR)
MVVLTSKETKPSVAEFYAGKSVFITGGTGFLGKVFIEKLLYSCPDIENIYMLIREKKGLS
VSERIKQFLDDPLFTRLKDKRPADLEKIVLIPGDITAPDLGINSENEKMLIEKVSVIIHS
AATVKFNEPLPTAWKINVEGTRMMLALSRRMKRIEVFIHISTAYTNTNREVVDEILYPAP
ADIDQVHQYVKDGISEEDTEKILNGRPNTYTFTKALTEHLVAENQAYVPTIIVRPSVVAA
IKDEPLKGWLGNWFGATGLTVFTAKGLNRVIYGHSSYIVDLIPVDYVANLVIAAGAKSSK
STELKVYNCCSSSCNPVTIGTLMSMFADDAIKQKSYAMPLPGWYIFTKYKWLVLLLTFLF
QVIPAYVTDLSRHLIGKSPRYIKLQSLVNQTRSSIDFFTNHSWVMKADRVRELYASLSPA
DKYLFPCDPTDINWTHYIQDYCWGVRHFLEKKSYE SEQ ID NO: 42  HaFAR S60A
MVVLTSKETKPSVAEFYAGKSVFITGGTGFLGKVFIEKLLYSCPDIENIYMLIREKKGLAV
SERIKQFLDDPLFTRLKDKRPADLEKIVLIPGDITAPDLGINSENEKMLIEKVSVIIHSAA
TVKFNEPLPTAWKINVEGTRMMLALSRRMKRIEVFIHISTAYTNTNREVVDEILYPAPADI
DQVHQYVKDGISEEDTEKILNGRPNTYTFTKALTEHLVAENQAYVPTIIVRPSVVAAIKDE
PLKGWLGNWFGATGLTVFTAKGLNRVIYGHSSYIVDLIPVDYVANLVIAAGAKSSKSTELK
VYNCCSSSCNPVTIGTLMSMFADDAIKQKSYAMPLPGWYIFTKYKWLVLLLTFLFQVIPAY
VTDLSRHLIGKSPRYIKLQSLVNQTRSSIDFFTNHSWVMKADRVRELYASLSPADKYLFPC
DPTDINWTHYIQDYCWGVRHFLEKKSYE SEQ ID NO: 43  HaFAR S195A
MVVLTSKETKPSVAEFYAGKSVFITGGTGFLGKVFIEKLLYSCPDIENIYMLIREKKGLSV
SERIKQFLDDPLFTRLKDKRPADLEKIVLIPGDITAPDLGINSENEKMLIEKVSVIIHSAA
TVKFNEPLPTAWKINVEGTRMMLALSRRMKRIEVFIHISTAYTNTNREVVDEILYPAPADI
DQVHQYVKDGIAEEDTEKILNGRPNTYTFTKALTEHLVAENQAYVPTIIVRPSVVAAIKDE
PLKGWLGNWFGATGLTVFTAKGLNRVIYGHSSYIVDLIPVDYVANLVIAAGAKSSKSTELK
VYNCCSSSCNPVTIGTLMSMFADDAIKQKSYAMPLPGWYIFTKYKWLVLLLTFLFQVIPAY
VTDLSRHLIGKSPRYIKLQSLVNQTRSSIDFFTNHSWVMKADRVRELYASLSPADKYLFPC
DPTDINWTHYIQDYCWGVRHFLEKKSYE SEQ ID NO: 44  HaFAR S298A
MVVLTSKETKPSVAEFYAGKSVFITGGTGFLGKVFIEKLLYSCPDIENIYMLIREKKGLSV
SERIKQFLDDPLFTRLKDKRPADLEKIVLIPGDITAPDLGINSENEKMLIEKVSVIIHSAA
TVKFNEPLPTAWKINVEGTRMMLALSRRMKRIEVFIHISTAYTNTNREVVDEILYPAPADI
DQVHQYVKDGISEEDTEKILNGRPNTYTFTKALTEHLVAENQAYVPTIIVRPSVVAAIKDE
PLKGWLGNWFGATGLTVFTAKGLNRVTYGHSSYIVDLIPVDYVANLVIAAGAKASKSTELK
VYNCCSSSCNPVTIGTLMSMFADDAIKQKSYAMPLPGWYIFTKYKWLVLLLTFLFQVIPAY
VTDLSPHLIGKSPRYIKLQSLVNQTRSSIDFFTNHSWVMKADRVRELYASLSPADKYLFPC
DPTDINWTHYIQDYCWGVRHFLEKKSYE SEQ ID NO: 45  HaFAR S378A
MVVLTSKETKPSVAEFYAGKSVFITGGTGFLGKVFIEKLLYSCPDIENIYMLIREKKGLSV
SERIKQFLDDPLFTRLKDKRPADLEKIVLIPGDITAPDLGINSENEKMLIEKVSVIIHSAA
TVKFNEPLPTAWKINVEGTRMMLALSRRMKRIEVFIHISTAYTNTNREVVDEILYPAPADI
DQVHQYVKDGISEEDTEKILNGRPNTYTFTKALTEHLVAENQAYVPTIIVRPSVVAAIKDE
PLKGWLGNWFGATGLTVFTAKGLNRVIYGHSSYIVDLIPVDYVANLVIAAGAKSSKSTELK
VYNCCSSSCNPVTIGTLMSMFADDAIKQKSYAMPLPGWYIFTKYKWLVLLLTFLFQVIPAY
VTDLSRHLIGKAPRYIKLQSLVNQTRSSIDFFTNHSWVMKADRVRELYASLSPADKYLFPC
DPTDINWTHYIQDYCWGVRHFLEKKSYE SEQ ID NO: 46  HaFAR S394A
MVVLTSKETKPSVAEFYAGKSVFITGGTGFLGKVFIEKLLYSCPDIENIYMLIREKKGLSV
SERIKQFLDDPLFTRLKDKRPADLEKIVLIPGDITAPDLGINSENEKMLIEKVSVIIHSAA
TVKFNEPLPTAWKINVEGTRMMLALSRRMKRIEVFIHISTAYTNTNREVVDEILYPAPADI
DQVHQYVKDGISEEDTEKILNGRPNTYTFTKALTEHLVAENQAYVPTIIVRPSVVAAIKDE

SEQUENCE LISTING

PLKGWLGNWFGATGLTVFTAKGLNRVIYGHSSYIVDLIPVDYVANLVIAAGAKSSKSTELK
VYNCCSSSCNPVTIGTLMSMFADDAIKQKSYAMPLPGWYIFTKYKWLVLLLTFLFQVIPAY
VTDLSRHLIGKSPRYIKLQSLVNQTRSAIDFFTNHSWVMKADRVRELYASLSPADKYLFPC
DPTDINWTHYIQDYCWGVRHFLEKKSYE

SEQ ID NO: 47  HaFAR S418A
MVVLTSKETKPSVAEFYAGKSVFITGGTGFLCKVFIEKLLYSCPDIENIYMLIREKKGLSV
SERIKQFLDDPLFTRLKDKRPADLEKIVLIPGDITAPDLGINSENEKMLIEKVSVIIHSAA
TVKFNEPLPTAWKINVEGTRMMLALSRRMKRIEVFIHISTAYTNTNREVVDEILYPAPADI
DQVHQYVKDGISEEDTEKILNGRPNTYTFTKALTEHLVAENQAYVPTIIVRPSVVAAIKDE
PLKGWLGNWFGATGLTVFTAKGLNRVIYGHSSYIVDLIPVDYVANLVIAAGAKSSKSTELK
VYNCCSSSCNPVTIGTLMSMFADDAIKQKSYAMPLPGWYIFTKYKWLVLLLTFLFQVIPAY
VTDLSRHLIGKSPRYIKLQSLVNQTRSSIDFFTNHSWVMKADRVRELYASLAPADKYLFPC
DPTDINWTHYIQDYCWGVRHFLEKKSYE

SEQ ID NO: 48  HaFAR S453A
MVVLTSKETKPSVAEFYAGKSVFITGGTGFLGKVFIEKLLYSCPDIENIYMLIREKKGLSV
SERIKQFLDDPLFTRLKDKRPADLEKIVLIPGDITAPDLGINSENEKMLIEKVSVIIHSAA
TVKFNEPLPTAWKINVEGTRMMLALSRRMKRIEVFIHISTAYTNTNREVVDEILYPAPADI
DQVHQYVKDGISEEDTEKILNGRPNTYTFTKALTEHLVAENQAYVPTIIVRPSVVAAIKDE
PLKGWLGNWFGATGLTVFTAKGLNRVIYGHSSYIVDLIPVDYVANLVIAAGAKSSKSTELK
VYNCCSSSCNPVTIGTLMSMFADDAIKQKSYAMPLPGWYIFTKYKWLVLLLTFLFQVIPAY
VTDLSRHLIGKSPRYIKLQSLVNQTRSSIDFFTNHSWVMKADRVRELYASLSPADKYLFPC
DPTDINWTHYIQDYCWGVRHFLEKKAYE

SEQ ID NO: 49  *Trichoplusia ni* desaturase
MAVMAQTVQETATVLEEEARTVTLVAPKTTPRKYKYIYTNFLTFSYAHLAALYGLYLCFTS
AKWETLLFSFVLFHMSNIGITAGAHRLWTHKTFKAKLPLEIVLMIFNSLAFQNTAITWARE
HRLHHKYSDTDADPHNASRGFFYSHVGWLLVKKHPDVLKYGKTIDMSDVYNNPVLKFQKKY
AVPLIGTVCFALPTLIPVYCWGESWNNAWHIALFRYIFNLNVTFLVNSAAHIWGNKPYDKS
ILPAQNLLVSFLASGEGFHNYHHVFPWDYRTAELGNNFLNLTTLFIDFCAWFGWAYDLKSV
SEDIIKQRAKRTGDGSSGVIWGWDDKDMRDIKSKANIFYAKKE SEQ ID NO: 50  *T. pseudonana* desaturase encoded by SEQ ID NO: 11
TSMDFLSGDPFRTLVLAALVVIGFAAAWQCFYPPSIVGKPRTLSNGKLNTRIHGKLYDLSS
FQHPGGPVALSLVQGRDGTALFESHHPFIPRKNLLQILSKYEVPSTEDSVSFIATLDELNG
ESPYDWKDIENDDFVSDLRALVIEHFSPLAKERGVSLVESSKATPQRWMVVLLLLASFFLS
IPLYLSGSWTFVVVTPILAWLAVVNYWHDATHFALSSNWILNAALPYLLPLLSSPSMWYHH
HVIGHHAYTNISKRDPDLAHAPQLMREHKSIKWRPSHLNQTQLPRILFIWSIAVGIGLNLL
NDVRALTKLSYNNVVRVEKMSSSRTLLHFLGRMLHIFVTTLWPFLAFPVWKAIVWATVPNA
ILSLCFMLNTQINHLINTCAHASDNNFYKHQVVTAQNFGRSSAFCFIFSGGLNYQIEHHLL
PTVNHCHLPALAPGVERLCKKHGVTYNSVEGYREAIIAHFAHTKDMSTKPTD SEQ ID NO: 51  *T. pseudonana* Z11 desaturase encoded by SEQ ID NO: 23
MDFLSGDPFRTLVLAALVVIGFAAAWQCFYPPSIVGKPRTLSNGKLNTRIHGKLYDLSSFQ
HPGGPVALSLVQGRDGTALFESHHPFIPRKNLLQILSKYEVPSTEDSVSFIATLDELNGES
PYDWKDIENDDFVSDLRALVIEHFSPLAKERGVSLVESSKATPQRWMVVLLLLASFFLSIP
LYLSGSWTFVVVTPILAWLAVVNYWHDATHFALSSNWILNAALPYLLPLLSSPSMWYHHHV
IGHHAYTNISKRDPDLAHAPQLMREHKSIKWRPSHLNQTQLPRILFIWSIAVGIGLNLLND
VRALTKLSYNNVVRVEKMSSSRTLLHFLGRMLHIFVTTLWPFLAFPVWKAIVWATVPNAIL
SLCFMLNTQINHLINTCAHASDNNFYKHQVVTAQNFGRSSAFCFIFSGGLNYQIEHHLLPT
VNHCHLPALAPGVERLCKKHGVTYNSVEGYREAIIAHFAHTKDMSTKPTD SEQ ID NO: 52  *Amyelois transitella* desaturase
MVPNKGSSDVLSEHSEPQFTKLIAPQAGPRKYKIVYRNLLTFGYWHLSAVYGLYLCFTCAK
WATILFAFFLYVIAEIGITGGAHRLWAHRTYKAKLPLEILLLIMNSIAFQDTAFTWARDHR
LHHKYSDTDADPHNATRGFFYSHVGWLLVKKHPEVKARGKYLSLDDLKNNPLLKFQKKYAI
LVIGTLCFLMPTFVPVYFWGEGISTAWNINLLRYVMNLNMTFLVNSAAHIFGNKPYDKSIA
SVQNISVSLATFGEGFHNYHHTYPWDYRAAELGNNRLNMTTAFIDFFAWIGWAYDLKSVPQ
EAIAKRCAKTGDGTDMWGRKR SEQ ID NO: 53  *Agrotis segetum* desaturase
MAQGVQTTTILREEEPSLTFVVPQEPRKYQIVYPNLITFGYWHIAGLYGLYLCFTSAKWQT
ILFSFMLVVLAELGITAGAHRLWAHKTYKAKLPLQIILMILNSIAFQNSAIDWVRDHRLHH
KYSDTDADPHNATRGFFYSHVGWLLVRKHPEVKRRGKELDMSDIYNNPVLRFQKKYAIPFI
GAMCFGLPTFIPVYFWGETWSNAWHITMLRYILNLNITFLVNSAAHIWGYKPYDIKILPAQ
NIAVSIVTGGEVSITTTTFFPWDYRAAELGNNYLNLTTKFIDFFAWIGWAYDLKTVSSDVI
KSKAERTGDGTNLWGLEDKGEEDFLKIWKDN SEQ ID NO: 54  *Helicoverpa zea* desaturase
MAQSYQSTTVLSEEKELTLQHLVPQASPRKYQIVYPNLITFGYWHIAGLYGLYLCFTSAKW
ATILFSYILFVLAEIGITAGAHRLWAHKTYKAKLPLEILLMVFNSIAFQNSAIDWVRDHRL
HHKYSDTDADPHNASRGFFYSHVGWLLVRKHPEVKKRGKELNMSDIYNNPVLRFQKKYAIP
FIGAVCFLAPTMIPVYFWGETWSNAWHITMLRYIMNLNVTFLVNSAAHIWGNKPYDAKILP
AQNVAVSVATGGEGFHNYHHVFPWDYRAAELGNNSLNLTTKFIDLFAAIGWAYDLKTVSED
MIKQRIKRTGDGTDLWGHEQNCDEVWDVKDKSS

SEQUENCE LISTING

SEQ ID NO: 55 *Agrotis segetum* FAR encoded by SEQ ID NO: 1
MPVLTSREDEKLSVPEFYAGKSIFVTGGTGFLGKVFIEKLLYCCPDIDKIYMLIREKKNLS
IDERMSKFLDDPLFSRLKEERPGDLEKIVLIPGDITAPNLGLSAENERILLEKVSVIINSA
ATVKFNEPLPIAWKINVEGTRMLLALSRRMKRIEVFIHISTAYSNASSDRIVVDEILYPAP
ADMDQVYQLVKDGVTEEETERLLNGLPNTYTFTKALTEHLVAEHQTYVPTIIIRPSVVASI
KDEPIRGWLCNWFGATGISVFTAKGLNRVLLGKASNIVDVIPVDYVANLVIVAGAKSGGQK
SDELKIYNCCSSDCNPVTLKKIIKEFTEDTIKNKSHIMPLPGWFVFTKYKWLLTLLTIIFQ
MLPMYLADVYRVLTGKIPRYMKLHHLVIQTRLGIDFFTSHSWVMKTDRVRELFGSLSLAEK
HMFPCDPSSIDWTDYLQSYCYGVRRFLEKKK

SEQ ID NO: 56 *Spodoptera littoralis* FAR encoded by SEQ ID NO: 2
MVVLTSKEKSNMSVADFYAGKSVFITGGTGFLGKVFIEKLLYSCPDIDKIYMLIREKKGQS
IRERLTKIVDDPLFNRLKDKRPDDLGKIVLIPGDITVPGLGISEENETILTEKVSVVIHSA
ATVKFNEPLATAWNVNVEGTRMIMALSRRMKRIEVFIHISTAYTNTNRAVIDEVLYPPPAD
INDVHQHVKNGVTEEETEKILNGRPNTYTFTKALTEHLVAENQSYMPTIIVRPSIVGAIKD
DPIRGWLANWYGATGLSVFTAKGLNRVIYGHSNHVVDLIPVDYVANLVIVAGAKTYHSNEV
TIYNSCSSSCNPITMKRLVGLFIDYTVKHKSYVMPLPGWYVYSNYKWLVFLVTVIFQVIPA
YLGDIGRRLLGKNPRYYKLQNLVAQTQEAVHFFTSHTWEIKSKRTSELFSSLSLTDQRMFP
CDANRIDWTDYITDYCSGYRQFLEKIK

SEQ ID NO: 57 *Helicoverpa armigera* FAR encoded by SEQ ID NO: 3 or 32
MVVLTSKETKPSVAEFYAGKSVFITGGTGFLGKVFIEKLLYSCPDIENIYMLIREKKGLSV
SERIKQFLDDPLFTRLKDKRPADLEKIVLIPGDITAPDLGINSENEKMLIEKVSVIIHSAA
TVKFNEPLPTAWKINVEGTRMMLALSRRMKRIEVFIHISTAYTNTNREVVDEILYPAPADI
DQVHQYVKDGISEEDTEKILNGRPNTYTFTKALTEHLVAENQAYVPTIIVRPSVVAAIKDE
PLKGWLGNWFGATGLTVFTAKGLNRVIYGHSSYIVDLIPVDYVANLVIAAGAKSSKSTELK
VYNCCSSSCNPVTIGTLMSMFADDAIKQKSYAMPLPGWYIFTKYKWLVLLLTFLFQVIPAY
VTDLSRHLIGKSPRYIKLQSLVNQTRSSIDFFTNHSWVMKADRVRELYASLSPADKYLFPC
DPTDINWTHYIQDYCWGVRHFLEKKSYE

SEQ ID NO: 58 *Ostrinia furnacalis* Z9 desaturase encoded by SEQ ID NO: 20
MAPNIKDGADLNGVLFEDDASTPDYALATAPVQKADNYPRKLVWRNIILFAYLHLAAVYGA
YLFLFSAKWQTDIFAYILYVISGLGITAGAHRLWAHKSYKAKWPLRLILIIFNTVSFQDSA
LDWSRDHRMHHKYSETDADPHNATRGFFFSHIGWLLVRKHPELKRKGKGLDLSDLYADPIL
RFQKKYYLLLMPLGCFIMPTVVPVYFWGETWTNAFFVAALFRYTFILNVTWLVNSAAHKWG
HKPYDSSIKPSENLSVSLFALGEGFHNYHHTFPWDYKTAELGNNRLNFTTNFINFFAKIGW
AYDLKTVSDEIIQNRVKRTGDGSHHLWGWGDKDQPKEEVNAAIRINPKDE

SEQ ID NO: 59 *Lampronia capitella* Z9 desaturase encoded by SEQ ID NO: 21
MPPNVTEANGVLFENDVQTPDMGLEVAPVQKADERKIQLVWRNIIAFACLHLAAVYGAYLF
FTSAIWQTDIFAYILYVMSGLGITAGAHRLWAHKSYKAKWPLRLILVAFNTLAFQDSAIDW
ARDHRMHHKYSETDADPHNATRGFFFSHIGWLLCRKHPELKRKGQGLDLSDLYADPIIRFQ
KKYYLLLMPLACFVLPTIIPVYLWGESWKNAFFVAAMFRYTFILNVTWLVNSAAHKWGGKP
YDKNIQPAQNISVAIFALGEGFHNYHHTFPWDYKTAELGNNRLNFTTSFINFFASFGWAYD
LKTVSDEIIQQRVKRTGDGSHHLRGWGDQDIPAEEEAQAALRINRKDD

SEQ ID NO: 60 *Helicoverpa zea* Z9 desaturase encoded by SEQ ID NO: 22
MAPNISEDVNGVLFESDAATPDLALSTPPVQKADNRPKQLVWRNILLFAYLHLAALYGGYL
FLFSAKWQTDIFAYILYVISGLGITAGAHRLWAHKSYKAKWPLRVILVIFNTVAFQDAAMD
WARDHRMHHKYSETDADPHNATRGFFFSHIGWLLVRKHPDLKEKGKGLDMSDLLADPILRF
QKKYYLILMPLACFVMPTVIPVYFWGETWTNAFFVAAMFRYAFILNVTWLVNSAAHKWGDK
PYDKSIKPSENLSVAMFALGEGFHNYHHTFPWDYKTAELGNNKLNFTTTFINFFAKIGWAY
DLKTVSDDIVKNRVKRTGDGSHHLWGWGDENQSKEEIDAAIRINPKDD

SEQ ID NO: 61 *Trichoplusia ni* desaturase with *Yarrowia lipolytica* OLE1
leader sequence encoded by SEQ ID NO: 28
MVKNVDQVDLSQVDTIASGRDVNYKVKYTSGVKTTPRKYKYIYTNFLTFSYAHLAALYGLY
LCFTSAKWETLLFSVLFHMSNIGITAGAHRLWTHKTFKAKLPLEIVLMIFNSLAFQNTAI
TWAREHRLHHKYSDTDADPHNASRGFFYSHVGWLLVKKHPDVLKYGKTIDMSDVYNNPVLK
FQKKYAVPLIGTVCFALPTLIPVYCWGESWNNAWHIALFRYIFNLNVTFLVNSAAHIWGNK
PYDKSILPAQNLLVSFLASGEGFHNYHHVFPWDYRTAELGNNFLNLTTLFIDFCAWFGWAY
DLKSVSEDIIKQRAKRTGDGSSGVIWGWDDKDMDRDIKSKANIFYAKKE

SEQ ID NO: 62 *Helicoverpa zea* desaturase with *Yarrowia lipolytica* OLE1
leader sequence encoded by SEQ ID NO: 29
MVKNVDQVDLSQVDTIASGRDVNYKVKYTSGVRKYQIVYPNLITFGYWHIAGLYGLYLCFT
SAKWATILFSYILFVLAEIGITAGAHRLWAHKTYKAKLPLEILLMVFNSIAFQNSAIDWVR
DHRLHHKYSDTDADPHNASRGFFYSHVGWLLVRKHPEVKKRGKELNMSDIYNNPVLRFQKK
YAIPFIGAVCFALPTMIPVYFWGETWSNAWHITMLRYIMNLNVTFLVNSAAHIWGNKPYDA
KILPAQNVAVSVATGGEGFHNYHHVFPWDYRAAELGNNSLNLTTKFIDLFAAIGWAYDLKT
VSEDMIKQRIKRTGDTDLWGHEQNCDEVWDVKDKSS

SEQ ID NO: 63 *Agrotis segetum* desaturase with *Candida albicans* OLE1
leader sequence encoded by SEQ ID NO: 15
MTTVEQLETVDITKLNAIAAGTNKKVPMAQGVQTTTILREEEPSLTFVVPQEPRKYQIVYP
NLITFGYWHIAGLYGLYLCFTSAKWQTILFSFMLVVLAELGITAGAHRLWAHKTYKAKLPL
QIILMLNSIAFQNSAIDWVRDHRLHHKYSDTDADPHNATRGFFYSHVGWLLVRKHPEVKR

SEQUENCE LISTING

SEQ ID NO: 64  *Amyelois transitella* desaturase from DTU WO 2016/
207339_SEQ ID NO: 2
```
MVPNKGSSDVLSEHSEPQFTKLIAPQAGPRKYKIVYRNLLTFGYWHLSAVYGLYLCFTCAK
WATILFAFFLYVIAEIGITGGAHRLWAHRTYKAKLPLEILLLIMNSIAFQDTAFTWARDHR
LHHKYSDTDADPHNATRGFFYSHVGWLLVKKHPEVKARGKYLSLDDLKNNPLLKFQKKYAI
LVIGTLCFLMPTFVPVYFWGEGISTAWNINLLRYVMNLNMTFLVNSAAHIFGNKPYDKSIA
SVQNISVSLATFGEGFHNYHHTYPWDYRAAELGNNRLNMTTAFIDFFAWIGWAYDLKSVPQ
EAIAKRCAKTGDGTDMWGRKR
```

RGKELDMSDIYNNPVLRFQKKYAIPFIGAMCFGLPTFIPVYFWGETWSNAWHITMLRYILN
LNITFLVNSAAHIWGYKPYDIKILPAQNIAVSIVTGGEVSITTTTFFPWDYRAAELGNNYL
NLTTKFIDFFAWIGWAYDLKTVSSDVIKSKAERTGDGTNLWGLEDKGEEDFLKIWKDN

SEQ ID NO: 65  *Spodoptera littoralis* desaturase from DTU WO 2016/
207339_SEQ ID NO: 41
```
MAQCVQTTTILEQKEEKTVTLLVPQAGKRKFEIVYFNIITFAYWHIAGLYGLYLCFTSTKW
ATVLFSFFLFVVAEVGVTAGSHRLWSHKTYKAKLPLQILLMVMNSLAFQNTVIDWVRDHRL
HHKYSDTDADPHNASRGFFYSHVGWLLVRKHPDVKKRGKEIDISDIYNNPVLRFQKKYAIP
FIGAVCFVLPTLIPVYGWGETWTNAWHVAMLRYIMNLNVTFLVNSAAHIYGKRPYDKKILP
SQNIAVSIATFGEGFHNYHHVFPWDYRAAELGNNSLNFPTKFIDFFAWIGWAYDLK
TVSKEMIKQRSKRTGDGTNLWGLEDVDTPEDLKNTKGE
```

SEQ ID NO: 66  *Agrotis segetum* desaturase from DTU WO 2016/
207339_SEQ ID NO: 43
```
MAQGVQTTTILREEEPSLTFVVPQEPRKYQIVYPNLITFGYWHIAGLYGLYLCFTSAKWQT
ILFSFMLVVLAELGITAGAHRLWAHKTYKAKLPLQIILMILNSIAFQNSAIDWVRDHRLHH
KYSDTDADPHNATRGFFYSHVGWLLVRKHPEVKRRGKELDMSDIYNNPVLRFQKKYAIPFI
GAMCFGLPTFIPVYFWGETWSNAWHITMLRYILNLNITFLVNSAAHIWGYKPYDIKILPAQ
NIAVSIVTGGEVSITTTTFFPWDYRAAELGNNYLNLTTKFIDFFAWIGWAYDLKTVSSDVI
KSKAERTGDGTNLWGLEDKGEEDFLKIWKDN
```

SEQ ID NO: 67  *Trichoplusia ni* desaturase from DTU WO 2016/
207339_SEQ ID NO: 45
```
MAVMAQTVQETATVLEEEARTVTLVAPKTTPRKYKYIYTNFLTFSYAHLAALYGLYLCFTS
AKWETLLFSFVTFHMSNIGITAGAHRLWTHKTFKAKLPLEIVLMIFNSLAFQNTAITWARE
HRLHHKYSDTDADPHNASRGFFYSHVGWLLVKKHPDVLKYGKTIDMSDVYNNPVLKFQKKY
AVPLIGTVCFALPTLIPVYCWGESWNNAWHIALFRYIFNLNVTFLVNSAAHIWGNKPYDKS
ILPAQNLLVSFLASGEGFHNYHHVFPWDYRTAELGNNFLNLTTLFIDFCAWFGWAYDLKSV
SEDIIKQRAKRTGDGSSGVIWGWDDKDMDRDIKSKANIFYAKKE
```

SEQ ID NO: 68  *Amyelois transitella* desaturase from DTU WO 2016/
207339_SEQ ID NO: 1
```
atggttccaaacaagggttcctctgatgttttgtctgaacattctgaaccacaattcacca
agttgattgctccacaagctggtccaagaaagtacaaaatcgtttacagaaacttgttgac
cttcggttactggcatttgtctgctgtttatggtttgtacttgtgtttcacttgtgctaag
tgggctactattttgttcgctttcttcttgtacgttatcgccgaaattggtattactggtg
gtgctcatagattatgggctcatagaacttacaaagccaagttgccattggaaatcttgtt
gttgatcatgaactccattgccttccaagatactgcttttacttgggctagagatcataga
ttgcatcacaagtactctgatactgatgctgatccacataatgctactagaggtttcttct
actctcatgttggttggttgttggttaagaaacacccagaagttaaggctagaggtaagta
cttgtctcttggatgacttgaagaacaaccctttgttgaagttccaaaagaagtacgccatt
ttggtcattggtactttgtgctttttgatgccaactttcgttccagtttacttttggggtg
aaggtatttctactgcctggaacattaacttgttaagatacgtcatgaacttgaacatgac
cttttttggttaactccgctgctcatatttttggtaacaagccatacgataagtctatcgcc
tctgttcaaaacatctctgtttcttggctactttcggtgaaggtttccataactaccatc
atacttatccatgggattacagagctgctgaattgggtaacaatagttga&tatgaccac
cgccttcattgatttctttgcttggattggttgggcctacgatttgaaatctgttccacaa
gaagctattgctaagagatgtgctaaaactggtgatggtactgatatgtggggtagaaaga
gatga
```

SEQ ID NO: 69  *Spodoptera littoralis* desaturase from DTU WO 2016/
207339_SEQ ID NO: 40
```
ggacactgacatggactgaaggagtagagaatcggcccgtggagttggccttcattttcag
tcttatctctcggtgttatggtagtcacttatatcggtattaaataagtgaataaggctt
gtaaaaatggcgcaatgtgtacaaacaacaacgattttggaacaaaagaagagaaaacag
taactttgctggtacctcaagcgggaaagaggaagtttgaaattgtgtattttaatatcat
caccttcgctactggcatatagctggactatatggcctttatttgtgcttcacttcaaca
aaatgggcgacagttttattctcattcttcctattcgtcgtagcagaagtaggggtcacgg
ctggctcccacagactttggtcgcataaaaacttacaaagcaaaactacctttacaaattct
gctaatggtgatgaattcccttgcatttcaaaacacagtcattgattgggtgagagaccat
cgactccatcataagtatagcgacactgatgccgatccccataatgcctcccgaggatttt
tctattcgcacgtcggttggctgcttgtgagaaaacaccctgattgtcaagaaacgaggaaa
ggaaattgatatatctgatatttacaacaatccggtactgaggttccagaagaagtacgca
attccttctcatcgggcagtttgttcgtcttaccaacattgataccggtttacggttggg
gagaaacctggactaatgcctggcacgtcgccatgctgcggtacattatgaacccttaacgt
caccttcctggtcaacagcgctgctcatatatgtgaaagagaccttatgacaagaagatc
ctaccatctcaaaacatagctgtgtccattgcaaccttggggaaggtttccataattatc
```

| SEQUENCE LISTING |
| --- |

```
                atcatgtatttccatgggattatcgcgcagctgaacttggaaataacagtttgaatttccc
                tacgaaatttattgatttctttgcgtggatcggatgggcgtatgacctaaagactgtttcg
                aaagaaatgataaaacaaaggtcaaaaagaactggtgatggaactaatctatgggggttag
                aagatgtggatacccccggaggatttaaaaaatacaaaaggcgaataggcaaacccttaaac
                tcaaacagtgaggtttaatgtgatatttagaattagaattaatttatttgaaattaaatga
                aggttttggataactgttttaataataaaaatagttttcgattaaattccttagattat
                tttaaaggaaatgtataaggtactcgcgtggttagcaacccagcagtccctgtttatctgt
                ttttatgaatttattctatgaatgtagatgtcgcatgaaattttaaaatgttgcatttgta
                taattttacttatgaataaataaatttattttaaaaaaaaaaaaaaaaaaaaaaaaaaa
                aaaaaa SEQ ID NO: 70   Agrotis segetum desaturase from DTU WO 2016/
                207339_SEQ ID NO: 42
                atggctcaaggtgtccaaacaactacgatattgagggaggaagagccgtcattgactttcg
                tggtacctcaagaaccgagaaagtatcaaatcgtgtacccaaaccttatcacatttgggta
                ctggcatatagctggtttatacgggctatatttgtgcttacttcggcaaaatggcaaaca
                atttattcagtttcatgctcgttgtgttagcagagttgggaataacagccggcgctcaca
                ggttatgggcccacaaaacatataaagcgaagcttcccttacaaatcatcctgatgatact
                gaactccattgccttccaaaattccgccattgattgggtgagggaccaccgtctccatcat
                aagtacagtgacactgatgcagaccctcacaatgctactcgtggtttcttctattctcatg
                ttggatggttgctcgtaagaaaacatccagaagtcaagagacgtggaaaggaacttgacat
                gtctgatatttacaacaatccagtgctgagatttcaaaagaagtatgctatacccttcatc
                ggggcaatgtgcttcggattaccaacttttatccctgtttacttctggggagaaacctgga
                gtaatgcttggcatatcaccatgcttcggtacatcctcaacctaaacattactttcctggt
                caacagtgctgctcatatctggggatacaaacctatgacatcaaaatattgcctgcccaa
                aatatagcagtttccatagtaaccggcggcgaagtttccataactaccaccacgttttc
                cttgggattatcgtgcagcagaattggggaacaattatcttaatttgacgactaagttcat
                agatttcttcgcttggatcggatgggcttacgatcttaagacggtgtccagtgatgttata
                aaaagtaaggcggaaagaactggtgatgggacgaatctttggggtttagaagacaaaggtg
                aagaagatttttttgaaaatctggaaagacaattaa SEQ ID NO: 71   Trichoplusia ni desaturase from DTU WO 2016/
                207339_SEQ ID NO: 44
                atggctgtgatggctcaaacagtacaagaaacggctacagtgttggaagaggaagctcgca
                cagtgactcttgtggctccaaagacaacgccaaggaaatataaatatatatacaccaactt
                tcttacattttcatatgcgcatttagctgcattatacggactttatttgtgcttcacctct
                gcgaaatgggaaacattgctattctctttcgtactcttccacatgtcaaatataggcatca
                ccgcaggggctcaccgactctggactcacaagactttcaaagccaaattgcctttggaaat
                tgtcctcatgatattcsactctttagcctttcaaaacacggctattacatgggctagagaa
                catcggctacatcacaaatacagcgatactgatgctgatcccacaatgcgtcaagagggt
                tcttctactcgcatgttggctggctattagtaaaaaaacatcccgatgtcctgaaatatgg
                aaaaactatagacatgtcggatgtatacaataatcctgtgttaaaatttcagaaaaagtac
                gcagtaccccttaattggaacagtttgttttgctcttccaactttgattccagtctactgtt
                ggggcaatcgtggaacaacgcttggcacatagccttatttcgatacatattcaatcttaa
                cgtgacttcctagtcaacagtgctgcgcatatctgggggaataagccttatgataaaagc
                atcttgcccgctcaaaacctgctggtttccttcctagcaagtggagaaggcttccataatt
                accatcacgtctcttccatgggattaccgcacagcagaattagggaataacttcctgaattt
                gacgacgctgttcattgattttgtgcctggtttggatgggcttatgacttgaagtctgta
                tcagaggatattataaaacagagagctaaacgaacaggtgacggttcttcaggggtcattt
                ggggatgggacgacaaagacatggaccgcgatataaaatctaaagctaacatttttttatgc
                taaaaaggaatga SEQ ID NO: 72   Spodoptera exigua FAR-like protein VIII nucleotide sequence
                (Genbank ID KR781121.1, codon optimized)
                ATGGTGGTGCTGACCAGCAAGGAGAAGTCCAACATGTCTGTGGCCGACTTCTACGCCGGCA
                AGTCCGTGTTTATCACAGGCGGCACCGGCTTCCTGGGCAAGGTGTTTATCGAGAAGCTGCT
                GTACTCTTGCCCAGACATCGATAAGATCTATATGCTGATCCGGGAGAAGAAGGGCCAGAGC
                ATCAGGGAGCGCCTGAGCAAGATCGTGGAGGATCCCCTGTTCAATAGGCTGAAGGAGAAGC
                GCGCTGGCGACCTGGATAAGATCGTGCTGATCCCAGGCGATGTGACAGTGCCCGGCCTGGG
                CATCTCCGACGAGAACGAGGCCATCCTGATCGATAAGGTGTCTGTGGTCATCCACAGCGCC
                GCCACAGTGAAGTTCAATGAGCCCCTGGAGACCGCCTGGAACGTGAATGTGGAGGGCACAA
                GGATGATCATGGCCCTGTCTCGGAAGATGAAGAGAATCGAGATCTTTATCCACATCAGCAC
                CGCCTACACCAACACAAATAGGGCAGTGGTGGACGAGGTGCTGTACCCACCTCCAGCCGAC
                ATCAACGAGGTGCACCAGTATGTGAAGAATGGCATCACAGAGGAGGAGACCGAGAAGATCC
                TGAACGGCAGGCCCAATACCTACACATTCACCAAGGCCCTGACCGAGCACCTGGTGGCAGA
                GAACCAGGCCTATATGCCTACAATCATCGTGCGGCCATCCATCGTGGGCGCCATCAAGGAC
                GATCCTATCAGAGGCTGGCTGGCAAACTGGTACGGAGCAACAGGACTGAGCGTGTTCACCG
                CCAAGGGCCTGAATCGCGTGATCTACGGCCAGAGCAGCCACGTGGTGGACCTGATCCCTGT
                GGATTATGTGGCAAACCTGGTCATCGTGGCAGGAGCAAAGACATACCGGTCCAACGAGGTG
                ACCATCTATAATTCTTGCTCTAGCTCCTGTAATCCAATCACAATGGAGCGGCTGGTGGGCC
                TGTTCATCGACGATACAGTGAAGCACAACAGCTACGTGATGCCCCTGCCTGGCTGGTACGT
                GTATTCCAATTACCGGTGGCTGGTGTATCTGGTGACCATCATCTTTCAGATGATCCCAGCC
                TATCTGGCAGACATCGGCCGGAGACTGCTGGGCAAGAATCCCAGATACTATAAGCTGCAGT
                CCCTGGTGGCACAGACCCAGGAGGCAGTGCACTTCTTTACATCTCACACCTGGGAGATCAA
                GAGCAAGAGGACCTCCGAGCTGTTCGCCTCTCTGAGCCACACAGACCAGCGCATCTTTCCT
                TGCGATGCCAAGAAGATCGACTGGACAGATTAGATCACCGATTATTGTAGCGGCGTGCGGC
                AGTTCCTGGAGAAGAAGAAGTGA
```

SEQUENCE LISTING

SEQ ID NO: 73   *Spodoptera exigua* FAR-like protein VIII amino acid sequence
(Genbank ID ALJ94061.1)
MVVLTSKEKSNMSVADFYAGKSVFITGGTGFLGKVFIEKLLYSCPDIDKIYMLIREKKGQS
IRERLTKIVDDPLFNRLKEKRPGDLDKIVLIPGDVTVPGLGISDENEAILIDKVSVVIHSA
ATVKFNEPLETAWNVNVEGTRMIMALSRKMKRIEIFIHISTAYTNTNRAVVDEVLYPPPAD
INEVHQYVKNGITEEETEKILNGRPNTYTFTKALTEHLVAENQAYMPTIIVRPSIVGAIKD
DPIRGWLANWYGATGLSVFTAKGLNRVIYGQSSHVVDLIPVDYVANLVIVAGAKTYRSNEV
TIYNSCSSSCNPITMERLVGLFIDDTVKHNSYVMPLPGWYVYSNYRWLVYLVTIIFQMIPA
YLADIGRRLLGKNPRYYKLQSLVAQTQEAVHFFTSHTWEIKSKRTSELFASLSHTDQRIFP
CDAKKIDWTDYITDYCSGVRQFLEKKK SEQ ID NO: 74   *Euglena gracilis* fatty acyl-coenzyme A reductase nucleotide
sequence, codon optimized
ATGAACGACTTCTACGCCGGCAAGGGCGTGTTTCTGACAGGCGTGACCGGCTTCGTGGGCA
AGATGGTGGTGGAGAAGATCCTGCGGTCTCTGCCAACCGTGGGCAGGCTGTATGTGCTGGT
GCGCCCAAAGGCAGGCACAGATCCTCACCAGAGACTGCACAGCGAAGTGTGGAGCAGCGC
GGATTTGACGTGGTGAGGGAGAAAGTGGGAGGACCTGCAGCCTTCGATGCACTGATCCGCG
AGAAGGTGGTGCCTGTGCCAGGCGACATGGTGAAGGATAGGTTTGGCCTGGACGATGCAGC
ATACCGCTCCCTGGCAGCCAACGTGAATGTGATCATCCACATGGCCGCCACAATCGACTTC
ACCGAGAGGCTGGATGTGGCCGTGTCTCTGAACGTGCTGGGCACAGTGCGGGTGCTGACCC
TGGCAAGGAGAGCCAGAGAGCTGGGCGCCCTGCACAGCGTGGTGCACGTGTCCACCTGCTA
CGTGAACTCCAATCAGCCCCTGGCGCCCGGCTGAGAGAGCAGCTGTATCCCCTGCCTTTT
GACCCACGGGAGATGTGCACAAGAATCTGGACATGAGCCCTCGGGAGATCGATCTGTTCG
GCCCACAGCTGCTGAAGCAGTACGGCTTCCCCAATACCTATACCTTCACCAAGTGCATGGC
AGAGCAGCTGGGCGCCCAGATCGCACACGACCTGCCATTCGCCATCTTTAGACCAGCAATC
ATCGGAGCCGCCCTGTCCGAGCCATTTCCCGGCTGGTGCGATTCTGCCAGCGCCTGTGGAG
CCGTGTTCCTGGCAGTGGGACTGGGCGTGCTGCAGGAGCTGCAGGGAAACGCCTCTAGCGT
GTGCGACCTGATCCCTGTGGATCACGTGGTGAATATGCTGCTGGTGACAGCAGCATATACC
GCATCTGCCCCACCAGCCGACCCTAGCCCATCCTCTCTGGCCCTGTCCCCTCCACAGCTGC
CACTGGCCACACTGCCCCCTGGCACCGTGGCAGATGTGCCAATCTACCACTGTGGCACCTC
TGCCGGCCCTAACGCCGTGAATTGGGGCAGGATCAAGGTGAGCCTGGTGGAGTATTGGAAC
GCACACCCAATCGCAAAGACCAAGGCAGCAATCGCCCTGCTGCCCGTGTGGAGGTTCGAGC
TGAGCTTTCTGCTGAAGAGGCGCCTGCCTGCAACAGCCCTGTCCCTGGTGGCCTCTCTGCC
AGGCGCATCCGCCGCCGTGCGGAGACAGGCAGAGCAGACAGAGCGGCTGGTGGGCAAGATG
AGAAAGCTGGTGGACACCTTCAGTCCTTCGTGTTTGGGCCTGGTACTTCCAGACAGAA
GCAGCGCCAGGCTGCTGGCCTCTCTGTGCCCAGAGGACCGCGAGACCTTTAACTGGGACCC
CAGGAGGATCGGATGGAGGGCCTGGGTGGAGAATTACTGTTATGGCCTGGTGCGGTATGTG
CTGAAGCAGCCAATCGGCGATAGACCACCAGTGGCAGCAGAGGAGCTGGCAAGCAATAGGT
TCCTGCGCGCCATGCTGTGA SEQ ID NO: 75   *Euglena gracilis* fatty acyl-coenzyme A reductase amino acid
sequence (ADI60057.1)
MNDFYAGKGVFLTGVTGFVGKMVVEKILRSLPTVGRLYVLVRPKAGTDPHQRLHSEVWSSA
GFDVVREKVGGPAAFDALIREKVVPVPGDMVKDRFGLDDAAYRSLAANVNVIIHMAATIDF
TERLDVAVSLNVLGTVRVLTLARRARELGALHSVVHVSTCYVNSNQPPGARLREQLYPLPF
DPREMCTRILDMSPREIDLFGPQLLKQYGFPNTYTFTKCMAEQLGAQIAHDLPFAIFRPAI
IGAALSEPFPGWCDSASACGAVFLAVGLGVLQELQGNASSVCDLIPVDHVVNMLLVTAAYT
ASAPPADPSPSSLALSPPQLPLATLPPGTVADVPIYHCGTSAGPNAVNWGRIKVSLVEYWN
AHPIAKTKAAIALLPVWRFELSFLLKRRLPATALSLVASLPGASAAVRRQAEQTERLVGKM
RKLVDTFQSFVFWAWYFQTESSARLLASLCPEDRETFNWDPRRIGWRAWVENYCYGLVRYV
LKQPIGDRPPVAAEELASNRFLRAML SEQ ID NO: 76   *Yponomeuta evonymellus* fatty-acyl CoA reductase II nucleotide
sequence, codon optimized
ATGGTGCAGCTGAAGGAGGACTCCGTGGCCGCCTTTTACGCCGAGAAGTCTATCTTCATCA
CAGGCGGCACCGGCTTTCTGGGCAAGGTGCTGATCGAGAAGCTGCTGTACTCCTGCAAGGC
CGTGGACCAGATCTATGTGCTGATCCGGAAGAAGAAGGATCAGACACCTTCTGAGCGCATC
GCCGAGCTGCTGGAGTCTGAGCTGTTCAGCCGGCTGAGAAAGGACGATCCAAGCGCCCTGA
AGAAGGTGGTGCCCGTGGTGGGCGACCTGACCATGCCTAACCTGGGACTGAGCGCCGCAGT
GCAGGATCTGATCGTGACAAAGGTGTCCATCATCTTCCACGTGGCCGCCACCGTGAAGTTT
AACGAGAGGATGAAGAATGCCCTGGCCAACAATGTGGAGGCCACCAGAGAAGTGATCAACC
TGTGCCACCGCCTGGAGAAGGTGGACGCCTTCATCCACGTGTCCACAGCCTATTCTAATAC
CGATCAGAAGGTGGTGGAGGAGCGCGTGTACCCACCTCCAGCACCTCTGAGCGAGGTGTAT
GCCTTTGTGACCAACAATGGCGACGATATGGACATCATCCAGAACCTGCTGAATGGCCGGC
CAAATACCTACACATATACGAAGGCCCTGGCCGAGGACATCGTGCTGAAGGAGCACGGCGG
CATCCCTACAGCCATCATCAGACGAAGCATCGTGCTGTCCGTGCTGAAGGAGCCCATCCCT
GGCTGGCTGGACAACTGGAATGGACAACCGGACTGCTGCACGCCAGCTCCCAGGGAGTGC
ACTGCTCCATGCTGGGCTCTGGCAGCAACGTGGCCGACCTGATCCCTGTGGACATCGTGAC
AAATCTGATGATCGTGGTGGCCTCTCGGTGCAAGAAGAGCAACGGCCTGAAGGTGTACAAT
TCCGTGTTCTGGCACCACAAACCCAATCGCCTATCAGGCCTTCACCAAGATGTTTCTGGATA
GCTGTATCTCCAGGGGCTGGAACAAGGTGCCATTCCCCATGCTGCTGTTTGTGAAGTGGGC
CTTCCTGAATCGCGTGCTGAAGTTCTTCCTGGTGATCGTGCCATTCTTTCTGATCGACGTG
TACCTGCGGTTCTTTGGCAAGCCCAATTACATGAGAATGATCACATATACCAAGAAGGCCG

```
                AGGATCTGATGACATTCTTTACCTCTCACGAGTGGCAGTTCAAGGACGGCAACGTGCGGGA
                TCTGATCAATATGATGAGCCCCGAGGATAGAAAGATCTTTTACTGCGACCCCGATGAGATC
                CACTGGAAGCCTTACTTCGACGATTATTGCGTGGGCGTGTTTAAGTATCTGCTGAAGAGGA
                AGGTGTGA

SEQ ID NO: 77   Yponomeuta evonymellus fatty-acyl CoA reductase II amino acid
                sequence (ADD62439.1)
                MVQLKEDSVAAFYAEKSIFITGGTGFLGKVLIEKLLYSCKAVDQIYVLIRKKKDQTPSERI
                AQLLESELFSRLRKDDPSALKKVVPVVGDLTMPNLGLSAAVQDLIVTKVSIIFHVAATVKF
                NERMKNALANNVEATREVINLCHRLEKVDAFIHVSTAYSNTDQKVVEERVYPPPAPLSEVY
                AFVTNNGDDMDIIQNLLNGRPNTYTYTKALAEDIVLKEHGGIPTAIIRPSIVLSVLKEPIP
                GWLDNWNGPTGLLHASSQGVHCSMLGSGSNVADLIPVDIVTNLMIVVASRCKKSNGLKVYN
                SCSGTTNPIAYQAFTKMFLDSCISRGWNKVPFPMLLFVKWAFLNRVLKFFLVIVPFFLIDV
                YLRFFGKPNYMRMITYTKKAEDLMTFFTSHEWQFKDGNVRDLINMMSPEDRKIFYCDPDEI
                HWKPYFDDYCVGVFKYLLKRKV SEQ ID NO: 78   Drosophila melanogaster fatty acid desaturase (Q9N9Z8)
                mapysriyhqdkssretgvlfeddaqtvdsdlttdrfqlkraekrrlplvwrniilfalvh
                laalyglhsiftraklattlfaaglyiigmlgvtagahrlwahrtykakwplrlllvifnt
                iafqdavyhwardhrvhhkysetdadphnatrgfffshvgwllckkhpdikekgrgldlsd
                lradpilmfqrkhyyilmplacfvlptvipmvywnetlasswfvatmfrwcfqlnmtwlvn
                saahkfgnrpydktmnptqnafvsaftfgegwhnyhhafpwdyktaewgcyslnittafid
                lfakigwaydlktvapdviqrrvlrtgdgshelwgwgdkdltaedarnvllvdksr SEQ ID NO: 79   Lampronia capitella acyl-CoA-delta 11-desaturase (ABX71630.1)
                mppypeevdtnhifeedisheeskpalkplvapqadnrkpeivplnlitfgyghlaaiygi
                ylcftsakwativfafvlyicaelgitagahrlwshrsykaklplrlilllfntlafqnta
                idwvrdhrmhhkysdtdadphnatrgfffshvgwlltrkhpevkrrgkdidmmdiyndsll
                kfqkkyaipfvglvcfviptlmpmyfwnetlnnswhiatmlryivnlnmtflvnsaahiwg
                ykpydksikpvqnitvsililgegfhnyhhvfpwdyrtselgndflnfttlfinlfakigw
                aydlktasdkvvaarrkrtgdgtnlwgwedkslneeerqaatvlypnkylnlkd SEQ ID NO: 80   Cydia pomonella desaturase (AIM40221.1)
                mapnvtdvngvlfesdaatpdlalanapvqqaddspriyvwrniilfaylhiaalyggylf
                lvsakwqtdifayflyvasglgitagahrlwahksykakwplrlilvifntiafqdsaidw
                ardhrmhhkysetdadphnatrgfffshigwllvrkhpelkrkgkgldlsdlyadpilrfq
                kkyylilmplacfvlptvipvylwnetwtnaffvaalfryafilnvtwlvnsaahkwgdkp
                ydksikpsenisvslfafgegfhnyhhtfpwdyktaelssnrlnftttkfinffakigwayd
                mktvsdeiiqkrvnrtgdgshhlwgwgdkdhskeevnaavrinpkdd SEQ ID NO: 81   Spodoptera exigua FAR-like protein VII nucleotide
                sequence(KF805977.1), codon optimized
                ATGACGTATAGACAAATAAATGAATTTGATGCTGAAAAGTTTACGGCAGCTACAGTACCGA
                CAAGCTACGTATCAGTACCAGATTTTTATGCGGGCAAGACAATTTTTATCACTGGTGGAAC
                TGGATTTCTTGGAAAGGTGTTTCTAGAGAAACTTCTTTACAGTTGTTAAAGATGTTGAAACC
                GTATACATTTTGATCAGAGAGAAAAAGGCAAAACACCTCAGCAAAGAGTTGAAGATCTTT
                TTAACAAACCGATTTTCTCAAGATTGAAACAGAAGGACTCTCAGTGTATGAAGAAGTCAC
                TGCAATAATTGGTGACCTTAGTGAACCTGGTCTTGGCATATCAAAAGATGATGAAGAACTA
                CTTTTGCAAAAGGTATCTGTAGTATTCCATGTCGCAGCCAATGTTCAGTTTTACAAGGAAT
                TCAAAGAGATTATAAATACGAATGTTGGTGGGACAAAATACGTACTCCAATTGTGTCAGCG
                AATAAAAGATATTAAGGCATTTGTCCATATTTCCACAGCCTACTGTCACACAGACCAAAAG
                GTATTAGAAGAGAGAATATACCCCCTCCAGCAGAACTCAGTGAAGTCCTGAAGTTCCTTC
                AGCAGCCACAGCATGACAAGAAACAGATTAAGGAATTATTTAAGAAACAACCAAACAGTTA
                CACCTTTGCCAAGGCTTTAGCAGAAACCTACATTGCTGAGAACTGCGGACGCGTCCCCACA
                ATTATCATCAGACCTTCTATTATATCAGCATCACTGAAAGAGCCGCTACCAGGATGGGTGG
                ATTCATGGAACGGAGCCACAGGCCTCATCACAGCTAGCTACAACGGCGCCAACAGAGTGCT
                TCTCGGCGAAGGCAGCAACTTCCTCGACCTGATCCCAGTTGACTTTGTTGCTAACCTGGCA
                ATTGTAGCTGCTGCTAAATGTACTAGCTCTTTGAAAGTTTACAATTGCTGCTCAAGCGGAT
                GTAACCCTTTAACATTGAAACAATTGGTCAGCCACATGAATAATGTCGGATTTGATAAAAA
                CGTCTCCATAATATTCACCAATAACAAAGCCTCGCTTTCCACATTGACATTTTTCCTTCAA
                ACAACGCCATCTTTCACCGCTGATATGTTTCTGAGAGTCACGGGAAAGTCACCAAGGTACA
                TGAAAATCCAGTCAAAACTGACCATCGCTCGGAATGCCTTAAATTTTTTCACCTGTCATTC
                CTGGGTCATGAAGGCTGATAATTCTAGAAGACTGTATGCTTCCTTGTCATTACACGACCGA
                CATACGTTCCCTTGTGATCCTACAGACATAGACTGGAAGAAGTACATAAATATATACATAG
                AAGGAATTAATCAGTTCTTAATGAAGAAACGTAGTTAA SEQ ID NO: 82   Spodoptera exigua FAR-like protein VII amino acid
                sequence (AIS85928.1)
                MTYRQINEFDAEKFTAATVPTSYVSVPDFYAGKTIFITGGTGFLGKVFLEKLLYSCKDVET
                VYILIREKKGKTPQQRVEDLFNKPIFSRLKQKDSQCMKKVTAIIGDLSEPGLGISKDDEEL
                LLQKVSVVFHVAANVQFYKEFKEIINTNVGGTKYVLQLCQRIKDIKAFVHISTAYCHTDQK
                VLEERIYPPPAELSEVLKFLQQPQHDKKQIKELFKKQPNSYTFAKALAETYIAENCGRVPT
                IIIRPSIISASLKEPLPGWVDSWNGATGLITASYNGANRVLLGEGSNFLDLIPVDFVANLA
                IVAAAKCTSSLKVYNCCSSGCNPLTLKQLVSHMNNVGFDKNVSIIFTNNKASLSTLTFFLQ
                TTPSFTADMFLRVTGKSPRYMKIQSKLTIARNALNFFTCHSWVMKADNSRRLYASLSLHDR
                HTFPCDPTDIDWKKYINIYIEGINQFLMKKRS
```

| | |
|---|---|
| SEQ ID NO: 83 | HaFAR S60A FAR2<br>ATGGTGGTGCTGACCTCCAAGGAGACAAAGCCCTCTGTGGCCGAGTTCTACGCCGGCAAGA<br>GCGTGTTCATCACAGGCGGCACCGGCTTCCTGGGCAAGGTGTTTATCGAGAAGCTGCTGTA<br>CAGCTGCCCTGACATCGAGAACATCTATATGCTGATCCGGGAGAAGAAGGGCCTGGCCGTG<br>TCCGAGAGAATCAAGCAGTTCCTGGACGATCCCTGTTTACAAGGCTGAAGGACAAGCGCC<br>CTGCCGATCTGGAGAAGATCGTGCTGATCCCAGGCGACATCACCGCACCAGATCTGGGCAT<br>CAACAGCGAGAATGAGAAGATGCTGATCGAGAAGGTGAGCGTGATCATCCACTCCGCCGCC<br>ACCGTGAAGTTCAACGAGCCCCTGCCTACAGCCTGGAAGATCAATGTGGAGGGCACCAGGA<br>TGATGCTGGCCCTGTCTCGGAGAATGAAGCGCATCGAGGTGTTTATCCACATGAGCACAGC<br>CTACACCAACACAAATAGGGAGGTGGTGGACGAGATCCTGTACCCAGCCCCCGCCGACATC<br>GATGAGGTGCACCAGTATGTGAAGGACGGCATCAGCGAGGAGGATACCGAGAAGATCCTGA<br>ACGGCAGACCCAATACCTACACATTCACCAAGGCCCTGACAGAGCACCTGGTGGCCGAGAA<br>CCAGGCCTATGTGCCTACCATCATCGTGAGACCATCCGTGGTGGCCGCCATCAAGGATGAG<br>CCTCTGAAGGGATGGCTGGGAAACTGGTTCGGAGCAACAGGACTGACCGTGTTTACAGCCA<br>AGGGCCTGAATAGAGTGATCTACGGCCACACCTCCTATATCGTGGACCTGATCCCAGTGGA<br>TTACGTGGCAAACCTGGTCATCGCAGCAGGAGCCAAGTCTAGCAAGTCCACCGAGCTGAAG<br>GTGTATAACTGCTGTTCCTCTAGCTGTAATCCCGTGACCATCGGCACACTGATGAGCATGT<br>TCGCCGACGATGCCATCAAGCAGAAGTCCTACGCCATGCCTCTGCCAGGCTGGTACATCTT<br>TACAAAGTATAAGTGGCTGGTGCTGCTGCTGACCTTCCTGTTTCAGGTCATCCCTGCCTAC<br>GTGACCGACCTGTCTAGGCACCTGATCGGCAAGAGCCCACGCTATATCAAGCTGCAGAGCC<br>TGGTGAACCAGACCAGGTCCTCTATCGACTTCTTTACAAATCACTCCTGGGTCATGAAGGC<br>CGATAGGGTGCGCGAGCTGTACGCATCTCTGAGCCCAGCCGACAAGTATCTGTTCCCTTGC<br>GACCCAACCGATATCAACTGGACACACTACATCCAGGATTATTGTTGGGGCGTGCGCCACT<br>TTCTGGAGAAGAAGTCCTATGAGTGA |
| SEQ ID NO: 84 | HaFAR S195A FAR3<br>ATGGTGGTGCTGACCTCCAAGGAGACAAAGCCCTCTGTGGCCGAGTTCTACGCCGGCAAGA<br>GCGTGTTCATCACAGGCGGCACCGGCTTCCTGGGCAAGGTGTTTATCGAGAAGCTGCTGTA<br>CAGCTGCCCTGACATCGAGAACATCTATATGCTGATCCGGGAGAAGAAGGGCCTGAGCGTG<br>TCCGAGAGAATCAAGCAGTTCCTGGACGATCCCTGTTTACAAGGCTGAAGGACAAGCGCC<br>CTGCCGATCTGGAGAAGATCGTGCTGATCCCAGGCGACATCACCGCACCAGATCTGGGCAT<br>CAACAGCGAGAATGAGAAGATGCTGATCGAGAAGGTGAGCGTGATCATCCACTCCGCCGCC<br>ACCGTGAAGTTCAACGAGCCCCTGCCTACAGCCTGGAAGATCAATGTGGAGGGCACCAGGA<br>TGATGCTGGCCCTGTCTCGGAGAATGAAGCGCATCGAGGTGTTTATCCACATCAGCACAGC<br>CTACACCAACACAAATAGGGAGGTGGTGGACGAGATCCTGTACCCAGCCCCCGCCGACATC<br>GATCAGGTGCACCAGTATGTGAAGGACGGCATCGCCGAGGAGGATACCGAGAAGATCCTGA<br>ACGGCAGACCCAATACCTACACATTCACCAAGGCCCTGACAGAGCACCTGGTGGCCGAGAA<br>CCAGGCCTATGTGCCTACCATCATCGTGAGACCATCCGTGGTGGCCGCCATCAAGGATGAG<br>CCTCTGAAGGGATGGCTGGGAAACTGGTTCGGAGCAACAGGACTGACCGTGTTTACAGCCA<br>AGGGCCTGAATAGAGTGATCTACGGCCACAGCTCCTATATCGTGGACCTGATCCCAGTGGA<br>TTACGTGGCAAACCTGGTCATCGCAGCAGGAGCCAAGTCTAGCAAGTCCACCGAGCTGAAG<br>GTGTATAACTGCTGTTCCTCTAGCTGTAATCCCGTGACCATCGGCACACTGATGAGCATGT<br>TCGCCGACGATGCCATCAAGCAGAAGTCCTACGCCATGCCTCTGCCAGGCTGGTACATCTT<br>TACAAAGTATAAGTGGCTGGTGCTGCTGCTGACCTTCCTGTTTCAGGTCATCCCTGCCTAC<br>GTGACCGACCTGTCTAGGCACCTGATCGGCAAGAGCCCACGCTATATCAAGCTGCAGAGCC<br>TGGTGAACCAGACCAGGTCCTCTATCGACTTCTTTACAAATCACTCCTGGGTCATGAAGGC<br>CGATAGGGTGCGCGAGCTGTACGCATCTCTGAGCCCAGCCGACAAGTATCTGTTCCCTTGC<br>GACCCAACCGATATCAACTGGACAGACTACATCCAGGATTATTGTTGGGGCGTGCGCCACT<br>TTCTGGAGAAGAAGTCCTATGAGTGA |
| SEQ ID NO: 85 | HaFAR S298A FAR4<br>ATGGTGGTGCTGACCTCCAAGGAGACAAAGCCCTCTGTGGCCGAGTTCTACGCCGGCAAGA<br>GCGTGTTCATCACAGGCGGCACCGGCTTCCTGGGCAAGGTGTTTATCGAGAAGCTGCTGTA<br>CAGCTGCCCTGACATCGAGAACATCTATATGCTGATCCGGGAGAAGAAGGGCCTGAGCGTG<br>TCCGAGAGAATCAAGCAGTTCCTGGACGATCCCTGTTTACAAGGCTGAAGGACAAGCGCC<br>CTGCCGATCTGGAGAAGATCGTGCTGATCCCAGGCGACATCACCGGACCAGATCTGGGCAT<br>CAACAGCGAGAATGAGAAGATGCTGATCGAGAAGGTGAGCGTGATCATCCACTCCGCCGCC<br>ACCGTGAAGTTCAACGAGCCCCTGCCTACAGCCTGGAAGATCAATGTGGAGGGCACCAGGA<br>TGATGCTGGCCCTGTCTCGGAGAATGAAGCGCATCGAGGTGTTTATCCACATCAGCACAGC<br>CTACACCAACACAAATAGGGAGGTGGTGGACGAGATCCTGTACCCAGCCCCCGCCGACATC<br>GATCAGGTGCACCAGTATGTGAAGGACGGCATCAGCGAGGAGGATACCGAGAAGATCCTGA<br>ACGGCAGACCCAATACCTACACATTCACCAAGGCCCTGACAGAGCACCTGGTGGCCGAGAA<br>CCAGGCCTATGTGCCTACCATCATCGTGAGACCATCCGTGGTGGCCGCCATCAAGGATGAG<br>CCTCTGAAGGGATGGCTGGGAAACTGGTTCGGAGCAACAGGACTGACCGTGTTTACAGCCA<br>AGGGCCTGAATAGAGTGATCTACGGCCACAGCTCCTATATCGTGGACCTGATCCCAGTGGA<br>TTACGTGGCAAACCTGGTCATCGCAGCAGGAGCCAAGGCCAGCAAGTCCACCGAGCTGAAG<br>GTGTATAACTGCTGTTCCTCTAGCTGTAATCCCGTGACCATCGGCACACTGATGAGCATGT<br>TCGCCGACGATGCCATCAAGCAGAAGTCCTACGCCATGCCTCTGCCAGGCTGGTACATCTT<br>TACAAAGTATAAGTGGCTGGTGCTGCTGCTGACCTTCCTGTTTCAGGTCATCCCTGCCTAC<br>GTGACCGACCTGTCTAGGCACCTGATCGGCAAGAGCCCACGCTATATCAAGCTGCAGAGCC<br>TGGTGAACCAGACCAGGTCCTCTATCGACTTCTTTACAAATCACTCCTGGGTCATGAAGGC<br>CGATAGGGTGCGCGAGCTGTACGCATCTCTGAGCCCAGCCGACAAGTATCTGTTCCCTTGC<br>GACCCAACCGATATCAACTGGACACACTACATCCAGGATTATTGTTGGGGCGTGCGCCACT<br>TTCTGGAGAAGAAGTCCTATGAGTGA |

SEQUENCE LISTING

SEQ ID NO: 86    HaFAR S378A FAR5
ATGGTGGTGCTGACCTCGAAGGAGAGAAAGCCCTCTGTGGCCGAGTTCTACGCCGGCAAGA
GCGTGTTCATCACAGGCGGCACCGGCTTCCTGGGCAAGGTGTTTATCGAGAAGCTGCTGTA
CAGCTGCCCTGACATCGAGAAGATCTATATGCTGATCGGGAGAAGAAGGGCCTGAGCGTG
TCCGAGAGAATCAAGCAGTTCCTGGACGATCCCCTGTTTACAAGGCTGAAGGACAAGCGCC
CTGCCGATCTGGAGAAGATCGTGCTGATCCCAGGCGACATCACCGCACCAGATCTGGGCAT
CAACAGCGAGAATGAGAAGATGCTGATCGAGAAGGTGAGCGTGATCATCCACTCCGCCGCC
ACCGTGAAGTTCAACGAGCCCCTGCCTACAGCCTGGAAGATCAATGTGGAGGGCACCAGGA
TGATGCTGGCCCTGTCTCGGAGAATGAAGCGCATCGAGGTGTTTATCCACATCAGCACAGC
CTACACCAACACAAATAGGGAGGTGGTGGACGAGATCCTGTACCCAGCCCCCGCCGACATC
GATCAGGTGCACCAGTATGTGAAGGACGGCATCAGCGAGGAGGATACCGAGAAGATCCTGA
ACGGCAGACCCAATACCTACACATTCACCAAGGCCCTGACAGAGCACCTGGTGGCCGAGAA
CCAGGCCTATGTGCCTACCATCATCGTGAGACCATCCGTGGTGGCCGCCATCAAGGATGAG
CCTCTGAAGGGATGGCTGGGAAACTGGTTCGGAGCAACAGGACTGACCGTGTTTACAGCCA
AGGGCCTGAATAGAGTGATCTACGGCCACAGCTCCTATATCGTGGACCTGATCCCAGTGGA
TTACGTGGCAAACCTGGTCATCGCAGCAGGAGCCAAGTCTAGCAAGTCCACCGAGCTGAAG
GTGTATAACTGCTGTTCCTCTAGCTGTAATCCCGTGACCATCGGCACACTGATGAGCATGT
TCGCCGACGATGCCATCAAGCAGAAGTCCTACGCCATGCCTCTGCCAGGCTGGTACATCTT
TACAAAGTATAAGTGGCTGGTGCTGCTGCTGACCTTCCTGTTTCAGGTCATCCCTGCCTAC
GTGACCGACCTGTCTAGGCACCTGATCGGCAAGGCCCGACGCTATATCAAGCTGCAGAGCC
TGGTGAACCAGACCAGGTCCTCTATCGACTTCTTTACAAATCACTCCTGGGTCATGAAGGC
CGATAGGGTGCGCGAGCTGTACGCATCTCTGAGCCCAGCCGACAAGTATCTGTTCCCTTGC
GACCCAACCGATATCAACTGGACACACTACATCCAGGATTATTGTTGGGGCGTGCGCCACT
TTCTGGAGAAGAAGTCCTATGAGTGA

SEQ ID NO: 87    HaFAR S394A FAR6
ATGGTGGTGCTGACCTCCAAGGAGACAAAGCCCTCTGTGGCCGAGTTCTACGCCGGCAAGA
GCGTGTTCATCACAGGCGGCACCGGCTTCCTGGGCAAGGTGTTTATCGAGAAGCTGCTGTA
CAGCTGCCCTGACATCGAGAACATCTATATGCTGATCGGGAGAAGAAGGGCCTGAGCGTG
TCCGAGAGAATCAAGCAGTTCCTGGACGATCCCCTGTTTACAAGGCTGAAGGACAAGCGCC
CTGCCGATCTGGAGAAGATCGTGCTGATCCCAGGCGACATCACCGCACCAGATCTGGGCAT
CAACAGCGAGAATGAGAAGATGCTGATCGAGAAGGTGAGCGTGATCATCCACTCCGCCGCC
ACCGTGAAGTTCAACGAGCCCCTGCCTACAGCCTGGAAGATCAATGTGGAGGGCACCAGGA
TGATGCTGGCCCTGTCTCGGAGAATGAAGCGCATCGAGGTGTTTATCCACATCAGCACAGC
CTACACCAACACAAATAGGGAGGTGGTGGACGAGATCCTGTACCCAGCCCCCGCCGACATC
GATCAGGTGCACCAGTATGTGAAGGACGGCATCAGCGAGGAGGATACCGAGAAGATCCTGA
ACGGCAGACCCAATACCTACACATTCACCAAGGCCCTGACAGAGCAGCTGGTGGCCGAGAA
CCAGGCCTATGTGCCTACCATCATCGTGAGACCATCCGTGGTGGCCGCCATCAAGGATGAG
CCTCTGAAGGATGGCTGGGAAACTGGTTCGGAGCAACAGGACTGACCGTGTTTACAGCCA
AGGGCCTGAATAGAGTGATCTACGGCCACAGCTCCTATATCGTGGACCTCATCCCAGTGGA
TTACGTGGCAAACCTGGTCATCGCAGCAGGAGCGAAGTCTAGCAAGTCCACCGAGCTGAAG
GTGTATAACTGCTGTTCCTCTAGCTGTAATCCCGTGACCATCGGCACACTGATGAGGATGT
TCGCCGACGATGCCATCAAGCAGAAGTCCTACGCCATGCCTCTGCCAGGCTGGTACATCTT
TACAAAGTATAAGTGGCTGGTGCTGCTGCTGACCTTCCTGTTTCAGGTCATCCCTGCCTAC
GTGACCGACCTGTCTAGGCACCTGATCGGCAAGAGCCCACGCTATATCAAGCTGCAGAGCC
TGGTGAACCAGACCAGGTCCGCCATCGACTTCTTTACAAATCACTCCTGGGTGATGAAGGC
CGATAGGGTGCGCGAGCTGTACGCATCTCTGAGCCCAGCCGACAAGTATCTGTTCCCTTGC
GACCCAACCGATATCAACTGGACACACTACATCCAGGATTATTGTTGGGGCGTGCGCCACT
TTCTGGAGAAGAAGTCCTATGAGTGA

SEQ ID NO: 88    HaFAR S418A FAR7
ATGGTGGTGCTGACCTCCAAGGAGACAAAGCCCTCTGTGGCCGAGTTCTACGCCGGCAAGA
GCGTGTTCATCACAGGCGGCACCGGCTTCCTGGGCAAGGTGTTTATCGAGAAGCTGCTGTA
CAGCTGCCCTGACATCGAGAACATCTATATGCTGATCCGGAGAAGAAGGGCCTGAGCGTG
TCCGAGAGAATCAAGCAGTTCCTGGACGATCCCCTGTTTACAAGGCTGAAGGACAAGCGCC
CTGCCGATCTGGAGAAGATCGTGCTGATCCCAGGCGACATCACCGCACCAGATCTGGGCAT
CAACAGCGAGAATGAGAAGATGCTGATCGAGAAGGTGAGCGTGATCATCCACTCCGCCGCC
ACCGTGAAGTTCAACGAGCCCCTGCCTACAGCCTGGAAGATCAATGTGGAGGGCACCAGGA
TGATGCTGGCCCTGTCTCGGAGAATGAAGCGCATCGAGGTGTTTATCCACATCAGCACAGC
CTACACCAACACAAATAGGGAGGTGGTGGACGAGATCCTGTACCCAGCCCCCGCCGACATC
GATCAGGTGCACCAGTATGTGAAGGACGGCATCAGCGAGGAGGATACCGAGAAGATCCTGA
ACGGCAGACCCAATACCTACACATTCACCAAGGCCCTGACAGAGCACCTGGTGGCCGAGAA
CCAGGCCTATGTGCCTACCATCATCGTGAGACCATCCGTGGTGGCCGCCATCAAGGATGAG
CCTCTGAAGGGATGGCTGGGAAACTGGTTCGGAGCAACAGGACTGACCGTGTTTACAGCCA
AGGGCCTGAATAGAGTGATCTACGGCCACAGCTCCTATATCGTGGACCTGATCCCAGTGGA
TTACGTGGCAAACCTGGTCATCGCAGCAGGAGCCAAGTCTAGCAAGTCCACCGAGCTGAAG
GTGTATAACTGCTGTTCCTCTAGCTGTAATCCCGTGACCATCGGCACACTGATGAGCATGT
TCGCCGACGATGCCATCAAGCAGAAGTCCTACGCCATGCCTCTGCCAGGCTGGTACATCTT
TACAAAGTATAAGTGGCTGGTGCTGCTGCTCACCTTCCTGTTTCAGGTCATCCCTGCCTAC
GTGACCGACCTGTCTAGGCACCTGATCGGCAAGAGCCCACGCTATATCAAGCTGCAGAGCC
TGGTGAACCAGACCAGGTCCTCTATCGACTTCTTTACAAATCACTCCTGGGTCATGAAGGC
CGATAGGGTGCGCGAGCTGTACGCATCTCTGGCCCCAGCCGACAAGTATCTGTTCCCTTGC
GACCGAACCGATATCAACTGGACACACTACATCCAGGATTATTGTTGGGGCGTGCGCCACT
TTCTGGAGAAGAAGTCCTATGAGTGA

SEQUENCE LISTING

SEQ ID NO: 89  HaFAR S453A FAR8
ATGGTGGTGCTGACCTCCAAGGAGACAAAGCCCTCTGTGGCCGAGTTCTACGCCGGCAAGA
GCGTGTTCATCACAGGCGGCACCGGCTTCCTGGGCAAGGTGTTTATCGAGAAGCTGCTGTA
CAGCTGCCCTGACATCGAGAACATCTATATGCTGATCGGGGAAGAAGGGCCTGAGCGTG
TCCGAGAGAATCAAGCAGTTCCTGGACGATCCCCTGTTTACAAGGCTGAAGGACAAGCGCC
CTGCCGATCTGGAGAAGATCGTGCTGATCCCAGGCGACATCACCGCACCAGATCTGGGCAT
CAACAGCGAGAATGAGAAGATGCTGATCGAGAAGGTGAGCGTGATCATCCACTCCGCCGCC
ACCGTGAAGTTCAACGAGCCCCTGCCTACAGCCTGGAAGATCAATGTGGAGGGCACCAGGA
TGATGCTGGCCCTGTCTCGGAGAATGAAGCGCATCGAGGTGTTTATCCACATCAGCACAGC
CTACACCAACACAAATAGGGAGGTGGTGGACGAGATCCTGTACCCAGCCCCCGCCGACATC
GATCAGGTGCACCAGTATGTGAAGGACGGCATCAGCGAGGAGGATACCGAGAAGATCCTGA
ACGGCAGACCCAATACCTACACATTCACCAAGGCCCTGACAGAGCACCTGGTGGCCGAGAA
CCAGGCCTATGTGCCTACCATCATCGTGAGACCATCCGTGGTGGCCGCCATCAAGGATGAG
CCTCTGAAGGGATGGCTGGGAAACTGGTTCGGAGCAACAGGACTGACCGTGTTTACAGCGA
AGGGCCTGAATAGAGTGATCTACGGCCACAGCTCCTATATCGTGGACCTGATCCCAGTGGA
TTACGTGGCAAACCTGGTCATCGCAGCAGGAGCCAAGTCTAGGAAGTCCACCGAGCTGAAG
GTGTATAACTGCTGTTCCTCTAGCTGTAATCCCGTGACCATCGGCACACTGATGAGCATGT
TCGCCGACGATGCGATCAAGCAGAAGTCCTACGCCATGCCTCTGCCAGGCTGGTACATCTT
TACAAAGTATAAGTGGCTGGTGCTGCTGCTGACCTTCCTGTTTCAGGTCATCCCTGCCTAC
GTGACCGACCTGTCTAGGCACCTGATCGGCAAGAGCCCACGCTATATCAAGCTGCAGAGCC
TGGTGAACCAGACCAGGTCCTCTATCGACTTCTTTACAAATCACTCCTGGGTCATGAAGGC
CGATAGGGTGCGCGAGCTGTACGCATCTCTGAGCCCAGCCGACAAGTATCTGTTCCCTTGC
GACCCAACCGATATCAACTGGACACACTACATCCAGGATTATTGTTGGGGCGTGCGCCACT
TTCTGGAGAAGAAGGCCTATGAGTGA

SEQ ID NO: 90  Codon optimized wild type HaFAR (FAR9; Strain SPV916)
ATGGTGGTGCTGACCTCCGAAGGAGACAAAGCCCTCTGTGGCCGAGTTCTACGCCGGCAAGA
GCGTGTTCATCACAGGCGGCACCGGCTTCCTGGGCAAGGTGTTTATCGAGAAGCTGCTGTA
CAGCTGCCCTGACATCGAGAACATCTATATGCTGATCGGGGAAGAAGGGCCTGAGCGTG
TCCGAGAGAATCAAGCAGTTCCTGGACGATCCCCTGTTTACAAGGCTGAAGGACAAGCGCC
CTGCCGATCTGGAGAAGATCGTGCTGATCCCAGGCGACATCACCGCACCAGATCTGGGCAT
CAACAGCGAGAATGAGAAGATGCTGATCGAGAAGGTGAGCGTGATCATCCACTCCGCCGCC
ACCGTGAAGTTCAACGAGCCCCTGCCTACAGCCTGGAAGATCAATGTGGAGGGCACCAGGA
TGATGCTGGCCCTGTCTCGGAGAATGAAGCGCATCGAGGTGTTTATCCACATCAGCACAGC
CTACACCAACACAAATAGGGAGGTGGTGGACGAGATCCTGTACCCAGCCCCCGCCGACATC
GATCAGGTGCACCAGTATGTGAAGGACGGCATCAGCGAGGAGGATACCGAGAAGATCCTGA
ACGGCAGACCCAATACCTACACATTCACCAAGGCCCTGACAGAGCACCTGGTGGCCGAGAA
CCAGGCCTATGTGCCTACCATCATCGTGAGACCATCCGTGGTGGCCGCCATCAAGGATGAG
CCTCTGAAGGGATGGCTGGGAAACTGGTTCGGAGCAACAGGACTGACCGTGTTTACAGCCA
AGGGCCTGAATAGAGTGATCTACGGCCACAGCTCCTATATCGTGGACCTGATCCCAGTGGA
TTACGTGGCAAACCTGGTCATCGCAGCAGGAGCCAAGTCTAGCAAGTCCACCGAGCTGAAG
GTGTATAACTGCTGTTCCTCTAGCTGTAATCCCGTGACCATCGGCACACTGATGAGCATGT
TCGCCGACGATGCCATCAAGCAGAAGTCCTACGCCATGCCTCTGCCAGGCTGGTACATCTT
TACAAAGTATAAGTGGCTGGTGCTGCTGCTGACCTTCCTGTTTCAGGTCATCCCTGCCTAC
GTGACCGACCTGTCTAGGCACCTGATCGGCAAGAGCCCACGCTATATCAAGCTGCAGAGCC
TGGTGAACCAGACCAGGTCCTCTATCGACTTCTTTACAAATCACTCCTGGGTCATGAAGGC
CGATAGGGTGCGCGAGCTGTACGCATCTCTGAGCCCAGCCGACAAGTATCTGTTCCCTTGC
GACCCAACCGATATCAACTGGACACACTACATCCAGGATTATTGTTGGGGCGTGCGCCACT
TTCTGGAGAAGAAGTCCTATGAGTGA SEQ ID NO: 91  PdDGAT1A (Phoenix dactylifera DGAT1A)
ATGGCCATCCCATCCGATAGAGAGACCCTGGAGAGGGCACCAGAGCCTTCTCCAGCAAGCG
ACCTGCAGAGCTCCCTGCGGAGAAGGCTGCACTCTACCGTGGCAGCAGTGGTGGTGCCAGA
TTCTAGCTCCAAGACATCTAGCCCCAGCGCCGAGAACCTGACCACAGACAGCGGAGAGGAT
TCCAGGGGCGACACCTCCTCTGACGCCGATACAAGGGATAGGGTGGTGGACGGAGTGGATA
GGGAGGAGGAGAACAAGACCGTGAGCGTGCTGAATGGCAGACAGTACGAGGACGGAGGCGG
CAGGGGACAGGGACAGGGCACAGGCGGCGGCGTGCCCGCCAAGTTTCTGTATAGGGCATCT
GCCCCTGCACACAGGAAGGTGAAGGAGAGCCCACTGAGCTCCGATGCCATCTTCAAGCAGA
GCCACGCCGGCCTGCTGAACCTGTGCATCGTGGTGCTGATCGCCGTGAACTCCAGGCTGAT
CATCGAGAATCTGATGAAGTACGGCCTGCTGATCCGCGCCGGCTATTGTTTTCTAGCAAG
TCCCTGCGGGACTGGCCTCTGCTGATGTGCGTCTGACCCTGCCAGCATTTCCTCTGGGAG
CCTTCATGGTGGAGAAGCTGGCCCAGCACAATTTGATCTCCGAGTCTGTGGTCATGAGCCT
GCACGTGATCATCACCACAGCCGAGCTGCTGTACCCAGTGATCGTGATCCTGAGATGCGAT
TCTGCCGTGCTGAGCGGCATCACACTGATGCTGTTTGCCAGCGTGGTGTGGCTGAAGCTGG
TGTCCTACGCCCACACCAACTATGACATGAGGACACTGAGCAAGTCCATCGACAAGGAGGA
TATGTACTCCAAGTGTCAGAGATCGATAATCTGAAGGGCACTCCTTTAAGTCTCTGGTG
TATTTCATGGTGGCCCCCACCCTGTGCTACCAGCCAAGCTATCCAAGGACCACCTGCATCA
GGAAGGGATGGGTCATCCGCCAGGTGGTGAAGCTGGTCATCTTCACCGGCCTGATGGGCTT
CATCATCGAGCAGTACATCAACCCCATCGTGCAGAATTCCCAGCACCCTCTGAAGGGCAAC
TTTCTGAATGCCATCGAGCGGGTGCTGAAGCTGTCTGTGCCCACCCTGTACGTGTGGCTGT
GCATGTTCTATTGTTTCTTTCACCTGTGGCTGAACATCCTGGCCGAGCTGCTGTGCTTTGG
CGATAGAGAGTTCTACAAGGACTGGTGGAACGCCAAGACAATGGAGGAGTATTGGAGGATG
TGGAATATGCCTGTGCACCGCTGGATGATCCGGCACATCTACTTCCCTTGTCTGAGAAATG
GCCTGCCAAGGGCCGTGGCCATCCTGATCTCCTTTCTGGTGTCTGCCATCTTCCACGAGAT
CTGCATCGCCGTGCCCTGTCACATCTTTAAGTTCTGGGCCTTTATCGGCATCATGTTCCAG
ATCCCCCTGGTCATCCTGACCAAGTATCTGCAGCACAAGTTTACAAACTCCATGGTGGGCA

SEQUENCE LISTING

| | |
|---|---|
| | ATATGATCTTCTGGTTCTTTTTCTCTATCCTGGGCCAGCCTATGTGCGTGCTGCTGTACTA<br>TCACGACGTGATGAATAGAAAGGTGAGGACCGAGTGA |
| SEQ ID NO: 92 | PdDGAT1A (*Phoenix dactylifera* DGAT1A) protein encoded by SEQ ID NO 91<br>MAIPSDRETLERAPEPSPASDLQSSLRRRLHSTVAAVVVPDSSSKTSSPSAENLTTDSGED<br>SRGDTSSDADTRDRVVDGVDREEENKTVSVLNGRQYEDGGGRGQGQGTGGGVPAKFLYRAS<br>APAHRKVKESPLSSDAIFKQSHAGLLNLCIVVLIAVNSRLIIENLMKYGLLIRAGYWFSSK<br>SLRDWPLLMCCLTLPAFPLGAFMVEKLAQHNFISESVVISLHVIITTAELLYPVIVILRCD<br>SAVLSGITLMLFASVVWLKLVSYAHTNYDMRTLSKSIDKEDMYSKCPEIDNLKGDSFKSLV<br>YFMVAPTLCYQPSYPRTTCIRKGWVIRQVVKLVIFTGLMGFIIEQYINPIVQNSQHPLKGN<br>FLNAIERVLKLSVPTLYVWLCMFYCFFHLWLNILAELLCFGDREFYKDWWNAKTIEEYWRM<br>WNMPVHRWMIRHIYFPCLRNGLPRAVAILISFLVSAIFHEICIAVPCHIFKFWAFIGIMFQ<br>IPLVILTKYLQHKFTNSMVGNMIFWFFFSILGQPMCVLLYYHDVMNRKVRTE |
| SEQ ID NO: 93 | TEF Promoter for enzyme expression<br>GAGACCGGGTTGGCGGCGCATTTGTGTCCCAAAAAACAGCCCCAATTGCCCCAATTGACCC<br>CAAATTGACCCAGTAGCGGGCCCAACCCCGGCGAGAGCCCCCTTCTCCCCACATATCAAAC<br>CTCCCCCGGTTCCCACACTTGCCGTTAAGGGCGTAGGGTACTGCAGTCTGGAATCTACGCT<br>TGTTCAGACTTTGTACTAGTTTCTTTGTCTGGCCATCCGGGTAACCCATGCCGGACGCAAA<br>ATAGACTACTGAAAATTTTTTGCTTTGTGGTTGGGACTTTAGCCAAGGGTATAAAAGACC<br>ACCGTCCCCGAATTACCTTTCCTCTTCTTTTCTCTCTCCTTGTCAACTCACACCCGAAA<br>TCGTTAAGCATTTCCTTCTGAGTATAAGAATGATTCAAA |
| SEQ ID NO: 94 | DST076_coding_sequence Z9 Desaturase<br>ATGCACATCGAGTCTGAGAACTGCCCCGGCAGGTTTAAGGAGGTGAACATGGCCCCTAATG<br>CCACCGATGCCAATGGCGTGCTGTTCGAGACCGATGCCGCCACACCTGACCTGGCCCTGCC<br>ACACGCACCTGTGCAGCAGGCCGAGAACTAGCCAAAGAAGTACGTGTGGCGCAATATCATC<br>CTGTTTGCCTACCTGCACATCGCCGCCCTGTACGGCGGCTATCTGTTTCTGTTCCACGCCA<br>AGTGGGAGACCGATATCTTGGCCTACATCCTGTATGTGATGTCTGGAGTGGGAATGACAGC<br>AGGAGCACACAGGCTGTGGGCCCACAAGAGCTACAAGGCCAAGTGGCCTCTGAGACTGATC<br>CTGGTCATCTTCAACACACTGGCCTTTCAGGACTCTGCCATCGATTGGAGCAGGGACCACC<br>GCATGCACCACAAGTATTCCGAGAGCGACGCCGATCCCCACAATGGCACACGGGGCTTCTT<br>TTTCTCTCACATCGGCTGGCTGCTGGTGCGGAAGCACCCTGAGCTGAAGAGAAAGGGCAAG<br>GGCCTGGACCTGTGCGATCTGTATGCCGACCCAATCCTGAGATTTCAGAAGAAGTACTATC<br>TGATCCTGATGCCCCTGACCTGTTTCGTGCTGCCAACAGTGATCCCCGTGTACTATTGGGG<br>CGAGACCTGGACAAACGCCTTTTTCGTGGCCGCCCTGTTTAGGTACGCCTTCATCCTGAAC<br>GTGACCTGGCTGGTGAATAGCGCCGCCCACAAGTGGGGGGATAAGGCTTATGAGCGCAACA<br>TCAAGCCATCCGAGAATATCAGCGTGTCCATGTTTGCCCTGGGCGAGGGCTTCCACAACTA<br>CCACCACACCTTCCCATGGGATTATAAGACAGCCGAGCTGGGCAACAATATGCTGAACTTC<br>ACCACAAACTTCATCAACTTCTTCGCCAAGATCGGCTGGGCCTACGATCTGAAGACCGTGT<br>CCGACGAGATCGTGCGGTCTACAGCAAAGAGGACAGGCGACGGAAGCCACCACCTGTGGGG<br>ATGGGGCGACAAGGATCACTCCAGGGAGGAGATGGCTGCCGCCATGCGCATCGACCCCAAG<br>GACGATTGA |
| SEQ ID NO: 95 | DST076_amino_acid Z9 Desaturase encoded by SEQ ID NO 94<br>MHIESENCPGRFKEVNMAPNATDANGVLFETDAATPDLALPHAPVQQADNYPKKYVWRNII<br>LFAYLHIAALYGGYLFLFHAKWQTDIFAYILYVMSGLGITAGAHRLWAHKSYKAKWPLRLI<br>LVIFNTLAFQDSAIDWSRDHRMHHKYSETDADPHNATRGFFFSHIGWLLVRKHPELKRKGK<br>GLDLSDLYADPILRFQKKYYLILMPLTCFVLPTVIPVYYWGETWTNAFFVAALFRYAFILN<br>VTWLVNSAAHKWGDKPYDRNIKPSENISVSMFALGEGFHNYHHTFPWDYKTAELGNNMLNF<br>TTNFINFFAKIGWAYDLKTVSDEIVRSRAKRTGDGSHHLWGWGDKDHSREEMAAAIRIHPK<br>DD |
| SEQ ID NO: 96 | DST180_coding_sequence Z9 Desaturase<br>ATGGCCCCAAACATCTCTGACGATGTGAATGGCGTGCTGTTTGAGAGCGATGGAGCAACAC<br>CAGACCTGGCCCTGGCAAGCCCCCCTGTGCAGAAGGCCGATAACGGGCCCAAGCAGTACGT<br>GTGGAGAAATATCCTGCTGTTCGCATATCTGCACGCCGCCGCCCTGTACGGCGGCTATCTG<br>TTTCTGACAAGCGGCAAGTGGCAGACGGACGTGTTCGCCTAGATCCTGTATGTGATGTCCG<br>GACTGGGAATCACAGCAGGAGCACACAGGCTGTGGGCACACAAGTCTTACAAGGCCAAGTG<br>GCCGCTGAAAGTGATCCTGATCATGTTTAACACCATCGCCTTTCAGGACGCAGCAATGGAT<br>TGGGCAAGGGACCACAGAATGCACCACAAGTATAGCGAGACAGACGCCGATCCTCACAATG<br>CCACCAGGGGCTTCTTTTTCTCCCACATCGGCTGGCTGCTGGTGCGCAAGCACCCAGATCT<br>GAAGGAGAAGGGCAAGGGCGTGGACATGAGCGATGTGCAGGGCGACCCCATCCTGCGGTTT<br>CAGAAGAAGTACTATCTGCTGCTGATGCCTCTGGCCTGCTTTGTGATGCCAACAGTGATCC<br>CCGTGTACTTCTGGGGCGAGACCTGGAACAATGCCTTTTTCGTGGCCGCCATGTTTAGATA<br>TGCCTTCATCCTGAACGTGACCTGGCTGGTGAATTCCGCCGCCCACAAGTGGGGCGATAAG<br>CCTTACGACAAGAGCATCAAGCCATCCGAGAACATGAGCGTGGCCATGTTTGCCCTGGGCG<br>AGGGCTTCCACAATTACCACCACACATTCCCCTGGGATTATAAGACCGCCGAGCTGGGCAA<br>CAATAAGCTGAACTTTACCACAACCTTCATCAACTTCTTCGCCAAGCTGGGCTGGGCCTAC<br>GACATGAAGACAGTGTCCGACGATATCGTGAAGAACAGGTGAAGCGCACCGGCGATGGAT<br>CTCACCACCTGTGGGGATGGGGCGACAAGAACCCAGAGCAAGGAGGAGATCGCCTCCGCCAT<br>CCGGATCAATCCTAAGGACGATTGA |
| SEQ ID NO: 97 | DST180_amino_acid Z9 Desaturase encoded by SEQ ID NO: 96<br>MAPNISDDVNGVLFESDAATPDLALASPPVQKADNRPKQYVWRNILLFAYLHAAALYGGYL<br>FLTSAKWQTDVFAYILYVMSGLGITAGAHRLWAHKSYKAKWPLKVILIIFNTIAFQDAAMD |

SEQUENCE LISTING

| | |
|---|---|
| | WARDHRMHHKYSETDADPHNATRGFFFSHIGWLLVRKHPDLKEKGKGLDMSDLQADPILRF<br>QKKYYLLLMPLACFVMPTVIPVYFWGETWNNAFFVAAMFRYAFILNVTWLVNSAAHKWGDK<br>PYDKSIKPSENMSVAMFALGEGFHNYHHTFPWDYKTAELGNNKLNFTTTFINFFAKLGWAY<br>DMKTVSDDIVKNRVKRTGDGSHHLWGWGDKNQSKEEIASAIRINPKDD |
| SEQ ID NO: 98 | DST181_coding_sequence Z9 Desaturase<br>ATGGCCCCAAACATCTCTGAGGATGCCAATGGCGTGCTGTTTGAGAGCGATGCAGCAACAC<br>CAGACCTGGCCCTGGCAAGCCCACCTGTGCAGAAGGCAGACAACAGGCCCAAGGAGTACGT<br>GTGGAGAAATATCATCCTGTTTGCCTATCTGCACCTGGCCGCCCTGTACGGCGGCTATCTG<br>TTTCTGTTCAGCGCCAAGTGGCAGACAGACGTGTTCGCCTACATCCTGTATGTGATGTCCG<br>GACTGGGAATCACCGCAGGAGCACACAGAGTGTGGGCACACAAGTCTTAGAAGGCCAAGTG<br>GCCCCTGAAAGTGATCCTGATCATCTTTAACACCATCGCCTTTCAGGACGCAGCAATGGAT<br>TGGGCAAGGGACCACAGAATGCACCACAAGTATAGCGAGACAGACGCCGATCCTCACAATG<br>CCACCAGGGGCTTCTTTTTCTCCCACATCGGCTGGCTGCTGGTGCGCAAGCACCCAGACCT<br>GAAGAAGAAGGGCAAGGGCCTGGACATGAGCGATCTGCTGAACGACCCCATCCTGAAGTTT<br>CAGAAGAAGTACTATCTGCTGCTGATGCCTCTGGCCTGCTTCGTGATGCCAACAATGATCC<br>CCGTGTACCTGTGGGGCGAGACATGGACCAATGCCTTTTTCGTGGCCGCCATGTTTCGGTA<br>TGCCTTCATCCTGAACGTGACCTGGCTGGTGAATTCCGCCGCCCACAAGTGGGGCGATAAG<br>CCTTAGGACAAGAGCATCAAGCCATCCGAGAACCTGTCTGTGGCCATGTTTGCCCTGGGCG<br>AGGGCTTCCACAATTACCACCACACATTCCCCTGGGATTATAAGACCGCCGAGCTGGGCAA<br>CCAGAAGCTGAACTTCACCACAACCTTCATCAACTTTTTCGCCAAGCTGGGCTGGGCCTAC<br>GACATGAAGACAGTGTCCGACGATATCGTGAAGAATAGGGTGAAGCGCACCGGCGATGGAT<br>CTCACCACCTGTGGGGATGGGGCGACAAGAACCAGAGCAAGGAGGAGATCGCCTCCGCCAT<br>CCGGATCAATCCTAAGGACGATTGA |
| SEQ ID NO: 99 | DST181_amino_acid Z9 Desaturase encoded by SEQ ID NO: 98<br>MAPNISEDANGVLFESDAATPDLALASPPVQKADNRPKQYVWRNIILFAYLHLAALYGGYL<br>FLFSAKWQTDVFAYILYVMSGLGITAGAHRLWAHKSYKAKWPLKVILIIFNTIAFQDAAMD<br>WARDHRMHHKYSETDADPHNATRGFFFSHIGWLLVRKHPDLKKKGKGLDMSDLLMDPILKF<br>QKKYYLLLMPLACFVMPTMIPVYLWGETWTNAFFVAAMFRYAFILNVTWLVNSAAHKWGDK<br>PYDKSIKPSENLSVAMFALGEGFHNYHHTFPWDYKTAELGNQKLNFTTTFINFFAKLGWAY<br>DMKTVSDDIVKNRVKRTGDGSHHLWGWGDKNQSKEEIASAIRINPKDD |
| SEQ ID NO: 100 | DST183_coding_sequence Z9 Desaturase<br>ATGGCCCCAAACATCAGCGAGGATGTGAATGGCGTGCTGTTCGAGTCCGATGCCGCCACAC<br>CAGACCTGGCCCTGTCTACCCCCACCTGTGCAGAAGGCAGACAACAGGCCCAAGCAGCTGGT<br>GTGGAGAAATATCCTGCTGTTTGCATACCTGCACCTGGCAGCACAGTACGGAGGCTATCTG<br>TTTCTGTTCTCTGCCAAGTGGCAGACAGATATCTTCGCCTACATCCTGTATGTGATCAGCG<br>GACTGGGAATCACCGCAGGAGCACACCGGCTGTGGGCCCACAAGTCCTACAAGGCCAAGTG<br>GCCTCTGAGAGTGATCCTGGTCATCTTCAACACCGTGGCCTTTCAGGACGCAGCAATGGAT<br>TGGGCAAGGGACCACAGAATGCACCACAAGTATTCTGAGACAGACGCCGATCCTCACAATG<br>CCACCAGGGGCTTCTTTTTCAGCCACATCGGCTGGCTGCTGGTGCGCAAGCACCCAGATCT<br>GAAGGAGAAGGGCAAGGGCCTGGACATGAGCGATCTGCTGGCCGACCCCATCCTGAGGTTT<br>CAGAAGAAGTACTATCTGATCCTGATGCCTCTGGCCTGCTTTGTGATGCCAACAGTGATCC<br>CCGTGTACTTCTGGGGCGAGACATGGACCAACGCCTTTTTCGTGGCCGCCATGTTTCGCTA<br>TGCCTTCATCCTGAACGTGACCTGGCTGGTGAATTCTGCCGCCCACAAGTGGGGCGATAAG<br>CCTTAGGACAAGAGCATCAAGCCATCCGAGAACCTGTCTGTGGCCATGTTTGCCCTGGGCG<br>AGGGCTTCCACAATTACCACCACACATTCCCCTGGGACTATAAGACCGCCGAGCTGGGCAA<br>CAATAAGCTGAACTTTACCACAACCTTCATCAACTTCTTCGCCAAGATCGGCTGGGCCTAT<br>GATCTGAAGACAGTGTCCGACGATATCGTGAAGAATAGGGTGAAGAGGACCGGCGACGGAA<br>GCCACCACCTGTGGGGCTGGGGCGATGAGAACCAGTCCAAGGAGGAGATCGACGCCGCCAT<br>CCGGATCAATCCTAAGGACGATTGA |
| SEQ ID NO: 101 | DST183_amino_acid Z9 Desatursae encoded by SEQ ID NO: 100<br>MAPNISEDVNGVLFESDAATPDLALSTPPVQKADNRPKQLVWRNILLFAYLHLAAQYGGYL<br>FLFSAKWQTDIFAYILYVISGLGITAGAHRLWAHKSYKAKWPLRVILVIFMTVAFQDAAMD<br>WARDHRMHHKYSETDADPHNATRGFFFSHIGWLLVRKHPDLKEKGKGLDMSDLLADPILRF<br>QKKYYLILMPLACFVMPTVIPVYFWGETWTNAFfVAAMFRYAFILNVTWLVNSAAHKWGDK<br>PYDKSIKPSENLSVAMFALGEGFHNYHHTFPWDYKTAELGNNKLNFTTTFINFFAKIGWAY<br>DLKTVSDDIVKNRVKRTGDGSHHLWGWGDENQSKEEIDAAIRINPKDD |
| SEQ ID NO: 102 | DST189_coding_sequence Z9 Desaturase<br>ATGGCCCCTAACGTGACCGAGGAGAATGGCGTGCTGTTCGAGTCTGATGCAGCAACACCTG<br>ACCTGGCCCTGGCAAGAGAGCCAGTGGAGCAGGCAGATAGCTCCCCACGGGTGTACGTGTG<br>GAGAAACATCATCCTGTTTGCCTATCTGCACATCGCCGCCGTGTACGGCGGCTATCTGTTT<br>CTGTTCTCCGCCAAGTGGCAGACCGACATCTTCGCCTACCTGCTGTATGTGGCCTCTGAC<br>TGGGAATCACAGCAGGAGCACACAGGCTGTGGGCCCACAAGAGCTACAAGGCCAAGTGGCC<br>CCTGAGACTGATCCTGACCATCTTTAACACCACAGCCTTTCAGGACAGCGCCATCGATTGG<br>GCCCGGGACCACAGAATGCACCACAAGTATTCCGAGACCGACGCCGATCCCCACAATGCCA<br>CAAGGGGCTTCTTTTTCTCCCACATCGGCTGGCTGGTGAGGAAGCACCCTGAGCTGAA<br>GCGCAAGGGCAAGGGCCTGGACCTGTCTGATCTGTACGCCGATCCTATCCTGCGCTTTCAG<br>AAGAAGTACTATCTGATCCTGATGCCACTGGCCTGCTTCATCCTGCCCACCGTGATCCCCG<br>TGTACCTGTGGAACGAGACATGGAGCAATGCCTTTTTCGTGGCCGCCCTGTTTCGGTATAC<br>CTTCATCCTGAACGTGACATGGCTGCTGAATTCCGCCGCCCACAAGTGGGGCGATAAGCCA<br>TACGACAAGTCCATCAAGCCCTCTGAGAACCTGTCTGTGAGCCTGTTTGCCTTCGGCGAGG<br>GCTTTCACAATTACCACCACACCTTCCCATGGGATTATAAGACAGCCGAGCTGGGCAACCA<br>CCGGCTGAACTTCACCACAAAGTTCATCAACTTTTTCGCCAAGATCGGCTGGGCCTATGAT |

| | SEQUENCE LISTING |
|---|---|
| | ATGAAGACCGTGTCTCACGAGATCGTGCAGCAGAGGGTGAAGAGGACAGGCGACGGAAGCC<br>ACCACCTGTGGGGATGGGGCGACAAGGATCACGCACAGGAGGAGATCGACGCCGCCATCAG<br>AATCAATCCCAAGGACGATTGA |
| SEQ ID NO: 103 | DST189_amino_acid Z9 Desaturase encoded by SEQ ID NO: 102<br>MAPNVTEENGVLFESDAATPDLALAREPVQQADSSPRVYVWRNIILFAYLHIAAVYGGYLF<br>LFSAKWQTDIFAYLLYVASGLGITAGAHRLWAHKSYKAKWPLRLILTIFNTTAFQDSAIDW<br>ARDHRMHHKYSETDADPHNATRGFFFSHIGWLLVRKHPELKRKGKGLDLSDLYADPILRFQ<br>KKYYLILMPLACFILPTVIPVYLWNETWSNAFFVAALFRYTFILNVTWLVNSAAHKWGDKP<br>YDKSIKPSENLSVSLFAFGEGFHNYHHTFPWDYKTAELGNHRLNFTTKFINFFAKIGWAYD<br>MKTVSHEIVQQRVKRTGDGSHHLWGWGDKDHAQEEIDAAIRINPKDD |
| SEQ ID NO: 104 | DST192_coding_sequence Z9 Desaturase<br>ATGGATTTTCTGAACGAGATCGACAATTGCCCCGAGCGGCTGAGAAAGCCAGAGAAGATGG<br>CCCCCAACGTGACCGAGGAGAATGGCGTGCTGTTCGAGTCCGATGCAGCAACCCCAGACCT<br>GGCCCTGGCAAGGACACCTGTGGAGCAGGCCGACGATTCTCCAAGGATCTACGTGTGGCGC<br>AACATCATCCTGTTTGCCTATCTGCACCTGGCCGCCATCTACGGCGGCTATCTGTTTCTGT<br>TCTCCGCCAAGTGGCAGACCGATATCTTCGCCTACCTGCTGTATGTGGCATCTGGACTGGG<br>AATCACAGCAGGAGCACACAGGCTGTGGGCACACAAGAGCTACAAGGCCAAGTGGCCTCTG<br>CGCCTGATCCTGACCATCTTTAACACAATCGCCTTTCAGGACAGCGCCATCGATTGGGCCA<br>GGGACCACCGCATGCACCACAAGTATTCCGAGACCGACGCCGATCCACACAATGCCACACG<br>GGGCTTCTTTTTCTCTCACATCGGATGGCTGCTGGTCGGAAGCACCCAGAGCTGAAGAGA<br>AAGGGCAAGGGCCTGGACCTGTCTGATCTGTACAGCGATCCCATCCTGAGATTTCAGAAGA<br>AGTACTATATGATCCTGATGCCTCTGGCCTGTTTCATCCTGCCCACCGTGATCCCCGTGTA<br>TATGTGGAACGAGACATGGAGCAATGCCTTTTTCGTGGCCGCCCTGTTTAGGTATACCTTC<br>ATCCTGAACGTGACATGGCTGGTGAATTCCGCCGCCCACAAGTGGGGCGATAAGCCTTACG<br>ACAAGTCCATCAAGCCATCTGAGAACATGAGCGTGTCCCTGTTTGCCTTCGGCGAGGGCTT<br>TCACAATTACCACCACACCTTCCCTTGGGACTATAAGACAGCCGAGCTGGGCAACCACCGG<br>CTGAACTTCACCACAAAGTTCATCAACTTCTTCGCCAAGATCGGCTGGGCCTATGATATGA<br>AGACCGTGTCTCAGGAGATCGTGCAGCAGCGGGTGAAGAGAACACGCGACGGAAGCCACCA<br>CCTGTGGGGATGGGGCGACAAGGATCACGCACAGGAGGAGATCAACGCCGCCATCCGCATC<br>AATCCAAAGGACGATTGA |
| SEQ ID NO: 105 | DST192_amino_acid Z9 Desaturase encoded by SEQ ID NO: 104<br>MDFLNEIDNCPER1RKPEKMAPNVTeENGVLFESDAATPDLALARTPVEQADDSPRIYVWR<br>NIILFAYLHLAAIYGGYLFLFSAKWQTDIFAYLLYVASGLGITAGAHRLWAHKSYKAKWPL<br>RLILTIFNTIAFQDSAIDWARDHRMHHKYSETDADPHNATRGFFFSHIGWLLVRKHPELKR<br>KGKGLDLSDLYSDPILRFQKKYYMILMPLACFILPTVIPVYMWNETWSNAFFVAALFRYTF<br>ILNVTWLVNSAAHKWGDKPYDKSIKPSENMSVSLFAFGEGFHNYHHTFPWDYKTAELGNHR<br>LNFTTKFINFFAKIGWAYDMKTVSQEIVQQRVKRTGDGSHHLWGWGDKDHAQEEINAAIRI<br>NPKDD |

The foregoing detailed description has been given for clearness of understanding only and no unnecessary limitations should be understood there from as modifications will be obvious to those skilled in the art.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

INCORPORATION BY REFERENCE

All references, articles, publications, patents, patent publications, and patent applications cited herein are incorporated by reference in their entireties for all purposes. The current application hereby incorporates by reference each of the following in its entirety: U.S. Provisional Application Ser. No. 62/257,054, filed Nov. 18, 2015, U.S. Provisional Application Ser. No. 62/351,605, filed Jun. 17, 2016, and PCT application no. PCT/US2016/062852, filed Nov. 18, 2016.

However, mention of any reference, article, publication, patent, patent publication, and patent application cited herein is not, and should not be taken as, an acknowledgment or any form of suggestion that they constitute valid prior art or form part of the common general knowledge in any country in the world.

Further Embodiments of the Invention

Other subject matter contemplated by the present disclosure is set out in the following numbered embodiments:

1. A recombinant *Yarrowia lipolytica* microorganism capable of producing a mono- or poly-unsaturated $C_6$-$C_{24}$ fatty alcohol from an endogenous or exogenous source of saturated $C_6$-$C_{24}$ fatty acid, wherein the recombinant *Yarrowia lipolytica* microorganism comprises:

(a) at least one nucleic acid molecule encoding a fatty acyl desaturase having at least 95% sequence identity to a fatty acyl desaturase selected from the group consisting of SEQ ID NOs: 39, 54, 60, 62, 78, 79, 80, 95, 97, 99, 101, 103, and 105 that catalyzes the conversion of a saturated $C_6$-$C_{24}$ fatty acyl-CoA to a corresponding mono- or poly-unsaturated $C_6$-$C_{24}$ fatty acyl-CoA; and (b) at least one nucleic acid molecule encoding a fatty alcohol forming fatty acyl reductase having at least 95% sequence identity to a fatty alcohol forming fatty acyl reductase selected from the group consisting of SEQ ID NOs: 41-48, 57, 73, 75 and 77 that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol.

2. The recombinant *Yarrowia lipolytica* microorganism of embodiment 1, wherein the recombinant *Yarrowia lipolytica* microorganism comprises a deletion, disruption, mutation, and/or reduction in the activity of one or more endogenous enzymes that catalyzes a reaction in a pathway that competes with the biosynthesis pathway for the production of a mono- or poly-unsaturated $C_6$-$C_{24}$ fatty alcohol.

3. The recombinant *Yarrowia lipolytica* microorganism of embodiments 1 or 2, wherein the recombinant *Yarrowia lipolytica* microorganism comprises a deletion, disruption, mutation, and/or reduction in the activity of one or more endogenous enzyme selected from the following:
(i) one or more acyl-CoA oxidase selected from the group consisting of YALI0E32835g (POX1), YALI0F10857g (POX2), YALI0D24750g (POX3), YALI0E27654g (POX4), YALI0C23859g (POX5), YALI0E06567g (POX6);
(ii) one or more (fatty) alcohol dehydrogenase selected from the group consisting of YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), YALI0E07766g (ADH7);
(iii) a (fatty) alcohol oxidase YALI0B14014g (FAO1);
(iv) one or more cytochrome P450 enzyme selected from the group consisting of YALI0E25982g (ALK1), YALI0F01320g (ALK2), YALI0E23474g (ALK3), YALI0B13816g (ALK4), YALI0B13838g (ALK5), YALI0B01848g (ALK6), YALI0A15488g (ALK7), (YALI0C12122g (ALK8), YALI0B06248g (ALK9), YALI0B20702g (ALK10), YALI0C10054g (ALK11) and YALI0A20130g (Alk12); and
(v) one or more diacylglycerol acyltransferase selected from the group consisting of YALI0E32791g (DGA1) and YALI0D07986g (DGA2).

4. The recombinant *Yarrowia lipolytica* microorganism of embodiments 1 or 2, wherein the recombinant *Yarrowia lipolytica* microorganism comprises a deletion of one or more endogenous enzyme selected from the following:
(i) one or more acyl-CoA oxidase selected from the group consisting of YALI0E32835g (POX1), YALI0F10857g (POX2), YALI0D24750g (POX3), YALI0E27654g (POX4), YALI0C23859g (POX5), YALI0E06567g (POX6);
(ii) one or more (fatty) alcohol dehydrogenase selected from the group consisting of YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), YALI0E07766g (ADH7);
(iii) a (fatty) alcohol oxidase YALI0B14014g (FAO1);
(iv) one or more cytochrome P450 enzyme selected from the group consisting of YALI0E25982g (ALK1), YALI0F01320g (ALK2), YALI0E23474g (ALK3), YALI0B13816g (ALK4), YALI0B13838g (ALK5), YALI0B01848g (ALK6), YALI0A15488g (ALK7), (YALI0C12122g (ALK8), YALI0B06248g (ALK9), YALI0B20702g (ALK10), YALI0C10054g (ALK11) and YALI0A20130g (Alk12); and
(v) one or more diacylglycerol acyltransferase selected from the group consisting of YALI0E32791g (DGA1) and YALI0D07986g (DGA2).

5. The recombinant *Yarrowia lipolytica* microorganism of any one of embodiments 1-4, wherein the fatty acyl desaturase catalyzes the conversion of a saturated fatty acyl-CoA into a mono- or poly-unsaturated intermediate selected from Z9-14:Acyl-CoA, Z11-14:Acyl-CoA, E11-14:Acyl-CoA, Z9-16:Acyl-CoA, and Z11-16:Acyl-CoA.

6. The recombinant *Yarrowia lipolytica* microorganism of any one of embodiments 1-5, wherein the mono- or poly-unsaturated $C_6$-$C_{24}$ fatty alcohol is selected from the group consisting of Z9-14:OH, Z11-14:OH, E11-14:OH, Z9-16:OH, Z11-16:OH, Z11Z13-16:OH, and Z13-18:OH.

7. The recombinant *Yarrowia lipolytica* microorganism of any one of embodiments 1-6, wherein the recombinant *Yarrowia lipolytica* microorganism further comprises at least one endogenous or exogenous nucleic acid molecule encoding an alcohol oxidase or an alcohol dehydrogenase capable of catalyzing the conversion of the mono- or poly-unsaturated $C_6$-$C_{24}$ fatty alcohol into a corresponding $C_6$-$C_{24}$ fatty aldehyde.

8. The recombinant *Yarrowia lipolytica* microorganism of embodiment 7, wherein the alcohol dehydrogenase is selected from Table 3a.

9. The recombinant *Yarrowia lipolytica* microorganism of embodiments 7 or 8, wherein the $C_6$-$C_{24}$ fatty aldehyde is selected from the group consisting of Z9-14:Ald, Z11-14:Ald, E11-14:Ald, Z9-16:Ald, Z11-16:Ald, Z11Z13-16:Ald and Z13-18:Ald.

10. The recombinant *Yarrowia lipolytica* microorganism of any one of embodiments 1-9, wherein the recombinant *Yarrowia lipolytica* microorganism further comprises at least one endogenous or exogenous nucleic acid molecule encoding an acetyl transferase capable of catalyzing the conversion of the mono- or poly-unsaturated $C_6$-$C_{24}$ fatty alcohol into a corresponding $C_6$-$C_{24}$ fatty acetate.

11. The recombinant *Yarrowia lipolytica* microorganism of embodiment 10, wherein the acetyl transferase is selected from Table 5d.

12. The recombinant *Yarrowia lipolytica* microorganism of embodiments 10 or 11, wherein the $C_6$-$C_{24}$ fatty acetate is selected from the group consisting of Z9-14:Ac, Z11-14:Ac, E11-14:Ac, Z9-16:Ac, Z11-16:Ac, Z11Z13-16:Ac, and Z13-18:Ac.

13. The recombinant *Yarrowia lipolytica* microorganism of any one of embodiments 1-12, wherein the recombinant *Yarrowia lipolytica* microorganism further comprises:
at least one endogenous or exogenous nucleic acid molecule encoding an alcohol oxidase or an alcohol dehydrogenase capable of catalyzing the conversion of the mono- or poly-unsaturated $C_6$-$C_{24}$ fatty alcohol into a corresponding $C_6$-$C_{24}$ fatty aldehyde; and
at least one endogenous or exogenous nucleic acid molecule encoding an acetyl transferase capable of catalyzing the conversion of the mono- or poly-unsaturated $C_6$-$C_{24}$ fatty alcohol into a corresponding $C_6$-$C_{24}$ fatty acetate.

14. The recombinant *Yarrowia lipolytica* microorganism of embodiment 13, wherein the mono- or poly-unsaturated $C_6$-$C_{24}$ fatty aldehyde and $C_6$-$C_{24}$ fatty acetate is selected from the group consisting of Z9-14:Ac, Z11-14:Ac, E11-14:Ac, Z9-16:Ac, Z11-16:Ac, Z11Z13-16:Ac, Z13-18:Ac, Z9-14:Ald, Z11-14:Ald, E11-14:Ald, Z9-16:Ald, Z11-16:Ald, Z11Z13-16:Ald and Z13-18:Ald.

15. The recombinant *Yarrowia lipolytica* microorganism of any one of embodiments 1-14, wherein the fatty acyl desaturase does not comprise a fatty acyl desaturase comprising an amino acid sequence selected from the group consisting of SEQ ID NOs: 64, 65, 66 and 67.

16. The recombinant *Yarrowia lipolytica* microorganism of any one of embodiments 1-15, wherein the fatty acyl desaturase does not comprise a fatty acyl desaturase selected from an *Amyelois transitella*, *Spodoptera littoralis*, *Agrotis segetum*, or *Trichoplusia ni* derived desaturase.

17. A method of producing a mono- or poly-unsaturated $C_6$-$C_{24}$ fatty alcohol from an endogenous or exogenous source of saturated $C_6$-$C_{24}$ fatty acid, comprising: cultivating the recombinant *Yarrowia lipolytica* microorganism of any one of embodiments 1-16 in a culture medium containing a feedstock that provides a carbon source adequate for the production of the mono- or poly-unsaturated $C_6$-$C_{24}$ fatty alcohol.

18. The method of embodiment 17, wherein the mono- or poly-unsaturated $C_6$-$C_{24}$ fatty alcohol is selected from the group consisting of Z9-14:OH, Z11-14:OH, E11-14:OH, Z9-16:OH, Z11-16:OH, Z11Z13-16:OH, and Z13-18:OH.

19. The method of embodiments 17 or 18, wherein the recombinant *Yarrowia lipolytica* microorganism comprises a deletion, disruption, mutation, and/or reduction in the activity of one or more endogenous enzyme selected from the following:
(i) one or more acyl-CoA oxidase selected from the group consisting of YALI0E32835g (POX1), YALI0F10857g (POX2), YALI0D24750g (POX3), YALI0E27654g (POX4), YALI0C23859g (POX5), YALI0E06567g (POX6);
(ii) one or more (fatty) alcohol dehydrogenase selected from the group consisting of YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), YALI0E07766g (ADH7);
(iii) a (fatty) alcohol oxidase YALI0B14014g (FAO1);
(iv) one or more cytochrome P450 enzyme selected from the group consisting of YALI0E25982g (ALK1), YALI0E1320g (ALK2), YALI0E23474g (ALK3), YALI0B13816g (ALK4), YALI0B13838g (ALK5), YALI0B01848g (ALK6), YALI0A15488g (ALK7), (YALI0C12122g (ALK8), YALI0B06248g (ALK9), YALI0B20702g (ALK10), YALI0C10054g (ALK11) and YALI0A20130g (Alk12); and
(v) one or more diacylglycerol acyltransferase selected from the group consisting of YALI0E32791g (DGA1) and YALI0D07986g (DGA2).

20. The method of embodiments 17 or 18, further comprising a step of recovering the mono- or poly-unsaturated $C_6$-$C_{24}$ fatty alcohol.

21. The method of embodiment 20, wherein said recovery step comprises distillation.

22. The method of embodiment 20, wherein said recovery step comprises membrane-based separation.

23. A method of producing a mono- or poly-unsaturated $C_6$-$C_{24}$ fatty aldehyde from an endogenous or exogenous source of saturated $C_6$-$C_{24}$ fatty acid, comprising: cultivating the recombinant *Yarrowia lipolytica* microorganism of any one of embodiment 1-16 in a culture medium containing a feedstock that provides a carbon source adequate for the production of the mono- or poly-unsaturated $C_6$-$C_{24}$ fatty aldehyde.

24. The method of embodiment 23, wherein the $C_6$-$C_{24}$ fatty aldehyde is selected from the group consisting of Z9-14:Ald, Z11-14:Ald, E11-14:Ald, Z9-16:Ald, Z11-16:Ald, Z11Z13-16:Ald and Z13-18:Ald.

25. The method of embodiments 23 or 24, further comprising a step of recovering the mono- or poly-unsaturated $C_6$-$C_{24}$ fatty aldehyde.

26. The method of embodiment 25, wherein said recovery step comprises distillation.

27. The method of embodiment 25, wherein said recovery step comprises membrane-based separation.

28. A method of producing a mono- or poly-unsaturated $C_6$-$C_{24}$ fatty acetate from an endogenous or exogenous source of saturated $C_6$-$C_{24}$ fatty acid, comprising: cultivating the recombinant *Yarrowia lipolytica* microorganism of any one of embodiments 1-16 in a culture medium containing a feedstock that provides a carbon source adequate for the production of the mono- or poly-unsaturated $C_6$-$C_{24}$ fatty acetate.

29. The method of embodiment 28, wherein the $C_6$-$C_{24}$ fatty acetate is selected from the group consisting of Z9-14:Ac, Z11-14:Ac, E11-14:Ac, Z9-16:Ac, Z11-16:Ac, Z11Z13-16:Ac, and Z13-18:Ac.

30. The method of embodiment 28, further comprising a step of recovering the mono- or poly-unsaturated $C_6$-$C_{24}$ fatty acetate.

31. The method of embodiment 28, wherein said recovery step comprises distillation.

32. The method of embodiment 28, wherein said recovery step comprises membrane-based separation.

33. A method of producing a mono- or poly-unsaturated $C_6$-$C_{24}$ fatty aldehyde and $C_6$-$C_{24}$ fatty acetate from an endogenous or exogenous source of saturated $C_6$-$C_{24}$ fatty acid, comprising: cultivating the recombinant *Yarrowia lipolytica* microorganism of any one of embodiments 1-16 in a culture medium containing a feedstock that provides a carbon source adequate for the production of the mono- or poly-unsaturated $C_6$-$C_{24}$ fatty aldehyde and $C_6$-$C_{24}$ fatty acetate.

34. The method of embodiment 33, wherein the mono- or poly-unsaturated $C_6$-$C_{24}$ fatty aldehyde and $C_6$-$C_{24}$ fatty acetate is selected from the group consisting of Z9-14:Ac, Z11-14:Ac, E11-14:Ac, Z9-16:Ac, Z11-16:Ac, Z11Z13-16:Ac, Z13-18:Ac, Z9-14:Ald, Z11-14:Ald, E11-14:Ald, Z9-16:Ald, Z11-16:Ald, Z1Z13-16:Ald and Z13-18:Ald.

35. A method of engineering a *Yarrowia lipolytica* microorganism that is capable of producing a mono- or poly-unsaturated $C_6$-$C_{24}$ fatty alcohol from an endogenous or exogenous source of saturated $C_6$-$C_{24}$ fatty acid, wherein the method comprises introducing into a *Yarrowia lipolytica* microorganism the following:
(a) at least one nucleic acid molecule encoding a fatty acyl desaturase having at least 95% sequence identity to a fatty acyl desaturase selected from the group consisting of SEQ ID NOs: 39, 54, 60, 62, 78, 79, 80, 95, 97, 99, 101, 103, and 105 that catalyzes the conversion of a saturated $C_6$-$C_{24}$ fatty acyl-CoA to a corresponding mono- or poly-unsaturated $C_6$-$C_{24}$ fatty acyl-CoA; and
(b) at least one nucleic acid molecule encoding a fatty alcohol forming fatty acyl reductase having at least 95% sequence identity to a fatty alcohol forming fatty acyl reductase selected from the group consisting of SEQ ID NOs: 41-48, 57, 73, 75 and 77 that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol.

36. The method of embodiment 35, wherein the method further comprises introducing into the *Yarrowia lipolytica* microorganism one or more modifications comprising a deletion, disruption, mutation, and/or reduction in the activity of one or more endogenous enzymes that catalyzes a reaction in a pathway that competes with the biosynthesis pathway for the production of a mono- or poly-unsaturated $C_6$-$C_{24}$ fatty alcohol.

37. The method of embodiment 35 or 36, wherein the *Yarrowia lipolytica* microorganism is MATA ura3-302:: SUC2 Δpox1 Δpox2 Δpox3 Δpox4 Δpox5 Δpox6 Δfadh Δadh1 Δadh2 Δadh3 Δadh4 Δadh5 Δadh6 Δadh7 Δfao1:: URA3.

38. The method of any one of embodiments 35-37, wherein the method further comprises introducing into the *Yarrowia lipolytica* microorganism one or more modifications comprising a deletion, disruption, mutation, and/or reduction in the activity of one or more endogenous enzyme selected from the following:
(i) one or more acyl-CoA oxidase selected from the group consisting of YALI0E32835g (POX), YALI0F10857g (POX2), YALI0D24750g (POX3), YALI0E27654g (POX4), YALI0C23859g (POX5), YALI0E06567g (POX6);
(ii) one or more (fatty) alcohol dehydrogenase selected from the group consisting of YALI0F09603g (FADH). YALI0D25630g (ADH1), YALI0E17787g (ADH2). YALI0A16379g (ADH3), YALI0E15818g (ADH4), YALI0D02167g (ADH5), YALI0A15147g (ADH6), YALI0E07766g (ADH7);
(iii) a (fatty) alcohol oxidase YALI0B14014g (FAO1);
(iv) one or more cytochrome P450 enzyme selected from the group consisting of YALI0E25982g (ALK1), YALI0F01320g (ALK2), YALI0E23474g (ALK3), YALI0B13816g (ALK4), YALI0B3838g (ALK5), YALI0B01848g (ALK6), YALI0A15488g (ALK7), (YALI0C12122g (ALK8).YALI0B06248g (ALK9), YALI0B20702g (ALK10), YALI0C10054g (ALK1) and YALI0A20130g (Alk12), and
(v) one or more diacylglycerol acyltransferase selected from the group consisting of YALI0E32791g (DGA1) and YALI0D07986g (DGA2).

39. The method of any one of embodiments 35-38, wherein the fatty acyl desaturase catalyzes the conversion of a fatty acyl-CoA into a mono- or poly-unsaturated intermediate selected from Z9-14:Acyl-CoA, Z11-14:Acyl-CoA, E11-14:Acyl-CoA, Z9-16:Acyl-CoA, and Z11-16:Acyl-CoA.

40. The method of any one of embodiments 35-39, wherein the mono- or poly-unsaturated $C_6$-$C_{24}$ fatty alcohol is selected from the group consisting of Z9-14:OH, Z11-14:OH, E11-14:OH, Z9-16:OH, Z11-16:OH, Z11Z13-16:OH, and Z13-18:OH.

41. The method of any one of embodiments 35-40, wherein the method further comprises introducing into or expressing in the recombinant *Yarrowia lipolytica* microorganism at least one endogenous or exogenous nucleic acid molecule encoding an alcohol oxidase or an alcohol dehydrogenase capable of catalyzing the conversion of the mono- or poly-unsaturated $C_6$-$C_{24}$ fatty alcohol into a corresponding $C_6$-$C_{24}$ fatty aldehyde.

42. The method of embodiment 41, wherein the alcohol dehydrogenase is selected from Table 3a.

43. The method of embodiment 41, wherein the $C_6$-$C_{24}$ fatty aldehyde is selected from the group consisting of Z9-14:Ald, Z11-14:Ald, E11-14:Ald, Z9-16:Ald, Z11-16:Ald, Z11Z13-16:Ald and Z13-18:Ald.

44. The method of any one of embodiments 35-43, wherein the method further comprises introducing into or expressing in the recombinant *Yarrowia lipolytica* microorganism at least one endogenous or exogenous nucleic acid molecule encoding an acetyl transferase capable of catalyzing the conversion of the mono- or poly-unsaturated $C_6$-$C_{24}$ fatty alcohol into a corresponding $C_6$-$C_{24}$ fatty acetate.

45. The method of embodiment 44, wherein the acetyl transferase is selected from Table 5d.

46. The method of embodiment 44, wherein the $C_6$-$C_{24}$ fatty acetate is selected from the group consisting of Z9-14:Ac, Z11-14:Ac, E11-14:Ac, Z9-16:Ac, Z11-16:Ac, Z11Z13-16:Ac, and Z13-18:Ac.

47. The method of any one of embodiments 35-46, wherein the method further comprises introducing into or expressing in the recombinant *Yarrowia lipolytica* microorganism:
at least one endogenous or exogenous nucleic acid molecule encoding an alcohol oxidase or an alcohol dehydrogenase capable of catalyzing the conversion of the mono- or poly-unsaturated $C_6$-$C_{24}$ fatty alcohol into a corresponding $C_6$-$C_{24}$ fatty aldehyde; and
at least one endogenous or exogenous nucleic acid molecule encoding an acetyl transferase capable of catalyzing the conversion of the mono- or poly-unsaturated $C_6$-$C_{24}$ fatty alcohol into a corresponding $C_6$-$C_{24}$ fatty acetate.

48. The method of any one of embodiments 35-47, wherein the mono- or poly-unsaturated $C_6$-$C_{24}$ fatty aldehyde and $C_6$-$C_{24}$ fatty acetate is selected from the group consisting of Z9-14:Ac, Z11-14:Ac. E11-14:Ac, Z9-16:Ac, Z11-16:Ac, Z11Z13-16:Ac, Z13-18:Ac, Z9-14:Ald, Z11-14:Ald, E11-14:Ald, Z9-16:Ald, Z11-16:Ald, Z11Z13-16:Ald and Z13-18:Ald.

49. The method of any one of embodiments 35-48, wherein the fatty acyl desaturase does not comprise a fatty acyl desaturase comprising an amino acid sequence selected from the group consisting of SEQ ID NOs: 64, 65, 66 and 67.

50. The method of any one of embodiments 35-49, wherein the fatty acyl desaturase does not comprise a fatty acyl desaturase selected from an *Amyelois transitella, Spodoptera littoralis, Agrotis segetum,* or *Trichoplusia ni* derived desaturase.

51. The method of any one of embodiments 17-22, wherein the mono- or poly-unsaturated $C_6$-$C_{24}$ fatty alcohol is converted into a corresponding $C_6$-$C_{24}$ fatty aldehyde using chemical methods.

53. The method of any one of embodiments 17-22, wherein the mono- or poly-unsaturated $C_6$-$C_2$s fatty alcohol is converted into a corresponding $C_6$-$C_{24}$ fatty acetate using chemical methods.

54. The method of embodiment 53, wherein the chemical methods utilize a chemical agent selected from the group consisting of acetyl chloride, acetic anhydride, butyryl chloride, butyric anhydride, propanoyl chloride and propionic anhydride in the presence of 4-N, N-dimethylaminopyridine (DMAP) or sodium acetate to esterify the mono- or poly-unsaturated $C_6$-$C_{24}$ fatty alcohol to the corresponding $C_6$-$C_{24}$ fatty acetate.

55. A recombinant microorganism capable of producing a mono- or poly-unsaturated $\leq C_{18}$ fatty alcohol from an endogenous or exogenous source of saturated $C_6$-$C_{24}$ fatty acid, wherein the recombinant microorganism comprises:
(a) at least one exogenous nucleic acid molecule encoding a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA;
(b) at least one exogenous nucleic acid molecule encoding an acyl-CoA oxidase that catalyzes the conversion of the mono- or poly-unsaturated $C_6$-$C_{24}$ fatty acyl-CoA from (a) into a mono- or poly-unsaturated $\leq C_{18}$ fatty acyl-CoA after one or more successive cycle of acyl-CoA oxidase activity, with a given cycle producing a mono- or poly-unsaturated $C_4$-$C_{22}$ fatty acyl-CoA intermediate with a two carbon truncation relative to a starting mono- or poly-unsaturated $C_6$-$C_{24}$ fatty acyl-CoA substrate in that cycle; and
(c) at least one exogenous nucleic acid molecule encoding a fatty alcohol forming fatty acyl reductase that catalyzes the conversion of the mono- or poly-unsaturated $\leq C_{18}$ fatty acyl-CoA from (b) into the corresponding mono- or poly-unsaturated $\leq C_{18}$ fatty alcohol.

56. The recombinant microorganism of embodiment 55, wherein the recombinant microorganism further comprises at least one endogenous or exogenous nucleic acid molecule encoding an acyltransferase that preferably stores $\leq C_{18}$ fatty acyl-CoA.

57. The recombinant microorganism of any one of embodiments 55-56, wherein the recombinant microorganism further comprises at least one endogenous or exogenous nucleic acid molecule encoding an acyltransferase that preferably stores ≤$C_{18}$ fatty acyl-CoA, and wherein the acyltransferase is selected from the group consisting of glycerol-3-phosphate acyl transferase (GPAT), lysophosphatidic acid acyltransferase (LPAAT), glycerolphospholipid acyltransferase (GPLAT) and diacylglycerol acyltransferases (DGAT).

58. The recombinant microorganism of any one of embodiments 55-57, wherein the recombinant microorganism further comprises at least one endogenous or exogenous nucleic acid molecule encoding an acyltransferase that preferably stores ≤$C_{18}$ fatty acyl-CoA, and wherein the acyltransferase is selected from Table 5b.

59. The recombinant microorganism of any one of embodiments 55-58, wherein the recombinant microorganism further comprises at least one endogenous or exogenous nucleic acid molecule encoding an acylglycerol lipase that preferably hydrolyzes ester bonds of >C16, of >C14, of >C12 or of >C10 acylglycerol substrates.

60. The recombinant microorganism of any one of embodiments 55-59, wherein the recombinant microorganism further comprises at least one endogenous or exogenous nucleic acid molecule encoding an acylglycerol lipase that preferably hydrolyzes ester bonds of >C16, of >C14, of >C12 or of >C10 acylglycerol substrates, and wherein the acylglycerol lipase is selected from Table 5c.

61. The recombinant microorganism of any one of embodiments 55-60, wherein the recombinant microorganism comprises a deletion, disruption, mutation, and/or reduction in the activity of one or more endogenous enzymes that catalyzes a reaction in a pathway that competes with the biosynthesis pathway for the production of a mono- or polyunsaturated ≤$C_{18}$ fatty alcohol.

62. The recombinant microorganism of any one of embodiments 55-61, wherein the recombinant microorganism comprises a deletion, disruption, mutation, and/or reduction in the activity of one or more endogenous enzyme selected from:
(i) one or more acyl-CoA oxidase:
(ii) one or more acyltransferase;
(iii) one or more acylglycerol lipase and/or sterol ester esterase:
(iv) one or more (fatty) alcohol dehydrogenase:
(v) one or more (fatty) alcohol oxidase; and
(vi) one or more cytochrome P450 monooxygenase.

63. The recombinant microorganism of any one of embodiments 55-62, wherein the recombinant microorganism comprises a deletion, disruption, mutation, and/or reduction in the activity of one or more endogenous acyl-CoA oxidase enzyme selected from the group consisting of *Y. lipolytica* POX1(YALI0E32835g), *Y. lipolytica* POX2 (YALI0F10857g), *Y. lipolytica* POX3(YALI0D24750g), *Y. lipolytica* POX4(YALI0E27654g). *Y. lipolytica* POX5 (YALI0C23859g). *Y. lipolytica* POX6(YALI0E06567g); *S. cerevisiae* POX1(YGL205W); *Candida* POX2 (CaO19.1655, CaO19.9224, CTRG_02374, M18259), *Candida* POX4 (CaO19.1652, CaO19.9221, CTRG_02377, M12160), and *Candida* POX5 (CaO19.5723, CaO19.13146, CTRG_02721, M12161).

64. The recombinant microorganism of any one of embodiments 55-63, wherein the recombinant microorganism comprises a deletion, disruption, mutation, and/or reduction in the activity of one or more endogenous acyltransferase enzyme selected from the group consisting of *Y. lipolytica* YALI0C00209g, *Y. lipolytica* YALI0E18964g, *Y. lipolytica* YALI0F19514g, *Y. lipolytica* YALI0C14014g, *Y. lipolytica* YALI0E16797g, *Y. lipolytica* YALI0E32769g, and *Y. lipolytica* YALI0D07986g. *S. cerevisiae* YBL011w, *S. cerevisiae* YDL052c, *S. cerevisiae* YOR175C, *S. cerevisiae* YPR139C, *S. cerevisiae* YNR008w, and *S. cerevisiae* YOR245c, and *Candida* I503_02577, *Candida* CTRG_02630, *Candida* CaO19.250. *Candida* CaO19.7881, *Candida* CTRG_02437, *Candida* CaO19.1881, *Candida* CaO19.9437, *Candida* CTRG_01687, *Candida* CaO19.1043, *Candida* CaO19.8645, *Candida* CTRG_04750, *Candida* CaO19.13439, *Candida* CTRG_04390, *Candida* CaO19.6941, *Candida* CaO19.14203, and *Candida* CTRG_06209.

65. The recombinant microorganism of any one of embodiments 55-64, wherein the recombinant microorganism comprises a deletion, disruption, mutation, and/or reduction in the activity of one or more endogenous acylglycerol lipase and/or sterol ester esterase enzyme selected from the group consisting of *Y. lipolytica* YALI0E32035g, *Y. lipolytica* YALI0D17534g, *Y. lipolytica* YALI0F10010g, *Y. lipolytica* YALI0C14520g, and *Y. lipolytica* YALI0E00528g, *S. cerevisiae* YKL140w, *S. cerevisiae* YMR313c, *S. cerevisiae* YKR089c, *S. cerevisiae* YOR081c, *S. cerevisiae* YKL094W, *S. cerevisiae* YLL012W, and *S. cerevisiae* YLR020C, and *Candida* CaO19.2050, *Candida* CaO19.9598, *Candida* CTRG_01138. *Candida* W5Q_03398, *Candida* CTRG_00057, *Candida* CaO19.5426, *Candida* CaO19.12881, *Candida* CTRG_06185. *Candida* CaO19.4864. *Candida* CaO19.12328, *Candida* CTRG_03360, *Candida* CaO19.6501, *Candida* CaO19.13854. *Candida* CTRG_05049, *Candida* CaO19.1887, *Candida* CaO19.9443, *Candida* CTRG_01683, and *Candida* CTRG_04630.

66. The method of any one of embodiments 55-65, wherein the recombinant microorganism comprises a deletion, disruption, mutation, and/or reduction in the activity of one or more endogenous cytochrome P450 monooxygenases selected from the group consisting of *Y. lipolytica* YALI0E25982g (ALK1), *Y. lipolytica* YALI0F01320g (ALK2), *Y. lipolytica* YALI0E23474g (ALK3), *Y. lipolytica* YALI0B13816g (ALK4), *Y. lipolytica* YALI0B13838g (ALK5), *Y. lipolytica* YALI0B01848g (ALK6). *Y. lipolytica* YALI10A5488g (ALK7), *Y. lipolytica* YALI0C12122g (ALK8), *Y. lipolytica* YALI0B06248g (ALK9), *Y. lipolytica* YALI0B20702g (ALK10), *Y. lipolytica* YALI0C10054g (ALK11) and *Y. lipolytica* YALI0A20130g (ALK2).

67. The recombinant microorganism of any one of embodiments 55-66, wherein the fatty acyl desaturase is selected from an *Argyrotaenia velutinana, Spodoptera litura, Sesamia inferens, Manduca sexta, Ostrinia nubilalis, Helicoverpa zea, Choristoneura rosaceana, Drosophila melanogaster, Spodoptera littoralis, Lampronia capitella. Amyelois transitella, Trichoplusia ni, Agrotis segetum, Ostrinia furnicalis*, and *Thalassiosira pseudonana* derived fatty acyl desaturase.

68. The recombinant microorganism of any one of embodiments 55-67, wherein the fatty acyl desaturase has at least 95% sequence identity to a fatty acyl desaturase selected from the group consisting of: SEQ ID NOs: 39, 49-54, 58-63, 78-80 and GenBank Accession nos. AF416738, AGH12217.1, AII21943.1, CAJ43430.2, AF441221, AAF81787.1, AF545481, AJ271414, AY362879, ABX71630.1, NP001299594.1, Q9N9Z8, ABX71630.1 and A1M40221.1.

69. The recombinant microorganism of any one of embodiments 55-68, wherein the acyl-CoA oxidase is selected from Table 5a.

70. The recombinant microorganism of any one of embodiments 55-69, wherein the fatty alcohol forming fatty acyl reductase is selected from an *Agrotis segetum, Spodoptera exigua, Spodoptera littoralis, Euglena gracilis, Yponomeuta evonymellus* and *Helicoverpa armigera* derived fatty alcohol forming fatty acyl reductase.

71. The recombinant microorganism of any one of embodiments 55-70, wherein the fatty alcohol forming fatty acyl reductase has at least 95% sequence identity to a fatty alcohol forming fatty acyl reductase selected from the group consisting of: SEQ ID NOs: 1-3, 32, 41-48, 55-57, 73, 75, 77 and 82.

72. The recombinant microorganism of any one of embodiments 55-71, wherein the fatty acyl desaturase catalyzes the conversion of a fatty acyl-CoA into a mono- or poly-unsaturated intermediate selected from E5-10:Acyl-CoA, E7-12:Acyl-CoA, E9-14:Acyl-CoA, E11-16:Acyl-CoA, E13-18:Acyl-CoA, Z7-12:Acyl-CoA, Z9-14:Acyl-CoA, Z11-16:Acyl-CoA, Z13-18:Acyl-CoA, Z8-12:Acyl-CoA, Z10-14:Acyl-CoA, Z12-16:Acyl-CoA, Z14-18:Acyl-CoA, Z7-10:Acyl-coA, Z9-12:Acyl-CoA, Z11-14:Acyl-CoA, Z13-16:Acyl-CoA, Z15-18:Acyl-CoA, E7-10:Acyl-CoA, E9-12:Acyl-CoA, E11-14:Acyl-CoA, E13-16:Acyl-CoA, E15-18:Acyl-CoA, E5Z7-12:Acyl-CoA, E7Z9-12:Acyl-CoA, E9Z11-14:Acyl-CoA, E11Z13-16:Acyl-CoA, E13Z15-18:Acyl-CoA, E6E8-10:Acyl-CoA, E8E10-12:Acyl-CoA, E10E12-14:Acyl-CoA, E12E14-16:Acyl-CoA, Z5E8-10:Acyl-CoA, Z7E10-12:Acyl-CoA, Z9E12-14:Acyl-CoA, Z11E4-16:Acyl-CoA, Z3E16-18:Acyl-CoA, Z3-10:Acyl-CoA, Z5-12:Acyl-CoA, Z7-14:Acyl-CoA, Z9-16:Acyl-CoA, Z11-18:Acyl-CoA, Z3Z5-10:Acyl-CoA, Z5Z7-12:Acyl-CoA, Z7Z9-14:Acyl-CoA, Z9Z11-16:Acyl-CoA, Z11Z13-16:Acyl-CoA, and Z13Z15-18:Acyl-CoA.

73. The recombinant microorganism of any one of embodiments 55-72, wherein the mono- or poly-unsaturated ≤$C_{18}$ fatty alcohol is selected from the group consisting of E5-10:OH, Z8-12:OH. Z9-12:OH, Z11-14:OH, Z11-16:OH, E11-14:OH, E8E10-12:OH, E7Z9-12:OH, Z11Z13-16OH, Z9-14:OH, Z9-16:OH, and Z13-18:OH.

74. The recombinant microorganism of any one of embodiments 55-73, wherein the recombinant microorganism further comprises at least one endogenous or exogenous nucleic acid molecule encoding an aldehyde forming fatty acyl-CoA reductase capable of catalyzing the conversion of the mono- or poly-unsaturated ≤$C_{18}$ fatty alcohol into a corresponding ≤$C_{18}$ fatty aldehyde.

75. The recombinant microorganism of embodiment 74, wherein the aldehyde forming fatty acyl-CoA reductase is selected from the group consisting of *Acinetobacter calcoaceticus* A0A1C4HN78, *A. calcoaceticus* N9DA85, *A. calcoaceticus* R8XW24, *A. calcoaceticus* A0A1A0GGM5, *A. calcoaceticus* A0A117N158, and *Nostoc punctiforme* YP_001865324.

76. The recombinant microorganism of any one of embodiments 55-75, wherein the recombinant microorganism further comprises at least one endogenous or exogenous nucleic acid molecule encoding an alcohol oxidase or an alcohol dehydrogenase capable of catalyzing the conversion of the mono- or poly-unsaturated ≤$C_{18}$ fatty alcohol into a corresponding ≤$C_{18}$ fatty aldehyde.

77. The recombinant microorganism of any one of embodiments 55-76, wherein the ≤$C_{18}$ fatty aldehyde is selected from the group consisting of Z9-16:Ald, Z11-16:Ald, Z11Z13-16:Ald, and Z13-18:Ald.

78. The recombinant microorganism of any one of embodiments 55-77, wherein the recombinant microorganism further comprises at least one endogenous or exogenous nucleic acid molecule encoding an acetyl transferase capable of catalyzing the conversion of the mono- or poly-unsaturated ≤$C_{18}$ fatty alcohol into a corresponding ≤$C_{18}$ fatty acetate.

79. The recombinant microorganism of embodiment 78, wherein the acetyl transferase is selected from Table 5d.

80. The recombinant microorganism of embodiment 78, wherein the ≤$C_{18}$ fatty acetate is selected from the group consisting of E5-10:Ac, Z7-12:Ac, Z8-12:Ac, Z9-12:Ac. E7Z9-12:Ac, Z9-14:Ac, Z9E12-14:Ac, Z11-14:Ac, E11-14:Ac, Z9-16:Ac, and Z11-16:Ac.

81. The recombinant microorganism of any one of embodiments 55-80, wherein the recombinant microorganism further comprises:
at least one endogenous or exogenous nucleic acid molecule encoding an enzyme selected from an alcohol oxidase, an alcohol dehydrogenase, and an aldehyde forming fatty acyl-CoA reductase capable of catalyzing the conversion of the mono- or poly-unsaturated ≤$C_{18}$ fatty alcohol into a corresponding ≤$C_{18}$ fatty aldehyde; and
at least one endogenous or exogenous nucleic acid molecule encoding an acetyl transferase capable of catalyzing the conversion of the mono- or poly-unsaturated ≤$C_{18}$ fatty alcohol into a corresponding ≤$C_{18}$ fatty acetate.

82. The recombinant microorganism of embodiment 81, wherein the mono- or poly-unsaturated ≤$C_{18}$ fatty aldehyde and ≤$C_{18}$ fatty acetate is selected from the group consisting of E5-10:Ac, Z7-12:Ac, Z8-12:Ac, Z9-12:Ac, E7Z9-12:Ac, Z9-14:Ac, Z9E12-14:Ac, E11-14:Ac, Z11-14:Ac, Z11-16:Ac, Z9-16:Ac, Z9-16:Ald, Z11-16:Ald, Z11Z13-16:Ald, and Z13-18:Ald.

83. The recombinant microorganism of any one of embodiments 55-82, wherein the recombinant microorganism is a yeast selected from the group consisting of *Yarrowia lipolytica, Saccharomyces cerevisiae, Candida albicans, Candida tropicalis* and *Candida viswanathii*.

84. A method of producing a mono- or poly-unsaturated ≤$C_{18}$ fatty alcohol from an endogenous or exogenous source of saturated $C_6$-$C_{24}$ fatty acid, comprising: cultivating the recombinant microorganism of any one of embodiment 55-83 in a culture medium containing a feedstock that provides a carbon source adequate for the production of the mono- or poly-unsaturated ≤$C_{18}$ fatty alcohol.

85. The method of embodiment 84, wherein the mono- or poly-unsaturated ≤$C_{18}$ fatty alcohol is selected from the group consisting of E5-10:OH, Z8-12:OH, Z9-12:OH, Z11-14:OH, Z11-16:OH. E11-14:OH, E8E10-12:OH, E7Z9-12:OH, Z11Z13-16OH, Z9-14:OH, Z9-16:OH, and Z13-18:OH.

86. The method of any one of embodiments 84-85, further comprising a step of recovering the mono- or poly-unsaturated ≤$C_{18}$ fatty alcohol.

87. The method of embodiment 86, wherein said recovery step comprises distillation.

88. The method of embodiment 86, wherein said recovery step comprises membrane-based separation.

89. A method of engineering a microorganism that is capable of producing a mono- or poly-unsaturated ≤$C_{18}$ fatty alcohol from an endogenous or exogenous source of saturated $C_6$-$C_{24}$ fatty acid, wherein the method comprises introducing into a microorganism the following:
  (a) at least one exogenous nucleic acid molecule encoding a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA;
  (b) at least one exogenous nucleic acid molecule encoding an acyl-CoA oxidase that catalyzes the conversion of the mono- or poly-unsaturated $C_6$-$C_{24}$ fatty acyl-CoA from (a) into a mono- or poly-unsaturated ≤$C_{18}$ fatty acyl-CoA after one or more successive cycle of acyl-CoA oxidase activity, with a given cycle producing a mono- or poly-unsaturated $C_4$-$C_{22}$ fatty acyl-CoA intermediate with a two carbon truncation relative to a starting mono- or poly-unsaturated $C_6$-$C_{24}$ fatty acyl-CoA substrate in that cycle; and (c) at least one exogenous nucleic acid molecule encoding a fatty alcohol forming fatty acyl reductase that catalyzes the conversion of the mono- or poly-unsaturated ≤$C_{18}$ fatty acyl-CoA from (b) into the corresponding mono- or poly-unsaturated ≤$C_{18}$ fatty alcohol.

90. The method of embodiment 89, wherein the microorganism is MATA ura3-302::SUC2 Δpox1 Δpox2 Δpox3 Δpox4 Δpox5 Δpox6 Δfadh Δadh1 Δadh2 Δadh3 Δadh4 Δadh5 Δadh6 Δadh7 Δfao1::URA3.

91. The method of any one of embodiments 89-90, wherein the method further comprises introducing into the microorganism at least one endogenous or exogenous nucleic acid molecule encoding an acyltransferase that preferably stores ≤$C_{18}$ fatty acyl-CoA.

92. The method of any one of embodiments 89-91, wherein the method further comprises introducing into the microorganism at least one endogenous or exogenous nucleic acid molecule encoding an acyltransferase that preferably stores ≤$C_{18}$ fatty acyl-CoA, and wherein the acyltransferase is selected from the group consisting of glycerol-3-phosphate acyl transferase (GPAT), lysophosphatidic acid acyltransferase (LPAAT), glycerolphospholipid acyltransferase (GPLAT) and diacylglycerol acyltransferases (DGAT).

93. The method of any one of embodiments 89-92, wherein the method further comprises introducing into the microorganism at least one endogenous or exogenous nucleic acid molecule encoding an acyltransferase that preferably stores ≤$C_{18}$ fatty acyl-CoA, and wherein the acyltransferase is selected from Table 5b.

94. The method of any one of embodiments 89-93, wherein the method further comprises introducing into the microorganism at least one endogenous or exogenous nucleic acid molecule encoding an acylglycerol lipase that preferably hydrolyzes ester bonds of >C16, of >C14, of >C12 or of >C10 acylglycerol substrates.

95. The method of any one of embodiments 89-94, wherein the method further comprises introducing into the microorganism at least one endogenous or exogenous nucleic acid molecule encoding an acylglycerol lipase that preferably hydrolyzes ester bonds of >C16, of >C14, of >C12 or of >C10 acylglycerol substrates, and wherein the acylglycerol lipase is selected from Table 5c.

96. The method of any one of embodiments 89-95, wherein the method further comprises introducing into the microorganism one or more modifications comprising a deletion, disruption, mutation, and/or reduction in the activity of one or more endogenous enzyme that catalyzes a reaction in a pathway that competes with the biosynthesis pathway for the production of a mono- or poly-unsaturated ≤$C_{18}$ fatty alcohol.

97. The method of any one of embodiments 89-96, wherein the method further comprises introducing into the microorganism one or more modifications comprising a deletion, disruption, mutation, and/or reduction in the activity of one or more endogenous enzyme selected from:
(i) one or more acyl-CoA oxidase;
(ii) one or more acyltransferase;
(iii) one or more acylglycerol lipase and/or sterol ester esterase:
(iv) one or more (fatty) alcohol dehydrogenase;
(v) one or more (fatty) alcohol oxidase; and
(vi) one or more cytochrome P450 monooxygenase.

98. The method of any one of embodiments 89-97, wherein the method further comprises introducing into the microorganism one or more modifications comprising a deletion, disruption, mutation, and/or reduction in the activity of one or more endogenous acyl-CoA oxidase enzyme selected from the group consisting of *Y. lipolytica* POX1 (YALI0E32835g), *Y. lipolytica* POX2(YALI0F10857g). *Y. lipolytica* POX3(YALI0D24750g), *Y. lipolytica* POX4 (YALI0E27654g), *Y. lipolytica* POX5(YALI0C23859g), *Y. lipolytica* POX6(YALI0E06567g); *S. cerevisiae* POX1 (YGL205W)S *Candida* POX2 (CaO19.1655, CaO19.9224, CTRG_02374, M18259), *Candida* POX4 (CaO19.1652, CaO19.9221, CTRG_02377, M12160), and *Candida* POX5 (CaO19.5723, CaO19.13146, CTRG_02721, M12161).

99. The method of any one of embodiments 89-98, wherein the method further comprises introducing into the microorganism one or more modifications comprising a deletion, disruption, mutation, and/or reduction in the activity of one or more endogenous acyltransferase enzyme selected from the group consisting of *Y. lipolytica* YALI0C00209g, *Y. lipolytica* YALI0E18964g, *Y. lipolytica* YALI0F9514g, *Y. lipolytica* YALI0C14014g, *Y. lipolytica* YALI0E16797g, *Y. lipolytica* YALI0E32769g, and *Y. lipolytica* YALI0D07986g, *S. cerevisiae* YBL011w, *S. cerevisiae* YDL052c, *S. cerevisiae* YOR175C, *S. cerevisiae* YPR139C, *S. cerevisiae* YNR008w, and *S. cerevisiae* YOR245c, and *Candida* I503_02577, *Candida* CTRG_02630, *Candida* CaO19.250, *Candida* CaO19.7881. *Candida* CTRG_02437, *Candida* CaO19.1881, *Candida* CaO19.9437, *Candida* CTRG_01687, *Candida* CaO19.1043, *Candida* CaO19.8645, *Candida* CTRG_04750, *Candida* CaO19.13439, *Candida* CTRG_04390, *Candida* CaO19.6941, *Candida* CaO19.14203, and *Candida* CTRG_06209.

100. The method of any one of embodiments 89-99, wherein the method further comprises introducing into the microorganism one or more modifications comprising a deletion, disruption, mutation, and/or reduction in the activity of one or more endogenous acylglycerol lipase and/or sterol ester esterase enzyme selected from the group consisting of *Y. lipolytica* YALI0E32035g, *Y. lipolytica* YALI0D17534g, *Y. lipolytica* YALI0F10010g, *Y. lipolytica* YALI0C14520g, and *Y. lipolytica* YALI0E00528g, *S. cerevisiae* YKL140w, *S. cerevisiae* YMR313c, *S. cerevisiae* YKR089c, *S. cerevisiae* YOR081c, *S. cerevisiae* YKL094W, *S. cerevisiae* YLL012W, and *S. cerevisiae* YLR020C, and *Candida* CaO19.2050, *Candida* CaO19.9598, *Candida* CTRG_01138, *Candida* W5Q_03398. *Candida* CTRG_00057, *Candida* CaO19.5426, *Candida* CaO19.12881, *Candida* CTRG_06185, *Candida* CaO19.4864, *Candida* CaO19.12328, *Candida* CTRG_03360, *Candida* CaO19.6501, *Candida* CaO19.13854, *Candida* CTRG_05049, *Candida* CaO19.1887. *Candida* CaO19.9443, *Candida* CTRG_01683, and *Candida* CTRG_04630.

101. The method of any one of embodiments 89-100, wherein the method further comprises one or more modifications comprising a deletion, disruption, mutation, and/or reduction in the activity of one or more endogenous cytochrome P450 monooxygenases selected from the group consisting of *Y. lipolytica* YALI0E25982g (ALK1), *Y. lipolytica* YALI0F01320g (ALK2), *Y. lipolytica* YALI0E23474g (ALK3), *Y. lipolytica* YALI0B13816g (ALK4), *Y. lipolytica* YALI0B13838g (ALK5), *Y. lipolytica* YALI0B01848g (ALK6), *Y. lipolytica* YALI0A5488g (ALK7), *Y. lipolytica* YALI0C12122g (ALK8), *Y. lipolytica* YALI0B06248g (ALK9), *Y. lipolytica* YALI0B20702g (ALK10), *Y. lipolytica* YALI0C10054g (ALK11) and *Y. lipolytica* YALI0A20130g (ALK12).

102. The method of any one of embodiments 89-101, wherein the fatty acyl desaturase is selected from an *Argyrotaenia velutinana, Spodoptera litura, Sesamia inferens, Manduca sexta, Ostrinia nubilalis, Helicoverpa zea, Choristoneura rosaceana, Drosophila melanogaster, Spodoptera littoralis, Lampronia capitella, Amyelois transitella, Trichoplusia ni, Agrotis segetum, Ostrinia furnicalis*, and *Thalassiosira pseudonana* derived fatty acyl desaturase.

103. The method of any one of embodiments 89-102, wherein the fatty acyl desaturase has at least 95% sequence identity to a fatty acyl desaturase selected from the group consisting of: SEQ ID NOs: 39, 49-54, 58-63, and GenBank Accession nos. AF416738, AGH12217.1, AII21943.1, CAJ43430.2, AF441221, AAF81787.1, AF545481, AJ271414, AY362879, ABX71630.1, NP001299594.1, Q9N9Z8, ABX71630.1 and AIM40221.1.

104. The method of any one of embodiments 89-103, wherein the acyl-CoA oxidase is selected from Table 5a.

105. The method of any one of embodiments 89-104, wherein the fatty alcohol forming fatty acyl reductase is selected from an *Agrotis segetum, Spodoptera* exigua, *Spodoptera littoralis, Euglena gracilis, Yponomeuta evonymellus* and *Helicoverpa armigera* derived fatty alcohol forming fatty acyl reductase.

106. The method of any one of embodiments 89-105, wherein the fatty alcohol forming fatty acyl reductase has at least 90% sequence identity to a fatty alcohol forming fatty acyl reductase selected from the group consisting of: SEQ ID NOs: 1-3, 32, 41-48, 55-57, 73, 75, 77 and 82.

107. The method of any one of embodiments 89-106, wherein the fatty acyl desaturase catalyzes the conversion of a fatty acyl-CoA into a mono- or poly-unsaturated intermediate selected from E5-10:Acyl-CoA, E7-12:Acyl-CoA, E9-14:Acyl-CoA, E11-16:Acyl-CoA, E13-18:Acyl-CoA, Z7-12:Acyl-CoA, Z9-14:Acyl-CoA, Z11-16:Acyl-CoA, Z13-18:Acyl-CoA, Z8-12:Acyl-CoA, Z10-14:Acyl-CoA, Z12-16:Acyl-CoA, Z14-18:Acyl-CoA, Z7-10:Acyl-coA, Z9-12:Acyl-CoA, Z11-14:Acyl-CoA, Z13-16:Acyl-CoA, Z15-18:Acyl-CoA, E7-10:Acyl-CoA, E9-12:Acyl-CoA, E11-14:Acyl-CoA, E13-16:Acyl-CoA, E15-18:Acyl-CoA, E5Z7-12:Acyl-CoA, E7Z9-12:Acyl-CoA, E9Z11-14:Acyl-CoA, E11Z13-16:Acyl-CoA, E13Z15-18:Acyl-CoA, E6E8-10:Acyl-CoA, E8E10-12:Acyl-CoA, E10E12-14:Acyl-CoA, E12E14-16:Acyl-CoA, Z5E8-10:Acyl-CoA, Z7E10-12:Acyl-CoA, Z9E12-14:Acyl-CoA, Z11E14-16:Acyl-CoA, Z13E16-18:Acyl-CoA, Z3-10:Acyl-CoA, Z5-12:Acyl-CoA, Z7-14:Acyl-CoA, Z9-16:Acyl-CoA, Z11-18:Acyl-CoA, Z3Z5-10:Acyl-CoA, Z5Z7-12:Acyl-CoA, Z7Z9-14:Acyl-CoA, Z9Z11-16:Acyl-CoA, Z11Z13-16:Acyl-CoA, and Z3Z15-18:Acyl-CoA.

108. The method of any one of embodiments 89-107, wherein the mono- or poly-unsaturated $\leq C_{18}$ fatty alcohol is selected from the group consisting of E5-10:OH, Z8-12:OH, Z9-12:OH, Z11-14:OH, Z11-16:OH, E11-14:OH, E8E10-12:OH, E7Z9-12:OH, Z11Z13-16OH, Z9-14:OH. Z9-16:OH, and Z13-18:OH.

109. The method of any one of embodiments 89-108, wherein the method further comprises introducing into the microorganism at least one endogenous or exogenous nucleic acid molecule encoding an aldehyde forming fatty acyl-CoA reductase capable of catalyzing the conversion of the mono- or poly-unsaturated $\leq C_{18}$ fatty alcohol into a corresponding $\leq C_{18}$ fatty aldehyde.

110. The method of embodiment 109, wherein the aldehyde forming fatty acyl-CoA reductase is selected from the group consisting of *Acinetobacter calcoaceticus* A0A1C4HN78, *A. calcoaceticus* N9DA85, *A. calcoaceticus* R8XW24, *A. calcoaceticus* A0A1A0GGM5, *A. calcoaceticus* A0A117N158, and *Nostoc punctiforme* YP_001865324.

111. The method of any one of embodiments 89-110, wherein the method further comprises introducing into the microorganism at least one endogenous or exogenous nucleic acid molecule encoding an alcohol oxidase or an alcohol dehydrogenase capable of catalyzing the conversion of the mono- or poly-unsaturated $\leq C_{18}$ fatty alcohol into a corresponding $\leq C_{18}$ fatty aldehyde.

112. The method of any one of embodiments 109-111, wherein the $\leq C_{18}$ fatty aldehyde is selected from the group consisting of Z9-16:Ald, Z11-16:Ald, Z11Z13-16:Ald, and Z13-18:Ald.

113. The method of any one of embodiments 89-112, wherein method further comprises introducing into the microorganism at least one endogenous or exogenous nucleic acid molecule encoding an acetyl transferase capable of catalyzing the conversion of the mono- or poly-unsaturated $\leq C_{18}$ fatty alcohol into a corresponding $\leq C_{18}$ fatty acetate.

114. The method of embodiment 113, wherein the acetyl transferase is selected from Table 5d.

115. The method of any one of embodiment 113-114, wherein the $\leq C_{18}$ fatty acetate is selected from the group consisting of E5-10:Ac, Z7-12:Ac, Z8-12:Ac, Z9-12:Ac, E7Z9-12:Ac, Z9-14:Ac, Z9E12-14:Ac, E11-14:Ac, Z9-16:Ac, Z11-14:Ac and Z11-16:Ac.

116. The method of any one of embodiments 89-115, wherein the method further comprises introducing into the microorganism:

at least one endogenous or exogenous nucleic acid molecule encoding an enzyme selected from an alcohol oxidase, an alcohol dehydrogenase, and an aldehyde forming fatty acyl-CoA reductase capable of catalyzing the conversion of the mono- or poly-unsaturated $\leq C_{18}$ fatty alcohol into a corresponding $\leq C_{181}$ fatty aldehyde; and at least one endogenous or exogenous nucleic acid molecule encoding an acetyl transferase capable of catalyzing the conversion of the mono- or poly-unsaturated $\leq C_{18}$ fatty alcohol into a corresponding $\leq C_{18}$ fatty acetate.

117. The method of embodiment 116, wherein the mono- or poly-unsaturated $\leq C_{18}$ fatty aldehyde and $\leq C_{18}$ fatty acetate is selected from the group consisting of E5-10:Ac, Z7-12:Ac, Z8-12:Ac, Z9-12:Ac, E7Z9-12:Ac, Z9-14:Ac, Z9E12-14:Ac, Z11-14:Ac, E11-14:Ac, Z11-16:Ac, Z9-16:Ald, Z9-16:Ac, Z11-16:Ald, Z11Z13-16:Ald, and Z13-18:Ald.

118. A method of producing a mono- or poly-unsaturated $\leq C_{18}$ fatty aldehyde from an endogenous or exogenous source of saturated $C_6$-$C_{24}$ fatty acid, comprising: cultivating the recombinant microorganism of any one of embodiments 74-76 in a culture medium containing a feedstock that provides a carbon source adequate for the production of the mono- or poly-unsaturated $\leq C_{18}$ fatty aldehyde.

119. The method of embodiment 118, wherein the $\leq C_{18}$ fatty aldehyde is selected from the group consisting of Z9-16:Ald, Z11-16:Ald, Z11Z13-16:Ald, and Z13-18:Ald.

120. The method of any one of embodiments 118-119, further comprising a step of recovering the mono- or poly-unsaturated $\leq C_{18}$ fatty aldehyde.

121. The method of embodiment 120, wherein said recovery step comprises distillation.

122. The method of embodiment 120, wherein said recovery step comprises membrane-based separation.

123. A method of producing a mono- or poly-unsaturated ≤$C_{18}$ fatty acetate from an endogenous or exogenous source of saturated $C_6$-$C_{24}$ fatty acid, comprising: cultivating the recombinant microorganism of any one of embodiments 78-80 in a culture medium containing a feedstock that provides a carbon source adequate for the production of the mono- or poly-unsaturated ≤$C_{18}$ fatty acetate.

124. The method of embodiment 123, wherein the mono- or poly-unsaturated ≤$C_{18}$ fatty acetate is selected from the group consisting of E5-10:Ac, Z7-12:Ac, Z8-12:Ac, Z9-12:Ac, E7Z9-12:Ac, Z9-14:Ac, Z9E12-14:Ac, Z11-14:Ac, E11-14:Ac, Z9-16:Ac, and Z11-16:Ac.

125. The method of any one of embodiments 123-124, further comprising a step of recovering the mono- or poly-unsaturated ≤$C_{18}$ fatty acetate.

126. The method of embodiment 125, wherein said recovery step comprises distillation.

127. The method of embodiment 125, wherein said recovery step comprises membrane-based separation.

128. The method of any one of embodiments 89-115, wherein the recombinant microorganism is a yeast selected from the group consisting of *Yarrowia lipolytica*, *Saccharomyces cerevisiae*, *Candida* albicans, *Candida viswanathii* and *Candida tropicalis*.

129. The method of any one of embodiments 89-115, wherein the mono- or poly-unsaturated ≤$C_{18}$ fatty alcohol is converted into a corresponding ≤$C_{18}$ fatty aldehyde using chemical methods.

130. The method of embodiment 129, wherein the chemical methods are selected from TEMPO-bleach, TEMPO-copper-air, TEMPO-PhI(OAc)$_2$, Swern oxidation and noble metal-air.

131. The method of any one of embodiments 89-115, wherein the mono- or poly-unsaturated ≤$C_{18}$ fatty alcohol is converted into a corresponding ≤$C_{18}$ fatty acetate using chemical methods.

132. The method of embodiment 131, wherein the chemical methods utilize a chemical agent selected from the group consisting of acetyl chloride, acetic anhydride, butyryl chloride, butyric anhydride, propanoyl chloride and propionic anhydride in the presence of 4-N,N-dimethylaminopyridine (DMAP) or sodium acetate to esterify the mono- or poly-unsaturated ≤$C_{18}$ fatty alcohol to the corresponding ≤$C_{18}$ fatty acetate.

The invention claimed is:

1. A recombinant *Yarrowia lipolytica* microorganism capable of producing a mono- or poly-unsaturated C6-C24 fatty alcohol from an endogenous or exogenous source of mono- or poly-unsaturated C6-C24 fatty acyl-CoA, wherein the recombinant *Yarrowia lipolytica* microorganism comprises:

a) a heterologous nucleic acid molecule encoding and expressing a *Euglena* fatty alcohol-forming fatty acyl reductase that catalyzes the conversion of the mono- or poly-unsaturated $C_6$-$C_{24}$ fatty acyl-CoA into the corresponding mono- or poly-unsaturated $C_6$-$C_{24}$ fatty alcohol.

2. The recombinant *Yarrowia lipolytica* microorganism of claim 1, wherein the *Euglena* fatty alcohol-forming fatty acyl reductase uses NADH instead of NADPH as a reducing equivalent.

3. The recombinant *Yarrowia lipolytica* microorganism of claim 1, wherein the *Euglena* fatty alcohol-forming fatty acyl reductase is from *Euglena gracilis*.

4. The recombinant *Yarrowia lipolytica* microorganism of claim 1, wherein the *Euglena* fatty alcohol-forming fatty acyl reductase comprises an amino acid sequence having at least 95% sequence identity to SEQ ID NO: 75.

5. The recombinant *Yarrowia lipolytica* microorganism of claim 1, wherein the *Euglena* fatty alcohol-forming fatty acyl reductase comprises an amino acid sequence of SEQ ID NO: 75.

6. The recombinant *Yarrowia lipolytica* microorganism of claim 1, wherein the recombinant *Yarrowia lipolytica* microorganism comprises at least one nucleic acid molecule encoding a fatty acyl desaturase selected from the group consisting of SEQ ID NOs: 39, 54, 60, 62, 78, 79, 80, 95, 97, 99, 101, 103, and 105 that catalyzes the conversion of a saturated $C_6$-$C_{24}$ fatty acyl-CoA to a corresponding mono- or poly-unsaturated $C_6$-$C_{24}$ fatty acyl-CoA.

7. The recombinant *Yarrowia lipolytica* microorganism of claim 1, wherein the recombinant *Yarrowia lipolytica* microorganism comprises a deletion, disruption, mutation, and/or reduction of the fao1 gene.

8. The recombinant *Yarrowia lipolytica* microorganism of claim 1, wherein the recombinant *Yarrowia lipolytica* microorganism comprises a deletion, disruption, mutation, and/or reduction in the activity of one or more endogenous enzymes selected from the following:
   a) one or more enzymes that catalyze the conversion of a fatty acyl-CoA into $\alpha,\beta$-enoyl-CoA;
   b) one or more fatty alcohol dehydrogenases;
   c) one or more fatty alcohol oxidases;
   d) one or more enzymes that catalyzes the conversion of a fatty acid into a $\omega$-hydroxyfatty acid; and
   e) one or more diacylglycerol acyltransferases.

9. The recombinant *Yarrowia lipolytica* microorganism of claim 1, wherein the recombinant *Yarrowia lipolytica* microorganism comprises a deletion, disruption, mutation, and/or reduction in the activity of one or more endogenous enzymes selected from the following:
   (i) one or more acyl-CoA oxidases selected from the group consisting of YALI0E32835g (POX1), YALI0F10857g (PDX2), YALI0D24750g (PDX3), YALI0E27654g (PDX4), YALI0C23859g (PDX5), and YALI0E06567g (PDX6);
   (ii) one or more (fatty) alcohol dehydrogenases selected from the group consisting of YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), and YALI0E07766g (ADH7);
   (iii) a (fatty) alcohol oxidase YALI0B14014g (FAO1);
   (iv) one or more cytochrome P450 enzymes selected from the group consisting of YALI0E25982g (ALK1), YALI0F01320g (ALK2), YALI0E23474g (ALK3), YALI0B13816g (ALK4), YALI0B13838g (ALK5), YALI0B01848g (ALK6), YALI0A15488g (ALK7), YALI0C12122g (ALK8), YALI0B06248g (ALK9), YALI0B20702g (ALK10), YALI0C10054g (ALK11), and YALI0A20130g (Alk12); and
   (v) one or more diacylglycerol acyltransferases selected from the group consisting of YALI0E32791g (DGA1) and YALI0D07986g (DGA2).

10. The recombinant *Yarrowia lipolytica* microorganism of claim 1, wherein the recombinant *Yarrowia lipolytica* microorganism comprises a deletion, disruption, mutation, and/or reduction in the activity of each of the following enzymes that catalyze the conversion of a fatty acyl-CoA into $\alpha,\beta$-enoyl-CoA: CAA04659, CAA04660, CAA04661, CAA04662, CAA04663, and CAG79214.

11. The recombinant *Yarrowia lipolytica* microorganism of claim 1, wherein the recombinant *Yarrowia lipolytica* microorganism comprises a deletion, disruption, mutation, and/or reduction in the activity of the FAO1 enzyme and each of the following enzymes that catalyze the conversion of a fatty acyl-CoA into $\alpha,\beta$-enoyl-CoA: CAA04659, CAA04660, CAA04661, CAA04662, CAA04663, and CAG79214.

12. The recombinant *Yarrowia lipolytica* microorganism of claim 1, wherein the mono- or poly-unsaturated C6-C24 fatty alcohol is selected from the group consisting of Z9-14:OH, Z11-14:OH, E11-14:OH, Z9-16:OH, Z11-16:OH, Z11Z13-16:OH, and Z13-18: OH.

13. A recombinant *Yarrowia lipolytica* microorganism capable of producing a mono- or poly-unsaturated $C_6$-$C_{24}$ fatty alcohol from an endogenous or exogenous source of saturated $C_6$-$C_{24}$ fatty acid, wherein the recombinant *Yarrowia lipolytica* microorganism comprises:
   a) at least one nucleic acid molecule encoding a fatty acyl desaturase having at least 95% sequence identity to SEQ ID NO: 54 that catalyzes the conversion of a saturated $C_6$-$C_{24}$ fatty acyl-CoA to a corresponding mono- or poly-unsaturated $C_6$-$C_{24}$ fatty acyl-CoA; and
   b) at least one nucleic acid molecule encoding a fatty alcohol forming fatty acyl reductase having at least 95% sequence identity to SEQ ID NO: 75 that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol.

14. The recombinant *Yarrowia lipolytica* microorganism of claim 13, wherein the recombinant *Yarrowia lipolytica* microorganism comprises a deletion, disruption, mutation, and/or reduction in the activity of one or more endogenous enzymes selected from the following:
   a) one or more fatty alcohol dehydrogenase;
   b) one or more enzymes that catalyze the conversion of a fatty acid into a $\omega$-hydroxyfatty acid; and
   c) one or more diacylglycerol acyltransferases.

15. The recombinant *Yarrowia lipolytica* microorganism of claim 13, wherein the recombinant *Yarrowia lipolytica* microorganism comprises a deletion, disruption, mutation, and/or reduction in the activity of one or more endogenous enzymes selected from the following:
   a) one or more fatty alcohol dehydrogenases;
   b) one or more cytochrome P450 enzymes selected from the group consisting of YALI0E25982g (ALK1), YALI0F01320g (ALK2), YALI0E23474g (ALK3), YALI0B13816g (ALK4), YALI0B13838g (ALK5), YALI0B01848g (ALK6), YALI0A15488g (ALK7), YALI0C12122g (ALK8), YALI0B06248g (ALK9), YALI0B20702g (ALK10), YALI0C10054g (ALK11), and YALI0A20130g (Alk12); and
   c) one or more diacylglycerol acyltransferases selected from the group consisting of YALI0E32791g (DGA1) and YALI0D07986g (DGA2).

16. The recombinant *Yarrowia lipolytica* microorganism of claim 13, wherein the recombinant *Yarrowia lipolytica* microorganism comprises a deletion, disruption, mutation, and/or reduction in the activity of each of the following enzymes that catalyze the conversion of a fatty acyl-CoA into $\alpha,\beta$-enoyl-CoA: CAA04659, CAA04660, CAA04661, CAA04662, CAA04663, and CAG79214.

17. The recombinant *Yarrowia lipolytica* microorganism of claim 13, wherein the recombinant *Yarrowia lipolytica* microorganism comprises a deletion, disruption, mutation, and/or reduction in the activity of the FAO1 enzyme and each of the following enzymes that catalyze the conversion of a fatty acyl-CoA into α,β-enoyl-CoA: CAA04659, CAA04660, CAA04661, CAA04662, CAA04663, and CAG79214.

18. The recombinant *Yarrowia lipolytica* microorganism of claim 13, wherein the mono- or poly-unsaturated C6-C24 fatty alcohol is selected from the group consisting of Z9-14:OH, Z11-14:OH, E11-14:OH, Z9-16:OH, Z11-16:OH, Z11Z13-16:OH, and Z13-18:OH.

19. A method of producing a mono- or poly-unsaturated $C_6$-$C_{24}$ fatty alcohol from an endogenous or exogenous source of saturated $C_6$-$C_{24}$ fatty acid, comprising: cultivating the recombinant *Yarrowia lipolytica* microorganism of claim 1 in a culture medium containing a feedstock that provides a carbon source adequate for the production of the mono- or poly-unsaturated $C_6$-$C_{24}$ fatty alcohol.

\* \* \* \* \*

SEQUENCE LISTING

```
<160> NUMBER OF SEQ ID NOS: 105

<210> SEQ ID NO 1
<211> LENGTH: 1377
<212> TYPE: DNA
<213> ORGANISM: Artificial Sequence
<220> FEATURE:
<223> OTHER INFORMATION: Agrotis segetum FAR S. cerevisiae codon
      optimized

<400> SEQUENCE: 1
atgccagttt tgacttctag agaagatgaa aagttgtcag ttccagaatt ttacgctggt      60
aaatctatct tcgttacagg tggtactggt ttcttgggta agttttttat tgaaaagttg     120
ttgtactgtt gtccagatat tgataaaatc tatatgttaa ttagagaaaa gaaaaatttg     180
tctattgatg aaagaatgtc aaagttcttg gatgatccat tattttctag attgaaggaa     240
gaaagacctg gtgacttgga aaagattgtt ttgattccag gtgacattac agctccaaat     300
ttgggtttat cagcagaaaa cgaaagaatt ttgttagaaa aagtttctgt tattattaat     360
tcagctgcaa ctgttaagtt taatgaacca ttgccaatcg cttggaagat taatgttgaa     420
ggtacaagaa tgttgttggc attgtctaga agaatgaaga gaatcgaagt tttttattcat    480 atttctactg cttactcaaa tgcatcttca gatagaatcg ttgttgatga aatcttgtat    540
ccagctccag cagatatgga tcaagtttac caattggtta aagatggtgt tacagaagaa    600
gaaactgaaa gattgttgaa cggtttgcca aacacttaca cttttactaa ggctttgaca    660
gaacatttgg ttgcagaaca tcaaacatac gttccaacta tcatcatcag accatctgtt    720
gttgcttcaa ttaaagatga accaatcaga ggttggttat gtaattggtt tggtgctaca    780
ggtatctctg ttttttactgc aaagggtttg aacagagttt tgttgggtaa agcttcaaac    840
atcgttgatg ttatcccagt tgattacgtt gcaaatttgg ttattgttgc tggtgcaaaa    900
tctggtggtc aaaaatcaga tgaattaaag atctataact gttgttcttc agattgtaac    960
ccagttactt tgaagaaaat tattaaagag tttactgaag atactattaa aaataagtct   1020
catattatgc cattgccagg ttggttcgtt tttactaagt acaagtggtt gttgacattg   1080
ttaactatta tttttcaaat gttaccaatg tatttggctg atgtttacag agttttgaca   1140
```

| ggtaaaatcc caagatacat gaagttgcat catttggtta ttcaaacaag attgggtatc | 1200 |
| gatttcttta cttctcattc atgggttatg aagacagata gagttagaga attattcggt | 1260 |
| tctttgtcat tggcagaaaa gcatatgttt ccatgtgatc catcttcaat cgattggaca | 1320 |
| gattattgc aatcatactg ttacggtgtt agaagatttt tggaaaagaa gaaataa | 1377 |

<210> SEQ ID NO 2
<211> LENGTH: 1365
<212> TYPE: DNA
<213> ORGANISM: Artificial Sequence
<220> FEATURE:
<223> OTHER INFORMATION: Spodoptera littoralis FAR1 S. cerevisiae codon
      optimized

<400> SEQUENCE: 2

| atggttgttt tgacttcaaa ggaaaaatca aacatgtctg ttgctgattt ctacgctggt | 60 |
| aaatctgttt ttattacagg tggtactggt ttcttgggta agttttttat tgaaaagttg | 120 |
| ttgtactcat gtccagatat tgataaaatc tatatgttga tcagagaaaa gaaaggtcaa | 180 |
| tctatcagag aaagattaac taaaattgtt gatgatccat gtttaatag attgaaggat | 240 |
| aagagaccag atgatttggg taaatcgtt ttgatcccag gtgacatcac agttccaggt | 300 |
| ttgggtattt ctgaagaaaa cgaaacaatc ttgactgaaa agtttcagt tgttattcat | 360 |
| tctgctgcaa ctgttaagtt taatgaacca ttggctactg catggaacgt taacgttgaa | 420 |
| ggtacaagaa tgatcatggc attatcaaga agaatgaaga gaatcgaagt ttttattcat | 480 |
| atttctactg cttacactaa cacaaacaga gcagttattg atgaagtttt gtatccacca | 540 |
| ccagctgata tcaacgatgt tcatcaacat gttaaaaatg gtgttacaga agaagaaact | 600 |
| gaaaagattt tgaacggtag accaaacact tacactttta ctaaggcttt gactgaacat | 660 |
| ttggttgcag aaaaccaatc atacatgcca acaatcattg ttagaccatc tattgttggt | 720 |
| gctattaaag atgatccaat tagaggttgg tggctaatt ggtatggtgc aacaggtttg | 780 |
| tcagttttta ctgcaaaggg tttgaacaga gttatatatg gtcattctaa ccatgttgtt | 840 |
| gatttgattc cagttgatta cgttgctaat ttggttattg ttgctggtgc aaagacatac | 900 |
| cattcaaacg aagttactat ctataactct tgttcttcat cttgtaaccc aatcactatg | 960 |
| aagagattgg ttggtttgtt tattgattac acagttaagc ataagtcata cgttatgcca | 1020 |
| tgccaggtt ggtatgttta ctctaactac aagtggttgg ttttcttggt tactgttatt | 1080 |
| ttccaagtta ttccagctta cttaggtgac attggtagaa gattgttagg taaaaatcca | 1140 |
| agatactaca gttgcaaaa tttggttgct caaacacaag aagcagttca tttctttaca | 1200 |
| tcacatactt gggaaattaa atcaaagaga acttctgaat tgttttcatc tttgtctttg | 1260 |
| acagatcaaa gaatgtttcc atgtgatgct aacagaatcg attggacaga ttacatcact | 1320 |
| gattactgtt ctggtgttag acaatttttg gaaaagatta aataa | 1365 |

<210> SEQ ID NO 3
<211> LENGTH: 1368
<212> TYPE: DNA
<213> ORGANISM: Artificial Sequence
<220> FEATURE:
<223> OTHER INFORMATION: Helicoverpa armigera FAR3 S. cerevisiae codon
      optimized

<400> SEQUENCE: 3

| atggttgttt tgacttcaaa ggaaacaaag ccatctgttg ctgaatttta cgctggtaaa | 60 |

```
tcagttttta ttacaggtgg tactggtttc ttgggtaaag ttttttattga aaagttgttg    120 tactcttgtc cagatattga aaatatctat atgttgatca gagaaaagaa aggtttgtca    180
gtttctgaaa gaattaaaca attttttagat gatccattgt ttacaagatt gaaggataag   240
agaccagctg atttggaaaa gattgttttg atcccaggtg acatcactgc accagatttg    300
ggtattaatt ctgaaaacga aaagatgttg attgaaaaag tttcagttat tattcattct    360
gctgcaactg ttaagtttaa tgaaccatta ccaacagctt ggaagattaa tgttgaaggt    420
actagaatga tgttggcatt gtcaagaaga atgaagagaa tcgaagtttt tattcatatt    480
tctacagctt acactaacac aaacagagaa gttgttgatg aaatcttgta tccagctcca    540
gcagatatcg atcaagttca tcaatacgtt aaggatggta tctcagaaga agatactgaa    600
aagattttga acggtagacc aaacacttac acttttacta aggctttgac agaacatttg    660
gttgctgaaa atcaagcata cgttccaact attattgtta gaccatctgt tgttgctgca    720
attaaagatg aaccattgaa aggttggttg ggtaattggt ttggtgctac aggtttgact    780
gtttttacag caaagggttt gaacagagtt atatatggtc attcttcata catcgttgat    840
ttgatcccag ttgattacgt tgctaatttg gttattgctg caggtgcaaa atcttcaaag    900
tcaacagaat tgaaggttta caactgttgt tcttcatctt gtaacccagt tactatcggt    960
acattgatgt caatgttcgc tgatgatgca attaaacaaa aatcttacgc tatgccattg   1020
ccaggttggt acattttttac aaagtacaag tggttggttt tgttgttgac attttttgttc   1080 caagttattc cagcatacgt tactgatttg tcaagacatt tgatcggtaa atctccaaga   1140
tacatcaagt tgcaatcatt ggttaaccaa actagatcat ctatcgattt ctttacaaac   1200
cattcttggg ttatgaaagc tgatagagtt agagaattgt acgcttcatt gtctccagct   1260
gataagtact tattcccatg tgatccaact gatatcaact ggacacatta catccaagat   1320
tactgttggg gtgttagaca tttcttggaa aagaaatctt acgaataa                 1368
```

<210> SEQ ID NO 4
<211> LENGTH: 1199
<212> TYPE: DNA
<213> ORGANISM: Artificial Sequence
<220> FEATURE:
<223> OTHER INFORMATION: pOLE1 cassette

<400> SEQUENCE: 4

```
cttgctgaaa agatgatgtt ctgaggtatt cgtatcgcta gcttgatacg cttttaacaa     60
aagtaagctt tcgtttgca ggtttggtta cttttctgta cgagatgata tcgctaagtt    120
tatagtcatc tgtgaaattt ctcaaaaacc tcatggtttc tccatcaccc attttttcatt   180 tcatttgccg ggcggaaaaa aaaaggaaa aaaaaaaaaa aaaaaaataa atgacacatg    240
gaaataagtc aaggattagc ggatatgtag ttccagtccg ggttatacca tcacgtgata   300
ataaatccaa atgagaatga gggtgtcata tctaatcatt atgcacgtca agattctccg   360
tgactatggc tcttttctga agcatttttc gggcgcccgg tggccaaaaa ctaactccga   420
gcccgggcat gtcccggggt tagcgggccc aacaaaggcg cttatctggt gggcttccgt   480
agaagaaaaa aagctgttga gcgagctatt tcgggtatcc cagccttctc tgcagaccgc   540
cccagttggc ttggctctgg tgctgttcgt tagcatcaca tcgcctgtga caggcagagg   600
taataacggc ttaaggttct cttcgcatag tcggcagctt tctttcggac gttgaacact   660
caacaaacct tatctagtgc ccaaccaggt gtgcttctac gagtcttgct cactcagaca   720
cacctatccc tattgttacg gctatgggga tggcacacaa aggtggaaat aatagtagtt   780
```

```
aacaatatat gcagcaaatc atcggctcct ggctcatcga gtcttgcaaa tcagcatata    840
catatatata tgggggcaga tcttgattca tttattgttc tatttccatc tttcctactt    900
ctgtttccgt ttatattttg tattacgtag aatagaacat catagtaata gatagttgtg    960
gtgatcatat tataaacagc actaaaacat tacaacaaag aatgccaact tctggaacta   1020
ctattgaatt gattgacgac caatttccaa aggatgactc tgccagcagt ggcattgtcg   1080
acactagtgc ggccgctcac atatgaaagt atatacccgc ttttgtacac tatgtagcta   1140
taattcaatc gtattattgt agctccgcac gaccatgcct tagaaatatc cgcagcgcg    1199
```

<210> SEQ ID NO 5
<211> LENGTH: 655
<212> TYPE: DNA
<213> ORGANISM: Saccharomyces cerevisiae

<400> SEQUENCE: 5

```
cttgctgaaa agatgatgtt ctgaggtatt cgtatcgcta gcttgatacg cttttaacaa     60
aagtaagctt ttcgtttgca ggtttggtta cttttctgta cgagatgata tcgctaagtt    120
tatagtcatc tgtgaaattt ctcaaaaacc tcatggtttc tccatcaccc attttttcatt   180 tcatttgccg ggcggaaaaa aaaaggaaa aaaaaaaaaa aaaaaaataa atgacacatg    240
gaaataagtc aaggattagc ggatatgtag ttccagtccg ggttatacca tcacgtgata    300
ataaatccaa atgagaatga gggtgtcata tctaatcatt atgcacgtca agattctccg    360
tgactatggc tcttttctga agcatttttc gggcgcccgg tggccaaaaa ctaactccga    420
gcccgggcat gtcccggggt tagcgggccc aacaaaggcg cttatctggt gggcttccgt    480
agaagaaaaa aagctgttga gcgagctatt tcgggtatcc cagccttctc tgcagaccgc    540
cccagttggc ttggctctgg tgctgttcgt tagcatcaca tcgcctgtga caggcagagg    600
taataacggc ttaaggttct cttcgcatag tcggcagctt tctttcggac gttga         655
```

<210> SEQ ID NO 6
<211> LENGTH: 346
<212> TYPE: DNA
<213> ORGANISM: Saccharomyces cerevisiae

<400> SEQUENCE: 6

```
acactcaaca aaccttatct agtgcccaac caggtgtgct tctacgagtc ttgctcactc     60
agacacacct atccctattg ttacggctat ggggatggca cacaaaggtg gaaataatag    120
tagttaacaa tatatgcagc aaatcatcgg ctcctggctc atcgagtctt gcaaatcagc    180
atatacatat atatatgggg gcagatcttg attcatttat tgttctatttt ccatctttcc   240 tacttctgtt tccgtttata ttttgtatta cgtagaatag aacatcatag taatagatag    300
ttgtggtgat catattataa acagcactaa aacattacaa caaaga                   346
```

<210> SEQ ID NO 7
<211> LENGTH: 81
<212> TYPE: DNA
<213> ORGANISM: Saccharomyces cerevisiae

<400> SEQUENCE: 7

```
atgccaactt ctggaactac tattgaattg attgacgacc aatttccaaa ggatgactct     60
gccagcagtg gcattgtcga c                                               81
```

<210> SEQ ID NO 8

```
<211> LENGTH: 103
<212> TYPE: DNA
<213> ORGANISM: Saccharomyces cerevisiae

<400> SEQUENCE: 8
tcacatatga aagtatatac ccgcttttgt acactatgta gctataattc aatcgtatta      60
ttgtagctcc gcacgaccat gccttagaaa tatccgcagc gcg                       103

<210> SEQ ID NO 9
<211> LENGTH: 1050
<212> TYPE: DNA
<213> ORGANISM: Trichoplusia ni

<400> SEQUENCE: 9
atggctgtga tggctcaaac agtacaagaa acggctacag tgttggaaga ggaagctcgc      60
acagtgactc ttgtggctcc aaagacaacg ccaaggaaat ataaatatat atacaccaac     120
tttcttacat tttcatatgc gcatttagct gcattatacg actttatttt gtgcttcacc     180
tctgcgaaat gggaaacatt gctattctct ttcgtactct tccacatgtc aaatataggc     240
atcaccgcag gggctcaccg actctggact cacaagactt tcaaagccaa attgcctttg     300
gaaattgtcc tcatgatatt caactcttta gcctttcaaa acacggctat tacatgggct     360
agagaacatc ggctacatca caaatacagc gatactgatg ctgatcccca caatgcgtca     420
agagggttct tctactcgca tgttggctgg ctattagtaa aaaacatcc cgatgtcctg      480 aaatatggaa aaactataga catgtcggat gtatacaata atcctgtgtt aaaatttcag     540
aaaaagtacg cagtaccctt aattggaaca gtttgtttg ctctgccaac tttgattcca      600
gtctactgtt ggggcgaatc gtggaacaac gcttggcaca tagccttatt tcgatacata     660
ttcaatctta acgtgacttt cctagtcaac agtgctgcgc atatctgggg gaataagcct     720
tatgataaaa gcatcttgcc cgctcaaaac ctgctggttt ccttcctagc aagtggagaa     780
ggcttccata attaccatca cgtctttcca tgggattacc gcacagcaga attagggaat     840
aacttcctga atttgacgac gctgttcatt gattttgtg cctggtttgg atgggcttat     900
gacttgaagt ctgtatcaga ggatattata aaacagagag ctaaacgaac aggtgacggt     960
tcttcagggg tcatttgggg atgggacgac aaagacatgg accgcgatat aaaatctaaa    1020
gctaacattt tttatgctaa aaaggaatga                                     1050

<210> SEQ ID NO 10
<211> LENGTH: 1011
<212> TYPE: DNA
<213> ORGANISM: Agrotis segetum

<400> SEQUENCE: 10
atggctcaag gtgtccaaac aactacgata ttgagggagg aggagccgtc attgactttc      60
gtggtacctc aagaaccgag aaagtatcaa atcgtgtacc caaaccttat cacatttggg     120
tactggcata tagctggttt atacgggcta tatttgtgct ttacttcggc aaaatggcaa     180
acaattttat tcagtttcat gctcgttgtg ttagcagagt tgggaataac agccggcgct     240
cacaggttat gggcccacaa acatatataaa gcgaagcttc ccttacaaat tatcctgatg     300
atactgaact ccattgcctt ccaaaattcc gccattgatt gggtgaggga ccaccgtctc     360
catcataagt acagtgacac tgatgcagac cctcacaatg ctactcgtgg tttcttctat     420
tctcatgttg gatggttgct cgtaagaaaa catccagaag tcaagagacg tggaaaggaa     480
cttgacatgt ctgatattta caacaatcca gtgctgagat ttcaaaagaa gtatgctata     540
```

-continued

| | |
|---|---|
| cccttcatcg gggcaatgtg cttcggatta ccaacttttta tccctgttta cttctgggga | 600 |
| gaaacctgga gtaatgcttg gcatatcacc atgcttcggt acatcctcaa cctaaacatt | 660 |
| actttcctgg tcaacagtgc tgctcatatc tggggataca aaccttatga catcaaaata | 720 |
| ttgcctgccc aaaatatagc agtttccata gtaaccggcg gcgaagtttc cataactacc | 780 |
| accacgtttt ttccttggga ttatcgtgca gcagaattgg ggaacaatta tcttaatttg | 840 |
| acgactaagt tcatagattt cttcgcttgg atcggatggg cttacgatct taagacggtg | 900 |
| tccagtgatg ttataaaaag taaggcggaa agaactggtg atgggacgaa tctttggggt | 960 |
| ttagaagaca aaggtgaaga agatttttttg aaaatctgga aagacaatta a | 1011 |

<210> SEQ ID NO 11
<211> LENGTH: 1440
<212> TYPE: DNA
<213> ORGANISM: Thalassiosira pseudonana

<400> SEQUENCE: 11

| | |
|---|---|
| actagtatgg actttctctc cggcgatcct ttccggacac tcgtccttgc agcacttgtt | 60 |
| gtcatcggat ttgctgcggc gtggcaatgc ttctacccgc cgagcatcgt cggcaagcct | 120 |
| cgtacattaa gcaatggtaa actcaatacc agaatccatg gcaaattgta cgacctctca | 180 |
| tcgtttcagc atccaggagg ccccgtggct ctttctcttg ttcaaggtcg cgacggaaca | 240 |
| gctctatttg agtcacacca tcccttcata cctcgaaaga atctacttca gatcctctcc | 300 |
| aagtacgagg ttccgtcgac tgaagactct gtttccttca tcgccaccct agacgaactc | 360 |
| aatggtgaat ctccgtacga ttggaaggac attgaaaatg atgatttcgt atctgaccta | 420 |
| cgagctctcg taattgagca ctttttctcct ctcgccaagg aaagggggagt ttcactcgtt | 480 |
| gagtcgtcga aggcaacacc tcagcggtgg atggtggttc tactgctcct tgcgtcgttc | 540 |
| ttcctcagca tcccattata tttgagtggt tcgtggactt tcgttgtcgt cactcccatc | 600 |
| ctcgcttggc tggcggttgt caattactgg cacgatgcta ctcactttgc attgagcagc | 660 |
| aactggattt tgaatgctgc gctcccatat ctcctccctc tcctatcgag tccgtcaatg | 720 |
| tggtatcatc atcacgtcat tggacatcac gcatacacca acatttccaa aagagatcca | 780 |
| gatcttgctc acgctccaca actcatgaga gaacacaaga gtatcaaatg gagaccatct | 840 |
| cacttaaatc aaacacagct tccgcggatt ctcttcatct ggtcgattgc agtcggtatt | 900 |
| gggttgaact tactgaacga cgtgagagca ctaaccaagc tttcatacaa caacgttgtt | 960 |
| cgggtggaga agatgtcatc gtcgcgaaca ttactccatt tccttggacg tatgttgcac | 1020 |
| atctttgtga ctacactttg gccccttttg gcgtttccgg tgtggaaggc catcgtttgg | 1080 |
| gcgactgtac cgaatgccat actgagtttg tgcttcatgc tgaatacgca aatcaatcac | 1140 |
| ctcatcaaca cgtgtgcaca tgcttccgat aacaactttt acaagcatca agttgtaact | 1200 |
| gctcagaact ttggccgatc aagtgccttt tgcttcatct tctcgggagg tctcaactac | 1260 |
| caaattgaac atcatttgtt gccgacggtg aaccattgcc atttgccagc tttggccccg | 1320 |
| ggtgtagagc gtttgtgtaa gaaacacggg gtgacataca actctgttga aggatacaga | 1380 |
| gaggccatca ttgcacactt tgcacatacc aaagatatgt cgacgaagcc tactgattga | 1440 |

<210> SEQ ID NO 12
<211> LENGTH: 981
<212> TYPE: DNA
<213> ORGANISM: Amyelois transitella

<400> SEQUENCE: 12

```
atggtcccta caagggttc cagtgacgtt ttgtctgaac attctgagcc ccagttcact      60
aaactcatag ctccacaagc agggccgagg aaatacaaga tagtgtatcg aaatttgctc     120
acattcggct attggcactt atcagctgtt tatgggctct acttgtgctt tacttgtgcg    180
aaatgggcta ccatcttatt tgcatttttc ttatacgtga tcgcggaaat cggtataaca    240
ggtggcgctc ataggctatg ggcacatcgg acttataaag ccaagttgcc tttagagatt    300
ttgttactca taatgaactc tattgccttc caagacactg ctttcacctg ggctcgtgat    360
caccgccttc atcacaaata ttcggatact gacgctgatc cccacaatgc taccagaggg    420
tttttctatt cacatgtagg ctggcttttg gtgaagaaac ccctgaagt caaagcaaga     480
ggaaaatact tgtcgttaga tgatcttaag aataatccat tgcttaaatt ccaaaagaaa    540
tacgctattc tagttatagg cacgttatgc ttccttatgc aacatttgt gcccgtatac     600
ttctggggcg agggcatcag cacggcctgg aacatcaatc tattgcgata cgtcatgaat    660
cttaacatga ctttcttagt taacagtgca gcgcatatct ttggcaacaa accatacgat    720
aagagcatag cctcagtcca aaatatttca gttagcttag ctacttttgg cgaaggattc    780
cataattacc atcacactta cccctgggat tatcgtgcgg cagaattagg aaataatagg    840
ctaaatatga ctactgcttt catagatttc ttcgcttgga tcggctgggc ttatgacttg    900
aagtctgtgc cacaagaggc cattgcaaaa aggtgtgcga aaactggcga tggaacggat    960
atgtggggtc gaaaaagata a                                              981
```

<210> SEQ ID NO 13
<211> LENGTH: 1017
<212> TYPE: DNA
<213> ORGANISM: Helicoverpa zea

<400> SEQUENCE: 13

```
atggcccaaa gctatcaatc aactacggtt tgagtgagg agaaagaact aacactgcaa      60
catttggtgc cccaagcatc gcccaggaag tatcaaatag tgtatccgaa cctcattacg    120
tttggttact ggcacatagc cggactttat ggcctttact tgtgcttcac ttctgctaaa    180
tgggctacga tttattcag ctacatcctc ttcgtgttag cagaaatagg aatcacggct     240
ggcgctcaca gactctgggc ccacaaaact tacaaagcga aactaccatt agaaatactc    300
ttaatggtat tcaactccat cgcttttcaa aactcagcca ttgactgggt gagggaccac    360
cgactccacc ataagtatag cgatacagat gctgatcccc acaatgccag ccgagggttc    420
ttttattccc atgtaggatg gctacttgtg agaaaacatc ctgaagtcaa aaagcgaggg    480
aaagaactca atatgtccga tatttacaac aatcctgtcc tgcggtttca gaaaaaatac    540
gccataccct tcattgggc tgtttgtttc gccttaccta caatgatacc tgtttacttc    600
tggggagaaa cctggtccaa tgcttggcat atcaccatgc ttcgctacat catgaacctc    660
aatgtcacct ttttggtaaa cagcgctgct catatatggg aaacaagcc ttatgacgca     720
aaaatattac ctgcacaaaa tgtagctgtg tcggtcgcca ctggtggaga aggtttccat    780
aattaccacc atgtcttccc ctgggattat cgagcagcgg aactcggtaa caatagcctc    840
aatctgacga ctaaattcat agatttattc gcagcaatcg gatgggcata tgatctgaag    900
acggtttcgg aggatatgat aaaacaaagg attaaacgca ctggagatgg aacggatctt    960
tggggacacg aacaaaactg tgatgaagtg tgggatgtaa aagataaatc aagttaa      1017
```

<210> SEQ ID NO 14
<211> LENGTH: 711
<212> TYPE: DNA
<213> ORGANISM: Artificial Sequence
<220> FEATURE:
<223> OTHER INFORMATION: mCherry C. tropicalis optimized

<400> SEQUENCE: 14

```
atggtttcta agggtgaaga agacaacatg gcaatcatca aggaatttat gcgttttaag      60
gtccatatgg aaggctccgt taacggccac gagttcgaga tcgagggaga aggtgagggt     120
agaccatacg aaggtactca aaccgccaag ttgaaagtta caaagggtgg tccattgcca     180
tttgcttggg atatcttgtc cccacaattt atgtacggat caaaggcata tgtcaagcat     240
cctgccgaca tcccagatta cttgaagtta tcctttccag aaggttttaa gtgggagaga     300
gttatgaact tgaagatgg cggagttgtt actgttactc aggactcttc cttgcaagat     360
ggtgaattta tctataaagt gaaattgaga ggtactaact ttccatccga cggtccagtc     420
atgcaaaaga gacaatggg ttgggaggct cttccgaaa gaatgtaccc agaagacgt       480
gcattgaaag gtgaaatcaa gcaacgttta agttgaagg acggtggtca ctacgatgcc     540
gaggtcaaga ccacttataa ggctaagaag ccagtccaat gccaggtgc ttataacgtt      600
aacatcaagt tagatattac ttcacacaac gaagactaca caatcgttga acaatatgaa    660
agagccgaag gtagacattc taccggcggc atggacgagt tatataagta g             711
```

<210> SEQ ID NO 15
<211> LENGTH: 1092
<212> TYPE: DNA
<213> ORGANISM: Artificial Sequence
<220> FEATURE:
<223> OTHER INFORMATION: CaOLE1-A. segetum Z11 desaturase

<400> SEQUENCE: 15

```
atgactacag ttgaacaact tgaaactgtt gatatcacta aattgaatgc cattgctgct      60
ggtactaata agaaggtgcc aatggctcaa ggtgtccaaa caactacgat attgagggag    120
gaagagccgt cattgacttt cgtggtacct caagaaccga aaagtatca atcgtgtac      180
ccaaacctta tcacatttgg gtactggcat atagctggtt tatacgggct atatttgtgc    240
tttacttcgg caaaatggca acaattttta ttcagtttca tgctcgttgt gttagcagag    300
ttgggaataa cagccggcgc tcacaggtta tgggcccaca aaacatataa agcgaagctt    360
cccttacaaa ttatcttaat gatattaaac tccattgcct tccaaaattc cgccattgat    420
tgggtgaggg accaccgtct ccatcataag tacagtgaca ctgatgcaga ccctcacaat    480
gctactcgtg gtttcttcta ttctcatgtt ggatggttgc tcgtaagaaa acatccagaa    540
gtcaagagac gtggaaagga acttgacatg tctgatattt acaacaatcc agtgttaaga    600
tttcaaaaga gtatgctat accccttcatc ggggcaatgt gcttcggatt accaactttt    660
atccctgttt acttctgggg agaaacctgg agtaatgctt ggcatatcac catgcttcgg    720
tacatcctca acctaaacat tactttctta gtcaacagtg ctgctcatat ctggggatac    780
aaaccttatg acatcaaaat attgcctgcc caaaatatag cagtttccat agtaaccggc    840
ggcgaagttt ccataactac caccacgttt tttccttggg attatcgtgc agcagaattg    900
gggaacaatt atcttaattt gacgactaag ttcatagatt tcttcgcttg gatcggatgg    960
gcttacgatc ttaagacggt gtccagtgat gttataaaaa gtaaggcgga aagaactggt   1020
gatgggacga atctttgggg tttagaagac aaaggtgaag aagatttttt gaaaatctgg   1080
```
aaagacaatt aa                                                              1092

<210> SEQ ID NO 16
<211> LENGTH: 1011
<212> TYPE: DNA
<213> ORGANISM: Agrotis segetum

<400> SEQUENCE: 16
atggctcaag gtgtccaaac aactacgata ttgagggagg aagagccgtc attgactttc    60
gtggtacctc aagaaccgag aaagtatcaa atcgtgtacc caaaccttat cacatttggg   120
tactggcata tagctggttt atacgggcta tatttgtgct ttacttcggc aaaatggcaa   180
acaattttat tcagtttcat gctcgttgtg ttagcagagt tgggaataac agccggcgct   240
cacaggttat gggcccacaa acatataaa gcgaagcttc ccttacaaat tatcttaatg   300
atattaaact ccattgcctt ccaaaattcc gccattgatt gggtgaggga ccaccgtctc   360
catcataagt acagtgacac tgatgcagac cctcacaatg ctactcgtgg tttcttctat   420
tctcatgttg gatggttgct cgtaagaaaa catccagaag tcaagagacg tggaaaggaa   480
cttgacatgt ctgatattta caacaatcca gtgttaagat ttcaaaagaa gtatgctata   540
cccttcatcg gggcaatgtg cttcggatta ccaacttttta tccctgttta cttctgggga   600
gaaacctgga gtaatgcttg gcatatcacc atgcttcggt acatcctcaa cctaaacatt   660
actttcttag tcaacagtgc tgctcatatc tggggataca aacctatga catcaaaata   720
ttgcctgccc aaaatatagc agtttccata gtaaccggcg gcgaagtttc cataactacc   780
accacgtttt ttccttggga ttatcgtgca gcagaattgg ggaacaatta tcttaatttg   840
acgactaagt tcatagattt cttcgcttgg atcggatggg cttacgatct taagacggtg   900
tccagtgatg ttataaaaag taaggcgaa agaactggtg atgggacgaa tctttggggt   960
ttagaagaca aggtgaaga agatttttttg aaaatctgga aagacaatta a           1011

<210> SEQ ID NO 17
<211> LENGTH: 981
<212> TYPE: DNA
<213> ORGANISM: Amyelois transitella

<400> SEQUENCE: 17
atggtcccta caagggttc cagtgacgtt ttgtctgaac attctgagcc ccagttcact    60
aaactcatag ctccacaagc agggccgagg aaatacaaga tagtgtatcg aaatttgctc   120
acattcggct attggcactt atcagctgtt tatgggctct acttgtgctt tacttgtgcg   180
aaatgggcta ccatcttatt tgcatttttc ttatacgtga tcgcggaaat cggtataaca   240
ggtggcgctc ataggctatg ggcacatcgg acttataaag ccaagttgcc tttagagatt   300
ttgttactca taatgaattc tattgccttc caagacactg ctttcacctg gctcgagat    360
caccgccttc atcacaaata ttcggatact gacgctgatc cccacaatgc taccagaggg   420
tttttctatt cacatgtagg ctggcttttg gtgaagaaac accctgaagt caaagcaaga   480
ggaaaatact tgtcgttaga tgatcttaag aataatccat tgcttaaatt ccaaaagaaa   540
tacgctattc tagttatagg cacgttatgc ttccttatgc aacatttgt gcccgtatac   600
ttctggggcg agggcatcag cacggcctgg aacatcaatc tattgcgata cgtcatgaat   660
cttaacatga cttctcttagt taacagtgca gcgcatatct ttggcaacaa accatacgat   720
aagagccatag cctcagtcca aaatatttca gttagcttag ctactttttgg cgaaggattc   780
cataattacc atcacactta cccctgggat tatcgtgcgg cagaattagg aaataataag   840

```
ctaaatatga ctactgcttt catagatttc ttcgcttgga tcggctgggc ttatgacttg    900
aagtctgtgc cacaagaggc cattgcaaaa aggtgtgcga aaactggcga tggaacggat    960
atgtggggtc gaaaaagata a                                              981
```

<210> SEQ ID NO 18
<211> LENGTH: 1050
<212> TYPE: DNA
<213> ORGANISM: Trichoplusia ni

<400> SEQUENCE: 18

```
atggctgtga tggctcaaac agtacaagaa acggctacag tgttggaaga ggaagctcgc     60
acagtgactc ttgtggctcc aaagacaacg ccaaggaaat ataaatatat atacaccaac    120
tttcttacat tttcatatgc gcatttagct gcattatacg gactttattt gtgcttcacc    180
tctgcgaaat gggaaacatt gctattctct ttcgtactct tccacatgtc aaatataggc    240
atcaccgcag gggctcaccg actctggact cacaagactt caaagccaa attgcctttg     300 gaaattgtcc tcatgatatt caactcttta gcctttcaaa acacggctat tacatgggct    360
agagaacatc ggctcatcca caaatacagc gatactgatg ctgatcccca caatgcgtca    420
agagggttct tctactcgca tgttggctgg ctattagtaa aaaaacatcc cgatgtctta    480
aaatatggaa aaactataga catgtcggat gtatacaata atcctgtgtt aaaatttcag    540
aaaaagtacg cagtaccctt aattggaaca gtttgttttg ctcttccaac tttgattcca    600
gtctactgtt ggggcgaatc gtggaacaac gcttggcaca tagccttatt tcgatacata    660
ttcaatctta acgtgacttt cctagtcaac agtgctgcgc atatctgggg gaataagcct    720
tatgataaaa gcatcttgcc cgctcaaaac ttattagttt ccttcctagc aagtggagaa    780
ggcttccata attaccatca cgtctttcca tgggattacc gcacagcaga attagggaat    840
aacttcttaa atttgacgac gttattcatt gatttttgtg cctggtttgg atgggcttat    900
gacttgaagt ctgtatcaga ggatattata aaacagagag ctaaacgaac aggtgacggt    960
tcttcagggg tcatttgggg atgggacgac aaagacatgg accgcgatat aaaatctaaa   1020
gctaacattt tttatgctaa aaaggaatga                                    1050
```

<210> SEQ ID NO 19
<211> LENGTH: 1017
<212> TYPE: DNA
<213> ORGANISM: Helicoverpa zea

<400> SEQUENCE: 19

```
atggcccaaa gctatcaatc aactacggtt ttgagtgagg agaaagaact aacattacaa     60
catttggtgc cccaagcatc gcccaggaag tatcaaatag tgtatccgaa cctcattacg    120
tttggttact ggcacatagc cggactttat ggcctttact tgtgcttcac ttctgctaaa    180
tgggctacga tttttattcag ctacatcctc ttcgtgttag cagaaatagg aatcacggct    240
ggcgctcaca gactctgggc ccacaaaact tacaaagcga aactaccatt agaaatactc    300
ttaatggtat tcaactccat cgcttttcaa aactcagcca ttgactgggt gagggaccac    360
cgactccacc ataagtatag cgatacagat gctgatcccc acaatgccag ccgagggttc    420
ttttattccc atgtaggatg gctacttgtg agaaaacatc ctgaagtcaa aaagcgaggg    480
aaagaactca atatgtccga tatttacaac aatcctgtct acggtttca gaaaaaatac    540 gccataccct tcattggggc tgtttgtttc gccttaccta caatgatacc tgtttacttc    600
```

```
tggggagaaa cctggtccaa tgcttggcat atcaccatgc ttcgctacat catgaacctc      660
aatgtcacct ttttggtaaa cagcgctgct catatatggg gaaacaagcc ttatgacgca      720
aaaatattac ctgcacaaaa tgtagctgtg tcggtcgcca ctggtggaga aggtttccat      780
aattaccacc atgtcttccc ctgggattat cgagcagcgg aactcggtaa caatagcctc      840
aatttaacga ctaaattcat agatttattc gcagcaatcg gatgggcata tgatttaaag      900
acggtttcgg aggatatgat aaaacaaagg attaaacgca ctggagatgg aacggatctt      960
tggggacacg aacaaaactg tgatgaagtg tgggatgtaa agataaatc  aagttaa       1017
```

<210> SEQ ID NO 20
<211> LENGTH: 1068
<212> TYPE: DNA
<213> ORGANISM: Ostrinia furnacalis

<400> SEQUENCE: 20

```
atggctccta atattaagga cggagctgat ttgaacggag ttttatttga agatgacgct       60 agcaccccg  attatgccct tgccacggcc ccagtccaga aagcagacaa ctatcccaga      120
aaactagtgt ggagaaacat catactcttt gcataccttc accttgccgc tgtgtatgga      180
gcatacctat tcttattttc agcgaaatgg cagacagata ttttgcctta cattctttac       240
gtgatctcag gactcggcat cacagcggga gcccaccgcc tttgggcgca caagtcatac       300
aaggctaagt ggccacttag actcattctt attatcttca acactgtatc attccaggac      360
tctgctctcg actggtcacg tgaccaccgc atgcaccaca atactcgga  gaccgacgcc      420 gacccgcaca acgcgactcg agggttcttc ttctctcata tcggctggtt attagtccgc      480
aagcacccgg aattaaagag aaagggcaag ggattagact taagcgactt gtatgctgat      540
cccatcctcc gtttccagaa gaagtactat ttactattaa tgcctcttgg ctgcttcatc      600
atgccgacgg tggtcccggt gtacttctgg ggtgagactt ggactaacgc tttcttcgtc      660
gccgcgctct ccgatacac  cttcatcctc aatgtcacct ggttggtcaa ctccgccgcg      720
cacaagtggg gccacaagcc ctatgacagc agcatcaagc cttccgagaa cctctcagtc      780
tccttattcg cgttgggcga aggattccac aactaccacc acacattccc ctgggactac      840
aaaactgccg agctcggcaa caacagactc aatttcacaa caaacttcat caacttcttc      900
gctaaaatcg gatgggctta cgacttgaaa acggtctccg acgagattat tcagaataga      960
gtcaagcgca caggagatgg ctcccaccac ttatggggtt ggggcgacaa ggatcaacct     1020
aaagaggagg taaacgcagc cattagaatt aatcctaaag acgagtaa               1068
```

<210> SEQ ID NO 21
<211> LENGTH: 1059
<212> TYPE: DNA
<213> ORGANISM: Lampronia capitella

<400> SEQUENCE: 21

```
atgccgccga acgtgacaga ggcgaacgga gtgttatttg agaatgacgt gcagactcct       60
gacatggggc tagaagtggc ccctgtgcag aaggctgacg agcgtaagat ccagctcgtt      120
tggaggaaca tcatcgcttt tgcatgtctt catttagcag ctgtgtatgg agcttattta      180
ttcttcacct cggctatatg gcagacagac atatttgcat acatccttta cgttatgtct       240
ggattaggaa tcacggcggg agcgcacaga ttatgggctc ataagtcata caaggcgaag      300
tggccgttaa gattaatcct cgtcgcattc aacactttgg cattccagga ttcggcaatc      360
gactgggcgc gcgaccaccg catgcaccac aagtactcgg agacggatgc ggacccacat      420
```

```
aacgccactc gcggcttctt cttttcgcac attggttggt tactctgccg aaaacacccg      480
gagctaaagc gcaagggcca gggcctcgac ttaagtgacc tctacgcaga tcctattatt      540
cgcttccaaa agaagtacta cttattgtta atgccgttag cctgctttgt tcttcccacc      600
ataattccgg tctacctctg gggcgagtcc tggaaaaacg cgttcttcgt agctgcaatg      660
ttccgttaca cgttcatcct caacgtaaca tggctcgtca actccgccgc ccacaaatgg      720
ggaggcaagc cctatgataa aacatccag cccgctcaga acatctctgt agctatcttc      780
gcattaggcg agggcttcca caactaccac cacacgttcc cctgggacta caagaccgct      840
gaattaggaa acaacaggtt aaatttcaca acttcgttta tcaatttctt cgcaagcttc      900
ggatgggcct acgacttaaa gaccgtgtcg gacgagatta tacaacagcg cgttaagagg      960
acgggagatg ggagccatca cttacggggc tggggcgacc aggacatacc ggccgaagaa     1020
gctcaagctg ctttacgcat taaccgtaaa gatgattag                            1059

<210> SEQ ID NO 22
<211> LENGTH: 1062
<212> TYPE: DNA
<213> ORGANISM: Helicoverpa zea

<400> SEQUENCE: 22
atggctccaa atatatcgga ggatgtgaac ggggtgctct tcgagagtga tgcagcgacg       60
ccggacttag cgttatccac gccgcctgtg cagaaggctg acaacaggcc caagcaatta      120
gtgtggagga acatactatt attcgcgtat cttcacttag cggctcttta cggaggttat      180
ttattcctct tctcagctaa atggcagaca gacatatttg cctacatctt atatgtgatc      240
tccgggcttg gtatcacggc tggagcacat cgcttatggg cccacaagtc ctacaaagct      300
aaatggcctc tccgagttat cttagtcatc tttaacacag tggcattcca ggatgccgct      360
atggactggg cgcgcgacca ccgcatgcat cacaagtact cggaaaccga tgctgatcct      420
cataatgcga cccgaggatt cttcttctct cacattggct ggttacttgt caggaaacat      480
cccgacctta aggagaaggg caagggactc gacatgagcg acttacttgc tgaccccatt      540
ctcaggttcc agaaaaaata ctacttaatc ttaatgccct tggcttgctt cgtgatgcct      600
accgtgattc ctgtgtactt ctggggtgaa acctggacca acgcattctt tgtggcggcc      660
atgttccgct acgcgttcat cctaaatgtg acgtggctcg tcaactctgc cgctcacaag      720
tggggagaca gcccctacga caaaagcatt aagccttccg aaaacttgtc ggtcgccatg      780
ttcgctctcg gagaaggatt ccacaactac caccacactt tcccttggga ctacaaaact      840
gctgagttag caacaacaa actcaacttc actaccacct ttattaactt cttcgctaaa      900
attggctggg cttacgactt aaagacagtg tctgatgata tcgtcaagaa cagggtgaag      960
cgcactggtg acggctccca ccacttatgg ggctggggag acgaaaatca atccaaagaa     1020
gaaattgatg ccgctatcag aatcaatcct aaggacgatt aa                        1062

<210> SEQ ID NO 23
<211> LENGTH: 1434
<212> TYPE: DNA
<213> ORGANISM: Thalassiosira pseudonana

<400> SEQUENCE: 23
atggactttc tctccggcga tcctttccgg acactcgtcc ttgcagcact tgttgtcatc       60
ggatttgctg cggcgtggca atgcttctac ccgccgagca tcgtcggcaa gcctcgtaca      120
```

```
ttaagcaatg gtaaactcaa taccagaatc catggcaaat tgtacgacct ctcatcgttt      180
cagcatccag gaggccccgt ggctcttcct cttgttcaag gtcgcgacgg aacagctcta      240
tttgagtcac accatcccct catacctcga aagaatctac ttcagatcct ctccaagtac      300
gaggttccgt cgactgaaga ctctgtttcc ttcatcgcca ccctagacga actcaatggt      360
gaatctccgt acgattggaa ggacattgaa aatgatgatt tcgtatctga cctacgagct      420
ctcgtaattg agcacttttc tcctctcgcc aaggaaaggg gagtttcact cgttgagtcg      480
tcgaaggcaa cacctcagcg gtggatggtg gttctattac tccttgcgtc gttcttcctc      540
agcatcccat tatatttgag tggttcgtgg actttcgttg tcgtcactcc catcctcgct      600
tggttagcgg ttgtcaatta ctggcacgat gctactcact ttgcattgag cagcaactgg      660 atttgaatg ctgcgctccc atatctcctc cctctcctat cgagtccgtc aatgtggtat       720
catcatcacg tcattggaca tcacgcatac accaacattt ccaaaagaga tccagatctt      780
gctcacgctc cacaactcat gagagaacac aagagtatca aatggagacc atctcactta      840
aatcaaacac agcttccgcg gattctcttc atctggtcga ttgcagtcgg tattgggttg      900
aacttattaa acgacgtgag agcactaacc aagctttcat acaacaacgt tgttcgggtg      960
gagaagatgt catcgtcgcg aacattactc catttccttg gacgtatgtt gcacatcttt     1020
gtgactacac tttggccctt tttggcgttt ccggtgtgga aggccatcgt ttgggcgact     1080
gtaccgaatg ccatattaag tttgtgcttc atgttaaata cgcaaatcaa tcacctcatc     1140
aacacgtgtg cacatgcttc cgataacaac ttttacaagc atcaagttgt aactgctcag     1200
aactttggcc gatcaagtgc cttttgcttc atcttctcgg gaggtctcaa ctaccaaatt     1260
gaacatcatt tgttgccgac ggtgaaccat tgccatttgc cagctttggc cccgggtgta     1320
gagcgtttgt gtaagaaaca cggggtgaca tacaactctg ttgaaggata cagagaggcc     1380
atcattgcac actttgcaca taccaaagat atgtcgacga agcctactga ttga           1434
```

<210> SEQ ID NO 24
<211> LENGTH: 1050
<212> TYPE: DNA
<213> ORGANISM: Trichoplusia ni

<400> SEQUENCE: 24

```
atggctgtga tggctcaaac agtacaagaa acggctacag tgttggaaga ggaagctcgc       60
acagtgactc ttgtggctcc aaagacaacg ccaaggaaat ataaatatat atacaccaac      120
tttcttacat ttcatatgc gcatttagct gcattatacg gactttattt gtgcttcacc       180
tctgcgaaat gggaaacatt gctattctct ttcgtactct tccacatgtc aaatataggc      240
atcaccgcag gggctcaccg actctggact cacaagactt tcaaagccaa attgcctttg      300
gaaattgtcc tcatgatatt caactcttta gcctttcaaa acacggctat tacatgggct      360
agagaacatc ggctacatca caaatacagc gatactgatg ctgatcccca caatgcgtca      420
agagggttct tctactcgca tgttggctgg ctattagtaa aaaaacatcc cgatgtcctg      480
aaatatggaa aaactataga catgtcggat gtatacaata tcctgtgtt aaaatttcag      540 aaaaagtacg cagtacccct aattggaaca gtttgttttg ctctgccaac tttgattcca      600
gtctactgtt ggggcgaatc gtggaacaac gcttggcaca tagccttatt tcgatacata      660
ttcaatctta acgtgacttt cctagtcaac agtgctgcgc atatctgggg gaataagcct      720
tatgataaaa gcatcttgcc cgctcaaaac ctgctggttt ccttcctagc aagtggagaa      780
ggcttccata attaccatca cgtctttcca tgggattacc gcacagcaga attagggaat      840
```

```
aacttcctga atttgacgac gctgttcatt gattttgtg cctggtttgg atgggcttat      900
gacttgaagt ctgtatcaga ggatattata aaacagagag ctaaacgaac aggtgacggt      960
tcttcagggg tcatttgggg atgggacgac aaagacatgg accgcgatat aaaatctaaa     1020
gctaacattt tttatgctaa aaaggaatga                                      1050

<210> SEQ ID NO 25
<211> LENGTH: 1017
<212> TYPE: DNA
<213> ORGANISM: Helicoverpa zea

<400> SEQUENCE: 25
atggcccaaa gctatcaatc aactacggtt ttgagtgagg agaaagaact aacactgcaa       60
catttggtgc cccaagcatc gcccaggaag tatcaaatag tgtatccgaa cctcattacg      120
tttggttact ggcacatagc cggactttat ggcctttact tgtgcttcac ttctgctaaa      180
tgggctacga ttttattcag ctacatcctc ttcgtgttag cagaaatagg aatcacggct      240
ggcgctcaca gactctgggc ccacaaaact tacaaagcga aactaccatt agaaatactc      300
ttaatggtat tcaactccat cgcttttcaa aactcagcca ttgactgggt gagggaccac      360
cgactccacc ataagtatag cgatacagat gctgatcccc acaatgccag ccgagggttc      420
ttttattccc atgtaggatg gctacttgtg agaaaacatc ctgaagtcaa aaagcgaggg      480
aaagaactca atatgtccga tatttacaac aatcctgtcc tgcggtttca gaaaaaatac      540
gccatacccT tcattgggc tgtttgtttc gccttaccta caatgatacc tgtttacttc      600 tgggagaaa cctggtccaa tgcttggcat atcaccatgc ttcgctacat catgaacctc      660
aatgtcacct ttttggtaaa cagcgctgct catatatggg aaacaagcc ttatgacgca      720 aaaatattac ctgcacaaaa tgtagctgtg tcggtcgcca ctggtggaga aggtttccat      780
aattaccacc atgtcttccc ctgggattat cgagcagcgg aactcggtaa caatagcctc      840
aatctgacga ctaaattcat agatttattc gcagcaatcg gatgggcata tgatctgaag      900
acggtttcgg aggatatgat aaaacaaagg attaaacgca ctggagatgg aacggatctt      960
tggggacacg aacaaaactg tgatgaagtg tgggatgtaa aagataaatc aagttaa      1017

<210> SEQ ID NO 26
<211> LENGTH: 1050
<212> TYPE: DNA
<213> ORGANISM: Artificial Sequence
<220> FEATURE:
<223> OTHER INFORMATION: Trichoplusia ni Z11 desaturase Homo sapiens
      optimized

<400> SEQUENCE: 26
atggccgtga tggcccagac cgtgcaggag accgcaacag tgctggagga ggaggcaagg       60
accgtgacac tggtggcacc caagaccaca cctagaaagt acaagtatat ctacaccaac      120
ttcctgacct tcagctacgc acacctggcc gccctgtatg actgtacct gtgctttacc      180 tccgccaagt gggagacact gctgttctct tttgtgctgt tccacatgag caatatcgga      240
atcaccgcag agcacacag gctgtggacc cacaagacat caaggccaa gctgcctctg      300 gagatcgtgc tgatgatctt caactctctg gcctttcaga ataccgccat cacatgggcc      360
cgggagcaca gactgcacca caagtatagc gacaccgatg cagacccaca caacgcaagc      420
aggggcttct tttactccca cgtgggctgg ctgctggtga agaagcaccc cgacgtgctg      480
aagtatggca agacaatcga catgtccgac gtgtacaaca tcccgtgct gaagtttcag      540
```

```
aagaagtatg ccgtgcctct gatcggcacc gtgtgcttcg ccctgccaac actgatcccc       600
gtgtattgtt ggggcgagtc ttggaacaat gcctggcaca tcgccctgtt ccggtacatc       660
tttaacctga atgtgacctt tctggtgaac tccgccgccc acatctgggg caataagcct       720
tacgacaagt ctatcctgcc agcccagaac ctgctggtgt ccttcctggc ctctggcgag       780
ggctttcaca attatcacca cgtgttccca tgggactaca ggaccgcaga gctgggcaac       840
aattttctga acctgaccac actgttcatc gattttgtg cctggttcgg ctgggcctat        900
gacctgaagt ctgtgagcga ggatatcatc aagcagaggg caaagaggac aggcgatggc       960
agctccggcg tgatctgggg gatgggacgat aaggatatgg acagagatat caagagcaag      1020
gccaatatct tctacgccaa gaaggagtga                                        1050
```

<210> SEQ ID NO 27
<211> LENGTH: 1017
<212> TYPE: DNA
<213> ORGANISM: Artificial Sequence
<220> FEATURE:
<223> OTHER INFORMATION: Helicoverpa zea Z11 desaturase Homo sapiens
      optimized

<400> SEQUENCE: 27

```
atggcacagt catatcagag cactaccgtc ctgagcgaag agaaggaact gacactgcag       60
cacctggtcc cacaggcatc acctagaaag taccagatcg tgtatccaaa cctgatcacc      120
ttcggctact ggcacatcgc cggcctgtac ggcctgtatc tgtgctttac ctccgccaag      180
tgggccacaa tcctgttctc ttacatcctg tttgtgctgg cagagatcgg aatcaccgca      240
ggagcacaca gactgtgggc acacaagaca tataaggcca agctgcccct ggagatcctg      300
ctgatggtgt tcaacagcat cgcctttcag aattccgcca tcgattgggt gcgggaccac      360
agactgcacc acaagtactc cgacaccgat gccgacccc acaacgcctc tagggcttc        420 tttttatagcc acgtgggatg gctgctggtg cggaagcacc ctgaggtgaa gaagagaggc      480
aaggagctga atatgtctga tatctacaac aatcctgtgc tgcgcttcca gaagaagtat      540
gccatcccat tcatcggcgc cgtgtgcttt gccctgccca ccatgatccc cgtgtacttt      600
tggggcgaga catggagcaa cgcctggcac atcacaatgc tgcggtatat catgaacctg      660
aatgtgacat tcctggtgaa ctccgccgcc cacatctggg gcaataagcc atacgacgcc      720
aagatcctgc ccgcccagaa cgtggccgtg agcgtggcaa ccggaggaga gggcttccac      780
aattaccacc acgtgtttcc ttgggattat cgggccgccg agctgggcaa caattctctg      840
aatctgacca caaagttcat cgacctgttt gccgccatcg gctgggccta tgatctgaag      900
acagtgagcg aggacatgat caagcagagg atcaagcgca ccggcgatgg cacagacctg      960
tgggggcacg agcagaactg tgatgaagtg tgggatgtga aagacaagtc ctcctaa        1017
```

<210> SEQ ID NO 28
<211> LENGTH: 1065
<212> TYPE: DNA
<213> ORGANISM: Artificial Sequence
<220> FEATURE:
<223> OTHER INFORMATION: Y. lipolytica OLE1 leader - T. ni Z11
      desaturase Homo sapiens optimized

<400> SEQUENCE: 28

```
atggtgaaga acgtggacca ggtggatctg tctcaggtgg acaccatcgc aagcggaagg        60
gatgtgaatt ataaggtgaa gtacacatct ggcgtgaaga ccacaccaag aaagtacaag      120
```

| | |
|---|---|
| tatatctaca ccaacttcct gacatttttct tacgcccacc tggccgccct gtatggcctg | 180 |
| tacctgtgct ttaccagcgc caagtgggag acactgctgt tctcctttgt gctgttccac | 240 |
| atgtctaata tcggaatcac cgcaggagca cacaggctgt ggacccacaa gacattcaag | 300 |
| gccaagctgc ccctggagat cgtgctgatg atcttcaact ccctggcctt tcagaatacc | 360 |
| gccatcacat gggcccggga gcacagactg caccacaagt attctgacac cgatgcagac | 420 |
| ccacacaacg caagcagggg cttcttttac tcccacgtgg gctggctgct ggtgaagaag | 480 |
| caccctgacg tgctgaagta tggcaagaca atcgacatga gcgacgtgta caacaatcct | 540 |
| gtgctgaagt tcagaagaa gtatgccgtg ccactgatcg gcaccgtgtg cttcgccctg | 600 |
| cccacactga tccccgtgta ctgttggggc gagtcctgga caatgcctg gcacatcgcc | 660 |
| ctgttccggt acatctttaa cctgaatgtg acctttctgg tgaacagcgc cgcccacatc | 720 |
| tggggcaata agccatacga caagtccatc ctgcccgccc agaacctgct ggtgtccttc | 780 |
| ctggcctctg gcgagggctt tcacaattat caccacgtgt tcccttggga ctacaggacc | 840 |
| gcagagctgg gcaacaattt tctgaacctg accacactgt tcatcgattt ttgtgcctgg | 900 |
| ttcggctggg cctatgacct gaagtctgtg agcgaggata tcatcaagca gagggcaaag | 960 |
| aggacaggcg atggcagctc cggcgtgatc tggggatggg acgataagga tatggacaga | 1020 |
| gatatcaagt ccaaggccaa tatcttctac gccaagaagg agtga | 1065 |

<210> SEQ ID NO 29
<211> LENGTH: 1029
<212> TYPE: DNA
<213> ORGANISM: Artificial Sequence
<220> FEATURE:
<223> OTHER INFORMATION: Y. lipolytica OLE1 leader - H. zea Z11
 desaturase Homo sapiens optimized

<400> SEQUENCE: 29

| | |
|---|---|
| atggtgaaaa acgtggacca agtggatctc tcgcaggtcg acaccattgc ctccggccga | 60 |
| gatgtcaact acaaggtcaa gtacacctcc ggcgttcgca agtatcagat cgtgtatcct | 120 |
| aacctgatca ccttcggcta ctggcatatc gctggactgt acggactgta tctgtgcttc | 180 |
| acttccgcca gtgggccac catcctgttc tcttacatcc tgtttgtgct ggcagagatc | 240 |
| ggaatcaccg caggagcaca cagactgtgg gcacacaaga catataaggc caagctgcca | 300 |
| ctggagatcc tgctgatggt gttcaacagc atcgccttc agaattccgc catcgattgg | 360 |
| gtgcgggacc acagactgca ccacaagtac tccgacacag atgccgaccc ccacaacgcc | 420 |
| tctaggggct tcttttatag ccacgtggga tggctgctgg tgcggaagca ccctgaggtg | 480 |
| aagaagagag gcaaggagct gaatatgtct gatatctaca acaatcctgt gctgcgcttc | 540 |
| cagaagaagt atgccatccc attcatcggc gccgtgtgct tgccctgcc accatgatc | 600 |
| cccgtgtact tttggggcga cacatggagc aacgcctggc acatcacaat gctgcggtat | 660 |
| atcatgaacc tgaatgtgac attcctggtg aactccgccg cccacatctg ggcaataag | 720 |
| ccatacgacg ccaagatcct gcccgcccag aacgtggccg tgagcgtggc aaccggagga | 780 |
| gagggcttcc acaattacca ccacgtgttt ccatgggatt atgggcagc agagctggga | 840 |
| aacaattctc tgaatctgac cacaaagttc atcgacctgt tgccgccat cggctgggcc | 900 |
| tatgatctga agacagtgag cgaggacatg atcaagcaga ggatcaagcg caccggcgat | 960 |
| ggcacagacc tgtgggggca cgagcagaat tgtgatgaag tgtgggatgt gaaggataaa | 1020 |
| agcagttga | 1029 |

<210> SEQ ID NO 30
<211> LENGTH: 981
<212> TYPE: DNA
<213> ORGANISM: Amyelois transitella

<400> SEQUENCE: 30

| | | | | | |
|---|---|---|---|---|---|
| atggtccctα | acaagggttc | cagtgacgtt | ttgtctgaac | attctgagcc | ccagttcact | 60 |
| aaactcatag | ctccacaagc | agggccgagg | aaatacaaga | tagtgtatcg | aaatttgctc | 120 |
| acattcggct | attggcactt | atcagctgtt | tatgggctct | acttgtgctt | tacttgtgcg | 180 |
| aaatgggcta | ccatcttatt | tgcatttttc | ttatacgtga | tcgcggaaat | cggtataaca | 240 |
| ggtggcgctc | ataggctatg | gcacatcgg | acttataaag | ccaagttgcc | tttagagatt | 300 |
| ttgttactca | taatgaattc | tattgccttc | aagacactg | ctttcacctg | ggctcgagat | 360 |
| caccgccttc | atcacaaata | ttcggatact | gacgctgatc | cccacaatgc | taccagaggg | 420 |
| ttttctatt | cacatgtagg | ctggcttttg | gtgaagaaac | ccctgaagt | caaagcaaga | 480 |
| ggaaaatact | tgtcgttaga | tgatcttaag | aataatccat | tgcttaaatt | ccaaaagaaa | 540 |
| tacgctattc | tagttatagg | cacgttatgc | ttccttatgc | caacatttgt | gcccgtatac | 600 |
| ttctggggcg | agggcatcag | cacggcctgg | aacatcaatc | tattgcgata | cgtcatgaat | 660 |
| cttaacatga | ctttcttagt | taacagtgca | gcgcatatct | ttggcaacaa | accatacgat | 720 |
| aagagcatag | cctcagtcca | aaatatttca | gttagcttag | ctacttttgg | cgaaggattc | 780 |
| cataattacc | atcacactta | cccctgggat | tatcgtgcgg | cagaattagg | aaataatagg | 840 |
| ctaaatatga | ctactgcttt | catagatttc | ttcgcttgga | tcggctgggc | ttatgacttg | 900 |
| aagtctgtgc | cacaagaggc | cattgcaaaa | aggtgtgcga | aaactggcga | tggaacggat | 960 |
| atgtggggtc | gaaaaagata | a | | | | 981 |

<210> SEQ ID NO 31
<211> LENGTH: 1017
<212> TYPE: DNA
<213> ORGANISM: Helicoverpa zea

<400> SEQUENCE: 31

| | | | | | |
|---|---|---|---|---|---|
| atggcccaaa | gctatcaatc | aactacggtt | ttgagtgagg | agaaagaact | aacattacaa | 60 |
| catttggtgc | cccaagcatc | gcccaggaag | tatcaaatag | tgtatccgaa | cctcattacg | 120 |
| tttggttact | ggcacatagc | cggactttat | ggcctttact | tgtgcttcac | ttctgctaaa | 180 |
| tgggctacga | ttttattcag | ctacatcctc | ttcgtgttag | cagaaatagg | aatcacggct | 240 |
| ggcgctcaca | gactctgggc | ccacaaaact | tacaaagcga | aactaccatt | agaaatactc | 300 |
| ttaatggtat | tcaactccat | cgcttttcaa | aactcagcca | ttgactgggt | gagggaccac | 360 |
| cgactccacc | ataagtatag | cgatacagat | gctgatcccc | acaatgccag | ccgagggttc | 420 |
| ttttattccc | atgtaggatg | gctacttgtg | agaaaacatc | ctgaagtcaa | aaagcgaggg | 480 |
| aaagaactca | atatgtccga | tatttacaac | aatcctgtct | tacggtttca | gaaaaaatac | 540 |
| gccataccct | tcattggggc | tgtttgtttc | gccttaccta | caatgatacc | tgtttacttc | 600 |
| tggggagaaa | cctggtccaa | tgcttggcat | atcaccatgc | ttcgctacat | catgaacctc | 660 |
| aatgtcacct | ttttggtaaa | cagcgctgct | catatatggg | gaaacaagcc | ttatgacgca | 720 |
| aaaatattac | ctgcacaaaa | tgtagctgtg | tcggtcgcca | ctggtggaga | aggtttccat | 780 |
| aattaccacc | atgtcttccc | ctgggattat | cgagcagcgg | aactcggtaa | caatagcctc | 840 |
| aatttaacga | ctaaattcat | agatttattc | gcagcaatcg | gatgggcata | tgatttaaag | 900 |

```
acggtttcgg aggatatgat aaaacaaagg attaaacgca ctggagatgg aacggatctt      960
tggggacacg aacaaaactg tgatgaagtg tgggatgtaa agataaaatc aagttaa       1017
```

<210> SEQ ID NO 32
<211> LENGTH: 1368
<212> TYPE: DNA
<213> ORGANISM: Artificial Sequence
<220> FEATURE:
<223> OTHER INFORMATION: pPV0228 - Helicoverpa armigera reductase codon
      optimized

<400> SEQUENCE: 32

```
atggtcgttt taacttctaa agagacaaaa ccttcagtag ctgagtttta tgcgggaaaa       60
tctgttttta ttacgggtgg cactggattc cttggaaagg tattcataga gaacttttta      120
tatagctgtc cagatatcga gaatatctac atgctcatac gagagaagaa aggtcttttct     180 gttagcgaaa gaataaaaca gttccttgat gacccgctct ttaccagact aaaagacaaa      240
agaccagctg actagagaa gattgtatta ataccaggga atattactgc tcctgactta       300
ggcattaatt ctgaaaacga gaagatgctt atagagaagg tatcggtgat tattcattcg      360
gctgctacgg tgaagtttaa tgagcctctc cctacggctt ggaagatcaa cgtggaagga      420
accagaatga tgttagcttt gagtcgaaga tgaagcgga ttgaggtttt cattcacata      480
tcgacagcat acacgaacac aaacagggaa gtggttgacg atcttata cccagctcct       540 gctgatatcg accaagttca tcagtatgtc aaagatggaa tctctgagga agacactgag      600
aaaatattaa atggtcgtcc aaatacgtac acgtttacga aagcgttaac tgagcattta      660
gttgctgaga accaagccta cgtacccact attatcgtca ggccgtcagt cgtggcagca      720
ataaaagatg agccattaaa aggttggtta ggcaactggt ttggagcgac tggtctcacc      780
gtgttcaccg ctaagggtct caaccgagtc atctacggtc attctagcta catcgtagac      840
ttaattcctg tggattatgt cgctaattta gtgattgctg ctggggctaa gagtagcaag      900
tcaactgagt tgaaggtata caactgctgc agcagctcct gcaatcccgt cactattggc      960
acgttaatga gcatgtttgc tgacgatgcc atcaaacaga gtcgtatgc tatgccgcta      1020 ccggggtggt acatattcac gaaatataag tggttagttc ttcttttaac atttctcttc     1080
caagttatac cggcgtatgt cacagatctc tccaggcact tgattgggaa gagtccacgg      1140
tacataaaac tccaatcact agtaaatcaa acgcgctctt caatcgactt cttcacgaat      1200
cactcctggg tgatgaaggc agacagagtg agagagttat atgcgtctct ttcccccgca      1260
gacaagtact tatttccctg tgatcctacg gacattaact ggacacatta catacaagac      1320
tactgttggg gagtccgaca ttttttggag aaaaaaagct acgaataa                  1368
```

<210> SEQ ID NO 33
<211> LENGTH: 1478
<212> TYPE: DNA
<213> ORGANISM: Candida tropicalis

<400> SEQUENCE: 33

```
tattaggcga agaggcatct agtagtagtg gcagtggtga gaacgtgggc gctgctatag       60
tgaacaatct ccagtcgatg gttaagaaga agagtgacaa accagcagtg aatgacttgt      120
ctgggtccgt gaggaaaaga aagaagcccg cacacaaagga cagtaacgtc aagaaaccca     180
agaaataggg gggaccctgtt tagatgtata ggaataaaaa ctccgagatg atctcaatgt    240
gtaatggagt tgtaatattg caaggggga aaatcaagac tcaaacgtgt gtatgagtga      300
```

```
gcgtacgtat atctccgaga gtagtatgac ataatgatga ctgtgaatca tcgtaatctc    360
acacaaaaac cccattgtcg gccatatacc acaccaagca acaccacata tcccccggaa    420
aaaaaaacgt gaaaaaaaga aacaatcaaa actacaacct actccttgat cacacagtca    480
ttgatcaagt tacagttcct gctagggaat gaccaaggta caaatcagca ccttaatggt    540
tagcacgctc tcttactctc tctcacagtc ttccggcccc tattcaaaat tctgcacttc    600
catttgaccc cagggttggg aaacagggcc acaaagaaa acccgacgt gaatgaaaaa     660 actaagaaaa gaaaaaaat tatcacacca gaaatttacc taattgggta attcccatcg    720 gtgttttttcc tggattgtcg cacgcacgca tgctgaaaaa agtgttcgag ttttgctttt    780
gcctcggagt ttcacgcaag ttttcgatc tcggaaccgg agggcggtcg ccttgttgtt     840
tgtgatgtcg tgctttgggt gttctaatgt gctgttattg tgctcttttt ttttcttctt    900
tttttggtga tcatatgata ttgctcggta gattactttc gtgtgtaggt attcttttag    960
acgtttggtt attgggtaga tatgagagag agagagtggg tggggagga gttggttgta    1020 ggagggaccc ctgggaggaa gtgtagttga ttttccctg acgaatgaaa atacgttttt    1080
gagaagataa tacaggaaag gtgtgtcggt gaatttccat ctatccgagg atatgagtgg    1140
aggagagtcg tgtgcgtgtg gttaatttag gatcagtgga acacacaaag taactaagac    1200
agagagacag agagaaaaat ctggggaaga gacaaagagt cagagtgtgt gagttattct    1260
gtattgtgaa attttttttgc ccaactacat aatattgctg aaactaattt tacttaaaaa    1320
gaaaagccaa caacgtcccc agtaaaaactt ttctataaat atcagcagtt ttccctttcc    1380
tccattcctc ttcttgtctt ttttcttact ttccctttt tataccttt cattatcatc     1440 ctttataatt gtctaaccaa caactatata tctatcaa                          1478

<210> SEQ ID NO 34
<211> LENGTH: 586
<212> TYPE: DNA
<213> ORGANISM: Candida tropicalis

<400> SEQUENCE: 34
aggaagacaa ccaaaagaaa gatcaaattg actaaatgtt gaacagacca aaaaaaaga     60 acaacaaata gataaattac aacatattaa tcttttgata tgttgttgaa tattctagta    120
aatctaatga tctcaatagt ggttatcatt cactctcttc gtcctcctct ctcccctcct    180
cctcttgcag tatattaaaa gcaataaaaa aaaaaaaaa aagaaaatct gccaacacac    240
acaaaaaaaa cttacatagt cgtgtaccag tgtcaatatt tcaccagcgc agagaaaaga    300
agatgaacag aaaaattttc tctttggttt tgtctttggt tttgtattaa tctcattgaa    360 aaatttttc tctctctctc tctctctctc tcactcacac actcactcgc atttcgtttg    420
ggttacagca gaagtcagac agaaaaaaaa aatcgtatat aactctcatc aaatgcccta    480
gagaaaaatt tttcttctat cctttttttt ttcttcttct tcttcttttc cttttttctt    540
ttagaagatc ttttttgaatt catcaaagat atatatttaa tcaatc                  586

<210> SEQ ID NO 35
<211> LENGTH: 297
<212> TYPE: DNA
<213> ORGANISM: Candida tropicalis

<400> SEQUENCE: 35
aagaaaaaag aaaaggtaaa gaacttcatt tgagatgaac ttttgtatat gactttagt     60
```

```
ttctactttt tttttattt attgcttaat tttctttatt tcaatccccc atagtttgtg    120
tagaatatat ttattcattc tggtaactca aacacgtagc aagctcgttg catctcgcct    180
cgtcacgggt acagctctgg aaccaaagac aaaaaaaaaa gttgatccga accctctcgc    240
tattccttgc tatgctatcc acgagatggg gtttatcagc ccaggcaagt cactaaa      297
```

<210> SEQ ID NO 36
<211> LENGTH: 217
<212> TYPE: DNA
<213> ORGANISM: Candida tropicalis

<400> SEQUENCE: 36

```
gctgattaat gaataattaa taagtattgt ttttttgtt tttaatatat atatatcttg    60
aaattagtat aaaaaaaatc ttttttttt ctttttatt tattttatca atagtttata    120
tatatatata tataaacttg taagagatta ggtatatcta acagtgatac tactaatagt    180
gcttaatatc tttgttaaac aagaaaataa aataaac                            217
```

<210> SEQ ID NO 37
<211> LENGTH: 2487
<212> TYPE: DNA
<213> ORGANISM: Artificial Sequence
<220> FEATURE:
<223> OTHER INFORMATION: SapI-tLIP2-pEXP1-HA_FAR-SapI (insert into
      pPV199 creating pPV247)

<400> SEQUENCE: 37

```
gcctgaagag cgctatttat cactctttac aacttctacc tcaactatct actttaataa    60
atgaatatcg tttattctct atgattactg tatatgcgtt cctccatggg agtttggcgc    120
ccgttttttc gagccccaca cgtttcggtg agtatgagcg gcggcagatt cgagcgtttc    180
cggtttccgc ggctggacga gagcccatga tgggggctcc caccaccagc aatcagggcc    240
ctgattacac acccacctgt aatgtcatgc tgttcatcgt ggttaatgct gctgtgtgct    300
gtgtgtgtgt gttgtttggc gctcattgtt gcgttatgca gcgtacacca caatattgga    360
agcttattag cctttctatt ttttcgtttg caaggcttaa caacattgct gtggagaggg    420
atggggatat ggaggccgct ggagggagtc ggagaggcgt tttggagcgg cttggcctgg    480
cgcccagctc gcgaaacgca cctaggaccc tttggcacgc cgaaatgtgc cacttttcag    540
tctagtaacg ccttacctac gtcattccat gcatgcatgt ttgcgccttt tttcccttgc    600
ccttgatcgc cacacagtac agtgcactgt acagtggagg ttttgggggg gtcttagatg    660
ggagctaaaa gcggctagc ggtacactag tgggattgta tgggagtggca tggagcctag    720 gtggagcctg acaggacgca cgaccggcta gcccgtgaca gacgatgggt ggctcctgtt    780
gtccaccgcg tacaaatgtt tgggccaaag tcttgtcagc cttgcttgcg aacctaattc    840
ccaattttgt cacttcgcac ccccattgat cgagccctaa cccctgccca tcaggcaatc    900
caattaagct cgcattgtct gccttgttta gtttggctcc tgcccgtttc ggcgtccact    960
tgcacaaaca caaacaagca ttatatataa ggctcgtctc tccctcccaa ccacactcac    1020 tttttttgccc gtcttccctt gctaacacaa aagtcaagaa cacaaacaac cacccccaacc    1080 cccttacaca caagacatat ctacagcaat ggtggtgctg accagcaagg agacaaagcc    1140
ttccgtggcc gagttctacg ccggcaagtc cgtgtttatc acaggcggca ccggcttcct    1200
gggcaaggtg tttatcgaga agctgctgta ctccttgccca gacatcgaga acatctatat    1260
gctgatccgg gagaagaagg gcctgagcgt gtccgagaga atcaagcagt cctggacga    1320
```

-continued

| | |
|---|---|
| tcccctgttt acacggctga aggacaagag acctgccgat ctggagaaga tcgtgctgat | 1380 |
| cccaggcgac atcaccgcac cagatctggg catcaactcc gagaatgaga agatgctgat | 1440 |
| cgagaaggtg tccgtgatca tccactctgc cgccaccgtg aagttcaacg agcccctgcc | 1500 |
| tacagcctgg aagatcaatg tggagggcac caggatgatg ctggccctga gccggagaat | 1560 |
| gaagcgcatc gaggtgttta tccacatctc cacagcctac accaacacaa atcgggaggt | 1620 |
| ggtggacgag atcctgtacc cagccccgc cgacatcgat caggtgcacc agtatgtgaa | 1680 |
| ggacggcatc agcgaggagg ataccgagaa gatcctgaac ggccggccaa atacctacac | 1740 |
| attcaccaag gccctgacag agcacctggt ggccgagaac caggcctatg tgcctaccat | 1800 |
| catcgtgaga ccatccgtgg tggccgccat caaggatgag cccctgaagg gatggctggg | 1860 |
| aaactggttc ggagcaacag gactgaccgt gtttacagcc aagggcctga atagagtgat | 1920 |
| ctacggccac agctcctata tcgtggacct gatccccgtg gattacgtgg caaacctggt | 1980 |
| catcgcagca ggagccaagt ctagcaagtc taccgagctg aaggtgtata actgctgttc | 2040 |
| ctctagctgt aatcctgtga ccatcggcac actgatgtcc atgttcgccg acgatgccat | 2100 |
| caagcagaag tcttacgcca tgcctctgcc aggctggtac atctttacaa agtataagtg | 2160 |
| gctggtgctg ctgctgacct tcctgtttca ggtcatccca gcctacgtga ccgatctgtc | 2220 |
| taggcacctg atcggcaaga gccccgcta tatcaagctg cagtctctgg tgaaccagac | 2280 |
| caggtcctct atcgacttct ttacaaatca cagctgggtc atgaaggccg ataggtgcg | 2340 |
| cgagctgtac gcctctctga gccctgccga caagtatctg ttcccctgcg accctaccga | 2400 |
| tatcaattgg acacactaca tccaggatta ttgttggggc gtgcgccact tcctggagaa | 2460 |
| gaagtcctat gagtgagcct gaagagc | 2487 |

<210> SEQ ID NO 38
<211> LENGTH: 1012
<212> TYPE: DNA
<213> ORGANISM: Artificial Sequence
<220> FEATURE:
<223> OTHER INFORMATION: NcoI-pTAL-AleI (insert into pPV247 creating pPV248)

<400> SEQUENCE: 38

| | |
|---|---|
| ccatgggtaa gcaggtggct ccgtttgtgt ctttgtgttt ttcccctcct ttttggacca | 60 |
| tttgtcagca tgttgcgtag gtctgggtgt ttgactgttc aggtggtgga tgacggatgc | 120 |
| atcatctgac ggcagagtgg gtacctggca gtggcaggct cgcagacgag gtagagagat | 180 |
| tctgaaagga gccattgaca gatggagaat tggatactcc tggtatgtcc tccgtttcca | 240 |
| cttttgacgt tggtgacgtg ctctggaacg acttttttct ttttctttaa aacaaaaaaa | 300 |
| agaaagaaaa aaaaaacatt tactactacc agtagtacac ctcaacattg ggtccagaac | 360 |
| gtcccaactg catgagtcac tggagtcatg ccgaggtcgc taaggtgctg taaaatacaa | 420 |
| cgtcaattga gagagacaca ggcgcagcgc gccgagggag aaacgaggca tttatcttct | 480 |
| gaccctcctt tttactcgta atctgtatcc cggaaccgcg tcgcatccat gttaattaaa | 540 |
| tcaacactta cacttgcttg cttcgtatga tgaagatttc tgactggcaa cccagtcagc | 600 |
| agcagattgg ggcagatgta gtaatgaaaa acactgcaag gtgtgacgtt tgagacactc | 660 |
| caattggtta gaaagcgaca agaagacgt cggaaaaata ccggaaaaat cgagtctttt | 720 |
| tctttctgcg tattgggccc ttctgcctcc tttgccgccc tttccacgct ctttccacac | 780 |
| cctcacactc cctgagcact atgatctcat tgcgcaataa gatatacatg cacgtgcatt | 840 |

```
tggtgagcac gcagaacctt gttgggggaa gatgccctaa ccctaagggc gttccatacg    900
gttcgacaga gtaaccttgc tgtcgattat aacgcatata tagccccccc cttcggaccc    960
tccttctgat ttctgtttct gtatcaacat tacacacaaa cacacaatgg tg           1012
```

<210> SEQ ID NO 39
<211> LENGTH: 324
<212> TYPE: PRT
<213> ORGANISM: Sesamia inferens

<400> SEQUENCE: 39

```
Met Leu Ser Gln Glu Glu Pro Thr Asp Thr Ser Leu Val Pro Arg Ala
1               5                   10                  15

Ala Pro Arg Lys Tyr Gln Ile Val Tyr Pro Asn Leu Ile Thr Phe Gly
            20                  25                  30

Tyr Trp His Leu Ala Gly Leu Tyr Gly Leu Tyr Leu Cys Phe Thr Ser
        35                  40                  45

Ala Lys Trp Thr Thr Ile Leu Phe Ser Phe Ile Leu Cys Val Ile Ala
    50                  55                  60

Glu Ile Gly Val Thr Ala Gly Ala His Arg Leu Trp Ala His Lys Thr
65                  70                  75                  80

Tyr Lys Ala Asn Leu Pro Leu Gln Ile Leu Met Val Met Asn Ser
                85                  90                  95

Ile Ala Phe Gln Asn Ser Ala Ile Asp Trp Val Arg Asp His Arg Leu
            100                 105                 110

His His Lys Tyr Ser Asp Thr Asp Ala Asp Pro His Asn Ala Ser Arg
        115                 120                 125

Gly Phe Phe Tyr Ser His Val Gly Trp Leu Leu Val Lys Lys His Pro
    130                 135                 140

Glu Val Lys Lys Arg Gly Lys Glu Leu Asp Met Ser Asp Ile Tyr Ser
145                 150                 155                 160

Asn Pro Val Leu Arg Phe Gln Lys Gln Tyr Ala Ile Pro Phe Ile Gly
                165                 170                 175

Ala Val Cys Phe Ile Leu Pro Thr Val Ile Pro Val Tyr Cys Trp Gly
            180                 185                 190

Glu Thr Trp Thr Asn Ala Trp His Ile Thr Met Leu Arg Tyr Ile Thr
        195                 200                 205

Asn Leu Asn Val Thr Phe Leu Val Asn Ser Ala Ala His Ile Trp Gly
    210                 215                 220

Tyr Lys Pro Tyr Asp Glu Asn Ile Leu Pro Ala Gln Asn Ile Ala Val
225                 230                 235                 240

Ser Ile Ala Thr Cys Gly Glu Gly Phe His Asn Tyr His His Val Phe
                245                 250                 255

Pro Trp Asp Tyr Arg Ala Ala Glu Leu Gly Asn Asn Asn Leu Asn Leu
            260                 265                 270

Thr Thr Lys Phe Ile Asp Phe Phe Ala Trp Leu Gly Trp Ala Tyr Asp
        275                 280                 285

Leu Lys Thr Val Ser Ser Asp Met Ile Lys Leu Arg Ala Lys Arg Thr
    290                 295                 300

Gly Asp Gly Thr Asn Leu Trp Gly Glu His Asn Asp Glu Leu Lys Glu
305                 310                 315                 320

Gly Lys Glu Asp
```

<210> SEQ ID NO 40
<211> LENGTH: 1368

```
<212> TYPE: DNA
<213> ORGANISM: Artificial Sequence
<220> FEATURE:
<223> OTHER INFORMATION: Helicoverpa armigera FAR from SEQ ID NO: 37

<400> SEQUENCE: 40
atggtggtgc tgaccagcaa ggagacaaag ccttccgtgg ccgagttcta cgccggcaag      60
tccgtgttta tcacaggcgg caccggcttc ctgggcaagg tgtttatcga agctgctg      120
tactcttgcc agacatcga aacatctat atgctgatcc gggagaagaa gggcctgagc      180
gtgtccgaga aatcaagca gttcctggac gatcccctgt tacacggct aaggacaag      240
agacctgccg atctggagaa gatcgtgctg atcccaggcg acatcaccgc accagatctg      300
ggcatcaact ccgagaatga aagatgctg atcgagaagg tgtccgtgat catccactct      360
gccgccaccg tgaagttcaa cgagcccctg cctacagcct ggaagatcaa gtgagggc      420
accaggatga tgctggccct gagccggaga atgaagcgca tcgaggtgtt tatccacatc      480
tccacagcct acaccaacac aaatcgggag gtggtggacg agatcctgta cccagccccc      540
gccgacatcg atcaggtgca ccagtatgtg aaggacggca tcagcgagga ggataccgag      600
aagatcctga acgccggcc aaatacctac acattcacca aggccctgac agagcacctg      660
gtggccgaga accaggccta tgtgcctacc atcatcgtga ccatccgt ggtggccgcc      720
atcaaggatg agcccctgaa gggatggctg gaaaactggt tcggagcaac aggactgacc      780
gtgtttacag ccaagggcct gaatagagtg atctacggcc acagctccta tatcgtggac      840
ctgatcccg tggattacgt ggcaaacctg gtcatcgcag caggagccaa gtctagcaag      900
tctaccgagc tgaaggtgta taactgctgt tcctctagct gtaatcctgt gaccatcggc      960
acactgatgt ccatgttcgc cgacgatgcc atcaagcaga agtcttacgc catgcctctg     1020
ccaggctggt acatctttac aaagtataag tggctggtgc tgctgctgac cttcctgttt     1080
caggtcatcc cagcctacgt gaccgatctg tctaggcacc tgatcggcaa gagccccgc     1140
tatatcaagc tgcagtctct ggtgaaccag accaggtcct ctatcgactt ctttacaaat     1200
cacagctggg tcatgaaggc cgataggtg cgcgagctgt acgcctctct gagccctgcc     1260
gacaagtatc tgttcccctg cgaccctacc gatatcaatt ggacacacta catccaggat     1320
tattgttggg gcgtgcgcca cttcctggag aagaagtcct atgagtga                 1368

<210> SEQ ID NO 41
<211> LENGTH: 455
<212> TYPE: PRT
<213> ORGANISM: Artificial Sequence
<220> FEATURE:
<223> OTHER INFORMATION: Helicoverpa armigera alcohol forming reductase
      (HaFAR)

<400> SEQUENCE: 41

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
                20                  25                  30

Lys Val Phe Ile Glu Lys Leu Leu Tyr Ser Cys Pro Asp Ile Glu Asn
            35                  40                  45

Ile Tyr Met Leu Ile Arg Glu Lys Lys Gly Leu Ser Val Ser Glu Arg
        50                  55                  60

Ile Lys Gln Phe Leu Asp Asp Pro Leu Phe Thr Arg Leu Lys Asp Lys
65                  70                  75                  80
```

```
Arg Pro Ala Asp Leu Glu Lys Ile Val Leu Ile Pro Gly Asp Ile Thr
             85                  90                  95

Ala Pro Asp Leu Gly Ile Asn Ser Glu Asn Glu Lys Met Leu Ile Glu
        100                 105                 110

Lys Val Ser Val Ile Ile His Ser Ala Ala Thr Val Lys Phe Asn Glu
    115                 120                 125

Pro Leu Pro Thr Ala Trp Lys Ile Asn Val Glu Gly Thr Arg Met Met
130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Asp Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Leu Lys Gly Trp Leu Gly Asn Trp Phe Gly Ala
                245                 250                 255

Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Cys Asn Pro Val Thr Ile Gly
305                 310                 315                 320

Thr Leu Met Ser Met Phe Ala Asp Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Phe Leu Phe Gln Val Ile Pro Ala Tyr Val Thr
        355                 360                 365

Asp Leu Ser Arg His Leu Ile Gly Lys Ser Pro Arg Tyr Ile Lys Leu
    370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Tyr Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
        435                 440                 445

Leu Glu Lys Lys Ser Tyr Glu
    450                 455

<210> SEQ ID NO 42
<211> LENGTH: 455
<212> TYPE: PRT
<213> ORGANISM: Artificial Sequence
<220> FEATURE:
<223> OTHER INFORMATION: HaFAR S60A
```

<400> SEQUENCE: 42

| Met | Val | Val | Leu | Thr | Ser | Lys | Glu | Thr | Lys | Pro | Ser | Val | Ala | Glu | Phe |
| 1 | | | | 5 | | | | | 10 | | | | | 15 | |

Tyr Ala Gly Lys Ser Val Phe Ile Thr Gly Thr Gly Phe Leu Gly
            20                  25                  30

Lys Val Phe Ile Glu Lys Leu Leu Tyr Ser Cys Pro Asp Ile Glu Asn
        35                  40                  45

Ile Tyr Met Leu Ile Arg Glu Lys Lys Gly Leu Ala Val Ser Glu Arg
    50                  55                  60

Ile Lys Gln Phe Leu Asp Asp Pro Leu Phe Thr Arg Leu Lys Asp Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Asn Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Asp Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Leu Lys Gly Trp Leu Gly Asn Trp Phe Gly Ala
                245                 250                 255

Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ser Cys Asn Pro Val Thr Ile Gly
305                 310                 315                 320

Thr Leu Met Ser Met Phe Ala Asp Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Phe Leu Phe Gln Val Ile Pro Ala Tyr Val Thr
        355                 360                 365

Asp Leu Ser Arg His Leu Ile Gly Lys Ser Pro Arg Tyr Ile Lys Leu
    370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Tyr Ala Ser

```
                    405                 410                 415
Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
            435                 440                 445

Leu Glu Lys Lys Ser Tyr Glu
            450                 455

<210> SEQ ID NO 43
<211> LENGTH: 455
<212> TYPE: PRT
<213> ORGANISM: Artificial Sequence
<220> FEATURE:
<223> OTHER INFORMATION: HaFAR S195A

<400> SEQUENCE: 43

Met Val Val Leu Thr Ser Lys Glu Thr Lys Pro Ser Val Ala Glu Phe
1               5                   10                  15

Tyr Ala Gly Lys Ser Val Phe Ile Thr Gly Thr Gly Phe Leu Gly
            20                  25                  30

Lys Val Phe Ile Glu Lys Leu Leu Tyr Ser Cys Pro Asp Ile Glu Asn
            35                  40                  45

Ile Tyr Met Leu Ile Arg Glu Lys Lys Gly Leu Ser Val Ser Glu Arg
50                  55                  60

Ile Lys Gln Phe Leu Asp Asp Pro Leu Phe Thr Arg Leu Lys Asp Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Asn Ser Glu Asn Glu Lys Met Leu Ile Glu
            100                 105                 110

Lys Val Ser Val Ile Ile His Ser Ala Ala Thr Val Lys Phe Asn Glu
            115                 120                 125

Pro Leu Pro Thr Ala Trp Lys Ile Asn Val Glu Gly Thr Arg Met Met
            130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ala Glu Glu Asp Thr Glu Lys Ile Leu Asn Gly Arg Pro Asn
            195                 200                 205

Thr Tyr Thr Phe Thr Lys Ala Leu Thr Glu His Leu Val Ala Glu Asn
210                 215                 220

Gln Ala Tyr Val Pro Thr Ile Ile Val Arg Pro Ser Val Val Ala Ala
225                 230                 235                 240

Ile Lys Asp Glu Pro Leu Lys Gly Trp Leu Gly Asn Trp Phe Gly Ala
                245                 250                 255

Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
            275                 280                 285

Asn Leu Val Ile Ala Ala Gly Ala Lys Ser Ser Lys Ser Thr Glu Leu
            290                 295                 300

Lys Val Tyr Asn Cys Cys Ser Ser Ser Cys Asn Pro Val Thr Ile Gly
```

```
          305                 310                 315                 320
    Thr Leu Met Ser Met Phe Ala Asp Asp Ala Ile Lys Gln Lys Ser Tyr
                    325                 330                 335

Ala Met Pro Leu Pro Gly Trp Tyr Ile Phe Thr Lys Tyr Lys Trp Leu
                    340                 345                 350

Val Leu Leu Leu Thr Phe Leu Phe Gln Val Ile Pro Ala Tyr Val Thr
                    355                 360                 365

Asp Leu Ser Arg His Leu Ile Gly Lys Ser Pro Arg Tyr Ile Lys Leu
                    370                 375                 380

Gln Ser Leu Val Asn Gln Thr Arg Ser Ser Ile Asp Phe Phe Thr Asn
    385                 390                 395                 400

His Ser Trp Val Met Lys Ala Asp Arg Val Arg Glu Leu Tyr Ala Ser
                    405                 410                 415

Leu Ser Pro Ala Asp Lys Tyr Leu Phe Pro Cys Asp Pro Thr Asp Ile
                    420                 425                 430

Asn Trp Thr His Tyr Ile Gln Asp Tyr Cys Trp Gly Val Arg His Phe
                    435                 440                 445

Leu Glu Lys Lys Ser Tyr Glu
                    450                 455

<210> SEQ ID NO 44
<211> LENGTH: 455
<212> TYPE: PRT
<213> ORGANISM: Artificial Sequence
<220> FEATURE:
<223> OTHER INFORMATION: HaFAR S298A

<400> SEQUENCE: 44

Met Val Val Leu Thr Ser Lys Glu Thr Lys Pro Ser Val Ala Glu Phe
1               5                   10                  15

Tyr Ala Gly Lys Ser Val Phe Ile Thr Gly Thr Gly Phe Leu Gly
                20                  25                  30

Lys Val Phe Ile Glu Lys Leu Leu Tyr Ser Cys Pro Asp Ile Glu Asn
                35                  40                  45

Ile Tyr Met Leu Ile Arg Glu Lys Lys Gly Leu Ser Val Ser Glu Arg
50                  55                  60

Ile Lys Gln Phe Leu Asp Asp Pro Leu Phe Thr Arg Leu Lys Asp Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Asn Ser Glu Asn Glu Lys Met Leu Ile Glu
                100                 105                 110

Lys Val Ser Val Ile Ile His Ser Ala Ala Thr Val Lys Phe Asn Glu
                115                 120                 125

Pro Leu Pro Thr Ala Trp Lys Ile Asn Val Glu Gly Thr Arg Met Met
                130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
                180                 185                 190

Gly Ile Ser Glu Glu Asp Thr Glu Lys Ile Leu Asn Gly Arg Pro Asn
                195                 200                 205

Thr Tyr Thr Phe Thr Lys Ala Leu Thr Glu His Leu Val Ala Glu Asn
```

```
                    210                 215                 220
Gln Ala Tyr Val Pro Thr Ile Ile Val Arg Pro Ser Val Val Ala Ala
225                 230                 235                 240

Ile Lys Asp Glu Pro Leu Lys Gly Trp Leu Gly Asn Trp Phe Gly Ala
                    245                 250                 255

Thr Gly Leu Thr Val Phe Thr Ala Lys Gly Leu Asn Arg Val Ile Tyr
                260                 265                 270

Gly His Ser Ser Tyr Ile Val Asp Leu Ile Pro Val Asp Tyr Val Ala
            275                 280                 285

Asn Leu Val Ile Ala Ala Gly Ala Lys Ala Ser Lys Ser Thr Glu Leu
        290                 295                 300

Lys Val Tyr Asn Cys Cys Ser Ser Cys Asn Pro Val Thr Ile Gly
305                 310                 315                 320

Thr Leu Met Ser Met Phe Ala Asp Ala Ile Lys Gln Lys Ser Tyr
                325                 330                 335

Ala Met Pro Leu Pro Gly Trp Tyr Ile Phe Thr Lys Tyr Lys Trp Leu
                340                 345                 350

Val Leu Leu Leu Thr Phe Leu Phe Gln Val Ile Pro Ala Tyr Val Thr
                355                 360                 365

Asp Leu Ser Arg His Leu Ile Gly Lys Ser Pro Arg Tyr Ile Lys Leu
            370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Tyr Ala Ser
                405                 410                 415

Leu Ser Pro Ala Asp Lys Tyr Leu Phe Pro Cys Asp Pro Thr Asp Ile
                420                 425                 430

Asn Trp Thr His Tyr Ile Gln Asp Tyr Cys Trp Gly Val Arg His Phe
            435                 440                 445

Leu Glu Lys Lys Ser Tyr Glu
    450                 455

<210> SEQ ID NO 45
<211> LENGTH: 455
<212> TYPE: PRT
<213> ORGANISM: Artificial Sequence
<220> FEATURE:
<223> OTHER INFORMATION: HaFAR S378A

<400> SEQUENCE: 45

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
                20                  25                  30

Lys Val Phe Ile Glu Lys Leu Leu Tyr Ser Cys Pro Asp Ile Glu Asn
            35                  40                  45

Ile Tyr Met Leu Ile Arg Glu Lys Gly Leu Ser Val Ser Glu Arg
        50                  55                  60

Ile Lys Gln Phe Leu Asp Asp Pro Leu Phe Thr Arg Leu Lys Asp Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Asn Ser Glu Asn Glu Lys Met Leu Ile Glu
                100                 105                 110

Lys Val Ser Val Ile Ile His Ser Ala Ala Thr Val Lys Phe Asn Glu
```

```
                115                 120                 125
Pro Leu Pro Thr Ala Trp Lys Ile Asn Val Glu Gly Thr Arg Met Met
        130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
                180                 185                 190

Gly Ile Ser Glu Glu Asp Thr Glu Lys Ile Leu Asn Gly Arg Pro Asn
                195                 200                 205

Thr Tyr Thr Phe Thr Lys Ala Leu Thr Glu His Leu Val Ala Glu Asn
        210                 215                 220

Gln Ala Tyr Val Pro Thr Ile Ile Val Arg Pro Ser Val Ala Ala
225                 230                 235                 240

Ile Lys Asp Glu Pro Leu Lys Gly Trp Leu Gly Asn Trp Phe Gly Ala
                245                 250                 255

Thr Gly Leu Thr Val Phe Thr Ala Lys Gly Leu Asn Arg Val Ile Tyr
                260                 265                 270

Gly His Ser Ser Tyr Ile Val Asp Leu Ile Pro Val Asp Tyr Val Ala
                275                 280                 285

Asn Leu Val Ile Ala Ala Gly Ala Lys Ser Ser Lys Ser Thr Glu Leu
        290                 295                 300

Lys Val Tyr Asn Cys Cys Ser Ser Cys Asn Pro Val Thr Ile Gly
305                 310                 315                 320

Thr Leu Met Ser Met Phe Ala Asp Asp Ala Ile Lys Gln Lys Ser Tyr
                325                 330                 335

Ala Met Pro Leu Pro Gly Trp Tyr Ile Phe Thr Lys Tyr Lys Trp Leu
                340                 345                 350

Val Leu Leu Leu Thr Phe Leu Phe Gln Val Ile Pro Ala Tyr Val Thr
        355                 360                 365

Asp Leu Ser Arg His Leu Ile Gly Lys Ala Pro Arg Tyr Ile Lys Leu
        370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Tyr Ala Ser
                405                 410                 415

Leu Ser Pro Ala Asp Lys Tyr Leu Phe Pro Cys Asp Pro Thr Asp Ile
                420                 425                 430

Asn Trp Thr His Tyr Ile Gln Asp Tyr Cys Trp Gly Val Arg His Phe
                435                 440                 445

Leu Glu Lys Lys Ser Tyr Glu
        450                 455

<210> SEQ ID NO 46
<211> LENGTH: 455
<212> TYPE: PRT
<213> ORGANISM: Artificial Sequence
<220> FEATURE:
<223> OTHER INFORMATION: HaFAR S394A

<400> SEQUENCE: 46

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
```

```
                    20                  25                  30
Lys Val Phe Ile Glu Lys Leu Leu Tyr Ser Cys Pro Asp Ile Glu Asn
                35                  40                  45
Ile Tyr Met Leu Ile Arg Glu Lys Lys Gly Leu Ser Val Ser Glu Arg
                50                  55                  60
Ile Lys Gln Phe Leu Asp Asp Pro Leu Phe Thr Arg Leu Lys Asp Lys
65                  70                  75                  80
Arg Pro Ala Asp Leu Glu Lys Ile Val Leu Ile Pro Gly Asp Ile Thr
                85                  90                  95
Ala Pro Asp Leu Gly Ile Asn Ser Glu Asn Glu Lys Met Leu Ile Glu
                100                 105                 110
Lys Val Ser Val Ile Ile His Ser Ala Ala Thr Val Lys Phe Asn Glu
                115                 120                 125
Pro Leu Pro Thr Ala Trp Lys Ile Asn Val Glu Gly Thr Arg Met Met
                130                 135                 140
Leu Ala Leu Ser Arg Arg Met Lys Arg Ile Glu Val Phe Ile His Ile
145                 150                 155                 160
Ser Thr Ala Tyr Thr Asn Thr Asn Arg Glu Val Val Asp Glu Ile Leu
                165                 170                 175
Tyr Pro Ala Pro Ala Asp Ile Asp Gln Val His Gln Tyr Val Lys Asp
                180                 185                 190
Gly Ile Ser Glu Glu Asp Thr Glu Lys Ile Leu Asn Gly Arg Pro Asn
                195                 200                 205
Thr Tyr Thr Phe Thr Lys Ala Leu Thr Glu His Leu Val Ala Glu Asn
                210                 215                 220
Gln Ala Tyr Val Pro Thr Ile Ile Val Arg Pro Ser Val Val Ala Ala
225                 230                 235                 240
Ile Lys Asp Glu Pro Leu Lys Gly Trp Leu Gly Asn Trp Phe Gly Ala
                245                 250                 255
Thr Gly Leu Thr Val Phe Thr Ala Lys Gly Leu Asn Arg Val Ile Tyr
                260                 265                 270
Gly His Ser Ser Tyr Ile Val Asp Leu Ile Pro Val Asp Tyr Val Ala
                275                 280                 285
Asn Leu Val Ile Ala Ala Gly Ala Lys Ser Ser Lys Ser Thr Glu Leu
                290                 295                 300
Lys Val Tyr Asn Cys Cys Ser Ser Ser Cys Asn Pro Val Thr Ile Gly
305                 310                 315                 320
Thr Leu Met Ser Met Phe Ala Asp Asp Ala Ile Lys Gln Lys Ser Tyr
                325                 330                 335
Ala Met Pro Leu Pro Gly Trp Tyr Ile Phe Thr Lys Tyr Lys Trp Leu
                340                 345                 350
Val Leu Leu Leu Thr Phe Leu Phe Gln Val Ile Pro Ala Tyr Val Thr
                355                 360                 365
Asp Leu Ser Arg His Leu Ile Gly Lys Ser Pro Arg Tyr Ile Lys Leu
                370                 375                 380
Gln Ser Leu Val Asn Gln Thr Arg Ser Ala Ile Asp Phe Phe Thr Asn
385                 390                 395                 400
His Ser Trp Val Met Lys Ala Asp Arg Val Arg Glu Leu Tyr Ala Ser
                405                 410                 415
Leu Ser Pro Ala Asp Lys Tyr Leu Phe Pro Cys Asp Pro Thr Asp Ile
                420                 425                 430
Asn Trp Thr His Tyr Ile Gln Asp Tyr Cys Trp Gly Val Arg His Phe
                435                 440                 445
```

```
Leu Glu Lys Lys Ser Tyr Glu
    450                 455

<210> SEQ ID NO 47
<211> LENGTH: 455
<212> TYPE: PRT
<213> ORGANISM: Artificial Sequence
<220> FEATURE:
<223> OTHER INFORMATION: HaFAR S418A

<400> SEQUENCE: 47

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Glu Asn
        35                  40                  45

Ile Tyr Met Leu Ile Arg Glu Lys Gly Leu Ser Val Ser Glu Arg
50                  55                  60

Ile Lys Gln Phe Leu Asp Asp Pro Leu Phe Thr Arg Leu Lys Asp Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Asn Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Asp Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Leu Lys Gly Trp Leu Gly Asn Trp Phe Gly Ala
                245                 250                 255

Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Cys Asn Pro Val Thr Ile Gly
305                 310                 315                 320

Thr Leu Met Ser Met Phe Ala Asp Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350
```

```
Val Leu Leu Leu Thr Phe Leu Phe Gln Val Ile Pro Ala Tyr Val Thr
            355                 360                 365

Asp Leu Ser Arg His Leu Ile Gly Lys Ser Pro Arg Tyr Ile Lys Leu
        370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Tyr Ala Ser
                405                 410                 415

Leu Ala Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
            435                 440                 445

Leu Glu Lys Lys Ser Tyr Glu
            450                 455

<210> SEQ ID NO 48
<211> LENGTH: 455
<212> TYPE: PRT
<213> ORGANISM: Artificial Sequence
<220> FEATURE:
<223> OTHER INFORMATION: HaFAR S453A

<400> SEQUENCE: 48

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Glu Asn
        35                  40                  45

Ile Tyr Met Leu Ile Arg Glu Lys Lys Gly Leu Ser Val Ser Glu Arg
    50                  55                  60

Ile Lys Gln Phe Leu Asp Asp Pro Leu Phe Thr Arg Leu Lys Asp Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Asn Ser Glu Asn Glu Lys Met Leu Ile Glu
            100                 105                 110

Lys Val Ser Val Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Asp Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Leu Lys Gly Trp Leu Gly Asn Trp Phe Gly Ala
                245                 250                 255
```

```
Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
            275                 280                 285

Asn Leu Val Ile Ala Ala Gly Lys Ser Ser Lys Ser Thr Glu Leu
            290                 295                 300

Lys Val Tyr Asn Cys Cys Ser Ser Cys Asn Pro Val Thr Ile Gly
305                 310                 315                 320

Thr Leu Met Ser Met Phe Ala Asp Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Phe Leu Phe Gln Val Ile Pro Ala Tyr Val Thr
            355                 360                 365

Asp Leu Ser Arg His Leu Ile Gly Lys Ser Pro Arg Tyr Ile Lys Leu
            370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Tyr Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
            435                 440                 445

Leu Glu Lys Lys Ala Tyr Glu
            450                 455

<210> SEQ ID NO 49
<211> LENGTH: 349
<212> TYPE: PRT
<213> ORGANISM: Trichoplusia ni

<400> SEQUENCE: 49

Met Ala Val Met Ala Gln Thr Val Gln Glu Thr Ala Thr Val Leu Glu
1               5                   10                  15

Glu Glu Ala Arg Thr Val Thr Leu Val Ala Pro Lys Thr Thr Pro Arg
            20                  25                  30

Lys Tyr Lys Tyr Ile Tyr Thr Asn Phe Leu Thr Phe Ser Tyr Ala His
            35                  40                  45

Leu Ala Ala Leu Tyr Gly Leu Tyr Leu Cys Phe Thr Ser Ala Lys Trp
        50                  55                  60

Glu Thr Leu Leu Phe Ser Phe Val Leu Phe His Met Ser Asn Ile Gly
65              70                  75                  80

Ile Thr Ala Gly Ala His Arg Leu Trp Thr His Lys Thr Phe Lys Ala
                85                  90                  95

Lys Leu Pro Leu Glu Ile Val Leu Met Ile Phe Asn Ser Leu Ala Phe
            100                 105                 110

Gln Asn Thr Ala Ile Thr Trp Ala Arg Glu His Arg Leu His His Lys
            115                 120                 125

Tyr Ser Asp Thr Asp Ala Asp Pro His Asn Ala Ser Arg Gly Phe Phe
            130                 135                 140

Tyr Ser His Val Gly Trp Leu Leu Val Lys Lys His Pro Asp Val Leu
145                 150                 155                 160

Lys Tyr Gly Lys Thr Ile Asp Met Ser Asp Val Tyr Asn Asn Pro Val
```

```
                           165                 170                 175
Leu Lys Phe Gln Lys Lys Tyr Ala Val Pro Leu Ile Gly Thr Val Cys
                180                 185                 190

Phe Ala Leu Pro Thr Leu Ile Pro Val Tyr Cys Trp Gly Glu Ser Trp
            195                 200                 205

Asn Asn Ala Trp His Ile Ala Leu Phe Arg Tyr Ile Phe Asn Leu Asn
        210                 215                 220

Val Thr Phe Leu Val Asn Ser Ala Ala His Ile Trp Gly Asn Lys Pro
225                 230                 235                 240

Tyr Asp Lys Ser Ile Leu Pro Ala Gln Asn Leu Leu Val Ser Phe Leu
                245                 250                 255

Ala Ser Gly Glu Gly Phe His Asn Tyr His His Val Phe Pro Trp Asp
            260                 265                 270

Tyr Arg Thr Ala Glu Leu Gly Asn Asn Phe Leu Asn Leu Thr Thr Leu
        275                 280                 285

Phe Ile Asp Phe Cys Ala Trp Phe Gly Trp Ala Tyr Asp Leu Lys Ser
290                 295                 300

Val Ser Glu Asp Ile Ile Lys Gln Arg Ala Lys Arg Thr Gly Asp Gly
305                 310                 315                 320

Ser Ser Gly Val Ile Trp Gly Trp Asp Asp Lys Asp Met Asp Arg Asp
                325                 330                 335

Ile Lys Ser Lys Ala Asn Ile Phe Tyr Ala Lys Lys Glu
                340                 345

<210> SEQ ID NO 50
<211> LENGTH: 479
<212> TYPE: PRT
<213> ORGANISM: Thalassiosira pseudonana

<400> SEQUENCE: 50

Thr Ser Met Asp Phe Leu Ser Gly Asp Pro Phe Arg Thr Leu Val Leu
1               5                   10                  15

Ala Ala Leu Val Val Ile Gly Phe Ala Ala Ala Trp Gln Cys Phe Tyr
                20                  25                  30

Pro Pro Ser Ile Val Gly Lys Pro Arg Thr Leu Ser Asn Gly Lys Leu
            35                  40                  45

Asn Thr Arg Ile His Gly Lys Leu Tyr Asp Leu Ser Ser Phe Gln His
        50                  55                  60

Pro Gly Gly Pro Val Ala Leu Ser Leu Val Gln Gly Arg Asp Gly Thr
65                  70                  75                  80

Ala Leu Phe Glu Ser His His Pro Phe Ile Pro Arg Lys Asn Leu Leu
                85                  90                  95

Gln Ile Leu Ser Lys Tyr Glu Val Pro Ser Thr Glu Asp Ser Val Ser
            100                 105                 110

Phe Ile Ala Thr Leu Asp Glu Leu Asn Gly Glu Ser Pro Tyr Asp Trp
        115                 120                 125

Lys Asp Ile Glu Asn Asp Asp Phe Val Ser Asp Leu Arg Ala Leu Val
    130                 135                 140

Ile Glu His Phe Ser Pro Leu Ala Lys Glu Arg Gly Val Ser Leu Val
145                 150                 155                 160

Glu Ser Ser Lys Ala Thr Pro Gln Arg Trp Met Val Val Leu Leu Leu
                165                 170                 175

Leu Ala Ser Phe Phe Leu Ser Ile Pro Leu Tyr Leu Ser Gly Ser Trp
            180                 185                 190
```

```
Thr Phe Val Val Thr Pro Ile Leu Ala Trp Leu Ala Val Val Asn
            195                 200                 205

Tyr Trp His Asp Ala Thr His Phe Ala Leu Ser Ser Asn Trp Ile Leu
            210                 215                 220

Asn Ala Ala Leu Pro Tyr Leu Leu Pro Leu Leu Ser Ser Pro Ser Met
225                 230                 235                 240

Trp Tyr His His His Val Ile Gly His His Ala Tyr Thr Asn Ile Ser
                245                 250                 255

Lys Arg Asp Pro Asp Leu Ala His Ala Pro Gln Leu Met Arg Glu His
                260                 265                 270

Lys Ser Ile Lys Trp Arg Pro Ser His Leu Asn Gln Thr Gln Leu Pro
            275                 280                 285

Arg Ile Leu Phe Ile Trp Ser Ile Ala Val Gly Ile Gly Leu Asn Leu
            290                 295                 300

Leu Asn Asp Val Arg Ala Leu Thr Lys Leu Ser Tyr Asn Asn Val Val
305                 310                 315                 320

Arg Val Glu Lys Met Ser Ser Arg Thr Leu Leu His Phe Leu Gly
                325                 330                 335

Arg Met Leu His Ile Phe Val Thr Thr Leu Trp Pro Phe Leu Ala Phe
                340                 345                 350

Pro Val Trp Lys Ala Ile Val Trp Ala Thr Val Pro Asn Ala Ile Leu
            355                 360                 365

Ser Leu Cys Phe Met Leu Asn Thr Gln Ile Asn His Leu Ile Asn Thr
            370                 375                 380

Cys Ala His Ala Ser Asp Asn Asn Phe Tyr Lys His Gln Val Val Thr
385                 390                 395                 400

Ala Gln Asn Phe Gly Arg Ser Ser Ala Phe Cys Phe Ile Phe Ser Gly
                405                 410                 415

Gly Leu Asn Tyr Gln Ile Glu His His Leu Leu Pro Thr Val Asn His
            420                 425                 430

Cys His Leu Pro Ala Leu Ala Pro Gly Val Glu Arg Leu Cys Lys Lys
            435                 440                 445

His Gly Val Thr Tyr Asn Ser Val Glu Gly Tyr Arg Glu Ala Ile Ile
            450                 455                 460

Ala His Phe Ala His Thr Lys Asp Met Ser Thr Lys Pro Thr Asp
465                 470                 475

<210> SEQ ID NO 51
<211> LENGTH: 477
<212> TYPE: PRT
<213> ORGANISM: Thalassiosira pseudonana

<400> SEQUENCE: 51

Met Asp Phe Leu Ser Gly Asp Pro Phe Arg Thr Leu Val Leu Ala Ala
1               5                   10                  15

Leu Val Val Ile Gly Phe Ala Ala Ala Trp Gln Cys Phe Tyr Pro Pro
            20                  25                  30

Ser Ile Val Gly Lys Pro Arg Thr Leu Ser Asn Gly Lys Leu Asn Thr
            35                  40                  45

Arg Ile His Gly Lys Leu Tyr Asp Leu Ser Ser Phe Gln His Pro Gly
        50                  55                  60

Gly Pro Val Ala Leu Ser Leu Val Gln Gly Arg Asp Gly Thr Ala Leu
65                  70                  75                  80

Phe Glu Ser His His Pro Phe Ile Pro Arg Lys Asn Leu Leu Gln Ile
                85                  90                  95
```

```
Leu Ser Lys Tyr Glu Val Pro Ser Thr Glu Asp Ser Val Ser Phe Ile
            100                 105                 110

Ala Thr Leu Asp Glu Leu Asn Gly Glu Ser Pro Tyr Asp Trp Lys Asp
            115                 120                 125

Ile Glu Asn Asp Asp Phe Val Ser Asp Leu Arg Ala Leu Val Ile Glu
        130                 135                 140

His Phe Ser Pro Leu Ala Lys Glu Arg Gly Val Ser Leu Val Glu Ser
145                 150                 155                 160

Ser Lys Ala Thr Pro Gln Arg Trp Met Val Val Leu Leu Leu Leu Ala
                165                 170                 175

Ser Phe Phe Leu Ser Ile Pro Leu Tyr Leu Ser Gly Ser Trp Thr Phe
            180                 185                 190

Val Val Val Thr Pro Ile Leu Ala Trp Leu Ala Val Val Asn Tyr Trp
            195                 200                 205

His Asp Ala Thr His Phe Ala Leu Ser Ser Asn Trp Ile Leu Asn Ala
        210                 215                 220

Ala Leu Pro Tyr Leu Leu Pro Leu Leu Ser Ser Pro Ser Met Trp Tyr
225                 230                 235                 240

His His His Val Ile Gly His Ala Tyr Thr Asn Ile Ser Lys Arg
                245                 250                 255

Asp Pro Asp Leu Ala His Ala Pro Gln Leu Met Arg Glu His Lys Ser
            260                 265                 270

Ile Lys Trp Arg Pro Ser His Leu Asn Gln Thr Gln Leu Pro Arg Ile
        275                 280                 285

Leu Phe Ile Trp Ser Ile Ala Val Gly Ile Gly Leu Asn Leu Leu Asn
290                 295                 300

Asp Val Arg Ala Leu Thr Lys Leu Ser Tyr Asn Asn Val Val Arg Val
305                 310                 315                 320

Glu Lys Met Ser Ser Ser Arg Thr Leu Leu His Phe Leu Gly Arg Met
                325                 330                 335

Leu His Ile Phe Val Thr Thr Leu Trp Pro Phe Leu Ala Phe Pro Val
            340                 345                 350

Trp Lys Ala Ile Val Trp Ala Thr Val Pro Asn Ala Ile Leu Ser Leu
            355                 360                 365

Cys Phe Met Leu Asn Thr Gln Ile Asn His Leu Ile Asn Thr Cys Ala
        370                 375                 380

His Ala Ser Asp Asn Asn Phe Tyr Lys His Gln Val Val Thr Ala Gln
385                 390                 395                 400

Asn Phe Gly Arg Ser Ser Ala Phe Cys Phe Ile Phe Ser Gly Gly Leu
                405                 410                 415

Asn Tyr Gln Ile Glu His His Leu Leu Pro Thr Val Asn His Cys His
            420                 425                 430

Leu Pro Ala Leu Ala Pro Gly Val Glu Arg Leu Cys Lys Lys His Gly
            435                 440                 445

Val Thr Tyr Asn Ser Val Glu Gly Tyr Arg Glu Ala Ile Ile Ala His
            450                 455                 460

Phe Ala His Thr Lys Asp Met Ser Thr Lys Pro Thr Asp
465                 470                 475

<210> SEQ ID NO 52
<211> LENGTH: 326
<212> TYPE: PRT
<213> ORGANISM: Amyelois transitella
```

```
<400> SEQUENCE: 52

Met Val Pro Asn Lys Gly Ser Ser Asp Val Leu Ser Glu His Ser Glu
1               5                   10                  15

Pro Gln Phe Thr Lys Leu Ile Ala Pro Gln Ala Gly Pro Arg Lys Tyr
            20                  25                  30

Lys Ile Val Tyr Arg Asn Leu Leu Thr Phe Gly Tyr Trp His Leu Ser
        35                  40                  45

Ala Val Tyr Gly Leu Tyr Leu Cys Phe Thr Cys Ala Lys Trp Ala Thr
    50                  55                  60

Ile Leu Phe Ala Phe Phe Leu Tyr Val Ile Ala Glu Ile Gly Ile Thr
65                  70                  75                  80

Gly Gly Ala His Arg Leu Trp Ala His Arg Thr Tyr Lys Ala Lys Leu
                85                  90                  95

Pro Leu Glu Ile Leu Leu Leu Ile Met Asn Ser Ile Ala Phe Gln Asp
            100                 105                 110

Thr Ala Phe Thr Trp Ala Arg Asp His Arg Leu His His Lys Tyr Ser
        115                 120                 125

Asp Thr Asp Ala Asp Pro His Asn Ala Thr Arg Gly Phe Phe Tyr Ser
130                 135                 140

His Val Gly Trp Leu Leu Val Lys Lys His Pro Glu Val Lys Ala Arg
145                 150                 155                 160

Gly Lys Tyr Leu Ser Leu Asp Asp Leu Lys Asn Asn Pro Leu Leu Lys
                165                 170                 175

Phe Gln Lys Lys Tyr Ala Ile Leu Val Ile Gly Thr Leu Cys Phe Leu
            180                 185                 190

Met Pro Thr Phe Val Pro Val Tyr Phe Trp Gly Glu Gly Ile Ser Thr
        195                 200                 205

Ala Trp Asn Ile Asn Leu Leu Arg Tyr Val Met Asn Leu Asn Met Thr
210                 215                 220

Phe Leu Val Asn Ser Ala Ala His Ile Phe Gly Asn Lys Pro Tyr Asp
225                 230                 235                 240

Lys Ser Ile Ala Ser Val Gln Asn Ile Ser Val Ser Leu Ala Thr Phe
                245                 250                 255

Gly Glu Gly Phe His Asn Tyr His His Thr Tyr Pro Trp Asp Tyr Arg
            260                 265                 270

Ala Ala Glu Leu Gly Asn Asn Arg Leu Asn Met Thr Thr Ala Phe Ile
        275                 280                 285

Asp Phe Phe Ala Trp Ile Gly Trp Ala Tyr Asp Leu Lys Ser Val Pro
        290                 295                 300

Gln Glu Ala Ile Ala Lys Arg Cys Ala Lys Thr Gly Asp Gly Thr Asp
305                 310                 315                 320

Met Trp Gly Arg Lys Arg
                325

<210> SEQ ID NO 53
<211> LENGTH: 336
<212> TYPE: PRT
<213> ORGANISM: Agrotis segetum

<400> SEQUENCE: 53

Met Ala Gln Gly Val Gln Thr Thr Thr Ile Leu Arg Glu Glu Glu Pro
1               5                   10                  15

Ser Leu Thr Phe Val Val Pro Gln Glu Pro Arg Lys Tyr Gln Ile Val
            20                  25                  30
```

Tyr Pro Asn Leu Ile Thr Phe Gly Tyr Trp His Ile Ala Gly Leu Tyr
            35                  40                  45

Gly Leu Tyr Leu Cys Phe Thr Ser Ala Lys Trp Gln Thr Ile Leu Phe
 50                  55                  60

Ser Phe Met Leu Val Val Leu Ala Glu Leu Gly Ile Thr Ala Gly Ala
65                  70                  75                  80

His Arg Leu Trp Ala His Lys Thr Tyr Lys Ala Lys Leu Pro Leu Gln
                85                  90                  95

Ile Ile Leu Met Ile Leu Asn Ser Ala Phe Gln Asn Ser Ala Ile
                100                 105                 110

Asp Trp Val Arg Asp His Arg Leu His His Lys Tyr Ser Asp Thr Asp
            115                 120                 125

Ala Asp Pro His Asn Ala Thr Arg Gly Phe Phe Tyr Ser His Val Gly
        130                 135                 140

Trp Leu Leu Val Arg Lys His Pro Glu Val Lys Arg Gly Lys Glu
145                 150                 155                 160

Leu Asp Met Ser Asp Ile Tyr Asn Asn Pro Val Leu Arg Phe Gln Lys
                165                 170                 175

Lys Tyr Ala Ile Pro Phe Ile Gly Ala Met Cys Phe Gly Leu Pro Thr
            180                 185                 190

Phe Ile Pro Val Tyr Phe Trp Gly Glu Thr Trp Ser Asn Ala Trp His
        195                 200                 205

Ile Thr Met Leu Arg Tyr Ile Leu Asn Leu Asn Ile Thr Phe Leu Val
    210                 215                 220

Asn Ser Ala Ala His Ile Trp Gly Tyr Lys Pro Tyr Asp Ile Lys Ile
225                 230                 235                 240

Leu Pro Ala Gln Asn Ile Ala Val Ser Ile Val Thr Gly Gly Glu Val
                245                 250                 255

Ser Ile Thr Thr Thr Thr Phe Phe Pro Trp Asp Tyr Arg Ala Ala Glu
            260                 265                 270

Leu Gly Asn Asn Tyr Leu Asn Leu Thr Thr Lys Phe Ile Asp Phe Phe
        275                 280                 285

Ala Trp Ile Gly Trp Ala Tyr Asp Leu Lys Thr Val Ser Ser Asp Val
    290                 295                 300

Ile Lys Ser Lys Ala Glu Arg Thr Gly Asp Gly Thr Asn Leu Trp Gly
305                 310                 315                 320

Leu Glu Asp Lys Gly Glu Asp Phe Leu Lys Ile Trp Lys Asp Asn
                325                 330                 335

<210> SEQ ID NO 54
<211> LENGTH: 338
<212> TYPE: PRT
<213> ORGANISM: Helicoverpa zea

<400> SEQUENCE: 54

Met Ala Gln Ser Tyr Gln Ser Thr Thr Val Leu Ser Glu Glu Lys Glu
1               5                   10                  15

Leu Thr Leu Gln His Leu Val Pro Gln Ala Ser Pro Arg Lys Tyr Gln
            20                  25                  30

Ile Val Tyr Pro Asn Leu Ile Thr Phe Gly Tyr Trp His Ile Ala Gly
            35                  40                  45

Leu Tyr Gly Leu Tyr Leu Cys Phe Thr Ser Ala Lys Trp Ala Thr Ile
 50                  55                  60

Leu Phe Ser Tyr Ile Leu Phe Val Leu Ala Glu Ile Gly Ile Thr Ala
65                  70                  75                  80

Gly Ala His Arg Leu Trp Ala His Lys Thr Tyr Lys Ala Lys Leu Pro
                    85                  90                  95

Leu Glu Ile Leu Leu Met Val Phe Asn Ser Ile Ala Phe Gln Asn Ser
            100                 105                 110

Ala Ile Asp Trp Val Arg Asp His Arg Leu His Lys Tyr Ser Asp
        115                 120                 125

Thr Asp Ala Asp Pro His Asn Ala Ser Arg Gly Phe Phe Tyr Ser His
    130                 135                 140

Val Gly Trp Leu Leu Val Arg Lys His Pro Glu Val Lys Lys Arg Gly
145                 150                 155                 160

Lys Glu Leu Asn Met Ser Asp Ile Tyr Asn Asn Pro Val Leu Arg Phe
                165                 170                 175

Gln Lys Lys Tyr Ala Ile Pro Phe Ile Gly Ala Val Cys Phe Ala Leu
            180                 185                 190

Pro Thr Met Ile Pro Val Tyr Phe Trp Gly Glu Thr Trp Ser Asn Ala
        195                 200                 205

Trp His Ile Thr Met Leu Arg Tyr Ile Met Asn Leu Asn Val Thr Phe
    210                 215                 220

Leu Val Asn Ser Ala Ala His Ile Trp Gly Asn Lys Pro Tyr Asp Ala
225                 230                 235                 240

Lys Ile Leu Pro Ala Gln Asn Val Ala Val Ser Val Ala Thr Gly Gly
                245                 250                 255

Glu Gly Phe His Asn Tyr His His Val Phe Pro Trp Asp Tyr Arg Ala
            260                 265                 270

Ala Glu Leu Gly Asn Asn Ser Leu Asn Leu Thr Thr Lys Phe Ile Asp
        275                 280                 285

Leu Phe Ala Ala Ile Gly Trp Ala Tyr Asp Leu Lys Thr Val Ser Glu
    290                 295                 300

Asp Met Ile Lys Gln Arg Ile Lys Arg Thr Gly Asp Gly Thr Asp Leu
305                 310                 315                 320

Trp Gly His Glu Gln Asn Cys Asp Glu Val Trp Asp Val Lys Asp Lys
                325                 330                 335

Ser Ser

<210> SEQ ID NO 55
<211> LENGTH: 458
<212> TYPE: PRT
<213> ORGANISM: Agrotis segetum

<400> SEQUENCE: 55

Met Pro Val Leu Thr Ser Arg Glu Asp Glu Lys Leu Ser Val Pro Glu
1               5                   10                  15

Phe Tyr Ala Gly Lys Ser Ile Phe Val Thr Gly Gly Thr Gly Phe Leu
            20                  25                  30

Gly Lys Val Phe Ile Glu Lys Leu Leu Tyr Cys Cys Pro Asp Ile Asp
        35                  40                  45

Lys Ile Tyr Met Leu Ile Arg Glu Lys Lys Asn Leu Ser Ile Asp Glu
    50                  55                  60

Arg Met Ser Lys Phe Leu Asp Asp Pro Leu Phe Ser Arg Leu Lys Glu
65                  70                  75                  80

Glu Arg Pro Gly Asp Leu Glu Lys Ile Val Leu Ile Pro Gly Asp Ile
                85                  90                  95

Thr Ala Pro Asn Leu Gly Leu Ser Ala Glu Asn Glu Arg Ile Leu Leu
            100                 105                 110

```
Glu Lys Val Ser Val Ile Ile Asn Ser Ala Thr Val Lys Phe Asn
        115                 120                 125

Glu Pro Leu Pro Ile Ala Trp Lys Ile Asn Val Glu Gly Thr Arg Met
    130                 135                 140

Leu Leu Ala Leu Ser Arg Arg Met Lys Arg Ile Glu Val Phe Ile His
145                 150                 155                 160

Ile Ser Thr Ala Tyr Ser Asn Ala Ser Ser Asp Arg Ile Val Val Asp
                165                 170                 175

Glu Ile Leu Tyr Pro Ala Pro Ala Asp Met Asp Gln Val Tyr Gln Leu
            180                 185                 190

Val Lys Asp Gly Val Thr Glu Glu Thr Glu Arg Leu Leu Asn Gly
        195                 200                 205

Leu Pro Asn Thr Tyr Thr Phe Thr Lys Ala Leu Thr Glu His Leu Val
    210                 215                 220

Ala Glu His Gln Thr Tyr Val Pro Thr Ile Ile Arg Pro Ser Val
225                 230                 235                 240

Val Ala Ser Ile Lys Asp Glu Pro Ile Arg Gly Trp Leu Cys Asn Trp
                245                 250                 255

Phe Gly Ala Thr Gly Ile Ser Val Phe Thr Ala Lys Gly Leu Asn Arg
            260                 265                 270

Val Leu Leu Gly Lys Ala Ser Asn Ile Val Asp Val Ile Pro Val Asp
        275                 280                 285

Tyr Val Ala Asn Leu Val Ile Val Ala Gly Ala Lys Ser Gly Gly Gln
    290                 295                 300

Lys Ser Asp Glu Leu Lys Ile Tyr Asn Cys Cys Ser Ser Asp Cys Asn
305                 310                 315                 320

Pro Val Thr Leu Lys Lys Ile Ile Lys Glu Phe Thr Glu Asp Thr Ile
                325                 330                 335

Lys Asn Lys Ser His Ile Met Pro Leu Pro Gly Trp Phe Val Phe Thr
            340                 345                 350

Lys Tyr Lys Trp Leu Leu Thr Leu Leu Thr Ile Ile Phe Gln Met Leu
        355                 360                 365

Pro Met Tyr Leu Ala Asp Val Tyr Arg Val Leu Thr Gly Lys Ile Pro
    370                 375                 380

Arg Tyr Met Lys Leu His His Leu Val Ile Gln Thr Arg Leu Gly Ile
385                 390                 395                 400

Asp Phe Phe Thr Ser His Ser Trp Val Met Lys Thr Asp Arg Val Arg
                405                 410                 415

Glu Leu Phe Gly Ser Leu Ser Leu Ala Glu Lys His Met Phe Pro Cys
            420                 425                 430

Asp Pro Ser Ser Ile Asp Trp Thr Asp Tyr Leu Gln Ser Tyr Cys Tyr
        435                 440                 445

Gly Val Arg Arg Phe Leu Glu Lys Lys Lys
    450                 455

<210> SEQ ID NO 56
<211> LENGTH: 454
<212> TYPE: PRT
<213> ORGANISM: Spodoptera littoralis

<400> SEQUENCE: 56

Met Val Val Leu Thr Ser Lys Glu Lys Ser Asn Met Ser Val Ala Asp
1               5                   10                  15

Phe Tyr Ala Gly Lys Ser Val Phe Ile Thr Gly Gly Thr Gly Phe Leu
```

-continued

```
               20                  25                  30
Gly Lys Val Phe Ile Glu Lys Leu Leu Tyr Ser Cys Pro Asp Ile Asp
            35                  40                  45
Lys Ile Tyr Met Leu Ile Arg Glu Lys Lys Gly Gln Ser Ile Arg Glu
        50                  55                  60
Arg Leu Thr Lys Ile Val Asp Asp Pro Leu Phe Asn Arg Leu Lys Asp
65                  70                  75                  80
Lys Arg Pro Asp Asp Leu Gly Lys Ile Val Leu Ile Pro Gly Asp Ile
                85                  90                  95
Thr Val Pro Gly Leu Gly Ile Ser Glu Glu Asn Glu Thr Ile Leu Thr
            100                 105                 110
Glu Lys Val Ser Val Val Ile His Ser Ala Ala Thr Val Lys Phe Asn
            115                 120                 125
Glu Pro Leu Ala Thr Ala Trp Asn Val Asn Val Glu Gly Thr Arg Met
            130                 135                 140
Ile Met Ala Leu Ser Arg Arg Met Lys Arg Ile Glu Val Phe Ile His
145                 150                 155                 160
Ile Ser Thr Ala Tyr Thr Asn Thr Asn Arg Ala Val Ile Asp Glu Val
                165                 170                 175
Leu Tyr Pro Pro Pro Ala Asp Ile Asn Asp Val His Gln His Val Lys
            180                 185                 190
Asn Gly Val Thr Glu Glu Glu Thr Glu Lys Ile Leu Asn Gly Arg Pro
            195                 200                 205
Asn Thr Tyr Thr Phe Thr Lys Ala Leu Thr Glu His Leu Val Ala Glu
            210                 215                 220
Asn Gln Ser Tyr Met Pro Thr Ile Ile Val Arg Pro Ser Ile Val Gly
225                 230                 235                 240
Ala Ile Lys Asp Asp Pro Ile Arg Gly Trp Leu Ala Asn Trp Tyr Gly
                245                 250                 255
Ala Thr Gly Leu Ser Val Phe Thr Ala Lys Gly Leu Asn Arg Val Ile
            260                 265                 270
Tyr Gly His Ser Asn His Val Val Asp Leu Ile Pro Val Asp Tyr Val
            275                 280                 285
Ala Asn Leu Val Ile Val Ala Gly Ala Lys Thr Tyr His Ser Asn Glu
            290                 295                 300
Val Thr Ile Tyr Asn Ser Cys Ser Ser Ser Cys Asn Pro Ile Thr Met
305                 310                 315                 320
Lys Arg Leu Val Gly Leu Phe Ile Asp Tyr Thr Val Lys His Lys Ser
                325                 330                 335
Tyr Val Met Pro Leu Pro Gly Trp Tyr Val Tyr Ser Asn Tyr Lys Trp
            340                 345                 350
Leu Val Phe Leu Val Thr Val Ile Phe Gln Val Ile Pro Ala Tyr Leu
            355                 360                 365
Gly Asp Ile Gly Arg Arg Leu Leu Gly Lys Asn Pro Arg Tyr Tyr Lys
            370                 375                 380
Leu Gln Asn Leu Val Ala Gln Thr Gln Glu Ala Val His Phe Phe Thr
385                 390                 395                 400
Ser His Thr Trp Glu Ile Lys Ser Lys Arg Thr Ser Glu Leu Phe Ser
                405                 410                 415
Ser Leu Ser Leu Thr Asp Gln Arg Met Phe Pro Cys Asp Ala Asn Arg
            420                 425                 430
Ile Asp Trp Thr Asp Tyr Ile Thr Asp Tyr Cys Ser Gly Val Arg Gln
            435                 440                 445
```

Phe Leu Glu Lys Ile Lys
                450

<210> SEQ ID NO 57
<211> LENGTH: 455
<212> TYPE: PRT
<213> ORGANISM: Helicoverpa armigera

<400> SEQUENCE: 57

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Glu Asn
        35                  40                  45

Ile Tyr Met Leu Ile Arg Glu Lys Gly Leu Ser Val Ser Glu Arg
    50                  55                  60

Ile Lys Gln Phe Leu Asp Asp Pro Leu Phe Thr Arg Leu Lys Asp Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Asn Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Asp Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Leu Lys Gly Trp Leu Gly Asn Trp Phe Gly Ala
                245                 250                 255

Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ser Cys Asn Pro Val Thr Ile Gly
305                 310                 315                 320

Thr Leu Met Ser Met Phe Ala Asp Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Phe Leu Phe Gln Val Ile Pro Ala Tyr Val Thr

```
                355                 360                 365
Asp Leu Ser Arg His Leu Ile Gly Lys Ser Pro Arg Tyr Ile Lys Leu
    370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Tyr Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
                435                 440                 445

Leu Glu Lys Lys Ser Tyr Glu
    450                 455

<210> SEQ ID NO 58
<211> LENGTH: 355
<212> TYPE: PRT
<213> ORGANISM: Ostrinia furnacalis

<400> SEQUENCE: 58

Met Ala Pro Asn Ile Lys Asp Gly Ala Asp Leu Asn Gly Val Leu Phe
1               5                   10                  15

Glu Asp Asp Ala Ser Thr Pro Asp Tyr Ala Leu Ala Thr Ala Pro Val
                20                  25                  30

Gln Lys Ala Asp Asn Tyr Pro Arg Lys Leu Val Trp Arg Asn Ile Ile
            35                  40                  45

Leu Phe Ala Tyr Leu His Leu Ala Ala Val Tyr Gly Ala Tyr Leu Phe
50                  55                  60

Leu Phe Ser Ala Lys Trp Gln Thr Asp Ile Phe Ala Tyr Ile Leu Tyr
65                  70                  75                  80

Val Ile Ser Gly Leu Gly Ile Thr Ala Gly Ala His Arg Leu Trp Ala
                85                  90                  95

His Lys Ser Tyr Lys Ala Lys Trp Pro Leu Arg Leu Ile Leu Ile Ile
                100                 105                 110

Phe Asn Thr Val Ser Phe Gln Asp Ser Ala Leu Asp Trp Ser Arg Asp
            115                 120                 125

His Arg Met His His Lys Tyr Ser Glu Thr Asp Ala Asp Pro His Asn
130                 135                 140

Ala Thr Arg Gly Phe Phe Phe Ser His Ile Gly Trp Leu Leu Val Arg
145                 150                 155                 160

Lys His Pro Glu Leu Lys Arg Lys Gly Lys Gly Leu Asp Leu Ser Asp
                165                 170                 175

Leu Tyr Ala Asp Pro Ile Leu Arg Phe Gln Lys Lys Tyr Tyr Leu Leu
            180                 185                 190

Leu Met Pro Leu Gly Cys Phe Ile Met Pro Thr Val Val Pro Val Tyr
                195                 200                 205

Phe Trp Gly Glu Thr Trp Thr Asn Ala Phe Phe Val Ala Ala Leu Phe
            210                 215                 220

Arg Tyr Thr Phe Ile Leu Asn Val Thr Trp Leu Val Asn Ser Ala Ala
225                 230                 235                 240

His Lys Trp Gly His Lys Pro Tyr Asp Ser Ser Ile Lys Pro Ser Glu
                245                 250                 255

Asn Leu Ser Val Ser Leu Phe Ala Leu Gly Glu Gly Phe His Asn Tyr
            260                 265                 270
```

His His Thr Phe Pro Trp Asp Tyr Lys Thr Ala Glu Leu Gly Asn Asn
            275                 280                 285

Arg Leu Asn Phe Thr Thr Asn Phe Ile Asn Phe Phe Ala Lys Ile Gly
        290                 295                 300

Trp Ala Tyr Asp Leu Lys Thr Val Ser Asp Glu Ile Ile Gln Asn Arg
305                 310                 315                 320

Val Lys Arg Thr Gly Asp Gly Ser His His Leu Trp Gly Trp Gly Asp
                325                 330                 335

Lys Asp Gln Pro Lys Glu Glu Val Asn Ala Ala Ile Arg Ile Asn Pro
            340                 345                 350

Lys Asp Glu
        355

<210> SEQ ID NO 59
<211> LENGTH: 352
<212> TYPE: PRT
<213> ORGANISM: Lampronia capitella

<400> SEQUENCE: 59

Met Pro Pro Asn Val Thr Glu Ala Asn Gly Val Leu Phe Glu Asn Asp
1               5                   10                  15

Val Gln Thr Pro Asp Met Gly Leu Glu Val Ala Pro Val Gln Lys Ala
            20                  25                  30

Asp Glu Arg Lys Ile Gln Leu Val Trp Arg Asn Ile Ile Ala Phe Ala
        35                  40                  45

Cys Leu His Leu Ala Ala Val Tyr Gly Ala Tyr Leu Phe Phe Thr Ser
    50                  55                  60

Ala Ile Trp Gln Thr Asp Ile Phe Ala Tyr Ile Leu Tyr Val Met Ser
65                  70                  75                  80

Gly Leu Gly Ile Thr Ala Gly Ala His Arg Leu Trp Ala His Lys Ser
                85                  90                  95

Tyr Lys Ala Lys Trp Pro Leu Arg Leu Ile Leu Val Ala Phe Asn Thr
            100                 105                 110

Leu Ala Phe Gln Asp Ser Ala Ile Asp Trp Ala Arg Asp His Arg Met
        115                 120                 125

His His Lys Tyr Ser Glu Thr Asp Ala Asp Pro His Asn Ala Thr Arg
    130                 135                 140

Gly Phe Phe Phe Ser His Ile Gly Trp Leu Leu Cys Arg Lys His Pro
145                 150                 155                 160

Glu Leu Lys Arg Lys Gly Gln Gly Leu Asp Leu Ser Asp Leu Tyr Ala
                165                 170                 175

Asp Pro Ile Ile Arg Phe Gln Lys Tyr Tyr Leu Leu Met Pro
            180                 185                 190

Leu Ala Cys Phe Val Leu Pro Thr Ile Ile Pro Val Tyr Leu Trp Gly
        195                 200                 205

Glu Ser Trp Lys Asn Ala Phe Phe Val Ala Ala Met Phe Arg Tyr Thr
    210                 215                 220

Phe Ile Leu Asn Val Thr Trp Leu Val Asn Ser Ala Ala His Lys Trp
225                 230                 235                 240

Gly Gly Lys Pro Tyr Asp Lys Asn Ile Gln Pro Ala Gln Asn Ile Ser
                245                 250                 255

Val Ala Ile Phe Ala Leu Gly Glu Gly Phe His Asn Tyr His His Thr
            260                 265                 270

Phe Pro Trp Asp Tyr Lys Thr Ala Glu Leu Gly Asn Asn Arg Leu Asn
        275                 280                 285

```
Phe Thr Thr Ser Phe Ile Asn Phe Ala Ser Phe Gly Trp Ala Tyr
    290                 295                 300

Asp Leu Lys Thr Val Ser Asp Glu Ile Ile Gln Gln Arg Val Lys Arg
305                 310                 315                 320

Thr Gly Asp Gly Ser His His Leu Arg Gly Trp Gly Asp Gln Asp Ile
                325                 330                 335

Pro Ala Glu Glu Ala Gln Ala Ala Leu Arg Ile Asn Arg Lys Asp Asp
                340                 345                 350

<210> SEQ ID NO 60
<211> LENGTH: 353
<212> TYPE: PRT
<213> ORGANISM: Helicoverpa zea

<400> SEQUENCE: 60

Met Ala Pro Asn Ile Ser Glu Asp Val Asn Gly Val Leu Phe Glu Ser
1               5                   10                  15

Asp Ala Ala Thr Pro Asp Leu Ala Leu Ser Thr Pro Pro Val Gln Lys
            20                  25                  30

Ala Asp Asn Arg Pro Lys Gln Leu Val Trp Arg Asn Ile Leu Leu Phe
        35                  40                  45

Ala Tyr Leu His Leu Ala Ala Leu Tyr Gly Gly Tyr Leu Phe Leu Phe
    50                  55                  60

Ser Ala Lys Trp Gln Thr Asp Ile Phe Ala Tyr Ile Leu Tyr Val Ile
65                  70                  75                  80

Ser Gly Leu Gly Ile Thr Ala Gly Ala His Arg Leu Trp Ala His Lys
                85                  90                  95

Ser Tyr Lys Ala Lys Trp Pro Leu Arg Val Ile Leu Val Ile Phe Asn
            100                 105                 110

Thr Val Ala Phe Gln Asp Ala Ala Met Asp Trp Ala Arg Asp His Arg
        115                 120                 125

Met His His Lys Tyr Ser Glu Thr Asp Ala Asp Pro His Asn Ala Thr
    130                 135                 140

Arg Gly Phe Phe Phe Ser His Ile Gly Trp Leu Leu Val Arg Lys His
145                 150                 155                 160

Pro Asp Leu Lys Glu Lys Gly Lys Gly Leu Asp Met Ser Asp Leu Leu
                165                 170                 175

Ala Asp Pro Ile Leu Arg Phe Gln Lys Lys Tyr Tyr Leu Ile Leu Met
            180                 185                 190

Pro Leu Ala Cys Phe Val Met Pro Thr Val Ile Pro Val Tyr Phe Trp
        195                 200                 205

Gly Glu Thr Trp Thr Asn Ala Phe Phe Val Ala Ala Met Phe Arg Tyr
    210                 215                 220

Ala Phe Ile Leu Asn Val Thr Trp Leu Val Asn Ser Ala Ala His Lys
225                 230                 235                 240

Trp Gly Asp Lys Pro Tyr Asp Lys Ser Ile Lys Pro Ser Glu Asn Leu
                245                 250                 255

Ser Val Ala Met Phe Ala Leu Gly Glu Gly Phe His Asn Tyr His His
            260                 265                 270

Thr Phe Pro Trp Asp Tyr Lys Thr Ala Glu Leu Gly Asn Asn Lys Leu
        275                 280                 285

Asn Phe Thr Thr Thr Phe Ile Asn Phe Phe Ala Lys Ile Gly Trp Ala
    290                 295                 300

Tyr Asp Leu Lys Thr Val Ser Asp Asp Ile Val Lys Asn Arg Val Lys
```

```
                    305                 310                 315                 320
Arg Thr Gly Asp Gly Ser His His Leu Trp Gly Trp Gly Asp Glu Asn
                325                 330                 335

Gln Ser Lys Glu Glu Ile Asp Ala Ala Ile Arg Ile Asn Pro Lys Asp
                340                 345                 350

Asp

<210> SEQ ID NO 61
<211> LENGTH: 354
<212> TYPE: PRT
<213> ORGANISM: Artificial Sequence
<220> FEATURE:
<223> OTHER INFORMATION: Trichoplusia ni desaturase with Yarrowia
      lipolytica OLE1 leader sequence encoded by SEQ ID NO: 28

<400> SEQUENCE: 61

Met Val Lys Asn Val Asp Gln Val Asp Leu Ser Gln Val Asp Thr Ile
1               5                   10                  15

Ala Ser Gly Arg Asp Val Asn Tyr Lys Val Lys Tyr Thr Ser Gly Val
                20                  25                  30

Lys Thr Thr Pro Arg Lys Tyr Lys Tyr Ile Tyr Thr Asn Phe Leu Thr
                35                  40                  45

Phe Ser Tyr Ala His Leu Ala Ala Leu Tyr Gly Leu Tyr Leu Cys Phe
            50                  55                  60

Thr Ser Ala Lys Trp Glu Thr Leu Leu Phe Ser Phe Val Leu Phe His
65                  70                  75                  80

Met Ser Asn Ile Gly Ile Thr Ala Gly Ala His Arg Leu Trp Thr His
                85                  90                  95

Lys Thr Phe Lys Ala Lys Leu Pro Leu Glu Ile Val Leu Met Ile Phe
                100                 105                 110

Asn Ser Leu Ala Phe Gln Asn Thr Ala Ile Thr Trp Ala Arg Glu His
            115                 120                 125

Arg Leu His His Lys Tyr Ser Asp Thr Asp Ala Asp Pro His Asn Ala
            130                 135                 140

Ser Arg Gly Phe Phe Tyr Ser His Val Gly Trp Leu Leu Val Lys Lys
145                 150                 155                 160

His Pro Asp Val Leu Lys Tyr Gly Lys Thr Ile Asp Met Ser Asp Val
                165                 170                 175

Tyr Asn Asn Pro Val Leu Lys Phe Gln Lys Tyr Ala Val Pro Leu
                180                 185                 190

Ile Gly Thr Val Cys Phe Ala Leu Pro Thr Leu Ile Pro Val Tyr Cys
            195                 200                 205

Trp Gly Glu Ser Trp Asn Asn Ala Trp His Ile Ala Leu Phe Arg Tyr
        210                 215                 220

Ile Phe Asn Leu Asn Val Thr Phe Leu Val Asn Ser Ala Ala His Ile
225                 230                 235                 240

Trp Gly Asn Lys Pro Tyr Asp Lys Ser Ile Leu Pro Ala Gln Asn Leu
                245                 250                 255

Leu Val Ser Phe Leu Ala Ser Gly Glu Gly Phe His Asn Tyr His His
            260                 265                 270

Val Phe Pro Trp Asp Tyr Arg Thr Ala Glu Leu Gly Asn Asn Phe Leu
        275                 280                 285

Asn Leu Thr Thr Leu Phe Ile Asp Phe Cys Ala Trp Phe Gly Trp Ala
        290                 295                 300

Tyr Asp Leu Lys Ser Val Ser Glu Asp Ile Ile Lys Gln Arg Ala Lys
```

```
                305                 310                 315                 320
Arg Thr Gly Asp Gly Ser Ser Gly Val Ile Trp Gly Trp Asp Lys
                    325                 330                 335

Asp Met Asp Arg Asp Ile Lys Ser Lys Ala Asn Ile Phe Tyr Ala Lys
                340                 345                 350

Lys Glu

<210> SEQ ID NO 62
<211> LENGTH: 342
<212> TYPE: PRT
<213> ORGANISM: Artificial Sequence
<220> FEATURE:
<223> OTHER INFORMATION: Helicoverpa zea desaturase with Yarrowia
      lipolytica OLE1 leader sequence encoded by SEQ ID NO: 29

<400> SEQUENCE: 62

Met Val Lys Asn Val Asp Gln Val Asp Leu Ser Gln Val Asp Thr Ile
1               5                   10                  15

Ala Ser Gly Arg Asp Val Asn Tyr Lys Val Lys Tyr Thr Ser Gly Val
            20                  25                  30

Arg Lys Tyr Gln Ile Val Tyr Pro Asn Leu Ile Thr Phe Gly Tyr Trp
        35                  40                  45

His Ile Ala Gly Leu Tyr Gly Leu Tyr Leu Cys Phe Thr Ser Ala Lys
    50                  55                  60

Trp Ala Thr Ile Leu Phe Ser Tyr Ile Leu Phe Val Leu Ala Glu Ile
65                  70                  75                  80

Gly Ile Thr Ala Gly Ala His Arg Leu Trp Ala His Lys Thr Tyr Lys
                85                  90                  95

Ala Lys Leu Pro Leu Glu Ile Leu Leu Met Val Phe Asn Ser Ile Ala
            100                 105                 110

Phe Gln Asn Ser Ala Ile Asp Trp Val Arg Asp His Arg Leu His His
        115                 120                 125

Lys Tyr Ser Asp Thr Asp Ala Asp Pro His Asn Ala Ser Arg Gly Phe
    130                 135                 140

Phe Tyr Ser His Val Gly Trp Leu Leu Val Arg Lys His Pro Glu Val
145                 150                 155                 160

Lys Lys Arg Gly Lys Glu Leu Asn Met Ser Asp Ile Tyr Asn Asn Pro
                165                 170                 175

Val Leu Arg Phe Gln Lys Lys Tyr Ala Ile Pro Phe Ile Gly Ala Val
            180                 185                 190

Cys Phe Ala Leu Pro Thr Met Ile Pro Val Tyr Phe Trp Gly Glu Thr
        195                 200                 205

Trp Ser Asn Ala Trp His Ile Thr Met Leu Arg Tyr Ile Met Asn Leu
    210                 215                 220

Asn Val Thr Phe Leu Val Asn Ser Ala Ala His Ile Trp Gly Asn Lys
225                 230                 235                 240

Pro Tyr Asp Ala Lys Ile Leu Pro Ala Gln Asn Val Ala Val Ser Val
                245                 250                 255

Ala Thr Gly Gly Glu Gly Phe His Asn Tyr His His Val Phe Pro Trp
            260                 265                 270

Asp Tyr Arg Ala Ala Glu Leu Gly Asn Asn Ser Leu Asn Leu Thr Thr
        275                 280                 285

Lys Phe Ile Asp Leu Phe Ala Ala Ile Gly Trp Ala Tyr Asp Leu Lys
    290                 295                 300

Thr Val Ser Glu Asp Met Ile Lys Gln Arg Ile Lys Arg Thr Gly Asp
```

-continued

```
               305                 310                 315                 320
Gly Thr Asp Leu Trp Gly His Glu Gln Asn Cys Asp Glu Val Trp Asp
                325                 330                 335

Val Lys Asp Lys Ser Ser
                340

<210> SEQ ID NO 63
<211> LENGTH: 363
<212> TYPE: PRT
<213> ORGANISM: Artificial Sequence
<220> FEATURE:
<223> OTHER INFORMATION: Agrotis segetum desaturase with Candida
      albicans OLE1 leader sequence encoded by SEQ ID NO: 15

<400> SEQUENCE: 63

Met Thr Thr Val Glu Gln Leu Glu Thr Val Asp Ile Thr Lys Leu Asn
1               5                   10                  15

Ala Ile Ala Ala Gly Thr Asn Lys Lys Val Pro Met Ala Gln Gly Val
                20                  25                  30

Gln Thr Thr Thr Ile Leu Arg Glu Glu Pro Ser Leu Thr Phe Val
                35                  40                  45

Val Pro Gln Glu Pro Arg Lys Tyr Gln Ile Val Tyr Pro Asn Leu Ile
50                  55                  60

Thr Phe Gly Tyr Trp His Ile Ala Gly Leu Tyr Gly Leu Tyr Leu Cys
65                  70                  75                  80

Phe Thr Ser Ala Lys Trp Gln Thr Ile Leu Phe Ser Phe Met Leu Val
                85                  90                  95

Val Leu Ala Glu Leu Gly Ile Thr Ala Gly Ala His Arg Leu Trp Ala
                100                 105                 110

His Lys Thr Tyr Lys Ala Lys Leu Pro Leu Gln Ile Ile Leu Met Ile
                115                 120                 125

Leu Asn Ser Ile Ala Phe Gln Asn Ser Ala Ile Asp Trp Val Arg Asp
                130                 135                 140

His Arg Leu His His Lys Tyr Ser Asp Thr Asp Ala Asp Pro His Asn
145                 150                 155                 160

Ala Thr Arg Gly Phe Phe Tyr Ser His Val Gly Trp Leu Leu Val Arg
                165                 170                 175

Lys His Pro Glu Val Lys Arg Arg Gly Lys Glu Leu Asp Met Ser Asp
                180                 185                 190

Ile Tyr Asn Asn Pro Val Leu Arg Phe Gln Lys Lys Tyr Ala Ile Pro
                195                 200                 205

Phe Ile Gly Ala Met Cys Phe Gly Leu Pro Thr Phe Ile Pro Val Tyr
                210                 215                 220

Phe Trp Gly Glu Thr Trp Ser Asn Ala Trp His Ile Thr Met Leu Arg
225                 230                 235                 240

Tyr Ile Leu Asn Leu Asn Ile Thr Phe Leu Val Asn Ser Ala Ala His
                245                 250                 255

Ile Trp Gly Tyr Lys Pro Tyr Asp Ile Lys Ile Leu Pro Ala Gln Asn
                260                 265                 270

Ile Ala Val Ser Ile Val Thr Gly Gly Glu Val Ser Ile Thr Thr Thr
                275                 280                 285

Thr Phe Phe Pro Trp Asp Tyr Arg Ala Ala Glu Leu Gly Asn Asn Tyr
                290                 295                 300

Leu Asn Leu Thr Thr Lys Phe Ile Asp Phe Phe Ala Trp Ile Gly Trp
305                 310                 315                 320
```

```
Ala Tyr Asp Leu Lys Thr Val Ser Ser Asp Val Ile Lys Ser Lys Ala
            325                 330                 335

Glu Arg Thr Gly Asp Gly Thr Asn Leu Trp Gly Leu Glu Asp Lys Gly
            340                 345                 350

Glu Glu Asp Phe Leu Lys Ile Trp Lys Asp Asn
            355                 360

<210> SEQ ID NO 64
<211> LENGTH: 326
<212> TYPE: PRT
<213> ORGANISM: Amyelois transitella

<400> SEQUENCE: 64

Met Val Pro Asn Lys Gly Ser Ser Asp Val Leu Ser Glu His Ser Glu
1               5                   10                  15

Pro Gln Phe Thr Lys Leu Ile Ala Pro Gln Ala Gly Pro Arg Lys Tyr
            20                  25                  30

Lys Ile Val Tyr Arg Asn Leu Leu Thr Phe Gly Tyr Trp His Leu Ser
        35                  40                  45

Ala Val Tyr Gly Leu Tyr Leu Cys Phe Thr Cys Ala Lys Trp Ala Thr
    50                  55                  60

Ile Leu Phe Ala Phe Phe Leu Tyr Val Ile Ala Glu Ile Gly Ile Thr
65                  70                  75                  80

Gly Gly Ala His Arg Leu Trp Ala His Arg Thr Tyr Lys Ala Lys Leu
                85                  90                  95

Pro Leu Glu Ile Leu Leu Leu Ile Met Asn Ser Ile Ala Phe Gln Asp
            100                 105                 110

Thr Ala Phe Thr Trp Ala Arg Asp His Arg Leu His His Lys Tyr Ser
        115                 120                 125

Asp Thr Asp Ala Asp Pro His Asn Ala Thr Arg Gly Phe Phe Tyr Ser
    130                 135                 140

His Val Gly Trp Leu Leu Val Lys Lys His Pro Glu Val Lys Ala Arg
145                 150                 155                 160

Gly Lys Tyr Leu Ser Leu Asp Asp Leu Lys Asn Asn Pro Leu Leu Lys
                165                 170                 175

Phe Gln Lys Lys Tyr Ala Ile Leu Val Ile Gly Thr Leu Cys Phe Leu
            180                 185                 190

Met Pro Thr Phe Val Pro Val Tyr Phe Trp Gly Glu Gly Ile Ser Thr
        195                 200                 205

Ala Trp Asn Ile Asn Leu Leu Arg Tyr Val Met Asn Leu Asn Met Thr
    210                 215                 220

Phe Leu Val Asn Ser Ala Ala His Ile Phe Gly Asn Lys Pro Tyr Asp
225                 230                 235                 240

Lys Ser Ile Ala Ser Val Gln Asn Ile Ser Val Ser Leu Ala Thr Phe
                245                 250                 255

Gly Glu Gly Phe His Asn Tyr His His Thr Tyr Pro Trp Asp Tyr Arg
            260                 265                 270

Ala Ala Glu Leu Gly Asn Asn Arg Leu Asn Met Thr Thr Ala Phe Ile
        275                 280                 285

Asp Phe Phe Ala Trp Ile Gly Trp Ala Tyr Asp Leu Lys Ser Val Pro
    290                 295                 300

Gln Glu Ala Ile Ala Lys Arg Cys Ala Lys Thr Gly Asp Gly Thr Asp
305                 310                 315                 320

Met Trp Gly Arg Lys Arg
                325
```

<210> SEQ ID NO 65
<211> LENGTH: 338
<212> TYPE: PRT
<213> ORGANISM: Spodoptera littoralis

<400> SEQUENCE: 65

Met Ala Gln Cys Val Gln Thr Thr Thr Ile Leu Glu Gln Lys Glu Glu
1               5                   10                  15

Lys Thr Val Thr Leu Leu Val Pro Gln Ala Gly Lys Arg Lys Phe Glu
            20                  25                  30

Ile Val Tyr Phe Asn Ile Ile Thr Phe Ala Tyr Trp His Ile Ala Gly
        35                  40                  45

Leu Tyr Gly Leu Tyr Leu Cys Phe Thr Ser Thr Lys Trp Ala Thr Val
    50                  55                  60

Leu Phe Ser Phe Phe Leu Phe Val Val Ala Glu Val Gly Val Thr Ala
65                  70                  75                  80

Gly Ser His Arg Leu Trp Ser His Lys Thr Tyr Lys Ala Lys Leu Pro
                85                  90                  95

Leu Gln Ile Leu Leu Met Val Met Asn Ser Leu Ala Phe Gln Asn Thr
            100                 105                 110

Val Ile Asp Trp Val Arg Asp His Arg Leu His His Lys Tyr Ser Asp
        115                 120                 125

Thr Asp Ala Asp Pro His Asn Ala Ser Arg Gly Phe Phe Tyr Ser His
    130                 135                 140

Val Gly Trp Leu Leu Val Arg Lys His Pro Asp Val Lys Lys Arg Gly
145                 150                 155                 160

Lys Glu Ile Asp Ile Ser Asp Ile Tyr Asn Asn Pro Val Leu Arg Phe
                165                 170                 175

Gln Lys Lys Tyr Ala Ile Pro Phe Ile Gly Ala Val Cys Phe Val Leu
            180                 185                 190

Pro Thr Leu Ile Pro Val Tyr Gly Trp Gly Glu Thr Trp Thr Asn Ala
        195                 200                 205

Trp His Val Ala Met Leu Arg Tyr Ile Met Asn Leu Asn Val Thr Phe
    210                 215                 220

Leu Val Asn Ser Ala Ala His Ile Tyr Gly Lys Arg Pro Tyr Asp Lys
225                 230                 235                 240

Lys Ile Leu Pro Ser Gln Asn Ile Ala Val Ser Ile Ala Thr Phe Gly
                245                 250                 255

Glu Gly Phe His Asn Tyr His His Val Phe Pro Trp Asp Tyr Arg Ala
            260                 265                 270

Ala Glu Leu Gly Asn Asn Ser Leu Asn Phe Pro Thr Lys Phe Ile Asp
        275                 280                 285

Phe Phe Ala Trp Ile Gly Trp Ala Tyr Asp Leu Lys Thr Val Ser Lys
    290                 295                 300

Glu Met Ile Lys Gln Arg Ser Lys Arg Thr Gly Asp Gly Thr Asn Leu
305                 310                 315                 320

Trp Gly Leu Glu Asp Val Asp Thr Pro Glu Asp Leu Lys Asn Thr Lys
                325                 330                 335

Gly Glu

<210> SEQ ID NO 66
<211> LENGTH: 336
<212> TYPE: PRT
<213> ORGANISM: Agrotis segetum -continued

<400> SEQUENCE: 66

```
Met Ala Gln Gly Val Gln Thr Thr Thr Ile Leu Arg Glu Glu Pro
1               5                   10                  15

Ser Leu Thr Phe Val Val Pro Gln Glu Pro Arg Lys Tyr Gln Ile Val
            20                  25                  30

Tyr Pro Asn Leu Ile Thr Phe Gly Tyr Trp His Ile Ala Gly Leu Tyr
        35                  40                  45

Gly Leu Tyr Leu Cys Phe Thr Ser Ala Lys Trp Gln Thr Ile Leu Phe
    50                  55                  60

Ser Phe Met Leu Val Val Leu Ala Glu Leu Gly Ile Thr Ala Gly Ala
65                  70                  75                  80

His Arg Leu Trp Ala His Lys Thr Tyr Lys Ala Lys Leu Pro Leu Gln
                85                  90                  95

Ile Ile Leu Met Ile Leu Asn Ser Ile Ala Phe Gln Asn Ser Ala Ile
            100                 105                 110

Asp Trp Val Arg Asp His Arg Leu His His Lys Tyr Ser Asp Thr Asp
        115                 120                 125

Ala Asp Pro His Asn Ala Thr Arg Gly Phe Phe Tyr Ser His Val Gly
    130                 135                 140

Trp Leu Leu Val Arg Lys His Pro Glu Val Lys Arg Arg Gly Lys Glu
145                 150                 155                 160

Leu Asp Met Ser Asp Ile Tyr Asn Asn Pro Val Leu Arg Phe Gln Lys
                165                 170                 175

Lys Tyr Ala Ile Pro Phe Ile Gly Ala Met Cys Phe Gly Leu Pro Thr
            180                 185                 190

Phe Ile Pro Val Tyr Phe Trp Gly Glu Thr Trp Ser Asn Ala Trp His
        195                 200                 205

Ile Thr Met Leu Arg Tyr Ile Leu Asn Leu Asn Ile Thr Phe Leu Val
    210                 215                 220

Asn Ser Ala Ala His Ile Trp Gly Tyr Lys Pro Tyr Asp Ile Lys Ile
225                 230                 235                 240

Leu Pro Ala Gln Asn Ile Ala Val Ser Ile Val Thr Gly Gly Glu Val
                245                 250                 255

Ser Ile Thr Thr Thr Thr Phe Phe Pro Trp Asp Tyr Arg Ala Ala Glu
            260                 265                 270

Leu Gly Asn Asn Tyr Leu Asn Leu Thr Thr Lys Phe Ile Asp Phe Phe
        275                 280                 285

Ala Trp Ile Gly Trp Ala Tyr Asp Leu Lys Thr Val Ser Ser Asp Val
    290                 295                 300

Ile Lys Ser Lys Ala Glu Arg Thr Gly Asp Gly Thr Asn Leu Trp Gly
305                 310                 315                 320

Leu Glu Asp Lys Gly Glu Asp Phe Leu Lys Ile Trp Lys Asp Asn
                325                 330                 335
```

<210> SEQ ID NO 67
<211> LENGTH: 349
<212> TYPE: PRT
<213> ORGANISM: Trichoplusia ni

<400> SEQUENCE: 67

```
Met Ala Val Met Ala Gln Thr Val Gln Glu Thr Ala Thr Val Leu Glu
1               5                   10                  15

Glu Glu Ala Arg Thr Val Thr Leu Val Ala Pro Lys Thr Thr Pro Arg
            20                  25                  30
```

Lys Tyr Lys Tyr Ile Tyr Thr Asn Phe Leu Thr Phe Ser Tyr Ala His
        35                  40                  45

Leu Ala Ala Leu Tyr Gly Leu Tyr Leu Cys Phe Thr Ser Ala Lys Trp
 50                  55                  60

Glu Thr Leu Leu Phe Ser Phe Val Leu Phe His Met Ser Asn Ile Gly
 65                  70                  75                  80

Ile Thr Ala Gly Ala His Arg Leu Trp Thr His Lys Thr Phe Lys Ala
                 85                  90                  95

Lys Leu Pro Leu Glu Ile Val Leu Met Ile Phe Asn Ser Leu Ala Phe
             100                 105                 110

Gln Asn Thr Ala Ile Thr Trp Ala Arg Glu His Arg Leu His His Lys
         115                 120                 125

Tyr Ser Asp Thr Asp Ala Asp Pro His Asn Ala Ser Arg Gly Phe Phe
130                 135                 140

Tyr Ser His Val Gly Trp Leu Leu Val Lys Lys His Pro Asp Val Leu
145                 150                 155                 160

Lys Tyr Gly Lys Thr Ile Asp Met Ser Asp Val Tyr Asn Asn Pro Val
                165                 170                 175

Leu Lys Phe Gln Lys Lys Tyr Ala Val Pro Leu Ile Gly Thr Val Cys
            180                 185                 190

Phe Ala Leu Pro Thr Leu Ile Pro Val Tyr Cys Trp Gly Glu Ser Trp
        195                 200                 205

Asn Asn Ala Trp His Ile Ala Leu Phe Arg Tyr Ile Phe Asn Leu Asn
210                 215                 220

Val Thr Phe Leu Val Asn Ser Ala Ala His Ile Trp Gly Asn Lys Pro
225                 230                 235                 240

Tyr Asp Lys Ser Ile Leu Pro Ala Gln Asn Leu Leu Val Ser Phe Leu
                245                 250                 255

Ala Ser Gly Glu Gly Phe His Asn Tyr His His Val Phe Pro Trp Asp
            260                 265                 270

Tyr Arg Thr Ala Glu Leu Gly Asn Asn Phe Leu Asn Leu Thr Thr Leu
        275                 280                 285

Phe Ile Asp Phe Cys Ala Trp Phe Gly Trp Ala Tyr Asp Leu Lys Ser
290                 295                 300

Val Ser Glu Asp Ile Ile Lys Gln Arg Ala Lys Arg Thr Gly Asp Gly
305                 310                 315                 320

Ser Ser Gly Val Ile Trp Gly Trp Asp Asp Lys Asp Met Asp Arg Asp
                325                 330                 335

Ile Lys Ser Lys Ala Asn Ile Phe Tyr Ala Lys Lys Glu
            340                 345

<210> SEQ ID NO 68
<211> LENGTH: 981
<212> TYPE: DNA
<213> ORGANISM: Artificial Sequence
<220> FEATURE:
<223> OTHER INFORMATION: Amyelois transitella desaturase from DTU WO
      2016/207339 SEQ ID NO: 1

<400> SEQUENCE: 68
atggttccaa acaagggttc ctctgatgtt ttgtctgaac attctgaacc acaattcacc    60
aagttgattg ctccacaagc tggtccaaga aagtacaaaa tcgtttacag aaacttgttg   120
accttcggtt actggcattt gtctgctgtt tatggttttgt acttgtgttt cacttgtgct   180
aagtgggcta ctattttgtt cgctttcttc ttgtacgtta tcgccgaaat tggtattact   240

```
ggtggtgctc atagattatg ggctcataga acttacaaag ccaagttgcc attggaaatc      300
ttgttgttga tcatgaactc cattgccttc caagatactg cttttacttg gctagagat      360 catagattgc atcacaagta ctctgatact gatgctgatc cacataatgc tactagaggt      420
ttcttctact ctcatgttgg ttggttgttg gttaagaaac acccagaagt taaggctaga      480
ggtaagtact tgtctttgga tgacttgaag aacaacccct tgttgaagtt ccaaaagaag      540
tacgccattt tggtcattgg tactttgtgc ttttgatgc caactttcgt tccagtttac       600
ttttggggtg aaggtatttc tactgcctgg aacattaact tgttaagata cgtcatgaac      660
ttgaacatga ccttttggt taactccgct gctcatattt tggtaacaa gccatacgat        720 aagtctatcg cctctgttca aaacatctct gtttctttgg ctactttcgg tgaaggtttc      780
cataactacc atcatactta tccatgggat tacagagctg ctgaattggg taacaataga     840
ttgaatatga ccaccgcctt cattgatttc tttgcttgga ttggttgggc ctacgatttg     900
aaatctgttc cacaagaagc tattgctaag agatgtgcta aaactggtga tggtactgat     960
atgtggggta gaaagagatg a                                                981

<210> SEQ ID NO 69
<211> LENGTH: 1470
<212> TYPE: DNA
<213> ORGANISM: Artificial Sequence
<220> FEATURE:
<223> OTHER INFORMATION: Spodoptera littoralis desaturase from DTU WO
      2016/207339 SEQ ID NO: 40

<400> SEQUENCE: 69
ggacactgac atggactgaa ggagtagaga atcggcccgt ggagttggcc ttcattttca      60
gtcttatctc tcggtgttat ggtagtcact tatatcggta ttaaaataag tgaataaggc     120
ttgtaaaaat ggcgcaatgt gtacaaacaa caacgatttt ggaacaaaaa gaagagaaaa     180
cagtaacttt gctggtacct caagcgggaa agaggaagtt tgaaattgtg tattttaata    240
tcatcacctt cgcttactgg catatagctg gactatatgg cctttatttg tgcttcactt     300
caacaaaatg ggcgacagtt ttattctcat tcttttctatt cgtcgtagca gaagtagggg    360
tcacggctgg ctcccacaga ctttggtcgc ataaaactta caaagcaaaa ctacctttac     420
aaattctgct aatggtgatg aattcccttg catttcaaaa cacagtcatt gattgggtga    480
gagaccatcg actccatcat aagtatagcg acactgatgc cgatccccat aatgcctccc    540
gaggattttt ctattcgcac gtcggttggc tgcttgtgag aaaacacccct gatgtcaaga   600 aacgaggaaa ggaaattgat atatctgata tttacaacaa tccggtactg aggttccaga    660
agaagtacgc aattccttc atcggggcag tttgtttcgt cttaccaaca ttgataccgg      720
tttacggttg gggagaaacc tggactaatg cctggcacgt cgccatgctg cggtacatta    780
tgaaccttaa cgtcaccttc ctggtcaaca gcgctgctca tatatatgga aagagacctt     840
atgacaagaa gatcctacca tctcaaaaca tagctgtgtc cattgcaacc tttggggaag    900
gtttccataa ttatcatcat gtatttccat gggattatcg cgcagctgaa cttggaaata    960
acagtttgaa tttccctacg aaatttattg atttctttgc gtggatcgga tgggcgtatg    1020
acctaaagac tgtttcgaaa gaaatgataa acaaaggtc aaaagaact ggtgatggaa       1080 ctaatctatg ggggttagaa gatgtggata ccccggagga tttaaaaaat acaaaaggcg    1140
aataggcaaa cccttaaact caaacagtga ggtttaatgt gatatttaga attagaatta    1200 atttattga aattaaatga aggttttgga taactgtttt taataataaa aatagttttt     1260
```

```
cgattaaatt ccttagatta ttttaaagga aatgtataag gtactcgcgt ggttagcaac    1320
ccagcagtcc ctgtttatct gttttttatga atttattcta tgaatgtaga tgtcgcatga    1380 aatttttaaaa tgttgcattt gtataatttt acttatgaat aaataaattt attttttaaaa    1440 aaaaaaaaaa aaaaaaaaaa aaaaaaaaaa                                      1470

<210> SEQ ID NO 70
<211> LENGTH: 1011
<212> TYPE: DNA
<213> ORGANISM: Artificial Sequence
<220> FEATURE:
<223> OTHER INFORMATION: Agrotis segetum desaturase from DTU WO
      2016/207339 SEQ ID NO: 42

<400> SEQUENCE: 70
atggctcaag gtgtccaaac aactacgata ttgagggagg aagagccgtc attgactttc     60
gtggtacctc aagaaccgag aaagtatcaa atcgtgtacc caaaccttat cacatttggg    120
tactggcata tagctggttt atacgggcta tatttgtgct ttacttcggc aaaatggcaa    180
acaattttat tcagtttcat gctcgttgtg ttagcagagt tgggaataac agccggcgct    240
cacaggttat gggcccacaa acatataaaa gcgaagcttc ccttacaaat tatcctgatg    300
atactgaact ccattgcctt ccaaaattcc gccattgatt gggtgaggga ccaccgtctc    360
catcataagt acagtgacac tgatgcagac cctcacaatg ctactcgtgg tttcttctat    420
tctcatgttg atggttgct cgtaagaaaa catccagaag tcaagagacg tggaaaggaa    480
cttgacatgt ctgatattta caacaatcca gtgctgagat ttcaaaagaa gtatgctata    540
cccttcatcg gggcaatgtg cttcggatta ccaacttttta tccctgttta cttctgggga    600
gaaacctgga gtaatgcttg gcatatcacc atgcttcggt acatcctcaa cctaaacatt    660
actttcctgg tcaacagtgc tgctcatatc tggggataca aaccttatga catcaaaata    720
ttgcctgccc aaaatatagc agtttccata gtaaccggcg gcgaagtttc cataactacc    780
accacgtttt ttccttggga ttatcgtgca gcagaattgg ggaacaatta tcttaatttg    840
acgactaagt tcatagattt cttcgcttgg atcggatggg cttacgatct taagacggtg    900
tccagtgatg ttataaaaag taaggcggaa agaactggtg atgggacgaa tctttggggt    960
ttagaagaca aggtgaaga agatttttttg aaaatctgga agacaattaa a              1011

<210> SEQ ID NO 71
<211> LENGTH: 1050
<212> TYPE: DNA
<213> ORGANISM: Artificial Sequence
<220> FEATURE:
<223> OTHER INFORMATION: Trichoplusia ni desaturase from DTU WO
      2016/207339_SEQ ID NO: 44

<400> SEQUENCE: 71
atggctgtga tggctcaaac agtacaagaa acggctacag tgttggaaga ggaagctcgc     60
acagtgactc ttgtggctcc aaagacaacg ccaaggaaat ataaatatat atacaccaac    120
tttcttacat tttcatatgc gcatttagct gcattatacg gactttattt gtgcttcacc    180
tctgcgaaat gggaaacatt gctattctct ttcgtactct tccacatgtc aaatataggc    240
atcaccgcag gggctcaccg actctggact cacaagactt caaagccaa attgcctttg    300 gaaattgtcc tcatgatatt caactctta gcctttcaaa acacggctat tacatgggct    360
agagaacatc ggctacatca caaatacagc gatactgatg ctgatcccca caatgcgtca    420
```

```
agagggttct tctactcgca tgttggctgg ctattagtaa aaaaacatcc cgatgtcctg      480
aaatatggaa aaactataga catgtcggat gtatacaata atcctgtgtt aaaatttcag      540
aaaaagtacg cagtacccct taattggaaca gtttgttttg ctcttccaac tttgattcca     600
gtctactgtt ggggcgaatc gtggaacaac gcttggcaca tagccttatt tcgatacata     660
ttcaatctta acgtgacttt cctagtcaac agtgctgcgc atatctgggg gaataagcct     720
tatgataaaa gcatcttgcc cgctcaaaac ctgctggttt ccttcctagc aagtggagaa     780
ggcttccata attaccatca cgtctttcca tgggattacc gcacagcaga attagggaat     840
aacttcctga atttgacgac gctgttcatt gatttttgtg cctggtttgg atgggcttat     900
gacttgaagt ctgtatcaga ggatattata aaacagagag ctaaacgaac aggtgacggt     960
tcttcagggg tcatttgggg atgggacgac aaagacatgg accgcgatat aaaatctaaa    1020
gctaacattt tttatgctaa aaaggaatga                                      1050
```

<210> SEQ ID NO 72  
<211> LENGTH: 1365  
<212> TYPE: DNA  
<213> ORGANISM: Artificial Sequence  
<220> FEATURE:  
<223> OTHER INFORMATION: codon optimized Spodoptera exigua FAR-like protein VIII nucleotide sequence (Genbank ID KR781121.1)

<400> SEQUENCE: 72

```
atggtggtgc tgaccagcaa ggagaagtcc aacatgtctg tggccgactt ctacgccggc       60
aagtccgtgt ttatcacagg cggcaccggc ttcctgggca aggtgtttat cgagaagctg      120
ctgtactctt gcccagacat cgataagatc tatatgctga tccgggagaa gaagggccag      180
agcatcaggg agcgcctgac caagatcgtg gacgatcccc tgttcaatag gctgaaggag      240
aagcgccctg gcgacctgga taagatcgtg ctgatcccag gcgatgtgac agtgcccggc      300
ctgggcatct ccgacgagaa cgaggccatc ctgatcgata ggtgtctgt ggtcatccac       360 agcgccgcca cagtgaagtt caatgagccc ctggagaccg cctggaacgt gaatgtggag      420
ggcacaagga tgatcatggc cctgtctcgg aagatgaaga gaatcgagat cttatccac       480 atcagcaccg cctacaccaa cacaaatagg gcagtggtgg acgaggtgct gtacccacct      540
ccagccgaca tcaacgaggt gcaccagtat gtgaagaatg gcatcacaga ggaggagacc      600
gagaagatcc tgaacggcag gcccaatacc tacacattca ccaaggccct gaccgagcac      660
ctggtggcag agaaccaggc ctatatgcct acaatcatcg tgcggccatc catcgtgggc      720
gccatcaagg acgatcctat cagaggctgg ctggcaaact ggtacggagc aacaggactg      780
agcgtgttca ccgccaaggg cctgaatcgc gtgatctacg ccagagcag ccacgtggtg       840 gacctgatcc ctgtggatta tgtggcaaac ctggtcatcg tggcaggagc aaagacatac      900
cggtccaacg aggtgaccat ctataattct tgctctagct cctgtaatcc aatcacaatg      960
gagcggctgg tgggcctgtt catcgacgat acagtgaagc acaacagcta cgtgatgccc     1020
ctgcctggct ggtacgtgta ttccaattac cggtggctgg tgtatctggt gaccatcatc     1080
tttcagatga tcccagccta tctggcagac atcggccgga gactgctggg caagaatccc     1140
agatactata agctgcagtc cctggtggca cagacccagg aggcagtgca cttctttaca     1200
tctcacacct gggagatcaa gagcaagagg acctccgagc tgttcgcctc tctgagccac     1260
acagaccagc gcatctttcc ttgcgatgcc aagaagatcg actggacaga ttacatcacc     1320
gattattgta gcggcgtgcg gcagttcctg gagaagaaga agtga                     1365
```

<210> SEQ ID NO 73
<211> LENGTH: 454
<212> TYPE: PRT
<213> ORGANISM: Spodoptera exigua

<400> SEQUENCE: 73

```
Met Val Val Leu Thr Ser Lys Glu Lys Ser Asn Met Ser Val Ala Asp
1               5                   10                  15

Phe Tyr Ala Gly Lys Ser Val Phe Ile Thr Gly Gly Thr Gly Phe Leu
            20                  25                  30

Gly Lys Val Phe Ile Glu Lys Leu Leu Tyr Ser Cys Pro Asp Ile Asp
        35                  40                  45

Lys Ile Tyr Met Leu Ile Arg Glu Lys Lys Gly Gln Ser Ile Arg Glu
    50                  55                  60

Arg Leu Thr Lys Ile Val Asp Asp Pro Leu Phe Asn Arg Leu Lys Glu
65                  70                  75                  80

Lys Arg Pro Gly Asp Leu Asp Lys Ile Val Leu Ile Pro Gly Asp Val
                85                  90                  95

Thr Val Pro Gly Leu Gly Ile Ser Asp Glu Asn Glu Ala Ile Leu Ile
            100                 105                 110

Asp Lys Val Ser Val Val Ile His Ser Ala Ala Thr Val Lys Phe Asn
        115                 120                 125

Glu Pro Leu Glu Thr Ala Trp Asn Val Asn Val Glu Gly Thr Arg Met
    130                 135                 140

Ile Met Ala Leu Ser Arg Lys Met Lys Arg Ile Glu Ile Phe Ile His
145                 150                 155                 160

Ile Ser Thr Ala Tyr Thr Asn Thr Asn Arg Ala Val Val Asp Glu Val
                165                 170                 175

Leu Tyr Pro Pro Pro Ala Asp Ile Asn Glu Val His Gln Tyr Val Lys
            180                 185                 190

Asn Gly Ile Thr Glu Glu Glu Thr Glu Lys Ile Leu Asn Gly Arg Pro
        195                 200                 205

Asn Thr Tyr Thr Phe Thr Lys Ala Leu Thr Glu His Leu Val Ala Glu
    210                 215                 220

Asn Gln Ala Tyr Met Pro Thr Ile Ile Val Arg Pro Ser Ile Val Gly
225                 230                 235                 240

Ala Ile Lys Asp Asp Pro Ile Arg Gly Trp Leu Ala Asn Trp Tyr Gly
                245                 250                 255

Ala Thr Gly Leu Ser Val Phe Thr Ala Lys Gly Leu Asn Arg Val Ile
            260                 265                 270

Tyr Gly Gln Ser Ser His Val Val Asp Leu Ile Pro Val Asp Tyr Val
        275                 280                 285

Ala Asn Leu Val Ile Val Ala Gly Ala Lys Thr Tyr Arg Ser Asn Glu
    290                 295                 300

Val Thr Ile Tyr Asn Ser Cys Ser Ser Ser Cys Asn Pro Ile Thr Met
305                 310                 315                 320

Glu Arg Leu Val Gly Leu Phe Ile Asp Asp Thr Val Lys His Asn Ser
                325                 330                 335

Tyr Val Met Pro Leu Pro Gly Trp Tyr Val Tyr Ser Asn Tyr Arg Trp
            340                 345                 350

Leu Val Tyr Leu Val Thr Ile Ile Phe Gln Met Ile Pro Ala Tyr Leu
        355                 360                 365

Ala Asp Ile Gly Arg Arg Leu Leu Gly Lys Asn Pro Arg Tyr Tyr Lys
    370                 375                 380
```

```
Leu Gln Ser Leu Val Ala Gln Thr Gln Glu Ala Val His Phe Phe Thr
385                 390                 395                 400

Ser His Thr Trp Glu Ile Lys Ser Lys Arg Thr Ser Glu Leu Phe Ala
            405                 410                 415

Ser Leu Ser His Thr Asp Gln Arg Ile Phe Pro Cys Asp Ala Lys Lys
        420                 425                 430

Ile Asp Trp Thr Asp Tyr Ile Thr Asp Tyr Cys Ser Gly Val Arg Gln
        435                 440                 445

Phe Leu Glu Lys Lys Lys
    450

<210> SEQ ID NO 74
<211> LENGTH: 1545
<212> TYPE: DNA
<213> ORGANISM: Artificial Sequence
<220> FEATURE:
<223> OTHER INFORMATION: codon optimized Euglena gracilis fatty acyl-
      coenzyme A reductase nucleotide sequence

<400> SEQUENCE: 74
atgaacgact tctacgccgg caagggcgtg tttctgacag gcgtgaccgg cttcgtgggc        60
aagatggtgg tggagaagat cctgcggtct ctgccaaccg tgggcaggct gtatgtgctg      120
gtgcgcccaa aggcaggcac agatcctcac cagagactgc acagcgaagt gtggagcagc      180
gccggatttg acgtggtgag ggagaaagtg ggaggacctg cagccttcga tgcactgatc      240
cgcgagaagg tggtgcctgt gccaggcgac atggtgaagg ataggtttgg cctggacgat      300
gcagcatacc gctccctggc agccaacgtg aatgtgatca tccacatggc cgccacaatc      360
gacttcaccg agaggctgga tgtggccgtg tctctgaacg tgctgggcac agtgcgggtg      420
ctgaccctgg caaggagagc cagagagctg ggcgccctgc acagcgtggt gcacgtgtcc      480
acctgctacg tgaactccaa tcagccccct ggcgcccggc tgagagagca gctgtatccc      540 ctgcctttg acccacggga gatgtgcaca agaatcctgg acatgagccc tcgggagatc      600
gatctgttcg ccccacagct gctgaagcag tacggcttcc ccaataccta taccttcacc      660
aagtgcatgg cagagcagct gggcgcccag atcgcacacg acctgccatt cgccatcttt      720
agaccagcaa tcatcggagc cgccctgtcc gagccatttc ccggctggtg cgattctgcc      780
agcgcctgtg agccgtgtt cctggcagtg ggactgggcg tgctgcagga gctgcaggga      840
aacgcctcta gcgtgtgcga cctgatccct gtggatcacg tggtgaatat gctgctggtg      900
acagcagcat ataccgcatc tgccccacca gccgacccta gcccatcctc tctgccctg      960 tccctccac agctgccact ggccacactg cccctggca ccgtggcaga tgtgccaatc       1020
taccactgtg gcacctctgc cggccctaac gccgtgaatt ggggcaggat caaggtgagc      1080
ctggtggagt attggaacgc acacccaatc gcaaagacca aggcagcaat cgccctgctg      1140
cccgtgtgga ggttcgagct gagctttctg ctgaagaggc gcctgcctgc aacagccctg      1200
tccctggtgg cctctctgcc aggcgcatcc gccgccgtgc ggagacaggc agagcagaca      1260
gagcggctgg tggcaagat gagaaagctg gtggacacct tcagtcctt cgtgttttgg       1320 gcctggtact ccagacaga gagcagcgcc aggctgctgg cctctctgtg cccagaggac      1380
cgcgagacct taactggga ccccaggagg atcggatgga gggcctgggt ggagaattac      1440
tgttatggcc tggtgcggta tgtgctgaag cagccaatcg cgatagacc accagtggca      1500 gcagaggagc tggcaagcaa taggttcctg cgcgccatgc tgtga                    1545
```

<210> SEQ ID NO 75
<211> LENGTH: 514
<212> TYPE: PRT
<213> ORGANISM: Euglena gracilis

<400> SEQUENCE: 75

```
Met Asn Asp Phe Tyr Ala Gly Lys Gly Val Phe Leu Thr Gly Val Thr
1               5                   10                  15

Gly Phe Val Gly Lys Met Val Val Glu Lys Ile Leu Arg Ser Leu Pro
            20                  25                  30

Thr Val Gly Arg Leu Tyr Val Leu Val Arg Pro Lys Ala Gly Thr Asp
        35                  40                  45

Pro His Gln Arg Leu His Ser Glu Val Trp Ser Ser Ala Gly Phe Asp
    50                  55                  60

Val Val Arg Glu Lys Val Gly Gly Pro Ala Ala Phe Asp Ala Leu Ile
65                  70                  75                  80

Arg Glu Lys Val Val Pro Val Pro Gly Asp Met Val Lys Asp Arg Phe
                85                  90                  95

Gly Leu Asp Asp Ala Ala Tyr Arg Ser Leu Ala Ala Asn Val Asn Val
            100                 105                 110

Ile Ile His Met Ala Ala Thr Ile Asp Phe Thr Glu Arg Leu Asp Val
        115                 120                 125

Ala Val Ser Leu Asn Val Leu Gly Thr Val Arg Val Leu Thr Leu Ala
    130                 135                 140

Arg Arg Ala Arg Glu Leu Gly Ala Leu His Ser Val His Val Ser
145                 150                 155                 160

Thr Cys Tyr Val Asn Ser Asn Gln Pro Pro Gly Ala Arg Leu Arg Glu
                165                 170                 175

Gln Leu Tyr Pro Leu Pro Phe Asp Pro Arg Glu Met Cys Thr Arg Ile
            180                 185                 190

Leu Asp Met Ser Pro Arg Glu Ile Asp Leu Phe Gly Pro Gln Leu Leu
        195                 200                 205

Lys Gln Tyr Gly Phe Pro Asn Thr Tyr Thr Phe Thr Lys Cys Met Ala
    210                 215                 220

Glu Gln Leu Gly Ala Gln Ile Ala His Asp Leu Pro Phe Ala Ile Phe
225                 230                 235                 240

Arg Pro Ala Ile Ile Gly Ala Ala Leu Ser Glu Pro Phe Pro Gly Trp
                245                 250                 255

Cys Asp Ser Ala Ser Ala Cys Gly Ala Val Phe Leu Ala Val Gly Leu
            260                 265                 270

Gly Val Leu Gln Glu Leu Gln Gly Asn Ala Ser Ser Val Cys Asp Leu
        275                 280                 285

Ile Pro Val Asp His Val Val Asn Met Leu Leu Val Thr Ala Ala Tyr
    290                 295                 300

Thr Ala Ser Ala Pro Pro Ala Asp Pro Ser Pro Ser Ser Leu Ala Leu
305                 310                 315                 320

Ser Pro Pro Gln Leu Pro Leu Ala Thr Leu Pro Pro Gly Thr Val Ala
                325                 330                 335

Asp Val Pro Ile Tyr His Cys Gly Thr Ser Ala Gly Pro Asn Ala Val
            340                 345                 350

Asn Trp Gly Arg Ile Lys Val Ser Leu Val Glu Tyr Trp Asn Ala His
        355                 360                 365

Pro Ile Ala Lys Thr Lys Ala Ala Ile Ala Leu Leu Pro Val Trp Arg
    370                 375                 380
```

```
Phe Glu Leu Ser Phe Leu Leu Lys Arg Arg Leu Pro Ala Thr Ala Leu
385                 390                 395                 400

Ser Leu Val Ala Ser Leu Pro Gly Ala Ser Ala Val Arg Arg Gln
            405                 410                 415

Ala Glu Gln Thr Glu Arg Leu Val Gly Lys Met Arg Lys Leu Val Asp
            420                 425                 430

Thr Phe Gln Ser Phe Val Phe Trp Ala Trp Tyr Phe Gln Thr Glu Ser
            435                 440                 445

Ser Ala Arg Leu Leu Ala Ser Leu Cys Pro Glu Asp Arg Glu Thr Phe
        450                 455                 460

Asn Trp Asp Pro Arg Arg Ile Gly Trp Arg Ala Trp Val Glu Asn Tyr
465                 470                 475                 480

Cys Tyr Gly Leu Val Arg Tyr Val Leu Lys Gln Pro Ile Gly Asp Arg
                485                 490                 495

Pro Pro Val Ala Ala Glu Glu Leu Ala Ser Asn Arg Phe Leu Arg Ala
            500                 505                 510

Met Leu

<210> SEQ ID NO 76
<211> LENGTH: 1350
<212> TYPE: DNA
<213> ORGANISM: Artificial Sequence
<220> FEATURE:
<223> OTHER INFORMATION: codon optimized Yponomeuta evonymellus fatty-
      acyl CoA reductase II nucleotide sequence

<400> SEQUENCE: 76
atggtgcagc tgaaggagga ctccgtggcc gccttttacg ccgagaagtc tatcttcatc      60
acaggcggca ccggctttct gggcaaggtg ctgatcgaga gctgctgta ctcctgcaag     120 gccgtggacc agatctatgt gctgatccgg aagaagaagg atcagacacc ttctgagcgc     180
atcgcccagc tgctggagtc tgagctgttc agcggctga gaaaggacga tccaagcgcc     240
ctgaagaagg tggtgcccgt ggtgggcgac ctgaccatgc taacctggg actgagcgcc     300 gcagtgcagg atctgatcgt gacaaaggtg tccatcatct ccacgtggc cgccaccgtg     360 aagtttaacg agaggatgaa gaatgccctg ccaacaatg tggaggccac cagagaagtg     420
atcaacctgt gccaccgcct ggagaaggtg gacgccttca tccacgtgtc cacagcctat     480
tctaataccg atcagaaggt ggtggaggag cgcgtgtacc acctccagc acctctgagc     540 gaggtgtatg cctttgtgac caacaatggc gacgatatgg acatcatcca gaacctgctg     600 aatgccggc caaatacca cacatatacc aaggccctgg ccgaggacat cgtgctgaag     660
gagcacggcg catccctac agccatcatc agaccaagca tcgtgctgtc cgtgctgaag     720
gagcccatcc ctggctggct ggacaactgg aatggaccaa ccggactgct gcacgccagc     780
tcccagggag tgcactgctc catgctgggc tctggcagca acgtggccga cctgatccct     840
gtggacatcg tgacaaatct gatgatcgtg gtggcctctc ggtgcaagaa gagcaacggc     900
ctgaaggtgt acaattcctg ttctggcacc acaaacccaa tcgcctatca ggccttcacc     960
aagatgtttc tggatagctg tatctccagg ggctggaaca aggtgccatt ccccatgctg    1020
ctgtttgtga agtgggcctt cctgaatcgc gtgctgaagt tcttcctggt catcgtgcca    1080
ttctttctga tcgacgtgta cctgcggttc tttggcaagc ccaattacat gagaatgatc    1140
acatatacca agaaggccga ggatctgatg acattcttta cctctcacga gtggcagttc    1200
aaggacggca acgtgcggga tctgatcaat atgatgagcc ccgaggatag aaagatcttt    1260
```

-continued

```
tactgcgacc ccgatgagat ccactggaag ccttacttcg acgattattg cgtgggcgtg    1320
tttaagtatc tgctgaagag gaaggtgtga                                     1350
```

<210> SEQ ID NO 77
<211> LENGTH: 449
<212> TYPE: PRT
<213> ORGANISM: Yponomeuta evonymellus

<400> SEQUENCE: 77

| | | | | | | | | | | | | | | |
|---|---|---|---|---|---|---|---|---|---|---|---|---|---|---|
| Met | Val | Gln | Leu | Lys | Glu | Asp | Ser | Val | Ala | Ala | Phe | Tyr | Ala | Glu | Lys |
| 1 | | | | 5 | | | | | 10 | | | | | 15 | |
| Ser | Ile | Phe | Ile | Thr | Gly | Gly | Thr | Gly | Phe | Leu | Gly | Lys | Val | Leu | Ile |
| | | | 20 | | | | | 25 | | | | | 30 | | |
| Glu | Lys | Leu | Leu | Tyr | Ser | Cys | Lys | Ala | Val | Asp | Gln | Ile | Tyr | Val | Leu |
| | | | 35 | | | | 40 | | | | | 45 | | | |
| Ile | Arg | Lys | Lys | Lys | Asp | Gln | Thr | Pro | Ser | Glu | Arg | Ile | Ala | Gln | Leu |
| | 50 | | | | | 55 | | | | | 60 | | | | |
| Leu | Glu | Ser | Glu | Leu | Phe | Ser | Arg | Leu | Arg | Lys | Asp | Asp | Pro | Ser | Ala |
| 65 | | | | | 70 | | | | | 75 | | | | | 80 |
| Leu | Lys | Lys | Val | Val | Pro | Val | Val | Gly | Asp | Leu | Thr | Met | Pro | Asn | Leu |
| | | | | 85 | | | | | 90 | | | | | 95 | |
| Gly | Leu | Ser | Ala | Ala | Val | Gln | Asp | Leu | Ile | Val | Thr | Lys | Val | Ser | Ile |
| | | | | 100 | | | | | 105 | | | | | 110 | |
| Ile | Phe | His | Val | Ala | Ala | Thr | Val | Lys | Phe | Asn | Glu | Arg | Met | Lys | Asn |
| | | | 115 | | | | | 120 | | | | | 125 | | |
| Ala | Leu | Ala | Asn | Asn | Val | Glu | Ala | Thr | Arg | Glu | Val | Ile | Asn | Leu | Cys |
| | 130 | | | | | 135 | | | | | 140 | | | | |
| His | Arg | Leu | Glu | Lys | Val | Asp | Ala | Phe | Ile | His | Val | Ser | Thr | Ala | Tyr |
| 145 | | | | | 150 | | | | | 155 | | | | | 160 |
| Ser | Asn | Thr | Asp | Gln | Lys | Val | Val | Glu | Glu | Arg | Val | Tyr | Pro | Pro | Pro |
| | | | | 165 | | | | | 170 | | | | | 175 | |
| Ala | Pro | Leu | Ser | Glu | Val | Tyr | Ala | Phe | Val | Thr | Asn | Asn | Gly | Asp | Asp |
| | | | | 180 | | | | | 185 | | | | | 190 | |
| Met | Asp | Ile | Ile | Gln | Asn | Leu | Leu | Asn | Gly | Arg | Pro | Asn | Thr | Tyr | Thr |
| | | | 195 | | | | | 200 | | | | | 205 | | |
| Tyr | Thr | Lys | Ala | Leu | Ala | Glu | Asp | Ile | Val | Leu | Lys | Glu | His | Gly | Gly |
| | 210 | | | | | 215 | | | | | 220 | | | | |
| Ile | Pro | Thr | Ala | Ile | Ile | Arg | Pro | Ser | Ile | Val | Leu | Ser | Val | Leu | Lys |
| 225 | | | | | 230 | | | | | 235 | | | | | 240 |
| Glu | Pro | Ile | Pro | Gly | Trp | Leu | Asp | Asn | Trp | Asn | Gly | Pro | Thr | Gly | Leu |
| | | | | 245 | | | | | 250 | | | | | 255 | |
| Leu | His | Ala | Ser | Ser | Gln | Gly | Val | His | Cys | Ser | Met | Leu | Gly | Ser | Gly |
| | | | | 260 | | | | | 265 | | | | | 270 | |
| Ser | Asn | Val | Ala | Asp | Leu | Ile | Pro | Val | Asp | Ile | Val | Thr | Asn | Leu | Met |
| | | | 275 | | | | | 280 | | | | | 285 | | |
| Ile | Val | Val | Ala | Ser | Arg | Cys | Lys | Lys | Ser | Asn | Gly | Leu | Lys | Val | Tyr |
| | 290 | | | | | 295 | | | | | 300 | | | | |
| Asn | Ser | Cys | Ser | Gly | Thr | Thr | Asn | Pro | Ile | Ala | Tyr | Gln | Ala | Phe | Thr |
| 305 | | | | | 310 | | | | | 315 | | | | | 320 |
| Lys | Met | Phe | Leu | Asp | Ser | Cys | Ile | Ser | Arg | Gly | Trp | Asn | Lys | Val | Pro |
| | | | | 325 | | | | | 330 | | | | | 335 | |
| Phe | Pro | Met | Leu | Leu | Phe | Val | Lys | Trp | Ala | Phe | Leu | Asn | Arg | Val | Leu |
| | | | | 340 | | | | | 345 | | | | | 350 | |

```
Lys Phe Phe Leu Val Ile Val Pro Phe Phe Leu Ile Asp Val Tyr Leu
                355                 360                 365

Arg Phe Phe Gly Lys Pro Asn Tyr Met Arg Met Ile Thr Tyr Thr Lys
    370                 375                 380

Lys Ala Glu Asp Leu Met Thr Phe Phe Thr Ser His Glu Trp Gln Phe
385                 390                 395                 400

Lys Asp Gly Asn Val Arg Asp Leu Ile Asn Met Met Ser Pro Glu Asp
                405                 410                 415

Arg Lys Ile Phe Tyr Cys Asp Pro Asp Glu Ile His Trp Lys Pro Tyr
                420                 425                 430

Phe Asp Asp Tyr Cys Val Gly Val Phe Lys Tyr Leu Leu Lys Arg Lys
                435                 440                 445

Val

<210> SEQ ID NO 78
<211> LENGTH: 361
<212> TYPE: PRT
<213> ORGANISM: Drosophila melanogaster

<400> SEQUENCE: 78

Met Ala Pro Tyr Ser Arg Ile Tyr His Gln Asp Lys Ser Ser Arg Glu
1               5                   10                  15

Thr Gly Val Leu Phe Glu Asp Asp Ala Gln Thr Val Asp Ser Asp Leu
                20                  25                  30

Thr Thr Asp Arg Phe Gln Leu Lys Arg Ala Glu Lys Arg Arg Leu Pro
            35                  40                  45

Leu Val Trp Arg Asn Ile Ile Leu Phe Ala Leu Val His Leu Ala Ala
    50                  55                  60

Leu Tyr Gly Leu His Ser Ile Phe Thr Arg Ala Lys Leu Ala Thr Thr
65                  70                  75                  80

Leu Phe Ala Ala Gly Leu Tyr Ile Ile Gly Met Leu Gly Val Thr Ala
                85                  90                  95

Gly Ala His Arg Leu Trp Ala His Arg Thr Tyr Lys Ala Lys Trp Pro
            100                 105                 110

Leu Arg Leu Leu Leu Val Ile Phe Asn Thr Ile Ala Phe Gln Asp Ala
        115                 120                 125

Val Tyr His Trp Ala Arg Asp His Arg Val His His Lys Tyr Ser Glu
    130                 135                 140

Thr Asp Ala Asp Pro His Asn Ala Thr Arg Gly Phe Phe Phe Ser His
145                 150                 155                 160

Val Gly Trp Leu Leu Cys Lys Lys His Pro Asp Ile Lys Glu Lys Gly
                165                 170                 175

Arg Gly Leu Asp Leu Ser Asp Leu Arg Ala Asp Pro Ile Leu Met Phe
            180                 185                 190

Gln Arg Lys His Tyr Tyr Ile Leu Met Pro Leu Ala Cys Phe Val Leu
        195                 200                 205

Pro Thr Val Ile Pro Met Val Tyr Trp Asn Glu Thr Leu Ala Ser Ser
    210                 215                 220

Trp Phe Val Ala Thr Met Phe Arg Trp Cys Phe Gln Leu Asn Met Thr
225                 230                 235                 240

Trp Leu Val Asn Ser Ala Ala His Lys Phe Gly Asn Arg Pro Tyr Asp
                245                 250                 255

Lys Thr Met Asn Pro Thr Gln Asn Ala Phe Val Ser Ala Phe Thr Phe
            260                 265                 270
```

```
Gly Glu Gly Trp His Asn Tyr His His Ala Phe Pro Trp Asp Tyr Lys
            275                 280                 285

Thr Ala Glu Trp Gly Cys Tyr Ser Leu Asn Ile Thr Thr Ala Phe Ile
290                 295                 300

Asp Leu Phe Ala Lys Ile Gly Trp Ala Tyr Asp Leu Lys Thr Val Ala
305                 310                 315                 320

Pro Asp Val Ile Gln Arg Arg Val Leu Arg Thr Gly Asp Gly Ser His
                325                 330                 335

Glu Leu Trp Gly Trp Gly Asp Lys Asp Leu Thr Ala Glu Asp Ala Arg
            340                 345                 350

Asn Val Leu Leu Val Asp Lys Ser Arg
            355                 360

<210> SEQ ID NO 79
<211> LENGTH: 359
<212> TYPE: PRT
<213> ORGANISM: Lampronia capitella

<400> SEQUENCE: 79

Met Pro Pro Tyr Pro Glu Glu Val Asp Thr Asn His Ile Phe Glu Glu
1               5                   10                  15

Asp Ile Ser His Glu Glu Ser Lys Pro Ala Leu Lys Pro Leu Val Ala
            20                  25                  30

Pro Gln Ala Asp Asn Arg Lys Pro Glu Ile Val Pro Leu Asn Leu Ile
        35                  40                  45

Thr Phe Gly Tyr Gly His Leu Ala Ala Ile Tyr Gly Ile Tyr Leu Cys
    50                  55                  60

Phe Thr Ser Ala Lys Trp Ala Thr Ile Val Phe Ala Phe Val Leu Tyr
65                  70                  75                  80

Ile Cys Ala Glu Leu Gly Ile Thr Ala Gly Ala His Arg Leu Trp Ser
                85                  90                  95

His Arg Ser Tyr Lys Ala Lys Leu Pro Leu Arg Leu Ile Leu Leu Leu
            100                 105                 110

Phe Asn Thr Leu Ala Phe Gln Asn Thr Ala Ile Asp Trp Val Arg Asp
        115                 120                 125

His Arg Met His His Lys Tyr Ser Asp Thr Asp Ala Asp Pro His Asn
    130                 135                 140

Ala Thr Arg Gly Phe Phe Phe Ser His Val Gly Trp Leu Leu Thr Arg
145                 150                 155                 160

Lys His Pro Glu Val Lys Arg Arg Gly Lys Asp Ile Asp Met Met Asp
                165                 170                 175

Ile Tyr Asn Asp Ser Leu Leu Lys Phe Gln Lys Lys Tyr Ala Ile Pro
            180                 185                 190

Phe Val Gly Leu Val Cys Phe Val Ile Pro Thr Leu Met Pro Met Tyr
        195                 200                 205

Phe Trp Asn Glu Thr Leu Asn Asn Ser Trp His Ile Ala Thr Met Leu
    210                 215                 220

Arg Tyr Ile Val Asn Leu Asn Met Thr Phe Leu Val Asn Ser Ala Ala
225                 230                 235                 240

His Ile Trp Gly Tyr Lys Pro Tyr Asp Lys Ser Ile Lys Pro Val Gln
                245                 250                 255

Asn Ile Thr Val Ser Ile Leu Ile Leu Gly Glu Gly Phe His Asn Tyr
            260                 265                 270

His His Val Phe Pro Trp Asp Tyr Arg Thr Ser Glu Leu Gly Asn Asp
        275                 280                 285
```

```
Phe Leu Asn Phe Thr Thr Leu Phe Ile Asn Leu Phe Ala Lys Ile Gly
        290                 295                 300

Trp Ala Tyr Asp Leu Lys Thr Ala Ser Asp Lys Val Val Ala Ala Arg
305                 310                 315                 320

Arg Lys Arg Thr Gly Asp Gly Thr Asn Leu Trp Gly Trp Glu Asp Lys
                325                 330                 335

Ser Leu Asn Glu Glu Arg Gln Ala Ala Thr Val Leu Tyr Pro Asn
        340                 345                 350

Lys Tyr Leu Asn Leu Lys Asp
        355

<210> SEQ ID NO 80
<211> LENGTH: 352
<212> TYPE: PRT
<213> ORGANISM: Cydia pomonella

<400> SEQUENCE: 80

Met Ala Pro Asn Val Thr Asp Val Asn Gly Val Leu Phe Glu Ser Asp
1               5                   10                  15

Ala Ala Thr Pro Asp Leu Ala Leu Ala Asn Ala Pro Val Gln Gln Ala
            20                  25                  30

Asp Asp Ser Pro Arg Ile Tyr Val Trp Arg Asn Ile Ile Leu Phe Ala
        35                  40                  45

Tyr Leu His Ile Ala Ala Leu Tyr Gly Gly Tyr Leu Phe Leu Val Ser
    50                  55                  60

Ala Lys Trp Gln Thr Asp Ile Phe Ala Tyr Phe Leu Tyr Val Ala Ser
65                  70                  75                  80

Gly Leu Gly Ile Thr Ala Gly Ala His Arg Leu Trp Ala His Lys Ser
                85                  90                  95

Tyr Lys Ala Lys Trp Pro Leu Arg Leu Ile Leu Val Ile Phe Asn Thr
            100                 105                 110

Ile Ala Phe Gln Asp Ser Ala Ile Asp Trp Ala Arg Asp His Arg Met
        115                 120                 125

His His Lys Tyr Ser Glu Thr Asp Ala Asp Pro His Asn Ala Thr Arg
    130                 135                 140

Gly Phe Phe Phe Ser His Ile Gly Trp Leu Leu Val Arg Lys His Pro
145                 150                 155                 160

Glu Leu Lys Arg Lys Gly Lys Gly Leu Asp Leu Ser Asp Leu Tyr Ala
                165                 170                 175

Asp Pro Ile Leu Arg Phe Gln Lys Lys Tyr Tyr Leu Ile Leu Met Pro
            180                 185                 190

Leu Ala Cys Phe Val Leu Pro Thr Val Ile Pro Val Tyr Leu Trp Asn
        195                 200                 205

Glu Thr Trp Thr Asn Ala Phe Phe Val Ala Ala Leu Phe Arg Tyr Ala
    210                 215                 220

Phe Ile Leu Asn Val Thr Trp Leu Val Asn Ser Ala Ala His Lys Trp
225                 230                 235                 240

Gly Asp Lys Pro Tyr Asp Lys Ser Ile Lys Pro Ser Glu Asn Ile Ser
                245                 250                 255

Val Ser Leu Phe Ala Phe Gly Glu Gly Phe His Asn Tyr His His Thr
            260                 265                 270

Phe Pro Trp Asp Tyr Lys Thr Ala Glu Leu Ser Ser Asn Arg Leu Asn
        275                 280                 285

Phe Thr Thr Lys Phe Ile Asn Phe Ala Lys Ile Gly Trp Ala Tyr
```

```
    290                 295                 300

Asp Met Lys Thr Val Ser Asp Glu Ile Ile Gln Lys Arg Val Asn Arg
305                 310                 315                 320

Thr Gly Asp Gly Ser His His Leu Trp Gly Trp Gly Asp Lys Asp His
                325                 330                 335

Ser Lys Glu Glu Val Asn Ala Ala Val Arg Ile Asn Pro Lys Asp Asp
            340                 345                 350

<210> SEQ ID NO 81
<211> LENGTH: 1380
<212> TYPE: DNA
<213> ORGANISM: Artificial Sequence
<220> FEATURE:
<223> OTHER INFORMATION: codon optimized Spodoptera exigua FAR-like
      protein VII nucleotide sequence (KF805977.1)

<400> SEQUENCE: 81
atgacgtata gacaaataaa tgaatttgat gctgaaaagt ttacggcagc tacagtaccg     60
acaagctacg tatcagtacc agatttttat gcgggcaaga caatttttat cactggtgga    120
actggatttc ttggaaaggt gtttctagag aaacttcttt acagttgtaa agatgttgaa    180
accgtataca ttttgatcag agagaaaaaa ggcaaaacac ctcagcaaag agttgaagat    240
ctttttaaca aaccgatttt ctcaagattg aaacagaagg actctcagtg tatgaagaaa    300
gtcactgcaa taattggtga ccttagtgaa cctggtcttg gcatatcaaa agatgatgaa    360
gaactacttt tgcaaaaggt atctgtagta ttccatgtcg cagccaatgt tcagttttac    420
aaggaattca aagagattat aaatacgaat gttggtggga caaaatacgt actccaattg    480
tgtcagcgaa taaaagatat taaggcattt gtccatattt ccacagccta ctgtcacaca    540
gaccaaaagg tattagaaga gagaatatac ccccctccag cagaactcag tgaagtcctg    600
aagttccttc agcagccaca gcatgacaag aaacagatta aggaattatt taagaaacaa    660
ccaaacagtt acacctttgc caaggcttta gcagaaacct acattgctga gaactgcgga    720
cgcgtcccca caattatcat cagaccttct attatatcag catcactgaa agagccgcta    780
ccaggatggg tggattcatg gaacggagcc acaggcctca tcacagctag ctacaacggc    840
gccaacagag tgcttctcgg cgaaggcagc aacttcctcg acctgatccc agttgacttt    900
gttgctaacc tggcaattgt agctgctgct aaatgtacta gctctttgaa agtttacaat    960
tgctgctcaa gcggatgtaa ccctttaaca ttgaaacaat tggtcagcca catgaataat   1020
gtcggatttg ataaaaacgt ctccataata ttcaccaata acaaagcctc gctttccaca   1080
ttgacatttt tccttcaaac aacgccatct ttcaccgctg atatgtttct gagagtcacg   1140
ggaaagtcac caaggtacat gaaaatccag tcaaaactga ccatcgctcg gaatgcctta   1200 aatttttca cctgtcattc ctgggtcatg aaggctgata attctagaag actgtatgct   1260
tccttgtcat tacacgaccg acatacgttc ccttgtgatc ctacagacat agactggaag   1320
aagtacataa atatatacat agaaggaatt aatcagttct taatgaagaa acgtagttaa   1380

<210> SEQ ID NO 82
<211> LENGTH: 459
<212> TYPE: PRT
<213> ORGANISM: Spodoptera exigua

<400> SEQUENCE: 82

Met Thr Tyr Arg Gln Ile Asn Glu Phe Asp Ala Glu Lys Phe Thr Ala
1               5                   10                  15
```

-continued

```
Ala Thr Val Pro Thr Ser Tyr Val Ser Val Pro Asp Phe Tyr Ala Gly
             20                  25                  30

Lys Thr Ile Phe Ile Thr Gly Gly Thr Gly Phe Leu Gly Lys Val Phe
         35                  40                  45

Leu Glu Lys Leu Leu Tyr Ser Cys Lys Asp Val Glu Thr Val Tyr Ile
 50                  55                  60

Leu Ile Arg Glu Lys Lys Gly Lys Thr Pro Gln Gln Arg Val Glu Asp
 65                  70                  75                  80

Leu Phe Asn Lys Pro Ile Phe Ser Arg Leu Lys Gln Lys Asp Ser Gln
             85                  90                  95

Cys Met Lys Lys Val Thr Ala Ile Ile Gly Asp Leu Ser Glu Pro Gly
            100                 105                 110

Leu Gly Ile Ser Lys Asp Asp Glu Glu Leu Leu Gln Lys Val Ser
         115                 120                 125

Val Val Phe His Val Ala Ala Asn Val Gln Phe Tyr Lys Glu Phe Lys
130                 135                 140

Glu Ile Ile Asn Thr Asn Val Gly Gly Thr Lys Tyr Val Leu Gln Leu
145                 150                 155                 160

Cys Gln Arg Ile Lys Asp Ile Lys Ala Phe Val His Ile Ser Thr Ala
             165                 170                 175

Tyr Cys His Thr Asp Gln Lys Val Leu Glu Glu Arg Ile Tyr Pro Pro
             180                 185                 190

Pro Ala Glu Leu Ser Glu Val Leu Lys Phe Leu Gln Pro Gln His
         195                 200                 205

Asp Lys Lys Gln Ile Lys Glu Leu Phe Lys Lys Gln Pro Asn Ser Tyr
210                 215                 220

Thr Phe Ala Lys Ala Leu Ala Glu Thr Tyr Ile Ala Glu Asn Cys Gly
225                 230                 235                 240

Arg Val Pro Thr Ile Ile Arg Pro Ser Ile Ile Ser Ala Ser Leu
             245                 250                 255

Lys Glu Pro Leu Pro Gly Trp Val Asp Ser Trp Asn Gly Ala Thr Gly
             260                 265                 270

Leu Ile Thr Ala Ser Tyr Asn Gly Ala Asn Arg Val Leu Leu Gly Glu
         275                 280                 285

Gly Ser Asn Phe Leu Asp Leu Ile Pro Val Asp Phe Val Ala Asn Leu
         290                 295                 300

Ala Ile Val Ala Ala Ala Lys Cys Thr Ser Ser Leu Lys Val Tyr Asn
305                 310                 315                 320

Cys Cys Ser Ser Gly Cys Asn Pro Leu Thr Leu Lys Gln Leu Val Ser
             325                 330                 335

His Met Asn Asn Val Gly Phe Asp Lys Asn Val Ser Ile Ile Phe Thr
             340                 345                 350

Asn Asn Lys Ala Ser Leu Ser Thr Leu Thr Phe Phe Leu Gln Thr Thr
         355                 360                 365

Pro Ser Phe Thr Ala Asp Met Phe Leu Arg Val Thr Gly Lys Ser Pro
     370                 375                 380

Arg Tyr Met Lys Ile Gln Ser Lys Leu Thr Ile Ala Arg Asn Ala Leu
385                 390                 395                 400

Asn Phe Phe Thr Cys His Ser Trp Val Met Lys Ala Asp Asn Ser Arg
             405                 410                 415

Arg Leu Tyr Ala Ser Leu Ser Leu His Asp Arg His Thr Phe Pro Cys
             420                 425                 430

Asp Pro Thr Asp Ile Asp Trp Lys Lys Tyr Ile Asn Ile Tyr Ile Glu
```

Gly Ile Asn Gln Phe Leu Met Lys Lys Arg Ser
    450                 455

<210> SEQ ID NO 83
<211> LENGTH: 1368
<212> TYPE: DNA
<213> ORGANISM: Artificial Sequence
<220> FEATURE:
<223> OTHER INFORMATION: HaFAR S60A FAR2

<400> SEQUENCE: 83

| | | | | | |
|---|---|---|---|---|---|
| atggtggtgc | tgacctccaa | ggagacaaag | ccctctgtgg | ccgagttcta | cgccggcaag | 60 |
| agcgtgttca | tcacaggcgg | caccggcttc | ctgggcaagg | tgtttatcga | gaagctgctg | 120 |
| tacagctgcc | ctgacatcga | gaacatctat | atgctgatcc | gggagaagaa | gggcctggcc | 180 |
| gtgtccgaga | gaatcaagca | gttcctggac | gatcccctgt | tacaaggct | gaaggacaag | 240 |
| cgccctgccg | atctggagaa | gatcgtgctg | atcccaggcg | acatcaccgc | accagatctg | 300 |
| ggcatcaaca | gcgagaatga | gaagatgctg | atcgagaagg | tgagcgtgat | catccactcc | 360 |
| gccgccaccg | tgaagttcaa | cgagcccctg | cctacagcct | ggaagatcaa | tgtggagggc | 420 |
| accaggatga | tgctggccct | gtctcggaga | tgaagcgca | tcgaggtgtt | tatccacatc | 480 |
| agcacagcct | acaccaacac | aaatagggag | gtggtggacg | agatcctgta | cccagccccc | 540 |
| gccgacatcg | atcaggtgca | ccagtatgtg | aaggacggca | tcagcgagga | ggataccgag | 600 |
| aagatcctga | acggcagacc | caatacctac | acattcacca | aggccctgac | agagcacctg | 660 |
| gtggccgaga | ccaggcctca | tgtgcctacc | atcatcgtga | gaccatccgt | ggtggccgcc | 720 |
| atcaaggatg | agcctctgaa | gggatggctg | ggaaactggt | tcggagcaac | aggactgacc | 780 |
| gtgtttacag | ccaagggcct | gaatagagtg | atctacggcc | acagctccta | tatcgtggac | 840 |
| ctgatcccag | tggattacgt | ggcaaacctg | gtcatcgcag | caggagccaa | gtctagcaag | 900 |
| tccaccgagc | tgaaggtgta | taactgctgt | cctctagct | gtaatcccgt | gaccatcggc | 960 |
| acactgatga | gcatgttcgc | cgacgatgcc | atcaagcaga | agtcctacgc | catgcctctg | 1020 |
| ccaggctggt | acatctttac | aaagtataag | tggctggtgc | tgctgctgac | cttcctgttt | 1080 |
| caggtcatcc | ctgcctacgt | gaccgacctg | tctaggcacc | tgatcggcaa | gagcccacgc | 1140 |
| tatatcaagc | tgcagagcct | ggtgaaccag | accaggtcct | ctatcgactt | ctttacaaat | 1200 |
| cactcctggg | tcatgaaggc | cgatagggtg | cgcgagctgt | acgcatctct | gagcccagcc | 1260 |
| gacaagtatc | tgttcccttg | cgacccaacc | gatatcaact | ggacacacta | catccaggat | 1320 |
| tattgttggg | gcgtgcgcca | ctttctggag | aagaagtcct | atgagtga | | 1368 |

<210> SEQ ID NO 84
<211> LENGTH: 1368
<212> TYPE: DNA
<213> ORGANISM: Artificial Sequence
<220> FEATURE:
<223> OTHER INFORMATION: HaFAR S195A FAR3

<400> SEQUENCE: 84

| | | | | | |
|---|---|---|---|---|---|
| atggtggtgc | tgacctccaa | ggagacaaag | ccctctgtgg | ccgagttcta | cgccggcaag | 60 |
| agcgtgttca | tcacaggcgg | caccggcttc | ctgggcaagg | tgtttatcga | gaagctgctg | 120 |
| tacagctgcc | ctgacatcga | gaacatctat | atgctgatcc | gggagaagaa | gggcctgagc | 180 |
| gtgtccgaga | gaatcaagca | gttcctggac | gatcccctgt | tacaaggct | gaaggacaag | 240 |

```
cgccctgccg atctggagaa gatcgtgctg atcccaggcg acatcaccgc accagatctg    300
ggcatcaaca gcgagaatga gaagatgctg atcgagaagg tgagcgtgat catccactcc    360
gccgccaccg tgaagttcaa cgagcccctg cctacagcct ggaagatcaa tgtggagggc    420
accaggatga tgctggccct gtctcggaga atgaagcgca tcgaggtgtt tatccacatc    480
agcacagcct acaccaacac aaatagggag gtggtggacg agatcctgta cccagccccc    540
gccgacatcg atcaggtgca ccagtatgtg aaggacggca tcgccgagga ggataccgag    600
aagatcctga acggcagacc caataccatc acattcacca aggccctgac agagcacctg    660
gtggccgaga accaggccta tgtgcctacc atcatcgtga gaccatccgt ggtggccgcc    720
atcaaggatg agcctctgaa gggatggctg gaaactggt tcggagcaac aggactgacc    780
gtgtttacag ccaagggcct gaatagagtg atctacggcc acagctccta tatcgtggac    840
ctgatcccag tggattacgt ggcaaacctg gtcatcgcag caggagccaa gtctagcaag    900
tccaccgagc tgaaggtgta taactgctgt cctctagct gtaatcccgt gaccatcggc    960
acactgatga gcatgttcgc cgacgatgcc atcaagcaga agtcctacgc catgcctctg    1020
ccaggctggt acatctttac aaagtataag tggctggtgc tgctgctgac cttcctgttt    1080
caggtcatcc ctgcctacgt gaccgacctg tctaggcacc tgatcggcaa gagcccacgc    1140
tatatcaagc tgcagagcct ggtgaaccag accaggtcct ctatcgactt ctttacaaat    1200
cactcctggg tcatgaaggc cgatagggtg cgcgagctgt acgcatctct gagcccagcc    1260
gacaagtatc tgttcccttg cgacccaacc gatatcaact ggacacacta catccaggat    1320
tattgttggg gcgtgcgcca ctttctggag aagaagtcct atgagtga               1368
```

<210> SEQ ID NO 85
<211> LENGTH: 1368
<212> TYPE: DNA
<213> ORGANISM: Artificial Sequence
<220> FEATURE:
<223> OTHER INFORMATION: HaFAR S298A FAR4

<400> SEQUENCE: 85

```
atggtggtgc tgacctccaa ggagacaaag ccctctgtgg ccgagttcta cgccggcaag     60
agcgtgttca tcacaggcgg caccggcttc ctgggcaagg tgtttatcga gaagctgctg    120
tacagctgcc ctgacatcga gaacatctat atgctgatcc gggagaagaa gggcctgagc    180
gtgtccgaga gaatcaagca gttcctggac gatcccctgt ttacaaggct gaaggacaag    240
cgccctgccg atctggagaa gatcgtgctg atcccaggcg acatcaccgc accagatctg    300
ggcatcaaca gcgagaatga gaagatgctg atcgagaagg tgagcgtgat catccactcc    360
gccgccaccg tgaagttcaa cgagcccctg cctacagcct ggaagatcaa tgtggagggc    420
accaggatga tgctggccct gtctcggaga atgaagcgca tcgaggtgtt tatccacatc    480
agcacagcct acaccaacac aaatagggag gtggtggacg agatcctgta cccagccccc    540
gccgacatcg atcaggtgca ccagtatgtg aaggacggca tcgccgagga ggataccgag    600
aagatcctga acggcagacc caataccatc acattcacca aggccctgac agagcacctg    660
gtggccgaga accaggccta tgtgcctacc atcatcgtga gaccatccgt ggtggccgcc    720
atcaaggatg agcctctgaa gggatggctg gaaactggt tcggagcaac aggactgacc    780
gtgtttacag ccaagggcct gaatagagtg atctacggcc acagctccta tatcgtggac    840
ctgatcccag tggattacgt ggcaaacctg gtcatcgcag caggagccaa ggccagcaag    900
tccaccgagc tgaaggtgta taactgctgt cctctagct gtaatcccgt gaccatcggc    960
```

```
acactgatga gcatgttcgc cgacgatgcc atcaagcaga agtcctacgc catgcctctg    1020
ccaggctggt acatctttac aaagtataag tggctggtgc tgctgctgac cttcctgttt    1080
caggtcatcc ctgcctacgt gaccgacctg tctaggcacc tgatcggcaa gagcccacgc    1140
tatatcaagc tgcagagcct ggtgaaccag accaggtcct ctatcgactt ctttacaaat    1200
cactcctggg tcatgaaggc cgatagggtg cgcgagctgt acgcatctct gagcccagcc    1260
gacaagtatc tgttcccttg cgacccaacc gatatcaact ggacacacta catccaggat    1320
tattgttggg gcgtgcgcca ctttctggag aagaagtcct atgagtga                 1368
```

<210> SEQ ID NO 86
<211> LENGTH: 1368
<212> TYPE: DNA
<213> ORGANISM: Artificial Sequence
<220> FEATURE:
<223> OTHER INFORMATION: HaFAR S378A FAR5

<400> SEQUENCE: 86

```
atggtggtgc tgacctccaa ggagacaaag ccctctgtgg ccgagttcta cgccggcaag     60
agcgtgttca tcacaggcgg caccggcttc ctgggcaagg tgtttatcga aagctgctg    120 tacagctgcc ctgacatcga aacatctat atgctgatcc gggagaagaa gggcctgagc    180
gtgtccgaga gaatcaagca gttcctggac gatccctgt ttacaaggct gaaggacaag    240
cgccctgccg atctggagaa gatcgtgctg atcccaggcg acatcaccgc accagatctg    300
ggcatcaaca gcgagaatga aagatgctg atcgagaagg tgagcgtgat catccactcc    360
gccgccaccg tgaagttcaa cgagcccctg cctacagcct ggaagatcaa tgtggagggc    420
accaggatga tgctggccct gtctcggaga atgaagcgca tcgaggtgtt tatccacatc    480
agcacagcct acaccaacac aaatagggag gtggtggacg agatcctgta cccagccccc    540
gccgacatcg atcaggtgca ccagtatgtg aaggacggca tcagcgagga ggataccgag    600
aagatcctga acggcagacc caataccctac acattcacca aggccctgac agagcacctg    660
gtggccgaga accaggccta tgtgcctacc atcatcgtga accatccgt ggtggccgcc    720 atcaaggatg agcctctgaa gggatggctg ggaaactggt tcggagcaac aggactgacc    780
gtgtttacag ccaagggcct gaatagagtg atctacggcc acagctccta tatcgtggac    840
ctgatcccag tggattacgt ggcaaacctg gtcatcgcag caggagccaa gtctagcaag    900
tccaccgagc tgaaggtgta taactgctgt tcctctagct gtaatccgt gaccatcggc    960 acactgatga gcatgttcgc cgacgatgcc atcaagcaga agtcctacgc catgcctctg   1020
ccaggctggt acatctttac aaagtataag tggctggtgc tgctgctgac cttcctgttt   1080
caggtcatcc ctgcctacgt gaccgacctg tctaggcacc tgatcggcaa ggccccacgc   1140
tatatcaagc tgcagagcct ggtgaaccag accaggtcct ctatcgactt ctttacaaat   1200
cactcctggg tcatgaaggc cgatagggtg cgcgagctgt acgcatctct gagcccagcc   1260
gacaagtatc tgttcccttg cgacccaacc gatatcaact ggacacacta catccaggat   1320
tattgttggg gcgtgcgcca ctttctggag aagaagtcct atgagtga                1368
```

<210> SEQ ID NO 87
<211> LENGTH: 1368
<212> TYPE: DNA
<213> ORGANISM: Artificial Sequence
<220> FEATURE:
<223> OTHER INFORMATION: HaFAR S394A FAR6

<400> SEQUENCE: 87

```
atggtggtgc tgacctccaa ggagacaaag ccctctgtgg ccgagttcta cgccggcaag      60
agcgtgttca tcacaggcgg caccggcttc ctgggcaagg tgtttatcga gaagctgctg     120
tacagctgcc ctgacatcga gaacatctat atgctgatcc gggagaagaa gggcctgagc     180
gtgtccgaga gaatcaagca gttcctggac gatcccctgt ttacaaggct gaaggacaag     240
cgccctgccg atctggagaa gatcgtgctg atcccaggcg acatcaccgc accagatctg     300
ggcatcaaca gcgagaatga aagatgctg atcgagaagg tgagcgtgat catccactcc      360
gccgccaccg tgaagttcaa cgagcccctg cctacagcct ggaagatcaa tgtggagggc     420
accaggatga tgctggccct gtctcggaga atgaagcgca tcgaggtgtt tatccacatc     480
agcacagcct acaccaacac aaatagggag gtggtggacg atcctgta cccagccccc      540
gccgacatcg atcaggtgca ccagtatgtg aaggacggca tcagcgagga ggataccgag     600
aagatcctga acggcagacc caatacctac acattcacca aggccctgac agagcacctg     660
gtggccgaga ccaggccta tgtgcctacc atcatcgtga gaccatccgt ggtggccgcc      720
atcaaggatg agcctctgaa gggatggctg ggaaactggt tcggagcaac aggactgacc     780
gtgtttacag ccaagggcct gaatagagtg atctacggcc acagtcccta tatcgtggac     840
ctgatcccag tggattacgt ggcaaacctg gtcatcgcag caggagccaa gtctagcaag     900
tccaccgagc tgaaggtgta taactgctgt cctctagct gtaatcccgt gaccatcggc      960
acactgatga gcatgttcgc cgacgatgcc atcaagcaga gtcctacgc atgcctctg     1020
ccaggctggt acatctttac aaagtataag tggctggtgc tgctgctgac cttcctgttt    1080
caggtcatcc ctgcctacgt gaccgacctg tctaggcacc tgatcggcaa gagcccacgc    1140
tatatcaagc tgcagagcct ggtgaaccag accaggtccg ccatcgactt ctttacaaat    1200
cactcctggg tcatgaaggc cgataggggtg cgcgagctgt acgcatctct gagcccagcc   1260
gacaagtatc tgttcccttg cgacccaacc gatatcaact ggacacacta catccaggat    1320
tattgttggg gcgtgcgcca ctttctggag aagaagtcct atgagtga                 1368
```

<210> SEQ ID NO 88
<211> LENGTH: 1368
<212> TYPE: DNA
<213> ORGANISM: Artificial Sequence
<220> FEATURE:
<223> OTHER INFORMATION: HaFAR S418A FAR7

<400> SEQUENCE: 88

```
atggtggtgc tgacctccaa ggagacaaag ccctctgtgg ccgagttcta cgccggcaag      60
agcgtgttca tcacaggcgg caccggcttc ctgggcaagg tgtttatcga gaagctgctg     120
tacagctgcc ctgacatcga gaacatctat atgctgatcc gggagaagaa gggcctgagc     180
gtgtccgaga gaatcaagca gttcctggac gatcccctgt ttacaaggct gaaggacaag     240
cgccctgccg atctggagaa gatcgtgctg atcccaggcg acatcaccgc accagatctg     300
ggcatcaaca gcgagaatga aagatgctg atcgagaagg tgagcgtgat catccactcc      360
gccgccaccg tgaagttcaa cgagcccctg cctacagcct ggaagatcaa tgtggagggc     420
accaggatga tgctggccct gtctcggaga atgaagcgca tcgaggtgtt tatccacatc     480
agcacagcct acaccaacac aaatagggag gtggtggacg atcctgta cccagccccc      540
gccgacatcg atcaggtgca ccagtatgtg aaggacggca tcagcgagga ggataccgag     600
aagatcctga acggcagacc caatacctac acattcacca aggccctgac agagcacctg     660
```

```
gtggccgaga accaggccta tgtgcctacc atcatcgtga gaccatccgt ggtggccgcc      720
atcaaggatg agcctctgaa gggatggctg ggaaactggt tcggagcaac aggactgacc      780
gtgtttacag ccaagggcct gaatagagtg atctacggcc acagctccta tatcgtggac      840
ctgatcccag tggattacgt ggcaaacctg gtcatcgcag caggagccaa gtctagcaag      900
tccaccgagc tgaaggtgta taactgctgt tcctctagct gtaatcccgt gaccatcggc      960
acactgatga gcatgttcgc cgacgatgcc atcaagcaga agtcctacgc catgcctctg     1020
ccaggctggt acatctttac aaagtataag tggctggtgc tgctgctgac cttcctgttt     1080
caggtcatcc ctgcctacgt gaccgacctg tctaggcacc tgatcggcaa gagcccacgc     1140
tatatcaagc tgcagagcct ggtgaaccag accaggtcct ctatcgactt ctttacaaat     1200
cactcctggg tcatgaaggc cgatagggtg cgcgagctgt acgcatctct ggccccagcc     1260
gacaagtatc tgttcccttg cgacccaacc gatatcaact ggacacacta catccaggat     1320
tattgttggg gcgtgcgcca ctttctggag aagaagtcct atgagtga               1368

<210> SEQ ID NO 89
<211> LENGTH: 1368
<212> TYPE: DNA
<213> ORGANISM: Artificial Sequence
<220> FEATURE:
<223> OTHER INFORMATION: HaFAR S453A FAR8

<400> SEQUENCE: 89
atggtggtgc tgacctccaa ggagacaaag ccctctgtgg ccgagttcta cgccggcaag       60
agcgtgttca tcacaggcgg caccggcttc ctgggcaagg tgtttatcga gaagctgctg      120
tacagctgcc ctgacatcga gaacatctat atgctgatcc gggagaagaa gggcctgagc      180
gtgtccgaga gaatcaagca gttcctggac gatcccctgt ttacaaggct gaaggacaag      240
cgccctgccg atctggagaa gatcgtgctg atcccaggcg acatcaccgc accagatctg      300
ggcatcaaca gcgagaatga agatgctgct gatcgagaagg tgagcgtgat catccactcc      360
gccgccaccg tgaagttcaa cgagcccctg cctacagcct ggaagatcaa tgtggagggc      420
accaggatga tgctggccct gtctcggaga tgaagcgca tcgaggtgtt tatccacatc      480
agcacagcct acaccaacac aaatagggag gtggtggacg agatcctgta cccagccccc      540
gccgacatcg atcaggtgca ccagtatgtg aaggacggca tcagcgagga ggataccgag      600
aagatcctga cggcagacc caataccta cattcacca aggccctgac agagcacctg      660
gtggccgaga ccaggccta tgtgcctacc atcatcgtga gaccatccgt ggtggccgcc      720
atcaaggatg agcctctgaa gggatggctg ggaaactggt tcggagcaac aggactgacc      780
gtgtttacag ccaagggcct gaatagagtg atctacggcc acagctccta tatcgtggac      840
ctgatcccag tggattacgt ggcaaacctg gtcatcgcag caggagccaa gtctagcaag      900
tccaccgagc tgaaggtgta taactgctgt tcctctagct gtaatcccgt gaccatcggc      960
acactgatga gcatgttcgc cgacgatgcc atcaagcaga agtcctacgc catgcctctg     1020
ccaggctggt acatctttac aaagtataag tggctggtgc tgctgctgac cttcctgttt     1080
caggtcatcc ctgcctacgt gaccgacctg tctaggcacc tgatcggcaa gagcccacgc     1140
tatatcaagc tgcagagcct ggtgaaccag accaggtcct ctatcgactt ctttacaaat     1200
cactcctggg tcatgaaggc cgatagggtg cgcgagctgt acgcatctct ggccccagcc     1260
gacaagtatc tgttcccttg cgacccaacc gatatcaact ggacacacta catccaggat     1320
```

```
tattgttggg gcgtgcgcca ctttctggag aagaaggcct atgagtga       1368
```

<210> SEQ ID NO 90
<211> LENGTH: 1368
<212> TYPE: DNA
<213> ORGANISM: Artificial Sequence
<220> FEATURE:
<223> OTHER INFORMATION: Codon optimized wild type HaFAR (FAR9; Strain SPV916)

<400> SEQUENCE: 90

```
atggtggtgc tgacctccaa ggagacaaag ccctctgtgg ccgagttcta cgccggcaag       60
agcgtgttca tcacaggcgg caccggcttc ctgggcaagg tgtttatcga agctgctg        120
tacagctgcc ctgacatcga aacatctat atgctgatcc gggagaagaa gggcctgagc      180
gtgtccgaga gaatcaagca gttcctggac gatcccctgt tacaaggct gaaggacaag      240
cgccctgccg atctggagaa gatcgtgctg atcccaggcg acatcaccgc accagatctg     300
ggcatcaaca gcgagaatga aagatgctg atcgagaagg tgagcgtgat catccactcc     360
gccgccaccg tgaagttcaa cgagcccctg cctacagcct ggaagatcaa tgtggagggc    420
accaggatga tgctggccct gtctcggaga atgaagcgca tcgaggtgtt tatccacatc    480
agcacagcct acaccaacac aaatagggag gtggtggacg agatcctgta cccagccccc    540
gccgacatcg atcaggtgca ccagtatgtg aaggacggca tcagcgagga ggataccgag    600
aagatcctga acggcagacc caataccctac acattcacca aggccctgac agagcacctg    660
gtggccgaga accaggccta tgtgcctacc atcatcgtga accatccgt ggtggccgcc    720
atcaaggatg agcctctgaa gggatggctg ggaaactggt tcggagcaac aggactgacc    780
gtgtttacag ccaagggcct gaatagagt atctacggcc acagctccta tatcgtggac    840
ctgatcccag tggattacgt ggcaaacctg gtcatcgcag caggagccaa gtctagcaag    900
tccaccgagc tgaaggtgta taactgctgt tcctctagct gtaatcccgt gaccatcggc   960
acactgatga gcatgttcgc cgacgatgcc atcaagcaga agcctacgc catgcctctg    1020
ccaggctggt acatctttac aaagtataag tggctggtgc tgctgctgac cttcctgttt    1080
caggtcatcc ctgcctacgt gaccgacctg tctaggcacc tgatcggcaa gagccacgc    1140
tatatcaagc tgcagagcct ggtgaaccag accaggtcct ctatcgactt ctttacaaat    1200
cactcctggg tcatgaaggc cgatagggtg cgcgagctgt acgcatctct gagcccagcc    1260
gacaagtatc tgttccctg cgacccaacc gatatcaact ggacacacta catccaggat    1320
tattgttggg gcgtgcgcca ctttctggag aagaagtcct atgagtga                 1368
```

<210> SEQ ID NO 91
<211> LENGTH: 1623
<212> TYPE: DNA
<213> ORGANISM: Phoenix dactylifera

<400> SEQUENCE: 91

```
atggccatcc catccgatag agagaccctg gagagggcac cagagccttc tccagcaagc       60
gacctgcaga gctccctgcg gagaaggctg cactctaccg tggcagcagt ggtggtgcca     120
gattctagct ccaagacatc tagccccagc gccgagaacc tgaccacaga cagcggagag     180
gattccaggg gcgacacctc ctctgacgcc gatacaaggg ataggtggt ggacggagtg      240
gatagggagg aggagaacaa gaccgtgagc gtgctgaatg cagacagta cgaggacgga     300
ggcggcaggg gacagggaca gggcacaggc ggcggcgtgc ccgccaagtt tctgtatagg    360
```

```
gcatctgccc ctgcacacag gaaggtgaag gagagcccac tgagctccga tgccatcttc    420
aagcagagcc acgccggcct gctgaacctg tgcatcgtgg tgctgatcgc cgtgaactcc    480
aggctgatca tcgagaatct gatgaagtac ggcctgctga tccgcgccgg ctattggttt    540
tctagcaagt ccctgcggga ctggcctctg ctgatgtgct gtctgaccct gccagcattt    600
cctctgggag ccttcatggt ggagaagctg gcccagcaca atttcatctc cgagtctgtg    660
gtcatcagcc tgcacgtgat catcaccaca gccgagctgc tgtacccagt gatcgtgatc    720
ctgagatgcg attctgccgt gctgagcggc atcacactga tgctgtttgc cagcgtggtg    780
tggctgaagc tggtgtccta cgcccacacc aactatgaca tgaggacact gagcaagtcc    840
atcgacaagg aggatatgta ctccaagtgt ccagagatcg ataatctgaa gggcgactcc    900
tttaagtctc tggtgtattt catggtggcc ccacccctgt gctaccagcc aagctatcca    960
aggaccacct gcatcaggaa gggatgggtc atccgccagg tggtgaagct ggtcatcttc   1020
accggcctga tgggcttcat catcgagcag tacatcaacc ccatcgtgca gaattcccag   1080
caccctctga agggcaactt tctgaatgcc atcgagcggg tgctgaagct gtctgtgccc   1140
accctgtacg tgtggctgtg catgttctat tgtttctttc acctgtggct gaacatcctg   1200
gccgagctgc tgtgctttgg cgatagagag ttctacaagg actggtggaa cgccaagaca   1260
atcgaggagt attggaggat gtggaatatg cctgtgcacc gctggatgat ccggcacatc   1320
tacttcccctt gtctgagaaa tggcctgcca agggccgtgg ccatcctgat ctcctttctg   1380
gtgtctgcca tcttccacga gatctgcatc gccgtgccct gtcacatctt taagttctgg   1440
gcctttatcg gcatcatgtt ccagatcccc ctggtcatcc tgaccaagta tctgcagcac   1500
aagtttacaa actccatggt gggcaatatg atcttctggt tcttttctc tatcctgggc   1560
cagcctatgt gcgtgctgct gtactatcac gacgtgatga atagaaaggt gaggaccgag   1620
tga                                                                 1623

<210> SEQ ID NO 92
<211> LENGTH: 540
<212> TYPE: PRT
<213> ORGANISM: Phoenix dactylifera

<400> SEQUENCE: 92

Met Ala Ile Pro Ser Asp Arg Glu Thr Leu Glu Arg Ala Pro Glu Pro
1               5                   10                  15

Ser Pro Ala Ser Asp Leu Gln Ser Ser Leu Arg Arg Arg Leu His Ser
            20                  25                  30

Thr Val Ala Ala Val Val Val Pro Asp Ser Ser Ser Lys Thr Ser Ser
        35                  40                  45

Pro Ser Ala Glu Asn Leu Thr Thr Asp Ser Gly Glu Asp Ser Arg Gly
    50                  55                  60

Asp Thr Ser Ser Asp Ala Asp Thr Arg Asp Arg Val Val Asp Gly Val
65                  70                  75                  80

Asp Arg Glu Glu Glu Asn Lys Thr Val Ser Val Leu Asn Gly Arg Gln
                85                  90                  95

Tyr Glu Asp Gly Gly Gly Arg Gly Gln Gly Gln Gly Thr Gly Gly Gly
            100                 105                 110

Val Pro Ala Lys Phe Leu Tyr Arg Ala Ser Ala Pro Ala His Arg Lys
        115                 120                 125

Val Lys Glu Ser Pro Leu Ser Ser Asp Ala Ile Phe Lys Gln Ser His
    130                 135                 140
```

-continued

Ala Gly Leu Leu Asn Leu Cys Ile Val Val Leu Ile Ala Val Asn Ser
145                 150                 155                 160

Arg Leu Ile Ile Glu Asn Leu Met Lys Tyr Gly Leu Leu Ile Arg Ala
            165                 170                 175

Gly Tyr Trp Phe Ser Ser Lys Ser Leu Arg Asp Trp Pro Leu Leu Met
                180                 185                 190

Cys Cys Leu Thr Leu Pro Ala Phe Pro Leu Gly Ala Phe Met Val Glu
            195                 200                 205

Lys Leu Ala Gln His Asn Phe Ile Ser Glu Ser Val Val Ile Ser Leu
210                 215                 220

His Val Ile Ile Thr Thr Ala Glu Leu Leu Tyr Pro Val Ile Val Ile
225                 230                 235                 240

Leu Arg Cys Asp Ser Ala Val Leu Ser Gly Ile Thr Leu Met Leu Phe
            245                 250                 255

Ala Ser Val Val Trp Leu Lys Leu Val Ser Tyr Ala His Thr Asn Tyr
            260                 265                 270

Asp Met Arg Thr Leu Ser Lys Ser Ile Asp Lys Glu Asp Met Tyr Ser
            275                 280                 285

Lys Cys Pro Glu Ile Asp Asn Leu Lys Gly Asp Ser Phe Lys Ser Leu
290                 295                 300

Val Tyr Phe Met Val Ala Pro Thr Leu Cys Tyr Gln Pro Ser Tyr Pro
305                 310                 315                 320

Arg Thr Thr Cys Ile Arg Lys Gly Trp Val Ile Arg Gln Val Val Lys
            325                 330                 335

Leu Val Ile Phe Thr Gly Leu Met Gly Phe Ile Glu Gln Tyr Ile
            340                 345                 350

Asn Pro Ile Val Gln Asn Ser Gln His Pro Leu Lys Gly Asn Phe Leu
            355                 360                 365

Asn Ala Ile Glu Arg Val Leu Lys Leu Ser Val Pro Thr Leu Tyr Val
370                 375                 380

Trp Leu Cys Met Phe Tyr Cys Phe Phe His Leu Trp Leu Asn Ile Leu
385                 390                 395                 400

Ala Glu Leu Leu Cys Phe Gly Asp Arg Glu Phe Tyr Lys Asp Trp Trp
            405                 410                 415

Asn Ala Lys Thr Ile Glu Glu Tyr Trp Arg Met Trp Asn Met Pro Val
            420                 425                 430

His Arg Trp Met Ile Arg His Ile Tyr Phe Pro Cys Leu Arg Asn Gly
            435                 440                 445

Leu Pro Arg Ala Val Ala Ile Leu Ile Ser Phe Leu Val Ser Ala Ile
450                 455                 460

Phe His Glu Ile Cys Ile Ala Val Pro Cys His Ile Phe Lys Phe Trp
465                 470                 475                 480

Ala Phe Ile Gly Ile Met Phe Gln Ile Pro Leu Val Ile Leu Thr Lys
            485                 490                 495

Tyr Leu Gln His Lys Phe Thr Asn Ser Met Val Gly Asn Met Ile Phe
            500                 505                 510

Trp Phe Phe Phe Ser Ile Leu Gly Gln Pro Met Cys Val Leu Leu Tyr
            515                 520                 525

Tyr His Asp Val Met Asn Arg Lys Val Arg Thr Glu
530                 535                 540

<210> SEQ ID NO 93
<211> LENGTH: 405
<212> TYPE: DNA

<213> ORGANISM: Artificial
<220> FEATURE:
<223> OTHER INFORMATION: TEF promoter for enzyme expression

<400> SEQUENCE: 93

| | | | | | |
|---|---|---|---|---|---|
| gagaccgggt | tggcggcgca | tttgtgtccc | aaaaaacagc | cccaattgcc | ccaattgacc | 60 |
| ccaaattgac | ccagtagcgg | gcccaacccc | ggcgagagcc | cccttctccc | cacatatcaa | 120 |
| acctcccccg | gttcccacac | ttgccgttaa | gggcgtaggg | tactgcagtc | tggaatctac | 180 |
| gcttgttcag | actttgtact | agtttctttg | tctggccatc | cgggtaaccc | atgccggacg | 240 |
| caaaatagac | tactgaaaat | ttttttgctt | tgtggttggg | actttagcca | agggtataaa | 300 |
| agaccaccgt | ccccgaatta | cctttcctct | tcttttctct | ctctccttgt | caactcacac | 360 |
| ccgaaatcgt | taagcatttc | cttctgagta | taagaatcat | tcaaa | | 405 |

<210> SEQ ID NO 94
<211> LENGTH: 1107
<212> TYPE: DNA
<213> ORGANISM: Artificial
<220> FEATURE:
<223> OTHER INFORMATION: DST076_coding_sequence Z9 Desaturase

<400> SEQUENCE: 94

| | | | | | |
|---|---|---|---|---|---|
| atgcacatcg | agtctgagaa | ctgccccggc | aggtttaagg | aggtgaacat | ggcccctaat | 60 |
| gccaccgatg | ccaatggcgt | gctgttcgag | accgatgccg | ccacacctga | cctggccctg | 120 |
| ccacacgcac | ctgtgcagca | ggccgacaac | tacccaaaga | agtacgtgtg | cgcaatatc | 180 |
| atcctgtttg | cctacctgca | catcgccgcc | ctgtacggcg | gctatctgtt | tctgttccac | 240 |
| gccaagtggc | agaccgatat | cttcgcctac | atcctgtatg | tgatgtctgg | actgggaatc | 300 |
| acagcaggag | cacacaggct | gtgggcccac | aagagctaca | aggccaagtg | gcctctgaga | 360 |
| ctgatcctgg | tcatcttcaa | cacactggcc | tttcaggact | ctgccatcga | ttggagcagg | 420 |
| gaccaccgca | tgcaccacaa | gtattccgag | accgacgccg | atccccacaa | tgccacacgg | 480 |
| ggcttctttt | tctctcacat | cggctggctg | ctggtgcgga | agcaccctga | gctgaagaga | 540 |
| aagggcaagg | gcctggacct | gtccgatctg | tatgccgacc | caatcctgag | atttcagaag | 600 |
| aagtactatc | tgatcctgat | gcccctgacc | tgtttcgtgc | tgccaacagt | gatccccgtg | 660 |
| tactattggg | gcgagacctg | gacaaacgcc | ttttcgtgg | ccgccctgtt | taggtacgcc | 720 |
| ttcatcctga | acgtgacctg | gctggtgaat | agcgccgccc | acaagtgggg | cgataagcct | 780 |
| tatgaccgca | acatcaagcc | atccgagaat | atcagcgtgt | ccatgtttgc | cctgggcgag | 840 |
| ggcttccaca | actaccacca | caccttccca | tgggattata | agacagccga | gctgggcaac | 900 |
| aatatgctga | acttcaccac | aaacttcatc | aacttcttcg | ccaagatcgg | ctgggcctac | 960 |
| gatctgaaga | ccgtgtccga | cgagatcgtg | cggtctagag | caaagaggac | aggcgacgga | 1020 |
| agccaccacc | tgtggggatg | gggcgacaag | gatcactcca | gggaggagat | ggctgccgcc | 1080 |
| atccgcatcc | accccaagga | cgattga | | | | 1107 |

<210> SEQ ID NO 95
<211> LENGTH: 368
<212> TYPE: PRT
<213> ORGANISM: Artificial
<220> FEATURE:
<223> OTHER INFORMATION: DST076_amino_acid Z9 Desaturase encoded by SEQ ID NO 94

<400> SEQUENCE: 95

```
Met His Ile Glu Ser Glu Asn Cys Pro Gly Arg Phe Lys Glu Val Asn
1               5                   10                  15

Met Ala Pro Asn Ala Thr Asp Ala Asn Gly Val Leu Phe Glu Thr Asp
            20                  25                  30

Ala Ala Thr Pro Asp Leu Ala Leu Pro His Ala Pro Val Gln Gln Ala
        35                  40                  45

Asp Asn Tyr Pro Lys Lys Tyr Val Trp Arg Asn Ile Ile Leu Phe Ala
    50                  55                  60

Tyr Leu His Ile Ala Ala Leu Tyr Gly Gly Tyr Leu Phe Leu Phe His
65                  70                  75                  80

Ala Lys Trp Gln Thr Asp Ile Phe Ala Tyr Ile Leu Tyr Val Met Ser
                85                  90                  95

Gly Leu Gly Ile Thr Ala Gly Ala His Arg Leu Trp Ala His Lys Ser
            100                 105                 110

Tyr Lys Ala Lys Trp Pro Leu Arg Leu Ile Leu Val Ile Phe Asn Thr
        115                 120                 125

Leu Ala Phe Gln Asp Ser Ala Ile Asp Trp Ser Arg Asp His Arg Met
    130                 135                 140

His His Lys Tyr Ser Glu Thr Asp Ala Asp Pro His Asn Ala Thr Arg
145                 150                 155                 160

Gly Phe Phe Phe Ser His Ile Gly Trp Leu Leu Val Arg Lys His Pro
                165                 170                 175

Glu Leu Lys Arg Lys Gly Lys Gly Leu Asp Leu Ser Asp Leu Tyr Ala
            180                 185                 190

Asp Pro Ile Leu Arg Phe Gln Lys Lys Tyr Tyr Leu Ile Leu Met Pro
        195                 200                 205

Leu Thr Cys Phe Val Leu Pro Thr Val Ile Pro Val Tyr Tyr Trp Gly
    210                 215                 220

Glu Thr Trp Thr Asn Ala Phe Phe Val Ala Ala Leu Phe Arg Tyr Ala
225                 230                 235                 240

Phe Ile Leu Asn Val Thr Trp Leu Val Asn Ser Ala Ala His Lys Trp
                245                 250                 255

Gly Asp Lys Pro Tyr Asp Arg Asn Ile Lys Pro Ser Glu Asn Ile Ser
            260                 265                 270

Val Ser Met Phe Ala Leu Gly Glu Gly Phe His Asn Tyr His His Thr
        275                 280                 285

Phe Pro Trp Asp Tyr Lys Thr Ala Glu Leu Gly Asn Asn Met Leu Asn
    290                 295                 300

Phe Thr Thr Asn Phe Ile Asn Phe Phe Ala Lys Ile Gly Trp Ala Tyr
305                 310                 315                 320

Asp Leu Lys Thr Val Ser Asp Glu Ile Val Arg Ser Arg Ala Lys Arg
                325                 330                 335

Thr Gly Asp Gly Ser His His Leu Trp Gly Trp Gly Asp Lys Asp His
            340                 345                 350

Ser Arg Glu Glu Met Ala Ala Ile Arg Ile His Pro Lys Asp Asp
        355                 360                 365

<210> SEQ ID NO 96
<211> LENGTH: 1062
<212> TYPE: DNA
<213> ORGANISM: Artificial
<220> FEATURE:
<223> OTHER INFORMATION: DST180_coding_sequence Z9 Desaturase

<400> SEQUENCE: 96
```

```
atggccccaa acatctctga cgatgtgaat ggcgtgctgt ttgagagcga tgcagcaaca      60
ccagacctgg ccctggcaag ccccctgtg cagaaggccg ataaccggcc caagcagtac     120
gtgtggagaa atatcctgct gttcgcatat ctgcacgccg ccgccctgta cggcggctat    180
ctgtttctga caagcgccaa gtggcagacc gacgtgttcg cctacatcct gtatgtgatg    240
tccggactgg gaatcacagc aggagcacac aggctgtggg cacacaagtc ttacaaggcc    300
aagtggcccc tgaaagtgat cctgatcatc tttaacacca tcgcctttca ggacgcagca    360
atggattggg caagggacca cagaatgcac acaagtata gcgagacaga cgccgatcct     420
cacaatgcca ccaggggctt cttttctcc cacatcggct ggctgctggt gcgcaagcac     480
ccagatctga aggagaaggg caagggcctg gacatgagcg atctgcaggc cgaccccatc    540
ctgcggtttc agaagaagta ctatctgctg ctgatgcctc tggcctgctt tgtgatgcca    600
acagtgatcc ccgtgtactt ctggggcgag acctggaaca tgcctttttt cgtggccgcc    660
atgtttagat atgccttcat cctgaacgtg acctggctgg tgaattccgc cgcccacaag    720
tggggcgata agccttacga caagagcatc aagccatccg agaacatgag cgtggccatg    780
tttgccctgg gcgagggctt ccacaattac caccacacat cccctgggga ttataagacc    840
gccgagctgg caacaataa gctgaacttt accacaacct tcatcaactt cttcgccaag    900
ctgggctggg cctacgacat gaagacagtg tccgacgata tcgtgaagaa cagggtgaag    960
cgcaccggcg atggatctca ccacctgtgg ggatggggcg acaagaacca gagcaaggag   1020
gagatcgcct ccgccatccg gatcaatcct aaggacgatt ga                       1062
```

<210> SEQ ID NO 97
<211> LENGTH: 353
<212> TYPE: PRT
<213> ORGANISM: Artificial
<220> FEATURE:
<223> OTHER INFORMATION: DST180_amino_acid Z9 Desaturase encoded by SEQ
      ID NO: 96

<400> SEQUENCE: 97

```
Met Ala Pro Asn Ile Ser Asp Asp Val Asn Gly Val Leu Phe Glu Ser
1               5                   10                  15

Asp Ala Ala Thr Pro Asp Leu Ala Leu Ala Ser Pro Val Gln Lys
            20                  25                  30

Ala Asp Asn Arg Pro Lys Gln Tyr Val Trp Arg Asn Ile Leu Leu Phe
        35                  40                  45

Ala Tyr Leu His Ala Ala Leu Tyr Gly Gly Tyr Leu Phe Leu Thr
    50                  55                  60

Ser Ala Lys Trp Gln Thr Asp Val Phe Ala Tyr Ile Leu Tyr Val Met
65                  70                  75                  80

Ser Gly Leu Gly Ile Thr Ala Gly Ala His Arg Leu Trp Ala His Lys
                85                  90                  95

Ser Tyr Lys Ala Lys Trp Pro Leu Lys Val Ile Leu Ile Ile Phe Asn
            100                 105                 110

Thr Ile Ala Phe Gln Asp Ala Ala Met Asp Trp Ala Arg Asp His Arg
        115                 120                 125

Met His His Lys Tyr Ser Glu Thr Asp Ala Asp Pro His Asn Ala Thr
    130                 135                 140

Arg Gly Phe Phe Phe Ser His Ile Gly Trp Leu Leu Val Arg Lys His
145                 150                 155                 160

Pro Asp Leu Lys Glu Lys Gly Lys Gly Leu Asp Met Ser Asp Leu Gln
                165                 170                 175
```

Ala Asp Pro Ile Leu Arg Phe Gln Lys Lys Tyr Tyr Leu Leu Leu Met
            180                 185                 190

Pro Leu Ala Cys Phe Val Met Pro Thr Val Ile Pro Val Tyr Phe Trp
            195                 200                 205

Gly Glu Thr Trp Asn Asn Ala Phe Phe Val Ala Ala Met Phe Arg Tyr
210                 215                 220

Ala Phe Ile Leu Asn Val Thr Trp Leu Val Asn Ser Ala Ala His Lys
225                 230                 235                 240

Trp Gly Asp Lys Pro Tyr Asp Lys Ser Ile Lys Pro Ser Glu Asn Met
                245                 250                 255

Ser Val Ala Met Phe Ala Leu Gly Glu Gly Phe His Asn Tyr His His
            260                 265                 270

Thr Phe Pro Trp Asp Tyr Lys Thr Ala Glu Leu Gly Asn Asn Lys Leu
        275                 280                 285

Asn Phe Thr Thr Thr Phe Ile Asn Phe Phe Ala Lys Leu Gly Trp Ala
290                 295                 300

Tyr Asp Met Lys Thr Val Ser Asp Asp Ile Val Lys Asn Arg Val Lys
305                 310                 315                 320

Arg Thr Gly Asp Gly Ser His His Leu Trp Gly Trp Gly Asp Lys Asn
                325                 330                 335

Gln Ser Lys Glu Glu Ile Ala Ser Ala Ile Arg Ile Asn Pro Lys Asp
            340                 345                 350

Asp

<210> SEQ ID NO 98
<211> LENGTH: 1062
<212> TYPE: DNA
<213> ORGANISM: Artificial
<220> FEATURE:
<223> OTHER INFORMATION: DST181_coding_sequence Z9 Desaturase

<400> SEQUENCE: 98 atggcccaa acatctctga ggatgccaat ggcgtgctgt ttgagagcga tgcagcaaca      60
ccagacctgg ccctggcaag cccacctgtg cagaaggcag acaacaggcc aagcagtac     120
gtgtggagaa atatcatcct gtttgcctat ctgcacctgg ccgccctgta cggcggctat    180
ctgtttctgt tcagcgccaa gtggcagaca gacgtgttcg cctacatcct gtatgtgatg    240
tccggactgg gaatcaccgc aggagcacac agactgtggg cacacaagtc ttacaaggcc    300
aagtggcccc tgaaagtgat cctgatcatc tttaacacca tcgcctttca ggacgcagca    360
atggattggg caagggacca cagaatgcac acaagtata gcgagacaga cgccgatcct    420
cacaatgcca ccaggggctt cttttttctcc cacatcggct ggctgctggt cgcaagcac    480
ccagacctga agaagaaggg caagggcctg gacatgagcg atctgctgaa cgaccccatc    540
ctgaagttc agaagaagta ctatctgctg ctgatgcctc tggcctgctt cgtgatgcca    600
acaatgatcc ccgtgtacct gtggggcgag acatggacca tgcctttt cgtggccgcc    660
atgtttcggt atgccttcat cctgaacgtg acctggctgg tgaattccgc cgcccacaag    720
tggggcgata gccttacga caagagcatc aagccatccg agaacctgtc tgtggccatg    780
tttgccctgg gcgagggctt ccacaattac caccacacat cccctggga ttataagacc    840
gccgagctgg caaccagaa gctgaacttc accacaacct tcatcaactt tttcgccaag    900
ctgggctggg cctacgacat gaagacagtg tccgacgata tcgtgaagaa tagggtgaag    960
cgcaccggcg atggatctca ccacctgtgg ggatggggcg acaagaacca gagcaaggag   1020
gagatcgcct ccgccatccg gatcaatcct aaggacgatt ga                          1062

<210> SEQ ID NO 99
<211> LENGTH: 353
<212> TYPE: PRT
<213> ORGANISM: Artificial
<220> FEATURE:
<223> OTHER INFORMATION: DST181_amino_acid Z9 Desaturase encoded by SEQ
      ID NO: 98

<400> SEQUENCE: 99

Met Ala Pro Asn Ile Ser Glu Asp Ala Asn Gly Val Leu Phe Glu Ser
1               5                   10                  15

Asp Ala Ala Thr Pro Asp Leu Ala Leu Ala Ser Pro Pro Val Gln Lys
            20                  25                  30

Ala Asp Asn Arg Pro Lys Gln Tyr Val Trp Arg Asn Ile Ile Leu Phe
        35                  40                  45

Ala Tyr Leu His Leu Ala Ala Leu Tyr Gly Gly Tyr Leu Phe Leu Phe
    50                  55                  60

Ser Ala Lys Trp Gln Thr Asp Val Phe Ala Tyr Ile Leu Tyr Val Met
65                  70                  75                  80

Ser Gly Leu Gly Ile Thr Ala Gly Ala His Arg Leu Trp Ala His Lys
                85                  90                  95

Ser Tyr Lys Ala Lys Trp Pro Leu Lys Val Ile Leu Ile Ile Phe Asn
            100                 105                 110

Thr Ile Ala Phe Gln Asp Ala Ala Met Asp Trp Ala Arg Asp His Arg
        115                 120                 125

Met His His Lys Tyr Ser Glu Thr Asp Ala Asp Pro His Asn Ala Thr
    130                 135                 140

Arg Gly Phe Phe Phe Ser His Ile Gly Trp Leu Leu Val Arg Lys His
145                 150                 155                 160

Pro Asp Leu Lys Lys Lys Gly Lys Gly Leu Asp Met Ser Asp Leu Leu
                165                 170                 175

Asn Asp Pro Ile Leu Lys Phe Gln Lys Lys Tyr Tyr Leu Leu Leu Met
            180                 185                 190

Pro Leu Ala Cys Phe Val Met Pro Thr Met Ile Pro Val Tyr Leu Trp
        195                 200                 205

Gly Glu Thr Trp Thr Asn Ala Phe Phe Val Ala Ala Met Phe Arg Tyr
    210                 215                 220

Ala Phe Ile Leu Asn Val Thr Trp Leu Val Asn Ser Ala Ala His Lys
225                 230                 235                 240

Trp Gly Asp Lys Pro Tyr Asp Lys Ser Ile Lys Pro Ser Glu Asn Leu
                245                 250                 255

Ser Val Ala Met Phe Ala Leu Gly Glu Gly Phe His Asn Tyr His His
            260                 265                 270

Thr Phe Pro Trp Asp Tyr Lys Thr Ala Glu Leu Gly Asn Gln Lys Leu
        275                 280                 285

Asn Phe Thr Thr Thr Phe Ile Asn Phe Phe Ala Lys Leu Gly Trp Ala
    290                 295                 300

Tyr Asp Met Lys Thr Val Ser Asp Asp Ile Val Lys Asn Arg Val Lys
305                 310                 315                 320

Arg Thr Gly Asp Gly Ser His His Leu Trp Gly Trp Gly Asp Lys Asn
                325                 330                 335

Gln Ser Lys Glu Glu Ile Ala Ser Ala Ile Arg Ile Asn Pro Lys Asp
            340                 345                 350

Asp

<210> SEQ ID NO 100
<211> LENGTH: 1062
<212> TYPE: DNA
<213> ORGANISM: Artificial
<220> FEATURE:
<223> OTHER INFORMATION: DST183_coding_sequence Z9 Desaturase

<400> SEQUENCE: 100

```
atggccccaa acatcagcga ggatgtgaat ggcgtgctgt tcgagtccga tgccgccaca    60
ccagacctgg ccctgtctac cccacctgtg cagaaggcag acaacaggcc caagcagctg   120
gtgtggagaa atatcctgct gtttgcatac ctgcacctgg cagcacagta cggaggctat   180
ctgtttctgt tctctgccaa gtggcagaca gatatcttcg cctacatcct gtatgtgatc   240
agcggactgg gaatcaccgc aggagcacac cggctgtggg cccacaagtc ctacaaggcc   300
aagtggcctc tgagagtgat cctggtcatc ttcaacaccg tggcctttca ggacgcagca   360
atggattggg caagggacca cagaatgcac acaagtatt ctgagacaga cgccgatcct   420
cacaatgcca ccaggggctt ctttttcagc cacatcggct ggctgctggt cgcaagcac    480
ccagatctga aggagaaggg caagggcctg acatgagcg atctgctggc cgaccccatc   540
ctgaggtttc agaagaagta ctatctgatc ctgatgcctc tggcctgctt tgtgatgcca   600
acagtgatcc ccgtgtactt ctggggcgag acatggacca acgccttttt cgtggccgcc   660
atgtttcgct atgccttcat cctgaacgtg acctggctgg tgaattctgc cgcccacaag   720
tggggcgata gccttacga caagagcatc aagccatccg agaacctgtc tgtggccatg   780
tttgccctgg gcgagggctt ccacaattac caccacacat ccccctggga ctataagacc   840
gccgagctgg gcaacaataa gctgaacttt accacaacct tcatcaactt cttcgccaag   900
atcggctggg cctatgatct gaagacagtg tccgacgata tcgtgaagaa tagggtgaag   960
aggaccggcg acggaagcca ccacctgtgg ggctggggcg atgagaacca gtccaaggag  1020
gagatcgacg ccgccatccg gatcaatcct aaggacgatt ga                    1062
```

<210> SEQ ID NO 101
<211> LENGTH: 353
<212> TYPE: PRT
<213> ORGANISM: Artificial
<220> FEATURE:
<223> OTHER INFORMATION: DST183_amino_acid Z9 Desatursae encoded by SEQ
      ID NO: 100

<400> SEQUENCE: 101

Met Ala Pro Asn Ile Ser Glu Asp Val Asn Gly Val Leu Phe Glu Ser
1               5                   10                  15

Asp Ala Ala Thr Pro Asp Leu Ala Leu Ser Thr Pro Val Gln Lys
            20                  25                  30

Ala Asp Asn Arg Pro Lys Gln Leu Val Trp Arg Asn Ile Leu Leu Phe
        35                  40                  45

Ala Tyr Leu His Leu Ala Ala Gln Tyr Gly Gly Tyr Leu Phe Leu Phe
    50                  55                  60

Ser Ala Lys Trp Gln Thr Asp Ile Phe Ala Tyr Ile Leu Tyr Val Ile
65                  70                  75                  80

Ser Gly Leu Gly Ile Thr Ala Gly Ala His Arg Leu Trp Ala His Lys
                85                  90                  95

Ser Tyr Lys Ala Lys Trp Pro Leu Arg Val Ile Leu Val Ile Phe Asn

|     |     |     |     |     | 100 |     |     |     | 105 |     |     |     |     | 110 |
| --- | --- | --- | --- | --- | --- | --- | --- | --- | --- | --- | --- | --- | --- | --- |

Thr Val Ala Phe Gln Asp Ala Ala Met Asp Trp Ala Arg Asp His Arg
            115                  120                125

Met His His Lys Tyr Ser Glu Thr Asp Ala Asp Pro His Asn Ala Thr
130                  135                  140

Arg Gly Phe Phe Phe Ser His Ile Gly Trp Leu Val Arg Lys His
145                  150                  155                160

Pro Asp Leu Lys Glu Lys Gly Lys Gly Leu Asp Met Ser Asp Leu Leu
            165                  170                175

Ala Asp Pro Ile Leu Arg Phe Gln Lys Lys Tyr Tyr Leu Ile Leu Met
            180                  185                190

Pro Leu Ala Cys Phe Val Met Pro Thr Val Ile Pro Val Tyr Phe Trp
            195                  200                205

Gly Glu Thr Trp Thr Asn Ala Phe Phe Val Ala Ala Met Phe Arg Tyr
            210                  215                220

Ala Phe Ile Leu Asn Val Thr Trp Leu Val Asn Ser Ala Ala His Lys
225                  230                  235              240

Trp Gly Asp Lys Pro Tyr Asp Lys Ser Ile Lys Pro Ser Glu Asn Leu
            245                  250                255

Ser Val Ala Met Phe Ala Leu Gly Glu Gly Phe His Asn Tyr His His
            260                  265                270

Thr Phe Pro Trp Asp Tyr Lys Thr Ala Glu Leu Gly Asn Asn Lys Leu
            275                  280                285

Asn Phe Thr Thr Thr Phe Ile Asn Phe Phe Ala Lys Ile Gly Trp Ala
            290                  295                300

Tyr Asp Leu Lys Thr Val Ser Asp Asp Ile Val Lys Asn Arg Val Lys
305                  310                  315              320

Arg Thr Gly Asp Gly Ser His His Leu Trp Gly Trp Gly Asp Glu Asn
            325                  330                335

Gln Ser Lys Glu Glu Ile Asp Ala Ala Ile Arg Ile Asn Pro Lys Asp
            340                  345                350

Asp

<210> SEQ ID NO 102
<211> LENGTH: 1059
<212> TYPE: DNA
<213> ORGANISM: Artificial
<220> FEATURE:
<223> OTHER INFORMATION: DST189_coding_sequence Z9 Desaturase

<400> SEQUENCE: 102

```
atggcccta acgtgaccga ggagaatggc gtgctgttcg agtctgatgc agcaacacct    60
gacctggccc tggcaagaga gccagtgcag caggcagata gctccccacg ggtgtacgtg   120
tggagaaaca tcatcctgtt tgcctatctg cacatcgccg ccgtgtacgg cggctatctg   180
tttctgttct ccgccaagtg gcagaccgac atcttcgcct acctgctgta tgtggcctct   240
ggactgggaa tcacagcagg agcacacagg ctgtgggccc acaagagcta caaggccaag   300 tggccccctga gactgatcct gaccatcttt aacaccacag cctttcagga cagcgccatc   360
gattgggccc gggaccacag aatgcaccac aagtattccg agaccgacgc cgatccccac   420
aatgccacaa ggggcttctt tttctcccac atcggctggc tgctggtgag aagcaccct    480 gagctgaagc gcaagggcaa gggcctggac ctgtctgatc tgtacgccga tcctatcctg   540
cgctttcaga agaagtacta tctgatcctg atgccactgg cctgcttcat cctgcccacc   600
```

```
gtgatccccg tgtacctgtg aacgagaca tggagcaatg ccttttttcgt ggccgccctg    660 tttcggtata ccttcatcct gaacgtgaca tggctggtga attccgccgc ccacaagtgg    720
ggcgataagc catacgacaa gtccatcaag ccctctgaga acctgtctgt gagcctgttt    780
gccttcggcg agggctttca caattaccac cacaccttcc catgggatta taagacagcc    840
gagctgggca accaccggct gaacttcacc acaaagttca tcaacttttt cgccaagatc    900
ggctgggcct atgatatgaa gaccgtgtct cacgagatcg tgcagcagag ggtgaagagg    960
acaggcgacg gaagccacca cctgtgggga tggggcgaca aggatcacgc acaggaggag   1020
atcgacgccg ccatcagaat caatcccaag gacgattga                          1059
```

<210> SEQ ID NO 103
<211> LENGTH: 352
<212> TYPE: PRT
<213> ORGANISM: Unknown
<220> FEATURE:
<223> OTHER INFORMATION: DST189_amino_acid Z9 Desaturase encoded by SEQ
      ID NO: 102

<400> SEQUENCE: 103

```
Met Ala Pro Asn Val Thr Glu Glu Asn Gly Val Leu Phe Glu Ser Asp
1               5                   10                  15

Ala Ala Thr Pro Asp Leu Ala Leu Ala Arg Glu Pro Val Gln Gln Ala
            20                  25                  30

Asp Ser Ser Pro Arg Val Tyr Val Trp Arg Asn Ile Ile Leu Phe Ala
        35                  40                  45

Tyr Leu His Ile Ala Ala Val Tyr Gly Gly Tyr Leu Phe Leu Phe Ser
    50                  55                  60

Ala Lys Trp Gln Thr Asp Ile Phe Ala Tyr Leu Leu Tyr Val Ala Ser
65                  70                  75                  80

Gly Leu Gly Ile Thr Ala Gly Ala His Arg Leu Trp Ala His Lys Ser
                85                  90                  95

Tyr Lys Ala Lys Trp Pro Leu Arg Leu Ile Leu Thr Ile Phe Asn Thr
            100                 105                 110

Thr Ala Phe Gln Asp Ser Ala Ile Asp Trp Ala Arg Asp His Arg Met
        115                 120                 125

His His Lys Tyr Ser Glu Thr Asp Ala Asp Pro His Asn Ala Thr Arg
    130                 135                 140

Gly Phe Phe Phe Ser His Ile Gly Trp Leu Leu Val Arg Lys His Pro
145                 150                 155                 160

Glu Leu Lys Arg Lys Gly Lys Gly Leu Asp Leu Ser Asp Leu Tyr Ala
                165                 170                 175

Asp Pro Ile Leu Arg Phe Gln Lys Lys Tyr Tyr Leu Ile Leu Met Pro
            180                 185                 190

Leu Ala Cys Phe Ile Leu Pro Thr Val Ile Pro Val Tyr Leu Trp Asn
        195                 200                 205

Glu Thr Trp Ser Asn Ala Phe Phe Val Ala Ala Leu Phe Arg Tyr Thr
    210                 215                 220

Phe Ile Leu Asn Val Thr Trp Leu Val Asn Ser Ala Ala His Lys Trp
225                 230                 235                 240

Gly Asp Lys Pro Tyr Asp Lys Ser Ile Lys Pro Ser Glu Asn Leu Ser
                245                 250                 255

Val Ser Leu Phe Ala Phe Gly Glu Gly Phe His Asn Tyr His His Thr
            260                 265                 270

Phe Pro Trp Asp Tyr Lys Thr Ala Glu Leu Gly Asn His Arg Leu Asn
```

275                 280                 285
Phe Thr Thr Lys Phe Ile Asn Phe Phe Ala Lys Ile Gly Trp Ala Tyr
        290                 295                 300

Asp Met Lys Thr Val Ser His Glu Ile Val Gln Gln Arg Val Lys Arg
305                 310                 315                 320

Thr Gly Asp Gly Ser His His Leu Trp Gly Trp Gly Asp Lys Asp His
                325                 330                 335

Ala Gln Glu Glu Ile Asp Ala Ile Arg Ile Asn Pro Lys Asp Asp
        340                 345                 350

<210> SEQ ID NO 104
<211> LENGTH: 1116
<212> TYPE: DNA
<213> ORGANISM: Unknown
<220> FEATURE:
<223> OTHER INFORMATION: DST192_coding_sequence Z9 Desaturase

<400> SEQUENCE: 104
atggattttc tgaacgagat cgacaattgc cccgagcggc tgagaaagcc agagaagatg    60
gcccccaacg tgaccgagga gaatggcgtg ctgttcgagt ccgatgcagc aaccccagac   120
ctggccctgg caaggacacc tgtggagcag gccgacgatt ctccaaggat ctacgtgtgg   180
cgcaacatca tcctgtttgc ctatctgcac ctggccgcca tctacggcgg ctatctgttt   240
ctgttctccg ccaagtggca gaccgatatc ttcgcctacc tgctgtatgt ggcatctgga   300
ctgggaatca cagcaggagc acacaggctg tgggcacaca agagctacaa ggccaagtgg   360
cctctgcgcc tgatcctgac catctttaac acaatcgcct tcaggacagc gccatcgat   420 tgggccaggg accaccgcat gcaccacaag tattccgaga ccgacgccga tccacacaat   480
gccacacggg gcttcttttt ctctcacatc ggatggctgc tggtgcggaa gcacccagag   540
ctgaagagaa agggcaaggg cctggacctg tctgatctgt acagcgatcc catcctgaga   600
tttcagaaga gtactatat gatcctgatg cctctggcct gtttcatcct gcccaccgtg   660
atccccgtgt atatgtggaa cgagacatgg agcaatgcct ttttcgtggc cgccctgttt   720
aggtatacct tcatcctgaa cgtgacatgg ctggtgaatt ccgccgccca caagtggggc   780
gataagcctt acgacaagtc catcaagcca tctgagaaca tgagcgtgtc cctgtttgcc   840
ttcggcgagg gctttcacaa ttaccaccac accttcccctt gggactataa acagccgag   900 ctgggcaacc accggctgaa cttcaccaca aagttcatca cttcttcgc caagatcggc   960 tgggcctatg atatgaagac cgtgtctcag gagatcgtgc agcagcgggt gaagagaaca  1020
ggcgacggaa gccaccacct gtggggatgg ggcgacaagg atcacgcaca ggaggagatc  1080
aacgccgcca tccgcatcaa tccaaaggac gattga                             1116

<210> SEQ ID NO 105
<211> LENGTH: 371
<212> TYPE: PRT
<213> ORGANISM: Unknown
<220> FEATURE:
<223> OTHER INFORMATION: DST192_amino_acid Z9 Desaturase encoded by SEQ
      ID NO: 104

<400> SEQUENCE: 105

Met Asp Phe Leu Asn Glu Ile Asp Asn Cys Pro Glu Arg Leu Arg Lys
1               5                   10                  15

Pro Glu Lys Met Ala Pro Asn Val Thr Glu Glu Asn Gly Val Leu Phe
            20                  25                  30

-continued

```
Glu Ser Asp Ala Ala Thr Pro Asp Leu Ala Leu Ala Arg Thr Pro Val
     35                  40                  45

Glu Gln Ala Asp Asp Ser Pro Arg Ile Tyr Val Trp Arg Asn Ile Ile
 50                  55                  60

Leu Phe Ala Tyr Leu His Leu Ala Ala Ile Tyr Gly Gly Tyr Leu Phe
 65                  70                  75                  80

Leu Phe Ser Ala Lys Trp Gln Thr Asp Ile Phe Ala Tyr Leu Leu Tyr
             85                  90                  95

Val Ala Ser Gly Leu Gly Ile Thr Ala Gly Ala His Arg Leu Trp Ala
            100                 105                 110

His Lys Ser Tyr Lys Ala Lys Trp Pro Leu Arg Leu Ile Leu Thr Ile
            115                 120                 125

Phe Asn Thr Ile Ala Phe Gln Asp Ser Ala Ile Asp Trp Ala Arg Asp
    130                 135                 140

His Arg Met His His Lys Tyr Ser Glu Thr Asp Ala Asp Pro His Asn
145                 150                 155                 160

Ala Thr Arg Gly Phe Phe Phe Ser His Ile Gly Trp Leu Leu Val Arg
                165                 170                 175

Lys His Pro Glu Leu Lys Arg Lys Gly Lys Gly Leu Asp Leu Ser Asp
            180                 185                 190

Leu Tyr Ser Asp Pro Ile Leu Arg Phe Gln Lys Lys Tyr Tyr Met Ile
    195                 200                 205

Leu Met Pro Leu Ala Cys Phe Ile Leu Pro Thr Val Ile Pro Val Tyr
    210                 215                 220

Met Trp Asn Glu Thr Trp Ser Asn Ala Phe Phe Val Ala Ala Leu Phe
225                 230                 235                 240

Arg Tyr Thr Phe Ile Leu Asn Val Thr Trp Leu Val Asn Ser Ala Ala
                245                 250                 255

His Lys Trp Gly Asp Lys Pro Tyr Asp Lys Ser Ile Lys Pro Ser Glu
            260                 265                 270

Asn Met Ser Val Ser Leu Phe Ala Phe Gly Glu Gly Phe His Asn Tyr
            275                 280                 285

His His Thr Phe Pro Trp Asp Tyr Lys Thr Ala Glu Leu Gly Asn His
    290                 295                 300

Arg Leu Asn Phe Thr Thr Lys Phe Ile Asn Phe Phe Ala Lys Ile Gly
305                 310                 315                 320

Trp Ala Tyr Asp Met Lys Thr Val Ser Gln Glu Ile Val Gln Gln Arg
                325                 330                 335

Val Lys Arg Thr Gly Asp Gly Ser His His Leu Trp Gly Trp Gly Asp
            340                 345                 350

Lys Asp His Ala Gln Glu Glu Ile Asn Ala Ala Ile Arg Ile Asn Pro
            355                 360                 365

Lys Asp Asp
    370
```